(12) United States Patent
Wu et al.

(10) Patent No.: US 9,938,292 B2
(45) Date of Patent: Apr. 10, 2018

(54) QUINOLINE DERIVATIVES AS SMO INHIBITORS

(71) Applicant: GUANGDONG ZHONGSHENG PHARMACEUTICAL CO., LTD, Dongguan, Guangdong (CN)

(72) Inventors: Hao Wu, Shanghai (CN); Chaofeng Long, Dongguan (CN); Jun Lin, Shanghai (CN); Xiaoxin Chen, Dongguan (CN); Yunhui Li, Shanghai (CN); Zhuowei Liu, Dongguan (CN); Changqing Wei, Shanghai (CN); Lijuan Chen, Dongguan (CN); Shuhui Chen, Shanghai (CN)

(73) Assignee: Guangdong Zhongsheng Pharmaceutical Co., Ltd, Dongguan, Guangdong (CN)

( * ) Notice: Subject to any disclaimer, the term of this patent is extended or adjusted under 35 U.S.C. 154(b) by 0 days.

(21) Appl. No.: 15/128,064

(22) PCT Filed: Mar. 16, 2015

(86) PCT No.: PCT/CN2015/074268
§ 371 (c)(1),
(2) Date: Sep. 21, 2016

(87) PCT Pub. No.: WO2015/144001
PCT Pub. Date: Oct. 1, 2015

(65) Prior Publication Data
US 2017/0174703 A1 Jun. 22, 2017

(30) Foreign Application Priority Data

Mar. 24, 2014 (CN) .......................... 2014 1 0110890
Mar. 10, 2015 (CN) .......................... 2015 1 0104908

(51) Int. Cl.
| | | |
|---|---|---|
| C07D 413/10 | (2006.01) |
| C07D 413/14 | (2006.01) |
| C07D 403/10 | (2006.01) |
| C07D 403/14 | (2006.01) |
| C07D 498/04 | (2006.01) |
| C07D 401/10 | (2006.01) |
| C07D 491/08 | (2006.01) |
| C07D 487/04 | (2006.01) |
| C07D 417/12 | (2006.01) |
| C07D 417/14 | (2006.01) |
| C07D 471/04 | (2006.01) |
| C07D 487/08 | (2006.01) |
| C07D 487/10 | (2006.01) |
| C07D 471/10 | (2006.01) |

(52) U.S. Cl.
CPC ......... *C07D 498/04* (2013.01); *C07D 401/10* (2013.01); *C07D 413/10* (2013.01); *C07D 413/14* (2013.01); *C07D 417/12* (2013.01); *C07D 417/14* (2013.01); *C07D 471/04* (2013.01); *C07D 471/10* (2013.01); *C07D 487/04* (2013.01); *C07D 487/08* (2013.01); *C07D 487/10* (2013.01); *C07D 491/08* (2013.01)

(58) Field of Classification Search
None
See application file for complete search history.

(56) References Cited

U.S. PATENT DOCUMENTS

| | | |
|---|---|---|
| 7,888,364 B2 | 2/2011 | Gunzner et al. |
| 8,178,563 B2 | 5/2012 | Gao et al. |
| 8,222,263 B2 | 7/2012 | Bahceci et al. |
| 8,507,491 B2 | 8/2013 | Cheng et al. |
| 8,754,092 B2 | 6/2014 | Bahceci et al. |
| 2006/0063779 A1 | 3/2006 | Gunzner et al. |
| 2009/0105211 A1 | 4/2009 | Bahceci et al. |
| 2009/0203666 A1 | 8/2009 | Gao et al. |
| 2010/0311760 A1 | 12/2010 | de Vicente Fidalgo et al. |
| 2011/0092461 A1 | 4/2011 | Gunzner et al. |
| 2011/0152282 A1 | 6/2011 | Cheng et al. |
| 2012/0196849 A1 | 8/2012 | Gao et al. |
| 2012/0238570 A1 | 9/2012 | Bahceci et al. |
| 2012/0245139 A1 | 9/2012 | Bahceci et al. |
| 2012/0270858 A1 | 10/2012 | Tao et al. |
| 2013/0296333 A1 | 11/2013 | Cheng et al. |
| 2015/0105550 A1 | 4/2015 | Gunzner et al. |

FOREIGN PATENT DOCUMENTS

| | | |
|---|---|---|
| CN | 101679308 A | 3/2010 |
| CN | 102203067 A | 9/2011 |
| CN | 102573473 A | 7/2012 |
| CN | 102746285 A | 10/2012 |
| CN | 102964294 A | 3/2013 |
| CN | 103588771 A | 2/2014 |
| EP | 2471789 A1 | 7/2012 |

(Continued)

OTHER PUBLICATIONS

Quintela, et al., Eur. J. Med. Chem., 38:265 (2003).*
Caro I. and J.A. Low, The role of the hedgehog signaling pathway in the development of basal cell carcinoma and opportunities for treatment, Clin Cancer Res, 2010, 16 (13), 3335-3339.
Bale A. E. and K.P. Yu, The hedgehog pathway and basal cell carcinomas, Hum Mol Genet, 2001, 10 (7), 757-762.
Von Hoff D. D., et al., Inhibition of the hedgehog pathway in advanced basal-cell carcinoma, N Engl J Med, 2009, 361(12), 1164-1172.
Stone D.M. et al., The tumour-suppressor gene patched encodes a candidate receptor for Sonic hedgehog, Nature, 1996, 384(6605), 129-134.

(Continued)

*Primary Examiner* — Michael Barker
(74) *Attorney, Agent, or Firm* — Harness, Dickey & Pierce, P.L.C.

(57) ABSTRACT

Disclosed are quinoline derivatives as hedgehog pathway inhibitors, especially as SMO inhibitors. Compounds of the present invention can be used in treating diseases relating to hedgehog pathway including cancer.

20 Claims, No Drawings

(56) References Cited

FOREIGN PATENT DOCUMENTS

| | | |
|---|---|---|
| JP | H07-173138 A | 7/1995 |
| JP | H11-501668 A | 2/1999 |
| JP | H11-171883 A | 6/1999 |
| JP | 2004-035549 A | 2/2004 |
| JP | 2005-132834 A | 5/2005 |
| JP | 2012-529461 | 11/2012 |
| JP | 2013-028588 A | 2/2013 |
| WO | WO-9830560 A1 | 7/1998 |
| WO | WO-2005-070430 A1 | 8/2005 |
| WO | WO-2007-109154 A2 | 9/2007 |
| WO | WO-2007-109172 A2 | 9/2007 |
| WO | WO-2007-109192 A2 | 9/2007 |
| WO | WO-2008-012623 A1 | 1/2008 |
| WO | WO-2010-021381 A1 | 2/2010 |
| WO | WO-2010-023480 A1 | 3/2010 |
| WO | WO-2010-082044 A1 | 7/2010 |
| WO | WO-2011-097491 A1 | 8/2011 |
| WO | WO-2013-066736 A1 | 5/2013 |
| WO | WO-2014-139328 A1 | 9/2014 |

OTHER PUBLICATIONS

Lorusso PM. et al., Phase I trial of hedgehog pathway inhibitor vismodegib (GDC-0449) in patients with refractory, locally advanced or metastatic solid tumors, Clin Cancer Res, 2011, 17 (8), 2502-2511.

De Smaele E. et al., Vismodegib, a small-molecule inhibitor of the hedgehog pathway for the treatment of advanced cancers, Curr Opin Investig Drugs, 2010, 11(6), 707-718.

Berge S.M. et al., Pharmaceutical Salts, J Pharm Sci, 1977, 66(1), 1-19.

First Office Action issued by Moscow Federal Service for Intellectual Property/Federal Institute of Industrial Property (FIIP) regarding Application No. 2016141129 with English translation (13 pages).

First Office Action issued by Israel Ministry of Justice Patent Office regarding Application No. 247970 (2 pages).

First Office Action/First Examination Report issued by New Zealand Intellectual Property Office regarding Application No. 724691 (3 pages).

First Office Action issued by Republic of Colombia Superintendent of Industry and Commerce regarding Application No. NC2016/0003099 with English translation (4 pages).

Extended European Search Report issued by European Patent Office (EPO) dated Feb. 22, 2017 regarding Application No. 15768666.8 (13 pages).

Surajit Sinha, et al., "Purmorphamine Activates the Hedgehog Pathway by Targeting Smoothened", Nature Chemical Biology, vol. 2, No. 2, Nov. 20, 2005, pp. 29-30 (2 pages).

Francisco X, Talmas, et al., "Discovery of N-[4-[6-tert-Butyl-5-methoxy-8-(6-methoxy-2-oxo-1H-pyridin-3-yl)-3-quinolyl]phenyl]methanesulfonamide (RG7109), A Potent Inhibitor of the Hepatitis C Virus NS5B Polymerase", Journal of Medicinal Chemistry, Vo. 57, No. 5, Mar. 13, 2014, pp. 1914-1931 (18 pages).

First Office Action (in Japanese) issued in Japan Application No. 2017-501450 (50 pages).

Rajendra Kristam, et al., "3D-QSAR Analysis of TRPV1 Inhibitors Reveals a Pharmacophore Applicable to Diverse Scaffolds and Clinical Candidates", Journal of Molecular Graphics and Modeling (2013), vol. 45, pp. 157-172 (35 pages).

Alison Betts, et al., "Impact of Physicochemical and Structural Properties on the Pharmacokinetics of a Series of a1L-Adrenoceptor Antagonists", Drug Metabolism & Disposition (2007), vol. 35, No. 8, pp. 1435-1445 (11 pages).

Aleksandar R. Todorov, et al., "Tautomeric Switching and Metal-Cation Sensing of Ligand-Equipped 4-Hydroxy-/4-oxo-1,4-dihydroquinolines", Chemistry, A European Journal (2012), vol. 18, pp. 7269-7277 (9 pages).

Francisco Carrion, et al., "Cyclization of 2-dicyanomethylene-1,2-dihydropyridine-3-carbonitriles with amines: A Mechanistic Rationalization", Tetrahedron (2007), vol. 63, pp. 215-223 (9 pages).

S. Anandan, et al., "Synthesis and Characterization of Naphthyridine and Acridinedione Ligands Coordinated Ruthenium (II) Complexes and Their Applications in Dye-Sensitized Solar Cells", Solar Energy Materials & Solar Cells (2004), vol. 81, pp. 419-428 (10 pages).

V.K. Indirapriyadharshini, et al., "Spectral and Photophysical Properties of 1,6-naphthyridine Derivatives: A New Class of Compounds for Nonlinear Optics", Spectrochimica Acta Part A (2002), vol. 58, pp. 1535-1543 (9 pages).

R. Sankaranarayanan, et al., "5-Amino-4-(4-diethylaminophenyl)-2-(4-hydroxyphenyl)-7-(pyrrolidin-1-yl)-1,6-naphthyridine-8-carbonitrile", Acta Cryst. (2001), vol. C57, pp. 726-727 (2 pages).

L. Govindasamy, et al., "5-Amino-4-(4-diethylaminophenyl)-2-phenyl-7-(pyrrolidin-1-yl)-1,6-naphthyridine-carbonitrile", Acta Cryst. (2000), vol. C56, pp. 80-81 (2 pages).

R. Sankaranarayanan, et al., "5-Amino-4-(4-methoxyphenyl)-2-phenyl-7-(pyrrolidin-1-yl)-1,6-naphthyridine-8-carbonatrile", Acta Cryst. (1999), vol. C55, pp. 1670-1672 (3 pages).

Kandasamy Chinnakali, et al., "5-Amino-2,4-diphenyl-7-(pyrrolidin-1-yl)-1,6-naphthyridine-8-carbonitrile", Acta Cryst. (1998), vol. C54, pp. 781-783 (3 pages).

Eva Veverkova, et al., "Synthesis of Highly Substituted 1,6-Naphthyridines: A Reinvestigation", Synthetic Communications (2002) vol. 32, No. 18, pp. 2903-2910 (10 pages).

S.V. Roman, et al., "Synthesis of 1,6-naphthyridines Containing A Cyclic Amine Residue Using the Cascade Heterocyclization Method", Chemistry of Heterocyclic Compounds (1999), vol. 35, No. 10, p. 1253 (3 pages).

Periyasamy Murugan, et al., "A Facile One Pot Synthesis of Highly Substituted 1,6-Naphthyridines", Synthetic Communications (1999), vol. 29, No. 22, pp. 3881-3887 (9 pages).

Sundari Bhaskaran, et al., "5-Amino-4-(4-dimethylaminophenyl)-2-(4-methoxyphenyl)-7-(phrrolidin-1-yl)-1,6-naphthyridine-8-carbonitrile", Acta Cryst. (2003), vol. E59, No. 2, pp. o200-o202 (3 pages).

Search Report from related Columbia Application.

2nd Office Action issued in NC20100003099.

2nd Office Action issued in JP2017-501450.

3rd Office Action issued in NZ 724691.

Office Action issued in related European application 157689666.8.

* cited by examiner

QUINOLINE DERIVATIVES AS SMO INHIBITORS

CROSS-REFERENCE TO RELATED APPLICATIONS

This application is a National Stage of International Application No. PCT/CN2015/074268, filed on Mar. 16, 2015, and published in Chinese as WO2015/144001 A1 on Oct. 1, 2015. This application claims the priority to Chinese Application No. 201410110890.1, filed on Mar. 24, 2014 and Chinese Application No. 201510104908.1, filed on Mar. 10, 2015. The entire disclosures of the above applications are incorporated herein by reference.

FIELD OF INVENTION

The present invention relates to a series of quinoline derivatives, as hedgehog pathway inhibitors, especially as SMO inhibitors, compounds of the present invention can be used in treating diseases relating to hedgehog pathway including cancer.

PRIOR ARTS

Hedgehog proteins are secreted signal proteins originally found in *drosophila*, they are highly hydrophobic proteins and play a critical role in embryonic development. Three types of homologous hedgehog proteins have already been identified in humans, which are sonic hedgehog (Shh), Indian hedgehog (Ihh) and Desert hedgehog (Dhh) respectively. Thereinto, Shh is not only essential for embryonic development and there are a lot of evidence showing that it also plays an important role in the carcinogenesis mechanism of some cancers including basal cell carcinoma and so on. (Caro, I. and J. A. Low, Clin Cancer Res, 2010. 16 (13): 3335-9). In vivo Shh synthesizes a precursor protein with a molecular weight of 45 kDa, produces a N-terminal fragment with a molecular weight of 20 kDa by self-excision, the N-terminal fragment is of all the known biological activities in vivo, including activating an intracellular hedgehog signaling pathway whose key members embraces patched (PTCH), GPCRs-like receptors oncogene smoothened (SMO) and transcription factor Gli, etc. (Bale, A. E. and K. P. Yu, Hum Mol Genet, 2001. 10 (7): 757-62). Analysis results of the variation in basal cell carcinoma hedgehog signaling pathway show that most of the variation occurs in PTCH-1 and SMO. (Von Hoff, D. D., et al., N Engl J Med, 2009. 361 (12): 1164-72). PTCH-1 is a membrane protein with a 12-transmembrane structure, which is a direct receptor of Shh. In the absence of Shh, PTCH-1 interacts with SMO, which is a 7-transmembrane protein, to inhibit the biological activity of SMO. The binding of Shh and PTCH-1 leads to a removal of PTCH-1 from SMO thereby making SMO loose from being inhibited. Gli transcription factor is controlled by SMO which is as a switch of gene transcription and whose key members include Gli1, Gli2 and Gli3. The whole hedgehog pathway plays an important role in normal embryonic development. Disrupting this signaling pathway will cause serious malformation, the natural teratogenic compound cyclopamine is an example which is a hedgehog inhibitor. Usually, the concentration of hedgehog protein in an adult human body is very low. In the case of low hedgehog protein concentration, PTCH-1 binds to SMO thereby inhibiting the biological activity of SMO, so that the whole pathway is inactive or of very low activity. When the cells secrete hedgehog protein, the binding of hedgehog to the PTCH-1 receptor leads to its removal from SMO, thereby losing inhibition effect on SMO. SMO further activates transcription factor Gli-1 to regulate gene transcription and cell growth. Increasing evidence indicates that the majority of the basal cell carcinoma is caused by overhigh hedgehog signaling pathway activity led by mutations or other causes. Thus, inhibiting the overhigh activity of hedgehog signaling pathway can inhibit the growth of cancer cells so as to achieve the treatment of basal cell carcinoma or other cancers caused by the same mechanism. The evidence that SMO's constitutive activation leads to cancer (e.g. BCC) as well as relieving the inhibition from Ptch makes SMO cause cancer illustrates the use of SMO antagonist as therapeutic agents in the treatment of the diseases (Stone, et al., (1996) Nature 384: 129). A series of scientific and clinical trials show that hedgehog inhibitors are effective in the treatment of many cancers. The latest clinical trial data show that hedgehog inhibitor GDC-0449 is effective in the treatment of basal cell carcinoma and medullary cell carcinoma (Lorusso P M. et al. Clin Cancer Res. 2011; 17 (8): 2502-11), which was licensed by FDA in January 2012, and the other cancers cause by the same mechanism, such as basal cell nevus syndrome (BCNS) (Goldberg L H. et al. Arch Dermatol. 2011 Mar. 21.). Biochemical studies show that the inhibition position of GDC-0449 locates on SMO, inhibiting the activity of SMO means inhibiting the activity of the whole hedgehog pathway, so as to achieve the purpose of anti-cancer. In addition to the two types of cancers, basal cell carcinoma and medullary cell carcinoma, there are many other cancers related to the ultra-high activity of hedgehog signaling pathway, including pancreatic cancer, stomach cancer, colorectal cancer, ovarian cancer and prostate cancer, and part of leukemia etc. (De Smaele E. et al. Curr Opin Investig Drugs. 2010; 11(6): 707-18). Thus, there is a promising prospect of developing hedgehog inhibitors as novel anti-cancer drugs.

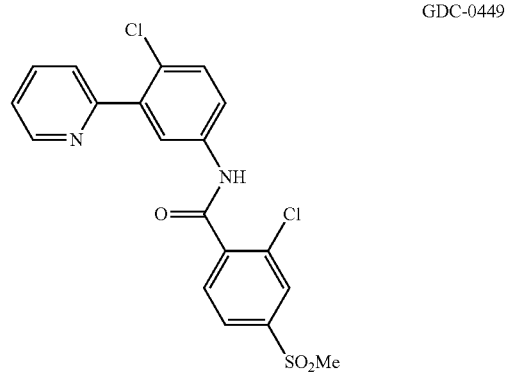 [SMILES: CS(=O)(=O)c1ccc(C(=O)Nc2ccc(Cl)c(-c3ccccn3)c2)c(Cl)c1]

GDC-0449

Although there are some SMO inhibitors in the prior art, it still need to be further improved in the aspects of activity, solubility, pharmacokinetics, druggability and so on.

Content of the Present Invention

The aim of the present invention is to provide a compound represented by formula (I) or a pharmaceutically acceptable salt thereof,

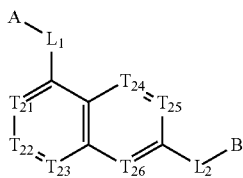

wherein, A is selected from

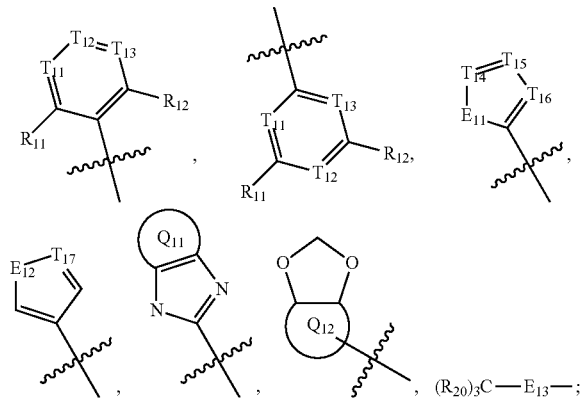, $(R_{20})_3C-E_{13}-$;

$(R_{20})_3C-E_{13}-$;

each of $T_{11-17}$ is independently selected from N, $C(R_{13})$;

each of $E_{11-13}$, $L_1$, $L_2$ is independently selected from $N(R_{14})$, $C(=O)N(R_{15})$, $S(=O)_2N(R_{16})$, $C=N(R_{17})$, $C(R_{18})(R_{19})$, S, $C(=O)O$, $C(=O)$, $C=S$, $S(=O)$ or $S(=O)_2$;

each of $L_1$, $L_2$ can also be independently selected from a single bond;

each of $R_{11-13}$, $R_{18-19}$ is independently selected from H, F, Cl, Br, I, CN, OH, SH, $NH_2$, an optionally $R_{01}$-substituted $C_{1-6}$ alkyl or heteroalkyl or alkyl-heteroatom group or heteroalkyl-heteroatom group, an optionally $R_{02}$-substituted $C_{3-8}$ cyclic group or heterocyclic group or cycle-heteroatom group or heterocycle-heteroatom group; preferably selected from a methyl, a trifluoromethyl, a trifluoromethoxy, F, Cl, Br, I, CN, a methylaminocarbonyl, a methylsulfonyl, a trifluoromethylsulfonyl, a trifluoromethoxy, a cyclopropyl, a morpholinylsulfonyl, a 2-imidazolyl, a dimethylamino, a n-, or iso-propyl;

each of $R_{14-17}$ is independently selected from H, an optionally $R_{01}$-substituted $C_{1-6}$ alkyl or $C_{3-6}$ cycloalkyl;

$R_{20}$ is selected from H, F, Cl, Br, I, CN, OH, SH, $NH_2$, a methoxy, a methylamino, a dimethylamino;

each of $Q_{11-12}$ is independently selected from a phenyl, a pyridyl, a thienyl, a furyl;

a structural unit

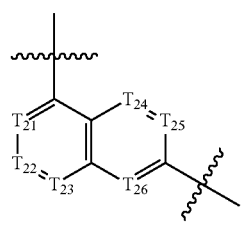

can be replaced by

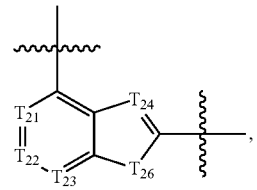,

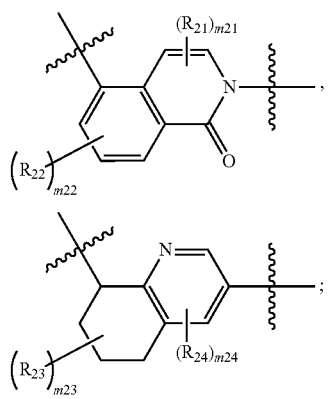

each of $T_{21-26}$ is independently selected from N, $C(R_{25})$; $T_{25}$ can also be selected from $N^{\oplus}(R_{25})$;

each of $R_{21-25}$ is independently selected from H, F, Cl, Br, I, CN, OH, SH, $NH_2$, an optionally $R_{01}$-substituted $C_{1-6}$ alkyl or heteroalkyl or alkyl-heteroatom group or heteroalkyl-heteroatom group, an optionally $R_{02}$-substituted $C_{3-8}$ cyclic group or heterocyclic group or cycle-heteroatom group or heterocycle-heteroatom group; preferably selected from F, Cl, Br, I, CN, OH, a methyl, an ethyl, an isopropyl, a methoxy, a trifluoromethyl, a difluoromethoxy, a n-, or iso-propoxy, a cyclopropyl, a formamido, a methanesulfonylamino, a dimethylamino, a dimethylaminoethoxy, a methylsulfonyl, a carbomethoxy,

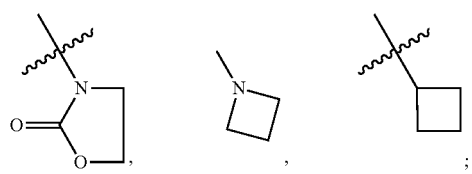

each of $m_{21-24}$ is independently selected from 0, 1 or 2; B is selected from

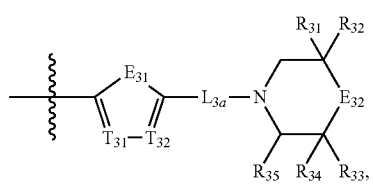

-continued

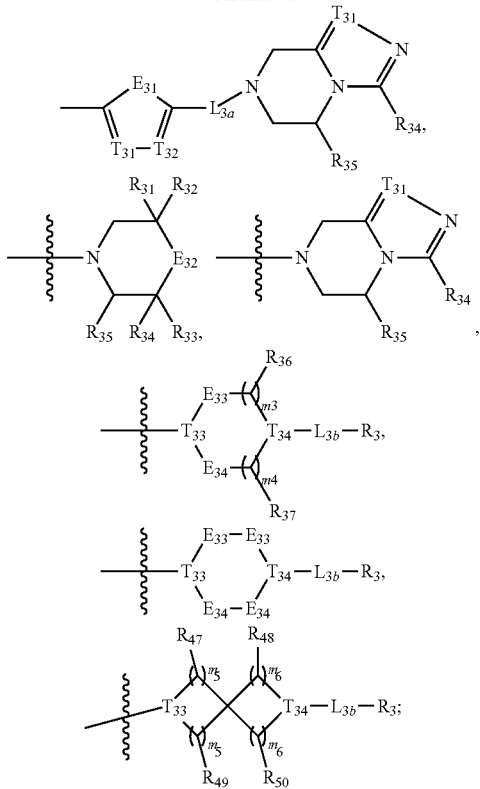

$R_3$ is selected from

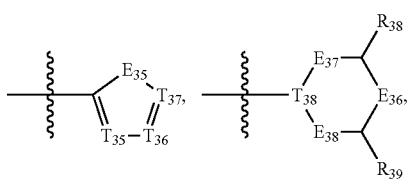

H, an optionally $R_{01}$-substituted $C_{1-6}$ alkyl or heteroalkyl or alkyl-heteroatom group or heteroalkyl-heteroatom group, an optionally $R_{02}$-substituted $C_{3-8}$ cyclic group or heterocyclic group or cycle-heteroatom group or heterocycle-heteroatom group;

each of $E_{31-38}$, $L_{3a}$, $L_{3b}$ is independently selected from $N(R_{40})$, $N(R_{40})(CH_2)_{1-3}$, $C(=O)N(R_{40})(CH_2)_{1-3}$, $C(=O)N(R_{41})$, $S(=O)_2N(R_{42})$, $C=N(R_{43})$, $C(R_{44})(R_{45})$, S, $C(=O)O$, $C(=O)$, $C=S$, $S(=O)$, $S(=O)_2$, O or $C(=O)C(R_{44})(R_{45})$;

each of $L_{3a}$, $L_{3b}$ can also be independently selected from a single bond or a $C_{1-5}$ alkyl;

each of $E_{31}$, $E_{35}$ can also be independently selected from $-T_{39}=T_{40}-$;

each of $T_{31-40}$ is independently selected from N, $C(R_{46})$;

each of $R_{40-43}$ is independently selected from H, an optionally $R_{01}$-substituted $C_{1-6}$ alkyl or $C_{3-6}$ cycloalkyl, an optionally $R_{01}$-substituted $C_{1-6}$ alkyl acyl or $C_{3-6}$ cycloalkyl acyl, an optionally $R_{01}$-substituted $C_{1-6}$ alkyl sulfonyl or $C_{3-6}$ cycloalkyl sulfonyl, an optionally $R_{01}$-substituted 5-6 membered aryl acyl, an optionally $R_{01}$-substituted 5-6 membered heteroaryl acyl, an optionally $R_{01}$-substituted 5-6 membered aryl sulfonyl, an optionally $R_{01}$-substituted $C_{1-6}$ alkyoxycarbonyl, an optionally $R_{01}$-substituted $C_{1-6}$ alkyl amino carbonyl;

each of $R_{31-49}$, $R_{44-50}$ is independently selected from H, F, Cl, Br, I, CN, OH, SH, $NH_2$, $C(=O)OH$, an optionally $R_{01}$-substituted $C_{1-6}$ alkyl or heteroalkyl or alkyl-heteroatom group or heteroalkyl-heteroatom group, an optionally $R_{02}$-substituted $C_{0-3}$ alkyl-$C_{3-8}$ cyclic group or heterocyclic group or cycle-heteroatom group or heterocycle-heteroatom group;

each of $R_{01}$, $R_{02}$ is independently selected from F, Cl, Br, I, CN, OH, SH, $NH_2$, $R_{03}$;

$R_{03}$ is selected from a $C_{1-6}$ alkyl amino, a di($C_{1-6}$ alkyl) amino, a $C_{1-6}$ alkoxy, a $C_{3-8}$ cycloalkyl amino, a $C_{3-8}$ heterocycloalkyl amino, a $C_{3-8}$ cycloalkoxy;

the heteroatom or the heteroatom group is independently selected from $C(=O)NR_{04}$, $N(R_{05})$, $C=N(R_{06})$, O, S, $C(=O)O$, $C(=O)$, $C=S$, $S(=O)$, $S(=O)_2$ and/or $S(=O)_2N(R_{07})$;

each of $R_{04-07}$ is independently selected from H, $R_{08}$;

$R_{08}$ is selected from a $C_{1-6}$ alkyl or a $C_{3-8}$ cycloalkyl;

$R_{03}$, $R_{08}$ are optionally substituted by $R_{001}$, $R_{001}$ is selected from OH, $N(CH_3)_2$, $NH(CH_3)$, $NH_2$, F, Cl, Br, I, CN, a methyl, a methoxy;

a number of $R_{01}$, $R_{02}$, $R_{001}$, the heteroatom or the heteroatom group is independently selected from 0, 1, 2, or 3;

each of $m_3$, $m_4$ is independently selected from 0 or 1, when $m_3$ or $m_4$ is selected from 0, the corresponding structural unit represents a single bond just for the linkage;

each of $m_5$, $m_6$ is independently selected from 1 or 2;

optionally, $R_{31}$ and $R_{32}$, $R_{31}$ and $R_{33}$, $R_{31}$ and $R_{35}$, $E_{33}$ and $E_{34}$ form a linking bond $(CH_2)_{1-6}$ together, preferably $(CH_2)_2$, $(CH_2)_3$, $(CH_2)_4$, $(CH_2)_5$;

optionally, $R_{32}$ and $R_{32}$ connect with each other to form a 5-membered carbocyclic ring or a heterocyclic ring;

optionally, when $E_{32}$ is selected from $N(R_{40})$ or O, $R_{31}$ and $R_{34}$ present a cis-arrangement; when $E_{32}$ is selected from $C(R_{43})(R_{44})$, $R_{31}$ and $R_{34}$ present a trans-arrangement; when $T_{34}$ is selected from N, $R_{36}$ and $R_{37}$ present a cis-arrangement; when $T_{34}$ is selected from $C(R_{45})$, $R_{36}$ and $R_{37}$ present a trans-arrangement;

preferably, the $C_{3-8}$ cyclic group or heterocyclic group or cycle-heteroatom group or heterocycle-heteroatom group is selected from a phenyl, a pyridyl, a thienyl, a furyl, an imidazolyl, an oxazolyl, a thiazolyl, an isothiazolyl.

preferably, the compound or the pharmaceutically acceptable salt thereof, wherein A is selected from

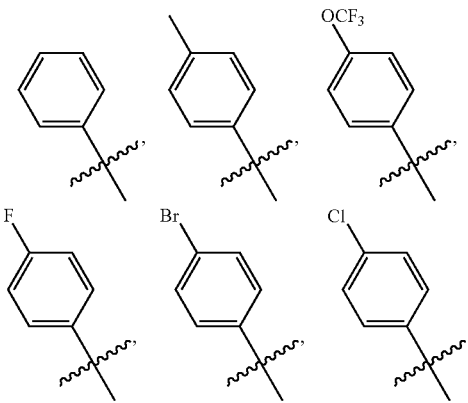

-continued
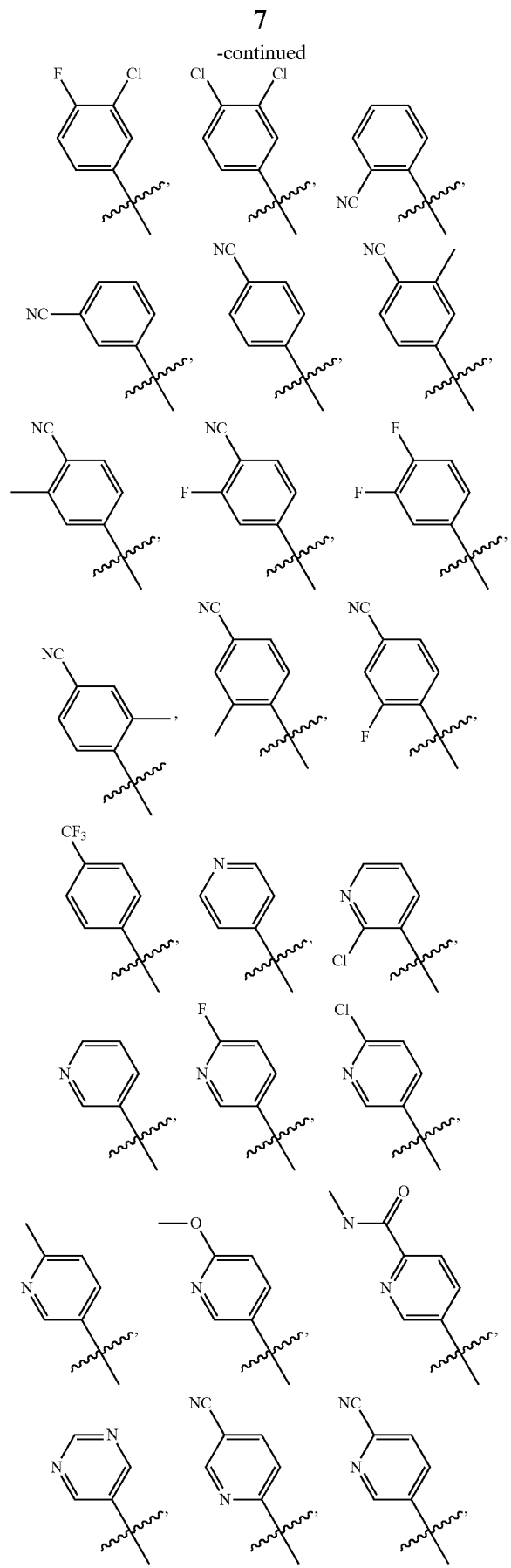
-continued
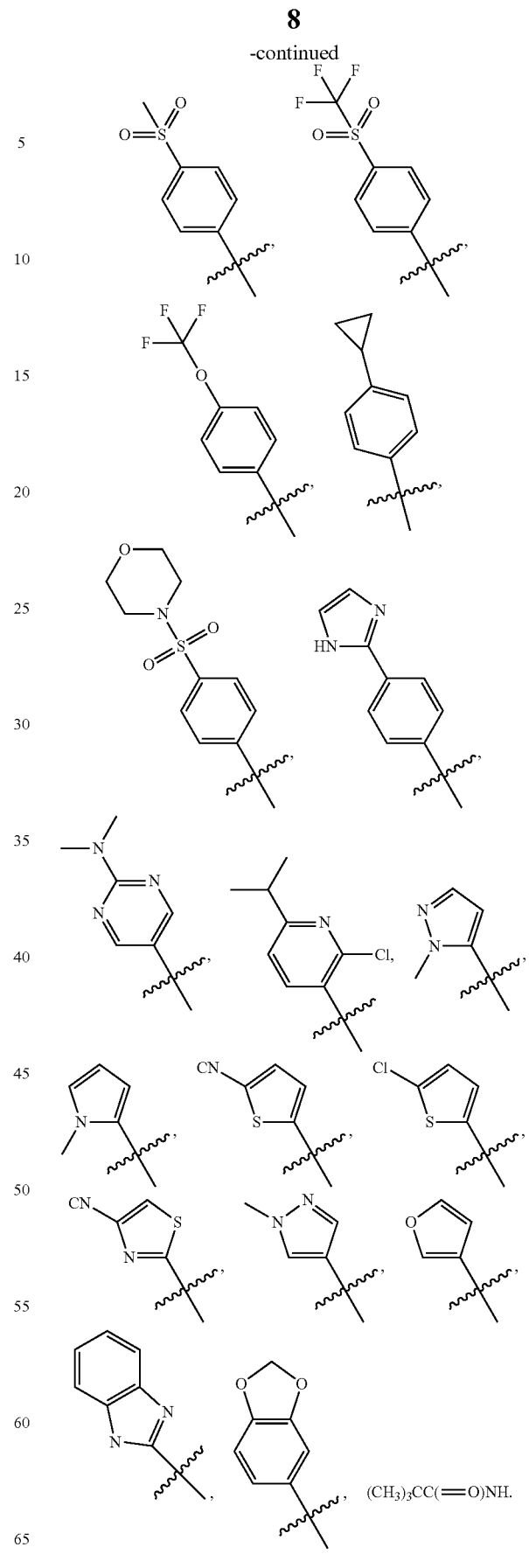
(CH₃)₃CC(=O)NH.

optionally, the compound or the pharmaceutically acceptable salt thereof, wherein the structural unit

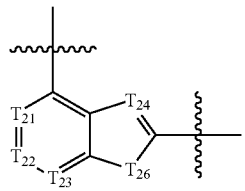

is selected from

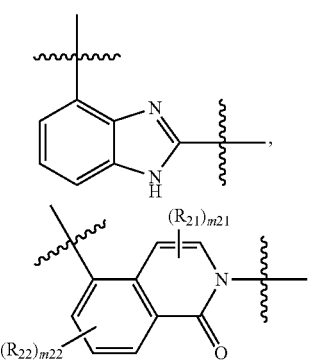

is selected from

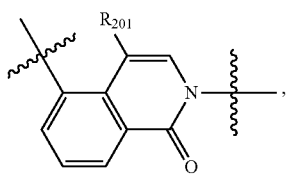

the structural unit

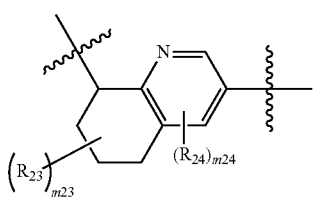

is selected from

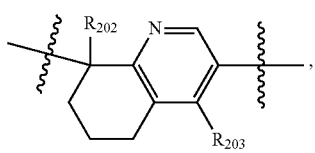

wherein,
each of $R_{201}$, $R_{202}$, $R_{203}$ is independently selected from H, F, Cl, Br, I, CN, OH, SH, $NH_2$, an optionally $R_{01}$-substituted $C_{1-6}$ alkyl or heteroalkyl or alkyl-heteroatom group or heteroalkyl-heteroatom group, an optionally $R_{02}$-substituted $C_{3-8}$ cyclic group or heterocyclic group or cycle-heteroatom group or heterocycle-heteroatom group;

preferably, $R_{201}$ is selected from a methyl, F, Cl, Br, I; each of $R_{202}$, $R_{203}$ is independently selected from a $C_{1-6}$ alkoxy, more preferably a methoxy.

Preferably, the compound or the pharmaceutically acceptable salt thereof, wherein the structural unit

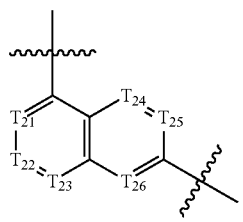

is selected from:

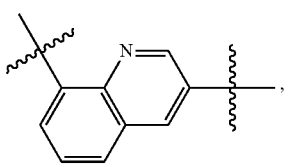

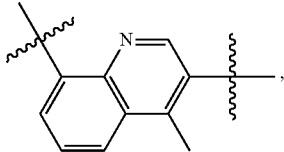

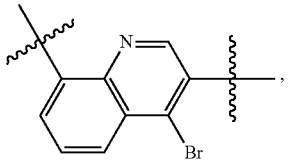

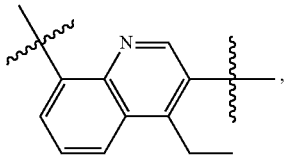

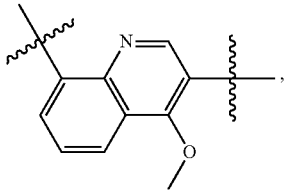

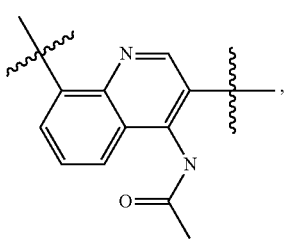

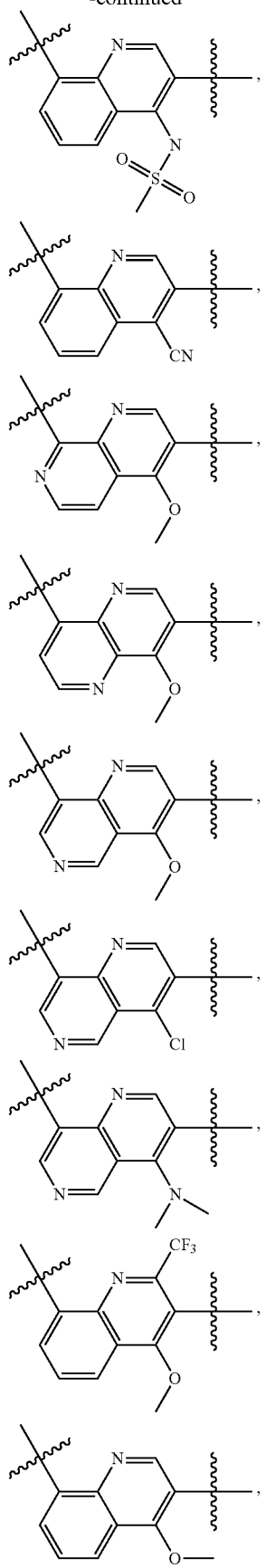
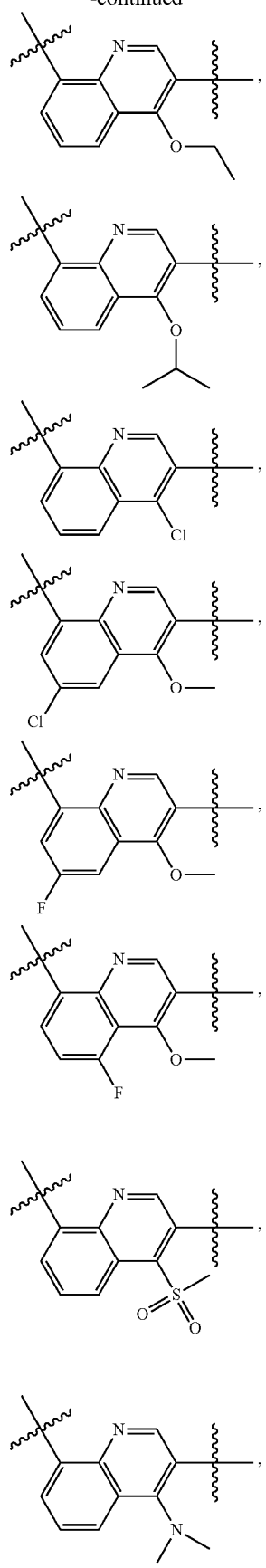

-continued
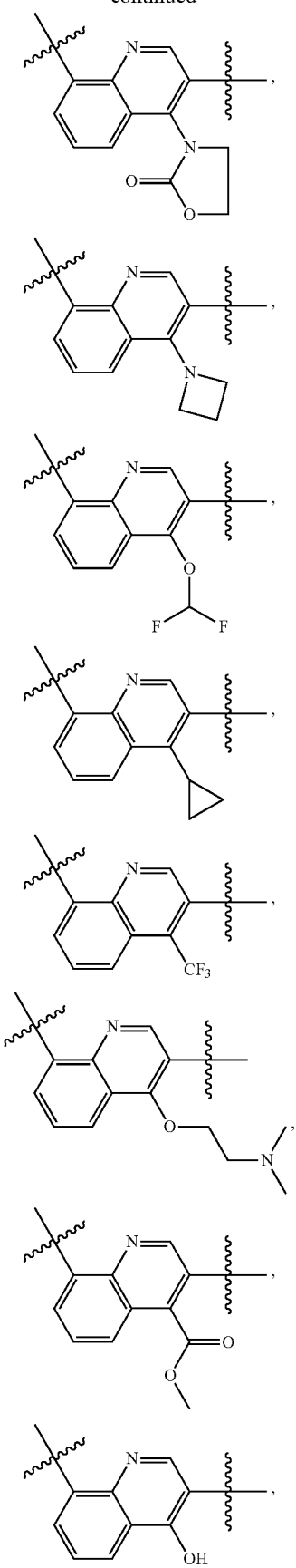
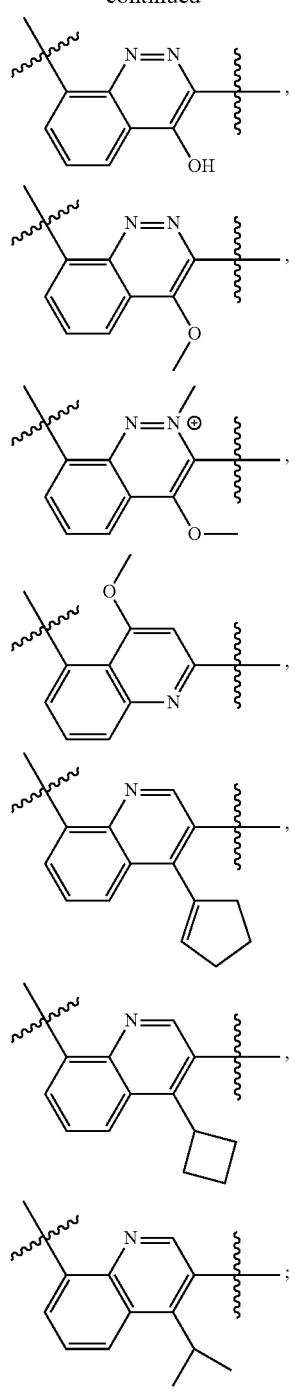
the structural unit
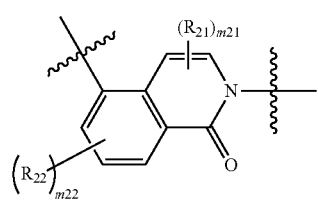

is selected from:

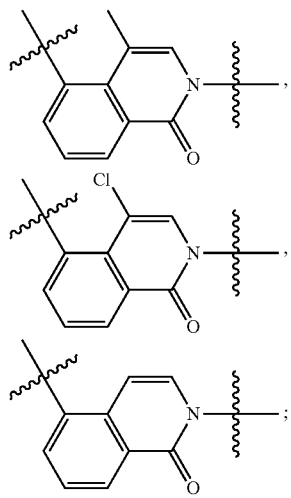

the structural unit

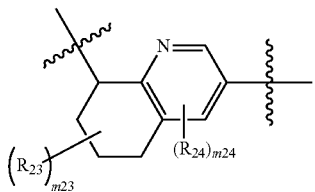

is selected from:

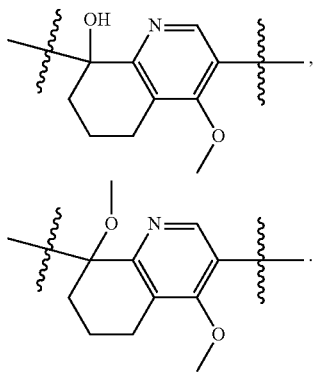

Preferably, the compound or the pharmaceutically acceptable salt thereof, wherein B is selected from

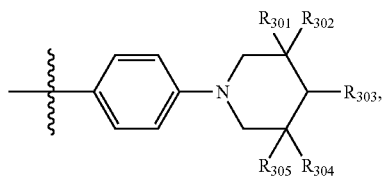

wherein
each of $R_{301-305}$ is independently selected from H, OH, $NH_2$, F, Cl, Br, I, CN, an optionally $R_{3001}$-substituted $C_{1-3}$ alkyl or alkoxy or alkyl amino or cyclopropyl;

$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
optionally, the structural unit

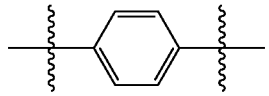

in the general structure can be replaced by a pyridyl, a thienyl, a furyl;
optionally,
each of $R_{301-305}$ is independently selected from a methyl, H, OH, $NH_2$, F, Cl, Br, I, CN;
further optionally,
B is selected from

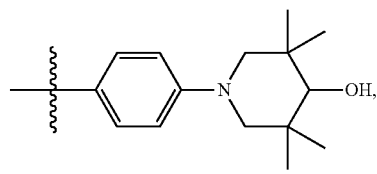

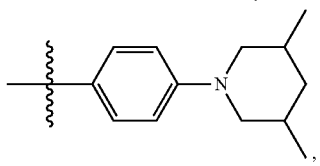

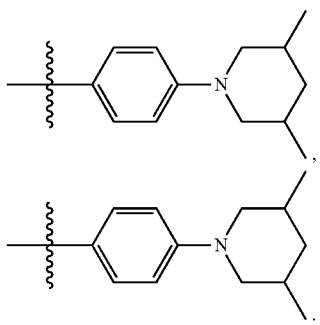

optionally, the compound or the pharmaceutically acceptable salt thereof, wherein B is selected from

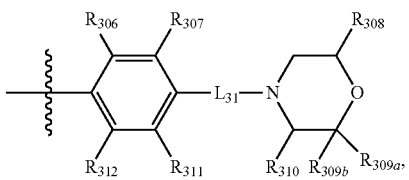

wherein
each of $R_{306-308}$, $R_{309a}$, $R_{309b}$, $R_{310-312}$ is independently selected from H, OH, $NH_2$, F, Cl, Br, I, CN, an optionally $R_{3001}$-substituted $C_{1-3}$ alkyl or alkoxy or alkyl amino or cyclopropyl;
$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;

$L_{31}$ is selected from a single bond, $R_{3002}N(R_{3003})R_{3004}$, O, S, C(=O)O, C(=O), C=S, S(=O) and/or S(=O)$_2$, $R_{3002}$ is selected from a single bond or C(=O);

$R_{3003}$ is selected from H, a $C_{1-3}$ alkyl or a cyclopropyl;

$R_{3004}$ is selected from (CH$_2$)$_{0-3}$;

optionally, $R_{308}$ and $R_{309a}$, $R_{308}$ and $R_{310}$ form a linking bond (CH$_2$)$_{1-3}$ together;

preferably, the $R_{308}$ and $R_{310}$ form a linking bond CH$_2$ together, $R_{308}$ and $R_{309a}$ form a linking bond CH$_2$CH$_2$ together.

preferably, each of $R_{306-308}$, $R_{309a}$, $R_{309b}$, $R_{310-312}$ is independently selected from a methyl, a cyclopropyl, C(CH$_3$)$_2$(OH), CH$_2$CH$_2$OH, CH$_2$N(CH$_3$)$_2$, H, OH, NH$_2$, F, Cl, Br, I, CN.

preferably, $L_{31}$ is selected from a single bond, NHCH$_2$CH$_2$;

preferably, B is selected from,

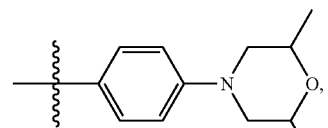

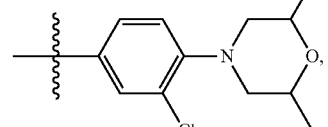

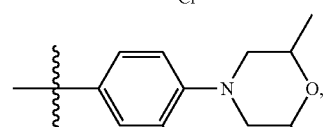

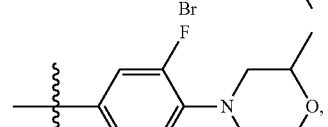

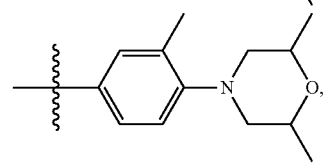

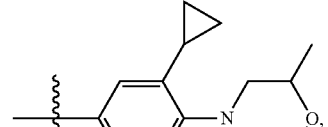

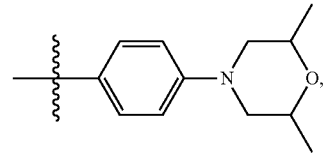

-continued

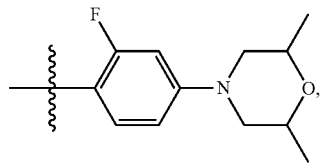

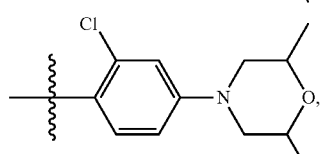

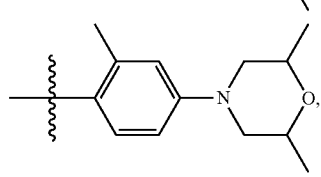

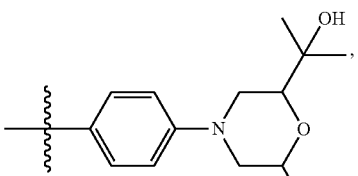

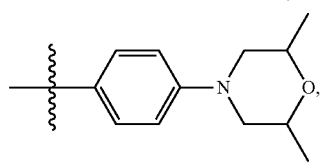

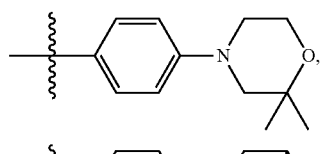

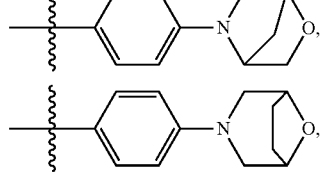

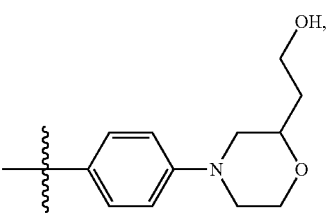

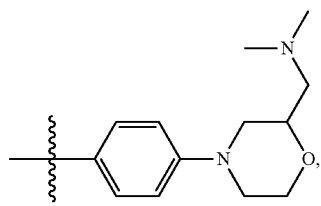

-continued

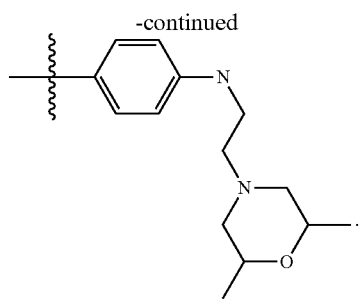

preferably, the compound or the pharmaceutically acceptable salt thereof, wherein B is selected from

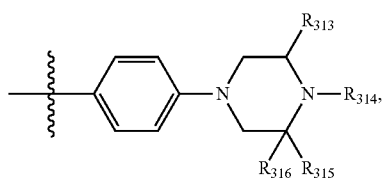

wherein
each of $R_{313}$, $R_{315}$, $R_{316}$ is independently selected from H, OH, $NH_2$, F, Cl, Br, I, CN, an optionally $R_{3001}$-substituted $C_{1-3}$ alkyl or alkoxy or alkyl amino or cyclopropyl;
$R_{314}$ is selected from H, OH, $NH_2$, F, Cl, Br, I, CN, an optionally $R_{3001}$-substituted $C_{1-3}$ alkyl or alkoxy or alkyl amino or cyclopropyl, $(CH_2)_{0-3}R_{3005}$,

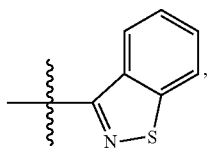

wherein $R_{3005}$ is optionally substituted by $R_{3001}$;
$R_{3005}$ is selected from a $C_{3-6}$ cycloalkyl, a phenyl, a pyridyl, a thienyl, a furyl, an imidazolyl, an oxazolyl, a thiazolyl, an isothiazolyl, each of the above-mentioned group is optionally fused with a benzene ring;
$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
optionally, the

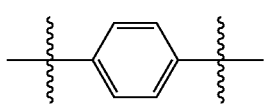

in the general structure can be replaced by a pyridyl, a thienyl, a furyl, an imidazolyl, an oxazolyl, a thiazolyl, an isothiazolyl.
Preferably, each of $R_{313}$, $R_{315}$, $R_{316}$ is independently selected from H, a methyl;
preferably, $R_{314}$ is selected from H, a methyl, an ethyl, a phenyl methylene, a cyclopropyl methylene, a methoxyphenyl,

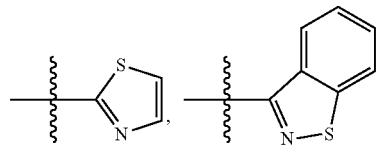

Preferably, B is selected from

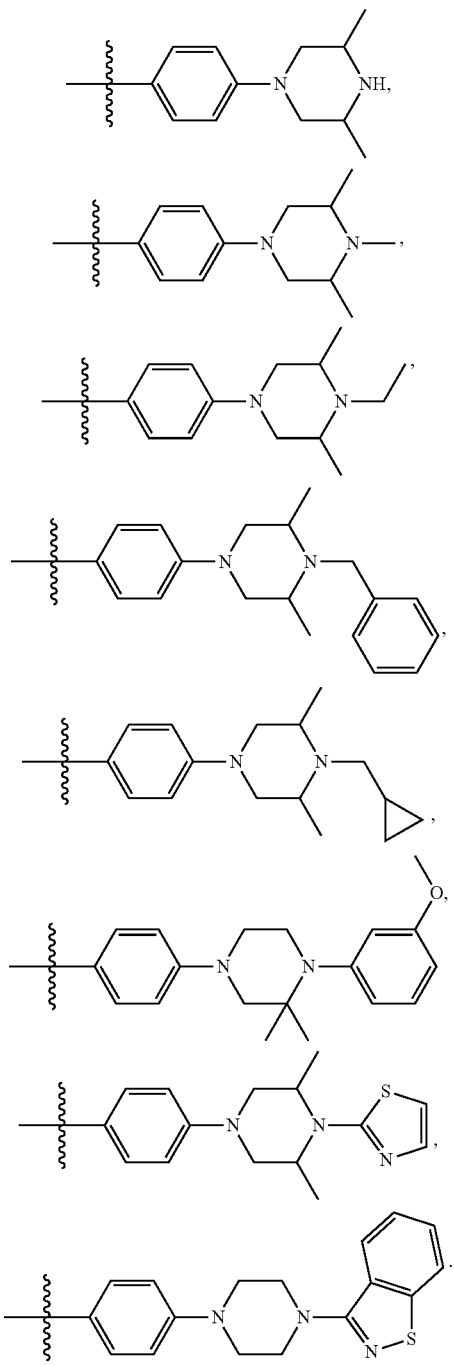

Preferably, the compound or the pharmaceutically acceptable salt thereof, wherein B is selected from

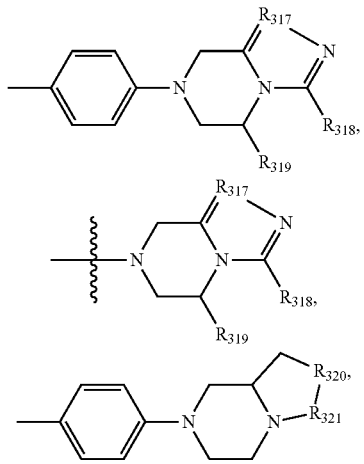

wherein

R$_{317}$ is selected from CR$_{3006}$ or N;

each of R$_{318}$, R$_{319}$, R$_{3006\text{-}3008}$ is independently selected from H, OH, NH$_2$, F, Cl, Br, I, CN, an optionally R$_{3001}$-substituted C$_{1\text{-}3}$ alkyl or alkoxy or alkyl amino or cyclopropyl;

each of R$_{320\text{-}321}$ is independently selected from C(R$_{3007}$)(R$_{3008}$), O, CON(R$_{3009}$), N(R$_{3010}$), C=N(R$_{3011}$), S, C(=O)O, C(=O), C=S, S(=O) and/or S(=O)$_2$;

each of R$_{3009\text{-}3011}$ is independently selected from H, an optionally R$_{3001}$-substituted C$_{1\text{-}3}$ alkyl or cyclopropyl;

R$_{3001}$ is selected from OH, N(CH$_3$)$_2$, NH(CH$_3$), NH$_2$, F, Cl, Br, I, CN, a methyl, a methoxyl, the number of R$_{3001}$ is selected from 1, 2 or 3;

optionally, the

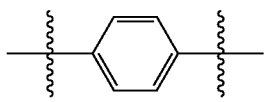

in the general structure can be replaced by a pyridyl, a thienyl, a furyl, an imidazolyl, an oxazolyl, a thiazolyl, an isothiazolyl.

Preferably, R$_{317}$ is selected from CR$_{3006}$ or N; each of R$_{3006}$, R$_{318}$, R$_{319}$ is selected from a methyl, a trifluoromethyl;

each of R$_{320\text{-}321}$ is independently selected from CH$_2$, O, C(=O).

Preferably, B is selected from

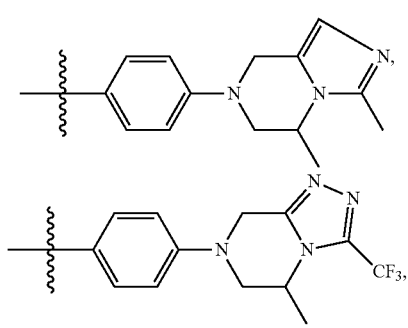

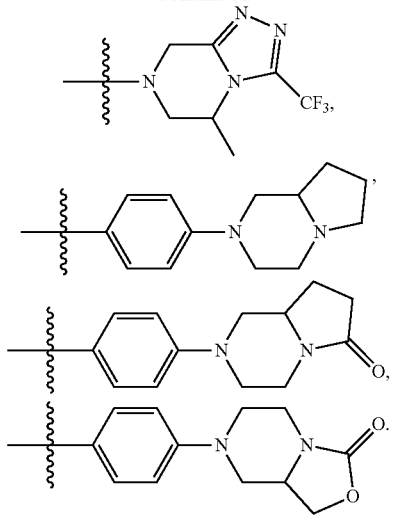

Preferably, the compound or the pharmaceutically acceptable salt thereof, wherein B is selected from

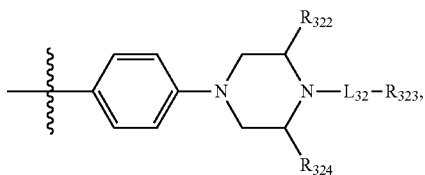

wherein,

L$_{32}$ is selected from C(R$_{3007}$)(R$_{3008}$), O, CON(R$_{3009}$), N(R$_{3010}$), C=N (R$_{3011}$), S, C(=O)O, C(=O), C=S, S(=O) and/or S(=O)$_2$;

R$_{323}$ is selected from a C$_{1\text{-}6}$ alkyl, a C$_{3\text{-}6}$ cycloalkyl, a phenyl, a pyridyl, an imidazolyl, a thienyl, a furyl, an oxazolyl, a thiazolyl, an isothiazolyl, each of the above-mentioned group is optionally substituted by R$_{3012}$;

each of R$_{322}$, R$_{324}$, R$_{3007}$, R$_{3008}$, R$_{3012}$ is independently selected from H, OH, NH$_2$, F, Cl, Br, I, CN, an optionally R$_{3001}$-substituted C$_{1\text{-}3}$ alkyl or alkoxy or alkyl amino or cyclopropyl;

each of R$_{3009\text{-}3011}$ is independently selected from H, an optionally R$_{3001}$-substituted C$_{1\text{-}3}$ alkyl or cyclopropyl;

R$_{3001}$ is selected from OH, N(CH$_3$)$_2$, NH(CH$_3$), NH$_2$, F, Cl, Br, I, CN, a methyl, a methoxy;

the number of each of R$_{3001}$, R$_{3012}$ is selected from 1, 2 or 3.

Optionally, the

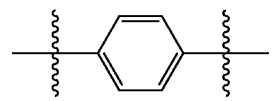

in the general structure can be replaced by a pyridyl, a thienyl, a furyl, an imidazolyl, an oxazolyl, a thiazolyl, an isothiazolyl.

Preferably, each of R$_{322}$, R$_{324}$ is independently selected from H, a methyl, a phenyl, C(CH$_3$)$_2$OH.

Preferably, L$_{32}$ is selected from C(=O), S(=O)$_2$;

preferably, $R_{323}$ is selected from a tert-butoxy, a methyl, a methoxy, an ethyl, an ethoxy, an propoxy, an isopropyl, a n-propyl, an isopropoxy, a cyclopropyl, a methylamino, a phenyl, a pyridyl, a 3-methyl pyridyl, an imidazolyl, $C(CH_3)_2OH$;
preferably, B is selected from
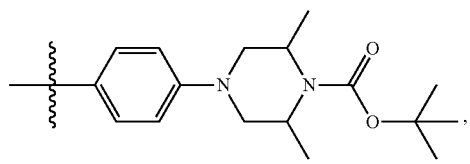
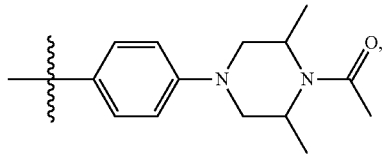
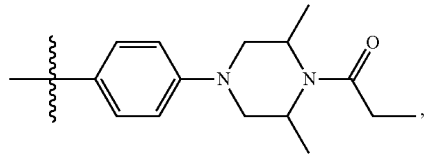
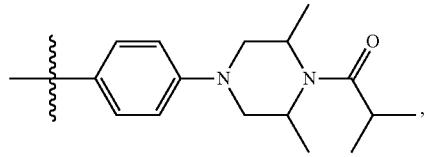
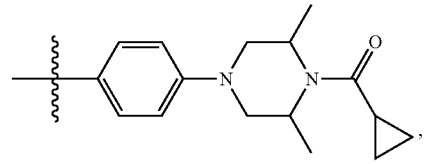
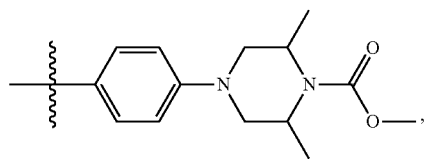
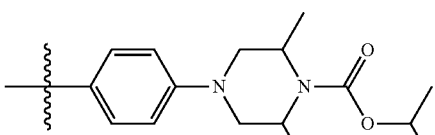
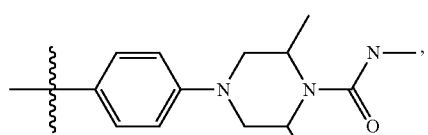
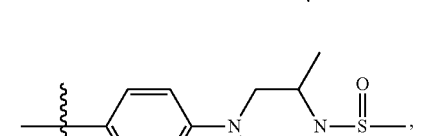
-continued
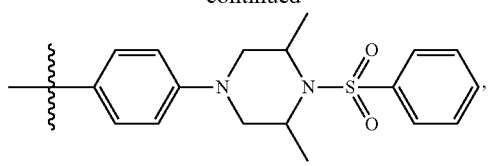
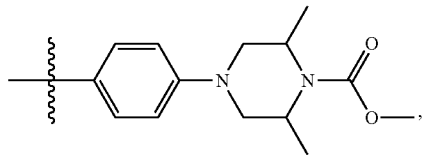
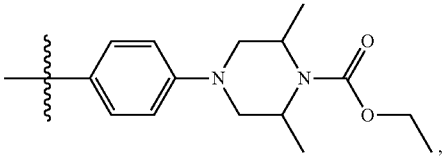
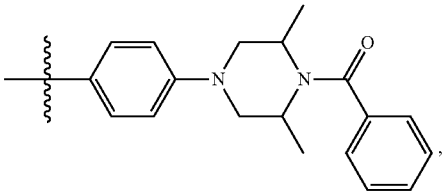
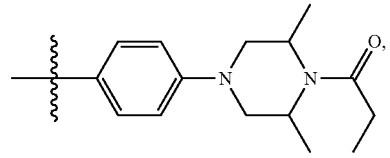
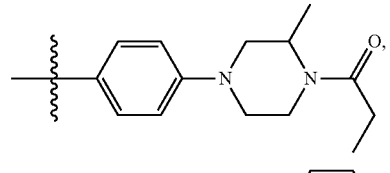
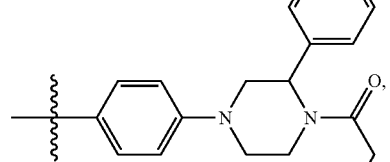
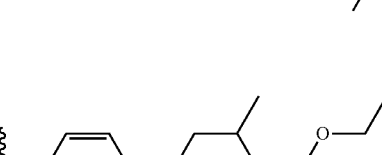
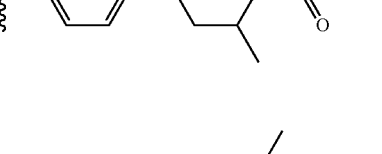
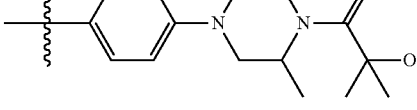

-continued

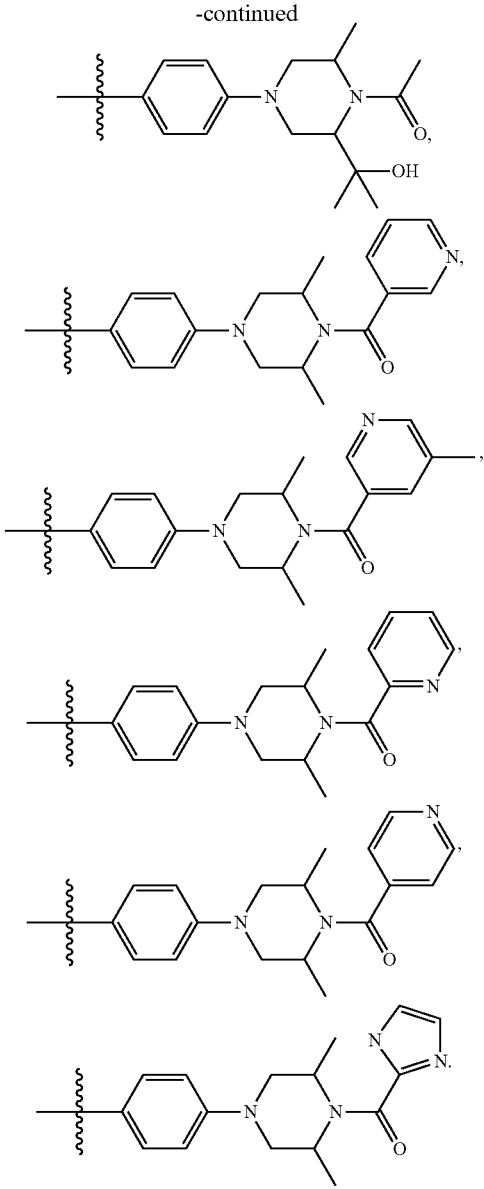

Preferably, the compound of the pharmaceutically acceptable salt thereof, wherein B is selected from

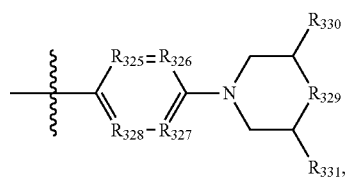

wherein,
one or two of $R_{325-328}$ is selected from N, the rest are selected from $C(R_{3013})$;
$R_{329}$ is selected from $N(R_{3014})$, O, $C(R_{3015})(R_{3016})$, CON$(R_{3017})$, $N(R_{3018})$, $C=N(R_{3019})$, S, $C(=O)O$, $C(=O)$, $C=S$, $S(=O)$ and/or $S(=O)_2$;
$R_{3014}$ is selected from $C(=O)R_{3020}$, $S(=O)_2R_{3020}$, a thiazolyl, an isothiazolyl, a phenyl, a pyridyl, an imidazolyl, a thienyl, a furyl, an oxazolyl;

$R_{3020}$ is selected from an optionally $R_{3001}$-substituted $C_{1-3}$ alkyl or alkoxyl;
each of $R_{3013}$, $R_{3015}$, $R_{3016}$, $R_{330-331}$ is independently selected from H, OH, $NH_2$, F, Cl, Br, I, CN, $C(=O)OH$, an optionally $R_{3001}$-substituted $C_{1-3}$ alkyl or alkoxy or alkyl amino or cyclopropyl;
each of $R_{3017-3019}$ is independently selected from H, an optionally $R_{3001}$-substituted $C_{1-3}$ alkyl or cyclopropyl;
$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
optionally, $R_{330}$ and $R_{331}$ form a linking bond $(CH_2)_{1-3}$ together;
optionally, when $R_{329}$ is selected from $N(R_{3014})$ or O, $R_{330}$ and $R_{331}$ present a cis-arrangement; when $R_{329}$ is selected from $C(R_{3015})(R_{3016})$, $R_{330}$ and $R_{331}$ present a trans-arrangement;
preferably, one or two of $R_{325-328}$ is selected from N, the rest are selected from CH, $CC(=O)OH$ or $CCH_3$.
Preferably, $R_{329}$ is selected from $N(R_{3014})$, O.
Preferably, $R_{3014}$ is selected from $C(=O)R_{3020}$,

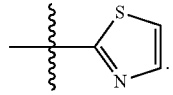

Preferably, $R_{3020}$ is selected from $C(CH_3)(F)_2$, $CH_3$, $CF_3$, $CH_2CH_3$, $CH_2CF_3$, $CH(F)(CH_3)$, $CH(OH)(CH_3)$, $CH_2(OH)$, $CH(NH_2)(CH_3)$, a methoxy, an ethoxy, an amino methyl.
Preferably, $R_{330-331}$ is selected from a methyl.
Preferably, B is selected from

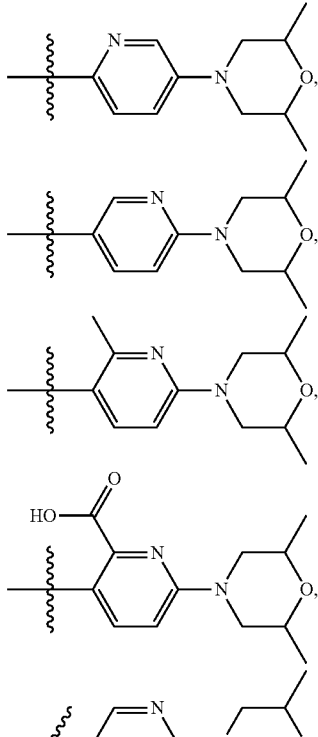

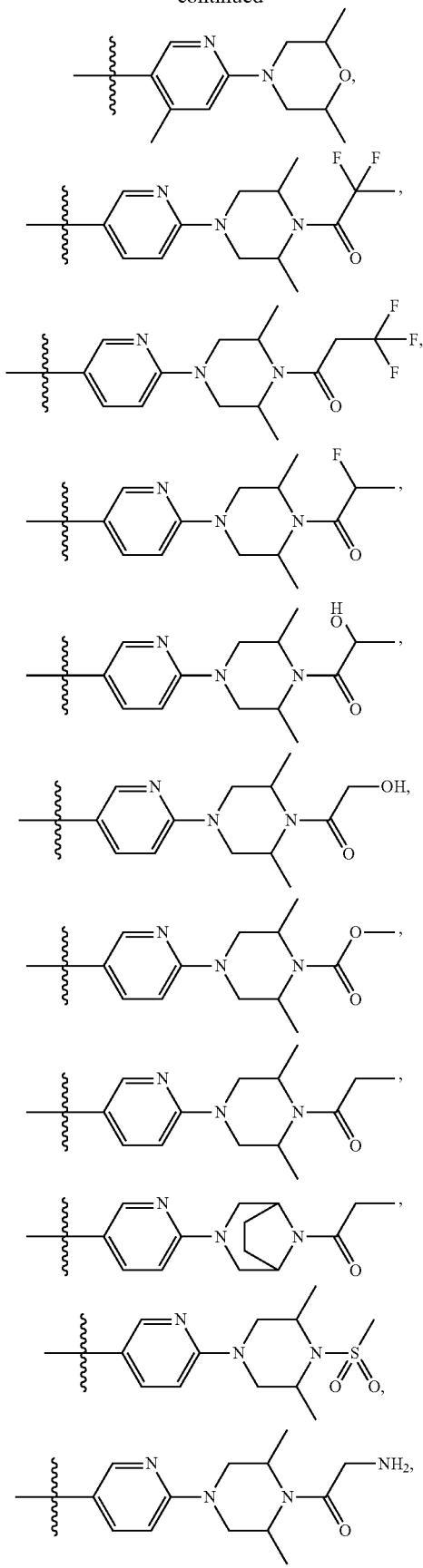

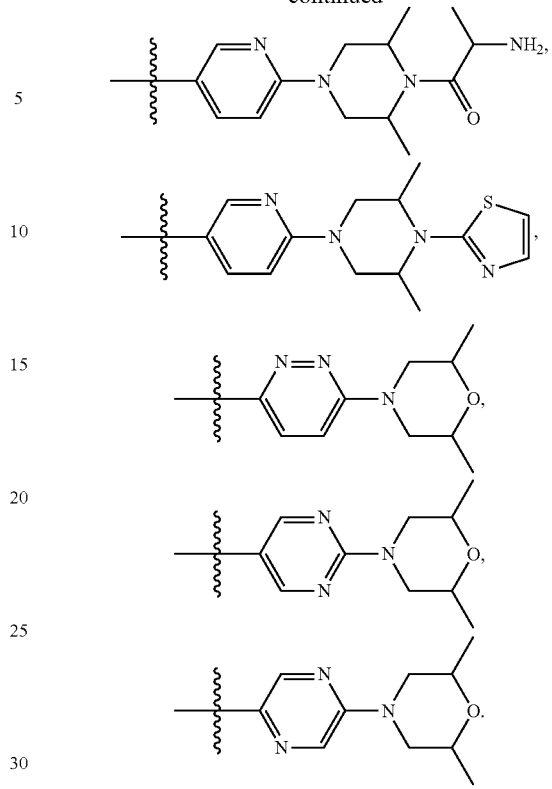

Preferably, the compound or the pharmaceutically acceptable salt thereof, wherein B is selected from

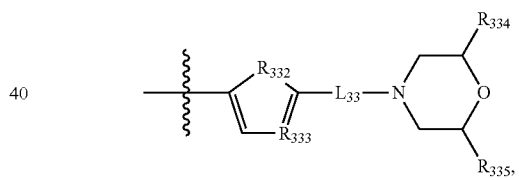

wherein, $R_{332}$ is selected from S, $N(R_{3021})$, O, $C(R_{3022})(R_{3023})$, $CON(R_{3024})$, $N(R_{3025})$, $C=N$ $(R_{3026})$, S, $C(=O)O$, $C(=O)$, $C=S$, $S(=O)$ and/or $S(=O)_2$;

$L_{33}$ is selected from a single bond, $C(=O)$, S, O, $C(R_{3022})(R_{3023})$, $CON(R_{3024})$, $N(R_{3025})$, $C=N(R_{3026})$, S, $C(=O)O$, $C=S$, $S(=O)$ and/or $S(=O)_2$;

$R_{333}$ is selected from N, $C(R_{3027})$;

each of $R_{3027}$, $R_{334}$, $R_{335}$, $R_{3022}$, $R_{3023}$ is independently selected from H, OH, $NH_2$, F, Cl, Br, I, CN, an optionally $R_{3001}$-substituted $C_{1-3}$ alkyl or alkoxy or alkyl amino or cyclopropyl;

each of $R_{3021}$, $R_{3024-3026}$ is independently selected from H, an optionally $R_{3001}$-substituted $C_{1-3}$ alkyl or cyclopropyl;

$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;

preferably, $R_{332}$ is selected from S, $R_{333}$ is selected from N or CH, $L_{33}$ is selected from a single bond, $C(=O)$, each of $R_{334}$, $R_{335}$ is selected from a methyl.

Preferably, B is selected from

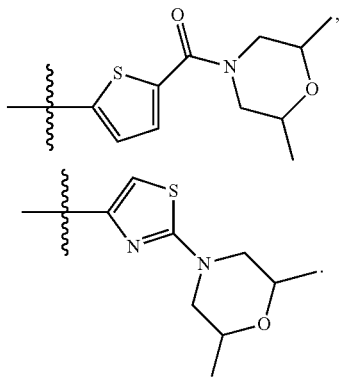

Preferably, the compound or the pharmaceutically acceptable salt thereof, wherein B is selected from

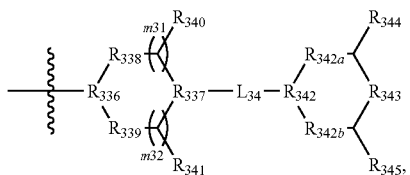

wherein,
each of $R_{336}$, $R_{337}$, $R_{342}$ is independently selected from N or $C(R_{3028})$;
each of $R_{338}$, $R_{339}$ is selected from $C(R_{3029})(R_{3030})$, optionally $R_{338}$ and $R_{339}$ connect to the same $(CH_2)_{1-3}$ together to form a ring;
each of $m_{31}$, $m_{32}$ is independently selected from 0 or 1;
each of $R_{342a}$, $R_{342b}$, $R_{343}$, $L_{34}$ is independently selected from a single bond, $C(=O)N(R_{3031})$, $C(=O)C(R_{3032})(R_{3033})$, $C(R_{3034})(R_{3035})$, $CON(R_{3036})$, $N(R_{3037})$, $C=N(R_{3038})$, O, S, $C(=O)O$, $C(=O)$, $C=S$, $S(=O)$ and/or $S(=O)_2$;
$L_{34}$ can also be selected from a single bond;
each of $R_{340}$, $R_{341}$, $R_{344}$, $R_{345}$, $R_{3028}$, $R_{3029}$, $R_{3030}$, $R_{3032-3035}$ is independently selected from H, OH, $NH_2$, F, Cl, Br, I, CN, an optionally $R_{3001}$-substituted $C_{1-3}$ alkyl or alkoxy or alkyl amino or cyclopropyl;
each of $R_{3031}$, $R_{3036-3038}$ is independently selected from H, an optionally $R_{3001}$-substituted $C_{1-3}$ alkyl or cyclopropyl;
$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
preferably, each of $R_{336}$, $R_{337}$, $R_{342}$ is independently selected from N or CH.
Preferably, each of $R_{338}$, $R_{339}$ is independently selected from $CH_2$, optionally $R_{338}$ and $R_{339}$ connect to the same $CH_2CH_2$ together to form a ring.
Preferably, each of $m_{31}$, $m_{32}$ is independently selected from 0 or 1.
Preferably, $L_{34}$ is independently selected from a single bond, $C(=O)NH$, $C(=O)N(CH_3)$, $C(=O)CH_2$.
Preferably, each of $R_{340}$, $R_{341}$, $R_{344}$, $R_{345}$ is independently selected from H or a methyl.
Preferably, each of $R_{342a}$, $R_{342b}$ is selected from $C(=O)$ or $CH_2$.

Preferably, B is selected from

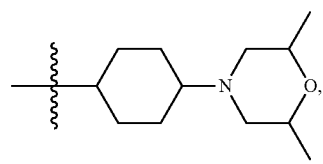

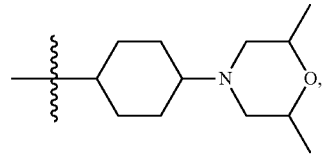

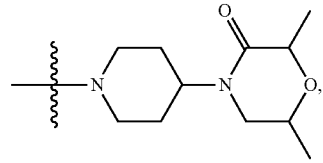

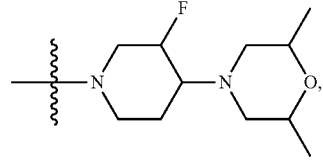

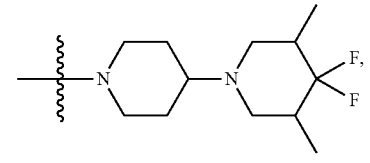

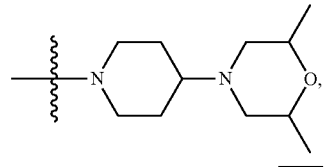

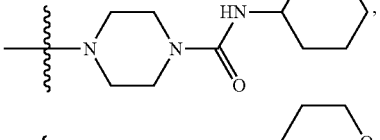

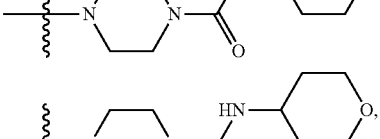

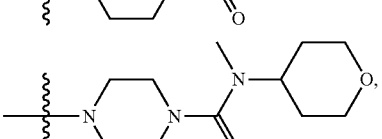

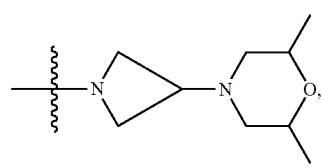

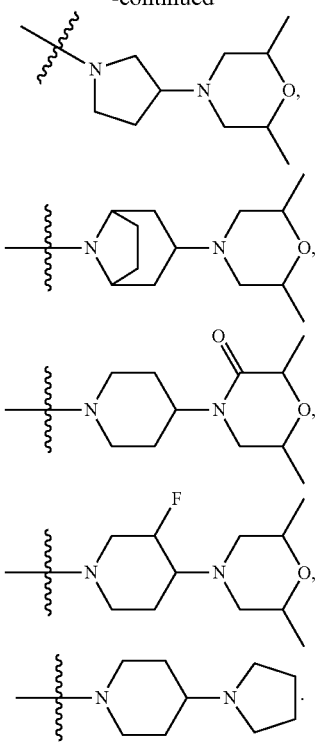

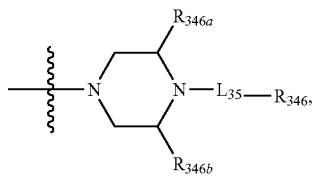

Preferably, the compound or the pharmaceutically acceptable salt thereof, wherein B is selected from

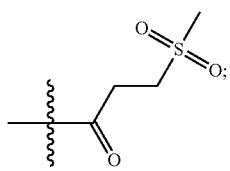

wherein $L_{35}$ is independently selected from a single bond, C(=O) N($R_{3031}$), C(=O)C($R_{3032}$)($R_{3033}$), C($R_{3034}$)($R_{3035}$), N($R_{3037}$), C=N ($R_{3038}$), O, S, C(=O)O, C(=O), C=S, S(=O) and/or S(=O)$_2$;

$L_{35}$ can also be selected from a single bond;

each of $R_{3032-3035}$ is independently selected from H, OH, NH$_2$, F, Cl, Br, I, CN, an optionally $R_{3001}$-substituted $C_{1-3}$ alkyl or alkoxy or alkyl amino or cyclopropyl;

each of $R_{346}$, $R_{346a}$, $R_{346b}$ is independently selected from H, an optionally $R_{3001}$-substituted $C_{1-3}$ alkyl or alkoxy or alkyl acyl or alkyl sulfonyl or alkyl amino or cyclopropyl, an optionally $R_{3001}$-substituted cyclopropyl acyl or cyclopropyl sulfonyl;

$R_{346}$ can also be selected from a phenyl, a pyridyl, an imidazolyl, a thienyl, a furyl, an oxazolyl, a thiazolyl, an isothiazolyl, a pyrrolidyl, a 2-pyridonyl;

each of $R_{3031}$, $R_{3037}$, $R_{3038}$ is independently selected from H, an optionally $R_{3001}$-substituted $C_{1-3}$ alkyl or cyclopropyl;

$R_{3001}$ is selected from OH, N(CH$_3$)$_2$, NH(CH$_3$), NH$_2$, F, Cl, Br, I, CN, —S(=O)CH$_3$, —S(=O)$_2$CH$_3$, a methyl, a methoxy, the number of $R_{3001}$ is selected from 1, 2 or 3;

preferably, $L_{35}$ is selected from a single bond, C(=O), CH$_2$;

preferably, $R_{346}$ is selected from H, a methyl, a phenyl, C(CH$_3$)$_2$(OH), CH$_2$C(CH$_3$)$_2$(OH), a cyclopropyl acyl, an isopropyl sulfonyl, a pyrrolidyl, a 2-pyridonyl,

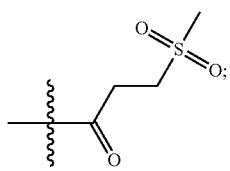 [SMILES: *C(=O)CCS(C)(=O)=O]

preferably, B is selected from

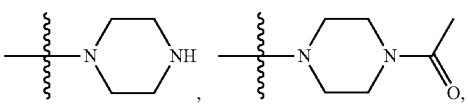

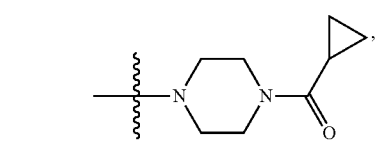

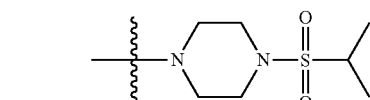

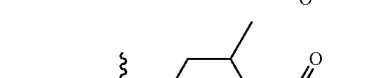

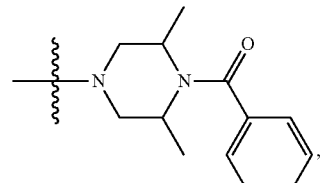

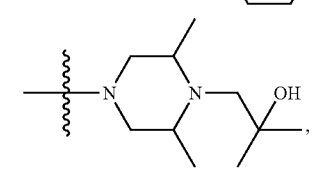

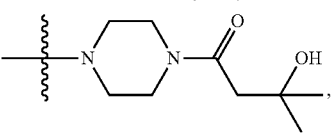

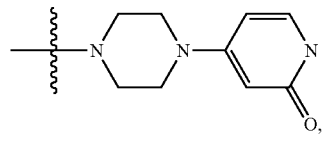

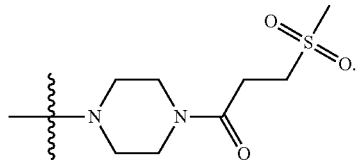

Preferably, the compound or the pharmaceutically acceptable salt thereof, wherein B is selected from

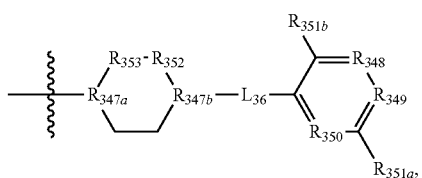

wherein, each of $R_{347a}$, $R_{347b}$ is independently selected from N or $C(R_{3028})$;

none, one or two of $R_{348-350}$ is selected from N, the rest are selected from $C(R_{3039})$;

each of $R_{352}$, $R_{353}$, $L_{36}$ is independently selected from a single bond, —C(=O)N($R_{3031}$)—, —C(=O)C($R_{3032}$)($R_{3033}$)—, C($R_{3034}$)($R_{3035}$), CON($R_{3036}$), N($R_{3037}$), C=N($R_{3038}$), O, S, C(=O)O, C(=O), C=S, S(=O) and/or S(=O)$_2$;

$L_{36}$ can also be selected from a single bond;

each of $R_{3028}$, $R_{3032-3035}$, $R_{3039}$, $R_{351a}$, $R_{351b}$ is independently selected from H, OH, NH$_2$, F, Cl, Br, I, CN, an optionally $R_{3001}$-substituted C$_{1-3}$ alkyl or alkoxy or alkyl amino or cyclopropyl;

each of $R_{3031}$, $R_{3036-3038}$ is independently selected from H, an optionally $R_{3001}$-substituted C$_{1-3}$ alkyl or cyclopropyl;

$R_{3001}$ is selected from OH, N(CH$_3$)$_2$, NH(CH$_3$), NH$_2$, F, Cl, Br, I, CN, a methyl, a methoxy, the number of $R_{3001}$ is selected from 1, 2 or 3; preferably, $L_{36}$ is selected from a single bond, C(=O)NH, C(=O)CH$_2$.

Preferably, $R_{347a}$, $R_{347b}$ is independently selected from N, CH or C(OH).

Preferably, none, one or two of $R_{348-350}$ is selected from N, the rest are selected from $C(R_{3039})$.

Preferably, $R_{3039}$ is selected from H, a methyl, a trifluoromethyl, C(CH$_3$)$_2$(OH).

Preferably, each of $R_{351a}$, $R_{351b}$ is independently selected from H, a methyl, a trifluoromethyl, an isopropyl.

Preferably, each of $R_{352}$, $R_{353}$ is independently selected from C(=O), C(CH$_3$)(OH).

Preferably, B is selected from

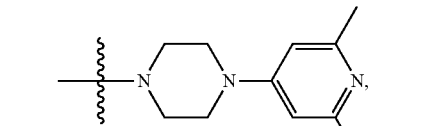

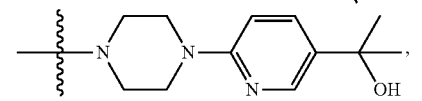

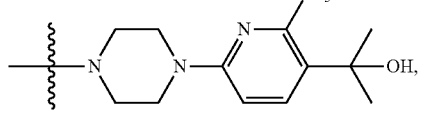

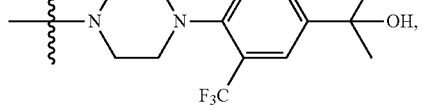

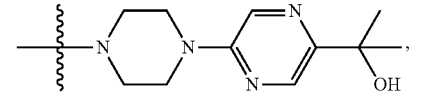

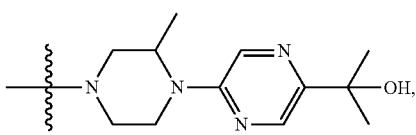

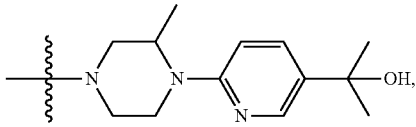

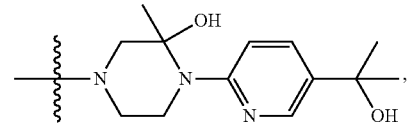

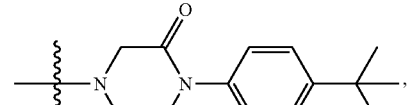

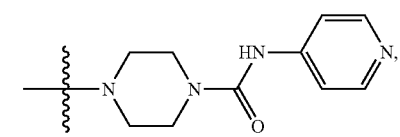

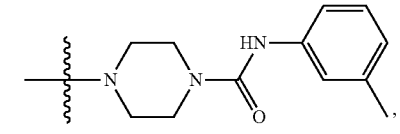

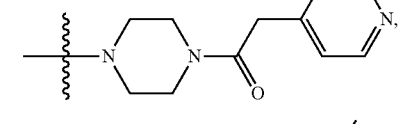

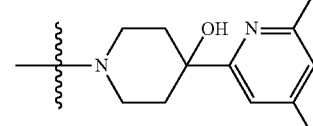

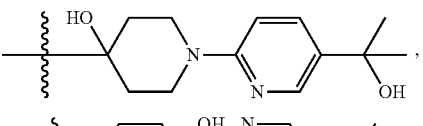

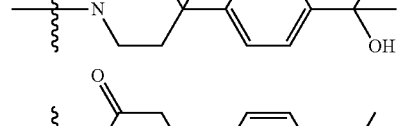

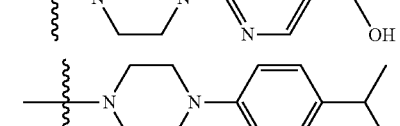

Preferably, the compound or the pharmaceutically acceptable salt thereof, wherein B is selected from

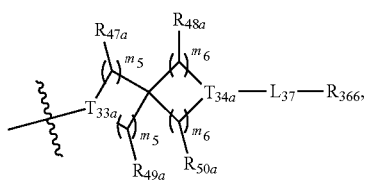

wherein each of $T_{33a}$, $T_{34a}$ is independently selected from N, CH or $C(R_{4001})$;

$L_{37}$ is independently selected from a single bond, a $C_{1-3}$ alkyl, O, S, C(=O), C=S, S(=O) and/or $S(=O)_2$;

each of $R_{366}$, $R_{47a}$, $R_{48a}$, $R_{49a}$, $R_{50a}$ is independently selected from H, an optionally $R_{4001}$-substituted $C_{1-3}$ alkyl or alkoxy or alkyl acyl or alkyl sulfonyl or alkyl amino or cyclopropyl, an optionally $R_{4001}$-substituted cyclopropyl acyl or cyclopropyl sulfonyl;

$R_{366}$ can also be selected from the group consisting of a phenyl, a pyridyl, an imidazolyl, a thienyl, a furyl, an oxazolyl, a thiazolyl and an isothiazolyl which is optionally substituted by $R_{4001}$;

$R_{4001}$ is selected from OH, $N(CH_3)_2$, $NH(CH_3)$, $NH_2$, $C(CH_3)_2(OH)$, F, Cl, Br, I, CN, a methyl, a methoxy, the number of $R_{4001}$ is selected from 1, 2 or 3;

preferably, $L_{37}$ is selected from a single bond, C(=O), $CH_2$.

Preferably, B is selected from

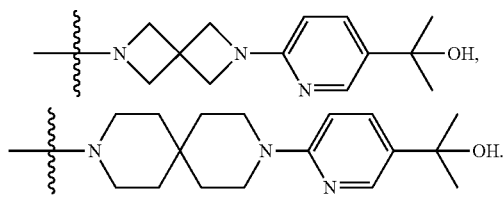

Preferably, the compound or the pharmaceutically acceptable salt thereof, wherein B is selected from the group consisting of

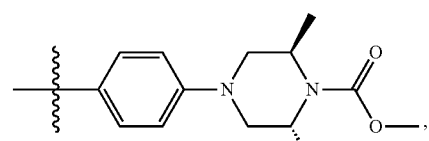

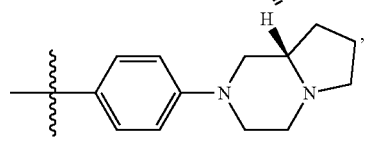

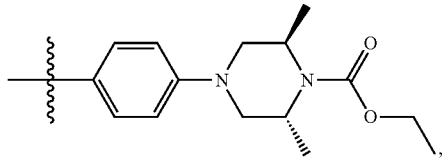

-continued

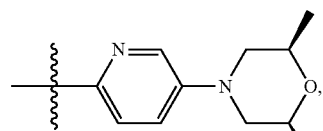

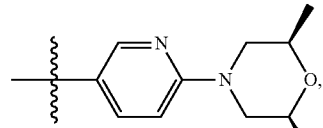

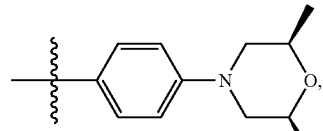

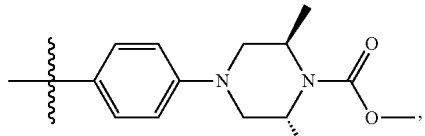

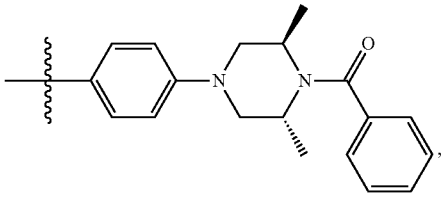

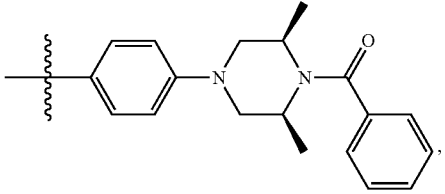

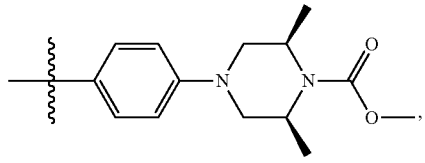

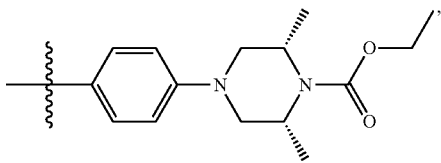

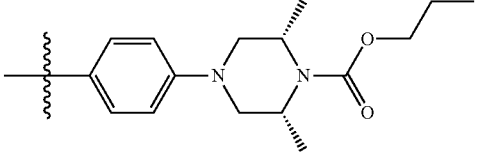

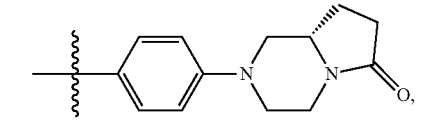

37
-continued
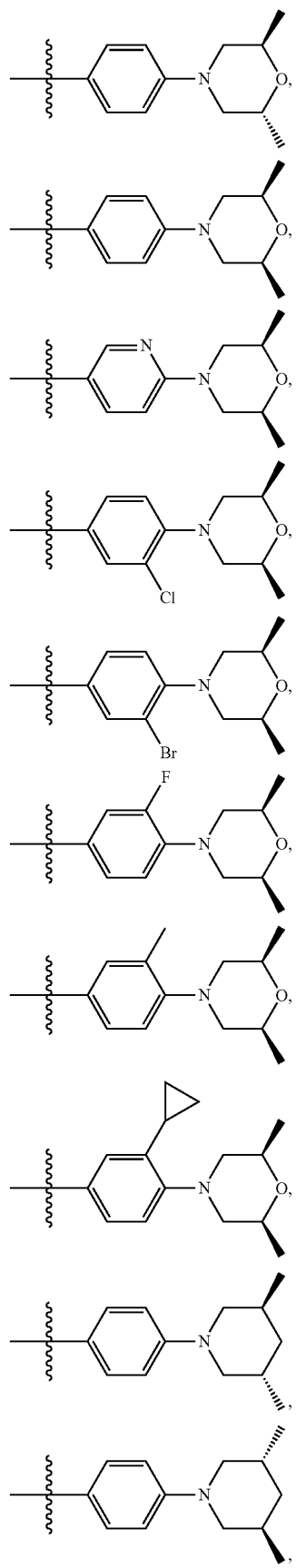
38
-continued
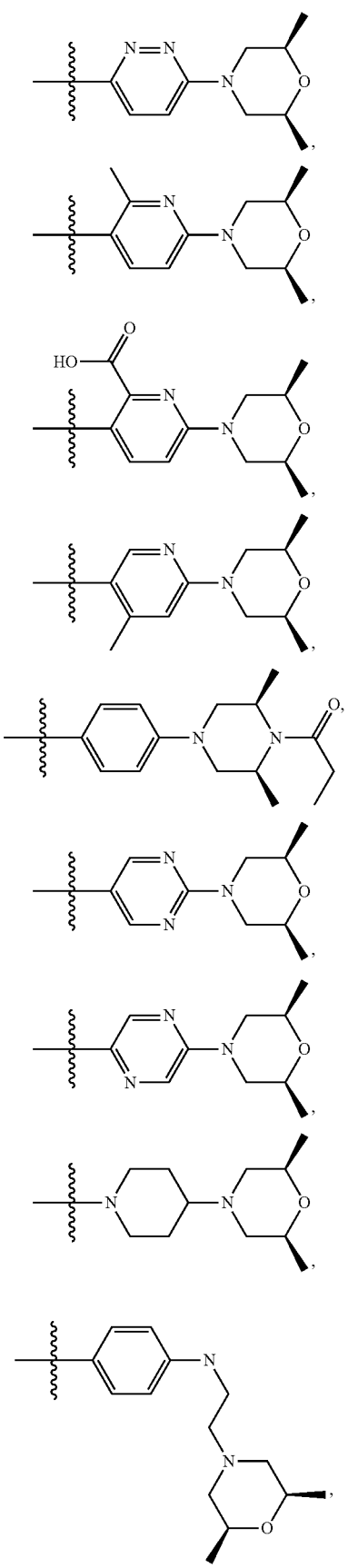

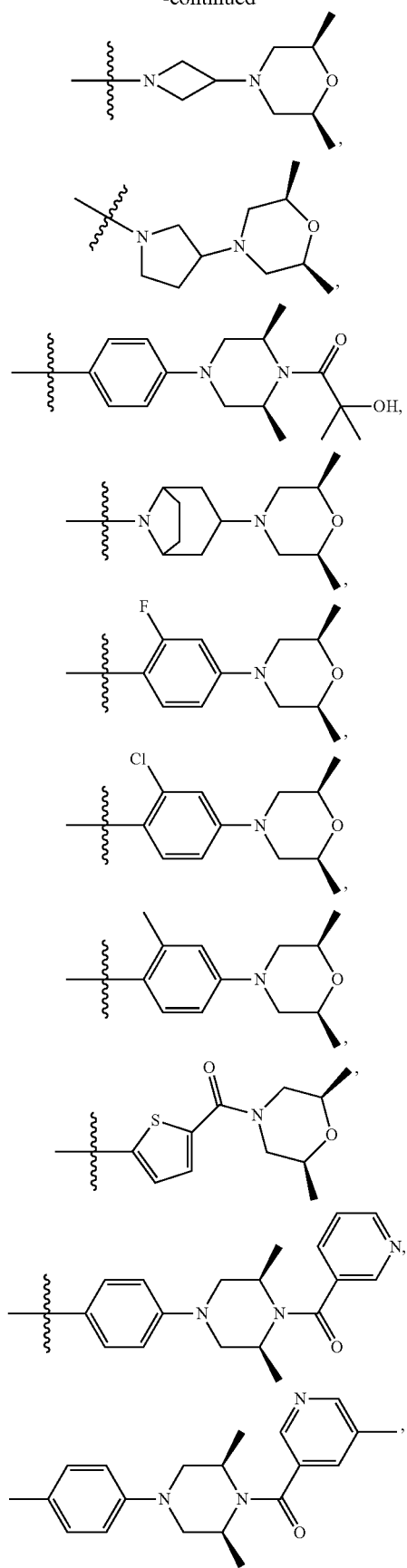
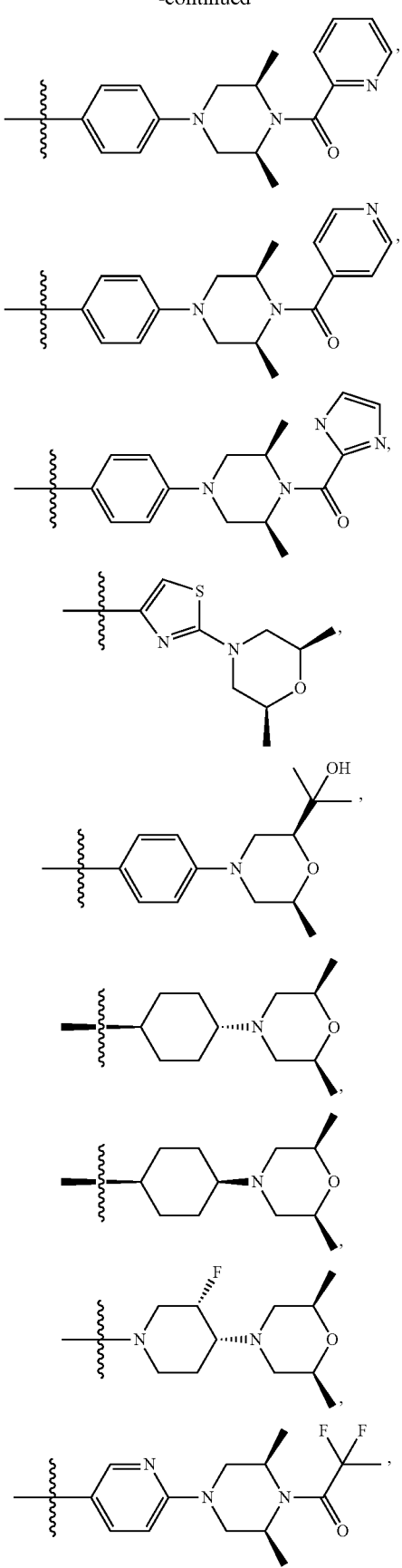

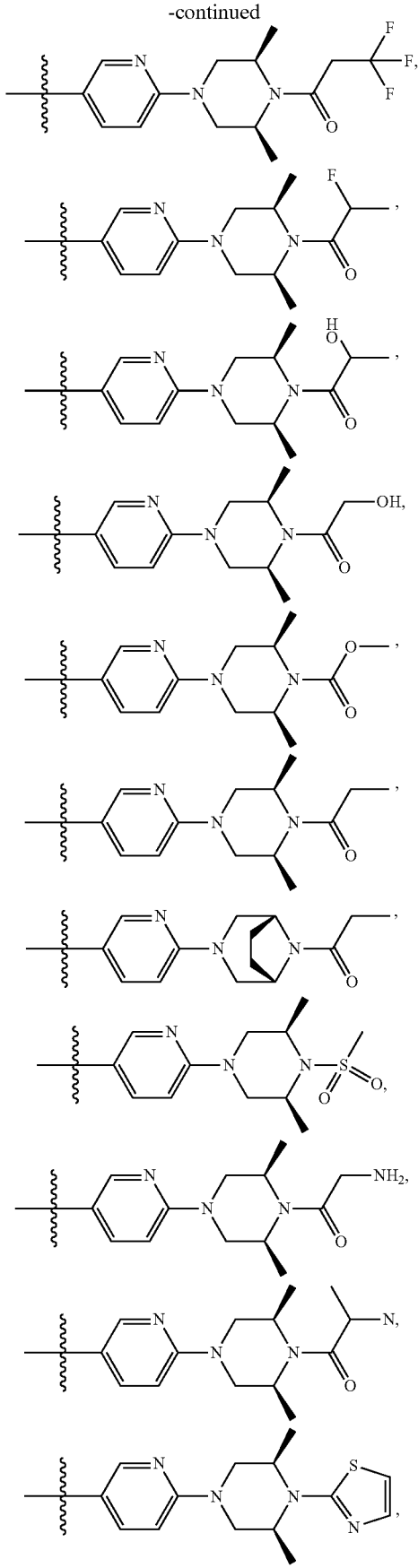
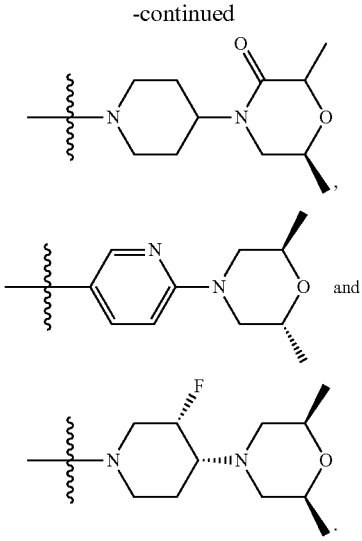
Preferably, the compound or the pharmaceutically acceptable salt thereof is selected from the group consisting of
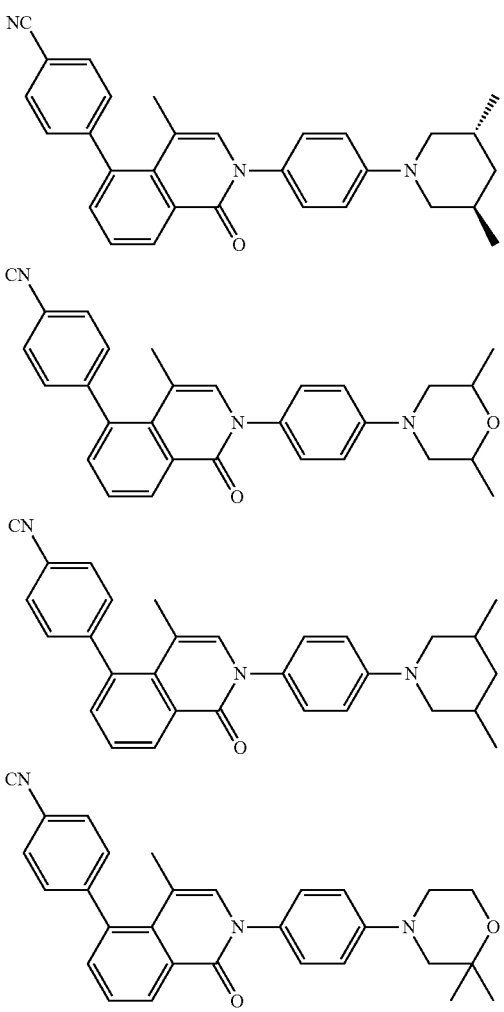

43
-continued
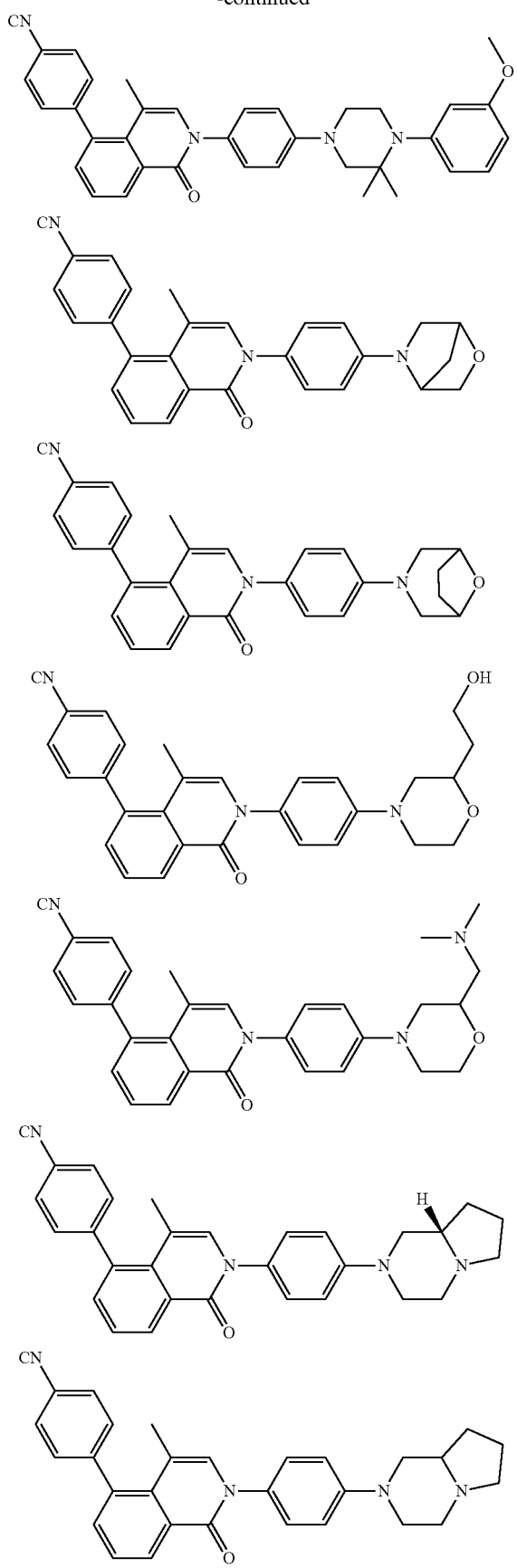
44
-continued
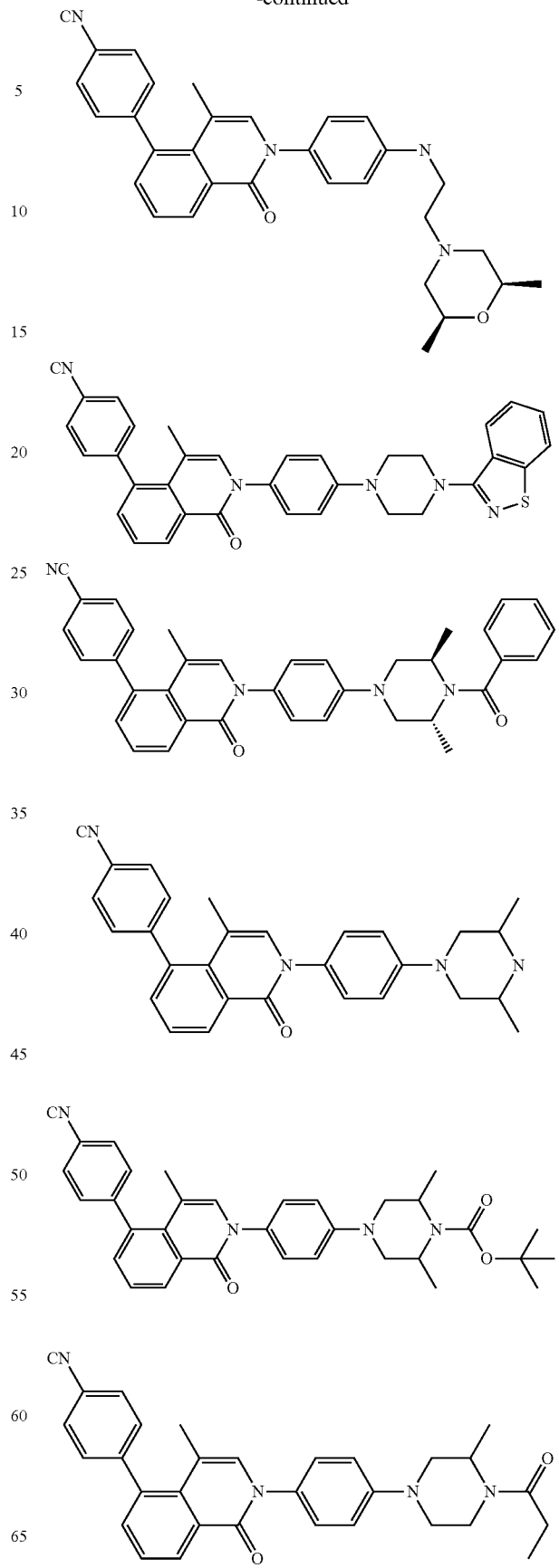

45
-continued
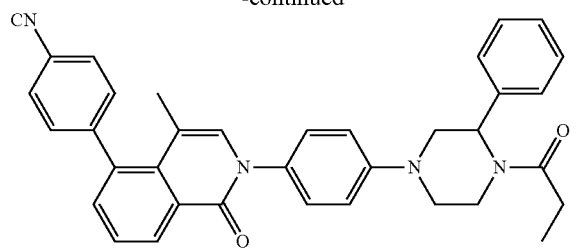
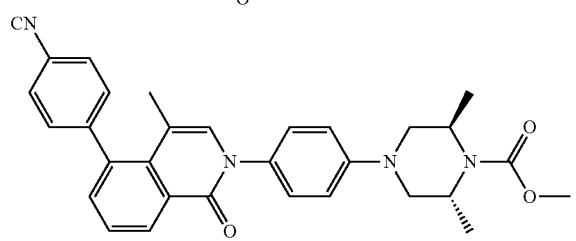
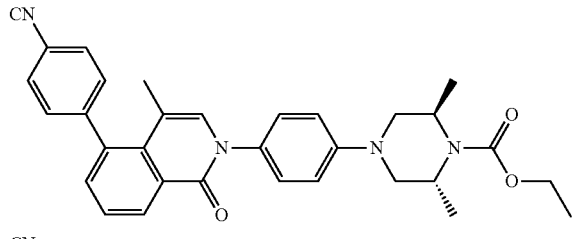
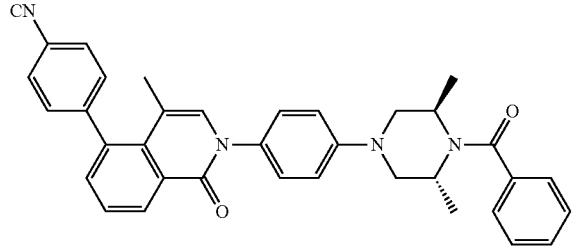
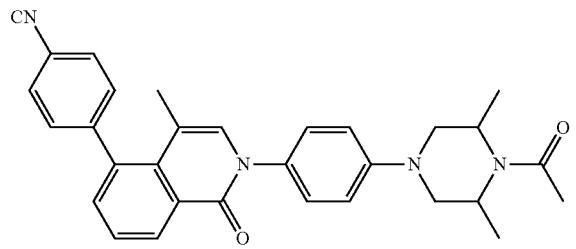
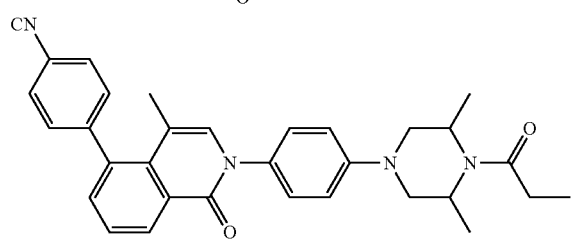
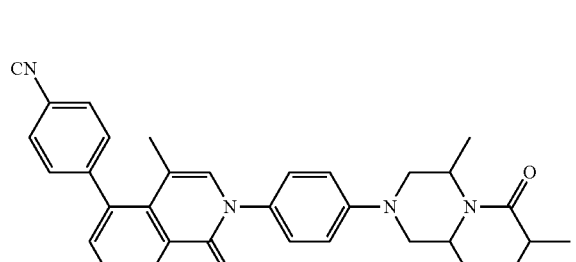
46
-continued
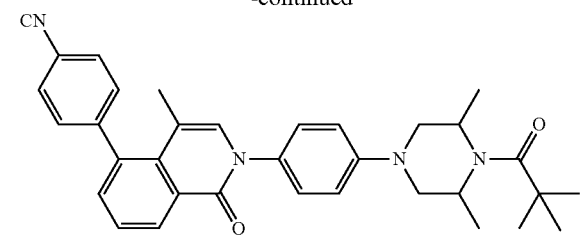
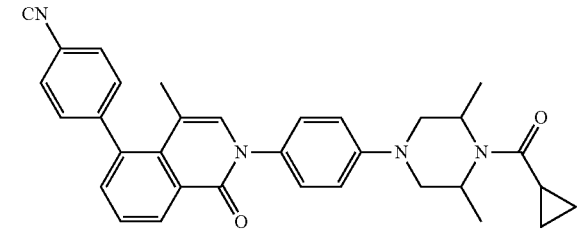
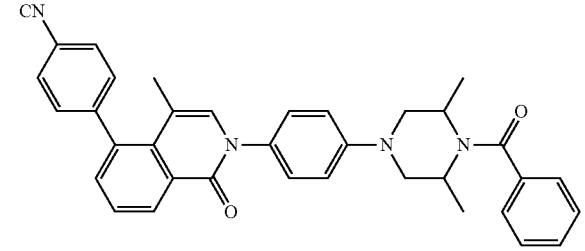
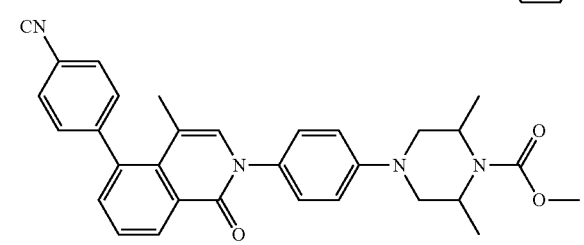
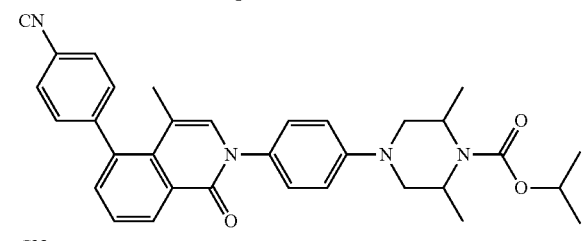
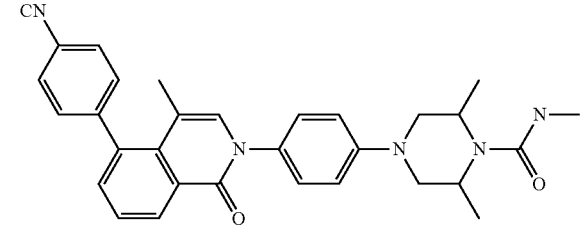
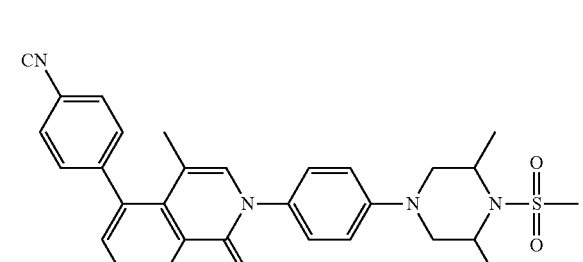

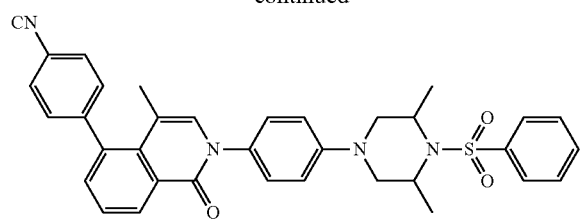
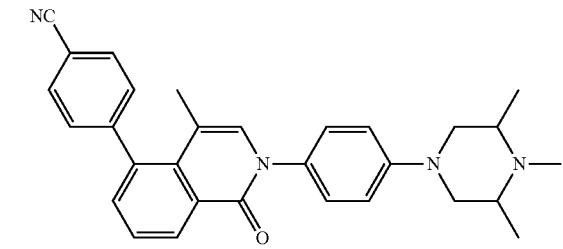
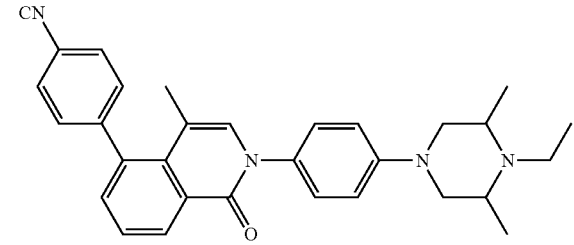
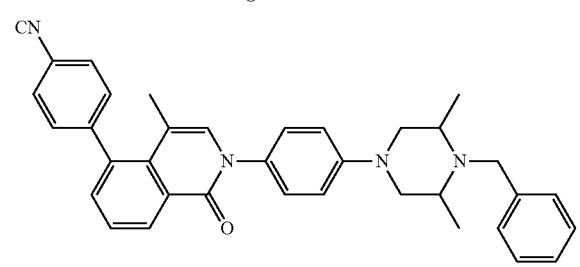
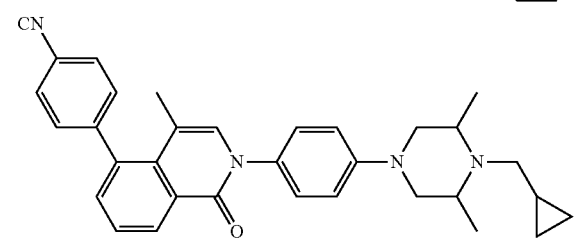
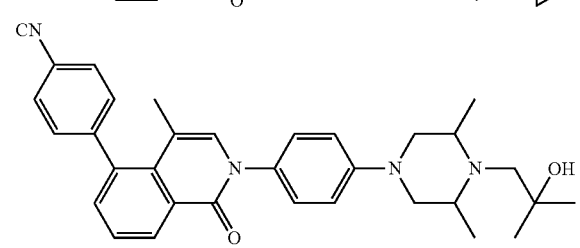
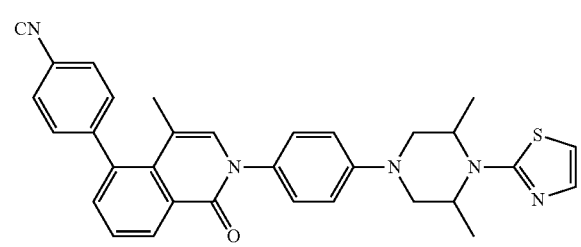
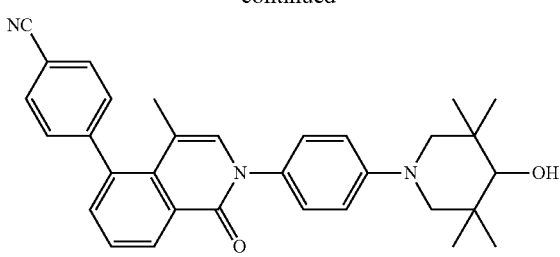
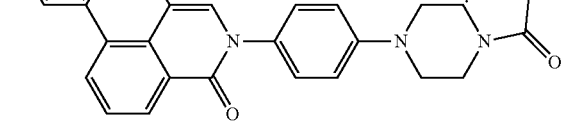
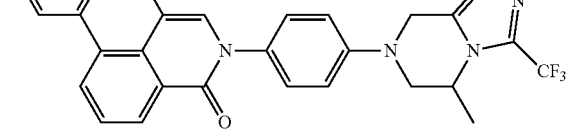
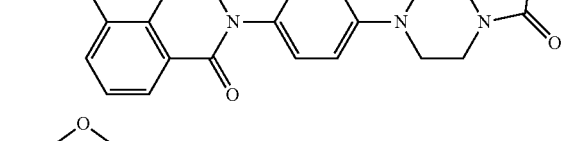
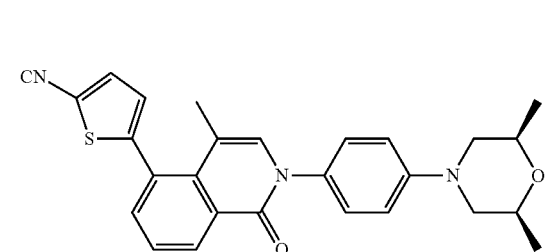
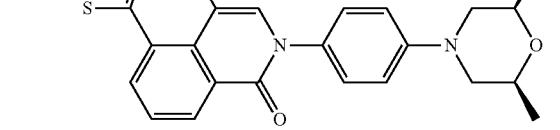

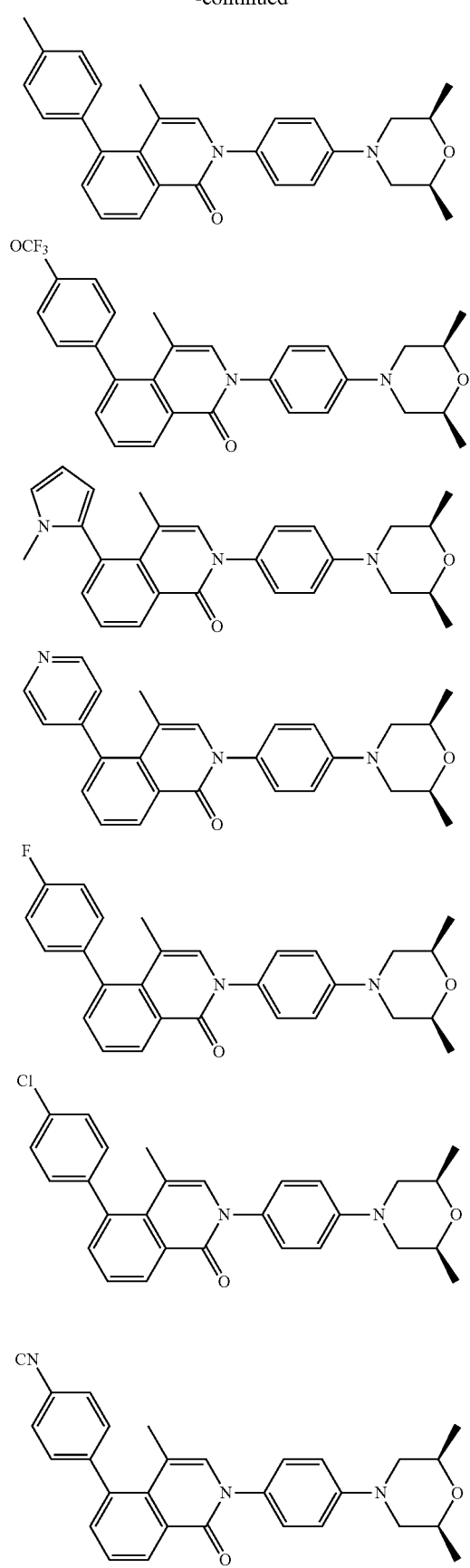
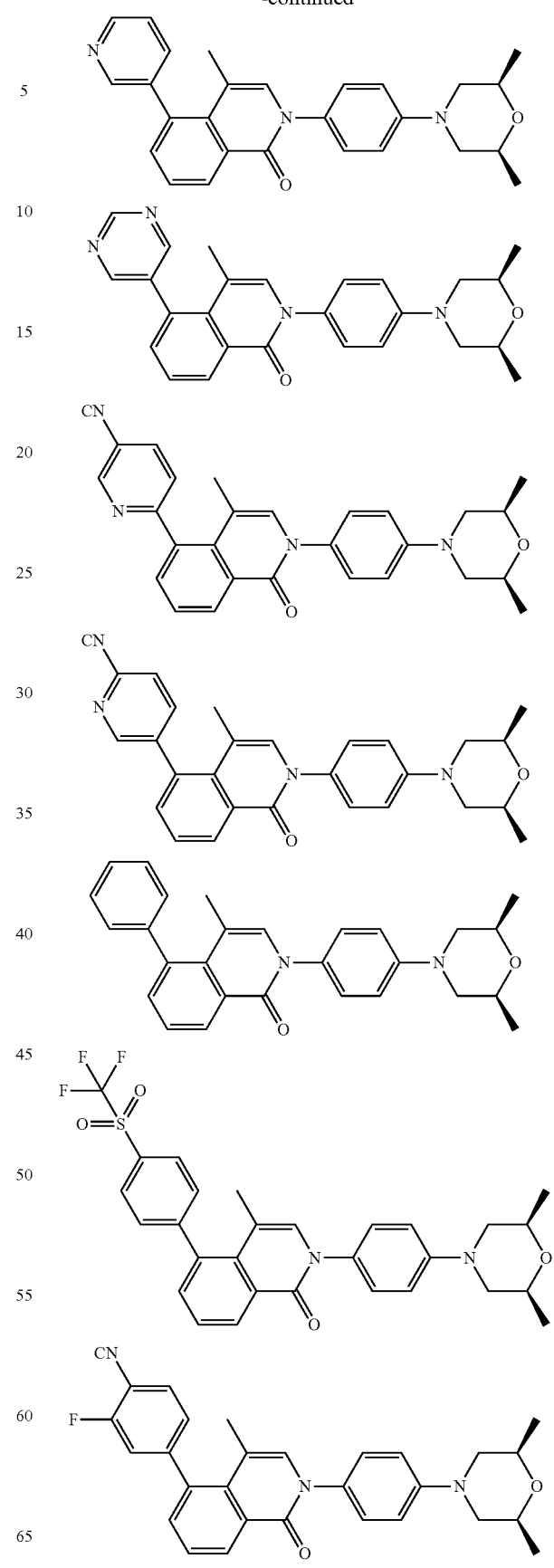

-continued
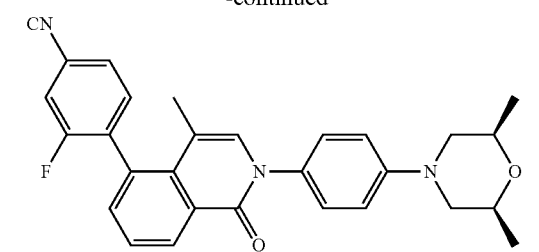
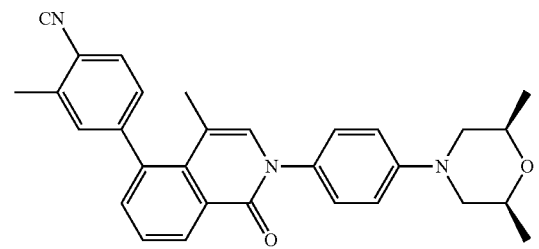
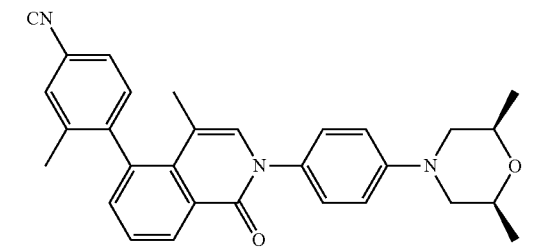
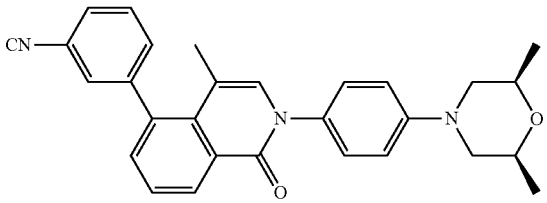
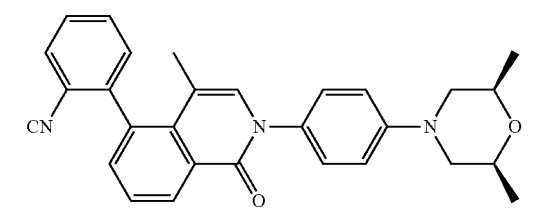
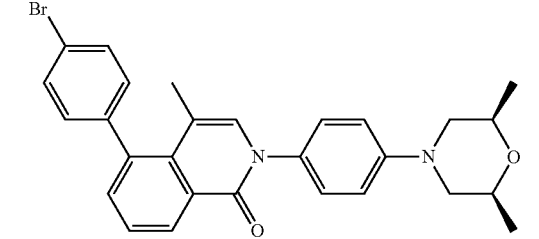
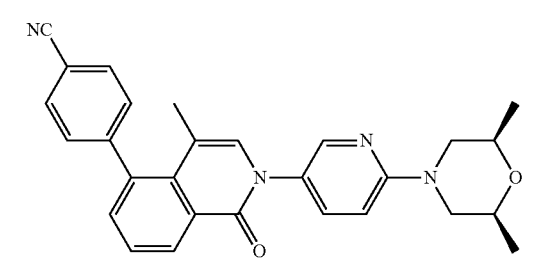
-continued
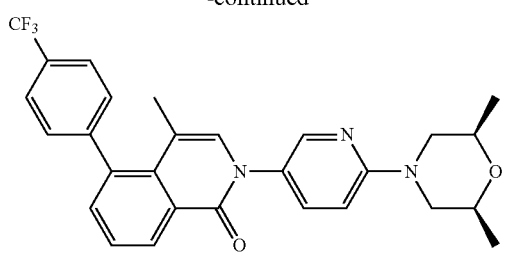
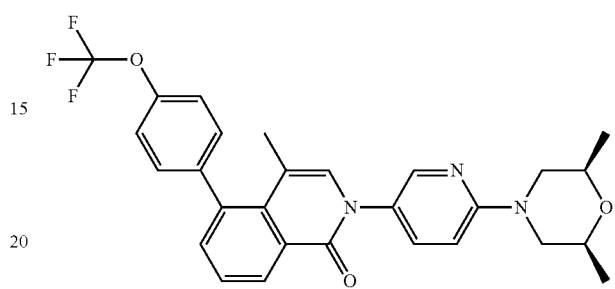
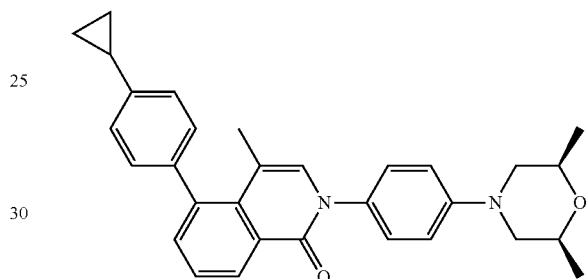
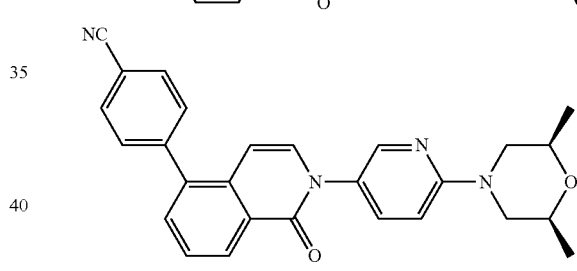
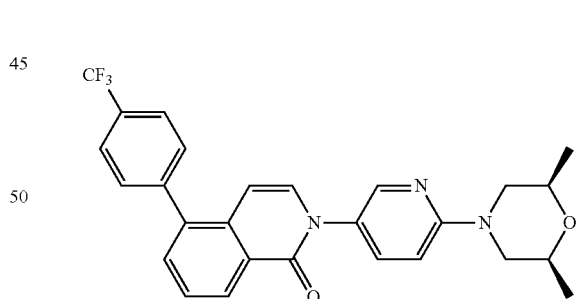
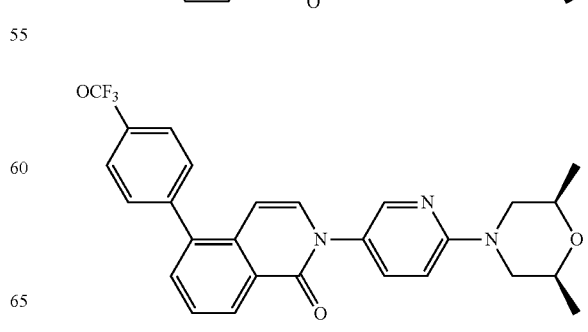

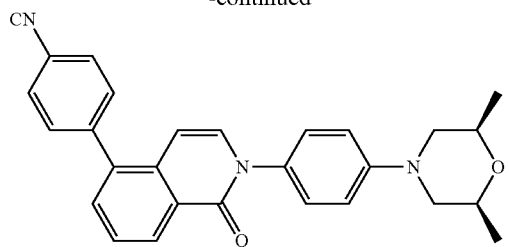
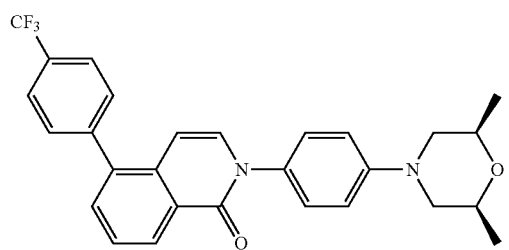
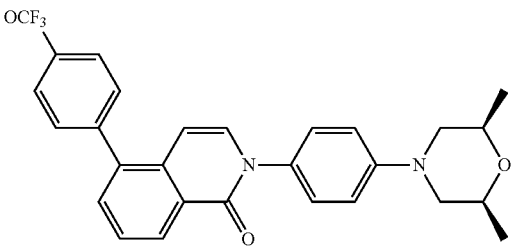
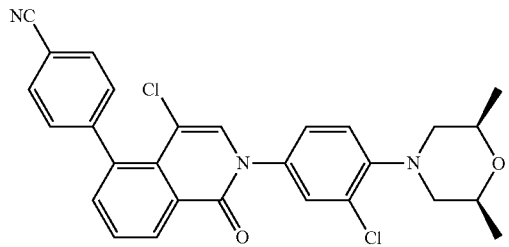
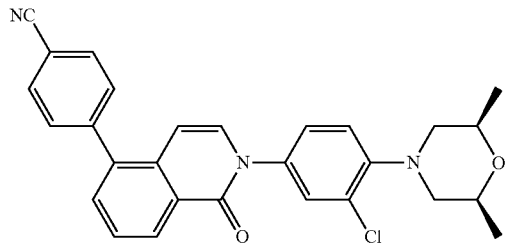
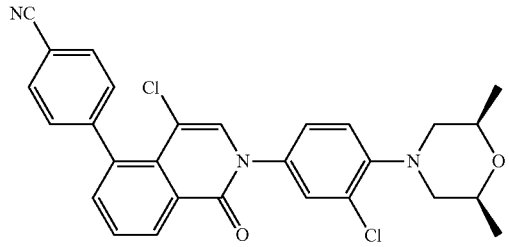
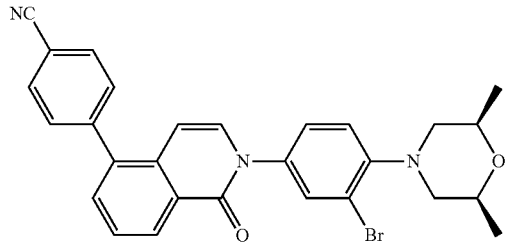
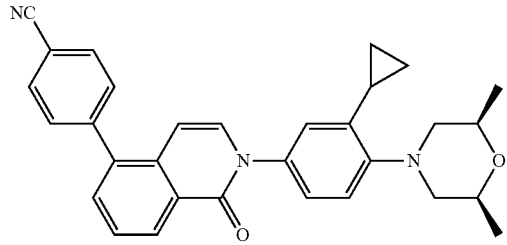
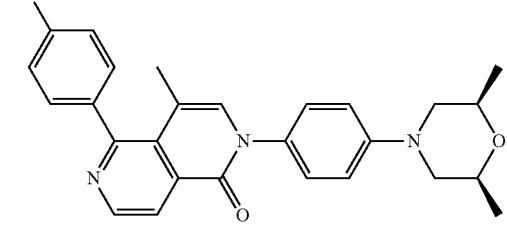
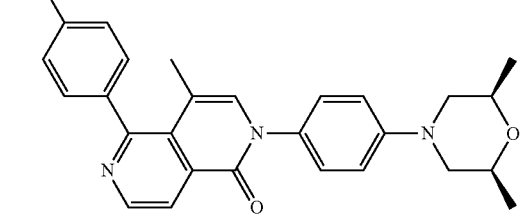
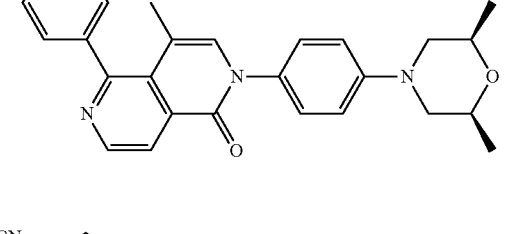
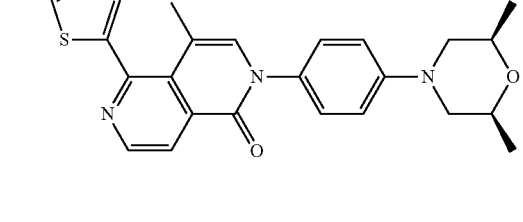
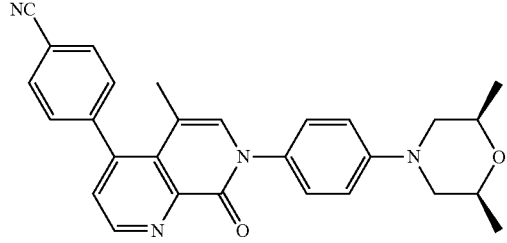

-continued
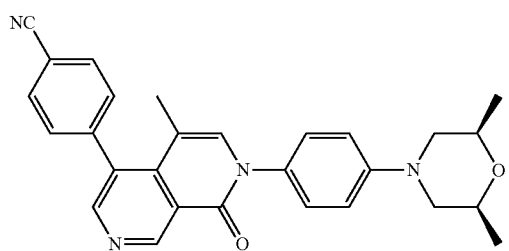
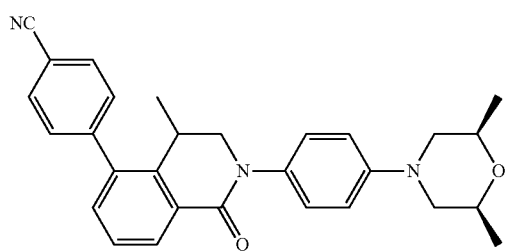
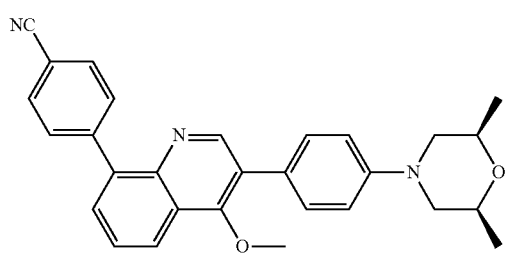
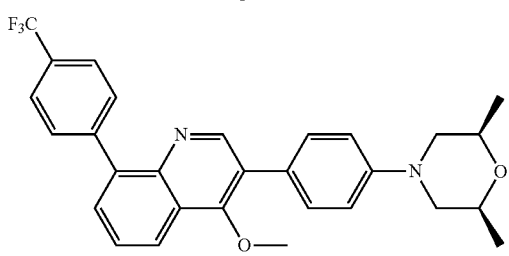
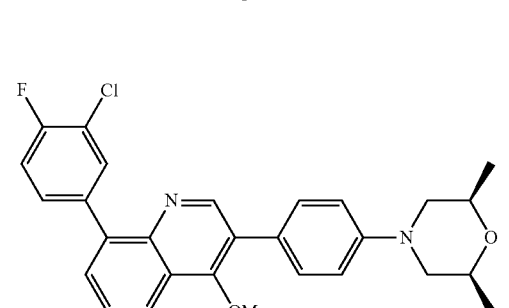
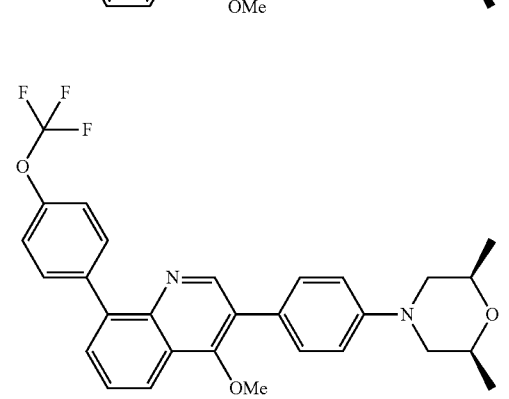
-continued
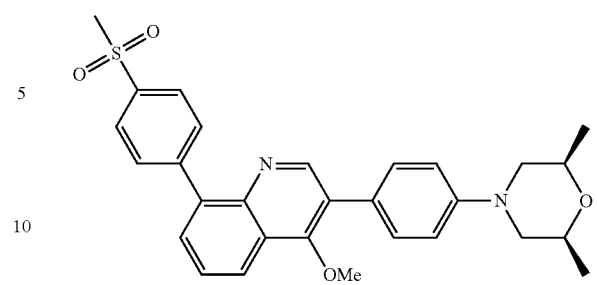
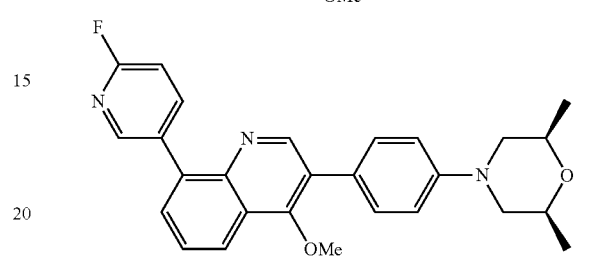
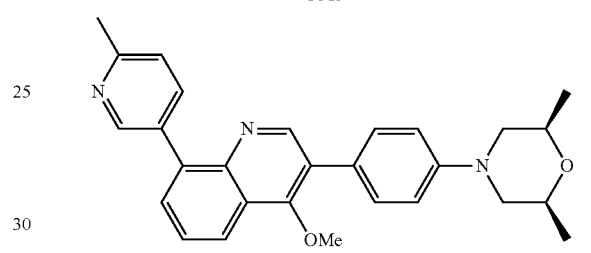
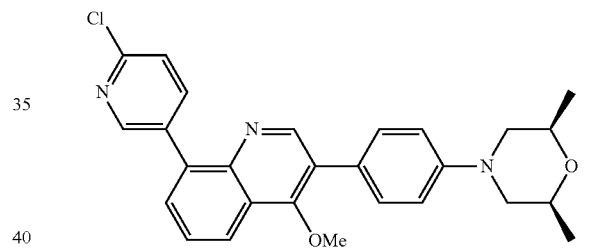
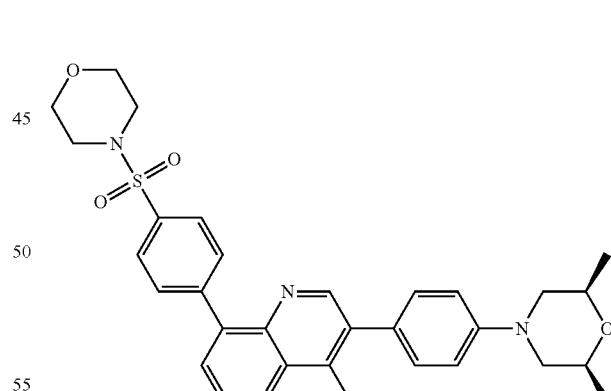
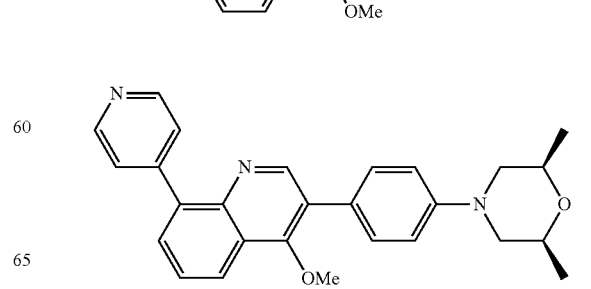

57
-continued
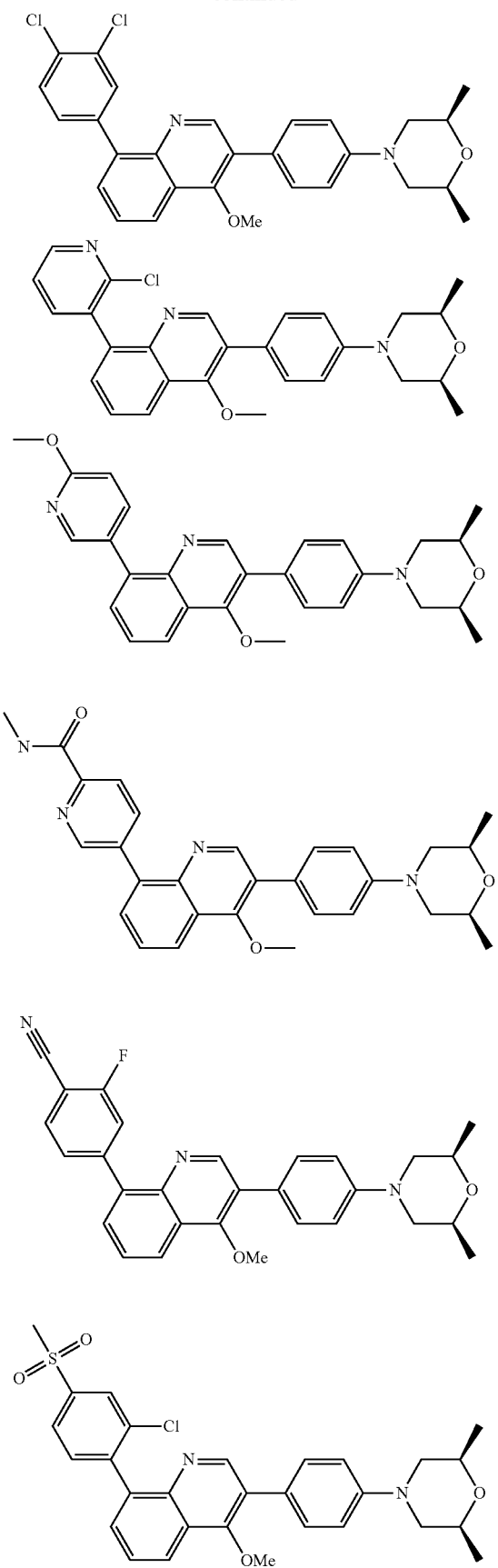
58
-continued
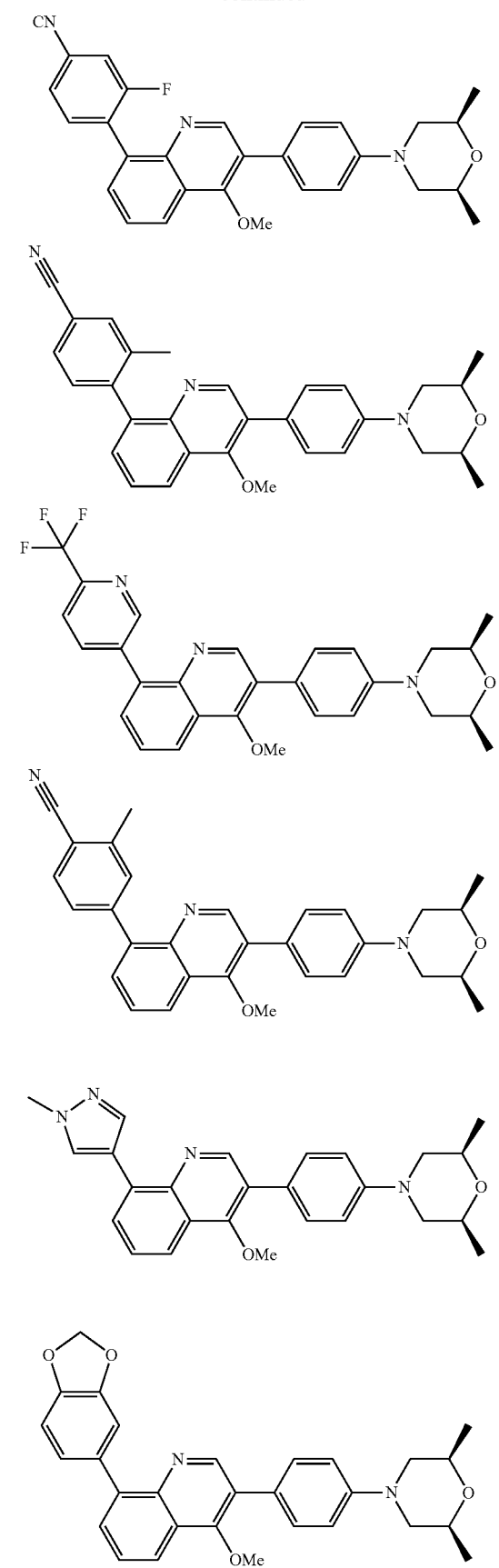

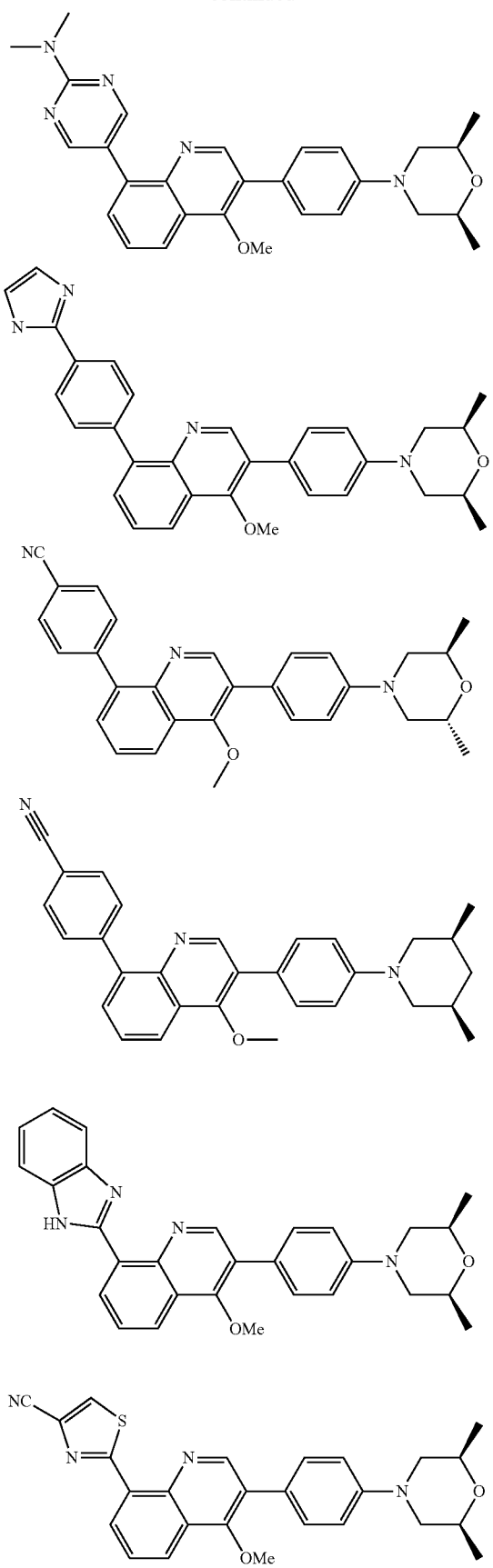
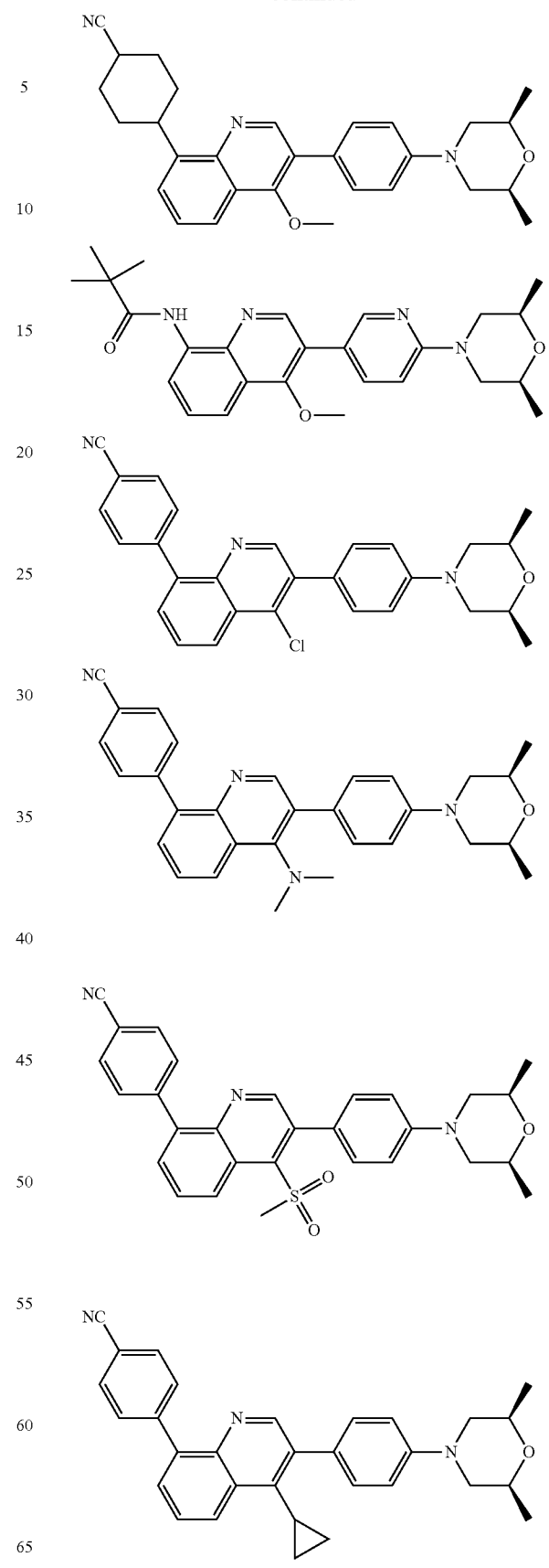

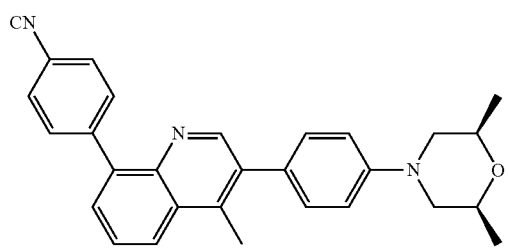
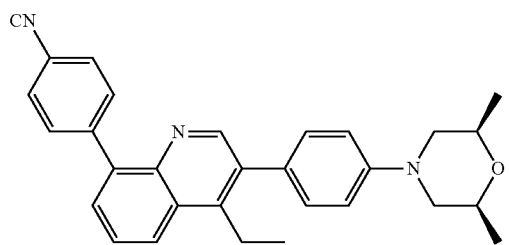
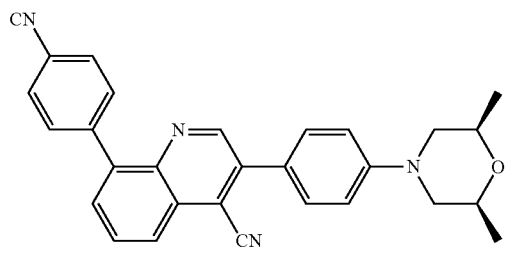
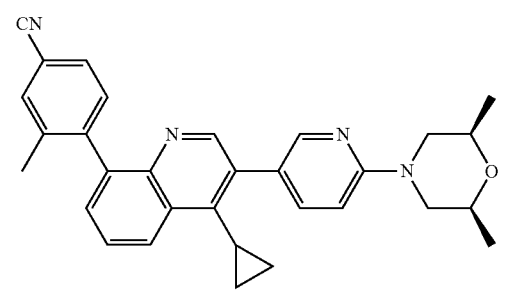
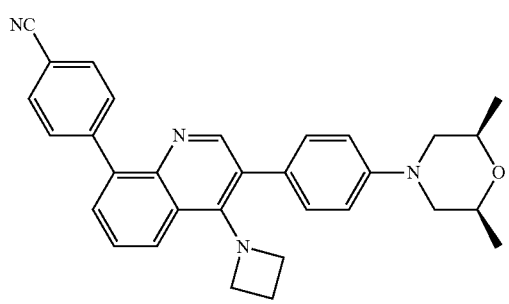
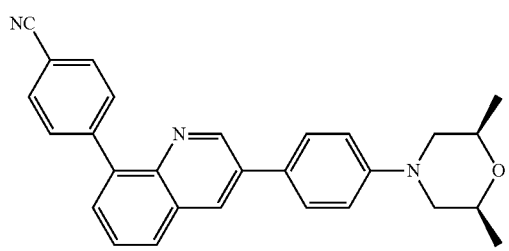
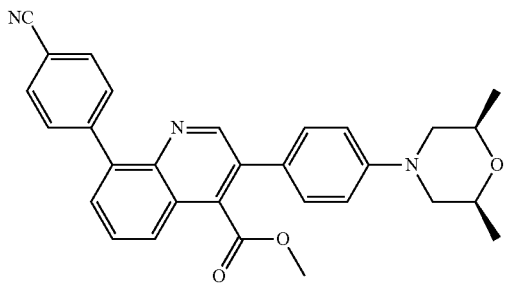
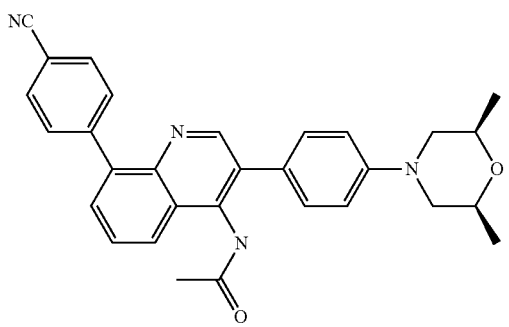
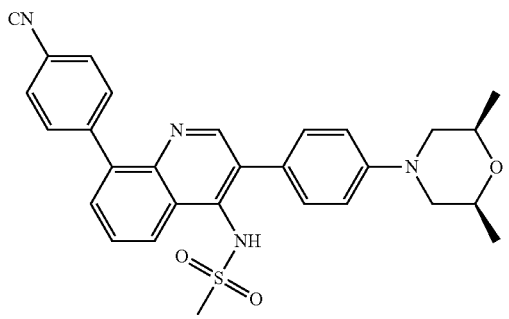
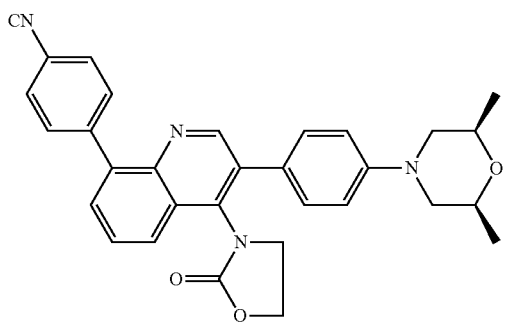
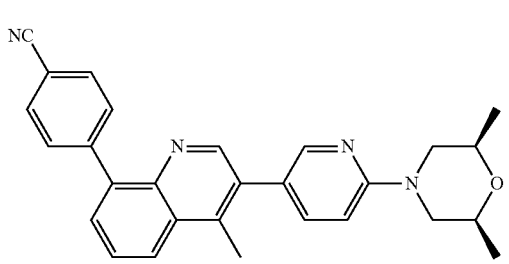

-continued
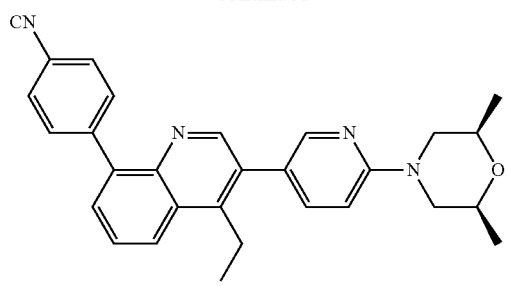
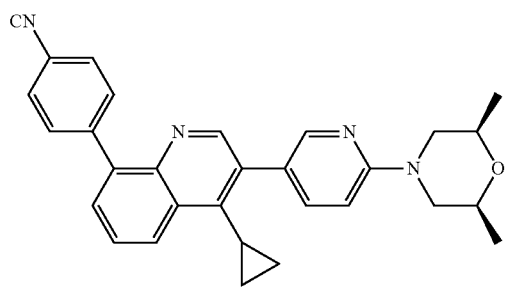
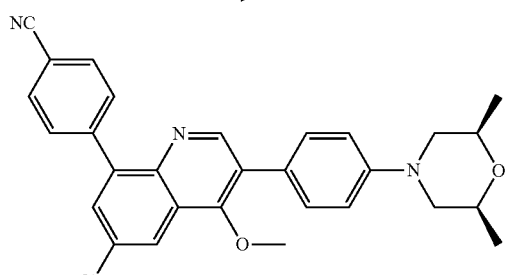
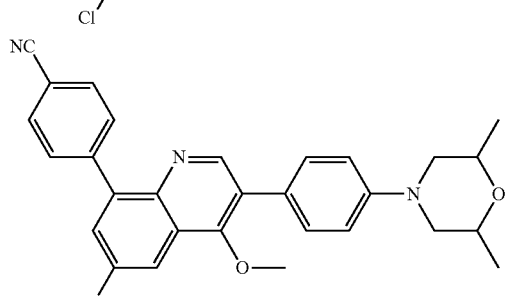
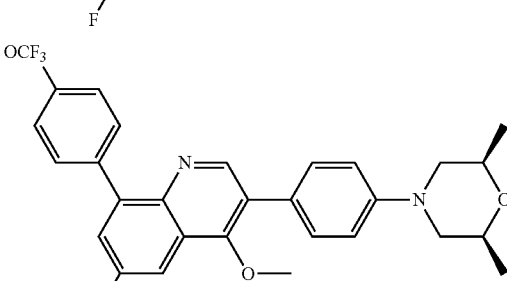
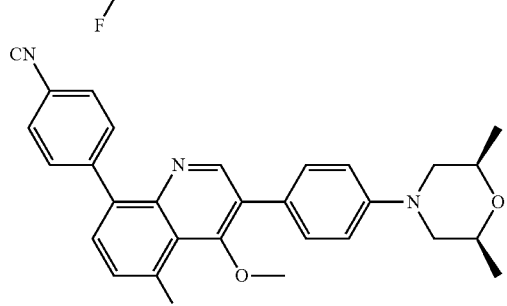
-continued
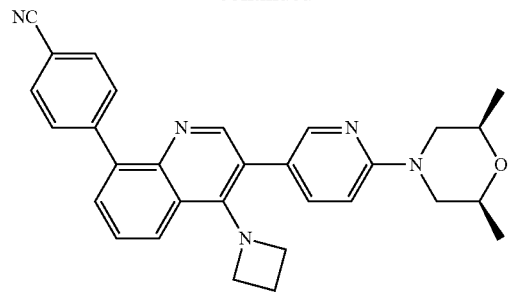
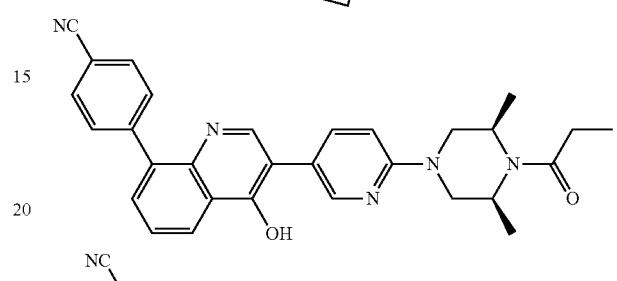
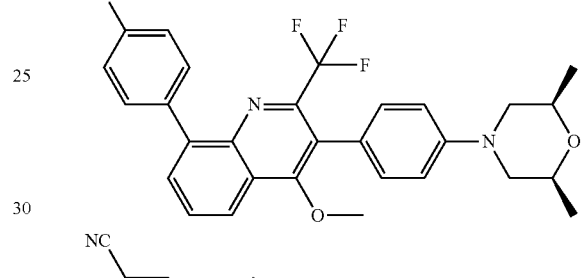
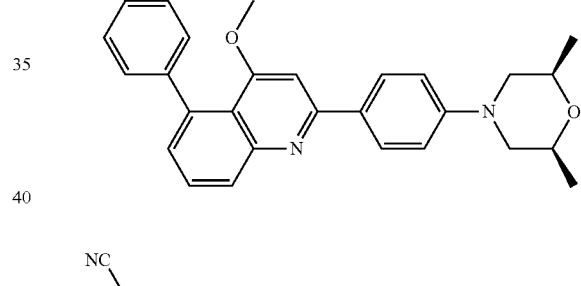
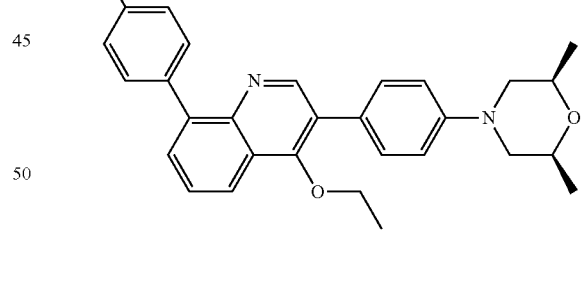
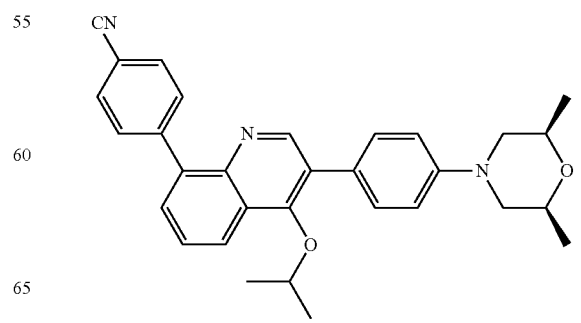

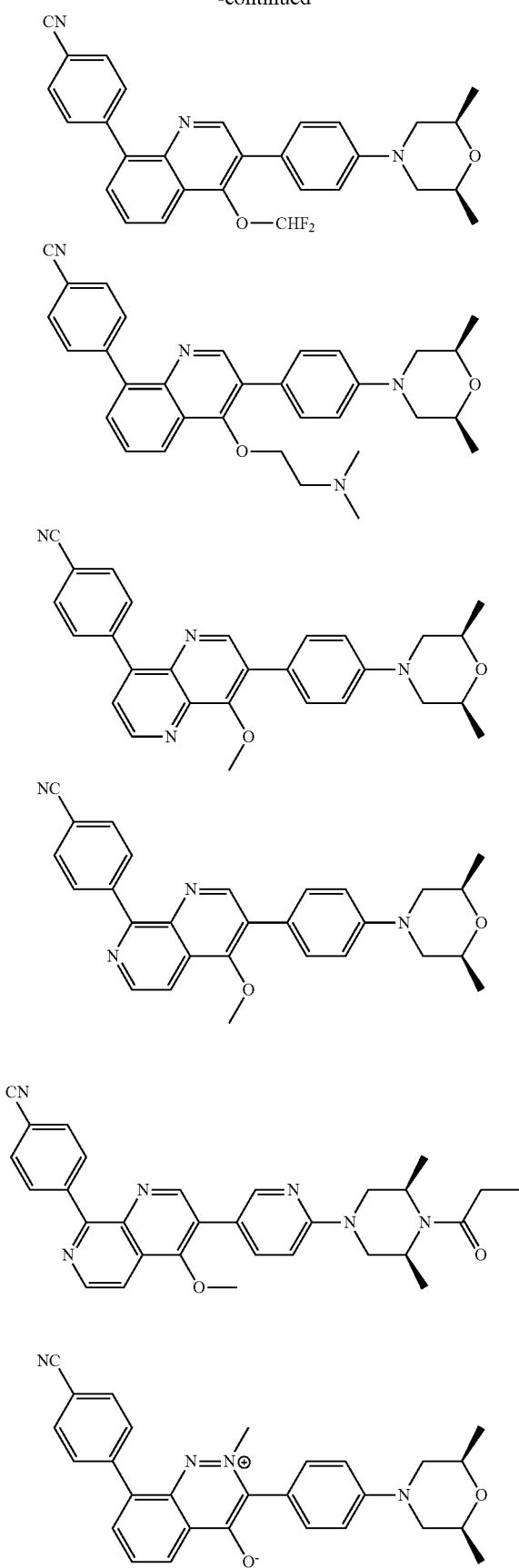
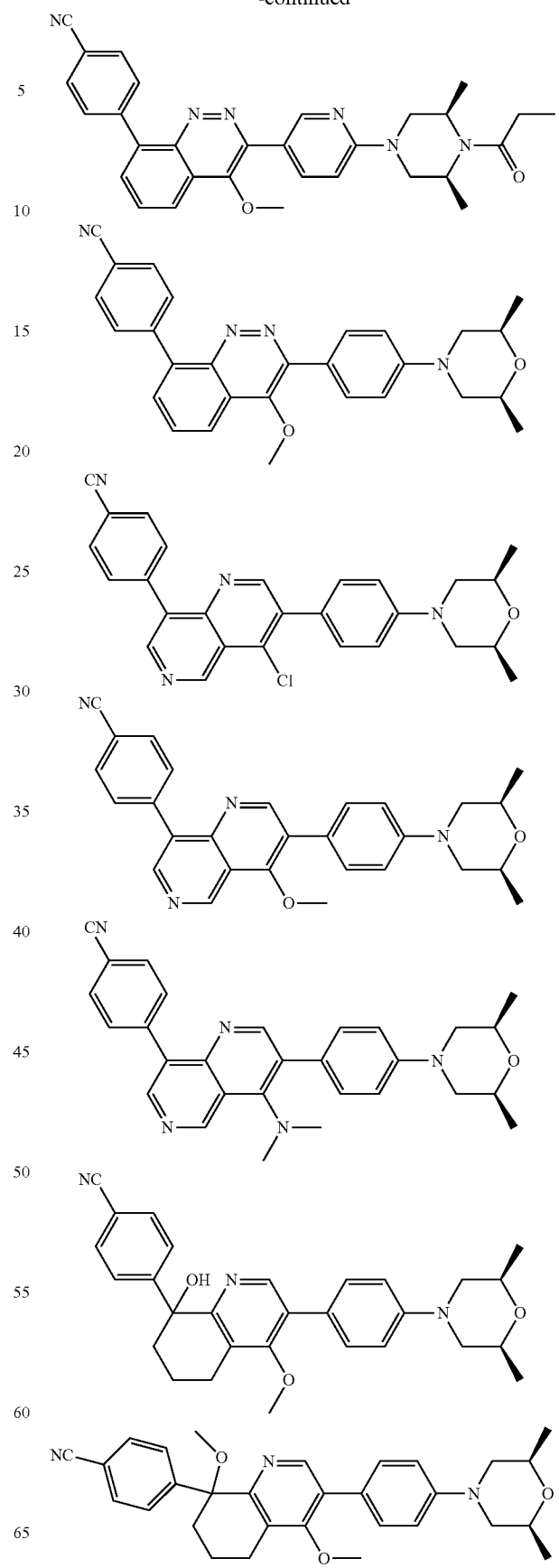

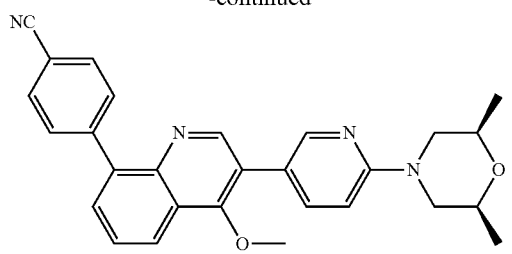
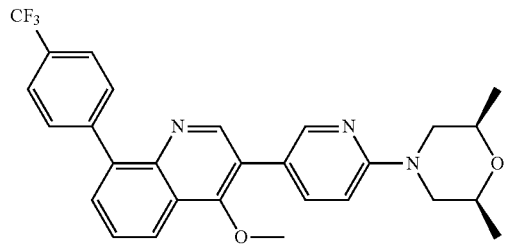
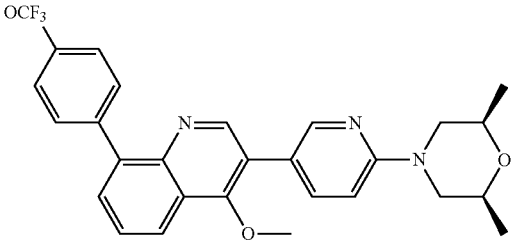
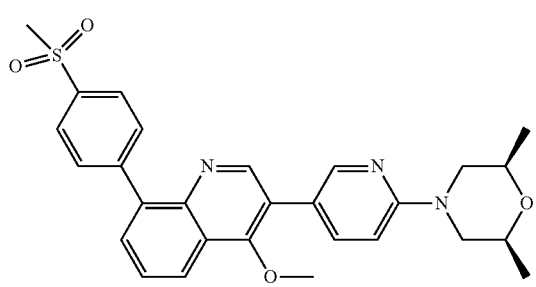
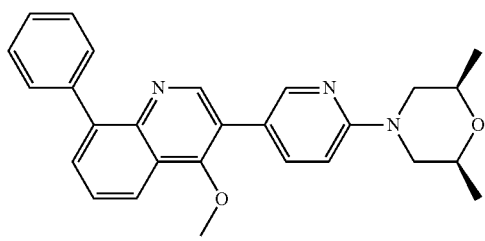
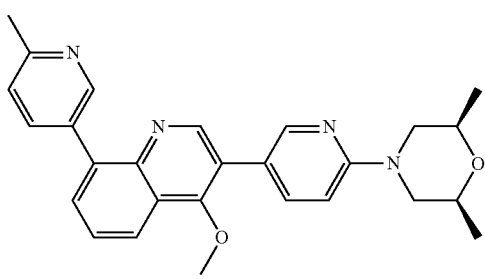
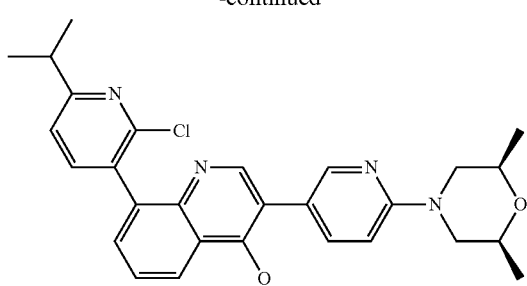
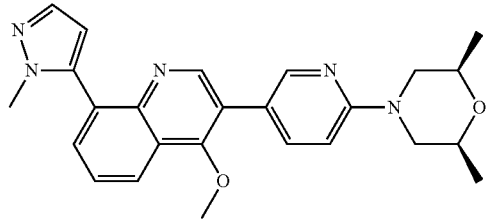
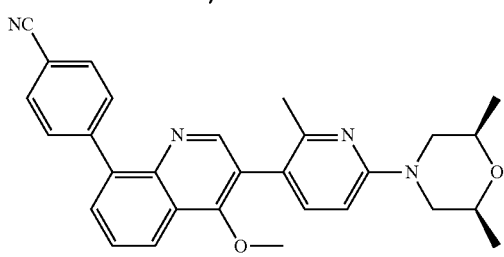
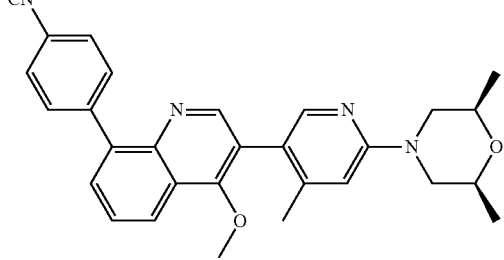
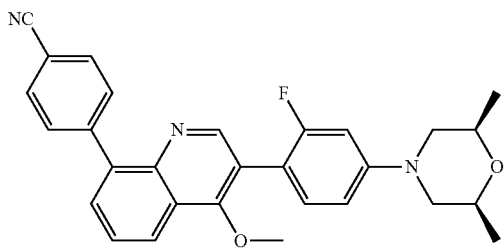
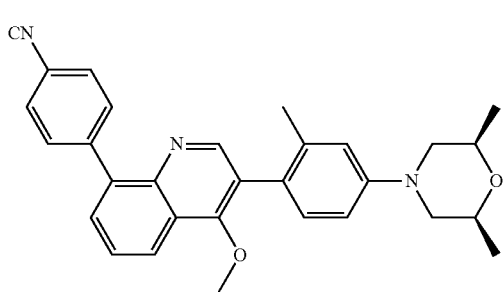

-continued
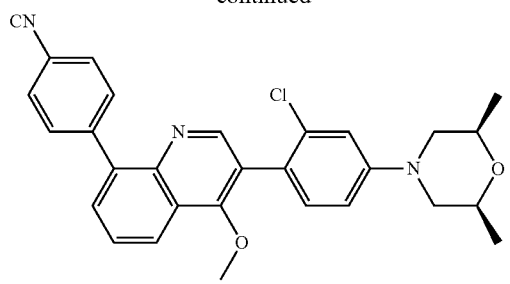
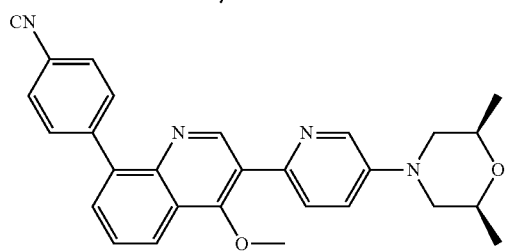
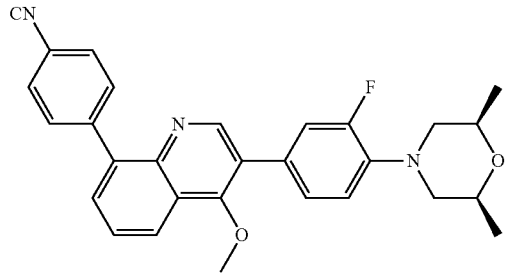
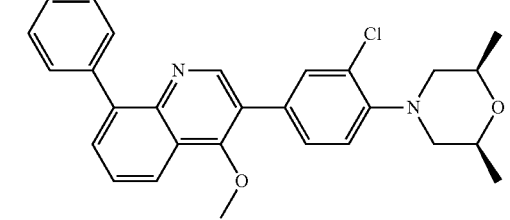
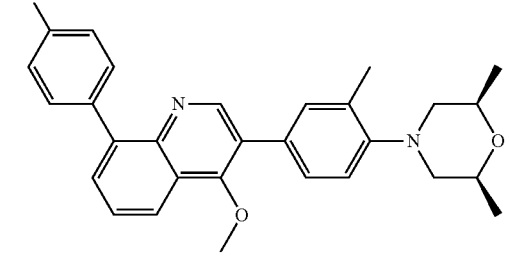
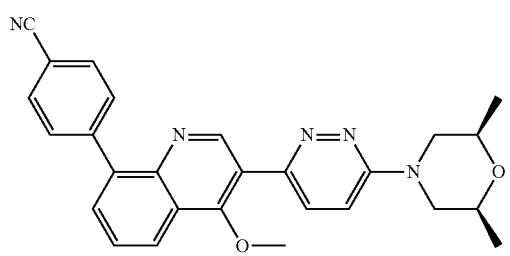
-continued
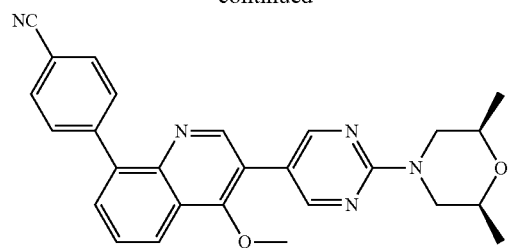
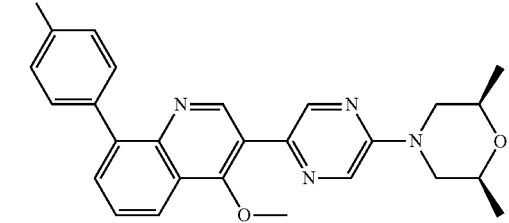
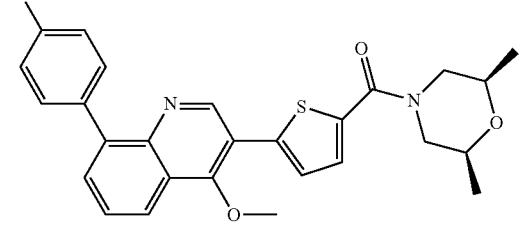
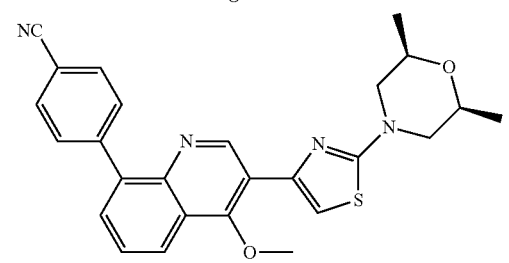
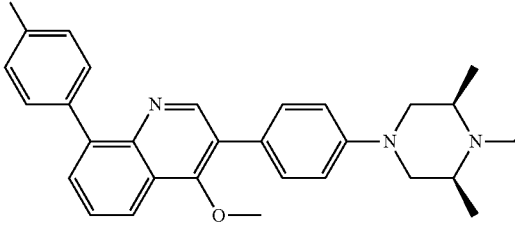
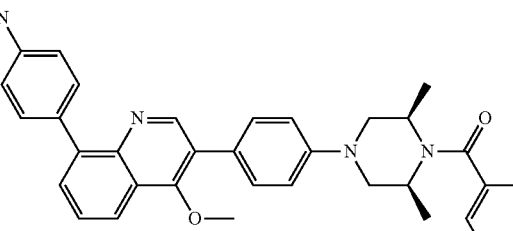
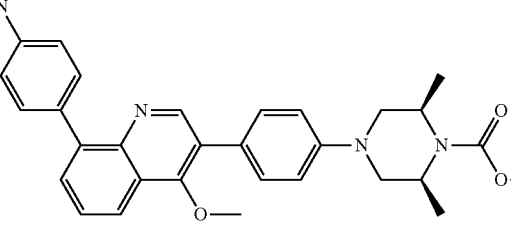

71
-continued
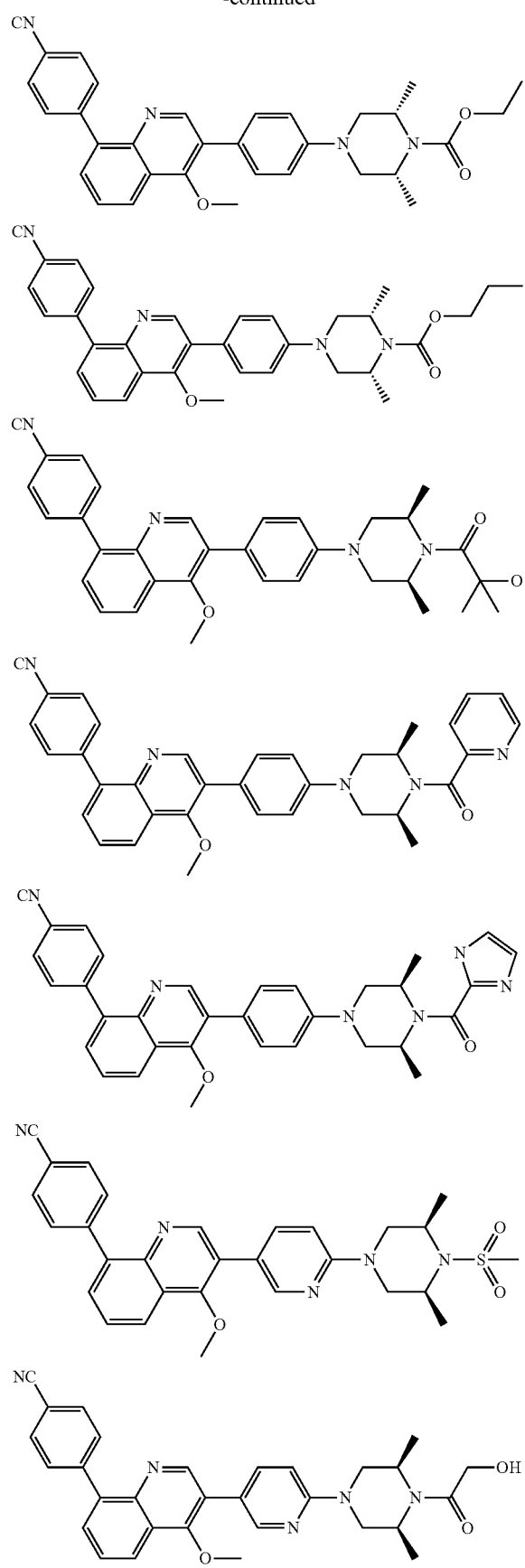
72
-continued
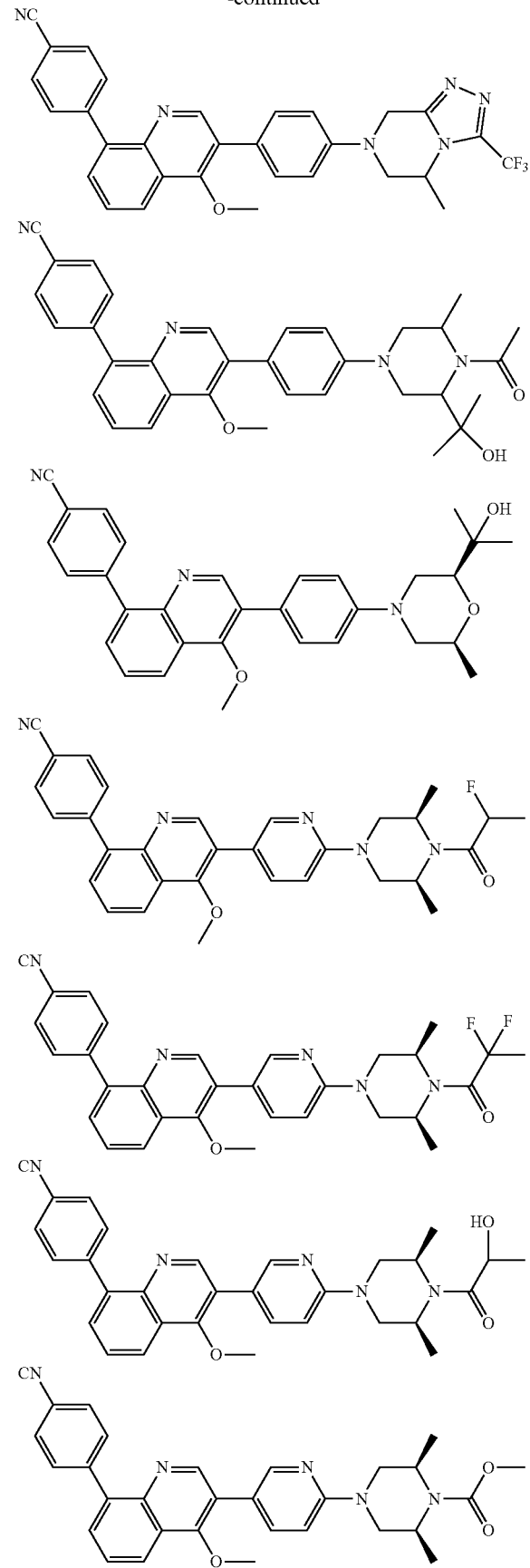

73
-continued
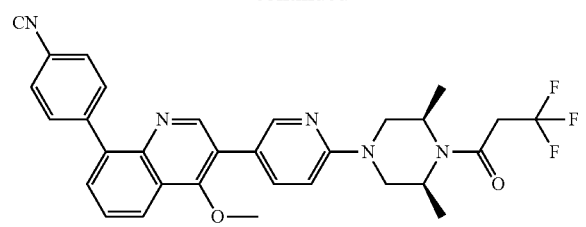
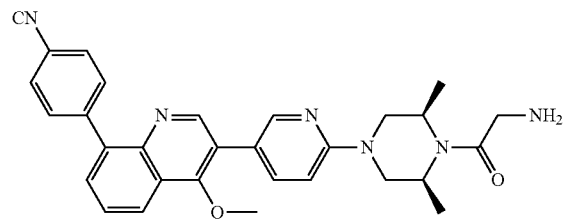
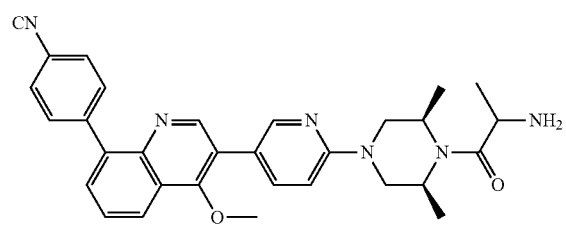
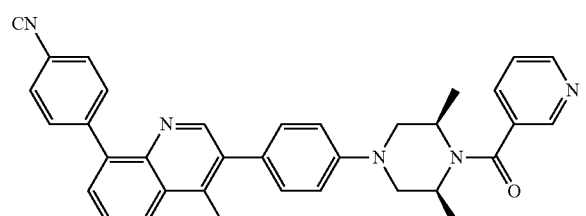
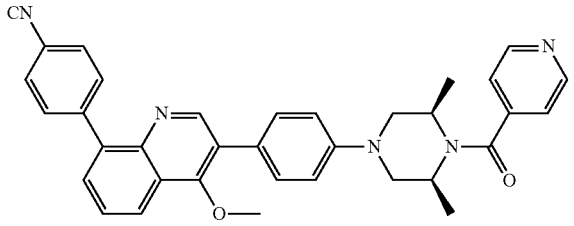
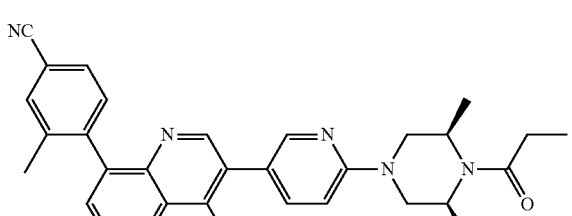
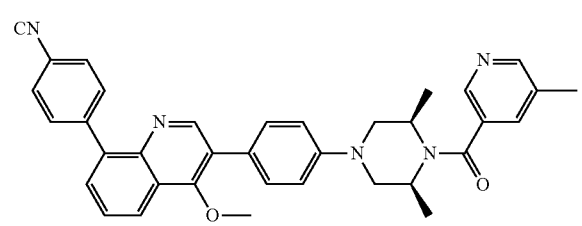
74
-continued
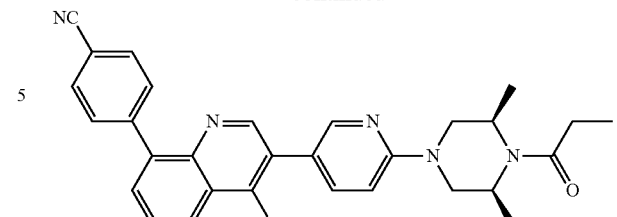
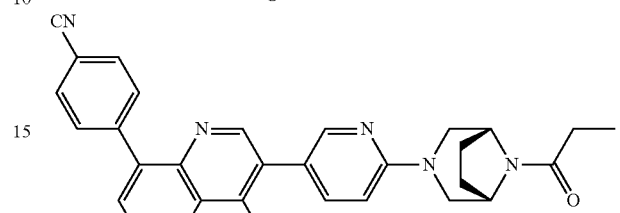
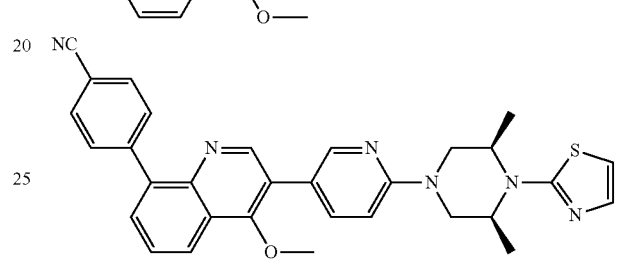
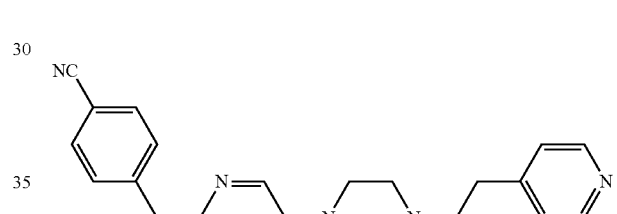
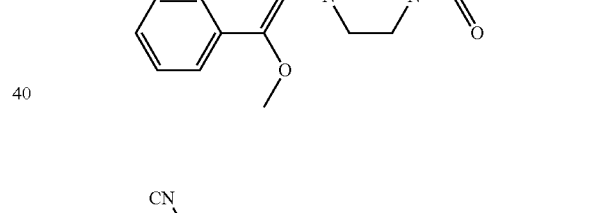
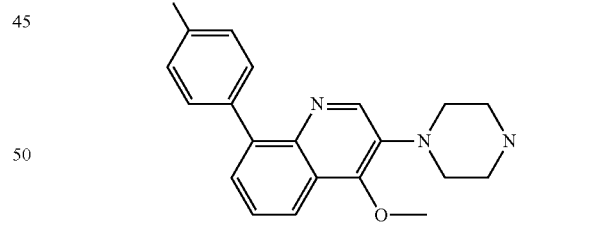
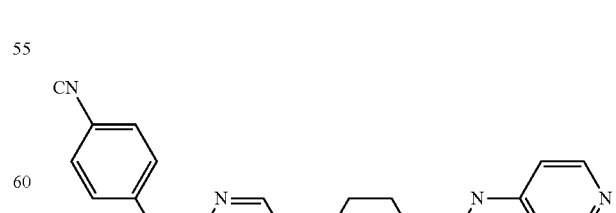

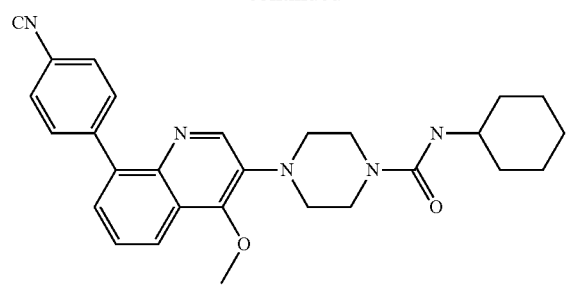
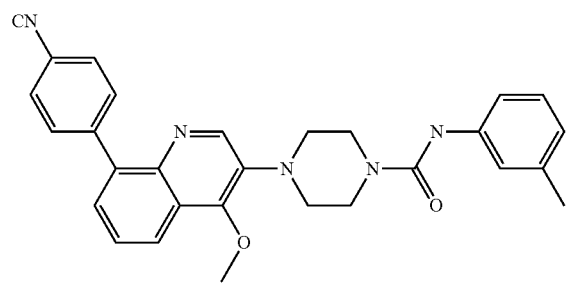
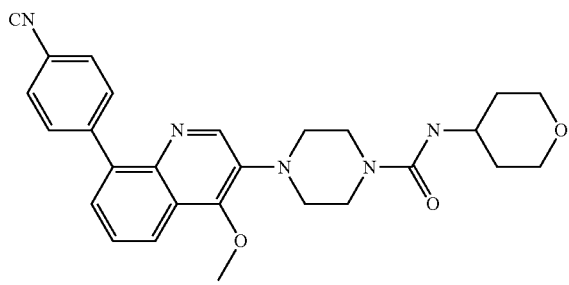
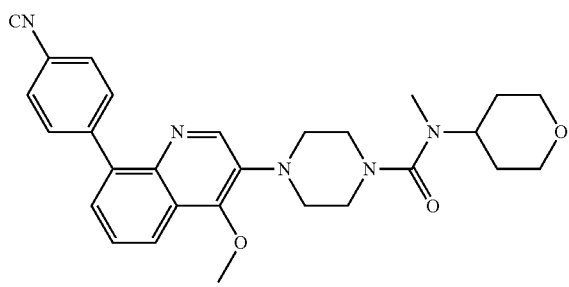
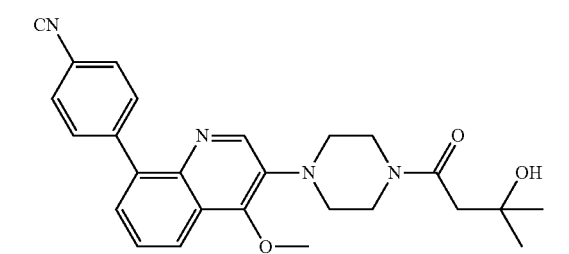
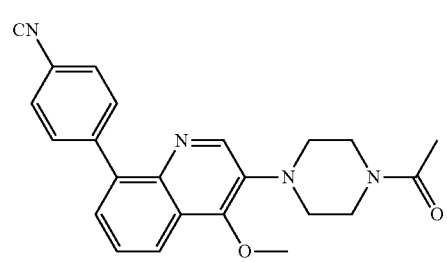
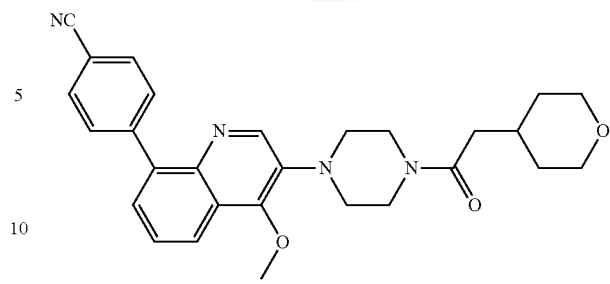
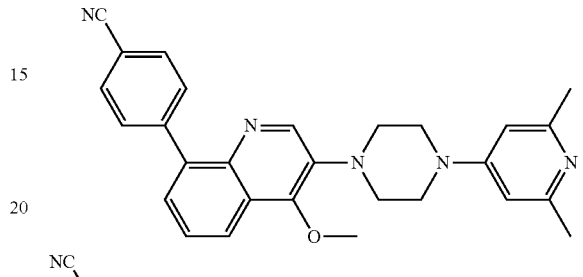
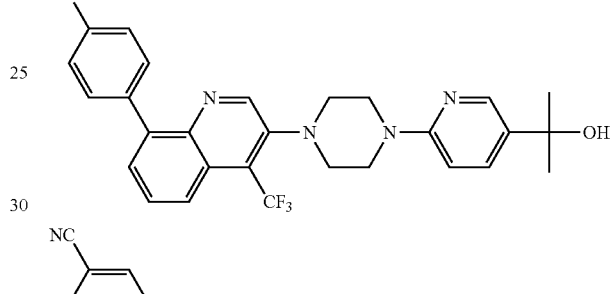
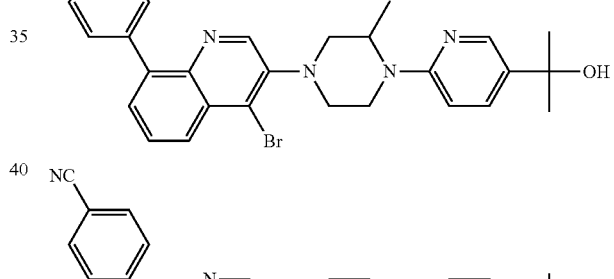
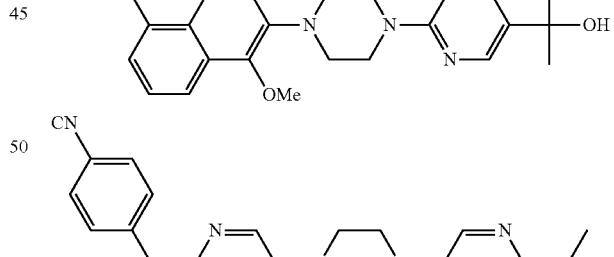
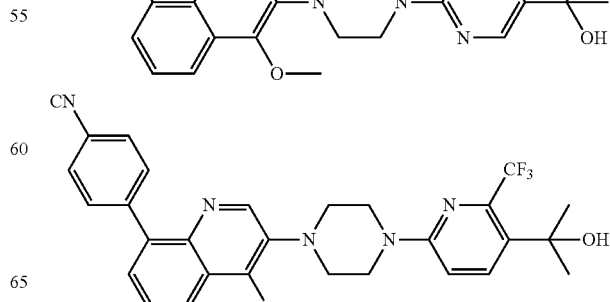

-continued
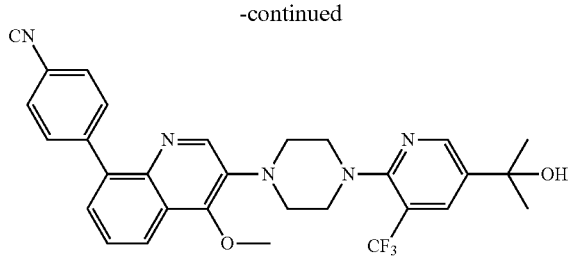
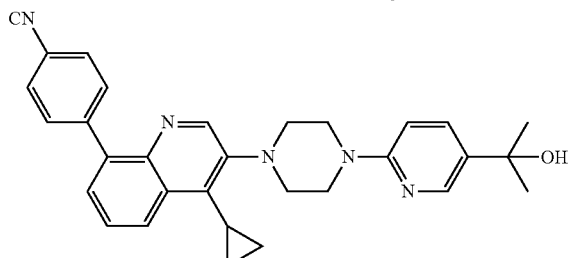
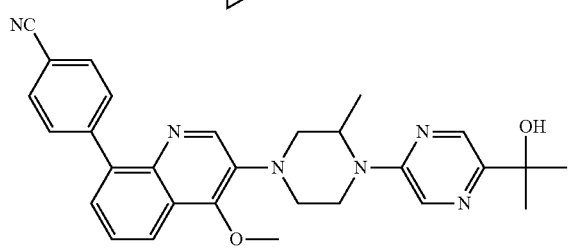
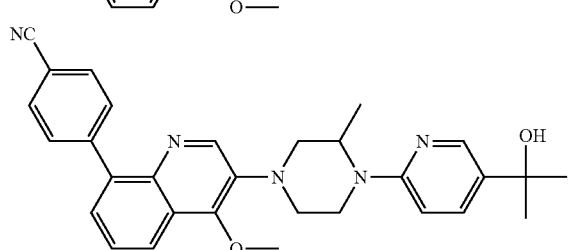
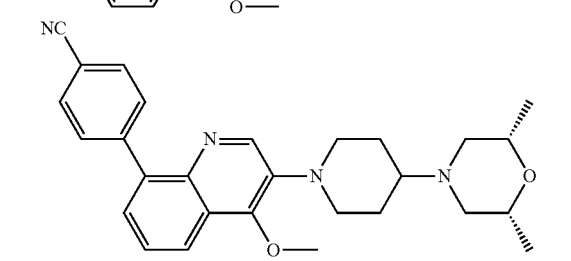
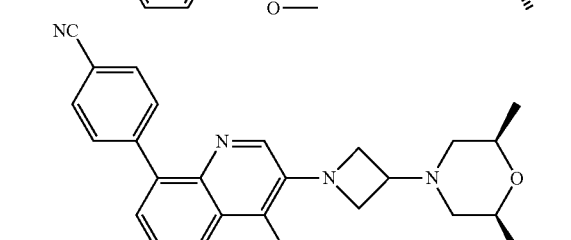
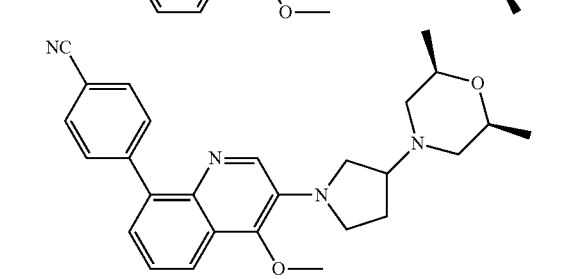
-continued
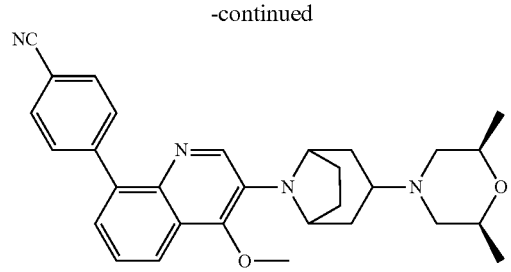
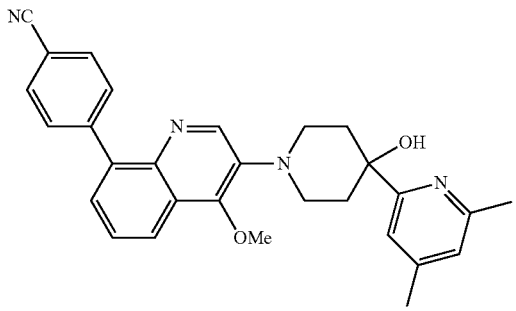
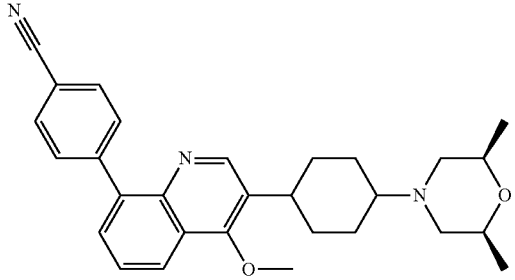
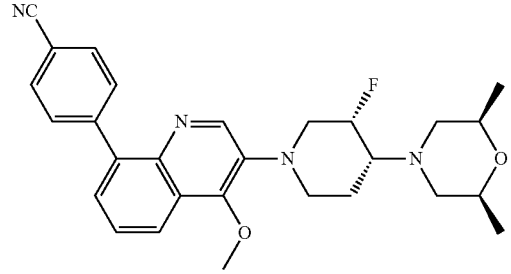
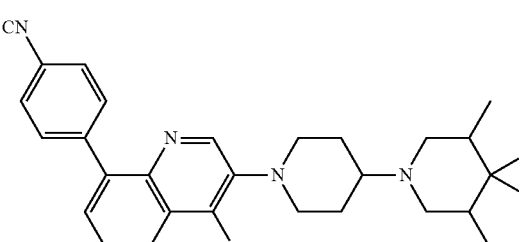
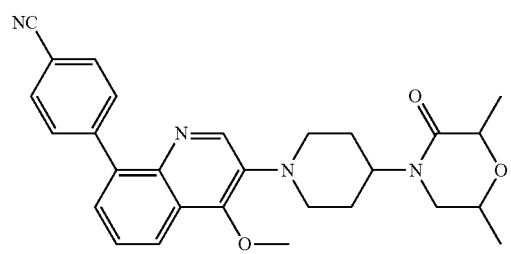

79
-continued
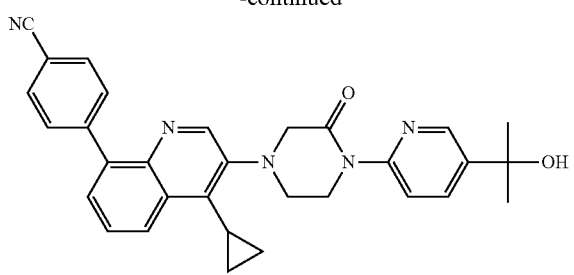
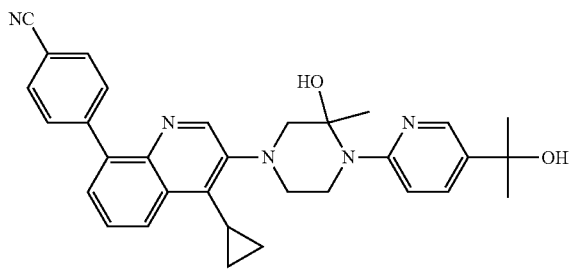
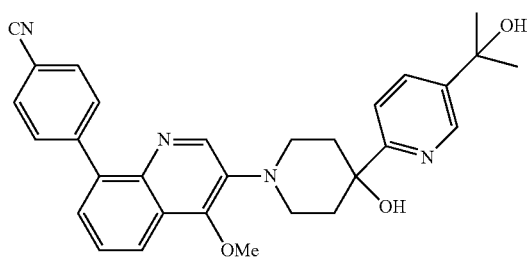
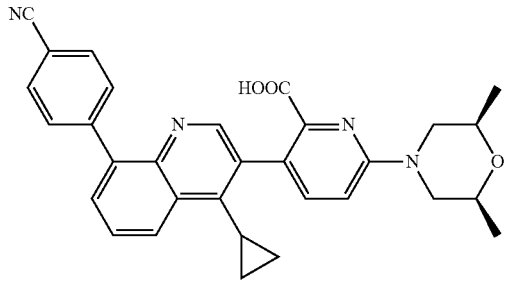
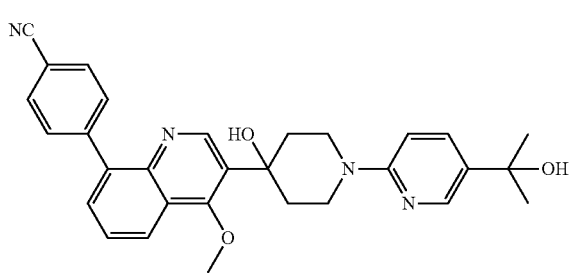
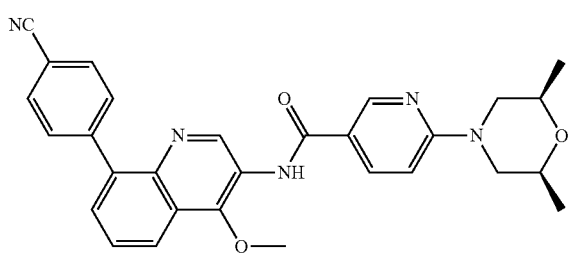
80
-continued
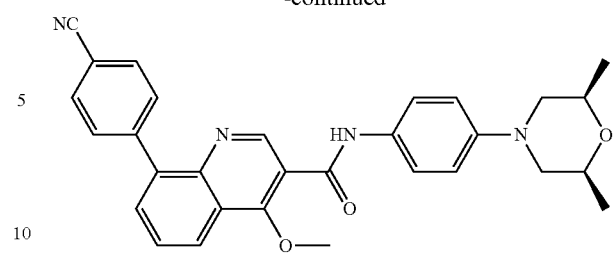
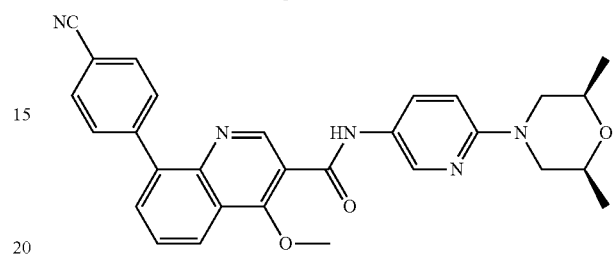
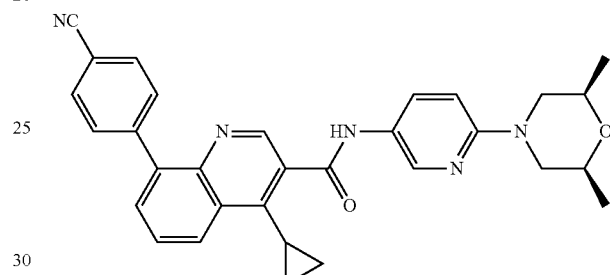
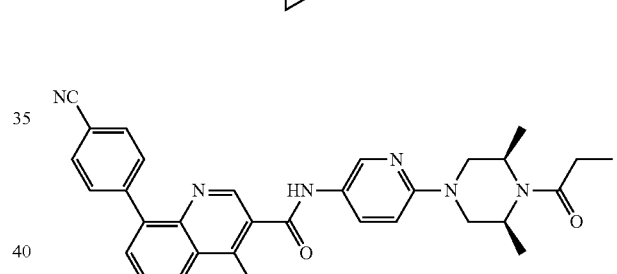
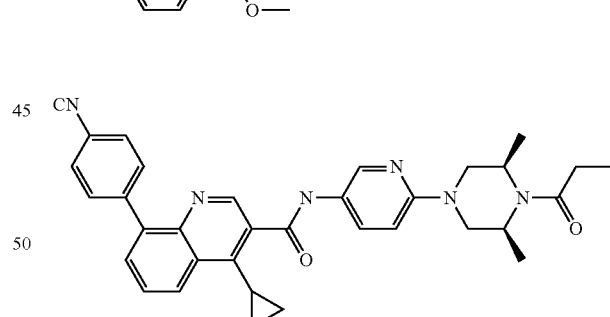
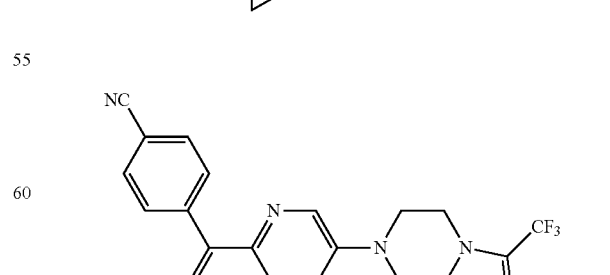
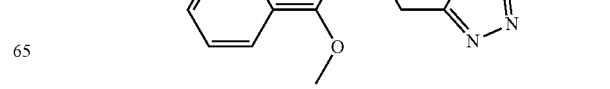

-continued
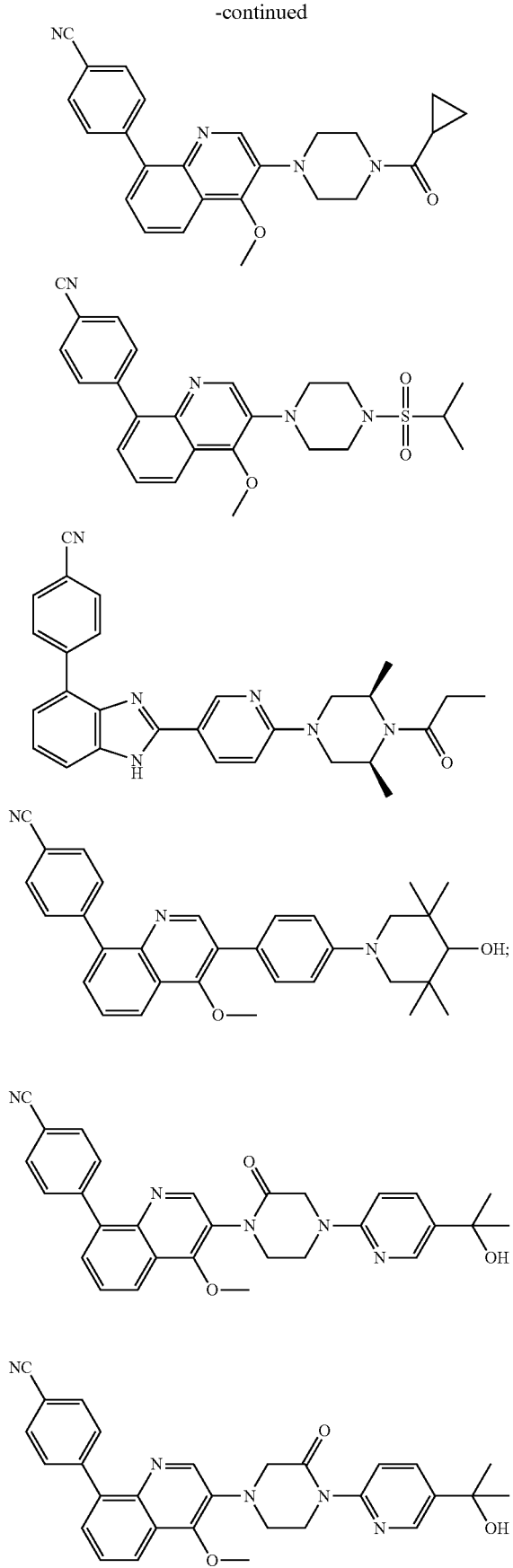
-continued
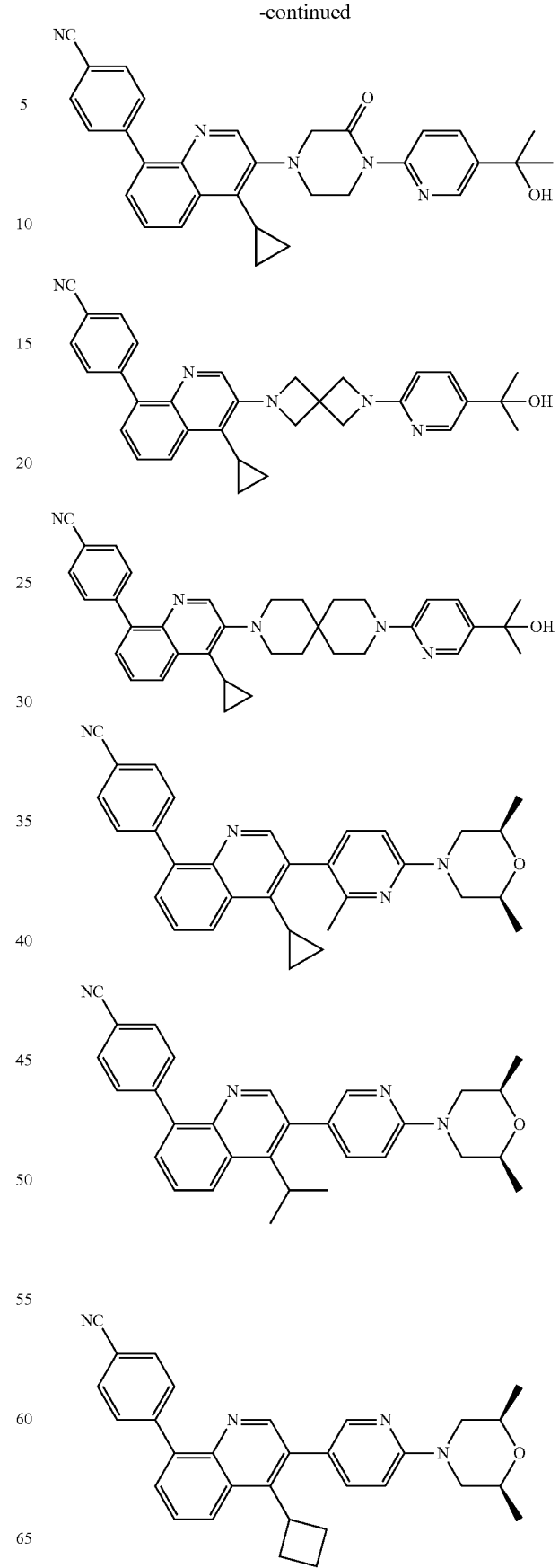

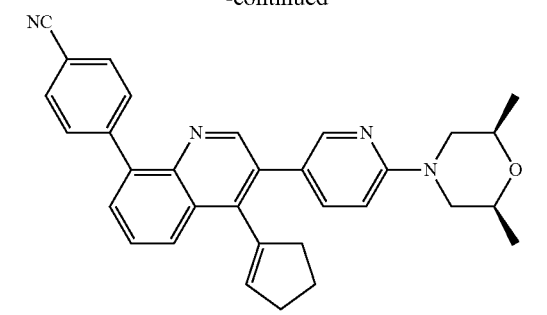
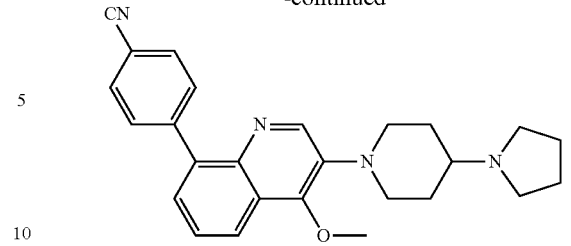
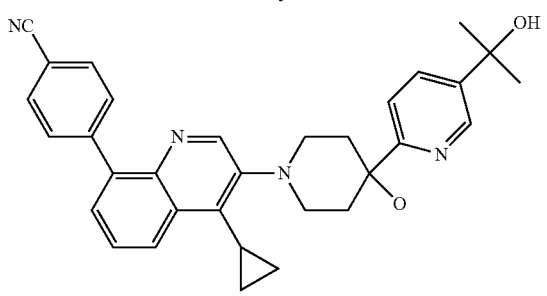
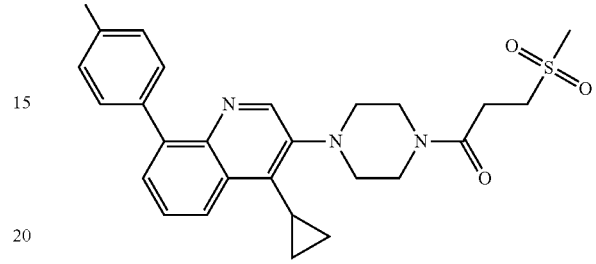
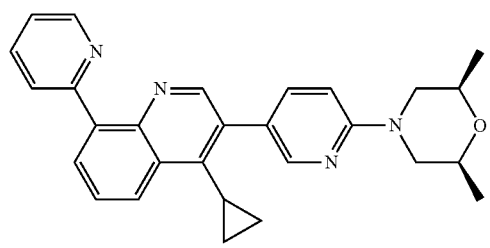
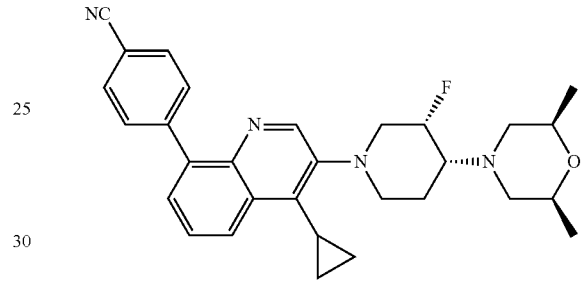
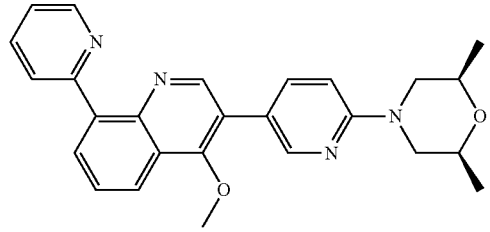
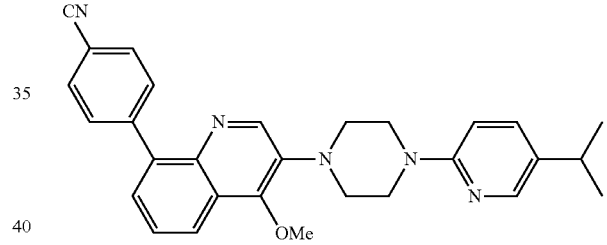
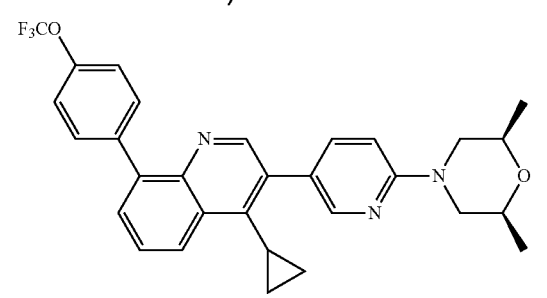
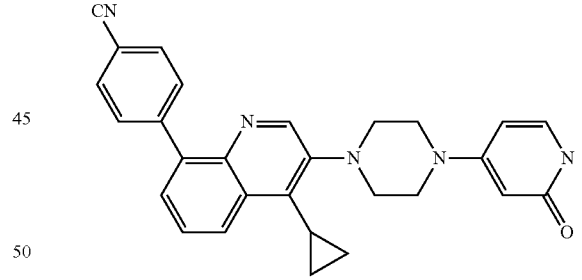
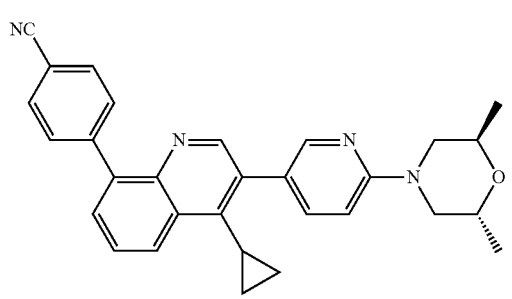
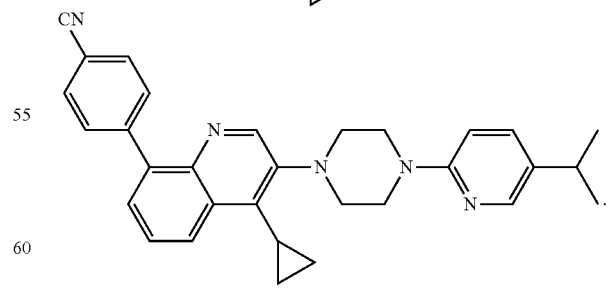
The term "pharmaceutically acceptable salt" refers to the salt of the compound of the present invention, which is prepared by the compound with specific substituent discovered by the present invention and relatively non-toxic acid or alkali. When the compound of the present invention contains a relatively acidic functional group, an alkali-addition salt can be obtained by contacting the compound in a neutral form with sufficient amount of alkali in a pure solution or suitable inert solvent. The pharmaceutically acceptable alkali-addition salt includes the salt of sodium, potassium, calcium, ammonium, organic ammonia or magnesium or the like. When the compound of the present invention contains a relatively alkaline functional group, an acid-addition salt can be obtained by contacting the compound in a neutral form with sufficient amount of acid in a pure solution or suitable inert solvent. Examples of the pharmaceutically acceptable acid-addition salt include a salt of inorganic acid, the inorganic acid includes such as hydrochloric acid, hydrobromic acid, nitric acid, carbonic acid, bicarbonate, phosphoric acid, hydrogen phosphate, dihydrogen phosphate, sulfuric acid, hydrogen sulfate, hydriodic acid, phosphorous acid etc; and salt of organic acid, the organic acid includes such as acetic acid, propionic acid, isobutyric acid, maleic acid, malonic acid, benzoic acid, succinic acid, suberic acid, fumaric acid, lactic acid, mandelic acid, phthalic acid, phenylsulfonic acid, p-toluene sulfonic acid, citric acid, tartaric acid, methylsulfonic acid and the like; and also includes salt of amino acid (e.g. arginine etc.), and salt of organic acid such as glucuronic acid and the like (see Berge et al., "Pharmaceutical Salts", Journal of Pharmaceutical Science 66: 1-19 (1977)). Some specific compound of the present invention contains both alkaline and acidic functional groups so as to be transformed to be any alkali-addition or acid-addition salt.

Preferably, the neutral form of a compound is regenerated by contacting a salt with a base or an acid in a conventional manner and then separating the parent compound. The difference between a parent form of a compound and the various salt forms lies in some physical properties, such as that the solubility in a polar solvent is different.

The "pharmaceutically acceptable salt" in the present invention is the derivatives of the compound of the present invention, wherein, the parent compound is modified by salifying with an acid or an alkali. Examples of the pharmaceutically acceptable salt include but not limited to: an inorganic acid or organic acid salt of an alkali such as amine, an alkali metal or organic salt of acid radical such as carboxylic acid and so on. The pharmaceutically acceptable salt includes conventionally non-toxic salts or quaternary ammonium salts of the parent compound, such as a salt formed by a non-toxic inorganic acid or organic acid. The conventionally non-toxic salt includes but not limited to those salts derived from inorganic acids and organic acids, the inorganic acids or organic acids are selected from 2-acetoxybenzoic acid, 2-isethionic acid, acetic acid, ascorbic acid, phenylsulfonic acid, benzoic acid, bicarbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydriodate, hydroxyl, hydroxynaphthoic, isethionic acid, lactic acid, lactose, dodecanesulfonic acid, maleic acid, malic acid, mandelic acid, methanesulfonic acid, nitric acid, oxalic acid, pamoic acid, pantothenic acid, phenylacetic acid, phosphoric acid, polygalacturonan, propionic acid, salicylic acid, stearic acid, folinate acid, succinic acid, aminosulfonic acid, sulfanilic acid, sulphuric acid, tannic acid, tartaric acid and p-toluene sulfonic acid.

The pharmaceutically acceptable salt of the present invention can be prepared by a conventional method with a parent compound containing an acidic or alkaline group. Generally, the preparation method of the salt comprises that in water or an organic solvent or the mixture of water and organic solvent, reacting these compounds in forms of free acids or alkalis with stoichiometric amount of proper alkalis or acids. In general, preferably choose non-aqueous media such as ether, ethyl acetate, ethanol, isopropanol or acetonitrile and so on.

Except for the form of salt, there is a form of prodrug for the compound in the present invention. The prodrug of the compound described in the present invention is easily transformed to be the compound of the present invention via chemical changes under physiological conditions. Besides, the prodrug can be transformed to be the compound of the present invention via chemical or biochemical method in vivo environment.

Some compounds of the present invention can exist in the form of non-solvate or solvate forms, including hydrate forms. In general, the solvate form is similar to the non-solvate form, both of which are included within the scope of the present invention. Some compounds of the present invention can exist in polycrystalline or amorphous form.

Some compounds of the present invention can contain asymmetric carbon atoms (optical center) or double bonds. The racemic isomers, diastereomers, geometric isomers and single isomers are included within the scope of the present invention.

Unless otherwise specified, the term "substituted" refers to one or more hydrogen atoms in a specific atom optionally substituted by a substituent, including a deuterium and a variant of hydrogen, as long as the valence state of the specific atom is normal and the compound obtained after substitution is stable. When the substituent is a ketone group (i.e. =O), it means that two hydrogen atoms are substituted. A substitution of ketone group does not occur in an aryl. The term "optionally substituted" means that it may be substituted or not be substituted, unless otherwise specified, the type and number of substituents can be arbitrary under the premise of stability available in chemistry.

Unless otherwise specified, when any parameter (e.g. R) shows an occurrence for more than one time in the composition or structure of the compound, the definition of each occurrence is independent. Therefore, for example, if a group is substituted by 0~2 of R, the group may optionally be substituted by at most two R, and R has an independent option in each case. In addition, the combination of substituents and/or their variants is allowed only if such a combination will lead to a stable compound.

When one parameter therein is selected from a single bond, it means that the two groups the parameter connects to connect to each other directly, for example when the L in A-L-Z refers a single bond, it means that the structure actually is A-Z.

Unless otherwise specified, when bonds of a substituent can be crossly connected to two atoms of a ring, the substituent can be bonded to arbitrary atoms in the ring. When it does not specify through which atom contained in the listed substituent is it connected to the general structure formula including the compound that is not specifically mentioned, the substituent can be bonded through any of its atoms. The combination of substituents and/or their variants is allowed only if such a combination will lead to a stable compound.

Unless otherwise specified, the term "hydrocarbon group" or its specific concept (such as alkyl, alkenyl, alkynyl, phenyl, etc.) itself or as a part of another substituent represents a linear, branched or cyclic hydrocarbon group or a combination thereof, which can be fully saturated, monocyclic or polycyclic unsaturated, can be monosubstituted, disubstituted or polysubstituted, can be univalent (such as methyl), bivalent (such as methylene) or multivalent (such as methenyl), can include bivalent or multivalent atomic groups, with a specified number of carbon atoms (such as that $C_1$-$C_{10}$ refers to having 1~10 carbon atoms). The term "alkyl" includes an aliphatic hydrocarbon group and aromatic hydrocarbon group, the aliphatic hydrocarbon group includes linear and cyclic structures, specifically includes but not limited to alkyl, alkenyl and alkynyl, the aromatic hydrocarbon group includes but not limited to 6- to 12-membered aromatic hydrocarbon group such as benzene, naphthalene and the like. In some embodiments, the term "alkyl" refers to linear or branched or cyclic groups or their combination, which can be completely saturated, monocyclic or polycyclic unsaturated, can include divalent and polyvalent groups. Examples of saturated hydrocarbon groups include but not limited to homologues or isomers of methyl, ethyl, n-propyl, iso-propyl, n-butyl, tert-butyl, iso-butyl, sec-butyl, iso-butyl, cyclohexyl, (cyclohexyl) methyl, cyclopropyl methyl, and n-amyl, n-hexyl, n-heptyl, n-octyl and the like. Unsaturated alkyl has one or more double or triple bond, examples of which includes but not limited to vinyl, 2-propenyl, butenyl, crotyl, 2-isopentenyl, 2-butadienyl, 2,4-(pentadienyl), 3-(1,4-pentadienyl), acetenyl, 1- and 3-propinyl, 3-butynyl, and more advanced homologues and isomers.

Unless otherwise specified, the terms "heterohydrocarbon group", "heterocycle group", "hydrocarbon-heteroatom group", "cycle-heteroatom group", "heterohydrocarbon-heteroatom group", "heterocycle-heteroatom group" refer that a heteroatom or a heteroatom group is contained on a specified group, the heteroatom or heteroatom group include but not limited to N, NH, a substituted or protected NH, O, S, S(═O), S(═O)$_2$, C(═O), C(═O)O, for a ring system, a heteroatom or a heteroatom group can be located in internal position or external position of the ring system (e.g. cyclopropyl sulfonyl, cyclopropyl acyl), wherein, the "heterohydrocarbon group", "heterocycle group" are connected with the rest part of the molecule through a carbon atom, that is, the heteroatom can be located in any position of the group (excluding the position where hydrocarbon group is attached to the rest part of the molecule); the "hydrocarbon-heteroatom group", "cycle-heteroatom group" are connected with the rest part of the molecule through a heteroatom, that is, the heteroatom is located in the position where the group is attached to the rest part of the molecule); the "heterohydrocarbon-heteroatom group", "heterocycle-heteroatom group" are connected with the rest part of the molecule through a heteroatom, wherein the heteroatom can be located in any position of the group (including the position where hydrocarbon group is attached to the rest part of the molecule).

Unless otherwise specified, the term "heterohydrocarbon group" or its specific concepts (such as heteroalkyl, heteroalkenyl, heteroalkynyl, heteroaryl, etc.) itself or the term combining with another term refers to a stable linear, branched or cyclic hydrocarbon group or their combinations, which consists of a certain number of carbon atoms and at least one heteroatom. In some embodiments, the term "heterohydrocarbon group" or its specific concepts (such as heteroalkyl, heteroalkenyl, heteroalkynyl, heteroaryl, etc.) itself or the term combining with another term refers to a stable linear, branched hydrocarbon group or their combinations, which consists of a certain number of carbon atoms and at least one heteroatom. In a typical embodiment, the heteroatom is selected from the group consisting of B, O, N and S, in which the nitrogen and sulfur atoms are optionally oxidized, and the nitrogen atom is optionally quaternized. Heteroatoms B, O, N and S can be located in any internal position of the heterohydrocarbon group (excluding the position where hydrocarbon group is attached to the rest part of the molecule). Examples include but not limited to —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH═CH—O—CH$_3$, —CH$_2$—CH═N—OCH$_3$ and —CH═CH—N(CH$_3$)—CH$_3$. At most two heteroatoms are adjacent, such as —CH$_2$—NH—OCH$_3$.

Unless otherwise specified, the terms "alkoxy", "alkyl amino" and alkylthio" (or thioalkoxy) are the idiomatic expressions, which refers to the alkyl group is attached to the rest of molecule through an oxygen, an amino, or a sulfur atom, respectively.

Unless otherwise specified, the term "cyclohydrocarbon group", "heterocyclo hydrocarbon group", "cyclohydrocarbon-heteroatom group" or its specific concepts (such as aryl, heteroaryl, aryl heteroatom group, cycloalkyl, heterocycloalkyl, cycloalkyl heteroatom group, cycloalkenyl, heterocycloalkenyl, cycloalkenyl heteroatom group, cycloalkynyl, heterocycloalkynyl, cycloalkynyl heteroatom group, etc.) itself or the term combining with other terms respectively refers to a cyclic "hydrocarbon group", "heterohydrocarbon group" or "hydrocarbon heteroatom group". Examples of the cycloalkyl include but not limited to cyclopentyl, cyclohexyl, 1-cyclohexenyl, 3-cyclohexenyl, cycloheptyl, etc. Unrestricted examples of the heterocyclic group include 1-(1,2,5,6-tetrahydropyridinyl), 1-piperidyl, 2-piperidyl, 3-piperidyl, 4-morpholinyl, 3-morpholinyl, tetrahydrofuran-2-yl, tetrahydrofuranylindol-3-yl, tetrahydrothiophene-2-yl, tetrahydrothiophene-3-yl, 1-piperazinyl and 2-piperazinyl.

Unless otherwise specified, the term "halogenated" or "halogen" itself or as a part of another substituent refers to fluorine, chlorine, bromine or iodine atom. In addition, the term "halogenated alkyl" is intended to include monohalogenated alkyl and polyhalogenated alkyl. For example, the term "halogenated ($C_1$-$C_4$) alkyl" is intended to include but not limited to trifluoromethyl, 2, 2, 2-trifluoroethyl, 4-chlorobutyl and 3-bromopropyl, etc.

Unless otherwise specified, the term "aryl" refers to a polyunsaturated aromatic hydrocarbon substituent, which can be monosubstituted, disubstituted or multisubstituted, it can be monocyclic or polycyclic (preferably 1 to 3 rings), they fuse together or connect by a covalent linkage. The term "heteroaryl" refers to an aryl (or ring) containing 1 to 4 heteroatoms. In an exemplary embodiment, the heteroatom is selected from the group consisting of B, N, O, and S, in which the nitrogen and sulfur atoms are optionally oxidized, and the nitrogen atom is optionally quaternized. The heteroaryl group can be connected to the rest part of the molecule via a heteroatom. Unrestricted examples of an aryl or a heteroaryl include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furanyl, 3-furanyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzoimidazolyl, 5-indolyl, 1-isoquinolyl, 5-isoquinolyl, 2-quinoxalyl, 5-quinoxalyl, 3-quinolyl and 6-quinolyl. Any one of the substituents in the aryl and heteroaryl ring system is selected from the acceptable substituents described below.

Unless otherwise specified, for the sake of briefness, when used in combination with other terms (e.g. aryloxy, arylthio, aralkyl), the aryl includes the definition of aryl and heteroaryl ring defined above. Therefore, the term "aralkyl"

is intended to include the groups that aryl attached to alkyl (e.g. benzyl, phenyl ethyl, pyridyl methyl), including those alkyls wherein carbon atoms (such as methylene) has been replaced by such as oxygen atoms, such as phenoxy methyl, 2-pyridyloxymethyl-3-(1-naphthoxy)propyl, etc.

Unless otherwise specified, the "ring" refers to substituted or unsubstituted cycloalkyl, substituted or unsubstituted heterocycloalkyl, substituted or unsubstituted aryl or substituted or unsubstituted heteroaryl. The ring includes a fused ring. A number of the atoms in the ring is usually defined as the member of the ring, for example, "5- to 7-membered ring" is a ring looped with 5 to 7 atoms. Unless otherwise specified, the ring optionally contains 1 to 3 of heteroatoms. Therefore, "5- to 7-membered ring" includes, for example, phenyl pyridine and piperidinyl; on the other hand, the term "5- to 7-membered heterocycloalkyl ring" includes pyridyl and piperidinyl, but does not include phenyl. The term "ring" also includes a ring system containing at least one ring, wherein each ring is of the above definition independently.

Unless otherwise specified, the term "heteroatom" includes atoms except carbon (C) and hydrogen (H), such as including oxygen (O), nitrogen (N), sulfur (S), silicon (Si), germanium (Ge), aluminum (Al) and boron (B) etc.

Unless otherwise specified, the term "leaving group" refers to a functional group or atom which can be replaced by another functional group or atom through a substitution reaction (e.g., nucleophilic substitution reaction). For example, representative leaving groups include triflate; chlorine, bromine, iodine; sulfonate, such as mesylate, tosylate, p-bromobenzene sulfonate, p-tosylate etc.; acyloxy, such as acetoxy, trifluoroacetoxy and so on.

Unless otherwise specified, the term "protecting group" includes but not limited to "the protecting group of an amino", "the protecting group of a hydroxyl", or "the protecting group of a mercapto". The term "the protecting group of an amino" refers to a protecting group that is suitable for preventing side reactions which occur at the nitrogen atom of an amino group. A representative protecting group of an amino includes but not limited to: formyl; acyl, such as alkanoyl (such as acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); aryl methyl, such as benzyl (Bn), triphenyl methyl (Tr), 1,1-bis-(4'-methoxyphenyl) methyl; silyl, such as trimethylsilyl (TMS) and tert-butyldimethylsilyl (TBS) and etc. The term "the protecting group of a hydroxyl" refers to a protecting group that is suitable for preventing side reactions of a hydroxyl group. A representative protecting group of a hydroxyl includes but not limited to: alkyl, such as methyl, ethyl, and tert-butyl; acyl, such as alkanoyl (such as acetyl); aryl methyl, such as benzyl (Bn), p-methoxybenzyl (PMB), 9-fluorenylmethyl (Fm) and diphenylmethyl (diphenylmethyl, DPM); silyl, such as trimethylsilyl (TMS) and tert-butyldimethylsilyl (TBS) and etc.

Unless otherwise specified, examples of halogenated alkyl include but not limited to: trifluoromethyl, trichloromethyl, pentafluoroethyl, and pentachloroethyl. The alkoxyl represents that the alkyl group with a specific number of carbon atoms is connected by an oxygen bridge. The $C_{1-6}$ alkoxyl includes $C_1$, $C_2$, $C_3$, $C_4$, $C_5$ and $C_6$ alkoxyl. Examples of alkoxyl include but not limited to: methoxy, ethoxy, n-propoxy, iso-propoxy, n-butoxy, sec-butoxy, tert-butoxy, n-pentyloxy and S-pentyloxy. The "cycloalkyl" includes saturated cyclic group, such as cyclopropyl, cyclobutyl or cyclopentyl. The 3- to 7-membered cycloalkyl includes $C_3$, $C_4$, $C_5$, $C_6$ and $C_7$ cycloalkyl. The "alkenyl" includes linear or branched hydrocarbon chain, wherein any stable sites on the chain exist one or more C—C double bonds, such as vinyl and propenyl.

Unless otherwise specified, the term "halo" or "halogen" refers to fluorine, chlorine, bromine and iodine.

Unless otherwise specified, the term "heterocycle" or "heterocyclic group" refers to a stable monocyclic, bicyclic or bicyclic hetero-ring, they can be saturated, partially unsaturated or unsaturated (aromatic), they contain carbon atoms and 1, 2, 3 or 4 of heteroatom in the ring which is independently selected from the group consisting of N, O and S, wherein any of the heterocycle can be fused to a benzene ring to form a bicyclic ring.

Unless otherwise specified, examples of heterocyclic compound include but not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolyl, 2H,6H-1,5,2-dithiazinyl, dihydrofuro[2,3-b] tetrahydrofuranyl, furanyl, furazanyl, imidazolidinyl, imidazolinyl, imidazolyl, 1H-indazolyl, indoalkenyl, indolinyl, indolizinyl, indolyl, 3H-indolyl, isatino group, isobenzofuranyl, pyran, isoindolyl, isoindolinyl, isoindolyl, indolyl, isoquinolyl, isothiazolyl, isoxazolyl, methylenedioxyphenyl, morpholinyl, naphthyridinyl, octahydroisoquinolyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, isooxazolyl, hydroxyl indyl, pyrimidyl, phenanthridinyl, phenanthrolinyl, phenazine, phenothiazine, benzopurinyl, phenoxazinyl, phthalazinyl, piperazinyl, piperidyl, oxopiperidinyl, 4-oxopiperidinyl, piperonyl, pteridyl, purinyl, pyranyl, pyrazinyl, pyrazolidinyl, pyrazolinyl, pyrazolyl, pyridazinyl, oxazolopyridine, pyridinoimidazole, pyridinothiazole, pyridyl, pyrimidyl, pyrrolidinyl, pyrrolinyl, 2H-pyrrolyl, pyrrolyl, pyrazolyl, quinazolinyl, quinolyl, 4H-quinolizinyl, quinoxalinyl, quinuclidinyl, tetrahydrofuryl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazyl, isothiazolylthienyl, thienyl, thiophenoxazolyl, thiophenothiazolyl, thiophenoimidazolyl, thienyl, triazinyl, 1,2, 3-triazolyl, 1,2,4-triazolyl, 1,2,5-triazolyl, 1,3,4-triazolyl and xanthenyl. Fused ring and spiro ring compound are also included. Unless otherwise specified, the compound of the present invention can be prepared through many synthetic methods which are well-known to the person skilled in the art, including the specific embodiments listed below and its combination with other chemical synthetic methods and the equivalent alternative methods which are known to the person skilled in the art, the preferred embodiments include but not limited to the embodiments of the present invention.

Unless otherwise specified, the solvents used in the present invention are commercially available.

Unless otherwise specified, the present invention adopts the following abbreviations: aq represents water; HATU represents 2-(7-azabenzotriazol-1-yl)-N,N,N',N'-tetramethyluronium hexafluorophosphate; EDC represents N-(3-dimethylaminopropyl)-N'-ethyl carbodiimide hydrochloride; m-CPBA represents m-chloroperbenzoic acid; eq represents equivalent, equal-quantitative; CDI represents carbonyl diimidazole; DCM represents dichloromethane; PE represents petroleum ether; DIAD represents diisopropyl azodicarboxylate; DMF represents N,N-dimethylformamide; DMSO represents dimethylsulfoxide; EtOAc represents ethyl acetate; EtOH represents ethanol; MeOH represents methanol; Cbz represents benzyloxycarbonyl, a protecting group of an amino; Boc represents tert-butoxycarbonyl, a protecting group of an amine; HOAc represents acetic acid; NaCNBH₃ represents sodium cyanoborohydride; r.t. represents room temperature; O/N represents overnight; THF represents tetrahydrofuran; Boc₂O represents di-tert-butyl dicarbonate; TFA represents trifluoroacetic acid; DIPEA represents diisopropylethylamine; SOCl₂ represents thionyl chloride; CS₂ represents carbon disulfide; TsOH represents p-toluene sulfonic acid; NFSI represents N-fluorobenzenesulfonimide; NCS represents N-chlorosuccinimide; n-Bu₄NF represents tetrabutylammonium fluoride; iPrOH represents 2-propanol; mp represents melting point.

Unless otherwise specified, compounds are named by manual work or software ChemDraw®, commercially available compounds are named in accordance with suppliers' catalogue.

Compared to the prior art, the compounds of the present invention are effective, lower-toxic, and make great and even incredible progresses on the aspects of activity, half-life, solubility and pharmacokinetics etc., which are more suitable for the pharmaceutical industry.

DETAILED DESCRIPTION OF THE PREFERRED EMBODIMENT

The following examples further illustrate the present invention, but it does not mean any unfavorable limitation to the present invention. The application has already described the present invention in details, in which the embodiments also have been disclosed, it is obvious for the person skilled in the art to vary and improve the embodiments of the present invention without departing from the spirit and scope of the present invention.

Embodiment 1

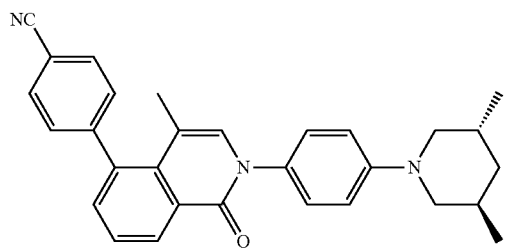 [SMILES: Cc1cn(-c2ccc(N3C[C@H](C)C[C@@H](C)C3)cc2)c(=O)c2cccc(-c3ccc(C#N)cc3)c12]

4-(2-(4-((3R,5R)-3,5-dimethylpiperidin-1-yl)phenyl)-4-methyl-1-oxo-1,2-dihydroisoquinolin-5-yl)benzonitrile

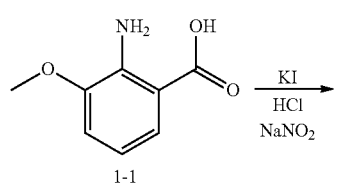

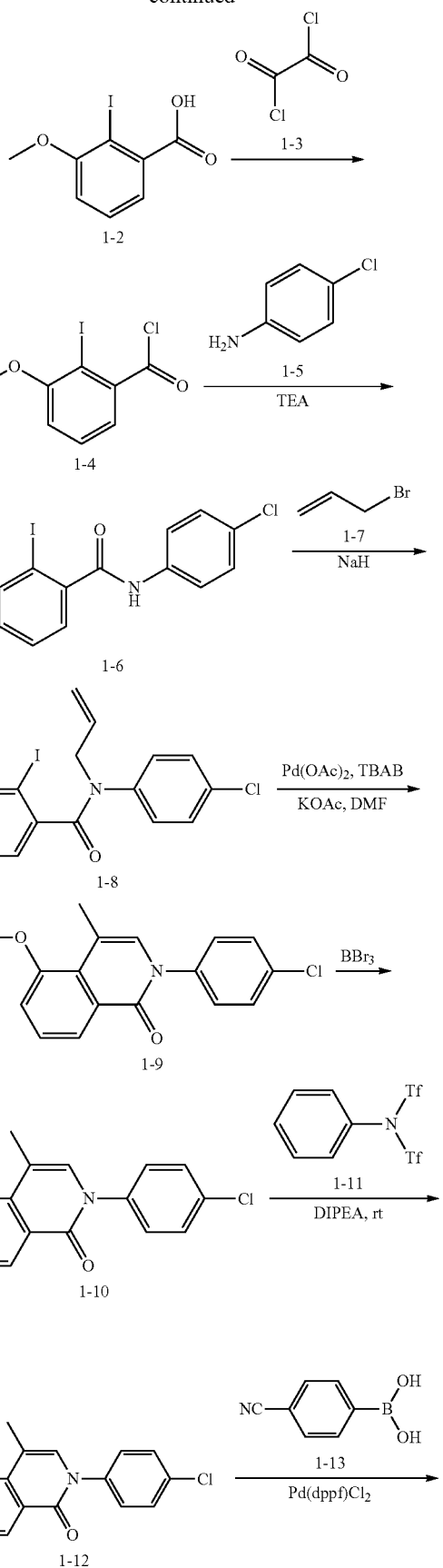

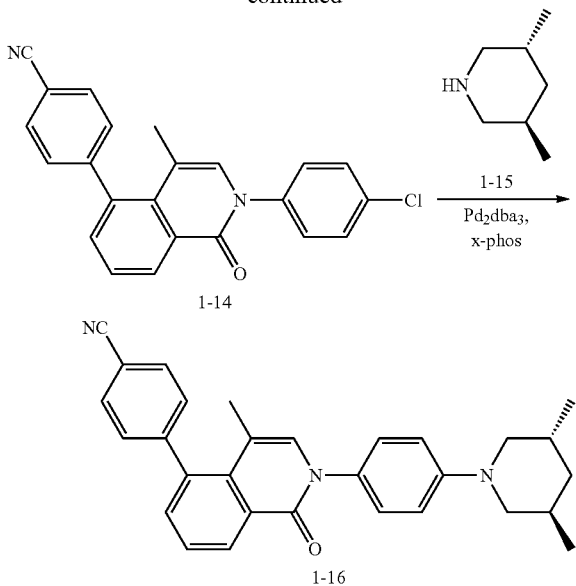

Step 1: Compound 1-1 (60 g, 0.36 mol) was dissolved in a solution of ice-water (900 mL), acetone (300 mL) and HCl aqueous solution (180 mL, 2.23 mol), then the mixture was added dropwise into an aqueous solution (360 mL) of sodium nitrite (50 g, 0.72 mol) slowly when the temperature was kept at 0-10° C. After stirring for 2 h, solid of potassium iodide (120 g, 0.72 mol) was added directly, and the temperature was kept at 7-10° C. for 30 min. The reaction mixture was heated to 80-90° C. until purple gas disappeared, and then cooled to room temperature. The reaction mixture was filtrated to deliver the compound 1-2 (85 g, yield 85%) as yellow solid. MS ESI calcd for $C_8H_7IO_3$ [M+H]$^+$ 279, found 279.

Step 2: Compound 1-2 (34.5 g, 0.12 mol) was dissolved in DCM (300 mL), DMF (0.1 mL) was added, and then compound 1-3 (12 mL, 0.135 mol) was added dropwise, the reaction mixture was stirred for 1 h to deliver the compound 1-4 as yellow oil. The crude product was used for the next step directly. MS ESI calcd for $C_8H_6ClIO_2$ [M+H]$^+$ 297, found 297.

Step 3: Compound 1-5 (15 g, 0.12 mol) was dissolved in DCM (150 mL), then DIPEA (77 g, 0.6 mol) was added, the reaction mixture was stirred at room temperature for 5 min. Compound 1-4 (46 g, 0.12 mol) was dissolved in DCM (300 mL), and was added dropwise into the reaction mixture at 0° C. After 3 h, the reaction was complete as detected by TLC (PE:EtOAc=3:1), the reaction mixture was poured into water and extracted with DCM. The organic phase was washed with brines, dried over anhydrous sodium sulfate, and concentrated under reduced pressure. The crude product was purified by silica gel column chromatography (PE:EtOAc=3:1) to deliver the target compound 1-6 (38 g, yield 75%) as yellow solid. MS ESI calcd for $C_{13}H_9ClINO_2$ [M+H]$^+$ 374, found 374.

Step 4: NaH (4.8 g, 0.2 mol) was added into a solution of compound 1-6 (38 g, 0.1 mol) in DMF (400 mL), the reaction mixture was added compound 1-7 (24 g, 0.2 mol) and stirred at 0° C. for 2 h. After the reaction was complete as detected by LC-MS, the reaction mixture was poured into water slowly and extracted with EtOAc. The organic phase was washed with brines, dried over anhydrous sodium sulfate, and concentrated under reduced pressure. The crude product was purified by silica gel column chromatography (PE:EtOAc=5:1) to deliver the target compound 1-8 (29 g, yield 69%) as yellow oil. MS ESI calcd for $C_{17}H_{15}ClINO_2$ [M+H]$^+$ 428, found 428.

Step 5: Compound 1-8 (28 g, 66 mmol), tetrabutyl ammonium bromide (53 g, 165 mmol), KOAc (9.7 g, 0.1 mol) and Pd(OAc)$_2$ (1.48 g, 6.6 mmol) were dissolved in DMF (250 mL), the reaction mixture was stirred at 100° C. for 16 h. The reaction was complete as detected by TLC (PE:EtOAc=3:1). The reaction mixture was quenched with water and extracted with EtOAc. The organic phase was washed with brines, dried over anhydrous sodium sulfate, and concentrated under reduced pressure. The crude product was purified by recrystallization to deliver the compound 1-9 as white solid (16 g, yield 81%). MS ESI calcd for $C_{17}H_{14}ClNO_2$ [M+H]$^+$ 300, found 300.

Step 6: BBr$_3$ (12.5 mL, 0.134 mol) was dripped into a solution of compound 1-9 (16 g, 0.054 mol) in DCM (150 mL) at 0° C., the reaction mixture was stirred at room temperature for 16 h. The reaction was detected by TLC (PE:EtOAc=3:1). The reaction mixture was quenched with saturated sodium carbonate solution and filtrated to deliver the compound 1-10 as white solid (13 g, yield 84%). MS ESI calcd for $C_{16}H_{12}ClNO_2$ [M+H]$^+$ 286, found 286.

Step 7: DIPEA (4.5 g, 35 mmol) and compound 1-11 (9.4 g, 26 mmol) were added into a solution of compound 1-10 (5 g, 17.5 mmol) in THF (50 mL), the reaction mixture was stirred at room temperature for 16 h. The reaction was detected by TLC (PE:EtOAc=2:1). The reaction mixture was poured into water, and extracted with EtOAc, the organic phase was washed with brines, dried over anhydrous sodium sulfate, and concentrated under reduced pressure. The crude product was purified by silica gel column chromatography (PE:EtOAc=5:1) to deliver the compound 1-12 as yellow oil (3.6 g, yield 50%). MS ESI calcd for $C_{17}H_{11}ClF_3NO_4S$ [M+H]$^+$ 418, found 418.

Step 8: Compound 1-12 (3.6 g, 8.6 mmol), compound 1-13 (1.7 g, 12 mmol), Pd(dppf)Cl$_2$ (630 mg, 0.86 mmol) and sodium carbonate (2.1 g, 19.8 mmol) were dissolved in dioxane/H$_2$O (48 mL), the reaction mixture was stirred at 110° C. and refluxed for 16 h. The reaction was detected by TLC (PE:EtOAc=3:1). The reaction mixture was poured into water, and filtrated to collect the residue, the crude product was purified by silica gel column chromatography (PE:EtOAc=5:1) to deliver the compound 1-14 as white solid (1.5 g, yield 50%). MS ESI calcd for $C_{23}H_{15}ClN_2O$ [M+H]$^+$ 371, found 371.

Step 9: Under nitrogen gas atmosphere, compound 1-14 (100 mg, 0.27 mmol), compound 1-15 (46 mg, 0.40 mmol), Pd$_2$(dba)$_3$ (25 mg, 0.03 mmol), Xantphos (26 mg, 0.06 mmol) and potassium tert-butoxide (61 mg, 0.54 mmol) were dissolved in toluene (10 mL), the reaction mixture was refluxing at 120° C. and stirred for 2 h. Then, the reaction mixture was filtrated with diatomite, concentrated by a rotary evaporator to remove the solvent, extracted with EtOAc (50 mL) and H$_2$O (20 mL), washed with brines, and dried over anhydrous sodium sulfate. After concentrated under reduced pressure, the residue was purified by preparative HPLC to deliver the title compound as white solid. $^1$H NMR (400 MHz, CDCl$_3$) δ 8.65 (d, J=7.2 Hz, 1H), 7.69 (d, J=8.0 Hz, 2H), 7.50-7.35 (m, 4H), 7.23 (d, J=8.4 Hz, 2H), 6.93 (t, J=8.8 Hz, 3H), 3.20 (dd, J=3.2 Hz, J=12.0 Hz, 2H), 2.85 (dd, J=2.4 Hz, J=11.6 Hz, 2H), 2.02 (dd, J=5.6 Hz, J=9.2 Hz, 2H), 1.56 (s, 3H), 1.45 (t, J=6.0 Hz, 2H), 1.01 (d, J=6.8 Hz, 6H). MS ESI calcd for $C_{30}H_{29}N_3O$ [M+H]$^+$ 448, found 448.

The compounds listed in table 1 can be synthesized by compound 1-14 and corresponding amines.

| Embodiment | Structure | NMR |
|---|---|---|
| 2 | 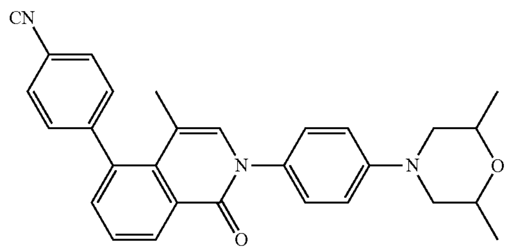 | $^1$H NMR (400 MHz, DMSO-d$_6$) δ 8.41 (d, J = 7.6 Hz, 1H), 7.87 (d, J = 8.0 Hz, 2H), 7.58-7.49 (m, 4H), 7.26 (d, J = 8.8 Hz, 2H), 7.17 (s, 1H), 7.01 (d, J = 9.2 Hz, 2H), 3.69-3.60 (m, 4H), 2.26 (t, J = 10.8 Hz, 2H), 1.49 (s, 3H), 1.13 (d, J = 5.6 Hz, 6H). MS ESI calcd for C$_{29}$H$_{27}$N$_3$O$_2$ [M + H]$^+$ 450, found 450. |
| 3 | 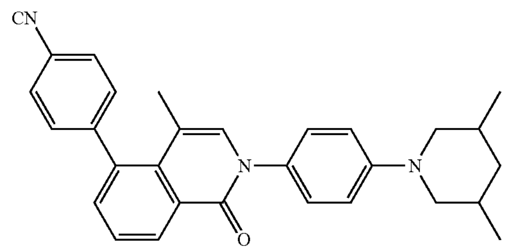 | $^1$H NMR (400 MHz, DMSO-d$_6$) δ 8.41 (d, J = 6.4 Hz, 1H), 7.87 (d, J = 8.4 Hz, 2H), 7.57-7.48 (m, 4H), 7.21 (d, J = 8.8 Hz, 2H), 7.17 (s, 1H), 6.98 (d, J = 9.2 Hz, 2H), 3.69 (d, J = 11.6 Hz, 2H), 2.20 (t, J = 12.0 Hz, 2H), 1.75-1.64 (m, 3H), 1.49 (s, 3H), 0.87 (d, J = 6.8 Hz, 6H), 0.74-0.67 (m, 1H). MS ESI calcd for C$_{30}$H$_{29}$N$_3$O [M + H]$^+$ 448, found 448. |
| 4 | 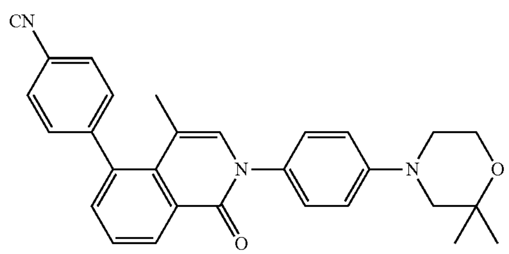 | $^1$H NMR (400 MHz, CDCl$_3$) δ 8.67 (d, J = 7.6 Hz, 1H), 7.72 (d, J = 8.0 Hz, 2H), 7.57-7.47 (m, 4H), 7.31 (d, J = 8.8 Hz, 2H), 7.00 (d, J = 8.8 Hz, 2H), 6.95 (s, 1H), 3.93 (t, J = 4.8 Hz, 2H), 3.03 (s, 2H), 1.61 (s, 3H), 1.36 (s, 6H). MS ESI calcd for C$_{29}$H$_{27}$N$_3$O$_2$ [M + H]$^+$ 450, found 450. |
| 5 | 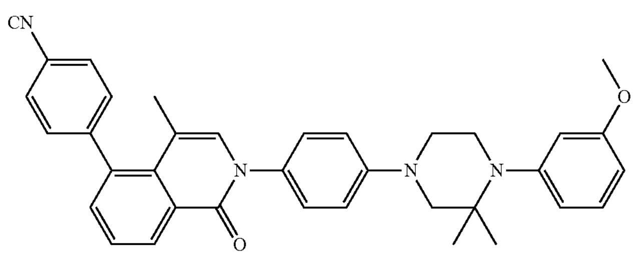 | $^1$H NMR (400 MHz, CDCl$_3$) δ 8.67 (d, J = 8.0 Hz, 1H), 7.72 (d, J = 7.6 Hz, 2H), 7.55-7.40 (m, 4H), 7.36 (d, J = 8.8 Hz, 3H), 7.23 (s, 1H), 7.05-7.02 (m, 4H), 6.93 (s, 1H), 3.81 (brs, 3H), 3.73 (brs, 4H), 3.59 (s, 2H), 1.60 (s, 3H), 1.47 (s, 6H). MS ESI calcd for C$_{36}$H$_{34}$N$_4$O$_2$ [M + H]$^+$ 555, found 555. |
| 6 | 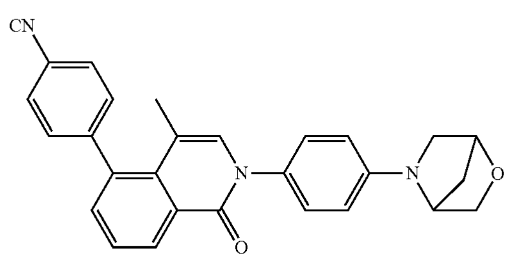 | $^1$H NMR (400 MHz, CDCl$_3$) δ 8.67 (d, J = 7.6 Hz, 1H), 7.72 (d, J = 8.0 Hz, 2H), 7.58 (t, J = 7.6 Hz, 1H), 7.49 (t, J = 4.4 Hz, 3H), 7.25 (d, J = 7.6 Hz, 2H), 6.97 (s, 1H), 6.67 (d, J = 9.2 Hz, 2H), 4.72 (s, 1H), 4.47 (s, 1H), 3.94 (dd, J = 24.8 Hz, J = 7.2 Hz, 2H), 3.59 (d, J = 8.8 Hz, 1H), 3.23 (d, J = 9.2 Hz, 1H), 2.05 (dd, J = 24.4 Hz, J = 9.6 Hz, 2H), 1.62 (s, 3H). MS ESI calcd for C$_{28}$H$_{23}$N$_3$O$_2$ [M + H]$^+$ 434, found 434. |
| 7 | 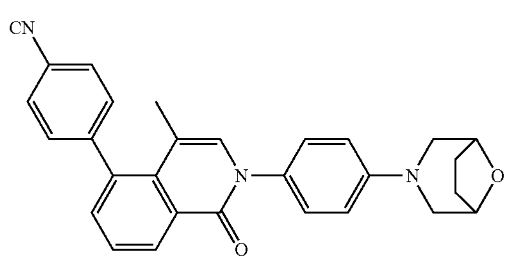 | $^1$H NMR (400 MHz, CDCl$_3$) δ 8.67 (d, J = 7.6 Hz, 1H), 7.72 (d, J = 7.6 Hz, 1H), 7.57 (t, J = 7.6 Hz, 1H), 7.48 (d, J = 7.6 Hz, 3H), 7.28 (d, J = 9.2 Hz, 2H), 6.95 (s, 1H), 6.88 (d, J = 8.4 Hz, 2H), 4.53 (s, 2H), 3.38 (d, J = 11.2 Hz, 2H), 3.08 (d, J = 11.2 Hz, 2H), 2.01-1.94 (m, 4H), 1.61 (s, 3H). MS ESI calcd for C$_{29}$H$_{25}$N$_3$O$_2$ [M + H]$^+$ 448, found 448. |

| Embodiment | Structure | NMR |
|---|---|---|
| 8 | 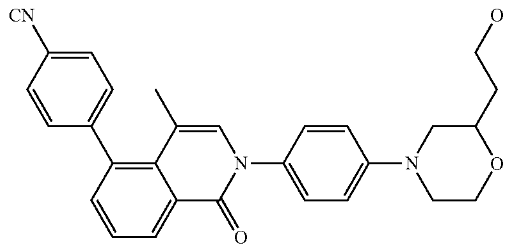 | ¹H NMR (400 MHz, CDCl₃) δ 8.66 (d, J = 8.0 Hz, 1H), 7.72 (d, J = 8.0 Hz, 2H), 7.58-7.41 (m, 6H), 7.23 (d, J = 8.8 Hz, 2H), 6.94 (s, 1H), 4.12-3.79 (m, 5H), 3.60 (dd, J = 24.8 Hz, J = 12.0 Hz, 2H), 3.09 (t, J = 3.2 Hz, 1H), 2.86 (t, J = 10.8 Hz, 1H), 1.88-7.75 (m, 2H), 1.62 (s, 3H). MS ESI calcd for $C_{28}H_{25}N_3O_3$ [M + H]⁺ 452, found 452. |
| 9 | 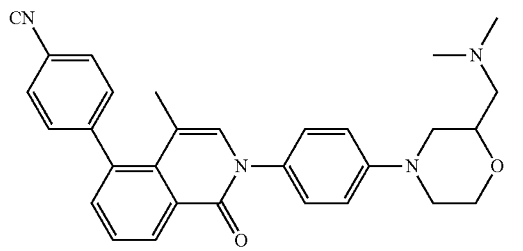 | ¹H NMR (400 MHz, CDCl₃) δ 8.65 (d, J = 7.6 Hz, 1H), 7.71 (d, J = 8.0 Hz, 2H), 7.56-7.43 (m, 4H), 7.33 (d, J = 8.4 Hz, 2H), 6.98 (d, J = 8.8 Hz, 2H), 6.92 (s, 1H), 4.20 (t, J = 21.6 Hz, 1H), 4.04 (t, J = 11.2 Hz, 1H), 3.82 (t, J = 10.4 Hz, 1H), 3.57 (d, J = 11.6 Hz, 1H), 3.46 (d, J = 12.0 Hz, 1H), 3.32 (d, J = 13.2 Hz, 1H), 3.09-2.85 (m, 8H), 2.60 (t, J = 10.8 Hz, 1H), 1.59 (s, 3H). MS ESI calcd for $C_{30}H_{30}N_4O_2$ [M + H]⁺ 479, found 479. |
| 10 | 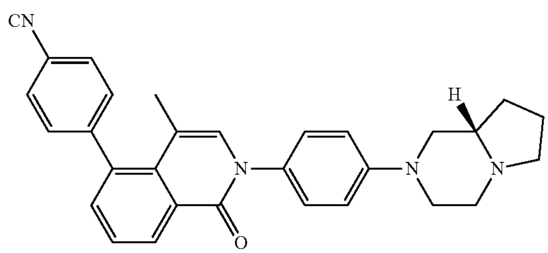 | ¹H NMR (400 MHz, CDCl₃) δ 8.65 (d, J = 8.0 Hz, 1H), 7.71 (d, J = 7.6 Hz, 2H), 7.54 (t, J = 8.0 Hz, 1H), 7.47 (d, J = 7.6 Hz, 3H), 7.35 (d, J = 8.4 Hz, 2H), 6.91 (s, 1H), 7.01 (dd, J = 21.6 Hz, J = 8.4 Hz, 2H), 3.95-3.32 (m, 7H), 3.27-3.07 (m, 1H), 3.02-2.72 (m, 1H), 2.37-2.05 (m, 14H), 1.60 (s, 3H). MS ESI calcd for $C_{30}H_{28}N_4O$ [M + H]⁺ 461, found 461. |
| 11 | 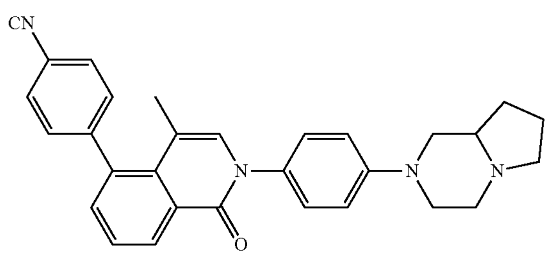 | ¹H NMR (400 MHz, CDCl₃) δ 8.65 (d, J = 7.2 Hz, 1H), 7.71 (d, J = 7.6 Hz, 2H), 7.51-7.58 (m, 1H), 7.40-7.50 (m, 3H), 7.35 (d, J = 8.8 Hz, 2H), 6.99 (dd, J = 8.4 Hz, J = 21.6 Hz, 2H), 6.91 (s, 1H), 3.33-4.15 (m, 5H), 2.90-3.30 (m, 4H), 2.05-2.40 (m, 4H), 1.59 (s, 3H). MS ESI calcd for $C_{30}H_{28}N_4O$ [M + H]⁺ 461, found 461. |
| 12 | 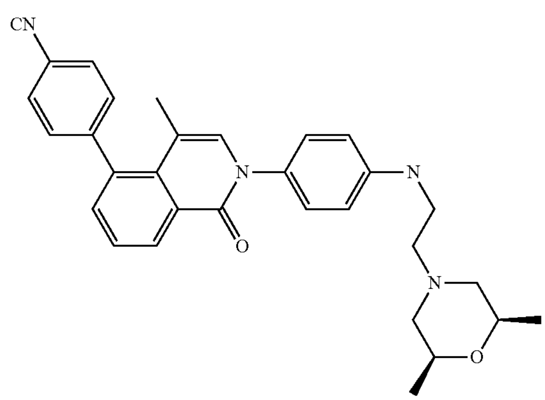 | ¹H NMR (400 MHz, CDCl₃) δ 8.64 (d, J = 7.2 Hz, 1H), 7.71 (d, J = 8.4 Hz, 2H), 7.56-7.46 (m, 4H), 7.21 (d, J = 8.8 Hz, 2H), 6.92 (s, 1H), 6.67 (d, J = 8.4 Hz, 2H), 4.09-4.05 (m, 2H), 3.60 (t, J = 4.8 Hz, 2H), 3.52 (d, J = 11.6 Hz, 2H), 3.28 (brs, 2H), 2.44 (t, J = 11.2 Hz, 2H), 1.59 (s, 3H), 1.24 (d, J = 6.0 Hz, 6H). MS ESI calcd for $C_{31}H_{32}N_4O_2$ [M + H]⁺ 493, found 493. |

| Embodiment | Structure | NMR |
|---|---|---|
| 13 | 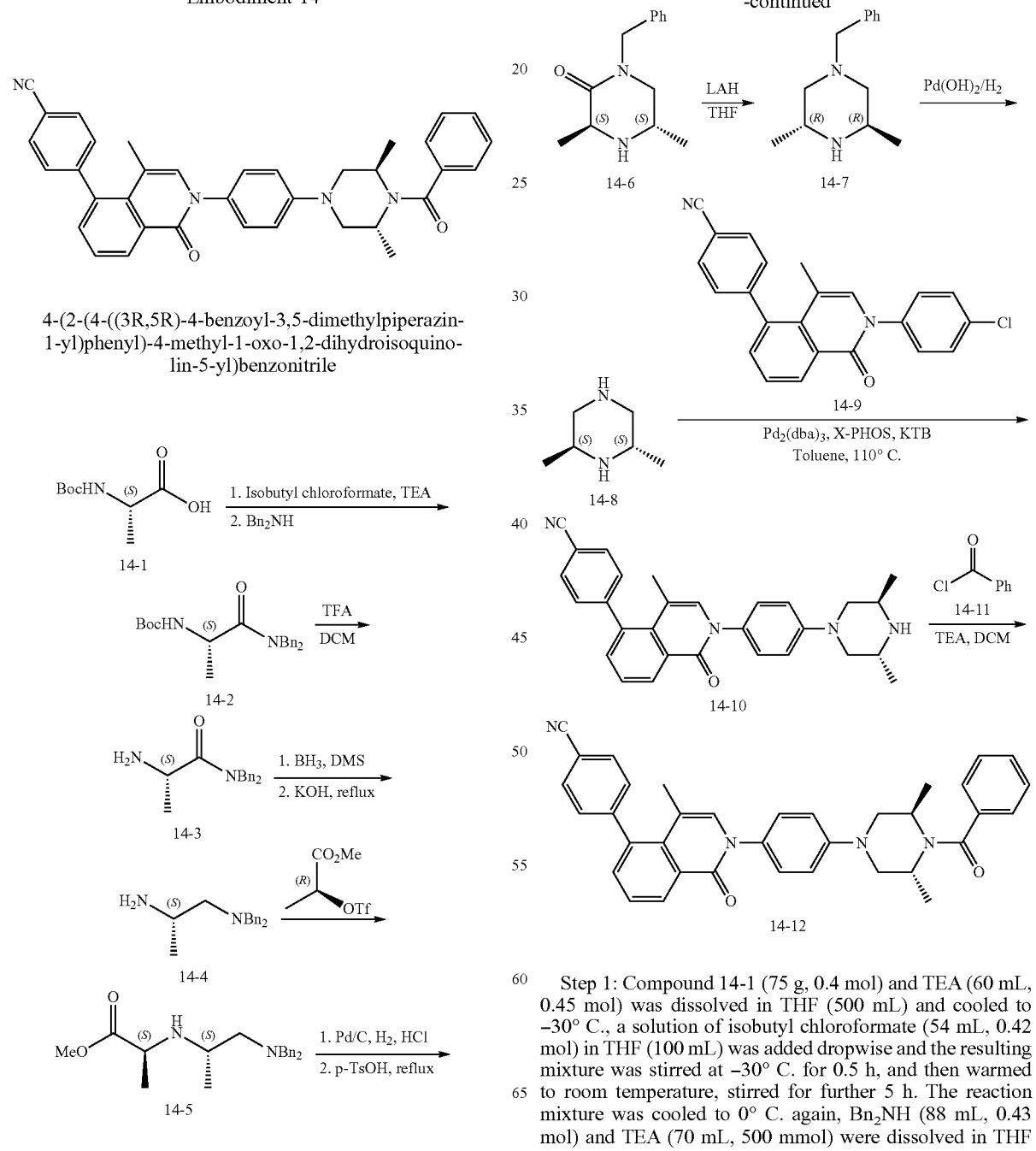 | $^1$H NMR (400 MHz, CDCl$_3$) δ 8.67 (d, J = 8.0 Hz, 1H), 7.94 (d, J = 8.0 Hz, 1H), 7.86 (d, J = 8.0 Hz, 1H), 7.73 (d, J = 8.4 Hz, 2H), 7.58-7.44 (m, 8H), 7.34 (d, J = 8.4 Hz, 2H), 6.96 (s, 1H), 3.94-3.84 (m, 4H), 3.64-3.58 (m, 4H), 1.62 (s, 3H). MS ESI calcd for C$_{34}$H$_{27}$N$_5$OS [M + H]$^+$ 554, found 554. |

Embodiment 14

4-(2-(4-((3R,5R)-4-benzoyl-3,5-dimethylpiperazin-1-yl)phenyl)-4-methyl-1-oxo-1,2-dihydroisoquinolin-5-yl)benzonitrile Step 1: Compound 14-1 (75 g, 0.4 mol) and TEA (60 mL, 0.45 mol) was dissolved in THF (500 mL) and cooled to −30° C., a solution of isobutyl chloroformate (54 mL, 0.42 mol) in THF (100 mL) was added dropwise and the resulting mixture was stirred at −30° C. for 0.5 h, and then warmed to room temperature, stirred for further 5 h. The reaction mixture was cooled to 0° C. again, Bn$_2$NH (88 mL, 0.43 mol) and TEA (70 mL, 500 mmol) were dissolved in THF (100 mL) and added dropwise, the reaction mixture was stirred at room temperature for 10 h. The reaction was detected by LC-MS. The reaction mixture was poured into water, and extracted with EtOAc. The organic phase was washed with brines, dried over anhydrous sodium sulfate, and concentrated under reduced pressure to deliver the compound 14-2 as white solid (84 g, yield 60%). MS ESI calcd for $C_{22}H_{28}N_2O_3$ [M+H]$^+$ 369, found 369.

Step 2: TFA (120 mL) was added into a solution of compound 14-2 (53 g, 0.15 mol) in DCM (450 mL), the reaction mixture was stirred at room temperature for 5 h. The reaction was detected by TLC (PE:EtOAc=5:1). The reaction mixture was poured into water, sodium bicarbonate was added to adjust pH to more than 7, and extracted with DCM. The organic phase was washed with brines, dried over anhydrous sodium sulfate, and concentrated under reduced pressure to deliver the compound 14-3 as yellow oil (38 g, yield 98%). MS ESI calcd for $C_{17}H_{20}N_2O$ [M+H]$^+$ 269, found 269.

Step 3: Borane-methyl sulfide (98 mL, 0.98 mol) was added into a solution of compound 14-3 (38 g, 0.14 mol) in THF (400 mL), the reaction mixture was stirred at room temperature for 48 h. The reaction was detected by LC-MS. The reaction mixture was quenched with hydrochloric acid, and adjusted to pH to more than 7 with NaOH aqueous solution, and then KOH (100 g) was added, the mixture was heated to reflux for 24 h. The reaction mixture was extracted with EtOAc, the organic phase was washed with brines, dried over anhydrous sodium sulfate, and concentrated under reduced pressure. The crude product was purified by silica gel column chromatography (DCM:MeOH=10:1) to deliver the compound 14-4 as white solid (25 g, yield 69%). MS ESI calcd for $C_{17}H_{22}N_2$ [M+H]$^+$ 255, found 255.

Step 4: A solution of compound 14-4 (25 g, 98.4 mmol) and TEA (15.9 g, 157.44 mmol) in DCM (150 mL) was added into a solution of 2-trifluoromethanesulfonyloxy methyl propionate (27.9 g, 118.1 mmol) in DCM (100 mL) at 0° C., the reaction mixture was stirred at 0° C. for 2 h and at room temperature for 2 h. The reaction was detected by LC-MS, and poured into DCM and NaHCO$_3$. The reaction mixture was extracted with DCM, the organic phase was washed with saturated brines, dried over anhydrous sodium sulfate, and concentrated under reduced pressure. The crude product was purified by silica gel column chromatography (EtOAc) to deliver the compound 14-5 as yellow oil (13.5 g, yield 40%). MS ESI calcd for $C_{21}H_{28}N_2O_2$ [M+H]$^+$ 341, found 341.

Step 5: Compound 14-5 (12 g, 35.2 mmol), hydrochloric acid (36%) (5 mL) and Pd/C (2.5 g) were dissolved in EtOH (100 mL), the reaction mixture was reacted under 40 psi for 2 h. The reaction mixture was filtrated, the filtrate was concentrated. The residue was dissolved in EtOH (100 mL), p-toluene-sulfonic acid (2 g) was added, the reaction mixture was stirred at 90° C. and refluxed for 16 h. The reaction was detected by LC-MS, the reaction mixture was concentrated under reduced pressure, DCM and NaHCO$_3$ were added. The reaction mixture was extracted with DCM, the organic phase was washed with brines, dried over anhydrous sodium sulfate, and concentrated under reduced pressure to deliver compound 14-6 as yellow solid (6 g, yield 78%). MS ESI calcd for $C_{13}H_{18}N_2O$ [M+H]$^+$ 219, found 219.

Step 6: Compound 14-6 (5.5 g, 25.2 mmol) was added into a solution of LAH (2.9 g, 75.6 mmol) in THF (50 mL) in portions, the reaction mixture was stirred at room temperature for 0.5 h, then heated to 70° C. and stirred for 6 h. The reaction was detected by LC-MS. The reaction system was quenched with H$_2$O (2.9 mL), 15% NaOH (2.9 mL) and H$_2$O (8.8 mL). The reaction mixture was stirred for 0.5 h, the solid was filtrated and washed with THF. The filtrate was dried over anhydrous sodium sulfate and concentrated under reduced pressure to deliver compound 14-7 as yellow solid (4.9 g, 96%). MS ESI calcd for $C_{13}H_{20}N_2$ [M+H]$^+$ 205, found 205.

Step 7: Compound 14-7 (2 g, 9.8 mmol) and Pd(OH)$_2$/C (0.9 g) were dissolved in MeOH (20 mL), the reaction mixture was reacted under 35 psi for 24 h. The reaction mixture was filtrated, the filtrate was concentrated under reduced pressure to deliver compound 14-8 as colorless oil (1 g, yield 91%). MS ESI calcd for $C_6H_{14}N_2$ [M+H]$^+$ 115, found 115.

Step 8: Compound 14-10 was prepared according to the above-mentioned method, as yellow solid (600 mg, yield 84%). MS ESI calcd for $C_{29}H_{28}N_4O$ [M+H]$^+$ 449, found 449.

Step 9: Compound 14-11 (93 mg, 0.66 mmol) was added into a solution of compound 14-10 (150 mg, 0.33 mmol) and TEA (100 mg, 0.99 mmol) in DCM (5 mL), the reaction mixture was stirred at room temperature for 5 h. The reaction was detected by LC-MS. The crude product was purified by preparative HPLC to deliver the title compound as white solid. $^1$H NMR (400 MHz, CDCl$_3$) δ 8.68 (d, J=7.6 Hz, 1H), 7.72 (d, J=7.2 Hz, 2H), 7.67-7.39 (m, 8H), 7.28 (t, J=8.0 Hz, 3H), 6.96 (s, 1H), 6.74 (d, J=8.4 Hz, 2H), 4.25 (brs, 2H), 3.85 (d, J=10.4 Hz, 2H), 3.40 (d, J=11.2 Hz, 2H), 1.61 (s, 3H), 1.31 (brs, 6H). MS ESI calcd for $C_{36}H_{32}N_4O_2$ [M+H]$^+$ 553, found 553.

The compounds listed in table 2 can be synthesized by compound 14-10 and corresponding acyl chlorides and sulfonyl chlorides.

| Embodiment | Structure | NMR |
|---|---|---|
| 15 | 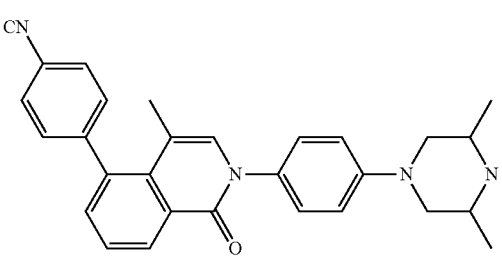 | $^1$H NMR (400 MHz, DMSO-d$_6$) δ 9.04 (d, J = 8.4 Hz, 1H), 8.41 (d, J = 8.0 Hz, 2H), 7.89 (d, J = 8.4 Hz, 2H), 7.58-7.50 (m, 4H), 7.32 (d, J = 8.4 Hz, 2H), 7.17 (s, 1H), 7.11 (d, J = 8.8 Hz, 2H), 3.93 (d, J = 12.8 Hz, 2H), 3.41-3.26 (brs, 2H), 2.65 (t, J = 12.8 Hz, 2H), 1.50 (s, 3H), 1.26 (d, J = 6.4 Hz, 6H). MS ESI calcd for $C_{29}H_{28}N_4O$ [M + H]$^+$ 449, found 449. |

-continued

| Embodiment | Structure | NMR |
|---|---|---|
| 16 | 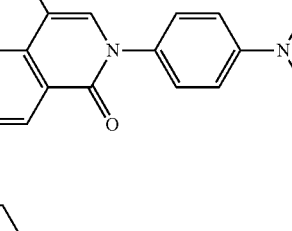 | $^1$H NMR (400 MHz, DMSO-d$_6$) δ 8.41 (d, J = 7.2 Hz, 1H), 7.87 (d, J = 7.6 Hz, 2H), 7.55-7.48 (m, 4H), 7.26 (d, J = 8.0 Hz, 2H), 7.18 (s, 1H), 7.02 (d, J = 8.0 Hz, 2H), 4.08 (brs, 2H), 3.55 (d, J = 12.0 Hz, 2H), 2.82 (d, J = 9.2 Hz, 2H), 1.48 (s, 3H), 1.39 (s, 9H), 1.22 (d, J = 6.0 Hz, 6H). MS ESI calcd for C$_{34}$H$_{36}$N$_4$O$_3$ [M + H]$^+$ 549, found 549. |
| 17 | 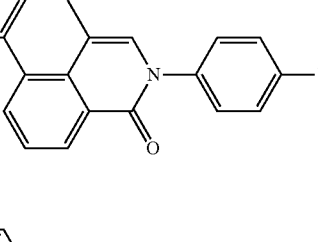 | $^1$H NMR (400 MHz, CDCl$_3$) δ 8.66 (d, J = 7.6 Hz, 1H), 7.01 (d, J = 8.0 Hz, 2H), 7.56-7.61 (m, 1H), 7.38-7.53 (m, 3H), 7.30 (d, J = 9.2 Hz, 2H), 6.96 (t, J = 8.8 Hz, 3H), 4.10-4.95 (m, 2H), 3.42-3.88 (m, 3H), 2.72-3.25 (m, 2H), 2.35-2.50 (m, 2H), 1.60 (s, 3H), 1.25-1.45 (m, 3H), 1.19 (t, J = 6.8 Hz, 3H). MS ESI calcd for C$_{31}$H$_{30}$N$_4$O$_2$ [M + H]$^+$ 491, found 491. |
| 18 | 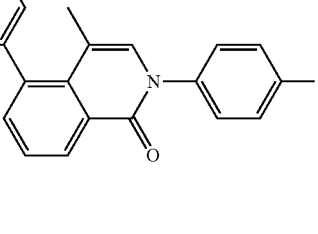 | $^1$H NMR (400 MHz, CDCl$_3$) δ 8.66 (d, J = 6.8 Hz, 1H), 7.71 (d, J = 8.4 Hz, 2H), 7.59-7.27 (m, 11H), 7.07-6.93 (m, 3H), 3.72-3.23 (m, 7H), 2.54-2.42 (m, 2H), 1.60 (s, 3H), 1.43-1.08 (m, 3H). MS ESI calcd for C$_{36}$H$_{32}$N$_4$O$_2$ [M + H]$^+$ 553, found 553. |
| 19 | 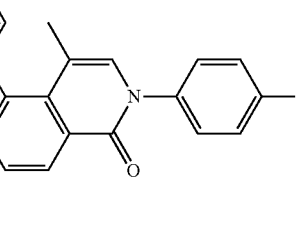 | $^1$H NMR (400 MHz, CDCl$_3$) δ 8.67 (d, J = 8.0 Hz, 1H), 7.71 (d, J = 8.0 Hz, 2H), 7.53-7.45 (m, 4H), 7.31-7.25 (m, 2H), 6.94 (s, 1H), 6.723 (d, J = 8.8 Hz, 2H), 4.26 (brs, 2H), 3.79-3.75 (m, 5H), 3.37 (d, J = 11.6 Hz, 2H), 1.58 (s, 3H), 1.42-1.23 (m, 6H). MS ESI calcd for C$_{31}$H$_{30}$N$_4$O$_3$ [M + H]$^+$ 507, found 507. |
| 20 | 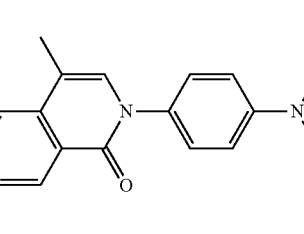 | $^1$H NMR (400 MHz, CDCl$_3$) δ 8.68 (d, J = 7.6 Hz, 1H), 7.72 (d, J = 8.0 Hz, 2H), 7.58 (t, J = 7.6 Hz, 1H), 7.49 (t, J = 8.0 Hz, 3H), 7.28 (d, J = 9.2 Hz, 2H), 6.98 (s, 1H), 6.72 (d, J = 8.8 Hz, 2H), 4.27-4.18 (m, 4H), 3.80-3.76 (m, 2H), 3.37 (d, J = 11.6 Hz, 2H), 1.61 (s, 3H), 1.32-1.27 (m, 9H). MS ESI calcd for C$_{32}$H$_{32}$N$_4$O$_3$ [M + H]$^+$ 521, found 521. |
| 21 | 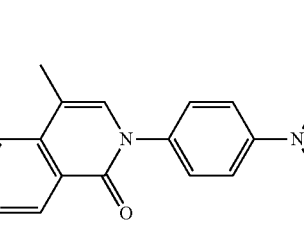 | $^1$H NMR (400 MHz, CDCl$_3$) δ 8.68 (d, J = 7.6 Hz, 1H), 7.72 (d, J = 8.4 Hz, 2H), 7.49-7.39 (m, 10H), 7.29 (d, J = 8.4 Hz, 2H), 6.97 (s, 1H), 6.74 (d, J = 8.8 Hz, 1H), 4.01 (brs, 2H), 3.87-3.78 (m, 2H), 3.46-3.38 (m, 2H), 1.61 (s, 3H), 1.37-1.23 (brs, 6H). MS ESI calcd for C$_{36}$H$_{32}$N$_4$O$_2$ [M + H]$^+$ 553, found 553. |

| Embodiment | Structure | NMR |
|---|---|---|
| 22 | 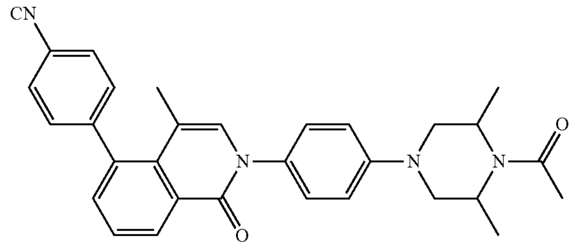 | ¹H NMR (400 MHz, DMSO-d₆) δ 8.42 (d, J = 7.2 Hz, 1H), 7.88 (d, J = 8.0 Hz, 2H), 7.59-7.49 (m, 4H), 7.28 (d, J = 8.4 Hz, 2H), 7.19 (s, 1H), 6.05 (d, J = 8.8 Hz, 2H), 3.59 (d, J = 12.0 Hz, 4H), 2.83 (brs, 2H), 2.04 (s, 3H), 1.50 (s, 3H), 1.26 (brs, 6H). MS ESI calcd for $C_{31}H_{30}N_4O_2$ [M + H]⁺ 491, found 491. |
| 23 | 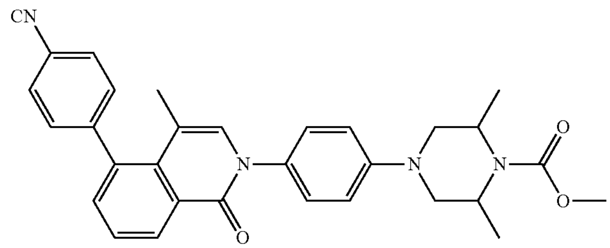 | ¹H NMR (400 MHz, DMSO-d₆) δ 8.44 (d, J = 6.4 Hz, 1H), 7.90 (d, J = 8.4 Hz, 2H), 7.60-7.51 (m, 4H), 7.29 (d, J = 8.8 Hz, 2H), 7.21 (s, 1H), 7.06 (d, J = 8.4 Hz, 2H), 3.97 (brs, 4H), 3.61 (d, J = 12.0 Hz, 2H), 2.85 (brs, 2H), 1.51 (s, 3H), 1.28 (brs, 6H), 1.01 (t, J = 7.2 Hz, 3H). MS ESI calcd for $C_{32}H_{32}N_4O_2$ [M + H]⁺ 505, found 505. |
| 24 | 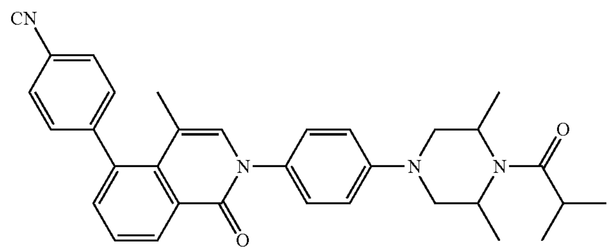 | ¹H NMR (400 MHz, DMSO-d₆) δ 8.43 (d, J = 6.4 Hz, 1H), 7.90 (d, J = 8.4 Hz, 2H), 7.61-7.51 (m, 4H), 7.30 (d, J = 8.8 Hz, 2H), 7.21 (s, 1H), 7.07 (d, J = 8.8 Hz, 2H), 3.85-3.52 (m, 4H), 2.86-2.81 (m, 3H), 1.51 (s, 3H), 1.42-1.17 (m, 6H), 1.03 (d, J = 6.4 Hz, 6H). MS ESI calcd for $C_{33}H_{34}N_4O_2$ [M + H]⁺ 519, found 519. |
| 25 | 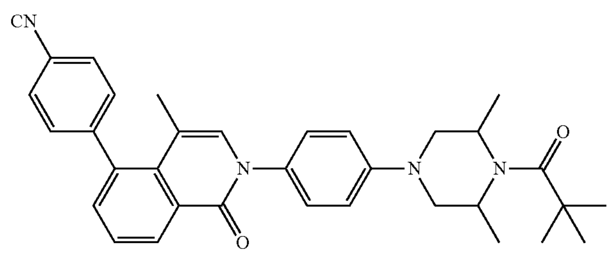 | ¹H NMR (400 MHz, DMSO-d₆) δ 8.43 (d, J = 7.6 Hz, 1H), 7.90 (d, J = 8.0 Hz, 2H), 7.60-7.51 (m, 4H), 7.30 (d, J = 8.4 Hz, 2H), 7.21 (s, 1H), 7.03 (d, J = 8.8 Hz, 2H), 4.52 (brs, 2H), 3.55 (d, J = 11.6 Hz, 2H), 2.86 (d, J = 11.6 Hz, 2H), 1.51 (s, 3H), 1.32 (d, J = 6.0 Hz, 6H), 1.23 (s, 9H). MS ESI calcd for $C_{34}H_{36}N_4O_2$ [M + H]⁺ 533, found 533. |
| 26 | 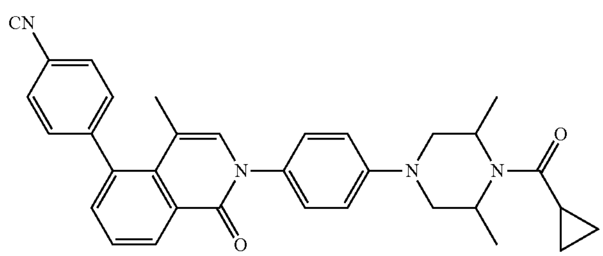 | ¹H NMR (400 MHz, DMSO-d₆) δ 8.44 (d, J = 6.8 Hz, 1H), 7.90 (d, J = 8.4 Hz, 2H), 7.61-7.51 (m, 4H), 7.30 (d, J = 9.2 Hz, 2H), 7.21 (s, 1H), 7.8 (d, J = 9.2 Hz, 2H), 4.56-4.47 (m, 2H), 3.67 (brs, 2H), 2.92-2.84 (m, 2H), 2.28-1.93 (m, 1H), 1.51 (s, 3H), 1.31 (brs, 6H), 0.76-0.72 (m, 4H). MS ESI calcd for $C_{33}H_{32}N_4O_2$ [M + H]⁺ 517, found 517. |
| 27 | 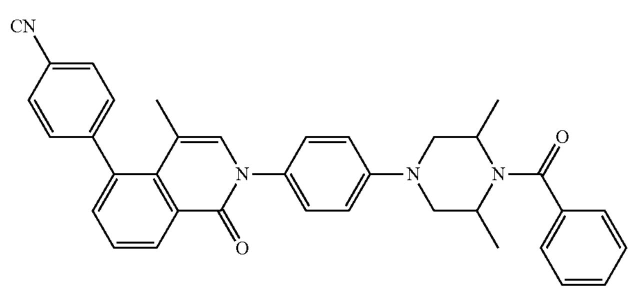 | ¹H NMR (400 MHz, DMSO-d₆) δ 8.43 (d, J = 7.2 Hz, 1H), 7.90 (d, J = 8.0 Hz, 2H), 7.91-7.39 (m, 9H), 7.29 (d, J = 8.8 Hz, 2H), 7.21 (s, 1H), 7.04 (d, J = 9.2 Hz, 2H), 4.02 (brs, 2H), 3.61 (d, J = 12.0 Hz, 2H), 2.97-2.93 (m, 2H), 1.51 (s, 3H), 1.32 (d, J = 6.0 Hz, 6H). MS ESI calcd for $C_{36}H_{32}N_4O_2$ [M + H]⁺ 553, found 553. |

-continued

| Embodiment | Structure | NMR |
|---|---|---|
| 28 | 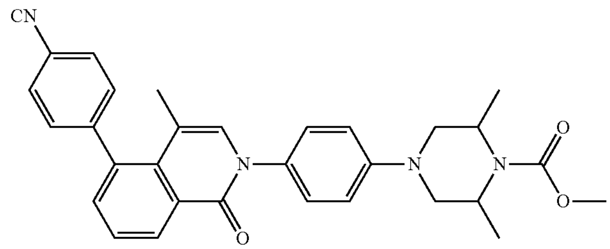 | ¹H NMR (400 MHz, MeOD) δ 8.54 (d, J = 6.4 Hz, 1H), 7.79 (d, J = 8.4 Hz, 2H), 7.62-7.53 (m, 4H), 7.30 (d, J = 9.2 Hz, 2H), 7.10 (d, J = 8.4 Hz, 3H), 4.28 (t, J = 5.6 Hz, 2H), 3.72 (s, 3H), 3.58 (d, J = 12.8 Hz, 2H), 2.95-2.91 (m, 2H), 1.63 (s, 3H), 1.36 (d, J = 6.4 Hz, 6H). MS ESI calcd for $C_{31}H_{30}N_4O_3$ [M + H]⁺ 507, found 507. |
| 29 | 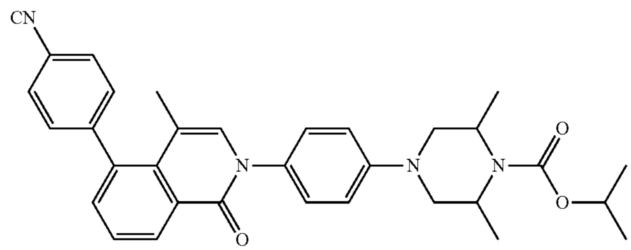 | ¹H NMR (400 MHz, MeOD) δ 8.53 (d, J = 6.8 Hz, 1H), 7.79 (d, J = 8.4 Hz, 2H), 7.61-7.53 (m, 4H), 7.28 (d, J = 8.8 Hz, 2H), 7.09 (d, J = 9.2 Hz, 3H), 4.95-4.88 (m, 1H), 4.27 (t, J = 5.2 Hz, 2H), 3.57 (d, J = 12.0 Hz, 2H), 2.92 (dd, J = 12.4 Hz, J = 4.0 Hz, 2H), 1.62 (s, 3H), 1.35 (d, J = 6.8 Hz, 6H), 1.26 (d, J = 6.0 Hz, 6H). MS ESI calcd for $C_{33}H_{34}N_4O_3$ [M + H]⁺ 535, found 535. |
| 30 | 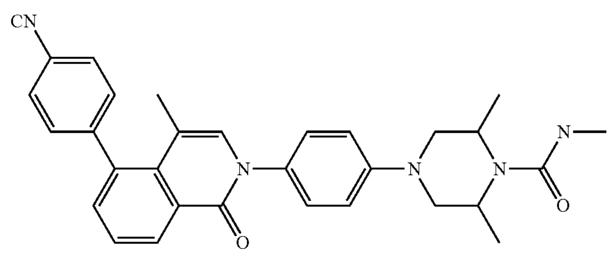 | ¹H NMR (400 MHz, MeOD) δ 8.53 (d, J = 7.6 Hz, 1H), 7.79 (d, J = 8.4 Hz, 2H), 7.61-7.52 (m, 4H), 7.28 (d, J = 8.8 Hz, 2H), 7.09 (d, J = 8.0 Hz, 3H), 4.19-4.16 (m, 2H), 3.58 (d, J = 12.0 Hz, 2H), 2.91 (dd, J = 12.0 Hz, J = 3.6 Hz, 2H), 2.75 (s, 3H), 1.62 (s, 3H), 1.33 (d, J = 6.8 Hz, 6H). MS ESI calcd for $C_{31}H_{31}N_5O_2$ [M + H]⁺ 506, found 506. |
| 31 | 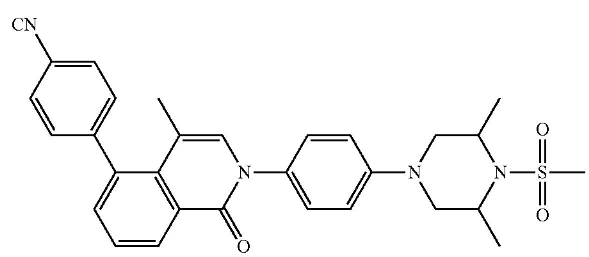 | ¹H NMR (400 MHz, MeOD) δ 8.53 (d, J = 6.8 Hz, 1H), 7.79 (d, J = 8.4 Hz, 2H), 7.61-7.53 (m, 4H), 7.29 (d, J = 8.0 Hz, 2H), 7.10-7.07 (m, 3H), 5.00 (brs, 1H), 4.14 (brs, 2H), 3.54 (t, J = 8.0 Hz, 2H), 3.20 (s, 1H), 3.12 (d, J = 3.6 Hz, 1H), 3.01 (dd, J = 12.4 Hz, J = 4.0 Hz, 1H), 2.94 (s, 1H), 1.62 (s, 3H), 1.48 (t, J = 8.0 Hz, 6H). MS ESI calcd for $C_{30}H_{30}N_4O_3S$ [M + H]⁺ 527, found 527. |
| 32 | 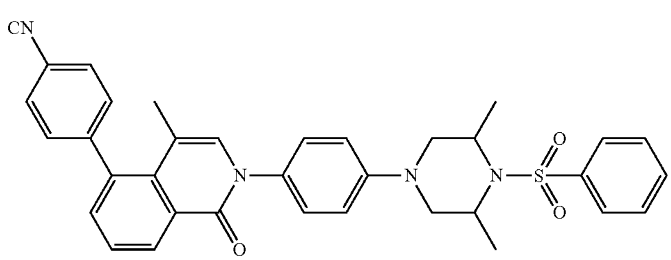 | ¹H NMR (400 MHz, MeOD) δ 8.52 (d, J = 6.8 Hz, 1H), 7.88 (d, J = 7.2 Hz, 2H), 7.79 (d, J = 8.4 Hz, 2H), 7.58-7.52 (m, 7H), 7.24 (d, J = 8.8 Hz, 2H), 7.07 (s, 1H), 6.97 (d, J = 8.8 Hz, 2H), 4.25-4.15 (m, 2H), 3.43 (d, J = 12.4 Hz, 2H), 2.64-2.60 (m, 2H), 1.61 (s, 3H), 1.47 (d, J = 6.8 Hz, 6H). MS ESI calcd for $C_{35}H_{32}N_4O_3S$ [M + H]⁺ 589, found 589. |

Embodiment 33

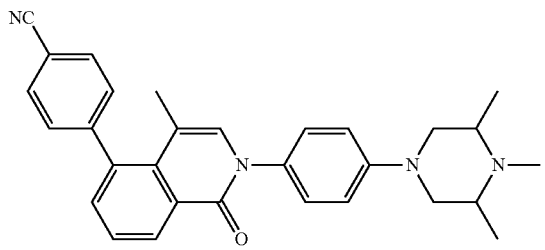 [SMILES: Cc1cn(-c2ccc(N3CC(C)N(C)C(C)C3)cc2)c(=O)c2cccc(-c3ccc(C#N)cc3)c12]

4-(4-methyl-1-oxo-2-(4-(3,4,5-trimethylpiperazin-1-yl)phenyl)-1,2-dihydroisoquinolin-5-yl)benzonitrile

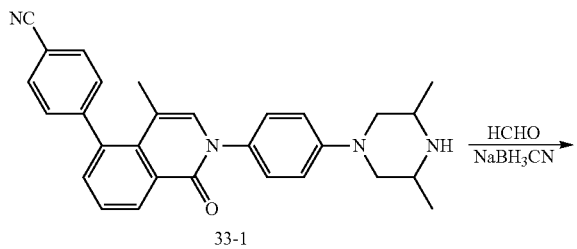

33-1

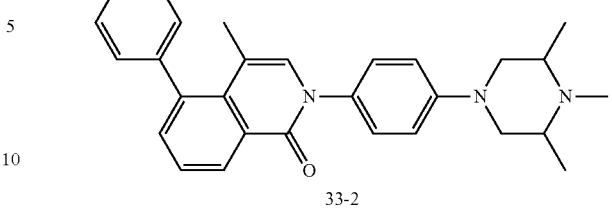

33-2

Compound 33-1 (200 mg, 0.45 mmol), formaldehyde (41 mg, 1.35 mmol) and NaBH$_3$CN (43 mg, 0.675 mmol) were dissolved in THF (5 mL), and the reaction mixture was stirred at room temperature for 16 h. The reaction was detected by LC-MS. The crude product was purified by preparative HPLC to deliver the title compound as white solid. $^1$H NMR (400 MHz, DMSO-d$_6$) δ 8.43 (d, J=8.0 Hz, 1H), 7.91 (d, J=8.0 Hz, 2H), 7.61-7.54 (m, 4H), 7.35 (d, J=8.8 Hz, 2H), 7.19 (s, 1H), 7.14 (d, J=8.4 Hz, 2H), 4.01 (d, J=12.8 Hz, 2H), 3.35 (d, J=6.4 Hz, 2H), 2.85 (t, J=12.4 Hz, 2H), 1.52 (s, 3H), 1.34 (d, J=6.4 Hz, 6H), 1.19 (t, J=6.4 Hz, 3H). MS ESI calcd for C$_{30}$H$_{30}$N$_4$O [M+H]$^+$ 463, found 463.

The compounds listed in table 3 can be synthesized by compound 33-1 and corresponding aldehydes.

| Embodiment | Structure | NMR |
|---|---|---|
| 34 | 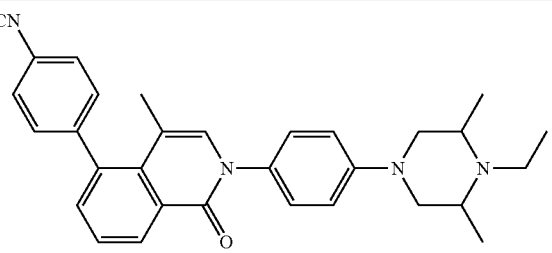 | $^1$H NMR (400 MHz, DMSO-d$_6$) δ 8.43 (d, J = 8.0 Hz, 1H), 7.91 (d, J = 8.0 Hz, 2H), 7.561-7.54 (m, 4H), 7.35 (d, J = 8.8 Hz, 2H), 7.19 (s, 1H), 7.14 (d, J = 8.4 Hz, 2H), 4.02 (d, J = 12.8 Hz, 2H), 3.53-3.46 (m, 4H), 2.85 (t, J = 12.4 Hz, 2H), 1.52 (s, 3H), 1.34 (d, J = 6.4 Hz, 6H), 1.19 (t, J = 6.4 Hz, 3H). MS ESI calcd for C$_{31}$H$_{32}$N$_4$O [M + H]$^+$ 477, found 477. |
| 35 | 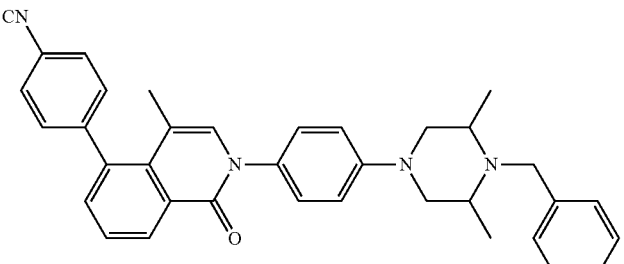 | $^1$H NMR (400 MHz, CDCl$_3$) δ 8.63 (d, J = 7.6 Hz, 1H), 7.70 (d, J = 8.0 Hz, 2H), 7.52-7.44 (m, 9H), 7.30 (d, J = 8.2 Hz, 2H), 6.93 (d, J = 8.4 Hz, 2H), 6.87 (s, 1H), 4.59 (s, 2H), 3.56 (d, J = 12.0 Hz, 2H), 3.43-3.31 (m, 4H), 1.78-1.67 (m, 4H), 1.78-1.67 (m, 4H), 1.57 (s, 3H). MS ESI calcd for C$_{36}$H$_{34}$N$_4$O [M + H]$^+$ 539, found 539. |
| 36 | 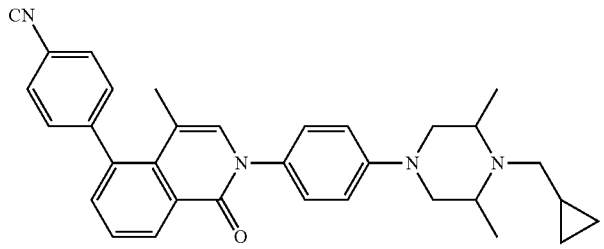 | $^1$H NMR (400 MHz, CDCl$_3$) δ 8.59 (d, J = 7.6 Hz, 1H), 7.65 (d, J = 8.0 Hz, 2H), 7.55-7.42 (m, 4H), 7.29 (d, J = 8.8 Hz, 2H), 6.95 (d, J = 8.8 Hz, 2H), 6.85 (s, 1H), 3.69-3.56 (m, 4H), 3.46-3.31 (m, 2H), 3.29 (d, J = 7.2 Hz, 2H), 2.36 (brs, 1H), 1.46 (d, J = 6.0 Hz, 6H), 0.97-0.73 (m, 3H), 0.43-0.34 (m, 2H). MS ESI calcd for C$_{33}$H$_{34}$N$_4$O [M + H]$^+$ 503, found 503. |

| Embodiment | Structure | NMR |
|---|---|---|
| 37 | 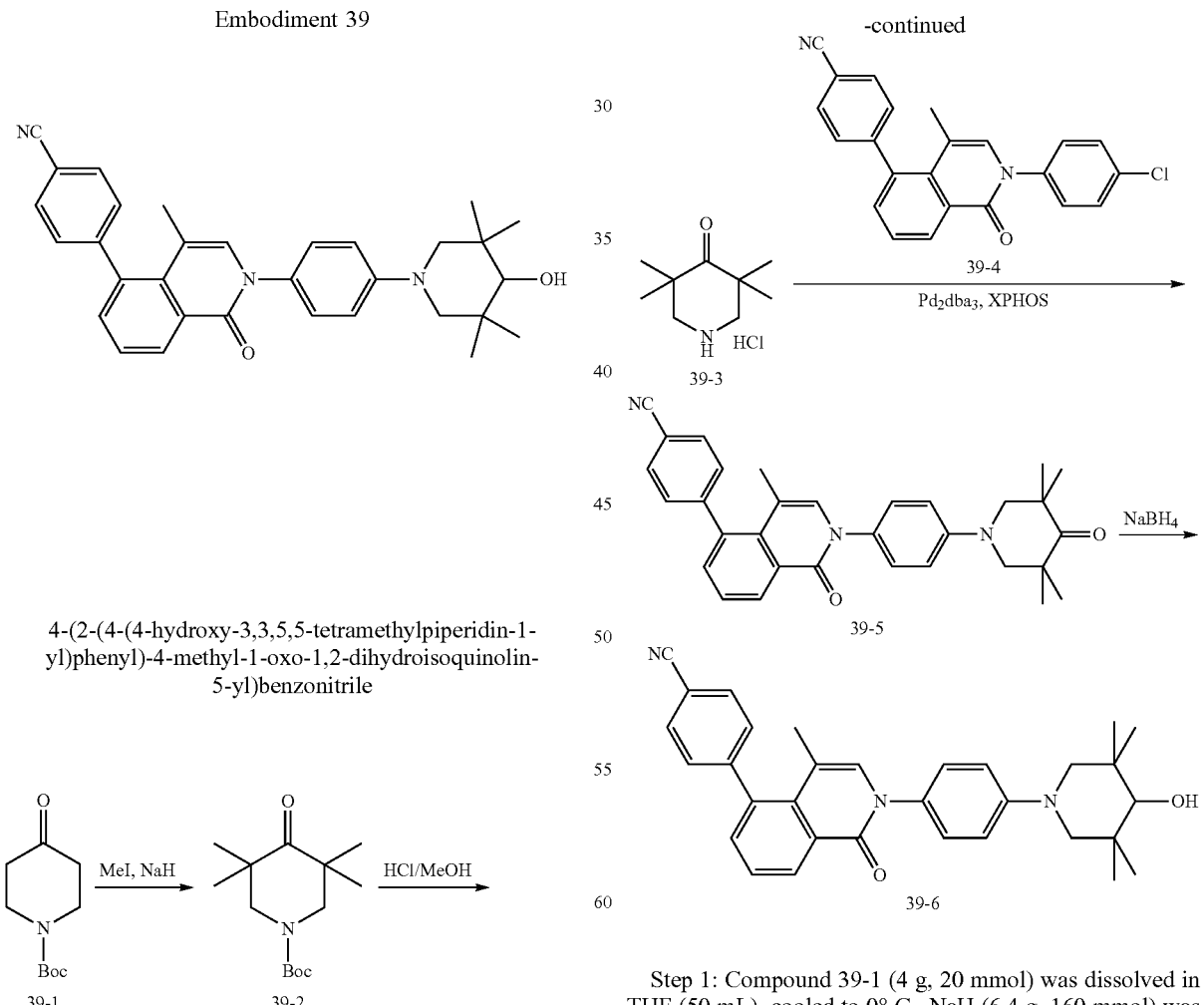 | $^1$H NMR (400 MHz, CDCl$_3$) δ 8.66 (d, J = 7.6 Hz, 1H), 7.72 (d, J = 7.6 Hz, 2H), 7.57-7.53 (m, 1H), 7.47 (d, J = 7.6 Hz, 3H), 7.36 (d, J = 6.4 Hz, 2H), 7.00 (d, J = 8.0 Hz, 2H), 6.92 (s, 1H), 4.02 (brs, 1H), 3.67-3.54 (m, 3H), 3.32 (brs, 1H), 3.20 (s, 1H), 3.17-2.85 (m, 3H), 2.67 (s, 5H), 1.60 (s, 3H), 1.43 (s, 6H). MS ESI calcd for C$_{33}$H$_{36}$N$_4$O$_2$ [M + H]$^+$ 521, found 521. |
| 38 | 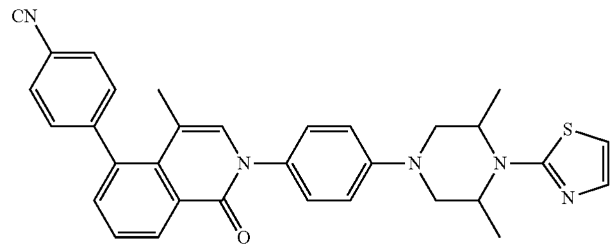 | $^1$H NMR (400 MHz, CDCl$_3$) δ 8.91 (s, 1H), 8.67 (d, J = 6.8 Hz, 2H), 7.72 (d, J = 8.0 Hz, 2H), 7.58-7.54 (m, 2H), 7.48 (d, J = 7.6 Hz, 3H), 7.36 (d, J = 9.2 Hz, 3H), 7.10 (d, J = 8.8 Hz, 2H), 6.94 (s, 1H), 3.62 (t, J = 11.2 Hz, 2H), 3.14-3.11 (m, 2H), 2.90 (t, J = 10.0 Hz, 2H), 2.17 (s, 1H), 1.61 (s, 3H), 1.02 (t, J = 6.4 Hz, 6H). MS ESI calcd for C$_{32}$H$_{29}$N$_5$OS [M + H]$^+$ 532, found 532. Q? |

Embodiment 39

4-(2-(4-(4-hydroxy-3,3,5,5-tetramethylpiperidin-1-yl)phenyl)-4-methyl-1-oxo-1,2-dihydroisoquinolin-5-yl)benzonitrile Step 1: Compound 39-1 (4 g, 20 mmol) was dissolved in THF (50 mL), cooled to 0° C., NaH (6.4 g, 160 mmol) was added, and then the reaction mixture was stirred at room temperature for 0.5 h, cooled to 0° C. again, iodomethane (10 mL, 160 mmol) was added dropwise, then warmed to room temperature and stirred for further 2 h. The reaction was detected by TLC, the reaction mixture was quenched with water and extracted with EtOAc, the organic phase was washed with brines, dried over anhydrous sodium sulfate and concentrated under reduced pressure to deliver the compound 39-2 as yellow solid (4.5 g, yield 88%). MS ESI calcd for $C_{14}H_{25}NO_3$ [M+H]$^+$ 256, found 256.

Step 2: Compound 39-2 (410 mg, 1.6 mmol) was dissolved in hydrochloric acid/methanol (10 mL) and stirred at room temperature for 2 h. After the reaction was complete, the mixture was concentrated under reduced pressure to deliver compound 39-3 as yellow oil (330 mg, yield 86%). MS ESI calcd for $C_9H_{17}NO$ [M+H]$^+$ 156, found 156.

Step 3: Compound 39-5 was prepared according to the above-mentioned method, as yellow solid (300 mg, yield 75%). MS ESI calcd for $C_{32}H_{31}N_3O_2$ [M+H]$^+$ 490, found 490.

Step 4: Compound 39-5 (490 mg, 1 mmol) was dissolved in THF (10 mL), NaBH$_4$ (57 mg, 1.5 mmol) was added, then the mixture was stirred at room temperature for 0.5 h. The reaction was detected by LC-MS, the residue was poured into H$_2$O, extracted with DCM. The organic phase was washed with brines, dried over anhydrous sodium sulfate and concentrated under reduced pressure to deliver the crude compound. The crude product was purified by preparative HPLC to deliver the title compound as white solid (64 mg, yield 13%). $^1$H NMR (400 MHz, CDCl3) δ 8.69 (d, J=7.2 Hz, 1H), 7.74 (d, J=7.6 Hz, 2H), 7.60-7.45 (m, 4H), 7.27 (d, J=6.4 Hz, 2H), 7.00-6.90 (m, 3H), 3.39 (d, J=12.0 Hz, 2H), 3.12 (s, 1H), 2.60 (d, J=12.0 Hz, 2H), 1.62 (s, 3H), 1.09 (s, 6H), 1.04 (s, 6H). MS ESI calcd for $C_{32}H_{33}N_3O_2$ [M+H]$^+$ 492, found 492.

Embodiment 40

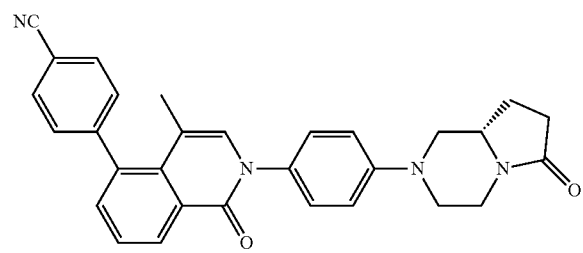 [SMILES: Cc1cn(-c2ccc(N3CCN4C(=O)CC[C@H]4C3)cc2)c(=O)c2cccc(-c3ccc(C#N)cc3)c12]

(S)-4-(4-methyl-1-oxo-2-(4-(6-oxo-hexahydropyrrolo[1,2-a]pyrazin-2(1H)-yl)phenyl)-1,2-dihydroisoquinolin-5-yl)benzonitrile

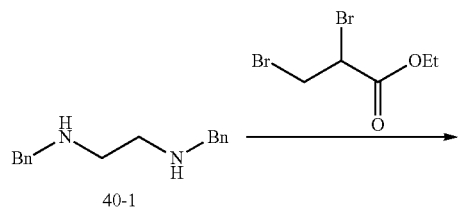

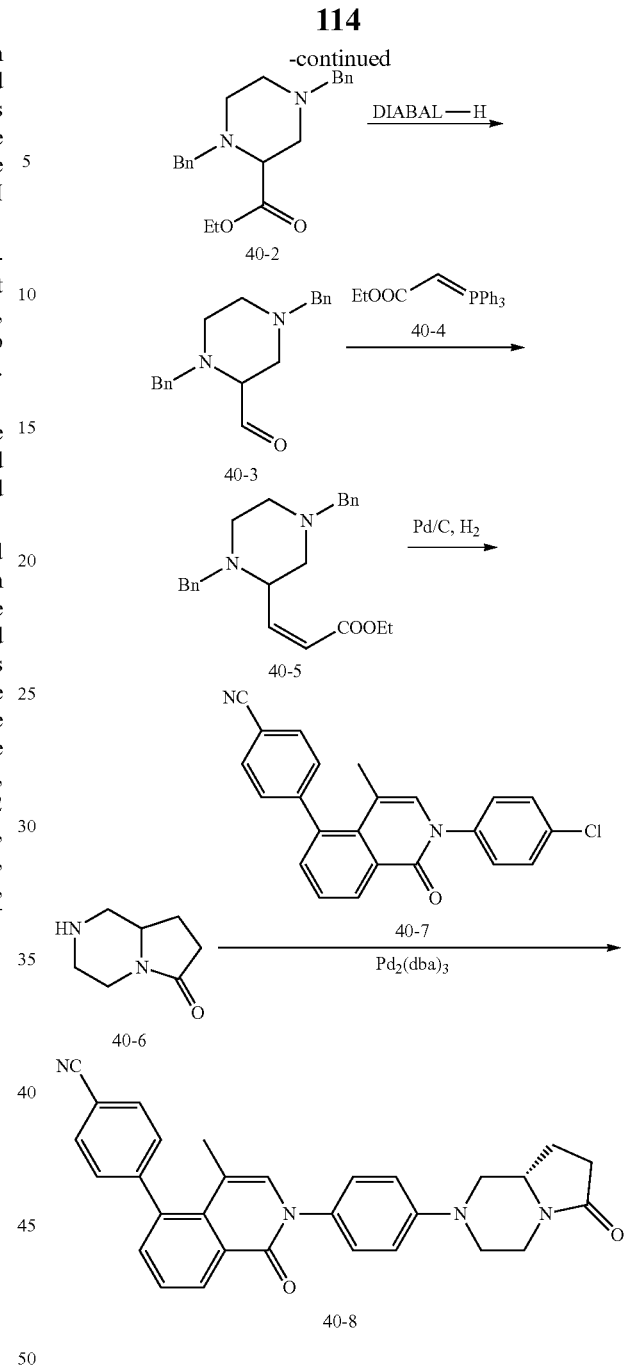

Step 1: Compound 40-1 (10 g, 4.20 mmol) and DIEA (10.8 g, 84 mmol) were dissolved in toluene (200 mL) and cooled to 0° C., ethyl 2,3-dibromopropionate (13.1 g, 50.4 mmol) was added, and then the reaction mixture was stirred at 100° C. overnight. The reaction was detected by TLC. The reaction mixture was quenched with H$_2$O, extracted with EtOAc. The organic phase was washed with brines, dried over anhydrous sodium sulfate and concentrated under reduced pressure, the residue was purified by silica gel column chromatography (PE/EtOAc=10/1) to deliver the compound 40-2 as yellow oil (8.5 g, yield 61%). MS ESI calcd for $C_{21}H_{26}N_2O_2$ [M+H]$^+$ 339, found 339.

Step 2: Under nitrogen gas atmosphere, DIBAL-H (45 mL, 45 mmol) was added into a solution of compound 40-2 (8.4 g, 24.85 mmol) in toluene (100 mL) at −78° C., and stirred at −78° C. for 1 h. After the reaction was complete, 20% sodium hydroxide (30.7 mL) was added. The reaction mixture was warmed to room temperature and 20% sodium hydroxide aqueous solution (76.8 mL) was added. The reaction solution was extracted with EtOAc, and the organic phase was washed with brines, dried over anhydrous sodium sulfate and concentrated under reduced pressure to deliver compound 40-3 as yellow oil (7.4 g crude). MS ESI calcd for $C_{19}H_{22}N_2O$ [M+H]$^+$ 295, found 295.

Step 3: Under nitrogen gas atmosphere, compound 40-3 (7.3 g, 24.75 mmol) was dissolved in toluene (100 mL), compound 40-4 (17.2 g, 49.50 mmol) was added, and the mixture was stirred at 80° C. overnight. The reaction was detected by LC-MS. The residue was poured into $H_2O$, extracted with EtOAc. The organic phase was washed with brines, dried over anhydrous sodium sulfate and concentrated under reduced pressure, the residue was purified by silica gel column chromatography (PE/EtOAc=10/1 to 4/1) to deliver compound 40-5 as yellow oil (5.6 g, yield 62%). MS ESI calcd for $C_{23}H_{28}N_2O_2$ [M+H]$^+$ 365, found 365.

Step 4: Pd/C (2.8 g, 10%) was added into a solution of compound 40-5 (5.6 g, 15.34 mmol) in ethanol (100 mL), the reaction mixture was heated to 70° C. under 55 psi and stirred overnight. The reaction was detected by TLC, and filtrated with diatomite, the filtrate was concentrated to deliver compound 40-6 as yellow oil (2 g, yield 71%). MS ESI calcd for $C_7H_{12}N_2O$ [M+H]$^+$ 141, found 141.

Step 5: The title compound was prepared according to the above-mentioned method, as white solid (30 mg, yield 12%). $^1$H NMR (400 MHz, CDCl$_3$) δ 8.66 (d, J=7.6 Hz, 1H), 7.72 (d, J=8.0 Hz, 2H), 7.42-7.58 (m, 4H), 7.34 (d, J=8.8 Hz, 2H), 7.04 (d, J=8.8 Hz, 2H), 6.94 (s, 1H), 4.13-4.18 (m, 1H), 3.76-3.90 (m, 2H), 2.69 (d, J=12.0 Hz, 1H), 3.05-3.18 (m, 1H), 2.75-2.85 (m, 1H), 2.52-2.63 (m, 3H), 2.25-2.35 (m, 1H), 1.65-1.78 (m, 1H), 1.61 (s, 3H). MS ESI calcd for $C_{30}H_{26}N_4O_2$ [M+H]$^+$ 475, found 475.

Embodiment 41

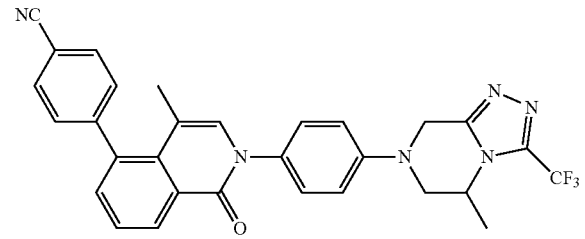 [SMILES: Cc1cn(-c2ccc(N3Cc4nnc(C(F)(F)F)n4C(C)C3)cc2)c(=O)c2cccc(-c3ccc(C#N)cc3)c12]

4-(4-methyl-2-(4-(5-methyl-3-(trifluoromethyl)-5,6-dihydro-[1,2,4]triazolo[4,3-a]pyrazin-7(8H)-yl)phenyl)-1-oxo-1,2-dihydroisoquinolin-5-yl)benzonitrile

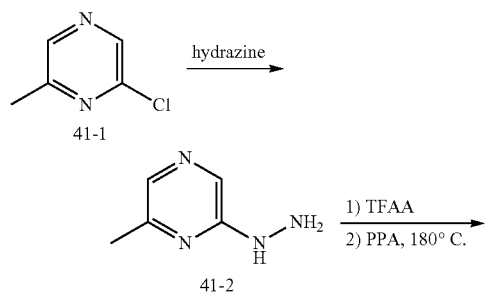

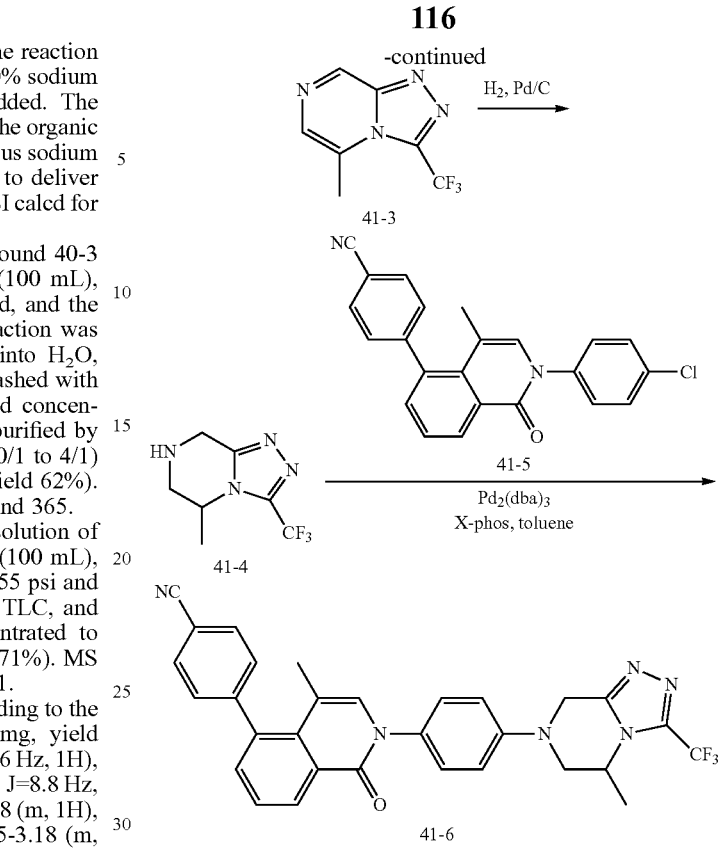

Step 1: Compound 41-1 (2.9 g, 22.75 mmol) was added into hydrazine hydrate (15 mL), the reaction mixture was subject to an preheated oil bath (50° C.), then warmed to 100° C. above for 30 min. After cooled to room temperature, the reaction mixture was cooled to 0° C. for 1 h. The residue was collected by filtration and dried to deliver compound 41-2 as white solid (1.6 g, yield 58%). MS ESI calcd for $C_5H_8N_4$ [M+H]$^+$ 125, found 125.

Step 2: TFAA (35 mL) was added into compound 41-2 (1.6 g, 13.2 mmol) dropwise at 0° C., the reaction mixture was stirred at room temperature for 1 h. The reaction mixture was concentrated under reduced pressure to deliver yellow solid. Then PPA (40 mL) was added. The reaction mixture was heated to 120° C. and stirred for 18 h. The hot PPA solution was poured into ice water and neutralized with ammonia. The aqueous phase was extracted with EtOAc, the organic phase was washed with brines, dried over anhydrous sodium sulfate and concentrated under reduced pressure. The crude product was purified by silica gel column chromatography (PE:EtOAc=1:1) to deliver compound 41-3 as yellow solid (2 g, yield 77%). MS ESI calcd for $C_7H_5F_3N_4$ [M+H]$^+$ 203, found 203.

Step 3: Compound 41-3 (2 g, 10 mmol) and Pd/C (1.1 g) were dissolved in EtOH (30 mL) and THF (15 mL), under hydrogen gas atmosphere, the reaction mixture was stirred at room temperature for 18 h. The reaction mixture was filtrated and the filtrate was concentrated to deliver compound 41-4 as yellow oil (1.9 g, yield 90%). MS ESI calcd for $C_7H_9F_3N_4$ [M+H]$^+$ 207, found 207.

Step 4: The title compound was prepared according to the above-mentioned method, as white solid (25 mg, yield 6.8%). $^1$H NMR (400 MHz, CDCl$_3$) δ 8.66 (d, J=7.6 Hz, 1H), 7.71 (d, J=8.4 Hz, 2H), 7.54 (t, J=8.0 Hz, 1H), 7.45 (dd, J=23.2 Hz, J=8.0 Hz 5H), 7.06 (d, J=8.8 Hz, 2H), 6.92 (s, 1H), 4.91 (d, J=16.0 Hz, 1H), 4.70 (brs, 1H), 4.44 (d, J=16.0 Hz, 1H), 3.83 (d, J=13.2 Hz, 1H), 3.53 (d, J=10.8 Hz, 1H), 1.68 (d, J=6.0 Hz, 3H), 1.59 (s, 3H). MS ESI calcd for $C_{30}H_{23}F_3N_6O$ [M+H]$^+$ 541, found 541.

Embodiment 42

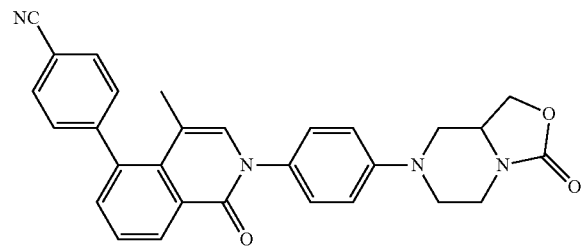 [SMILES: Cc1cn(-c2ccc(N3CCN4C(=O)OCC4C3)cc2)c(=O)c2cccc(-c3ccc(C#N)cc3)c12]

4-(4-methyl-1-oxo-2-(4-(3-oxotetrahydro-1H-oxazolo[3,4-a]pyrazin-7(3H)-yl)phenyl)-1,2-dihydroisoquinolin-5-yl)benzonitrile

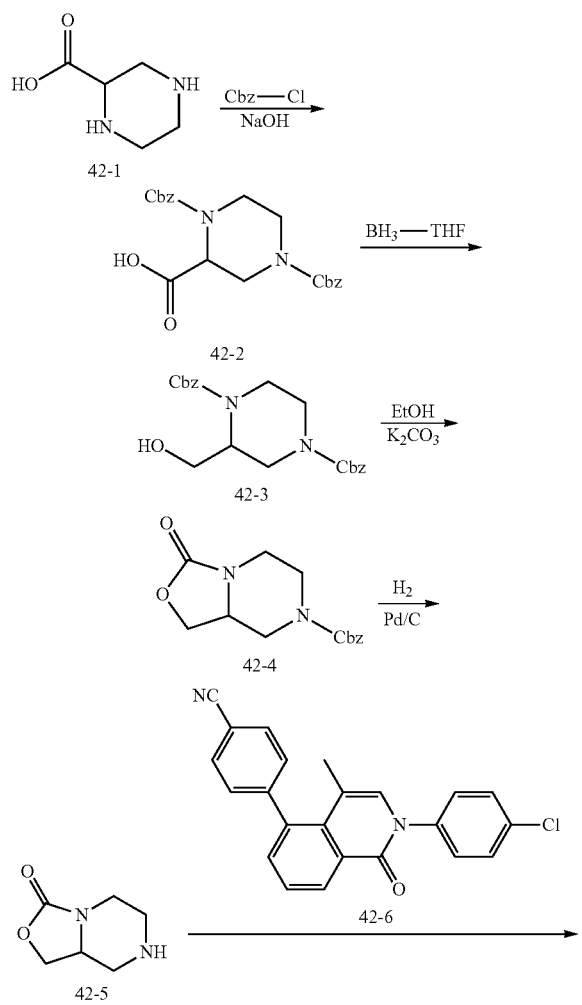

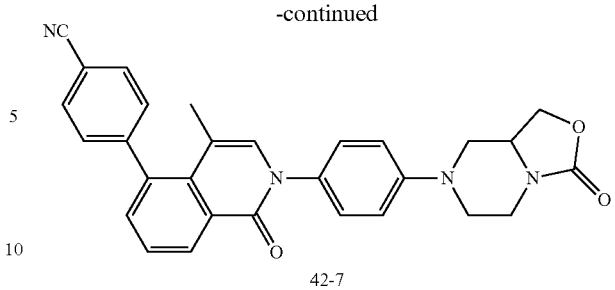

Step 1: Compound 42-1 (17 g, 84 mmol) was dissolved in dioxane (340 mL) and H$_2$O (210 mL), the solution was adjust to pH>11 with sodium hydroxide aqueous solution (50%), CbzCl (24 mL, 168 mmol) was added, the reaction mixture was stirred for 2 h, and then poured into 1 L H$_2$O. The aqueous phase was extracted with DCM, the organic phase was washed with brines, dried over anhydrous sodium sulfate and concentrated under reduced pressure to deliver compound 42-2 as colorless adhesive oil (18 g, 51%). MS ESI calcd for $C_{21}H_{22}N_2O_6$ [M+H]$^+$ 399, found 399.

Step 2: Compound 42-2 (14 g, 35 mmol) was dissolved in THF (150 mL), then BH$_3$-THF (70 mL, 70 mmol) was added dropwise, the reaction mixture was stirred at 50° C. for 3 h. After the reaction was complete as detected by LC-MS, MeOH was added slowly to quench the reaction. When no gas was released, the reaction mixture was warmed to 50° C. and stirred for 1 h, and then concentrated under reduced pressure to deliver compound 42-3 as colorless oil (4 g, 30%). MS ESI calcd for $C_{21}H_{24}N_2O_5$ [M+H]$^+$ 385, found 385.

Step 3: Compound 42-3 (4 g, 10.4 mmol) and potassium carbonate (1.7 g, 12.5 mmol) were dissolved in EtOH (40 mL), the reaction mixture was stirred at 70° C. overnight. After the reaction was complete as detected by LC-MS, the mixture was filtrated to remove the remained potassium carbonate. The filtrate was concentrated under reduced pressure, purified by silica gel column chromatography (PE:EtOAc=1:1) to deliver compound 42-4 as yellow solid (2.2 g, 78%). MS ESI calcd for $C_{14}H_{16}N_2O_4$ [M+H]$^+$ 277, found 277.

Step 4: Pd/C (100 mg) was added into a solution of compound 42-4 (500 mg, 1.8 mmol) in MeOH (50 mL), under hydrogen gas atmosphere (40 psi), the reaction mixture was stirred at room temperature for 12 h. Pd/C was removed by filtration, the filtrate was concentrated under reduced pressure to deliver compound 42-5 as yellow oil (240 mg, 95%). MS ESI calcd for $C_6H_{10}N_2O_2$ [M+H]$^+$ 143, found 143.

Step 5: The title compound was prepared according to the above-mentioned method, as white solid (55 mg, yield 20%). $^1$H NMR (400 MHz, CDCl$_3$) δ 8.67 (d, J=6.8 Hz, 1H), 7.72 (d, J=8.0 Hz, 2H), 7.55 (t, J=8.0 Hz, 1H), 7.48 (d, J=7.6 Hz, 3H), 7.35 (d, J=8.4 Hz, 2H), 7.02 (d, J=8.4 Hz, 2H), 6.92 (s, 1H), 4.51 (t, J=10.4 Hz, 1H), 4.04 (d, J=5.6 Hz, 2H), 3.96 (d, J=2.4 Hz, 1H), 3.71 (d, J=12.0 Hz, 1H), 3.61 (d, J=12.0 Hz, 1H), 3.37-3.22 (m, 1H), 2.94-2.78 (m, 1H), 2.76 (t, J=10.04 Hz, 1H), 1.59 (s, 3H). MS ESI calcd for $C_{29}H_{24}N_4O_3$ [M+H]$^+$ 477, found 477.

Embodiment 43

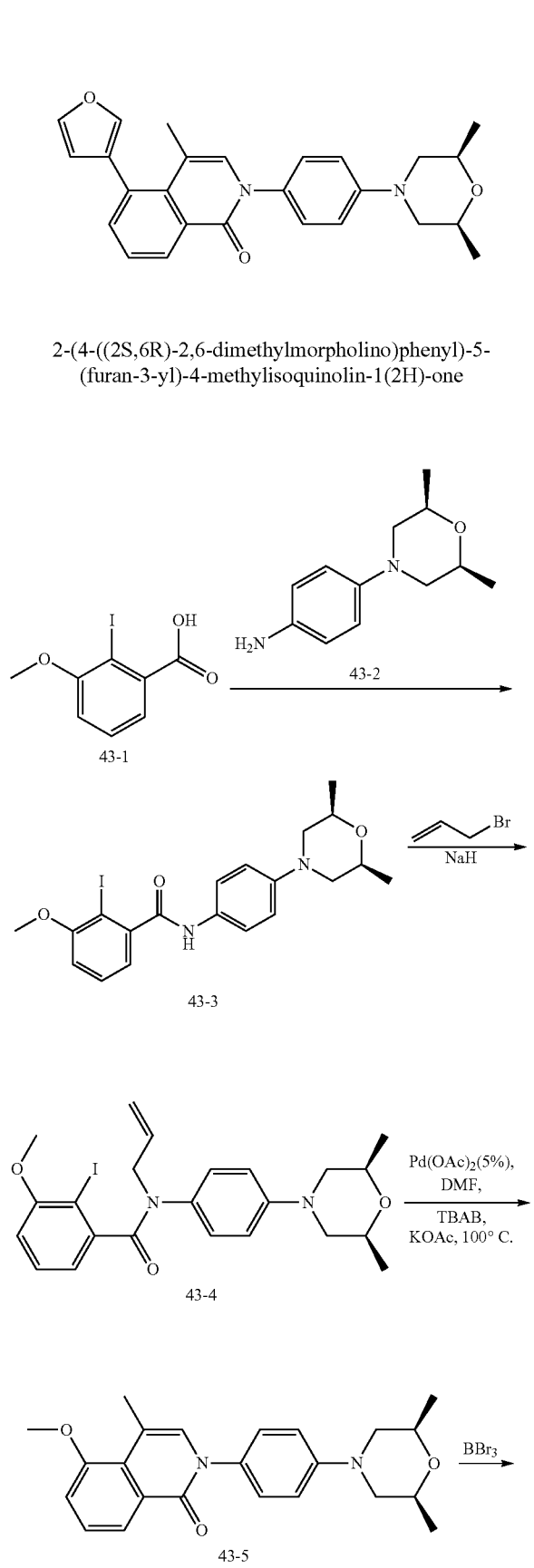

2-(4-((2S,6R)-2,6-dimethylmorpholino)phenyl)-5-(furan-3-yl)-4-methylisoquinolin-1(2H)-one

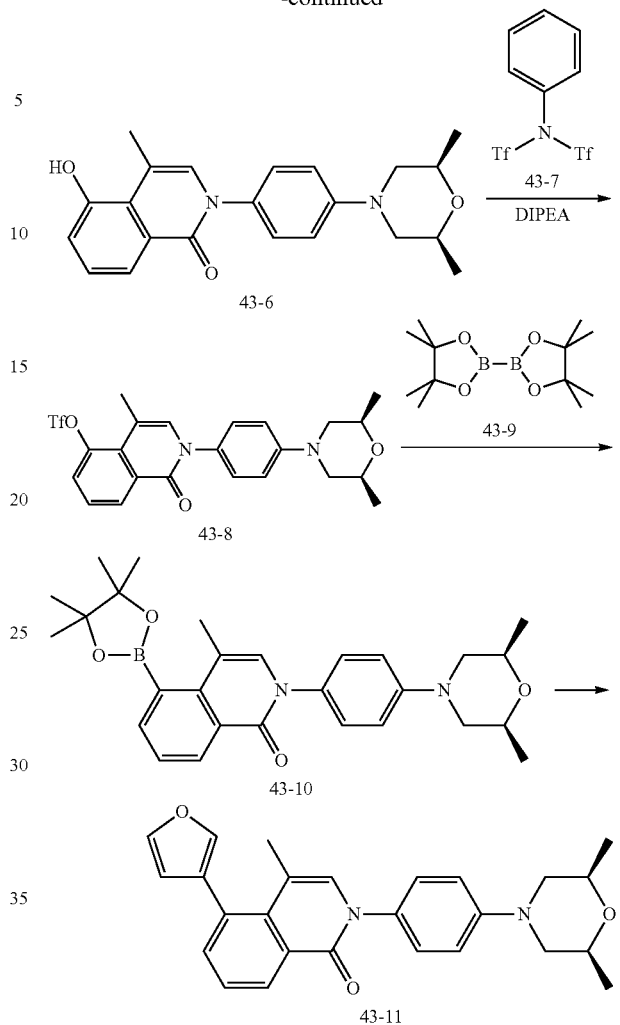

Step 1: HATU (5.5 g, 40.86 mmol) was added into a solution of compound 43-1 (9.7 g, 34.9 mmol) in DMF (100 mL) at 0° C. After stirring at room temperature for 30 min, DIEA (18 g, 69.8 mmol) and compound 43-2 (7.2 g, 34.9 mmol) was added at 0° C., and then the reaction mixture was reacted at room temperature overnight. The reaction mixture was poured into H₂O, extracted with EtOAc. The organic phase was washed with H₂O, dried over anhydrous sodium sulfate, filtrated and concentrated. The residue was purified by silica gel column chromatography to deliver compound 43-3 (13 g, yield 80%) as white solid. MS (ESI) m/z (M+H)⁺ 467.

Step 2: Under nitrogen gas atmosphere, NaH (1.34 g, 33.5 mmol), 3-bromo-1-propylene (6.8 g, 55.8 mmol) were added into a solution of compound 43-3 (13 g, 27.9 mmol) in DMF (100 mL) at 0° C., and then the reaction mixture was reacted at room temperature overnight. The reaction mixture was poured into H₂O, extracted with EtOAc, the organic phase was washed with H₂O, dried over anhydrous sodium sulfate, filtrated and concentrated, the residue was purified by silica gel column chromatography to deliver compound 43-4 (12 g, yield 85.7%). MS (ESI) m/z (M+H)⁺ 507.

Step 3: Compound 43-4 (11.1 g, 21.74 mmol), TBAB (17.50 g, 54.35 mmol), potassium acetate (3.2 g, 32.61 mmol), palladium acetate (487 mg, 2.17 mmol) were added into DMF (700 mL), heated to 100° C. and stirred overnight.

H₂O was added into the reaction mixture, EtOAc was used for extraction, the organic phase was washed with H₂O, dried over anhydrous sodium sulfate, filtrated and concentrated, the residue was purified by silica gel column chromatography to deliver compound 43-5 (4.5 g, yield 50%). MS (ESI) m/z (M+H)⁺ 379.

Step 4: Boron tribromide (12.6 g, 4.7 mL) was added into a solution of compound 43-5 (3.8 g, 10.05 mmol) in DCM (40 mL) at 0° C., the reaction mixture was stirred at room temperature overnight, then quenched with saturated sodium carbonate solution, the mixture was filtrated to deliver compound 43-6 (1.9 g, yield 53%). MS (ESI) m/z (M+H)⁺ 365.

Step 5: DIPEA (1.1 g, 8.24 mmol) and compound 43-7 (2.2 g, 6.18 mmol) were added into a solution of compound 43-6 (1.5 g, 4.12 mmol) in DMF (60 mL), the reaction mixture reacted at room temperature overnight, and then concentrated under reduced pressure to remove the solvent. The residue was purified by silica gel column chromatography to deliver compound 43-8 (1.5 g, yield 75%). MS (ESI) m/z (M+H)⁺ 497.

Step 6: Compound 43-9 (508 mg, 2.0 mmol), Pd(dppf)Cl₂ (73 mg, 0.10 mmol) and potassium acetate (196 mg, 2.0 mmol) were added into a solution of compound 43-8 (496 mg, 1.0 mmol) in 1,4-dioxane. Under nitrogen gas atmosphere, the reaction mixture reacted at 110° C. overnight, and then the solvent was evaporated. The residue was purified by silica gel column chromatography to deliver compound 43-10 (270 mg, yield 60%). MS (ESI) m/z (M+H)⁺ 475.

Step 7: 3-furanboronic acid (24 mg, 1.5 eq), potassium phosphate (59 mg, 0.28 mmol) and Pd(dppf)Cl₂ (10 mg) were added into a solution of compound 43-10 (70 mg, 0.14 mmol) in DMF and H₂O (6 mL, 5:1), then the reaction mixture was refluxed overnight, H₂O was added into the reaction mixture, DCM was used to extract for 3 times, the organic phases were combined and washed with brines, dried over anhydrous sodium sulfate, filtrated and concentrated under reduced pressure, the residue was purified by preparative HPLC to deliver the title compound as light yellow solid. ¹H NMR (400 MHz, Methanol-d₄) δ 8.57-8.59 (d, J=8.0 Hz, 1H) 7.55-7.60 (m, 4H) 7.33-7.35 (mz, 2H) 7.16-7.18 (d, J=8.4 Hz, 2H) 7.13 (s, 1H) 6.52 (s, 1H) 3.79-3.83 (d, J=14.4 Hz 2H) 3.60-3.63 (t, J=11.2 Hz, 2H) 2.50-2.56 (t, J=22.4 Hz, 2H) 1.97 (s, 3H) 1.24-1.25 (d, J=6.4 Hz, 6H). MS ESI calcd for C₂₆H₂₆N₂O₃ [M+H]⁺ 416, found 416.

The compounds listed in table 4 can be synthesized by compound 43-10 and corresponding boric acids.

| Embodiment | Structure | NMR |
|---|---|---|
| 44 | (CN-thiophene substituted structure) | ¹H NMR (400 MHz, Methanol-d₄) δ 8.57-8.59 (d, J = 8.0 Hz, 1H) 7.72-7.76 (d d, J = 8.0 Hz, 2H) 7.57-7.61 (t, J = 16 Hz, 1H) 7.31-7.33 (t, J = 9.2 Hz, 2H) 7.15-7.16 (d, J = 3.6 Hz, 3H) 7.13 (s, 1H) 3.79-3.83 (d, J = 14.4 Hz, 2H) 3.59-3.62 (t, J = 11.2 Hz, 2H) 2.43-2.49 (t, J = 22.4 Hz, 2H) 1.85 (s, 3H) 1.22-1.24 (d, J = 6.4 Hz, 6 H). MS ESI calcd for C₂₇H₂₅N₃O₂S [M + H]⁺ 456, found 456. |
| 45 | (Cl-thiophene substituted structure) | ¹H NMR (400 MHz, Methanol-d₄) δ 8.52-8.54 (d, J = 8.0 Hz, 1H) 7.70-7.72 (d, J = 6.8 Hz, 1H) 7.53-7.57 (t, J = 16 Hz, 1H) 7.31-7.33 (t, J = 8.8 Hz, 2H) 7.12-7.15 (d, J = 9.6 Hz, 3H) 6.97-6.98 (d, J = 3.2 Hz, 1H) 6.82-6.83 (d, J = 4.0 Hz, 1H) 3.79-3.83 (d, J = 12.0 Hz, 2H) 3.59-3.62 (t, J = 11.2 Hz, 2H) 2.43-2.49 (t, J = 22.4 Hz, 2H) 1.85 (s, 3H) 1.22-1.24 (d, J = 6.4 Hz, 6 H). MS ESI calcd for C₂₆H₂₅ClN₂O₂S [M + H]⁺ 466, found 466. |
| 46 | (p-tolyl substituted structure) | ¹H NMR (400 MHz, DMSO-d₆) δ 8.41-8.43 (m, 1H), 7.80-7.82 (d, J = 7.2 Hz, 2H) 7.58-7.63 (m, 4H), 7.30-7.32 (d, J = 7.2 Hz, 2H), 7.21 (s, 1H) 7.05-7.07 (d, J = 8.8 Hz, 2H) 3.66-3.69 (m, 1H), 2.28-2.34 (m, 4H), 1.54 (s, 3H), 1.18-1.19 (d, J = 5.6 Hz, 6 H). MS ESI calcd for C₂₉H₂₇F₃N₂O₂ [M + H]+ 493, found 493. |
| 47 | (OCF₃-phenyl substituted structure) | ¹H NMR (400 MHz, DMSO-d₆) δ 8.52-8.53 (m, 1H), 7.61-7.62 (d, J = 4.0 Hz, 2H) 7.48-7.5 (m, 2H), 7.30-7.36 (m, 4H), 7.10-7.12 (m, 2H), 3.63-3.65 (m, 2H), 2.38-2.44 (m, 2H), 2.16-2.18 (m, 2H), 1.68 (s, 3H), 1.26-1.28 (d, J = 6.0 Hz, 6 H). MS ESI calcd for C₂₉H₂₇F₃N₂O₃ [M + H]⁺ 509, found 509. |

-continued

| Embodiment | Structure | NMR |
|---|---|---|
| 48 | 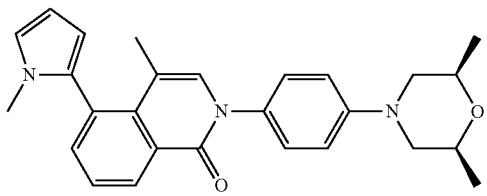 | $^1$H NMR (400 MHz, DMSO-$d_6$) δ 8.57-8.59 (d, J = 6.8 Hz, 1H), 7.56-7.57 (d, J = 6.0 Hz, 1H), 7.45-7.46 (d, J = 7.6 Hz, 1H), 7.24-7.26 (d, J = 9.2 Hz, 2H), 6.86-6.92 (m, 3H), 6.64 (s, 1H), 6.07-6.16 (m, 2H), 3.73-3.75 (m, 2H), 3.41-3.44 (m, 2H), 3.21 (s, 3H), 2.38-2.43 (m, 2H), 1.54 (s, 3H), 1.18-1.20 (d, J = 6.4 Hz, 6 H). MS ESI calcd for $C_{27}H_{29}N_3O_2$ [M + H]$^+$ 428, found 428. |
| 49 | 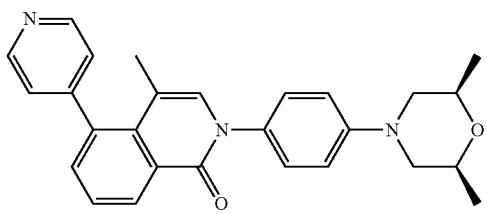 [SMILES: Cc1cn(-c2ccc(N3C[C@@H](C)O[C@@H](C)C3)cc2)c(=O)c2cccc(-c3ccncc3)c12] | $^1$H NMR (400 MHz, DMSO-$d_6$) δ 8.64-8.65 (d, J = 4.4 Hz, 2H), 8.46-8.48 (d, J = 8.0 Hz, 1H), 7.60-7.64 (m, 2H), 7.53-7.55 (d, J = 7.6 Hz, 2H), 7.44-7.45 (d, J = 4.8 Hz, 2H), 7.31-7.33 (d, J = 8.4 Hz, 2H), 7.23 (s, 1H), 7.06-7.08 (d, J = 8.4 Hz, 1H), 3.66-3.75 (m, 4H), 2.29-2.35 (m, 2H), 1.61 (s, 3H), 1.18-1.20 (d, J = 6.0 Hz, 6 H). MS ESI calcd for $C_{27}H_{27}N_3O_2$ [M + H]$^+$ 426, found 426. |
| 50 | 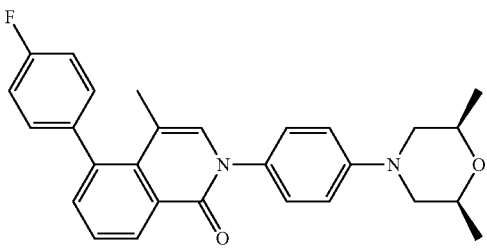 [SMILES: Cc1cn(-c2ccc(N3C[C@@H](C)O[C@@H](C)C3)cc2)c(=O)c2cccc(-c3ccc(F)cc3)c12] | $^1$H NMR (400 MHz, DMSO-$d_6$) δ 8.37-8.39 (d, J = 7.2 Hz, 1H), 7.49-7.53 (m, 2H), 7.34-7.35 (d, J = 5.6 Hz, 2H), 7.20-7.27 (m, 4H), 7.13 (s, 1H), 7.00-7.02 (d, J = 7.6 Hz, 2H), 3.61-3.69 (m, 4H), 2.23-2.29 (m, 2H), 1.51 (s, 3H), 1.13-1.14 (d, J = 6.0 Hz, 6 H). MS ESI calcd for $C_{28}H_{27}FN_2O_2$ [M + H]$^+$ 443, found 443. |
| 51 | 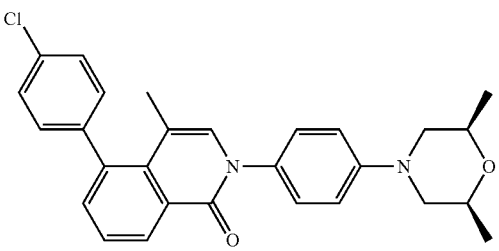 [SMILES: Cc1cn(-c2ccc(N3C[C@@H](C)O[C@@H](C)C3)cc2)c(=O)c2cccc(-c3ccc(Cl)cc3)c12] | $^1$H NMR (400 MHz, DMSO-$d_6$) δ 8.39-8.41 (d, J = 7.2 Hz, 1H), 7.49-7.55 (m, 3H), 7.35-7.37 (d, J = 7.6 Hz, 2H), 7.27-7.29 (d, J = 8.0 Hz, 2H), 7.16 (s, 1H), 7.02-7.04 (d, J = 8.0 Hz, 2H), 3.62-3.69 (m, 4H), 2.25-2.30 (m, 2H), 1.55 (s, 3H), 1.15-1.16 (d, J = 6.4 Hz, 6 H). MS ESI calcd for $C_{28}H_{27}ClN_2O_2$ [M + H]$^+$ 460, found 460. |
| 52 | 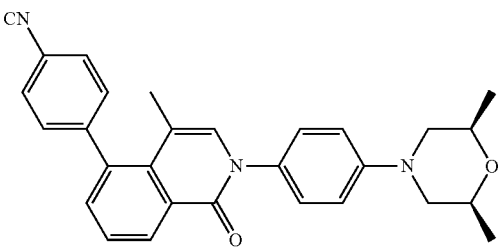 | $^1$H NMR (400 MHz, DMSO-$d_6$) δ 8.42-8.44 (d, J = 7.6 Hz, 1H), 7.88-7.90 (d, J = 8.0 Hz, 2H), 7.50-7.58 (m, 3H), 7.27-.29 (d, J = 8.4 Hz, 2H), 7.27-7.29 (d, J = 8.0 Hz, 2H), 7.19 (s, 1H), 7.02-7.04 (d, J = 8.0 Hz, 2H), 3.63-3.69 (m, 4H), 2.25-2.30 (m, 2H), 1.51 (s, 3H), 1.15-1.16 (d, J = 6.0 Hz, 6 H). MS ESI calcd for $C_{29}H_{27}N_3O_2$ [M + H]$^+$ 450, found 450. |
| 53 | 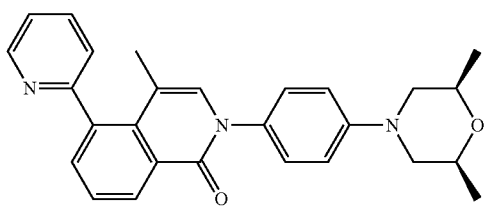 [SMILES: Cc1cn(-c2ccc(N3C[C@@H](C)O[C@@H](C)C3)cc2)c(=O)c2cccc(-c3ccccn3)c12] | $^1$H NMR (400 MHz, Methanol-$d_4$) δ 8.88 (s, 1H) 8.84-8.85 (d, J = 4.4 Hz, 1H) 8.59-8.62 (t, J = 9.6 Hz, 1H) 8.44-8.46 (d, J = 8.0 Hz, 1H) 7.97-8.00 (d d, J = 6.0 Hz, 1H) 7.64-7.66 (d, J = 4.8 Hz, 2H) 7.28-7.30 (d, J = 8.4 Hz, 2H) 7.17 (s, 1H) 7.08-7.10 (d, J = 8.8 Hz, 1H) 3.77-3.80 (d d, J = 4.4 Hz, 2H) 3.58-3.62 (t, J = 11.6 Hz, 2H) 2.36-2.41 (t, J = 22.4 Hz, 2H) 1.63 (s, 3H) 1.21-1.23 (d, J = 5.6 Hz, 6 H). MS ESI calcd for $C_{27}H_{27}N_3O_2$ [M + H]$^+$ 426, found 426. |

-continued

| Embodiment | Structure | NMR |
|---|---|---|
| 54 | 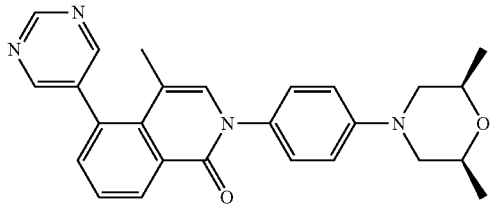 [SMILES: Cc1cn(-c2ccc(N3C[C@@H](C)O[C@@H](C)C3)cc2)c(=O)c2cccc(-c3cncnc3)c12] | ¹H NMR (400 MHz, Methanol-d₄) δ 9.21 (s, 1H) 8.42-8.49 (m, 2H) 7.82-7.84 (t, J = 8.0 Hz, 1H) 7.63-7.64 (d d, J = 4.4 Hz, 2H) 7.30-7.32 (d, J = 8.8 Hz, 2H) 7.24 (s, 1H) 7.05-7.07 (d, J = 8.8 Hz, 2H) 3.81-3.85 (t, J = 14.4 Hz, 2H) 3.60-3.62 (d, J = 11.6 Hz, 2H) 2.49-2.55 (t, J = 22.8 Hz, 2H) 1.64 (s, 3H) 1.23-1.24 (d, J = 6.0 Hz, 6 H). MS ESI calcd for C₂₆H₂₆N₄O₂ [M + H]⁺ 427, found 427. |
| 55 | 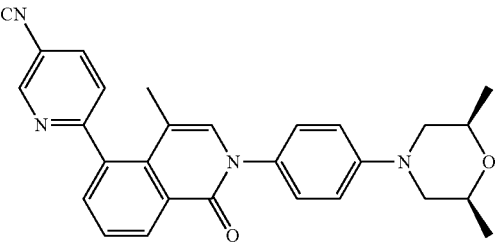 | ¹H NMR (400 MHz, Methanol-d₄) δ 9.11 (s, 1H) 8.83 (s, 2H) 8.57-8.59 (t, J = 6.8 Hz, 1H) 7.64-7.65 (t, J = 6.4 Hz, 2H) 7.34-7.36 (d d, J = 8.8 Hz, 2H) 7.16-7.20 (t, J = 10.8 Hz, 3H) 3.81-3.85 (t, J = 14.4 Hz, 2H) 3.60-3.62 (d, J = 11.6 Hz, 2H) 2.27-2.32 (t, J = 22.0 Hz, 2H) 1.47 (s, 3H) 1.16-1.18 (d, J = 6.0 Hz, 6 H). MS ESI calcd for C₂₈H₂₆N₄O₂ [M + H]⁺ 452, found 452. |
| 56 | 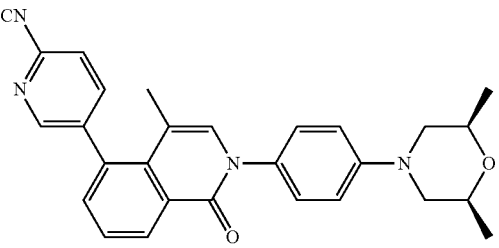 | ¹H NMR (400 MHz, Methanol-d₄) δ 8.72 (s, 1H) 8.56-8.58 (d, J = 7.2 Hz, 1H) 7.94-8.02 (m, 2H) 7.59-7.63 (t, J = 16.4 Hz, 2H) 7.31-7.33 (t, J = 8.8 Hz, 2H) 7.12-7.15 (t, J = 12 Hz, 3H) 3.80-3.84 (t, J = 16.0 Hz, 2H) 3.59-3.62 (d, J = 11.6 Hz, 2H) 2.41-2.47 (t, J = 22.8 Hz, 2H) 1.61 (s, 3H) 1.22-1.23 (d, J = 6.4 Hz, 6 H). MS ESI calcd for C₂₈H₂₆N₄O₂ [M + H]⁺ 452, found 452. |
| 57 | 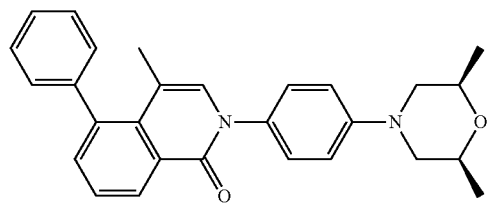 [SMILES: Cc1cn(-c2ccc(N3C[C@@H](C)O[C@@H](C)C3)cc2)c(=O)c2cccc(-c3ccccc3)c12] | ¹H NMR (400 MHz, Methanol-d₄) δ 8.48-8.50 (d d, J = 3.6 Hz, 1H) 7.56-8.57 (d, J = 4.0 Hz, 2H) 7.38-7.40 (m, 5H) 7.31-7.33 (t, J = 6.4 Hz, 2H) 7.23-7.25 (t, J = 9.2 Hz, 2H) 7.05 (s, 1H) 3.84-3.87 (t, J = 14.4 Hz, 2H) 3.61-3.64 (d, J = 11.6 Hz, 2H) 2.57-2.62 (t, J = 22.4 Hz, 2H) 1.62 (s, 3H) 1.24-1.25 (d, J = 6.4 Hz, 6 H). MS ESI calcd for C₂₈H₂₈N₂O₂ [M + H]⁺ 426, found 426. |
| 58 | 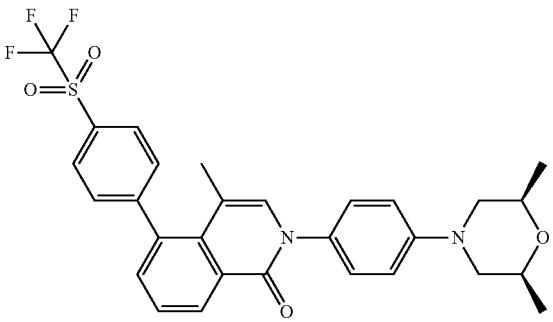 [SMILES: Cc1cn(-c2ccc(N3C[C@@H](C)O[C@@H](C)C3)cc2)c(=O)c2cccc(-c3ccc(S(=O)(=O)C(F)(F)F)cc3)c12] | ¹H NMR (400 MHz, Methanol-d₄) δ 8.56 (s, 1H) 8.14 (s, 2H) 7.78-7.80 (d, J = 5.6 Hz, 2H) 7.61 (s, 2H) 7.32 (m, 2H) 7.13 (m, 3H) 3.84 (m, 2H) 3.61-3.64 (d, J = 11.2 Hz, 2H) 2.44-2.49 (t, J = 20.4 Hz, 2H) 1.60 (s, 3H) 1.23-1.24 (d, J = 6.4 Hz, 6 H). MS ESI calcd for C₂₉H₂₉F₃N₂O₄S [M + H]⁺ 559, found 559. |
| 59 | 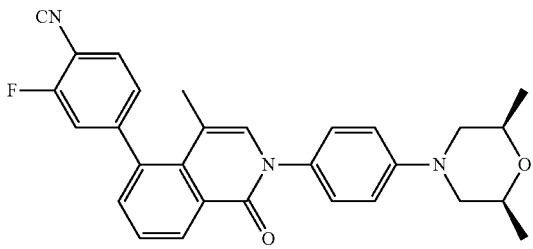 | ¹H NMR (400 MHz, CDCl₃) δ 8.67-8.69 (d, J = 8.0 Hz, 1H) 7.68-7.70 (m, 1H) 7.59-7.61 (m, 1H) 7.47-7.51 (m, 3H) 7.40-7.42 (d, J = 8.4 Hz 2H) 7.25-7.27 (t, J = 9.2 Hz, 2H) 6.97 (s, 1H) 3.61-3.64 (d, J = 10.4 Hz, 2H) 2.75-2.80 (t, J = 22.4 Hz, 2H) 1.68 (s, 3H) 1.30-1.31 (d, J = 6.4 Hz, 6 H). MS ESI calcd for C₂₉H₂₆FN₃O₂ [M + H]⁺ 469, found 469. |

| Embodiment | Structure | NMR |
|---|---|---|
| 60 | 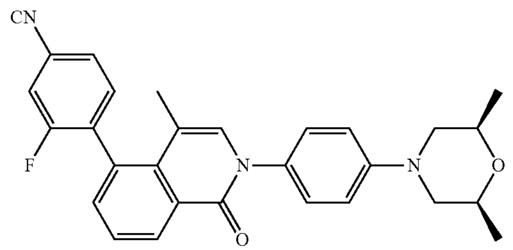 | $^1$H NMR (400 MHz, CDCL$_3$) δ 8.69-8.71 (d, J = 7.6 Hz, 1H) 7.54-7.58 (t, J = 13.2 Hz, 2H) 7.44-7.49 (d d, J = 8.0 Hz, 3H) 7.30-7.32 (d, J = 8.8 Hz, 3H) 6.95-6.99 (t, J = 16.4 Hz, 3H) 3.80-3.83 (d, J = 14.0 Hz, 2H) 3.48-3.51 (d, J = 11.6 Hz, 2H) 2.44-2.49 (t, J = 22.0 Hz, 2H) 1.66 (s, 3H) 1.27-1.28 (d, J = 6.4 Hz, 6 H). MS ESI calcd for C$_{29}$H$_{26}$FN$_3$O$_2$ [M + H]$^+$ 469, found 469. |
| 61 | 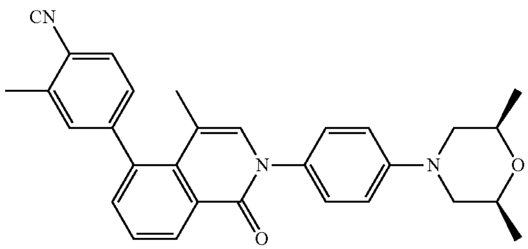 | $^1$H NMR (400 MHz, CDCl$_3$) δ 8.65-8.67 (d, J = 7.2 Hz, 1H) 7.66-7.67 (d, J = 3.6 Hz, 1H) 7.56-7.57 (d, J = 3.2 Hz, 1H) 7.49-7.51 (d, J = 7.2 Hz, 1H) 7.44-7.46 (d, J = 7.6 Hz, 2H) 7.33 (s, 1H) 6.94 (s, 1H) 3.99-4.01 (t, J = 8.0 Hz, 2H) 3.57-3.60 (d, J = 11.6 Hz, 2H) 2.67-2.72 (t, J = 22.4 Hz, 2H) 1.64 (s, 3H) 1.30-1.31 (d, J = 6.0 Hz, 6 H). MS ESI calcd for C$_{30}$H$_{29}$N$_3$O$_2$ [M + H]$^+$ 465, found 465. |
| 62 | 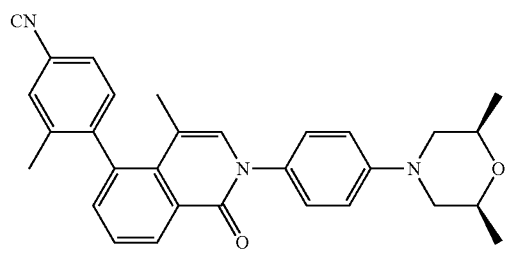 | $^1$H NMR (400 MHz, CDCl$_3$) δ 8.66-8.68 (d, J = 8.0 Hz, 1H) 7.66-7.67 (m, 5H) 7.38-7.47 (m, 3H) 7.27 (s, 1H) 6.93 (s, 1H) 4.08-4.10 (t, J = 8.0 Hz, 2H) 3.63-3.65 (d, J = 11.6 Hz, 2H) 2.79-2.85 (t, J = 22.0 Hz, 2H) 2.10 (s, 3H) 1.57 (s, 3H) 1.31-1.32 (d, J = 6.0 Hz, 6 H). MS ESI calcd for C$_{30}$H$_{29}$N$_3$O$_2$ [M + H]$^+$ 465, found 465. |
| 63 | 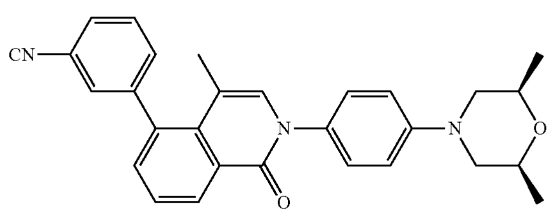 | $^1$H NMR (400 MHz, CDCl$_3$) δ 8.67-8.68 (d, J = 7.2 Hz, 1H) 7.50-7.71 (m, 6H) 7.38-7.40 (d, J = 8.4 Hz, 2H) 7.15-7.17 (d, J = 8.8 Hz, 2H) 6.94 (s, 1H) 3.91-3.95 (t, J = 15.2 Hz, 2H) 3.53-3.55 (d, J = 11.6 Hz, 2H) 2.57-2.62 (t, J = 22.8 Hz, 2H) 1.60 (s, 3H) 1.28-1.30 (d, J = 6.0 Hz, 6 H). MS ESI calcd for C$_{29}$H$_{27}$N$_3$O$_2$ [M + H]$^+$ 451, found 451. |
| 64 | 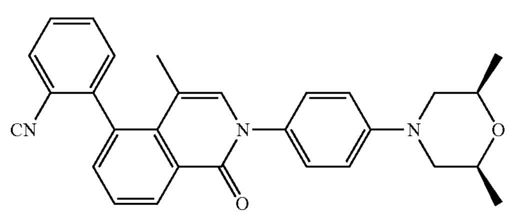 | $^1$H NMR (400 MHz, CDCl$_3$) δ 8.70-8.72 (d, J = 7.6 Hz, 1H) 7.55-7.76 (m, 5H) 7.47-7.49 (t, J = 8.8 Hz, 3H) 7.32-7.34 (d, J = 9.2 Hz, 2H) 6.94 (s, 1H) 4.01-4.04 (t, J = 14.8 Hz, 2H) 3.57-3.60 (d, J = 11.6 Hz, 2H) 2.69-2.75 (m, 2H) 1.60 (s, 3H) 1.29-1.31 (d, J = 6.0 Hz, 6 H). MS ESI calcd for C$_{29}$H$_{27}$N$_3$O$_2$ [M + H]$^+$ 451, found 451. |
| 65 | 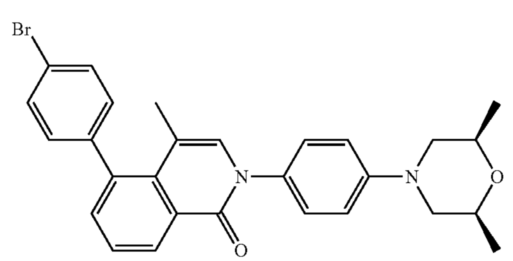 [SMILES: Cc1cn(-c2ccc(N3C[C@@H](C)O[C@@H](C)C3)cc2)c(=O)c2cccc(-c3ccc(Br)cc3)c12] | $^1$H NMR (400 MHz, CDCl$_3$) δ 8.63-8.65 (d, J = 6.0 Hz, 1H) 7.52-7.57 (m, 4H) 7.41-7.43 (d, J = 8.4 Hz, 2H) 7.22-7.24 (d, J = 8.4 Hz, 4H) 6.92 (s, 1H) 3.96-3.99 (t, J = 14.4 Hz, 2H) 3.55-3.57 (d, J = 11.2 Hz, 2H) 2.62-2.67 (t, J = 22.4 Hz, 2H) 1.66 (s, 3H) 1.29-1.31 (d, J = 6.4 Hz, 6 H). MS ESI calcd for C$_{28}$H$_{27}$BrN$_2$O$_2$ [M + H]$^+$ 504, found 504. |

-continued

| Embodiment | Structure | NMR |
|---|---|---|
| 66 | 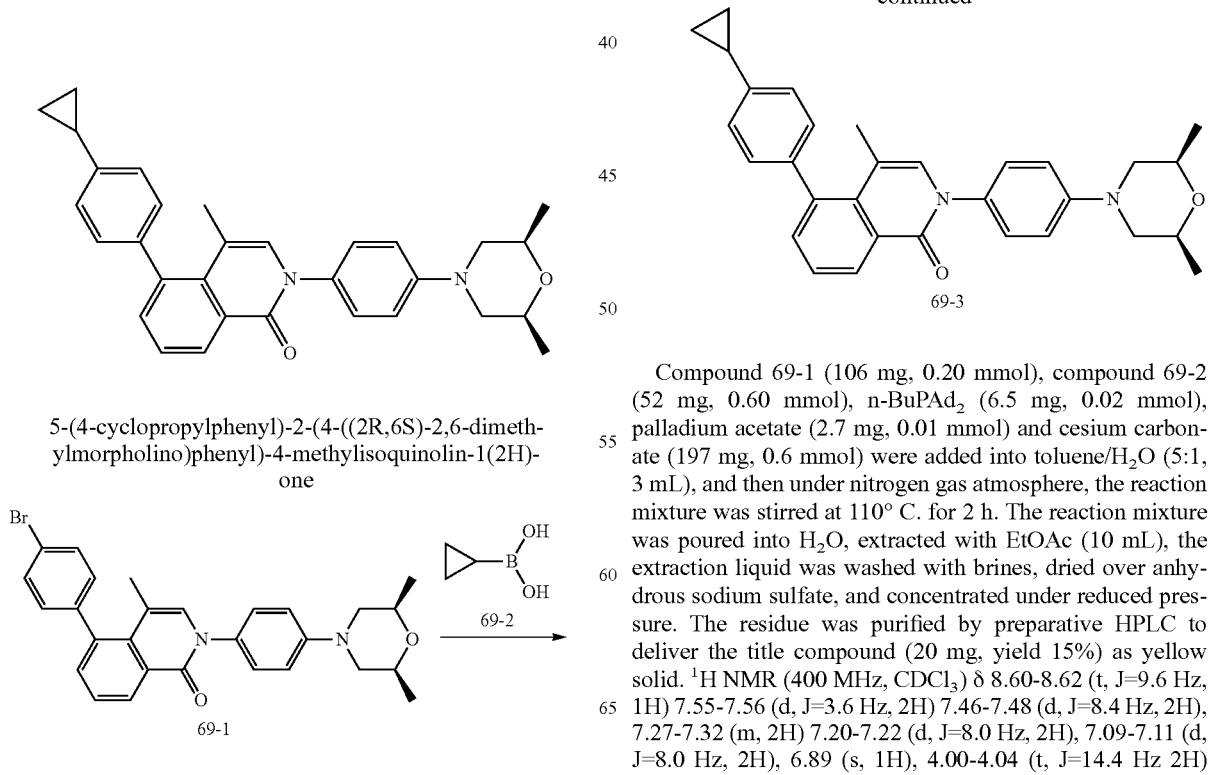 | $^1$H NMR (400 MHz, Methanol-$d_4$) δ 8.44 (d, J = 8.0 Hz, 1H), 8.08 (s, 1H), 7.72 (d, J = 8.4 Hz, 2H), 7.61-7.41 (m, 5H), 7.03 (s, 1H), 6.85 (d, J = 8.8 Hz, 1H), 4.10 d, J = 12.0 Hz, 2H), 3.71-3.15 (m, 2H), 2.44 (t, J = 12.0 Hz, 2H), 1.55 (s, 3H), 1.25-1.08 (m, 6H). MS ESI calcd for $C_{28}H_{36}N_4O_2$ [M + H]$^+$ 451, found 451. |
| 67 | 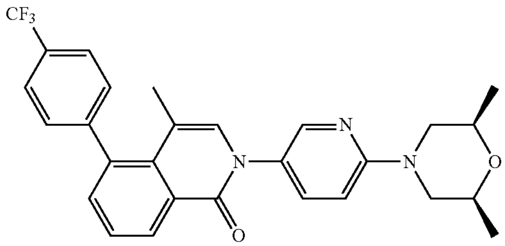 [SMILES: Cc1cn(-c2ccc(N3C[C@@H](C)O[C@@H](C)C3)nc2)c(=O)c2cccc(-c3ccc(C(F)(F)F)cc3)c12] | $^1$H NMR (400 MHz, CDCl$_3$) δ 8.59 (d, J = 7.6 Hz, 1H), 8.28 (s, 1H), 7.99 (d, J = 8.4 Hz, 1H), 7.75-7.41 (m, 6H), 6.93 (d, J = 9.2 Hz, 1H), 6.87 (s, 1H), 4.07 (d, J = 12.4 Hz, 2H), 3.80-3.61 (m, 2H), 2.84 (t, J = 12.0 Hz, 2H), 1.59 (s, 3H), 1.35-1.20 (m, 6H). MS ESI calcd for $C_{28}H_{26}F_3N_3O_2$ [M + H]$^+$ 494, found 494. |
| 68 | 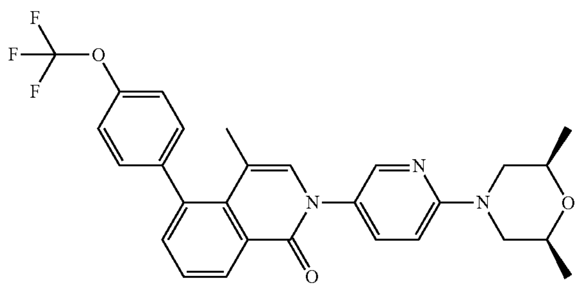 [SMILES: Cc1cn(-c2ccc(N3C[C@@H](C)O[C@@H](C)C3)nc2)c(=O)c2cccc(-c3ccc(OC(F)(F)F)cc3)c12] | $^1$H NMR (400 MHz, Methanol-$d_4$) δ 8.53 (t, J = 4.8 Hz, 1H), 8.20 (s, 1H), 7.90 (d, J = 7.2 Hz, 1H), 7.61 (d, J = 4.0 Hz, 2H), 7.45 (d, J = 8.4 Hz, 2H), 7.35 (d, J = 8.4 Hz, 2H), 7.21 (d, J = 9.6 Hz, 1H), 7.12 (s, 1H), 6.87 (s, 1H), 4.14 (d, J = 12.4 Hz, 2H), 3.81-3.71 (m, 2H), 2.73 (t, J = 12.0 Hz, 2H), 1.67 (s, 3H), 1.27 (d, J = 6.4 Hz, 6H). MS ESI calcd for $C_{28}H_{26}F_3N_3O_3$ [M + H]$^+$ 510, found 510. |

Embodiment 69

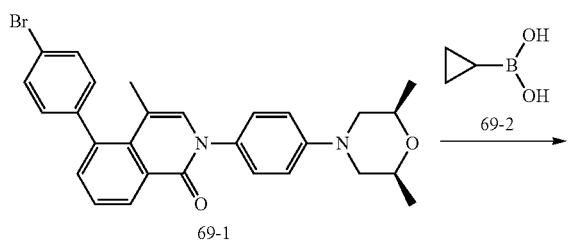

5-(4-cyclopropylphenyl)-2-(4-((2R,6S)-2,6-dimethylmorpholino)phenyl)-4-methylisoquinolin-1(2H)-one Compound 69-1 (106 mg, 0.20 mmol), compound 69-2 (52 mg, 0.60 mmol), n-BuPAd$_2$ (6.5 mg, 0.02 mmol), palladium acetate (2.7 mg, 0.01 mmol) and cesium carbonate (197 mg, 0.6 mmol) were added into toluene/H$_2$O (5:1, 3 mL), and then under nitrogen gas atmosphere, the reaction mixture was stirred at 110° C. for 2 h. The reaction mixture was poured into H$_2$O, extracted with EtOAc (10 mL), the extraction liquid was washed with brines, dried over anhydrous sodium sulfate, and concentrated under reduced pressure. The residue was purified by preparative HPLC to deliver the title compound (20 mg, yield 15%) as yellow solid. $^1$H NMR (400 MHz, CDCl$_3$) δ 8.60-8.62 (t, J=9.6 Hz, 1H) 7.55-7.56 (d, J=3.6 Hz, 2H) 7.46-7.48 (d, J=8.4 Hz, 2H), 7.27-7.32 (m, 2H) 7.20-7.22 (d, J=8.0 Hz, 2H) 7.09-7.11 (d, J=8.0 Hz, 2H), 6.89 (s, 1H), 4.00-4.04 (t, J=14.4 Hz 2H)

3.57-3.60 (t, J=11.2 Hz, 2H) 2.68-2.73 (t, J=22.4 Hz, 2H), 1.96-1.98 (m, 1H), 1.66 (s, 3H), 1.30-1.31 (d, J=6.0 Hz, 6H), 1.03-1.05 (m, 2H), 0.77-0.79 (m, 2H). MS ESI calcd for $C_{31}H_{32}N_2O_2$ [M+H]$^+$ 465, found 465.

Embodiment 70

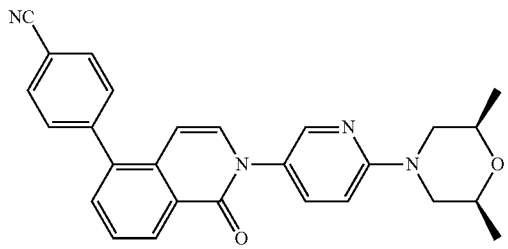 [SMILES: C[C@@H]1CN(c2ccc(-n3ccc4c(-c5ccc(C#N)cc5)cccc4c3=O)cn2)C[C@H](C)O1]

4-(2-(6-(2,6-dimethylmorpholino-4-yl)pyridin-3-yl)-1-oxo-1,2-dihydroisoquinolin-5-yl)benzonitrile

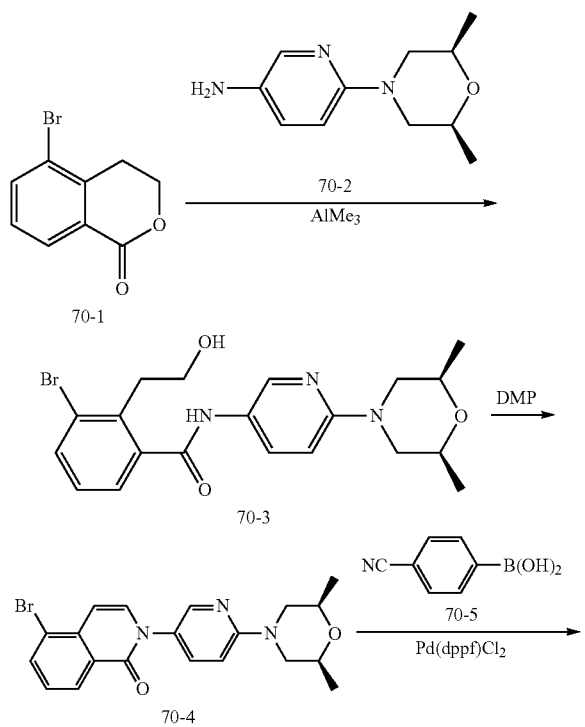

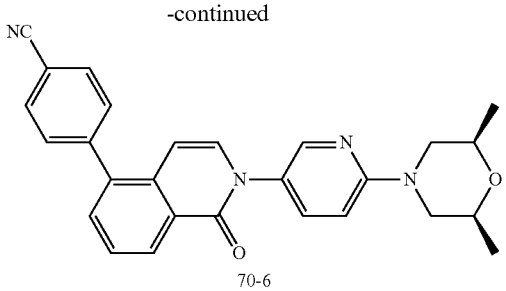

70-6

Step 1: A solution of trimethyl aluminum (2 mol/L, 3.85 mL) in toluene was added into a solution of compound 70-2 in dry DCM (20 mL) at 0° C., the reaction mixture was stirred at room temperature for 15 min. Then a solution of compound 70-1 (0.7 g, 3.1 mmol) in DCM (5 mL) was added dropwise, and the obtained solution was stirred at room temperature for 3 h. After the reaction was complete as detected by LCMS, Rochelle salt solution was added. The obtained mixture was extracted with DCM, washed with brines, dried over anhydrous sodium sulfate, and concentrated under reduced pressure. The residue was purified by silica gel column chromatography (PE/EtOAc=5:1) to deliver compound 70-3 (1.1 g, 85%) as yellow solid. MS ESI calcd for $C_{20}H_{24}BrN_3O_3$ [M+H]$^+$ 435, found 435.

Step 2: Dess-Martin periodinane (507 mg, 1.2 mmol) was added into a solution of compound 70-3 (434 mg, 1 mmol) in dry DCM (20 mL) at 0° C. The reaction mixture was stirred at room temperature overnight. Then the reaction mixture were quenched with saturated sodium thiosulfate aqueous solution and extracted with DCM, the organic phase was dried over anhydrous sodium sulfate and concentrated under reduced pressure. The residue was purified by silica gel column chromatography (PE/EtOAc=5:1) to deliver compound 70-4 (320 mg, 77%) as yellow solid. MS ESI calcd for $C_{20}H_{20}BrN_3O_2$ [M+H]$^+$ 415, found 415.

Step 3: Under nitrogen gas atmosphere, compound 70-5 (53 mg, 0.36 mmol), sodium carbonate (51 mg, 0.48 mmol) and Pd(dppf)Cl$_2$ (18 mg, 0.024 mmol) were added into a solution of compound 70-4 (0.10 g, 0.24 mmol) in 1,4-dioxane (5 mL) and H$_2$O (1 mL). Then the reaction mixture was heated to reflux and stirred overnight. After the reaction was complete, the residue was purified by preparative HPLC to deliver the title compound (56 mg, 53%) as white solid. $^1$H NMR (400 MHz, CDCl$_3$) δ 8.43 (d, J=8.0 Hz, 1H), 8.18 (d, J=2.0 Hz, 1H), 7.90-7.82 (m, 3H), 7.75-7.61 (m, 4H), 7.32 (d, J=8.0 Hz, 1H), 7.16 (d, J=8.8 Hz, 1H), 6.60 (d, J=7.6 Hz, 1H), 4.13 (d, J=12.8 Hz, 2H), 3.75-3.71 (m, 2H), 2.68 (t, J=12.0 Hz, 2H), 1.24 (d, J=5.6 Hz, 6H). MS ESI calcd for $C_{27}H_{24}N_4O_2$ [M+H]$^+$ 437, found 437.

The compounds listed in table 5 can be synthesized by compound 70-4 and corresponding boric acids.

| Embodiment | Structure | NMR |
|---|---|---|
| 71 | CF$_3$ (structure shown) | $^1$H NMR (400 MHz, CDCl$_3$) δ 8.42 (d, J = 8.0 Hz, 1H), 8.19 (s, 1H), 7.90-7.80 (m, 3H), 7.75-7.60 (m, 3H), 7.32 (d, J = 8.0 Hz, 1H), 7.20 (d, J = 8.8 Hz, 1H), 6.61 (d, J = 7.6 Hz, 1H), 4.13 (d, J = 12.4 Hz, 2H), 3.75-3.71 (m, 2H), 2.71 (t, J = 12.0 Hz, 2H), 1.24 (d, J = 5.6 Hz, 6H). MS ESI calcd for $C_{27}H_{24}F_3N_3O_2$ [M + H]$^+$ 480, found 480. |

-continued

| Embodi-ment | Structure | NMR |
|---|---|---|
| 72 | 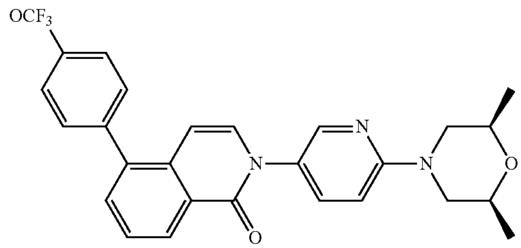 [SMILES: C[C@@H]1CN(c2ccc(-n3ccc4c(-c5ccc(OC(F)(F)F)cc5)cccc4c3=O)cn2)C[C@H](C)O1] | $^1$H NMR (400 MHz, CDCl$_3$) δ 8.40 (d, J = 8.0 Hz, 1H), 8.19 (s, 1H), 7.92-7.82 (m, 1H), 7.70 (d, J = 8.0 Hz, 1H), 7.65-7.60 (m, 1H), 7.50 (d, J = 8.0 Hz, 2H), 7.43 (d, J = 8.0 Hz, 2H), 7.31 (d, J = 8.0 Hz, 1H), 7.21 (d, J = 8.8 Hz, 1H), 6.61 (d, J = 7.6 Hz, 1H), 4.11 (d, J = 12.4 Hz, 2H), 3.70-3.61 (m, 2H), 2.72 (t, J = 12.0 Hz, 2H), 1.22 (d, J = 5.6 Hz, 6H). MS ESI calcd for C$_{27}$H$_{24}$F$_3$N$_3$O$_3$ [M + H]$^+$ 496, found 496. |
| 73 | 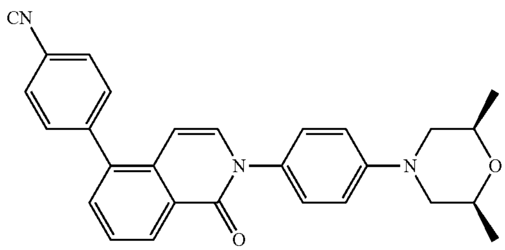 | $^1$H NMR (400 MHz, Methanol-d$_4$) δ 8.42-8.44 (d, J = 8.0 Hz, 1H) 7.85-7.87 (m, 2H), 7.61-7.71 (m, 4H) 7.29-7.34 (m, 3H) 7.15-7.17 (d, J = 8.4 Hz, 2H), 6.56-6.58 (d, J = 8.0 Hz, 1H), 3.79-3.83 (t, J = 14.4 Hz, 2H) 3.58-3.61 (t, J = 11.6 Hz, 2H) 2.46-2.51 (t, J = 22.4 Hz, 2H), 1.21-1.23 (d, J = 6.4 Hz, 6 H). MS ESI calcd for C$_{28}$H$_{25}$N$_3$O$_2$ [M + H]$^+$ 436, found 436. |
| 74 | 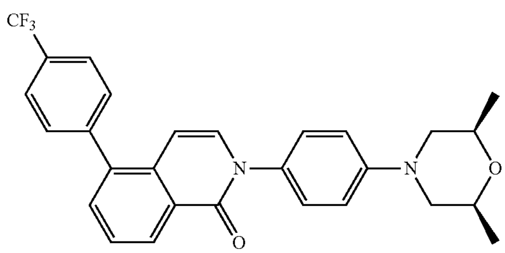 | $^1$H NMR (400 MHz, Methanol-d$_4$) δ 8.40-8.42 (d, J = 8.0 Hz, 1H) 7.61-7.85 (m, 6H), 7.27-7.33 (d d, J = 8.0 Hz, 3H) 7.13-7.15 (d, J = 9.2 Hz, 2H), 6.56-6.58 (d, J = 8.0 Hz, 1H), 3.79-3.83 (t, J = 14.4 Hz, 2H) 3.58-3.61 (t, J = 11.6 Hz, 2H) 2.44-2.50 (t, J = 22.0 Hz, 2H), 1.21-1.23 (d, J = 6.0 Hz, 6 H). MS ESI calcd for C$_{28}$H$_{25}$F$_3$N$_2$O$_2$ [M + H]$^+$ 479, found 479. |
| 75 | 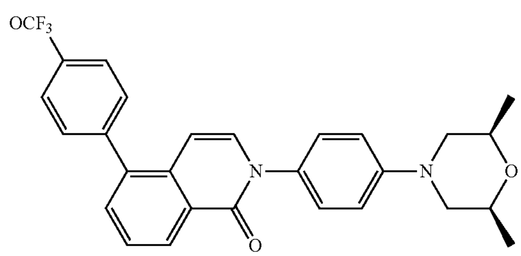 [SMILES: C[C@@H]1CN(c2ccc(-n3ccc4c(-c5ccc(OC(F)(F)F)cc5)cccc4c3=O)cc2)C[C@H](C)O1] | $^1$H NMR (400 MHz, Methanol-d$_4$) δ 8.39-8.41 (d, J = 8.4 Hz, 1H) 7.52-7.67 (m, 4H), 7.39-7.41 (m, J = 8.0 Hz, 2H) 7.28-7.33 (m, 3H), 7.12-7.15 (d, J = 9.6 Hz, 2H), 6.59-6.61 (d, J = 8.0 Hz, 1H), 3.78-3.82 (t, J = 14.4 Hz 2H) 3.58-3.61 (t, J = 11.6 Hz, 2H) 2.43-2.48 (t, J = 22.4 Hz, 2H), 1.21-1.23 (d, J = 6.4 Hz, 6 H). MS ESI calcd for C$_{28}$H$_{25}$F$_3$N$_2$O$_3$ [M + H]$^+$ 495, found 495. |

Embodiment 76

4-(4-chloro-2-(3-chloro-4-((2S,6R)-2,6-dimethyl-morpholino)phenyl)-1-oxo-1,2-dihydroisoquinolin-5-yl)benzonitrile

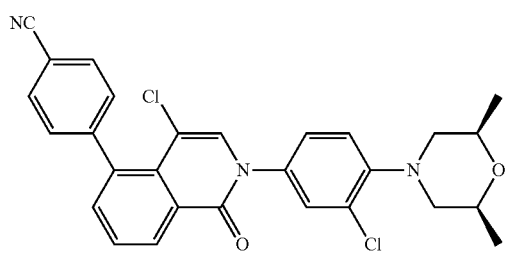 [SMILES: C[C@@H]1CN(c2ccc(-n3cc(Cl)c4c(-c5ccc(C#N)cc5)cccc4c3=O)cc2Cl)C[C@H](C)O1]

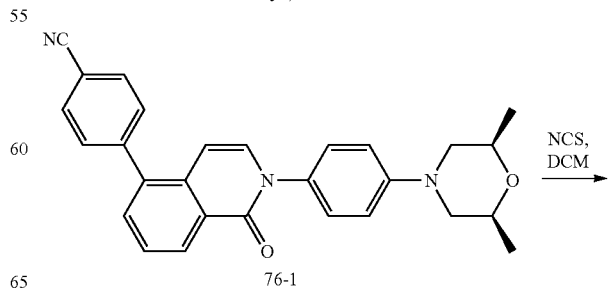

76-1

NCS, DCM

-continued

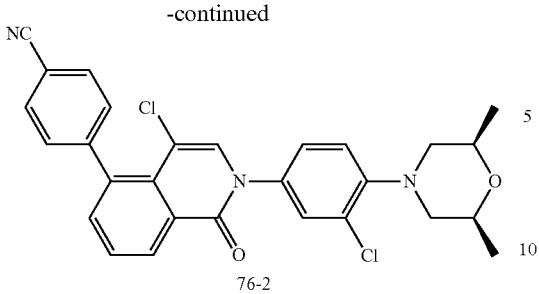

76-2

NCS (48 mg, 0.36 mmol) was added into a solution of compound 76-1 (100 mg, 0.24 mmol) in dry DCM (10 mL). Then the reaction mixture was stirred at room temperature overnight. After the reaction was complete, the residue was purified by preparative HPLC to deliver the title compound as white solid. $^1$H NMR (400 MHz, CDCl$_3$) δ 8.65 (d, J=8.0 Hz, 1H), 7.70 (d, J=8.4 Hz, 2H), 7.50-7.68 (m, 2H), 7.40-7.49 (m, 3H), 7.27-7.35 (m, 2H), 7.12 (d, J=8.0 Hz, 1H), 3.85-4.00 (m, 2H), 3.20-3.35 (m, 2H), 2.40-2.55 (m, 2H), 1.25 (s, 3H), 1.24 (s, 3H). MS ESI calcd for C$_{28}$H$_{27}$N$_5$O [M+H]$^+$ 450, found 450.

Embodiments 77, 78

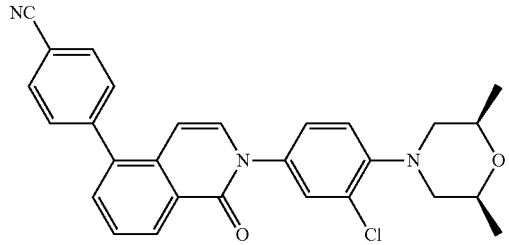

4-(2-(3-chloro-4-((2S,6R)-2,6-dimethylmorpholino)phenyl)-1-oxo-1,2-dihydroisoquinolin-5-yl)benzonitrile

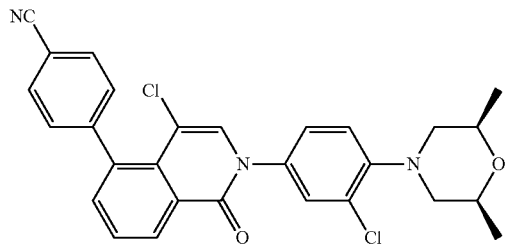

4-(4-chloro-2-(3-chloro-4-((2S,6R)-2,6-dimethylmorpholino)phenyl)-1-oxo-1,2-dihydroisoquinolin-5-yl)benzonitrile

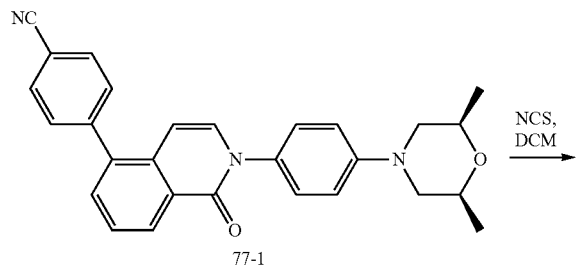

77-1

-continued

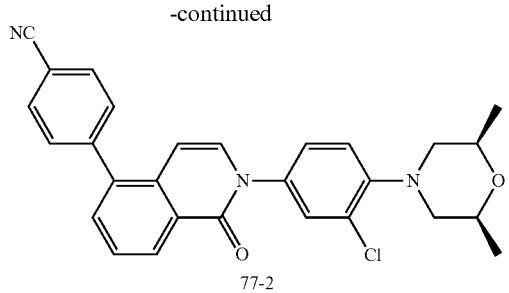

77-2

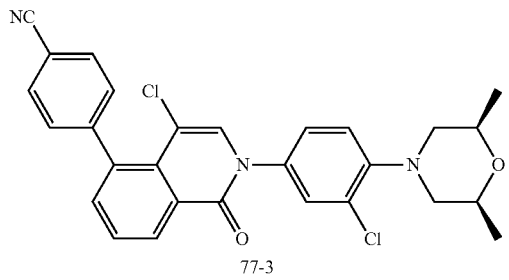

77-3

NCS (48 mg, 0.36 mmol) was added into a solution of compound 77-1 (100 mg, 0.24 mmol) in DCM (10 mL) in portions, and then the reaction mixture was stirred at room temperature overnight and the solvent was evaporated, the residue was purified by preparative HPLC to deliver the title compound of embodiment 77 as yellow solid. $^1$H NMR (400 MHz, CDCl$_3$) δ 8.57-8.59 (d, J=8.0 Hz, 1H) 7.80-7.82 (d, J=8.0 Hz, 2H) 7.63-7.64 (t, J=6.4 Hz, 2H), 7.56-7.58 (t, J=8.0 Hz, 2H), 7.46 (s, 1H) 7.29-7.34 (m, 1H) 7.12-7.14 (d, J=8.4 Hz, 2H), 6.52-6.54 (d, J=8.0 Hz, 1H), 3.93-3.95 (t, J=14.4 Hz 2H) 3.27-3.30 (t, J=10.8 Hz, 2H) 2.47-2.53 (t, J=23.2 Hz, 2H), 1.24-1.26 (d, J=6.0 Hz, 6H). MS ESI calcd for C$_{28}$H$_{24}$ClN$_3$O$_2$ [M+H]$^+$ 471, found 471. At the same time, the title compound of embodiment 78 was isolated as yellow solid. $^1$H NMR (400 MHz, Methanol-d$_4$) δ 8.64-8.66 (d, J=7.2 Hz, 1H) 7.57-7.71 (m, 4H), 7.44-7.47 (d d, J=8.0 Hz, 3H) 7.31 (s, 1H), 7.11-7.13 (d, J=8.0 Hz, 1H), 3.89-3.93 (t, J=14.4 Hz 2H), 3.26-3.29 (t, J=11.6 Hz, 2H) 2.44-2.50 (t, J=21.6 Hz, 2H), 1.24-1.26 (d, J=6.0 Hz, 6H). MS ESI calcd for C$_{28}$H$_{23}$Cl$_2$N$_3$O$_2$ [M+H]$^+$ 505, found 505.

Embodiment 79

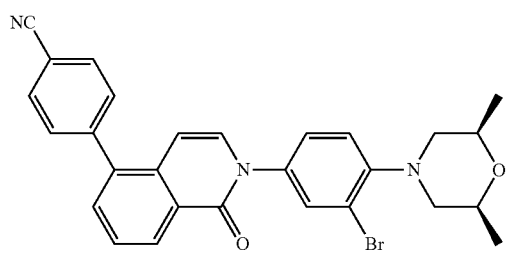 [SMILES: C[C@@H]1CN(c2ccc(-n3ccc4c(-c5ccc(C#N)cc5)cccc4c3=O)cc2Cl)C[C@H](C)O1]

4-(2-(3-bromo-4-((2S,6R)-2,6-dimethylmorpholino)phenyl)-1-oxo-1,2-dihydroisoquinolin-5-yl)benzonitrile

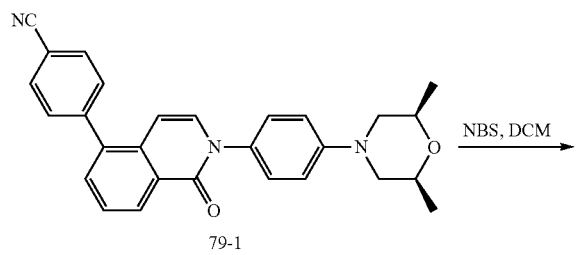

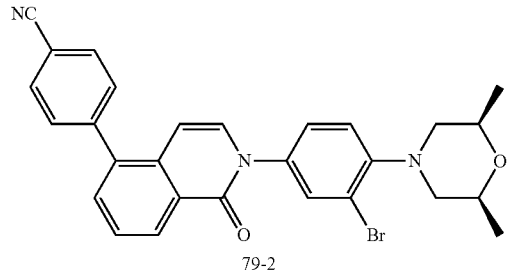

NBS (43 mg, 0.24 mmol) was added into a solution of compound 79-1 (100 mg, 0.24 mmol) in DCM (10 mL) in portions, then the reaction mixture was stirred at room temperature overnight and the solvent was evaporated, the residue was purified by preparative HPLC to deliver the title compound (20 mg, yield 25%) as white solid. $^1$H NMR (400 MHz, Methanol-$d_4$) δ 8.43-8.45 (d, J=7.6 Hz, 1H) 7.87-7.89 (d, J=8.4 Hz, 2H), 7.64-7.71 (m, 5H), 7.24-7.40 (m, 3H), 6.58-6.60 (d, J=7.6 Hz, 2H), 3.87-3.91 (t, J=14.4 Hz 2H), 2.42-2.47 (t, J=22.4 Hz, 2H), 1.18-1.20 (d, J=6.4 Hz, 6H). MS ESI calcd for $C_{28}H_{24}BrN_3O_2$ [M+H]$^+$ 515, found 515.

Embodiment 80

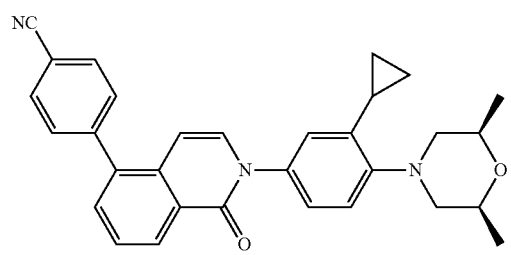 [SMILES: C[C@@H]1CN(c2ccc(-n3ccc4c(-c5ccc(C#N)cc5)cccc4c3=O)cc2C2CC2)C[C@H](C)O1]

4-(2-(3-cyclopropyl-4-((2S,6R)-2,6-dimethylmorpholino)phenyl)-1-oxo-1,2-dihydroisoquinolin-5-yl)benzonitrile

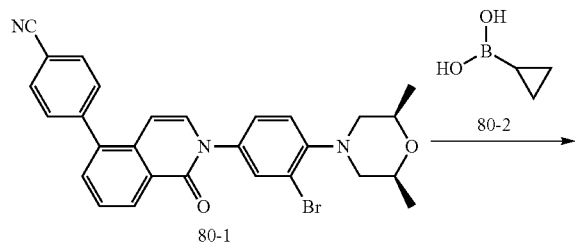

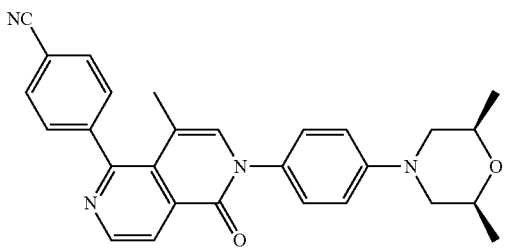

Compound 80-1 (100 mg, 0.19 mmol), 80-2 (49 mg, 0.57 mmol), n-BuPAd$_2$ (7.2 mg, 0.02 mmol), palladium acetate (3 mg, 0.01 mmol) and cesium carbonate (187 mg, 0.57 mmol) were added into toluene/H$_2$O (5:1, 3 mL), then under nitrogen gas atmosphere, the reaction mixture was stirred at 110° C. for 2 h. The reaction mixture was poured into H$_2$O, extracted with EtOAc (10 mL), the extraction liquid was washed with brines, dried over anhydrous sodium sulfate, and concentrated under reduced pressure. The residue was purified by preparative HPLC to deliver the title compound (250 mg, yield 20%) as yellow solid. $^1$H NMR (400 MHz, CDCl$_3$) δ 8.57-8.59 (t, J=9.2 Hz, 1H) 7.80-7.82 (d, J=8.0 Hz, 2H) 7.57-7.63 (m, 4H), 7.11-7.18 (m, 3H) 6.83-6.84 (d, J=1.6 Hz, 1H), 6.50-6.52 (d, J=7.6 Hz, 1H), 3.94-3.98 (t, J=14.4 Hz 2H) 3.27-3.30 (t, J=10.8 Hz, 2H) 2.55-2.60 (t, J=21.6 Hz, 2H), 2.29-2.34 (m, 2H), 1.24-1.26 (d, J=6.4 Hz, 6H), 1.03-1.05 (m, 2H), 0.75-0.76 (m, 2H). MS ESI calcd for $C_{31}H_{29}N_3O_2$ [M+H]$^+$ 476, found 476.

Embodiment 81

4-(6-(4-((2S,6R)-2,6-dimethylmorpholino)phenyl)-8-methyl-5-oxo-5,6-dihydro-2,6-naphthyridin-1-yl)benzonitrile

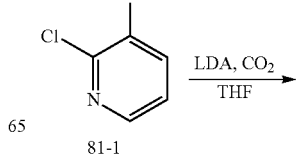

-continued

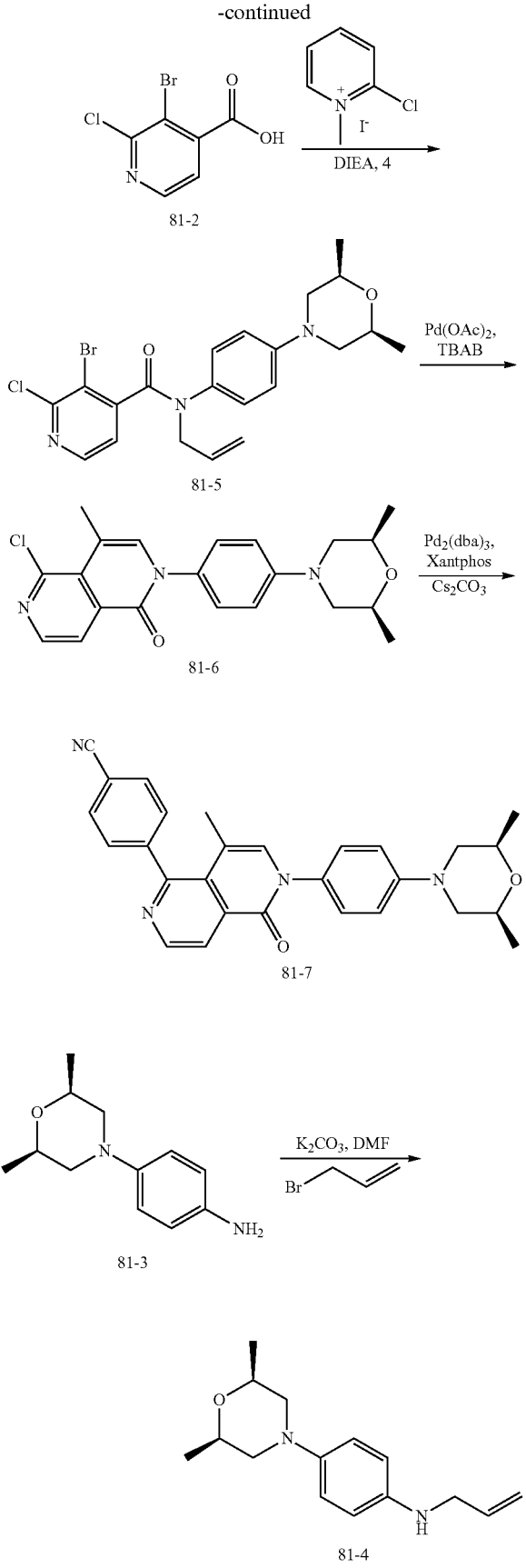

Step 1: LDA (60 mL, 0.12 mol) was dripped into a solution of compound 81-1 (20 g, 0.1 mol) in THF (200 mL) at −78° C., the reaction mixture was stirred at −78° C. for 2 h. The reaction mixture was poured into dry ice quickly. Then the mixture was stirred at room temperature for 30 min, and quenched with $H_2O$ in the end. The aqueous phase was extracted with EtOAc. The combined organic phase was washed with brines, dried over sodium sulfate, and concentrated under reduced pressure to deliver compound 81-2 (10 g, yield 43%) as white-off solid. MS ESI calcd for $C_6H_3BrClNO_2$ $[M+H]^+$ 236, found 236.

Step 2: A mixture of compound 81-3 (5 g, 24.3 mmol), allyl bromide (2.1 g, 17 mmol) and $K_2CO_3$ (6.7 g, 48.6 mmol) was added into DMF (50 mL), the reaction mixture was stirred at 80° C. for 5 h. The reaction mixture was poured into $H_2O$. The aqueous phase was extracted with EtOAc. The combined organic phase was washed with brines, dried over sodium sulfate, and concentrated under reduced pressure. The obtained crude product was purified by silica gel chromatography (PE:EtOAc=15:1) to deliver compound 81-4 (2.5 g, yield 42%) as brown solid. MS ESI calcd for $C_{15}H_{22}N_2O$ $[M+H]^+$ 247, found 247.

Step 3: CMPI (2.2 g, 8.9 mmol) was added into a solution of compound 81-2 (2.1 g, 8.9 mmol), compound 81-4 (2.2 g, 8.9 mmol) and DIEA (2.3 g, 17.8 mmol) in acetonitrile (20 mL). The reaction mixture was stirred at room temperature for 16 h. The crude product was used for the next step directly. MS ESI calcd for $C_{21}H_{23}BrClN_3O_2$ $[M+H]^+$ 464, found 464.

Step 4: Compound 81-5 (4.1 g, 8.9 mmol), tetra-butyl ammonium bromide (7.2 g, 22.3 mmol), palladium acetate (200 mg, 0.89 mmol) and TEA (2.7 g, 26.7 mmol) in acetonitrile (40 mL) were heated to reflux and stirred for 48 h. The reaction mixture was poured into $H_2O$. The aqueous phase was extracted with EtOAc. The combined organic phase was washed with brines, dried over anhydrous sodium sulfate, and concentrated under reduced pressure. The residue was purified by silica gel chromatography (PE: EtOAc=2:1) to deliver compound 81-6 (1 g, yield 30%) as brown solid. MS ESI calcd for $C_{21}H_{22}ClN_3O_2$ $[M+H]^+$ 384, found 384.

Step 5: Compound 81-6 (100 mg, 0.26 mmol), 4-cyanophenyl boronic acid (45.6 mg, 0.31 mmol), $Pd_2(dba)_3$ (24 mg, 0.026 mmol), Xantphos (25 mg, 0.052 mmol) and cesium carbonate (171 mg, 0.52 mmol) were added into dioxane (5 mL) and the mixture was heated to reflux, then stirred for 16 h. The crude product was purified by preparative HPLC to deliver the title compound as white solid. $^1$H NMR (400 MHz, DMSO-$d_6$) δ 8.79 (d, J=5.6 Hz, 1H), 7.77 (d, J=8.0 Hz, 2H), 7.67 (d, J=5.2 Hz, 1H), 7.61 (s, 1H), 7.54 (d, J=8.0 Hz, 2H), 7.17 (d, J=8.4 Hz, 2H), 6.97 (d, J=8.8 Hz, 2H), 3.45-3.52 (m, 4H), 2.15-2.30 (m, 4H), 1.13 (s, 3H), 1.11 (s, 3H). MS ESI calcd for $C_{28}H_{26}N_4O_2$ $[M+H]^+$ 451, found 451.

The compounds listed in table 6 can be synthesized by compound 81-6 and corresponding boric acids.

| Embodiment | structure | NMR |
|---|---|---|
| 82 | 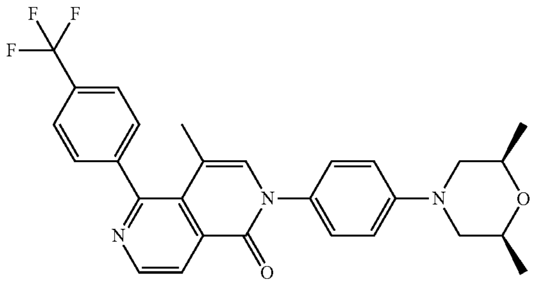 [SMILES: Cc1cn(-c2ccc(N3C[C@@H](C)O[C@@H](C)C3)cc2)c(=O)c2ccnc(-c3ccc(C(F)(F)F)cc3)c12] | $^1$H NMR (400 MHz, DMSO-d$_6$) δ 8.79 (d, J = 5.6 Hz, 1H), 7.64-7.63 (m, 3H), 7.52-7.62 (m, 3H), 7.17 (d, J = 8.8 Hz, 2H), 6.97 (d, J = 8.8 Hz, 2H), 3.40-3.50 (m, 4H), 2.15-2.35 (m, 5H), 1.20 (s, 3H), 1.13 (s, 3H). MS ESI calcd for C$_{28}$H$_{26}$F$_3$N$_3$O$_2$ [M + H]$^+$ 494, found 494. |
| 83 | 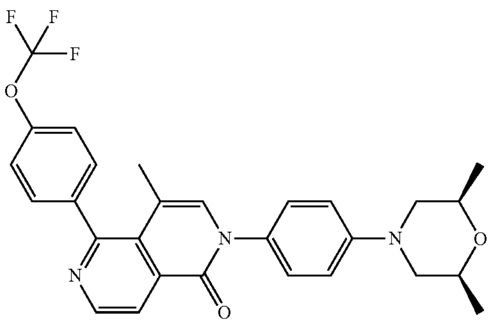 [SMILES: Cc1cn(-c2ccc(N3C[C@@H](C)O[C@@H](C)C3)cc2)c(=O)c2ccnc(-c3ccc(OC(F)(F)F)cc3)c12] | $^1$H NMR (400 MHz, DMSO-d$_6$) δ 8.77 (d, J = 5.6 Hz, 1H), 7.67 (d, J = 5.6 Hz, 1H), 7.62 (s, 1H), 7.50 (d, J = 8.0 Hz, 2H), 7.30 (d, J = 8.4 Hz, 2H), 7.18 (d, J = 8.4 Hz, 2H), 6.98 (d, J = 9.2 Hz, 2H), 3.40-3.50 (m, 4H), 2.15-2.33 (m, 5H), 1.13 (s, 3H), 1.11 (s, 3H). MS ESI calcd for C$_{28}$H$_{26}$F$_3$N$_3$O$_3$ [M + H]$^+$ 510, found 510. |
| 84 | 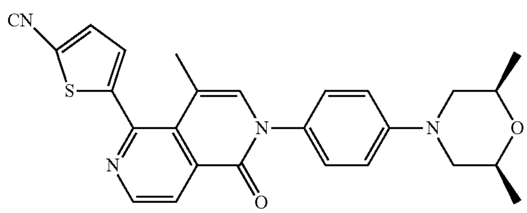 | $^1$H NMR (400 MHz, DMSO-d$_6$) δ 8.75 (d, J = 5.2 Hz, 1H), 7.84 (d, J = 8.0 Hz, 1H), 7.58-7.70 (m, 3H), 7.25 (d, J = 9.2 Hz, 2H), 7.01 (d, J = 8.8 Hz, 2H), 3.60-3.70 (m, 4H), 2.19-2.35 (m, 5H), 1.14 (s, 3H), 1.13 (s, 3H). MS ESI calcd for C$_{26}$H$_{24}$N$_4$O$_2$S [M + H]$^+$ 457, found 457. |

Embodiment 85

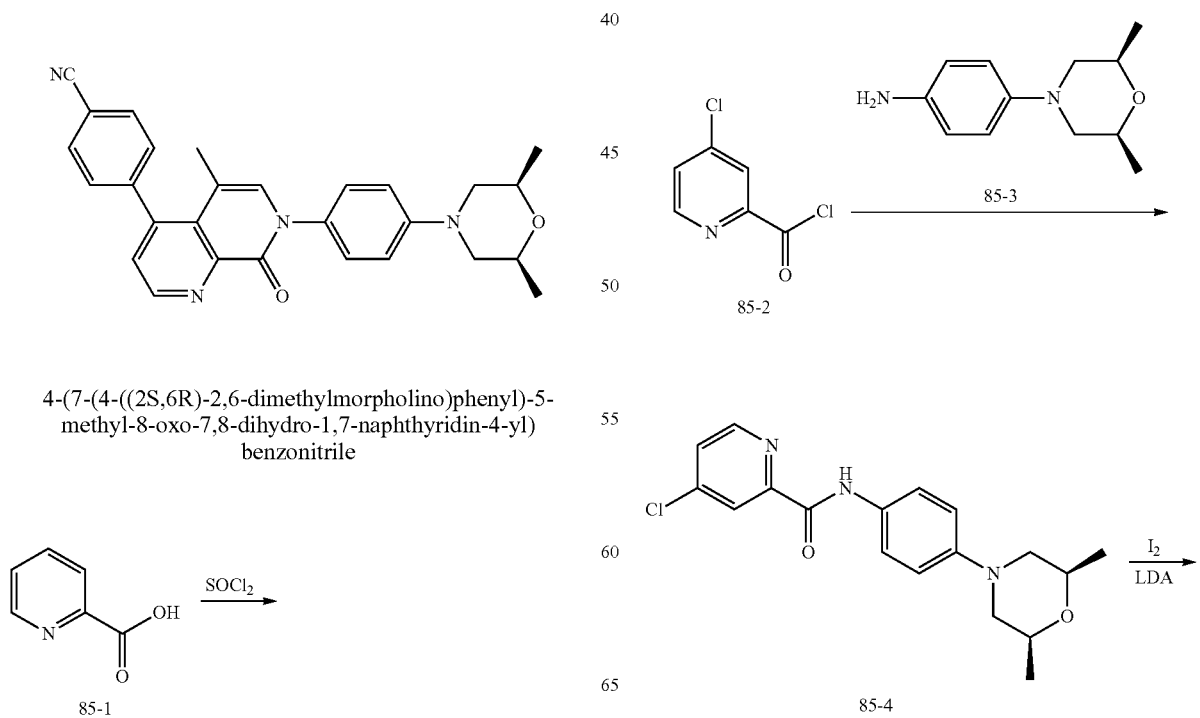

4-(7-(4-((2S,6R)-2,6-dimethylmorpholino)phenyl)-5-methyl-8-oxo-7,8-dihydro-1,7-naphthyridin-4-yl)benzonitrile

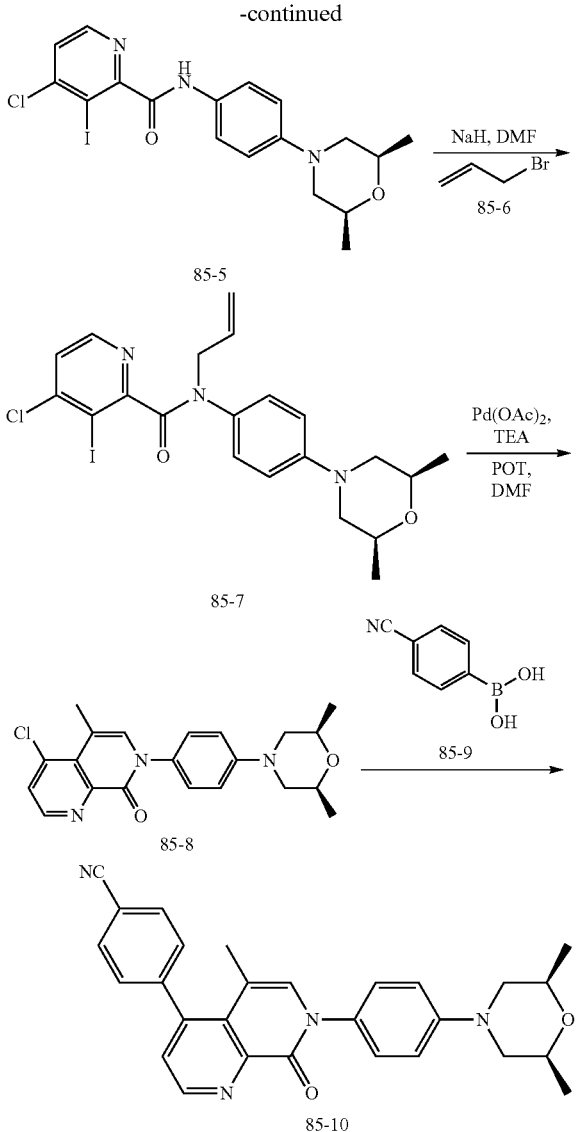

Step 1: Compound 85-1 (4.3 g, 35 mmol), DMF (0.5 mL) and thionyl chloride (13 mL, 181 mmol) were stirred at 80° C. for 12 h. The reaction mixture was concentrated to dry under reduced pressure to deliver compound 85-2 (6.1 g, yield 100%) as brown solid. MS ESI calcd for $C_6H_3Cl_2NO$ $[M+H]^+$ 176, found 176.

Step 2: Compound 85-2 (6.1 g, 35 mmol) was added into a solution of compound 85-3 (6 g, 29.1 mmol) in DCM (60 mL) at 0° C. After the addition, the reaction mixture was stirred at room temperature for 3 h. The reaction mixture was poured into $H_2O$ (200 mL), and the precipitate was collected by filtration. The filtrate cake was dissolved in EtOAc, dried over sodium sulfate, filtrated and concentrated to dry. In the end, the residue was purified by silica gel chromatography (PE:EtOAc=2:1) to deliver compound 85-4 (5.6 g, yield 56%) as white solid. MS ESI calcd for $C_{18}H_{20}ClN_3O_2$ $[M+H]^+$ 346, found 346.

Step 3: Under nitrogen gas atmosphere, LDA (22 mL, 43.5 mmol) was added into a solution of compound 85-4 (5 g, 14.5 mmol) in THF (20 mL) at −78° C. After 30 min, a solution of $I_2$ (5.5 g, 22.7 mmol) in THF (20 mL) was added into the solution. The obtained reaction mixture was stirred at −78° C. for further 2 h. Then the reaction mixture was poured into $H_2O$, extracted with EtOAc, the organic phases were combined and washed with brines, dried over anhydrous sodium sulfate, filtrated and concentrated under reduced pressure. The residue was purified by silica gel chromatography (PE:EtOAc=2:1) to deliver compound 85-5 (5 g, yield 74%) as yellow solid. MS ESI calcd for $C_{18}H_{19}ClIN_3O_2$ $[M+H]^+$ 472, found 472.

Step 4: NaH (848 mg, 21.2 mmol, containing 40% mineral oil) was added into a solution of compound 85-5 (5 g, 10.6 mmol) in DMF at 0° C. The reaction mixture was stirred under nitrogen gas atmosphere for 10 min. Compound 85-6 (2.56 g, 21.2 mmol) was added into the solution, and the obtained mixture was stirred at 0° C. for further 2 h. Then the reaction mixture was poured into $H_2O$, extracted with EtOAc. The combined organic phase was washed with brines, dried over anhydrous sodium sulfate, filtrated and concentrated under reduced pressure to deliver compound 85-7 (5.3 g, yield 99%) as white solid. MS ESI calcd for $C_{21}H_{23}ClIN_3O_2$ $[M+H]^+$ 512, found 512.

Step 5: Compound 85-7 (5.4 g, 10.6 mmol), palladium acetate (237 mg, 1.06 mmol), TEA (2.1 g, 21.2 mmol) and POT (322 mg, 1.06 mmol) were added into DMF (40 mL) and the reaction mixture was stirred at 120° C. for 12 h. The reaction mixture was poured into $H_2O$, extracted with EtOAc. The combined organic phase was washed with brines, dried over anhydrous sodium sulfate, filtrated and concentrated, finally purified by silica gel chromatography (PE:EtOAc=1:1) to deliver compound 85-8 (3 g, yield 75%) as white-off solid. MS ESI calcd for $C_{21}H_{22}ClN_3O_2$ $[M+H]^+$ 384, found 384.

Step 6: Compound 85-8 (300 mg, 0.78 mmol), compound 85-9 (160 mg, 1.09 mmol), $K_3PO_4$ (413 mg, 1.95 mmol), Pd(dppf)$Cl_2$ (57 mg, 0.078 mmol) were added into DMF (5 mL), and then under nitrogen gas atmosphere, the mixture was stirred at 120° C. for 12 h. The reaction mixture was poured into $H_2O$, extracted with EtOAc. The combined organic phase was washed with brines, dried over anhydrous sodium sulfate, filtrated and concentrated, purified by preparative HPLC to deliver the title compound (75 mg, yield 21%) as white solid. MS ESI calcd for $C_{28}H_{26}N_4O_2$ $[M+H]^+$ 451, found 451.

Embodiment 86

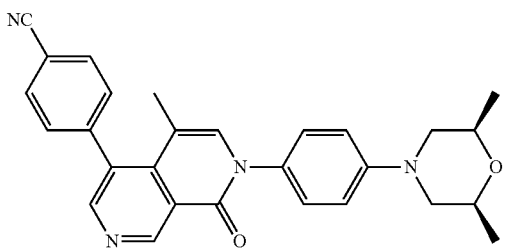

4-(7-(4-((2S,6R)-2,6-dimethylmorpholino)phenyl)-5-methyl-8-oxo-7,8-dihydro-2,7-naphthyridin-4-yl)benzonitrile

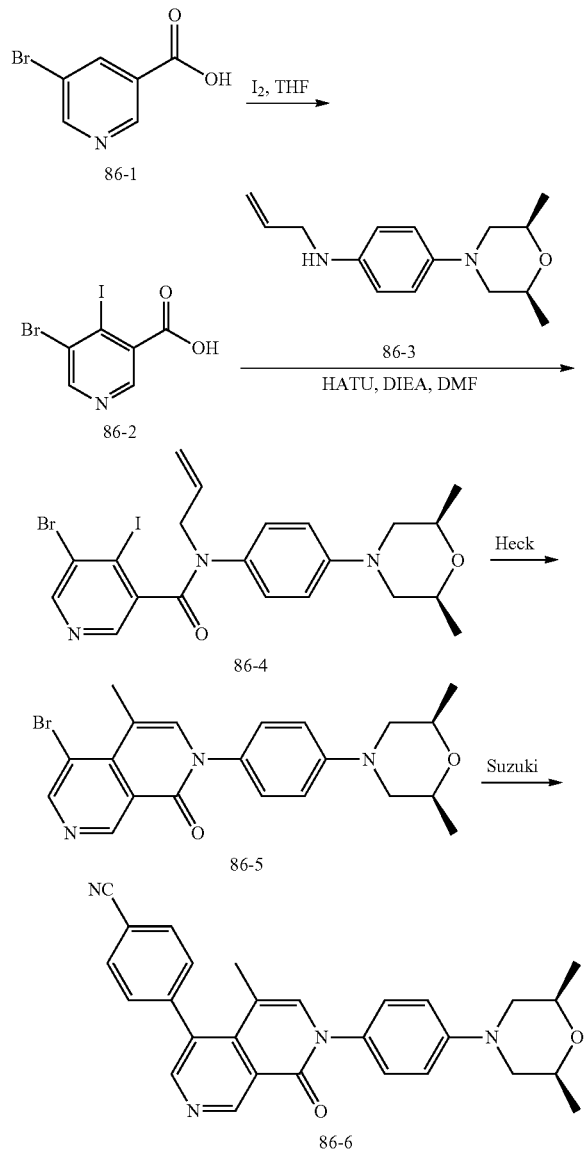

Step 1: Under nitrogen gas atmosphere, n-butyl lithium (1.8 mL, 4.4 mmol) was added dropwise into a solution of 2,2,6,6-tetramethyl piperidine (0.81 mL, 4.8 mmol) in THF (10 mL) at −50° C. After 5 min, 5-bromonicotinic acid (0.40 g, 2.0 mmol) was added. After 30 min, a solution of $I_2$ (0.61 g, 2.4 mmol) in THF (5 mL) was added dropwise at −50° C. The obtained reaction mixture was stirred at −50° C. for 2 h. The reaction mixture was quenched with $H_2O$ (10 mL), the aqueous phase was separated and extracted with $Et_2O$ (10 mL), then the aqueous phase was acidified with 1 M hydrochloric acid to pH=3. The precipitate was filtrated and the filtrate cake was dried to deliver compound 86-2 as beige powder. MS ESI calcd for $C_6H_3BrINO_2$ [M+H]$^+$ 328, found 328.

Step 2: Compound 86-2 (650 mg, 25 mmol), compound 86-3 (500 mg, 2 mmol), HATU (770 mg, 2 mmol) and DIEA (2 mL) were added into DMF (10 mL), and the mixture was stirred at 20° C. for 4 h. The reaction mixture was poured into $H_2O$, and extracted with EtOAc. The combined organic phase was dried over sodium sulfate. After concentration, the residue was purified by silica gel chromatography to deliver compound 86-4 (yield 70%) as white-off solid. MS ESI calcd for $C_{21}H_{23}BrIN_3O_2$ [M+H]$^+$ 556, found 556.

Step 3: Compound 86-5 as white solid was synthesized according to the method previously described. MS ESI calcd for $C_{21}H_{22}BrN_3O_2$ [M+H]$^+$ 428, found 428.

Step 4: The title compound (yield 48%) as white solid was synthesized according to the method previously described. $^1$H NMR (400 MHz, CDCl$_3$) δ 9.66 (s, 1H), 8.56 (s, 1H), 7.72 (d, J=8.4 Hz, 2H), 7.44 (d, J=8.4 Hz, 2H), 7.23 (d, J=8.4 Hz, 2H), 6.95 (d, J=8.8 Hz, 2H), 3.55-3.75 (m, 3H), 3.40-3.50 (m, 2H), 2.35-2.50 (m, 2H), 1.57 (s, 3H), 1.22 (s, 3H), 1.21 (s, 3H). MS ESI calcd for $C_{28}H_{26}N_4O_2$ [M+H]$^+$ 451, found 451.

Embodiment 87

4-(2-(4-((2S,6R)-2,6-dimethylmorpholino)phenyl)-4-methyl-1-oxo-1,2,3,4-tetrahydroisoquinolin-5-yl)benzonitrile

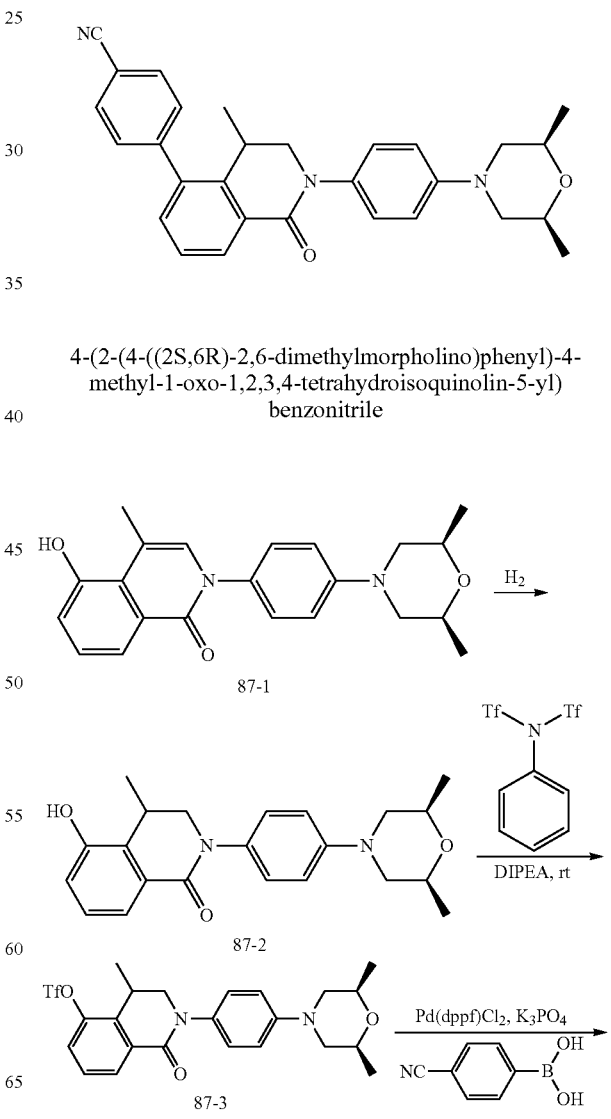

-continued

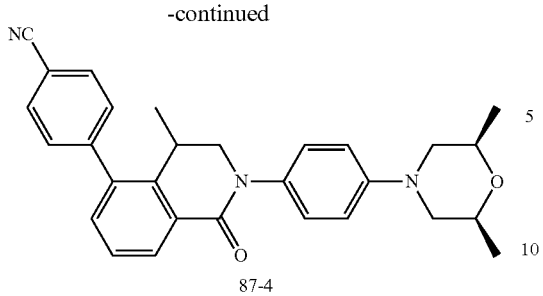

87-4

Step 1: 10% Pd/C (50 mg, 50% wet) was added into a solution of compound 87-1 (500 mg, 1.37 mmol) in MeOH (50 mL). Then under a hydrogen gas pressure of 55 psi, the reaction mixture was stirred at 40° C. for 48 h. After the reaction was complete, the reaction mixture was filtrated with diatomite, and the filtrate was concentrated under reduced pressure to deliver compound 87-2 (400 mg, yield 80%) as white solid. MS ESI calcd for $C_{22}H_{26}N_2O_3$ [M+H]$^+$ 367, found 367.

Step 2: Compound 87-3 (150 mg, yield 30%) as white-off solid was synthesized according to the method previously described. MS ESI calcd for $C_{22}H_{26}N_2O_3$ [M+H]$^+$ 499, found 499.

Step 3: The title compound as white solid was synthesized according to the method previously described. $^1$H NMR (400 MHz, CDCl$_3$) δ 8.25 (d, J=7.6 Hz, 1H), 7.78 (d, J=8.4 Hz, 2H), 7.35-7.56 (m, 8H), 4.33 (dd, J=8.4, 3.6 Hz, 1H), 4.06-4.16 (m, 2H), 3.50-3.57 (m, 3H), 3.07-3.16 (m, 1H), 2.75-2.85 (m, 2H), 1.31 (s, 3H), 1.30 (s, 3H), 1.24 (d, J=6.8 Hz, 1H). MS ESI calcd for $C_{29}H_{29}N_3O_2$ [M+H]$^+$ 452, found 452.

Embodiment 88

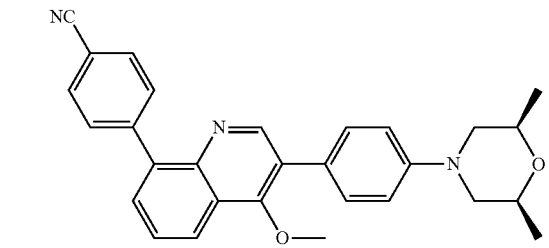 [SMILES: COc1c(-c2ccc(N3C[C@@H](C)O[C@@H](C)C3)cc2)cnc2c(-c3ccc(C#N)cc3)cccc12]

4-(3-(4-((2S,6R)-2,6-dimethylmorpholino)phenyl)-4-methoxyquinolin-8-yl) benzonitrile

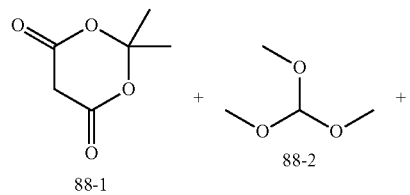

88-1   88-2

-continued

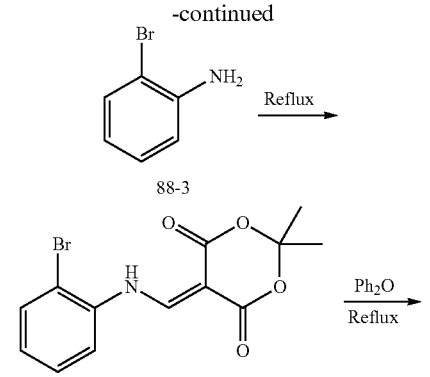

88-3

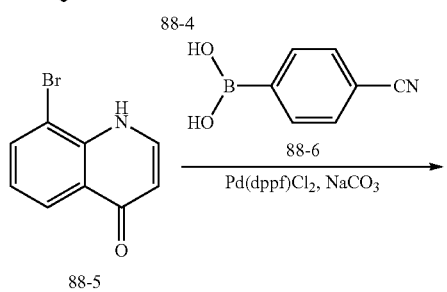

88-4

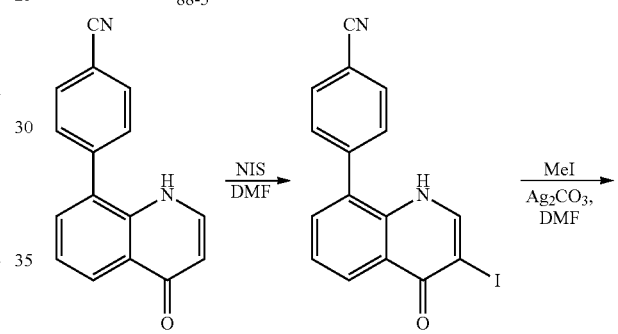

88-5    88-6

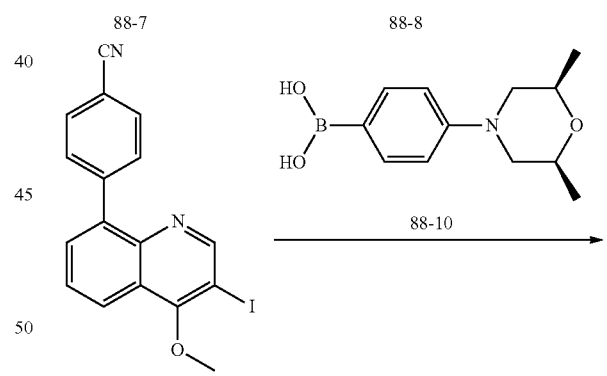

88-7    88-8

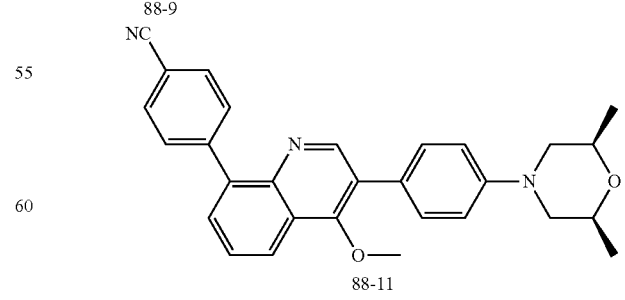

88-9    88-10    88-11

Step 1: Compound 88-1 (50 g, 350 mmol) was added into compound 88-2 (170 mL, 1 mol), then the reaction system was heated to reflux for 3 h. After the reaction system was cooled to room temperature, compound 88-3 (48 g, 280 mmol) was added. The reaction mixture was stirred for 12 h, monitored by LC-MS until the reaction was complete. Then the system was concentrated, the residue was washed with MeOH, dried to deliver light yellow compound 88-4 (80 g, 90%). MS ESI calcd for $C_{13}H_{12}BrNO_4$ [M+H]$^+$ 326, found 326.

Step 2: Compound 88-4 (80 g, 245 mmol) was dissolved in Ph$_2$O (560 mL), then the mixture was heated to reflux for 1 h. After the reaction was complete as monitored by LC-MS, 560 mL n-hexane was added into the solution in portions to deliver the product. The product was washed with n-hexane, dried under reduced pressure to deliver compound 88-5 (48 g, 87%) as gray solid. MS ESI calcd for $C_9H_6BrNO$ [M+H]$^+$ 225, found 225.

Step 3: Compound 88-5 (20 g, 89 mmol), compound 88-6 (14.4 g, 98 mmol), Pd(dppf)Cl$_2$ (6.5 g, 8.9 mmol) and Na$_2$CO$_3$ (18.8 g, 178 mmol) were dissolved in DMF (200 mL), and 40 mL H$_2$O was added into the solution. The reaction system reacted at 90° C. overnight. After the reaction was complete as monitored by LC-MS, the reaction system was poured into 500 mL H$_2$O, filtrated to deliver brown solid (19 g, 87%). MS ESI calcd for $C_{16}H_{10}N_2O$ [M+H]$^+$ 247, found 247.

Step 4: NIS (17.4 g, 77.2 mmol) was added into a solution of 88-7 (19 g, 77.2 mmol) in DMF (200 mL) in portions. The reaction system was stirred at room temperature for 3 h. The reaction was monitored by LC-MS and TLC until completion. The solution was poured into H$_2$O (500 mL), filtrated to deliver brown residue. The residue was washed with MeOH, and recrystallized with PE:EtOAc=1:1 to deliver the target compound 88-8 (25 g, 87%) as brown solid. MS ESI calcd for $C_{16}H_9IN_2O$ [M+H]$^+$ 373, found 373.

Step 5: Compound 88-8 (15 g, 40.3 mmol) and Ag$_2$CO$_3$ (25 g, 80.6 mmol) were dissolved in DMF (150 mL). Then MeI (3.8 mL, 60.5 mmol) was added into the reaction system. The reaction was stirred at 80° C. for 3 h. The reaction was monitored by LC-MS until completion, the reaction mixture was added into H$_2$O and extracted with EtOAc. The organic phases were combined and washed with brines, dried over anhydrous sodium sulfate, filtrated and concentrated to dry. The crude product was purified by column chromatography (PE:EtOAc=10:1) to deliver white compound 88-9 (3 g, 19%). MS ESI calcd for $C_{17}H_{11}IN_2O$ [M+H]$^+$ 387, found 387.

Step 5: Compound 88-9 (200 mg, 0.52 mmol), compound 88-13 (246 mg, 1.04 mmol), Pd(dppf)Cl$_2$ (38 mg, 0.052 mmol) and Na$_2$CO$_3$ (110 mg, 1.04 mmol) were dissolved in THF (5 mL) and H$_2$O (1 mL). The mixture was stirred at 60° C. overnight. The reaction was monitored by LC-MS until completion. The reaction system was extracted with EtOAc, the organic phases were combined and washed with brines, dried over anhydrous sodium sulfate, filtrated concentrated, the crude product was purified by preparative chromatography to deliver the title compound as light yellow solid (23 mg, yield 10%). $^1$H NMR (400 MHz, CDCl$_3$) δ 8.89 (s, 1H), 8.33-8.31 (m, 1H), 7.84-7.56 (m, 8H), 7.04 (d, J=8.8 Hz, 2H), 3.86-3.82 (m, 2H), 3.70 (s, 3H), 3.57 (d, J=11.2 Hz, 2H), 2.51 (t, J=11.2 Hz, 2H), 1.30 (d, J=6.0 Hz, 6H). MS ESI calcd for $C_{29}H_{27}N_3O_2$ [M+H]$^+$ 450, found 450.

Embodiment 89

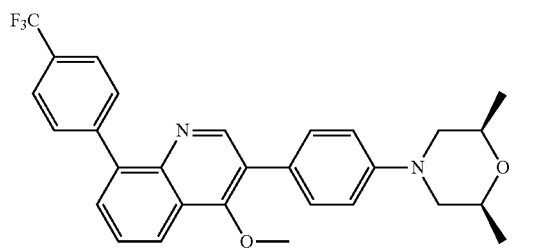

(2R,6S)-4-(4-(4-methoxy-8-(4-(trifluoromethyl)phenyl)quinolin-3-yl)phenyl)-2,6-dimethylmorpholine

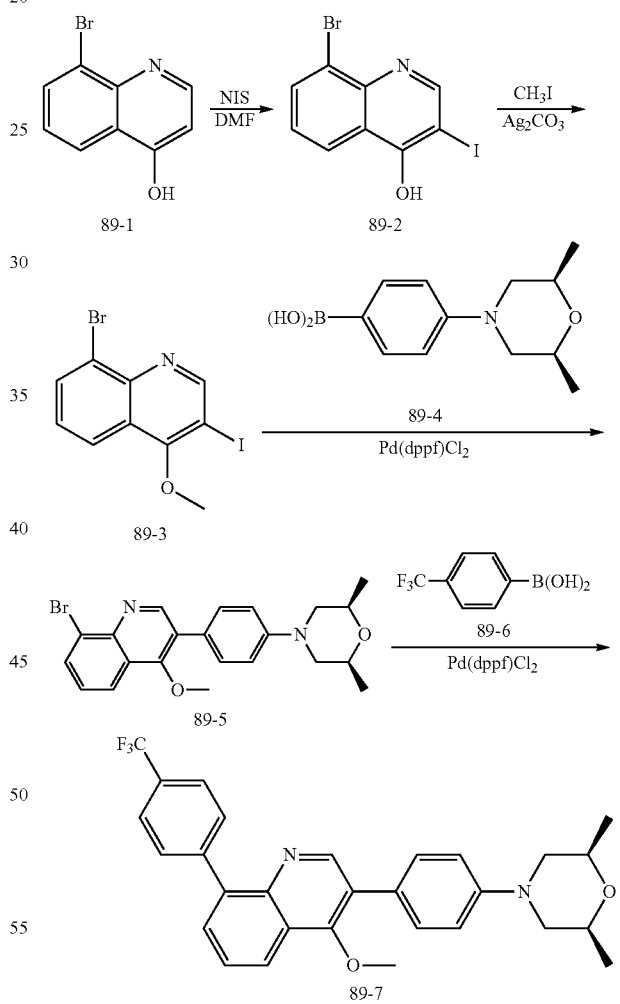

Step 1: NIS (3.8 g, 22 mmol) was added into a solution of compound 89-1 (4.9 g, 22 mmol) in DMF (40 mL) in portions. The reaction mixture was stirred at room temperature for 2 h. After the reaction was complete as detected by LC-MS, the reaction mixture was poured into H$_2$O (500 mL). The product 89-2 was obtained by filtration (5.5 g, 71%) as brown solid. MS ESI calcd for $C_9H_5BrINO$ [M+H]$^+$ 350, found 350.

Step 2: CH₃I (1.2 g, 8.7 mmol) was added into a solution of compound 89-2 (2.0 g, 5.8 mmol) and Ag₂CO₃ (2.4 g, 8.7 mmol) in DMF (20 mL). The reaction mixture was stirred at 60° C. for 2 h. After the reaction was complete as detected by LC-MS, the reaction mixture was poured into H₂O, then extracted with EtOAc (80×3 mL), the organic phase was dried over anhydrous sodium sulfate. After concentration, the crude product was further purified by column chromatography (PE:EtOAc=5:1) to deliver compound 89-3 (464 mg, 22%) as white solid. MS ESI calcd for $C_{10}H_7BrINO$ [M+H]⁺ 364, found 364.

Step 3: Compound 89-3 (1089 mg, 3 mmol), compound 89-4 (1050 mg, 3.3 mmol), Pd(dppf)Cl₂ (110 mg, 0.15 mmol) and Na₂CO₃ (636 mg, 6 mmol) were added into THF (20 mL)/H₂O (2 mL), under nitrogen gas atmosphere, the reaction mixture was stirred at 60° C. overnight. After the reaction was complete, the mixture was filtrated, the filtrate was extracted with EtOAc, the organic phase was washed with brines, dried over anhydrous sodium sulfate, concentrated under reduced pressure to deliver crude product 4 (140 mg, 11%) as white solid. MS ESI calcd for $C_{22}H_{23}BrN_2O_2$ [M+H]⁺ 427, found 427.

Step 4: Compound 89-5 (70 mg, 0.16 mmol), compound 89-6 (46 mg, 0.24 mmol) were added into a solution of Pd(dppf)Cl₂ (15 mg, 0.02 mmol), Na₂CO₃ (34 mg, 0.32 mmol) in THF (10 mL)/H₂O (1 mL), under nitrogen gas atmosphere, the reaction mixture was stirred at 80° C. overnight. After the reaction was complete, the mixture was filtrated, the filtrate was extracted with EtOAc, the organic phase was washed with brines, dried over anhydrous sodium sulfate, concentrated under reduced pressure to deliver the title compound (35 mg, 45%) as light yellow solid. ¹H NMR (400 MHz, CDCl₃) δ 8.91 (s, 1H), 8.32-8.30 (m, 1H), 7.83-7.57 (m, 8H), 7.04 (d, J=8.8 Hz, 2H), 3.84-3.83 (m, 2H), 3.71 (s, 3H), 3.57 (d, J=11.2 Hz, 2H), 2.51 (t, J=11.2 Hz, 2H), 1.30 (d, J=6.0 Hz, 6H). MS ESI calcd for $C_{29}H_{27}F_3N_2O_2$ [M+H]⁺ 493, found 493.

The compounds listed in table 7 were synthesized by compound 89-5 and corresponding boric acids.

| Embodiment | Strucuture | NMR |
|---|---|---|
| 90 | (F, Cl substituted phenyl–quinoline–OMe–phenyl–dimethylmorpholine) | ¹H NMR (400 MHz, CDCl₃) δ 8.91 (s, 1H), 8.30-8.28 (m, 1H), 7.80-7.58 (m, 6H), 7.24 (s, 1H), 7.06-7.03 (d, J = 12 Hz, 2H), 3.87-3.83 (m, 2H), 3.71 (s, 3H), 3.60-3.57 (d, J = 12 Hz, 2 H), 2.55-2.49 (m, 2H), 1.32-1.30 (d, J = 8 Hz, 6H). MS ESI calcd for $C_{28}H_{26}ClFN_2O_2$ [M + H]⁺ 477, found 477. |
| 91 | (OCF₃-phenyl–quinoline–OMe–phenyl–dimethylmorpholine) | ¹H NMR (400 MHz, CDCl₃) δ 8.91 (s, 1H), 8.30-8.28 (d, J = 8 Hz, 1H), 7.77-7.60 (m, 6H), 7.58-7.34 (m, 2H), 7.06-7.03 (d, J = 12 Hz, 2H), 3.87-3.85(d, J = 8 Hz, 2 H), 3.71 (s, 3H), 3.60-3.57 (d, J = 12 Hz, 2 H), 2.55-2.49 (m, 2H), 1.32-1.30 (d, J = 8 Hz, 6H). MS ESI calcd for $C_{29}H_{27}F_3N_2O_3$ [M + H]⁺ 509, found 509. |
| 92 | (MeSO₂-phenyl–quinoline–OMe–phenyl–dimethylmorpholine) | ¹H NMR (400 MHz, CDCl₃) δ 8.93 (s, 1H), 8.36 (m, 1H), 8.09-8.07 (m, 2H), 7.96-7.94 (d, J = 8.5 Hz, 2H), 7.74-7.60 (m, 3H), 7.07-7.05 (d, J = 8.8 Hz, 2H), 3.88-3.84 (m, 2H), 3.74 (s, 2H), 3.61-3.58 (m, 2H), 3.15 (s, 3H), 2.56-2.50 (m, 2H) 1.32-1.31 (m, 6H). MS ESI calcd for $C_{28}H_{28}N_2O_3S$ [M + H]⁺ 473, found 473. |

-continued

| Embodiment | Structure | NMR |
|---|---|---|
| 93 | 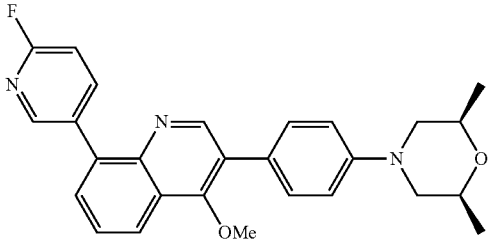 [SMILES: COc1c(-c2ccc(N3C[C@@H](C)O[C@@H](C)C3)cc2)cnc2c(-c3ccc(F)nc3)cccc12] | $^1$H NMR (400 MHz, CDCl$_3$) δ 8.89 (s, 1H), 8.52 (d, J = 2.0 Hz, 1H), 8.32 (dd, J = 1.4, 8.2 Hz, 1H), 8.23 (dt, J = 2.4, 8.1 Hz, 1H), 7.75-7.69 (m, 1H), 7.68-7.62 (m, 1H), 7.59 (d, J = 8.8 Hz, (2H), 7.12-6.98 (m, 3H), 3.91-3.76 (m, 2H), 3.71 (s, 3H), 3.58 (d, J = 11.0 Hz, 2H), 2.52 (t, J = 11.2 Hz, 2H), 1.35-1.21 (m, 6H). MS ESI calcd for C$_{27}$H$_{26}$FN$_3$O$_2$ [M + H]$^+$ 444, found 444. |
| 94 | 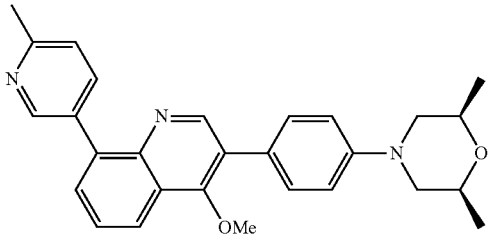 [SMILES: COc1c(-c2ccc(N3C[C@@H](C)O[C@@H](C)C3)cc2)cnc2c(-c3ccc(C)nc3)cccc12] | $^1$H NMR (400 MHz, CDCl$_3$) δ 8.91 (s, 1H), 8.83 (d, J = 1.8 Hz, 1H), 8.35-8.28 (m, 1H), 8.02 (dd, J = 2.1, 7.9 Hz, 1H), 7.73 (d, J = 5.8 Hz, 1H), 7.70-7.57 (m, 2H), 7.32 (d, J = 8.0 Hz, 1H), 7.06 (d, J = 8.8 Hz, 1H), 3.89-3.82 (m, 1H), 3.73 (s, 2H), 3.59 (d, J = 10.8 Hz, 1H), 2.67 (s, 2H), 2.53 (t, J = 11.2 Hz, 1H), 1.32 (d, J = 6.3 Hz, 6H). MS ESI calcd for C$_{28}$H$_{29}$N$_3$O$_2$ [M + H]$^+$ 440, found 440. |
| 95 | 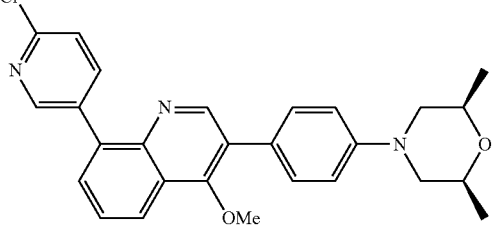 | $^1$H NMR (400 MHz, CDCl$_3$) δ 8.89 (S, 1H), 8.70 (s, 1H), 8.34-8.32 (d, J = 7.9 Hz, 1H), 8.11-8.09 (d, J = 7.1 Hz, 1H), 7.72-7.71 (d, J = 5.7 Hz, 1H), 7.67-7.65 (d, J = 7.5 Hz, 1H), 7.59(s, 1H), 7.57 (s, 2H), 7.47-7.45 (d, J = 7.9 Hz, 1 H), 7.05-7.03(d, J = 7.5 Hz, 2H), 3.85 (s, 2H), 3.71(s, 3H), 3.59-3.57 (d, J = 11.5 Hz, 2H), 2.54-2.49 (t, 2H), 1.31-1.30 (d, J = 5.3 Hz, 6H). MS ESI calcd for C$_{27}$H$_{26}$ClN$_3$O$_2$ [M + H]$^+$ 460, found 460. |
| 96 | 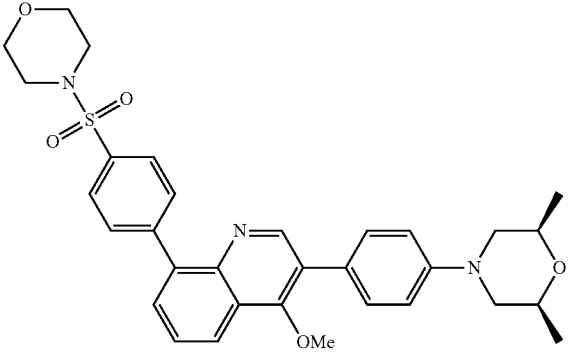 [SMILES: COc1c(-c2ccc(N3C[C@@H](C)O[C@@H](C)C3)cc2)cnc2c(-c3ccc(S(=O)(=O)N4CCOCC4)cc3)cccc12] | $^1$H NMR (400 MHz, CDCl$_3$) δ 8.91 (s, 1H), 8.35-8.32 (m, 1H), 7.94-7.87 (m, 4H), 7.73-7.71 (m, 1H), 7.86-7.64 (m, 1H), 7.60-7.58 (d, J = 8.5 Hz, 2H), 7.06-7.04 (d, J = 8.5 Hz, 2H), 3.85-3.79 (m, 6H), 3.72 (s, 3 H), 3.60-3.57 (d, J = 10.8 Hz, 2H), 3.15-3.13 (m, 4H), 2.55-2.49 (m, 2H), 1.31-1.30 (d, J = 6.3 Hz, 6H). MS ESI calcd for C$_{32}$H$_{35}$N$_3$O$_5$S [M + H]$^+$ 574, found 574. |
| 97 | 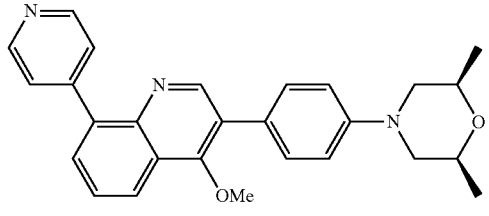 [SMILES: COc1c(-c2ccc(N3C[C@@H](C)O[C@@H](C)C3)cc2)cnc2c(-c3ccncc3)cccc12] | $^1$H NMR (400 MHz, CDCl$_3$) δ 8.92-8.90 (d, J = 6.2 Hz, 2H), 8.86 (s, 1H), 8.55-8.53 (m, 1H), 8.48-8.46 (d, J = 6.2 Hz, 2H), 8.06-8.04 (d, J = 6.2 Hz, 1H), 7.85-7.81 (m, 1H), 7.61-7.58 (d, J = 8.4 Hz, 2H), 7.17-7.14 (d, J = 8.8 Hz, 2H), 3.86-3.82 (m, 2H), 3.75 (s, 1H), 3.69-3.66 (d, J = 10.6 Hz, 2H), 2.47-2.42 (t, 2H), 1.27-1.26 (m, 6H). MS ESI calcd for C$_{27}$H$_{27}$N$_3$O$_2$ [M + H]$^+$ 426, found 426 |
| 98 | 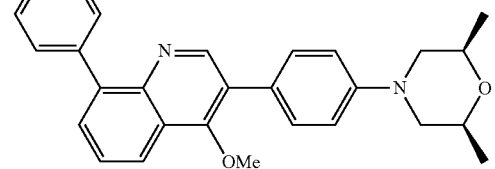 | $^1$H NMR (400 MHz, CDCl$_3$) δ 8.91 (s, 1H), 8.30-8.28 (d, J = 8 Hz, 1H), 7.81 (s, 1H), 7.67-7.56 (m, 6H), 7.05-7.03 (d, J = 8 Hz, 2H), 3.87-3.83 (m, 2H), 3.71 (s, 3H), 3.60-3.57 (d, J = 12 Hz, 2H), 2.55-2.49 (m, 2H), 1.32-1.30 (d, J = 8 Hz, 6H). MS ESI calcd for C$_{28}$H$_{26}$Cl$_2$N$_2$O$_2$ [M + H]$^+$ 493, found 493. |

| Embodiment | Structure | NMR |
|---|---|---|
| 99 | 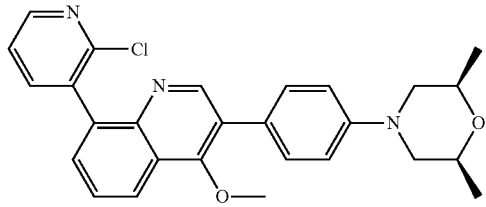 | ¹H NMR (400 MHz, CDCl₃) δ 8.87 (s, 1H), 8.50 (m, 1H), 8.37 (m, 1H), 7.82 (m, 1H), 7.68-7.58 (m, 3H), 7.40 (m, 1H), 7.05(d, J = 8.8 Hz, 2H) 3.88-3.84 (m, 2H), 3.74 (s, 2 H), 3.61-3.58 (d, J = 10.5 Hz, 2H), 2.56-2.50 (m, 2H), 1.32-1.31 (m, 6H). MS ESI calcd for $C_{26}H_{24}ClN_3O$ [M + H]⁺ 430, found 430. |
| 100 | 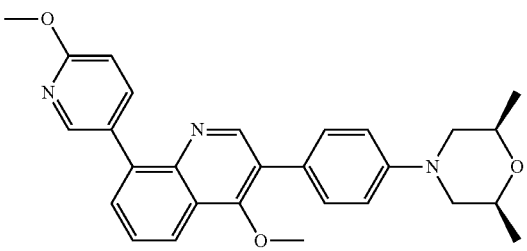 | ¹H NMR (400 MHz, CDCl₃) δ 8.90 (s, 1H), 8.50 (d, J = 2.0 Hz, 1H), 8.27 (d, J = 8.3 Hz, 1H), 8.03 (dd, J = 2.0, 8.5 Hz, 1H), 7.73-7.67 (m, 1H), 7.67-7.54 (m, 3H), 7.04 (d, J = 8.8 Hz, 2H), 6.89 (d, J = 8.5 Hz, 1H), 4.03 (s, 3H), 3.86 (d, J = 7.8 Hz, 2H), 3.71 (s, 3H), 3.58 (d, J = 11.5 Hz, 2H), 2.52 (t, J = 11.2 Hz, 2H), 1.31 (d, J = 6.3 Hz, 6H). MS ESI calcd for $C_{28}H_{29}N_3O_3$ [M + H]⁺ 456, found 456. |
| 101 | 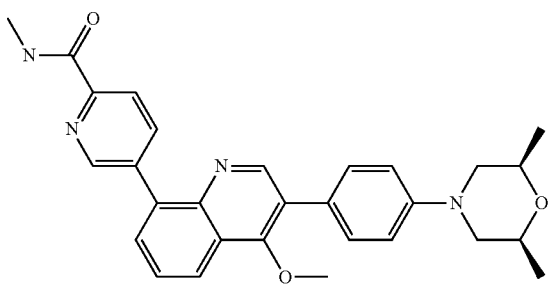 | ¹H NMR (400 MHz, CDCl₃) δ 8.95-8.86 (m, 2H), 8.34 (dd, J = 4.6, 7.7 Hz, 2H), 8.22 (dd, J = 1.6, 7.9 Hz, 1H), 8.10 (d, J = 4.5 Hz, 1H), 7.75 (d, J = 6.3 Hz, 1H), 7.71-7.64 (m, 1H), 7.59 (d, J = 8.8 Hz, 2H), 7.05 (d, J = 8.8 Hz, 2H), 3.93-3.78 (m, 2H), 3.72 (s, 3H), 3.58 (d, J = 11.3 Hz, 2H), 3.09 (d, J = 5.0 Hz, 3H), 2.52 (t, J = 11.0 Hz, 2H), 1.31 (d, J = 6.3 Hz, 6H). MS ESI calcd for $C_{29}H_{30}N_4O_3$ [M + H]⁺ 483, found 483. |
| 102 | 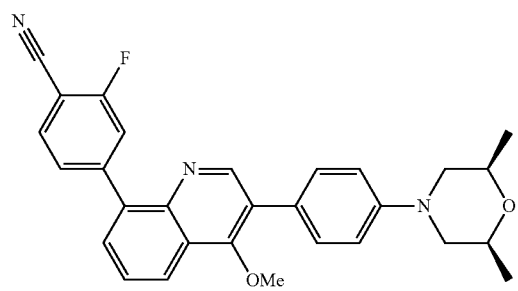 [SMILES: COc1c(-c2ccc(N3C[C@@H](C)O[C@@H](C)C3)cc2)cnc2c(-c3ccc(C#N)c(F)c3)cccc12] | ¹H NMR (400 MHz, CDCl₃) δ 8.89 (s, 1H), 8.36-8.33 (d, J = 12 Hz, 1H), 7.72-7.60 (m, 7H), 7.04-7.02 (d, J = 8 Hz, 2H), 3.86-3.82 (m, 2H), 3.75 (s, 3H), 3.59-3.56 (d, J = 12 Hz, 2H), 2.54-2.49 (m, 2H), 1.31-1.29 (d, J = 8 Hz, 6H). MS ESI calcd for $C_{29}H_{26}FN_3O_2$ [M + H]⁺ 468, found 468. |
| 103 | 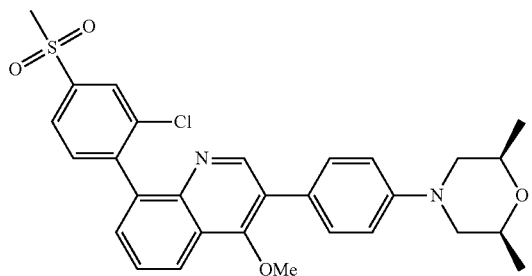 [SMILES: COc1c(-c2ccc(N3C[C@@H](C)O[C@@H](C)C3)cc2)cnc2c(-c3ccc(S(C)(=O)=O)cc3Cl)cccc12] | ¹H NMR (400 MHz, CDCl₃) δ 8.87 (s, 1H), 8.38 (m, 1H), 8.14 (m, 1H), 7.95 (m, 1H), 7.68-7.58 (m, 5H), 7.06-7.04(m, 2H), 3.85 (s, 1H), 3.74 (s, 3 H), 3.60-3.57 (m, 2H), 2.55-2.50 (m, 6H), 1.32-1.27 (m, 6H). MS ESI calcd for $C_{29}H_{29}ClN_2O_4S$ [M + H]⁺ 537, found 537. |

| Embodiment | Structure | NMR |
|---|---|---|
| 104 | | $^1$H NMR (400 MHz, CDCl$_3$) δ 8.861 (s, 1H) 8.38-8.36 (m, 1H) 7.68-7.51 (m, 7H) 7.05-7.03 (m, 2H) 3.86-3.83 (m, 2H) 3.72 (s, 3H) 3.59-3.56 (m, 2H) 2.54-2.49 (t, 2H) 1.31-1.29 (d, J = 6.8 Hz, 6H). MS ESI calcd for C$_{29}$H$_{26}$FN$_3$O$_2$ [M + H]$^+$ 468, found 468. |
| 105 | | $^1$H NMR (400 MHz, CDCl$_3$) δ 8.90 (s, 1H), 8.34-8.32 (d, J = 8 Hz, 1H), 7.63-7.53 (m, 6H), 7.42-7.40 (d, J = 8 Hz, 1H), 7.04-7.02 (d, J = 8 Hz, 2H), 3.84-3.82 (d, J = 8 Hz, 2H), 3.72 (s, 3 H), 3.59-3.56 (d, J = 12 Hz, 2H), 2.54-2.48 (m, 2H), 2.12 (s, 3 H), 1.31-1.29 (d, J = 8 Hz, 6H). MS ESI calcd for C$_{30}$H$_{29}$N$_3$O$_2$ [M + H]$^+$ 464, found 464. |
| 106 | | $^1$H NMR (400 MHz, CDCl$_3$) δ 9.06 (s, 1H) 8.89 (s, 1H) 8.38-8.36 (m, 1H) 8.30-8.28 (m, 1H) 7.68-7.51 (m, 7H) 7.05-7.03 (m, 2H) 3.86-3.83 (m, 2H) 3.72 (s, 3H) 3.59-3.56 (m, 2H) 2.54-2.49 (t, 2 H) 1.31-1.29 (d, J = 6.8 Hz, 6H). MS ESI calcd for C$_{28}$H$_{26}$F$_3$N$_3$O$_2$ [M + H]$^+$ 494, found 494. |
| 107 | | $^1$H NMR (400 MHz, CDCl$_3$) δ 8.90 (s, 1H), 8.32-8.30 (m, 1H), 7.74-7.57 (m, 7H), 7.05-7.01 (m, 2H), 3.86-3.82 (m, 2H), 3.71 (s, 3H), 3.59-3.57 (m, 2H), 2.65 (s, 3H), 2.55-2.49 (m, 2H), 1.31-1.30 (m, 6 H). MS ESI calcd for C$_{30}$H$_{29}$N$_3$O$_2$ [M + H]$^+$ 464, found 464. |
| 108 | | $^1$H NMR (400 MHz, CDCl$_3$) δ 8.90 (s, 1H), 8.60 (s, 1H), 8.18 (s, 1H), 7.97-8.06 (m, 2H), 7.56-7.63 (m, 3H), 7.10 (d, J = 8.82 Hz, 2H), 3.92 (s, 3H), 3.69 (d, J = 10.58 Hz, 4H), 3.63 (s, 3 H), 2.32 (t, J = 11.47 Hz, 2H), 1.17 (d, J = 5.73 Hz, 6H). MS ESI calcd for C$_{26}$H$_{28}$N$_4$O$_2$ [M + H]$^+$ 429, found 429. |

| Embodiment | Structure | NMR |
|---|---|---|
| 109 | 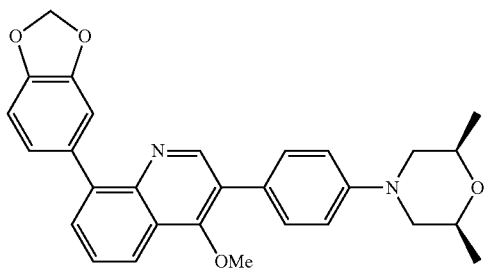 [SMILES: COc1c(-c2ccc(N3C[C@@H](C)O[C@@H](C)C3)cc2)cnc2c(-c3ccc4c(c3)OCO4)cccc12] | $^1$H NMR (400 MHz, CDCl$_3$) δ 8.84 (s, 1H), 8.17 (dd, J = 8.38, 1.32 Hz, 1H), 7.63-7.73 (m, 2H), 7.56 (d, J = 8.38 Hz, 2H), 7.23 (d, J = 1.32 Hz, 1H), 7.09 (d, J = 7.94 Hz, 3H), 6.98-7.02 (m, 1H), 6.06 (s, 2H), 3.69 (d, J = 10.58 Hz, 4H), 3.64 (s, 3H), 2.31 (t, J = 11.69 Hz, 2H), 1.16 (d, J = 6.17 Hz, 6H). MS ESI calcd for C$_{29}$H$_{28}$N$_2$O$_4$ [M + H]$^+$ 469, found 469. |
| 110 | 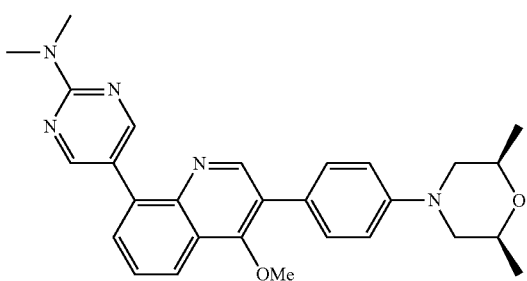 | $^1$H NMR (400 MHz, CDCl$_3$) δ 8.84 (s, 1H), 8.69 (s, 2H), 8.17 (d, J = 7.06 Hz, 1H), 7.79 (d, J = 5.73 Hz, 1H), 7.65-7.72 (m, 1H), 7.56 (d, J = 8.82 Hz, 2H), 7.09 (d, J = 8.82 Hz, 2H), 3.69 (d, J = 10.14 Hz, 4H), 3.18 (s, 6H) 3.64 (s, 3H), 2.31 (t, J = 11.47 Hz, 2H), 1.16 (d, J = 5.73 Hz, 6H). MS ESI calcd for C$_{28}$H$_{31}$N$_5$O$_2$ [M + H]$^+$ 470, found 470. |
| 111 | 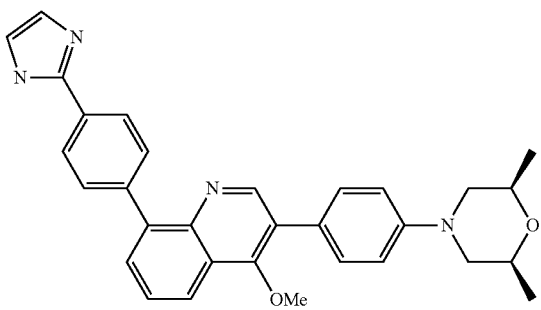 [SMILES: COc1c(-c2ccc(N3C[C@@H](C)O[C@@H](C)C3)cc2)cnc2c(-c3ccc(-c4ncc[nH]4)cc3)cccc12] | $^1$H NMR (400 MHz, CDCl$_3$) δ 8.92 (s, 1H) 8.30-8.28 (m, 1H) 7.87-7.74 (m, 2H) 7.73-7.72 (m, 3H)7.64-7.58(m, 3H) 7.15 (s, 2H) 7.05-7.03 (m, 2H) 3.86-3.83 (m, 2H)3.73 (s, 3H) 3.69-3.56 (m, 2H) 2.54-2.49 (m, 2H) 1.31-1.29 (m, 6H). MS ESI calcd for C$_{31}$H$_{30}$N$_4$O$_2$ [M + H]$^+$ +491, found 491. |
| 112 | 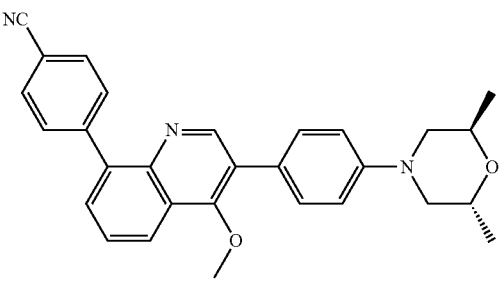 [SMILES: COc1c(-c2ccc(N3C[C@@H](C)O[C@H](C)C3)cc2)cnc2c(-c3ccc(C#N)cc3)cccc12] | $^1$H NMR (400 MHz, CDCl$_3$) δ 8.84 (s, 1 H), 8.27 (d, J = 7.94 Hz, 1 H), 7.88-7.96 (m, 2 H), 7.83-7.88 (m, 2 H), 7.77-7.82 (m, 1 H), 7.69-7.76 (m, 1 H), 7.55 (d, J = 8.82 Hz, 2 H), 7.06 (d, J = 8.82 Hz, 2 H), 4.06 (d, J = 3.09 Hz, 2 H), 3.66 (s, 3 H), 3.27 (br. s., 2 H), 2.94 (dd, J = 11.69, 5.95 Hz, 2 H), 1.20 (d, J = 6.17 Hz, 6 H). MS ESI calcd for C$_{29}$H$_{27}$N$_3$O$_2$ [M + H]$^+$ 450, found 450. |
| 113 | 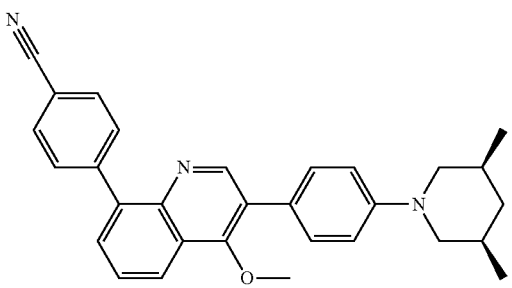 [SMILES: COc1c(-c2ccc(N3C[C@H](C)C[C@H](C)C3)cc2)cnc2c(-c3ccc(C#N)cc3)cccc12] | $^1$H NMR (400 MHz, CDCl$_3$) δ 8.91 (s, 1H), 8.31 (d, J = 4.0 Hz, 1H), 7.85-7.78 (m, 4H), 7.68-7.66 (m, 2H), 7.64-7.54 (m, 2H), 7.07-7.05 (m, 2H), 3.76-3.72 (m, 5H), 2.35-2.29 (m, 2 H), 1.87-1.84 (m, 1H), 1.30-1.27 (m, 1H), 0.99-0.97 (m, 6H), 0.93-0.89 (m, 1H), 0.78-0.75 (m, 1H). MS ESI calcd for C$_{30}$H$_{29}$N$_3$O [M + H]$^+$ 448, found 448. |

Embodiment 114

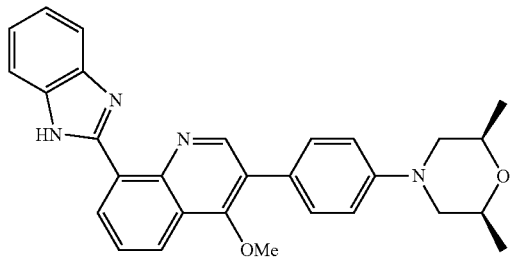 [SMILES: COc1c(-c2ccc(N3C[C@@H](C)O[C@@H](C)C3)cc2)cnc2c(-c3nc4ccccc4[nH]3)cccc12]

(2S,6R)-4-(4-(8-(1H-benzo[d]imidazol-2-yl)-4-methoxyquinolin-3-yl)phenyl)-2,6-dimethylmorpholine

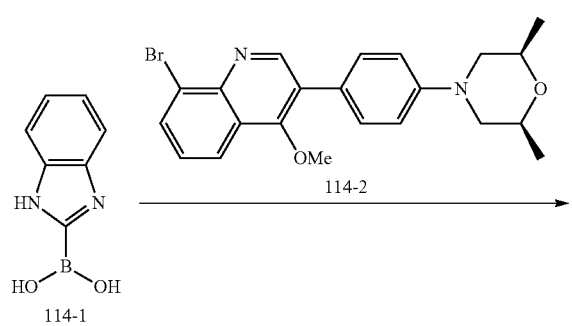

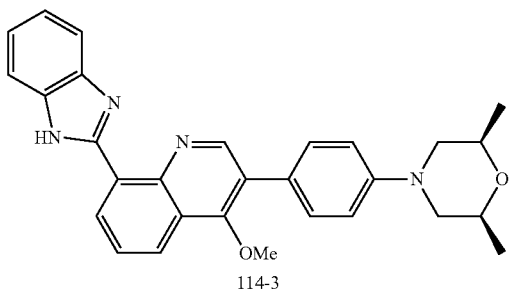

A mixture of compound 114-1 (100 mg, 0.61 mmol), Pd(dppf)Cl$_2$ (23.1 mg, 0.061 mmol), compound 114-2 (263.5 mg, 0.61 mmol) and Na$_2$CO$_3$ (161 mg, 1.53 mmol) was added into dioxane (2 mL). Under nitrogen gas atmosphere, the obtained reaction mixture was heated to 120° C. and stirred for 16 h. The reaction mixture were poured into H$_2$O, extracted with EtOAc. The combined extraction liquid was washed with brines, dried over sodium sulfate and concentrated to dry, finally purified by column chromatography (PE:EtOAc=3:1) to deliver the title compound (15 mg, yield 5.4%) as white solid. $^1$H NMR (400 MHz, CDCl$_3$) δ 9.10-9.20 (m, 1H), 9.02 (s, 1H), 8.37 (d, J=8.0 Hz, 1H), 7.65-7.80 (m, 1H), 7.62 (d, J=8.4 Hz, 2H), 7.20-7.35 (m, 5H), 7.08 (d, J=8.4 Hz, 1H), 3.80-3.92 (m, 2H), 3.74 (s, 3H), 3.55-3.62 (m, 2H), 2.50-2.60 (m, 2H), 1.20-1.40 (m, 6H). MS ESI calcd for C$_{29}$H$_{28}$N$_4$O$_2$ [M+H]$^+$ 465, found 465.

Embodiment 115

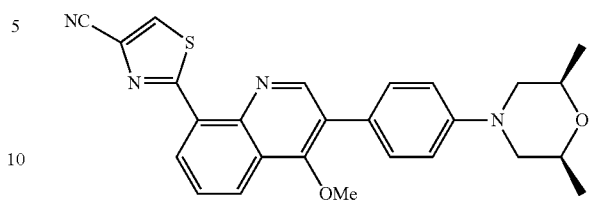

2-(3-(4-((2S,6R)-2,6-dimethylmorpholino)phenyl)-4-methoxyquinolin-8-yl)thiazole-4-carbonitrile

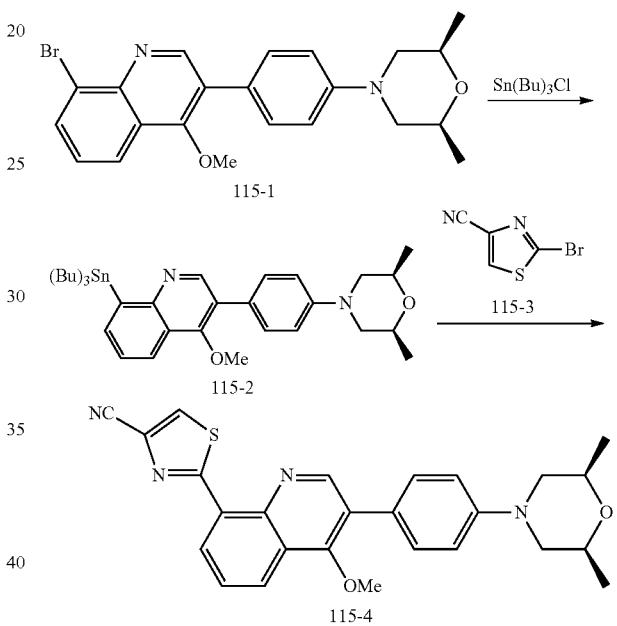

Step 1: Under nitrogen gas atmosphere, "BuLi (0.22 mL, 0.552 mmol) was added dropwise into a solution of compound 115-1 (200 mg, 0.46 mmol) in THF (10 mL) at −65° C. After the addition, the reaction mixture was stirred at this temperature for further 1 h. Then SnBu$_3$Cl (150 mg, 0.46 mmol) was added into the solution. The reaction mixture was stirred at −65° C. for further 4 h. After the reaction was complete, the reaction mixture was quenched with saturated NH$_4$Cl solution and extracted with EtOAc. The combined extraction liquid was washed with brines, dried over sodium sulfate and concentrated to dry, finally purified by column chromatography (PE:EtOAc=1:1) to deliver compound 115-2 (120 mg, yield 41%) as white solid. MS ESI calcd for C$_{34}$H$_{50}$N$_2$O$_2$Sn [M+H]$^+$ 639, found 639.

Step 2: Compound 115-2 (100 mg, 0.16 mmol), compound 115-3 (30 mg, 0.16 mmol), Na$_2$CO$_3$ (43 mg, 0.4 mmol) and Pd(dppf)Cl$_2$ (10 mg, 0.016 mmol) were added into dioxane (2 mL). Under nitrogen gas atmosphere, the reaction mixture was heated to 120° C. and stirred for 16 h. The reaction mixture was poured into H$_2$O, extracted with EtOAc. The combined extraction liquid was washed with brines, dried over sodium sulfate and concentrated to dry, finally purified by column chromatography (PE:EtOAc=1:1)

to deliver the title compound (25 mg, yield 34%) as white solid. $^1$H NMR (400 MHz, CDCl$_3$) δ 8.95 (s, 1H), 8.85 (d, J=2.0 Hz, 1H), 8.33 (d, J=2.0 Hz, 1H), 8.10 (s, 1H), 7.60-7.70 (m, 1H), 7.56 (d, J=8.4 Hz, 2H), 7.02 (d, J=8.4 Hz, 2H), 3.75-3.85 (m, 2H), 3.57 (s, 3H), 3.52-3.60 (m, 2H), 3.40-3.50 (m, 2H), 1.29 (s, 3H), 1.27 (s, 3H). MS ESI calcd for C$_{26}$H$_{24}$N$_4$O$_2$S [M+H]$^+$ 457, found 457.

Embodiment 116

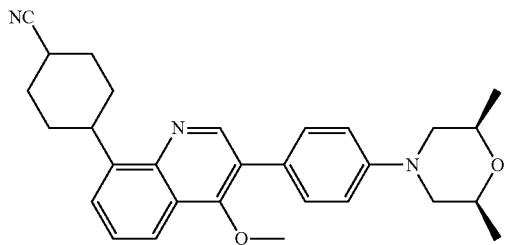 [SMILES: COc1c(-c2ccc(N3C[C@@H](C)O[C@@H](C)C3)cc2)cnc2c(C3CCC(C#N)CC3)cccc12]

4-(3-(4-((2S,6R)-2,6-dimethylmorpholino)phenyl)-4-methoxyquinolin-8-yl) cyclohexane carbonitrile

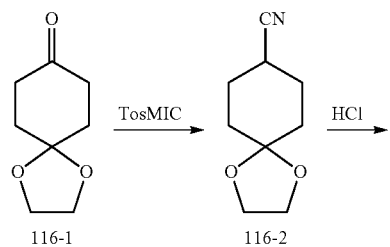

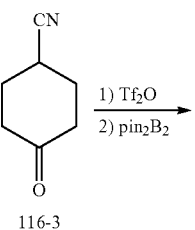

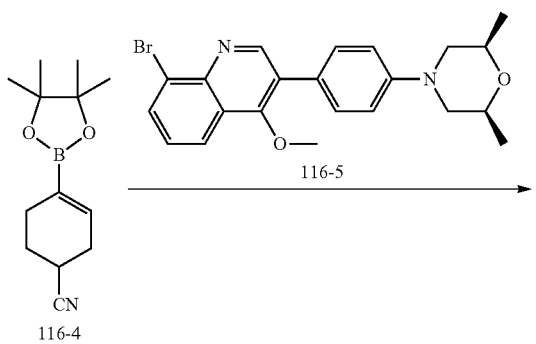

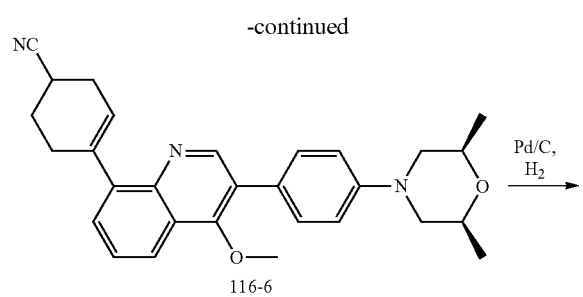

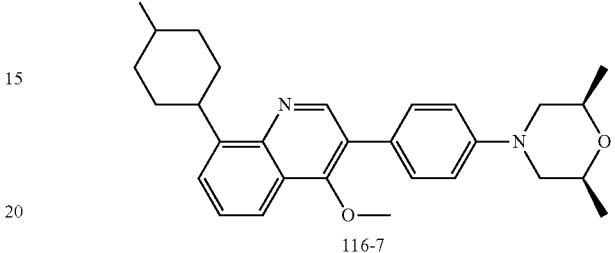

Step 1: t-BuOK (18.5 g, 165.2 mmol) was added into a solution of compound 116-1 (10 g, 64 mmol) and TosMIC (17.6 g, 90.27 mmol) in DME (10 mL) at 0° C. The reaction mixture was stirred at 0° C. for 2 h. After the reaction was complete, the reaction mixture was quenched with saturated NH$_4$Cl solution and extracted with EtOAc. The combined extraction liquid was washed with brines, dried over sodium sulfate and concentrated to dry, finally purified by column chromatography (PE:EtOAc=1:1) to deliver 116-2 (6.7 g, yield 50%) as colorless oil.

Step 2: A mixture of compound 116-2 (3 g, 18 mmol) in conc. hydrochloric acid/H$_2$O (v/v=1:1, 20 mL) was stirred at room temperature for 2 h. The reaction mixture was adjusted to pH=8 with NaOH, and extracted with EtOAc. The combined extraction liquid was washed with brines, dried over sodium sulfate and concentrated to dry, finally purified by column chromatography (PE:EtOAc=1:1) to deliver compound 116-3 (1.5 g, yield 68%) as colorless oil.

Step 3: LiHMDS (9.5 mL, 9.5 mmol) was added dropwise into a solution of compound 116-3 (1 g, 8 mmol) in THF (20 mL) at 0° C. After the addition, the reaction mixture was stirred for further 30 min. Then PhN(SO$_2$CF$_3$) (3.6 g, 8.6 mmol) was added into the solution. The obtained mixture was stirred at 25° C. for 6 h, finally quenched with H$_2$O and extracted with EtOAc. The combined extraction liquid was washed with brines, dried over sodium sulfate and concentrated to dry to deliver sulfonate as yellow oil. The obtained sulfonate, Pd(dppf)Cl$_2$ (80.4 mg, 0.11 mmol), bis(pinacolato)diboron (0.67 g, 2.6 mmol) and KOAc (0.65 g, 6.6 mmol) were added into dioxane (15 mL), under nitrogen gas atmosphere, the reaction mixture was heated to 100° C. and stirred for 18 h. The reaction mixture was poured into H$_2$O, extracted with EtOAc. The combined extraction liquid was washed with brines, dried over sodium sulfate and concentrated to dry, finally purified by column chromatography (PE:EtOAc=5:1) to deliver compound 116-4 (0.5 g, yield 28%) as white solid.

Step 4: A mixture of Pd(dppf)Cl$_2$ (180.8 mg, 0.23 mmol), compound 116-4 (500 mg, 2.1 mmol), compound 116-5 (1 g, 2.3 mmol) and Na$_2$CO$_3$ (556 mg, 5.25 mmol) was added into dioxane (20 mL). Under nitrogen gas atmosphere, the obtained suspension was heated to 80° C. and stirred for 4 h. The reaction mixture was poured into H$_2$O, extracted with EtOAc. The combined extraction liquid was washed with brines, dried over sodium sulfate and concentrated to dry, finally purified by column chromatography (PE:EtOAc=5:1) to deliver compound 116-6 (400 mg, yield 42%) as white solid. MS ESI calcd for $C_{29}H_{31}N_3O_2$ [M+H]$^+$ 454, found 454.

Step 5: Pd/C (100 mg, 10%) and compound 116-6 (100 mg, 0.22 mmol) were added into EtOAc (20 mL). Under hydrogen gas atmosphere provided by hydrogen balloon, the reaction mixture was stirred at room temperature for 50 h. The reaction mixture was filtered, the filtrate was concentrated to dry, finally purified by preparative HPLC to deliver the title compound (50 mg, yield 46%) as white solid. $^1$H NMR (400 MHz, CDCl$_3$) δ 8.90 (s, 1H), 8.14 (d, J=8.4 Hz, 1H), 7.50-7.65 (m, 6H), 7.06 (d, J=8.8 Hz, 2H), 4.00-4.15 (m, 1H), 3.80-3.95 (m, 2H), 3.69 (s, 3H), 3.55-3.65 (m, 2H), 3.15-3.20 (m, 1H), 2.45-2.55 (m, 2H), 1.90-2.25 (m, 7H), 1.55-1.65 (m, 1H), 1.33 (s, 3H), 1.31 (s, 3H). MS ESI calcd for $C_{29}H_{33}N_3O_2$ [M+H]$^+$ 456, found 456.

Embodiment 117

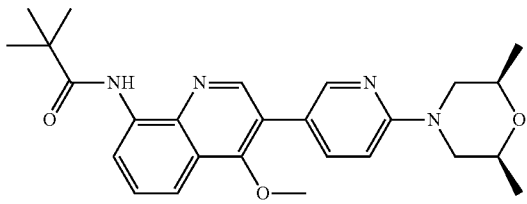 [SMILES: COc1c(-c2ccc(N3C[C@@H](C)O[C@@H](C)C3)nc2)cnc2c(NC(=O)C(C)(C)C)cccc12]

N-(3-(6-((2S,6R)-2,6-dimethylmorpholino)pyridin-3-yl)-4-methoxyquinolin-8-yl) pivalamide

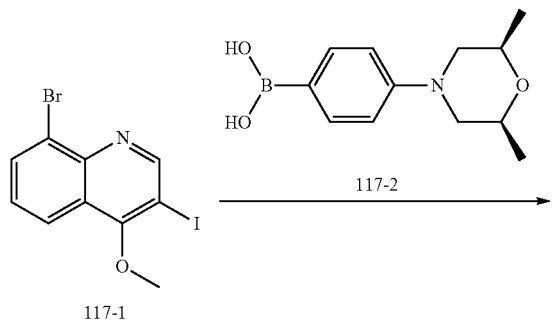

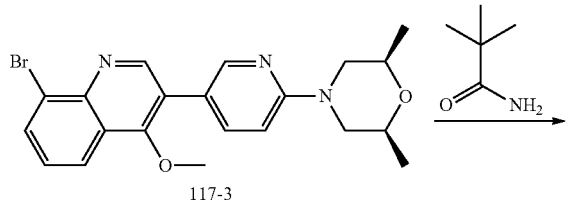

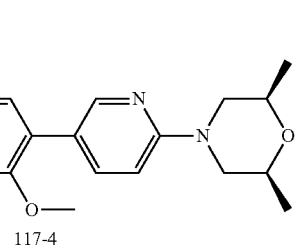

Step 1: A mixture of Na$_2$CO$_3$ (430 mg, 4 mmol), compound 117-1 (730 mg, 2 mmol), compound 117-2 (480 mg, 2 mmol) and Pd(dppf)Cl$_2$ (150 mg, 0.2 mmol) was added into a mixed solvent of THF/DMF/H$_2$O. Then the reaction mixture was heated to 80° C. and stirred for 4 h. The reaction mixture was poured into H$_2$O, extracted with EtOAc. The combined extraction liquid was dried over sodium sulfate and concentrated to dry, finally purified by column chromatography (PE:EtOAc=5:1) to deliver compound 117-3 (430 mg, yield 50%) as brown solid. MS ESI calcd for $C_{21}H_{22}BrN_3O_2$ [M+H]$^+$ 428, found 428.

Step 2: A mixture of compound 117-3 (130 mg, 0.3 mmol), trimethylacetamide (60 mg, 0.6 mmol), Cs$_2$CO$_3$ (190 mg, 0.6 mmol), Pd$_2$(dba)$_3$ (30 mg, 0.03 mmol) and Xantphos (36 mg, 0.06 mmol) was added into dioxane (5 mL). Under nitrogen gas atmosphere, the reaction mixture was heated to 120° C. and stirred for 4 h. The reaction mixture was poured into H$_2$O, extracted with EtOAc. The combined extraction liquid was dried over sodium sulfate and concentrated to dry, finally purified by preparative HPLC to deliver the title compound (30 mg, yield 21%) as white solid. $^1$H NMR (400 MHz, CDCl$_3$) δ 10.23 (brs, 1H), 8.77 (d, J=7.6 Hz, 1H), 8.74 (s, 1H), 8.47 (d, J=2.0 Hz, 1H), 7.90-7.95 (m, 2H), 7.69-7.80 (m, 1H), 6.78 (d, J=8.4 Hz, 1H), 4.05-4.10 (m, 2H), 3.35-3.46 (m, 5H), 2.26-2.85 (m, 2H), 1.42 (s, 9H), 1.31 (s, 9H), 1.29 (s, 3H). MS ESI calcd for $C_{26}H_{32}N_4O_3$ [M+H]$^+$ 449, found 449.

Embodiment 118

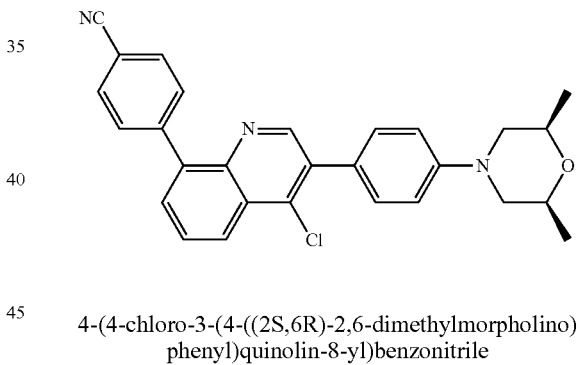

4-(4-chloro-3-(4-((2S,6R)-2,6-dimethylmorpholino)phenyl)quinolin-8-yl)benzonitrile

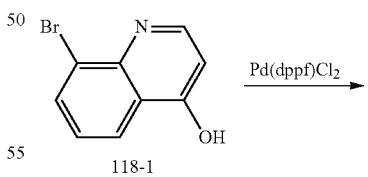

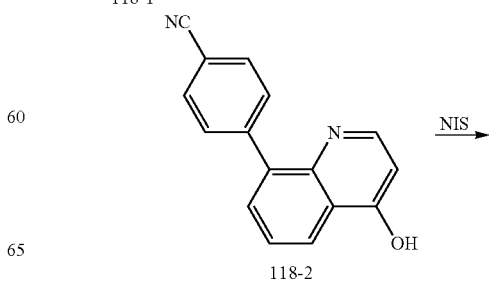

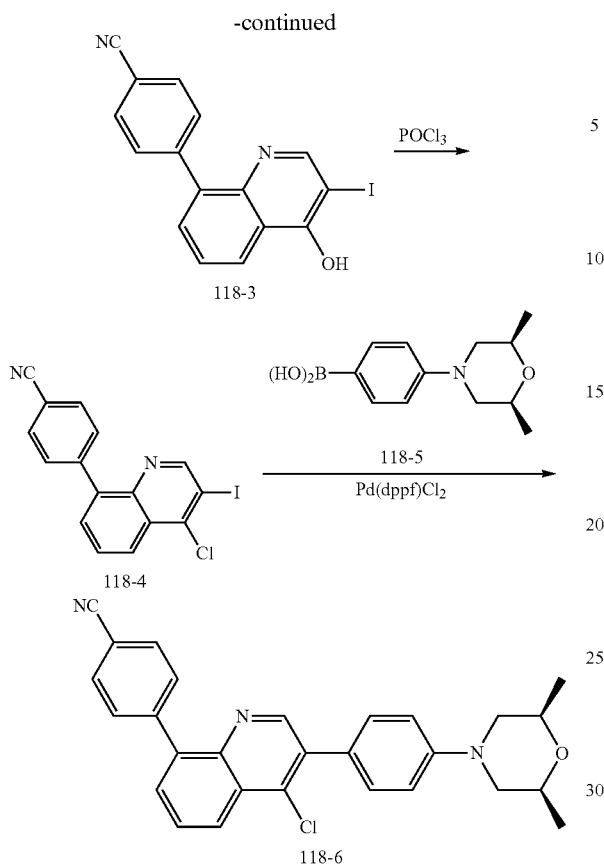

to deliver the desired product as brown solid (40 mg, 33%). $^1$H NMR (400 MHz, CDCl$_3$) δ 8.84 (s, 1H), 8.38-8.49 (m, 1H), 7.37-7.62 (m, 6H), 7.54 (d, 2H, J=8.0 Hz), 7.25 (d, 2H, J=8.4 Hz), 3.97 (t, 2H, J=7.6 Hz), 3.61 (d, 2H, J=11.6 Hz), 2.67 (t, 2H, J=11.6 Hz), 1.28 (d, 6H, J=6.4 Hz). MS ESI calcd for C$_{28}$H$_{24}$ClN$_3$O [M+H]$^+$ 454, found 454.

Embodiment 119

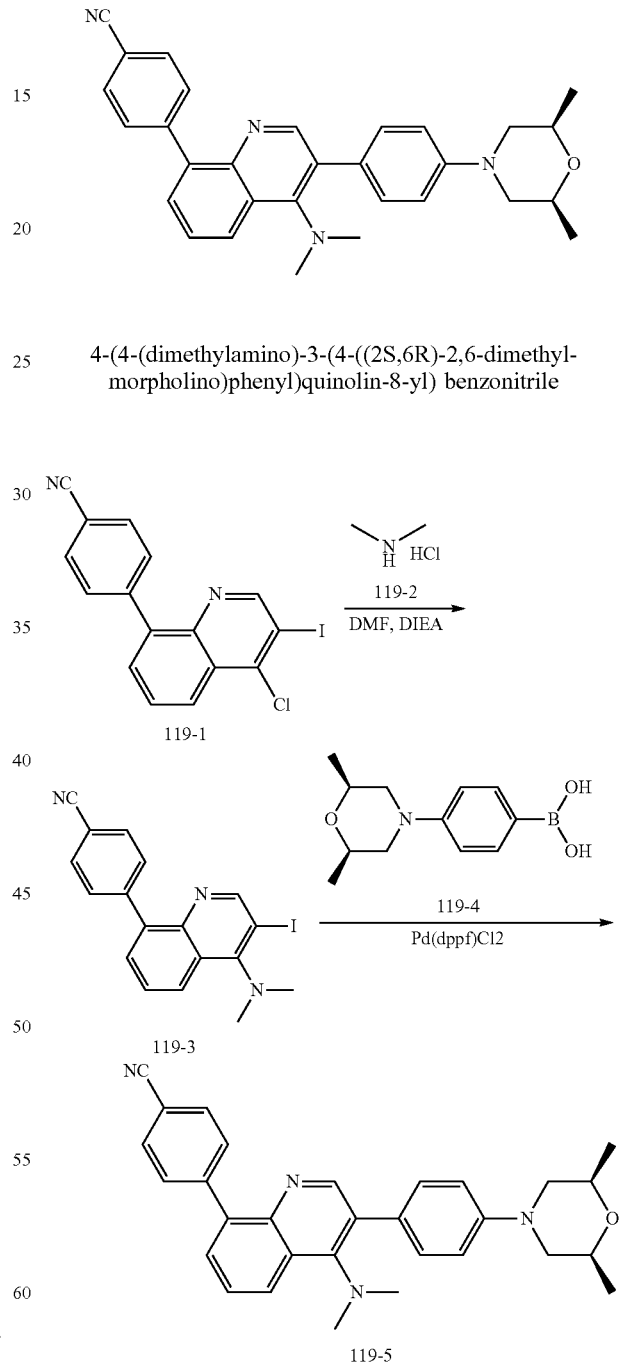

4-(4-(dimethylamino)-3-(4-((2S,6R)-2,6-dimethyl-morpholino)phenyl)quinolin-8-yl) benzonitrile Step 1: Pd(dppf)Cl$_2$ (1.6 g, 0.1 mmol), sodium carbonate (9.5 g, 89.23 mmol) and DMF/H$_2$O (100:20, 120 mL) were added into a suspension of compound 118-1 (10 g, 44.64 mmol), 4-cyanophenylboronic acid (7.2 g, 49.11 mmol). Under nitrogen gas atmosphere, the reaction mixture was stirred at 90° C. overnight. After the reaction was complete as detected by LC-MS, the reaction mixture was poured into H$_2$O (500 mL). The product 2 was obtained after filtration as brown solid (10.8 g, 98%). MS ESI calcd for C$_{16}$H$_{10}$N$_2$O [M+H]$^+$ 247, found 247.

Step 2: NIS (11.96 g, 53.17 mmol) was added into a solution of compound 118-2 (10.9 g, 44.31 mmol) in DMF (110 mL) in portions. The reaction mixture was stirred at room temperature for 3 h. After the reaction was complete as detected by LC-MS and TLC, the reaction mixture was poured into H$_2$O (500 mL). The product was obtained after filtration as brown residue (14 g and 85%). MS ESI calcd for C$_{16}$H$_9$IN$_2$O [M+H]$^+$ 373, found 373.

Step 3: compound 118-3 (5 g, 13.4 mmol) was added into phosphorus oxychloride (20 mL). The reaction mixture was stirred at reflux for 3 h. After the reaction was complete as detected by LC-MS, the reaction mixture was poured into H$_2$O (500 mL). The mixture was filtrated and dried under vacuum to deliver compound 4 (5.2 g, 99%) as brown solid. MS ESI calcd for C$_{16}$H$_8$ClIN$_2$ [M+H]$^+$ 391, found 391.

Step 4: Compound 118-1 (200 mg, 0.5 mmol), compound 118-5 (176 mg, 0.75 mmol) were added into a suspension of Pd(dppf)Cl$_2$ (18 mg, 0.03 mmol), sodium carbonate (106 mg, 1.0 mmol) in THF/H$_2$O (10:1, 11 mL), then under nitrogen gas atmosphere, the reaction mixture was stirred at 90 deg. C. overnight. The reaction was complete as detected by LC-MS. The mixture was purified by preparative HPLC Step 1: Compound 119-2 (1.1 g, 13 mmol) was added into a solution of compound 119-1 (500 mg, 1.3 mmol) in DMF (5 mL). DIEA (5 g, 39 mmol) was added. The reaction mixture was stirred at 120.deg. C. for 10 h. Then the reaction mixture was poured into H₂O (50 mL), and extracted with EtOAc. The organic phase was dried over sodium sulfate and concentrated under reduced pressure to deliver the desired compound as white solid (100 mg, 20%). MS ESI calcd for $C_{18}H_{14}IN_3$ [M+H]⁺ 400, found 400.

Step 2: Under nitrogen gas atmosphere, a mixture of compound 119-3 (18 mg, 0.03 mmol), sodium carbonate (100 mg, 0.25 mmol), compound 119-4 (88 mg, 0.37 mmol), Pd(dppf)Cl₂ (53 mg, 0.5 mmol) in THF/H₂O (11 mL, 10:1) was stirred at 90.deg. C. overnight. After the reaction was complete as detected by LC-MS, the reaction mixture was purified by preparative HPLC to deliver the title compound (20 mg, 20%) as white solid. ¹H NMR (400 MHz, CDCl₃) δ 8.37 (s, 1H), 8.26 (t, 1H, J=4.8 Hz), 7.80 (d, 2H, J=6.8 Hz), 7.74 (d, 2H, J=4.4 Hz), 7.59 (d, 2H, J=7.2 Hz), 7.19 (d, 2H, J=7.2 Hz), 7.05 (d, 2H, J=8.0 Hz), 3.85 (t, 2H, J=7.2 Hz), 3.12 (s, 6H), 2.53 (t, 2H, J=11.2 Hz), 1.28 (d, 6H, J=10.0 Hz). MS ESI calcd for $C_{30}H_{30}N_4O$ [M+H]⁺ 463, found 463.

Embodiment 120

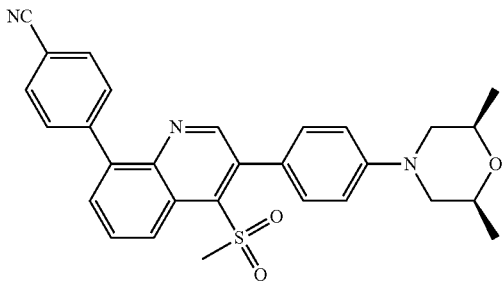 [SMILES: C[C@@H]1CN(c2ccc(-c3cnc4c(-c5ccc(C#N)cc5)cccc4c3S(C)(=O)=O)cc2)C[C@H](C)O1]

4-(3-(4-((2S,6R)-2,6-dimethylmorpholino)phenyl)-4-(methylsulfonyl)quinolin-8-yl) benzonitrile

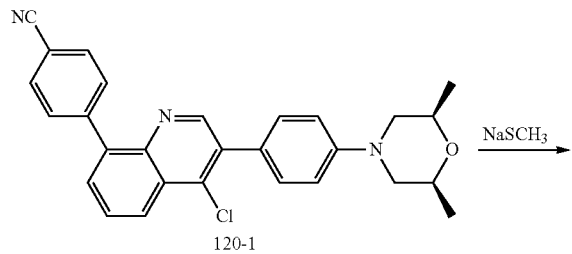

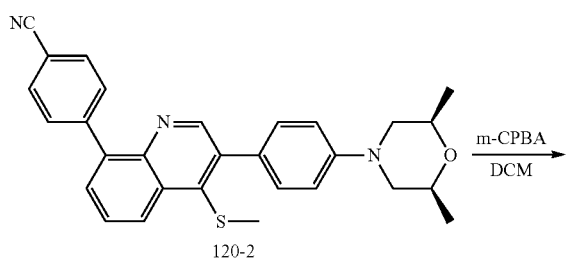

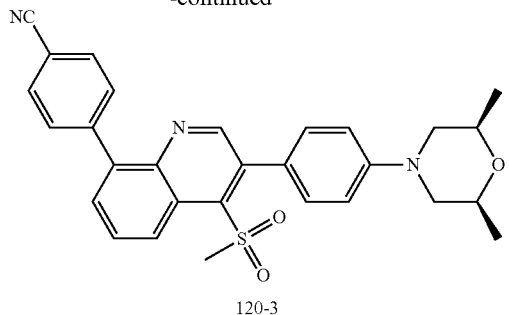

Step 1: NaSCH₃ (31 mg, 0.44 mmol) was added into a solution of compound 120-1 (200 mg, 0.44 mmol) in DMF (5 mL). Then the reaction mixture was stirred at 60° C. for 3 h. After the reaction was complete as detected by LC-MS, the reaction mixture was poured into H₂O and extracted with EtOAc. The organic phase was dried over sodium sulfate and concentrated under vacuum to deliver the desired compound (200 mg, 97.6%) as white solid. MS ESI calcd for $C_{29}H_{27}N_3OS$ [M+H]⁺ 466, found 466.

Step 2: m-chloroperbenzoic acid (186 mg, 1.08 mmol, 80%) was added into a solution of compound 120-2 (200 mg, 0.43 mmol) in DCM (20 mL). Then the reaction mixture was stirred at reflux overnight. After the reaction was complete as detected by LC-MS, the reaction mixture was poured into H₂O and extracted with DCM. The organic phase was dried over sodium sulfate and concentrated under vacuum, purified by preparative HPLC to deliver the desired product (120 mg, 55%) as white solid. ¹H NMR (400 MHz, CDCl₃) δ 9.36 (d, 1H, J=8.0 Hz), 8.77 (s, 1H), 7.99 (d, 2H, J=8.4 Hz), 7.68-7.88 (m, 6H), 7.62 (d, 2H, J=8.4 Hz), 4.67 (s, 2H), 4.19 (d, 2H, J=14.0 Hz), 3.48 (dd, 2H, J=10.0 Hz, 22.0 Hz), 3.06 (s, 3H), 1.22-1.42 (m, 6H). MS ESI calcd for $C_{29}H_{27}N_3O_3S$ [M+H]⁺ 498, found 498.

Embodiment 121

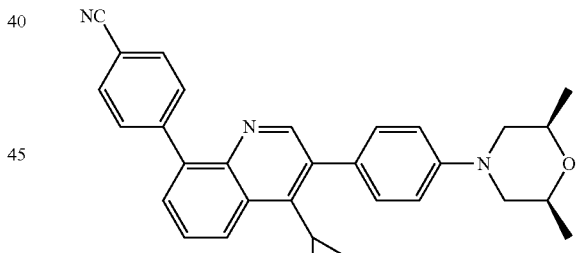

4-(4-cyclopropyl-3-(4-((2S,6R)-2,6-dimethylmorpholino)phenyl)quinolin-8-yl) benzonitrile

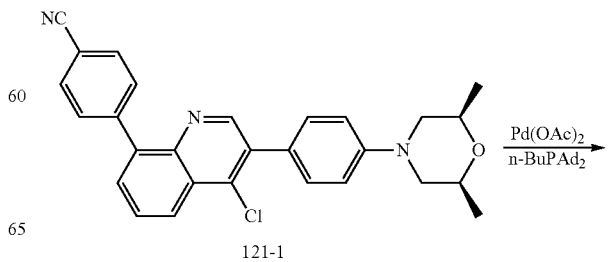

-continued

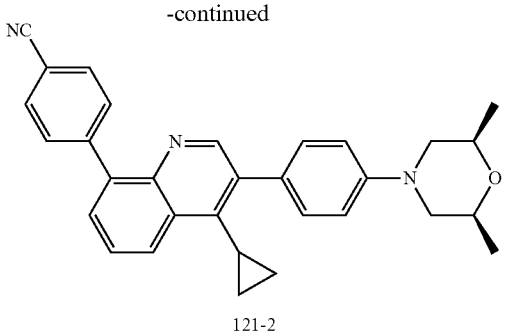

121-2

Under nitrogen gas atmosphere, a mixture of compound 121-1 (100 mg, 0.22 mmol), palladium acetate (4.5 mg, 0.02 mmol), n-BuPAd$_2$ (4.7 mg, 0.01 mmol), cesium carbonate (143 mg, 0.44 mmol) in toluene/H$_2$O (10:1, 11 mL) was stirred at 120 deg. C. overnight. After the reaction was complete as detected by LC-MS, the reaction mixture was purified by preparative HPLC to deliver the desired product (50 mg, 42%) as white solid. $^1$H NMR (400 MHz, CDCl$_3$) δ 8.80 (s, 1H), 8.70 (d, 1H, J=8.4 Hz), 7.77 (t, 2H, J=8.4 Hz), 7.65-7.75 (m, 3H), 7.50 (d, 2H, J=8.0 Hz), 7.38 (d, 2H, J=8.4 Hz), 7.04-7.13 (m, 2H), 3.85 (dd, 2H, J=6.0 Hz, J=8.0 Hz), 3.50 (d, 2H, J=11.2 Hz), 2.56 (t, 2H, J=11.2 Hz), 2.34 (t, 1H, J=6.4 Hz), 1.18 (d, 6H, J=6.0 Hz), 1.08 (d, 2H, J=8.0 Hz), 0.33 (d, 2H, J=5.6 Hz). MS ESI calcd for C$_{31}$H$_{29}$N$_3$O [M+H]$^+$ 460, found 460.

The compounds listed in table 8 were synthesized by compound 121-1 and corresponding boric acids.

| Embodiment | Structure | NMR |
|---|---|---|
| 122 | 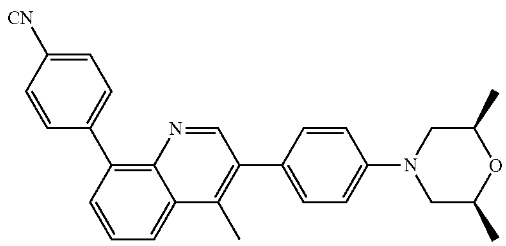 | $^1$H NMR (400 MHz, CDCl$_3$) δ 8.85 (s, 1H), 8.12-8.21 (m, 1H), 7.68-7.81 (m, 6H), 7.32 (d, 2H, J = 8.8 Hz), 7.08 (d, 2H, J = 8.4 Hz), 3.87 (t, 2H, J = 6.4 Hz), 3.57 (d, 2H, J = 10.8 Hz), 2.76 (s, 3H), 2.55 (t, 2H, J = 10.8 Hz), 1.30 (d, 6H, J = 6.4 Hz). MS ESI calcd for C$_{29}$H$_{27}$N$_3$O [M + H]$^+$ 434, found 434. |
| 123 | 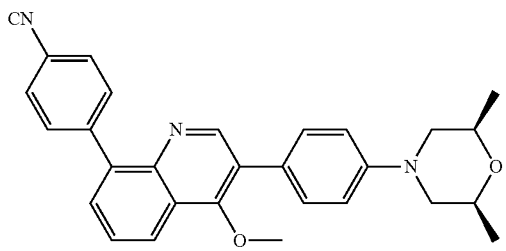 | $^1$H NMR (400 MHz, CDCl$_3$) δ 8.82 (s, 1H), 8.24 (d, 1H, J = 10.8 Hz), 7.66-7.80 (m, 6H), 7.31 (d, 2H, J = 8.4 Hz), 7.11 (d, 2H, J = 8.8 Hz), 3.86 (t, 2H, J = 6.4 Hz), 3.58 (d, 2H, J = 11.2 ( Hz), 3.20 (d, 2H, J = 7.6 Hz), 2.58 (t, 2H, J = 11.2 Hz), 1.23-1.40 (m, 9H). MS ESI calcd for C$_{30}$H$_{29}$N$_3$O [M + H]$^+$ 448, found 448. |
| 124 | 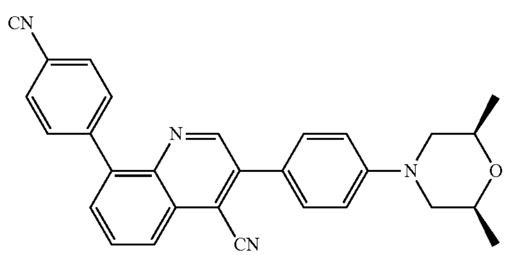 | $^1$H NMR (400 MHz, CDCl$_3$) δ 9.13 (s, 1H), 8.35 (d, 1H, J = 6.0 Hz), 7.78-7.86 (m, 6H), 7.68 (d, 2H, J = 8.8 Hz), 7.08 (d, 2H, J = 8.8 Hz), 3.79 (t, 2H, J = 6.4 Hz), 3.62 (d, 2H, J = 10.8 Hz), 2.56 (t, 2H, J = 10.8 Hz), 1.30 (d, 6H, J = 6.0 Hz). MS ESI calcd for C$_{29}$H$_{24}$N$_4$O [M + H]$^+$ 445, found 445. |
| 125 | 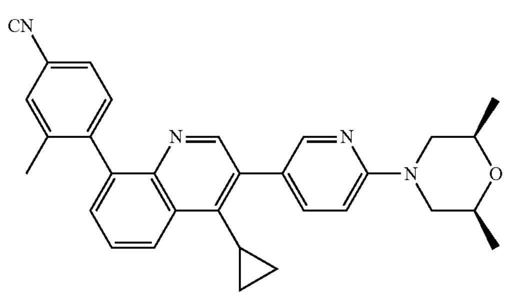 | $^1$H NMR (400 MHz, CDCl$_3$) δ 8.89 (s, 1H), 8.65-8.67 (d, J = 8.4 Hz, 1H), 8.38 (s, 1H), 7.53-7.70 (m, 5H) 7.39-7.41 (d, J = 7.6 Hz, 1H) 6.77-6.79 (d, J = 8.8 Hz, 1H) 4.14-4.17 (m, 2H), 3.79-3.81 (m, 2H) 2.61-2.67 (m, 2H) 2.32-2.34 (m, 1H) 2.24(s, 3H) 1.32-1.33 (d, J = 6.0 Hz 6H) 1.13-1.15 (m, 2H) 0.40-0.42 (m, 2H). MS ESI calcd for C$_{31}$H$_{30}$N$_4$O [M + H]$^+$ 475, found 475. |

Embodiment 126

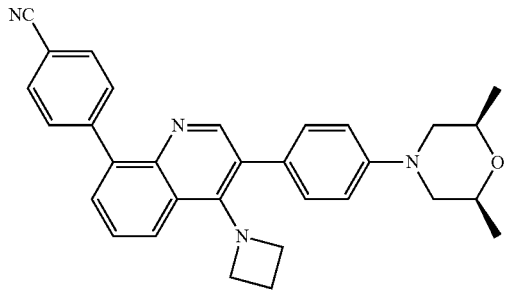

4-(4-(azetidin-1-yl)-3-(4-((2S,6R)-2,6-dimethylmorpholino)phenyl)quinolin-8-yl) benzonitrile

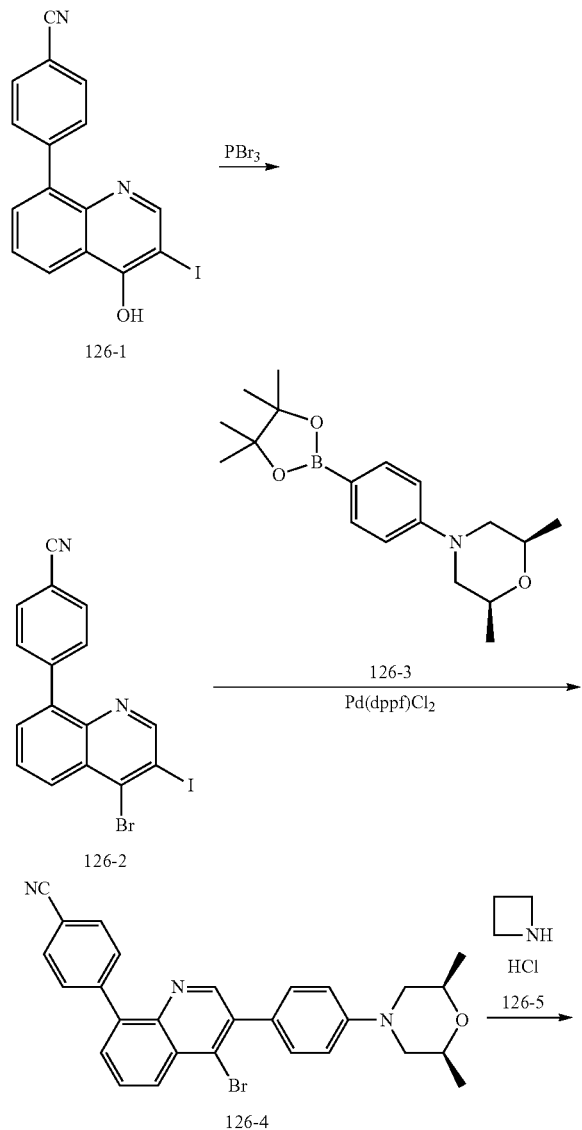

-continued

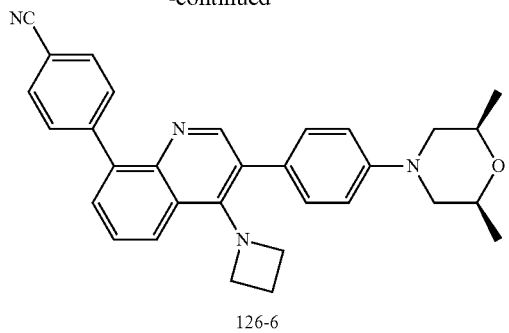

126-6

Step 1: PBr$_3$ (26.0 g, 97 mmol) solution was added dropwise into a solution of compound 126-1 (24.0 g, 65 mmol) in DMF (320 mL). The reaction mixture was stirred at room temperature for 1 h, and then filtrated to give the product 126-5 (26.0 g, yield 93%) as white solid. MS ESI calcd for $C_{16}H_8BrIN_2$ [M+H]$^+$ 434, found 434.

Step 2: To a solution of compound 126-2 (11 g, 25 mmol), compound 126-3 (9 g, 28 mmol) and sodium carbonate (5.3 g, 50 mmol) in THF/H$_2$O (5:1, 180 mL), was added Pd(dppf)Cl$_2$ (1.83 g, 2.5 mmol). The reaction mixture was stirred at 66° C. for 12 h. The reaction was complete as detected by LCMS. Then the reaction mixture was poured into H$_2$O, extracted with EtOAc, dried over anhydrous sodium sulfate. The crude product 126—was purified by column chromatography to deliver compound 126-4 (9.3 g, yield 74%) as yellow solid. MS ESI calcd for $C_{28}H_{24}BrN_3O$ [M+H]$^+$ 498, found 498.

Step 3: To a solution of compound 126-4 (100 mg, 0.2 mmol), compound 126-5 (37.6 mg, 0.4 mmol) and potassium tert-butoxide (112 mg, 1 mmol) in PhCH$_3$ (5 mL), were added Pd$_2$(dba)$_3$ (18.3 mg, 0.02 mmol) and Xantphos (19.1 mg, 0.04 mmol). The reaction mixture was heated to reflux for 12 h. The reaction was complete as detected by LCMS. Then the reaction mixture was poured into H$_2$O, extracted with ether (3×3 mL), the organic phase was dried over anhydrous sodium sulfate. After concentration, the residue was purified by preparative HPLC to deliver the title compound (yield 21%) as white solid. $^1$H NMR (400 MHz, CDCl$_3$) δ 8.30 (brs, 1H), 8.00 (d, 1H, J=8.0 Hz), 7.70-7.80 (m, 3H), 7.50-7.65 (m, 5H), 6.92 (d, 2H, J=5.6 Hz), 3.79 (t, 3H, J=8.0 Hz), 3.45-3.53 (m, 4H), 2.30-2.50 (m, 5H), 1.27 (d, 6H, J=6.0 Hz). MS ESI calcd for $C_{31}H_{30}N_4O$ [M+H]$^+$ 475, found 475.

Embodiment 127

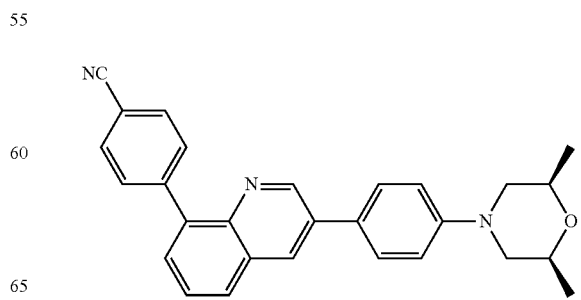

4-(3-(4-((2S,6R)-2,6-dimethylmorpholino)phenyl)quinolin-8-yl)benzonitrile

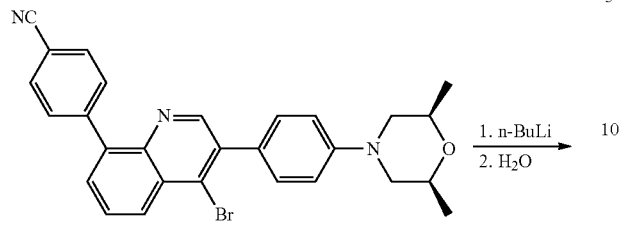
127-1

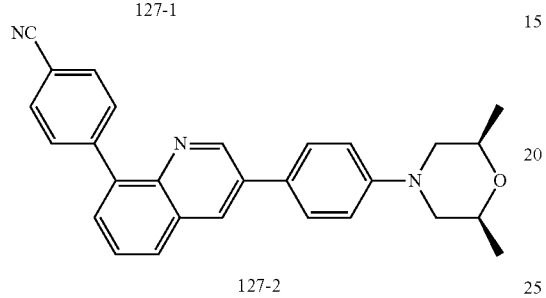
127-2 n-BuLi (0.5 mmol, 0.2 mL) was added into a solution of compound 127-1 (150 mg, 0.3 mmol) in THF at −70° C. The reaction mixture was poured into H$_2$O. The aqueous phase was extracted with EtOAc. The combined organic phase was washed with saturated brines, dried over anhydrous sodium sulfate, concentrated under reduced pressure. The crude product was purified by preparative HPLC to deliver the product (50 mg, yield: 50%) as white solid. MS ESI calcd for C$_{28}$H$_{25}$N$_3$O [M+H]$^+$ 420, found 420.

Embodiment 128

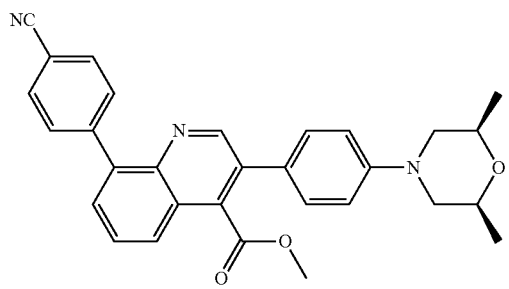 [SMILES: COC(=O)c1c(-c2ccc(N3C[C@@H](C)O[C@@H](C)C3)cc2)cnc2c(-c3ccc(C#N)cc3)cccc12]

methyl 8-(4-cyanophenyl)-3-(4-((2S,6R)-2,6-dimethylmorpholino)phenyl)quinoline-4-carboxylate

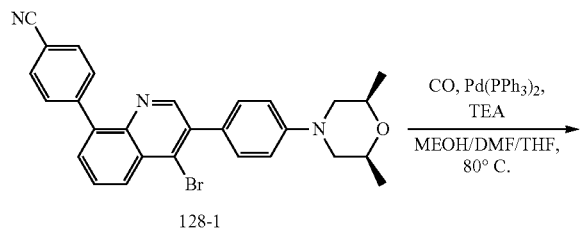
128-1

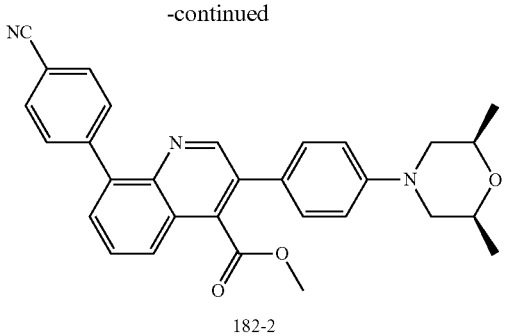
182-2

Pd(PPh$_3$)Cl$_2$ (21 mg, 0.03 mmol) and TEA (303 mg, 3 mmol) were added into a solution of compound 128-1 (150 mg, 0.3 mmol) in methanol/DMF/THF (25/5/5 mL), under CO gas atmosphere with a pressure of 50 psi, the reaction mixture was stirred at 70° C. for 48 h. After the reaction was complete as detected by LC-MS, the crude product was purified by preparative HPLC to deliver the title compound as white solid. $^1$H NMR (400 MHz, CDCl$_3$) δ 9.00 (s, 1H), 7.95 (d, 1H, J=7.6 Hz), 7.68-7.85 (m, 6H), 7.50 (d, 2H, J=8.8 Hz), 7.27 (d, 2H, J=8.8 Hz), 3.98 (d, 2H, J=6.4 Hz), 3.86 (s, 3H), 3.62 (d, 2H, J=11.6 Hz), 2.62-2.73 (m, 2H), 1.30 (d, 6H, J=6.0 Hz). MS ESI calcd for C$_{30}$H$_{27}$N$_3$O$_3$ [M+H]$^+$ 478, found 478.

Embodiment 129

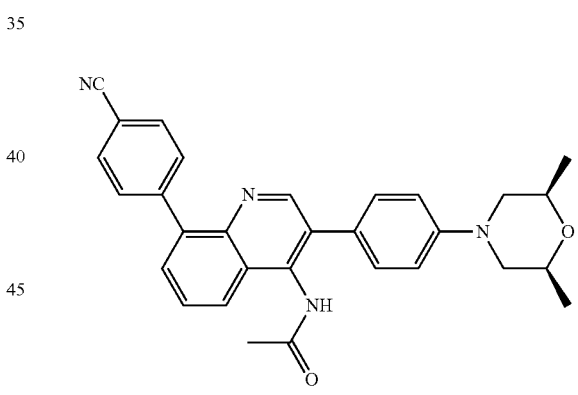

N-(8-(4-cyanophenyl)-3-(4-((2S,6R)-2,6-dimethylmorpholino)phenyl)quinolin-4-yl) acetamide

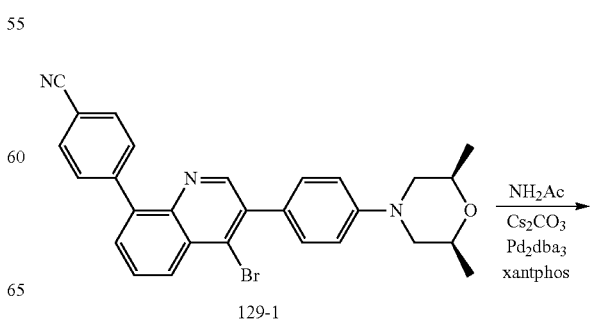
129-1

-continued

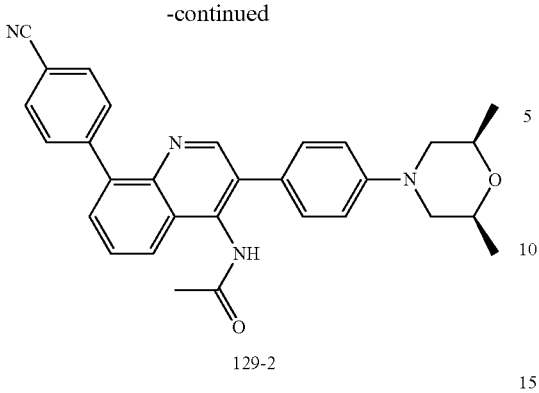

129-2

Embodiment 132

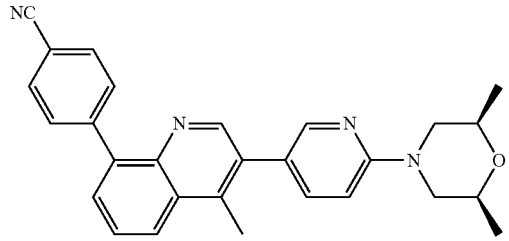 [SMILES: Cc1c(-c2ccc(N3C[C@@H](C)O[C@@H](C)C3)nc2)cnc2c(-c3ccc(C#N)cc3)cccc12]

Cesium carbonate (100 mg, 0.3 mmol), Pd₂dba₃ (9 mg, 0.01 mmol) and Xantphos (12 mg, 0.02 mmol) were added into a solution of compound 129-1 (50 mg, 0.1 mmol) and NH₂Ac (30 mg, 0.5 mmol) in dioxane (5 mL). The reaction mixture was heated to reflux for 12 h. After the reaction was complete as detected by LC-MS, the reaction mixture was poured into H₂O, extracted with EtOAc, dried over anhydrous sodium sulfate and dissolved in DMF. The crude product was purified by preparative HPLC to deliver the title compound (21 mg, yield 44%) as yellow solid. $^1$H NMR (400 MHz, CDCl₃) δ 8.93 (s, 1H), 8.00 (d, 1H, J=8.4 Hz), 7.65-7.80 (m, 6H), 7.37 (d, 2H, J=8.8 Hz), 7.10 (d, 2H, J=8.8 Hz), 3.87 (t, 2H, J=7.6 Hz), 3.58 (d, 2H, J=11.6 Hz), 3.56 (t, 2H, J=11.6 Hz), 2.22 (brs, 2H), 1.93 (s, 3H), 1.18 (d, 6H, J=6.0 Hz). MS ESI calcd for $C_{30}H_{28}N_4O_2$ [M+H]$^+$ 477 found 477.

The compounds listed in table 9 were synthesized by compound 129-1 and corresponding amides.

4-(3-(6-((2S,6R)-2,6-dimethylmorpholino)pyridin-3-yl)-4-methylquinolin-8-yl) benzonitrile

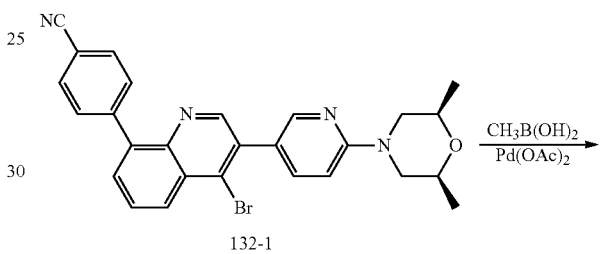

132-1

| Embodiment | Structure | NMR |
|---|---|---|
| 130 | 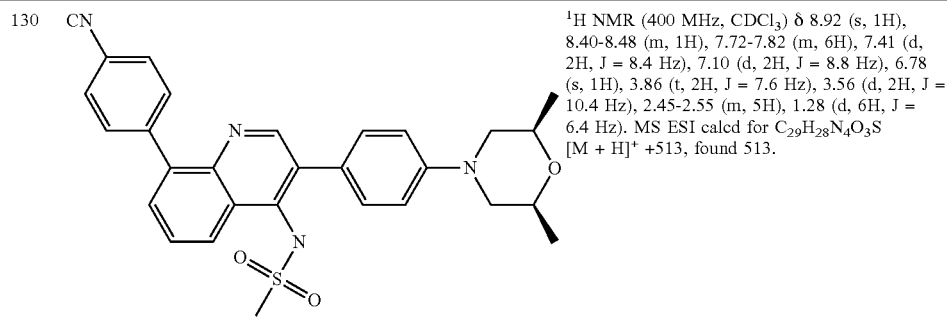 | $^1$H NMR (400 MHz, CDCl₃) δ 8.92 (s, 1H), 8.40-8.48 (m, 1H), 7.72-7.82 (m, 6H), 7.41 (d, 2H, J = 8.4 Hz), 7.10 (d, 2H, J = 8.8 Hz), 6.78 (s, 1H), 3.86 (t, 2H, J = 7.6 Hz), 3.56 (d, 2H, J = 10.4 Hz), 2.45-2.55 (m, 5H), 1.28 (d, 6H, J = 6.4 Hz). MS ESI calcd for $C_{29}H_{28}N_4O_3S$ [M + H]$^+$ +513, found 513. |
| 131 | 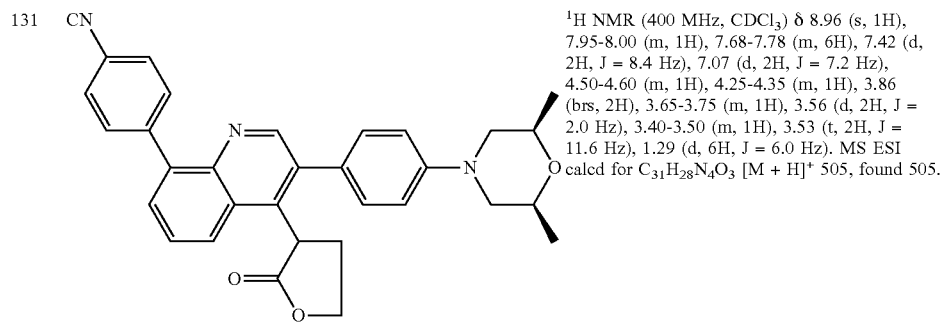 | $^1$H NMR (400 MHz, CDCl₃) δ 8.96 (s, 1H), 7.95-8.00 (m, 1H), 7.68-7.78 (m, 6H), 7.42 (d, 2H, J = 8.4 Hz), 7.07 (d, 2H, J = 7.2 Hz), 4.50-4.60 (m, 1H), 4.25-4.35 (m, 1H), 3.86 (brs, 2H), 3.65-3.75 (m, 1H), 3.56 (d, 2H, J = 2.0 Hz), 3.40-3.50 (m, 1H), 3.53 (t, 2H, J = 11.6 Hz), 1.29 (d, 6H, J = 6.0 Hz). MS ESI calcd for $C_{31}H_{28}N_4O_3$ [M + H]$^+$ 505, found 505. |

-continued

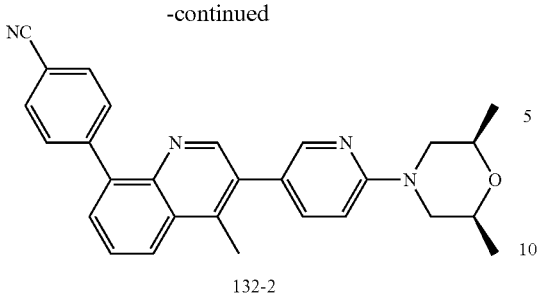

132-2

A mixture of n-BuPAd$_2$ (20 mg, 0.04 mmol), palladium acetate (5 mg, 0.02 mmol) and cesium carbonate (130 mg, 0.4 mmol) was added into a solution of compound 132-1 (100 mg, 0.2 mmol) and CH$_3$B(OH)$_2$ (120 mg, 2 mmol) in Toluene/H$_2$O (3 mL/1 mL), then the reaction mixture was stirred at 110° C. overnight. After poured into H$_2$O, the mixture was extracted with EtOAc, dried over sodium sulfate, concentrated to deliver the crude product which was purified by preparative HPLC to deliver the title compound (30 mg, yield 30%) as yellow solid. MS ESI calcd for C$_{28}$H$_{26}$N$_4$O [M+H]$^+$ 435 found 435.

The compounds listed in table 10 were synthesized by compound 132-1 and corresponding boric acids.

4-(6-chloro-3-(4-((2S,6R)-2,6-dimethylmorpholino)phenyl)-4-methoxyquinolin-8-yl) benzonitrile

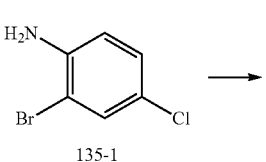

135-1

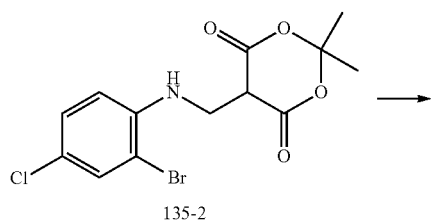

135-2

| Embodiment | structure | NMR |
|---|---|---|
| 133 | [structure with CN, quinoline, pyridine, dimethylmorpholine, ethyl] | $^1$H NMR (400 MHz, CDCl$_3$) δ 8.70 (s, 1H), 8.29 (s, 1H), 8.20 (dd, 1H, J = 2.8 Hz, J = 6.8 Hz), 7.65-7.80 (m, 7H), 6.93 (d, 1H, J = 8.0 Hz), 4.15 (d, 2H, J = 12.8 Hz), 3.70-3.83 (m, 2H), 3.11 (d, 2H, J = 7.6 Hz), 2.82 (t, 2H, J = 11.2 Hz), 1.25-1.38 (m, 9H). MS ESI calcd for C$_{29}$H$_{28}$N$_4$O [M + H]$^+$ 449, found 449. |
| 134 | [structure with CN, quinoline, pyridine, dimethylmorpholine, cyclopropyl] | $^1$H NMR (400 MHz, CDCl$_3$) 8.83 (s, 1H), 8.65-8.66 (d, J = 5.2 Hz, 1H), 8.37-8.38 (d, J = 2.8 Hz, 1H), 7.77-7.82 (d d, J = 8.0 Hz, 4H), 7.67-7.70 (d d, J = 3.6 Hz, 3H), 6.76-6.78 (d, J = 8.8 Hz, 1H), 4.13-4.16 (d, J = 11.6 Hz 2H), 3.77-3.81 (m, 2H), 2.61-2.66 (t, J = 22.8 Hz 2H), 2.31-2.33 (m, 1H), 1.31-1.33 (d, J = 6.8 Hz 6H), 1.11-1.13 (m, 2H), 0.38-0.39 (m, 2H). MS ESI calcd for C$_{30}$H$_{28}$N$_4$O [M + H]$^+$ 461, found 461. |

Embodiment 135

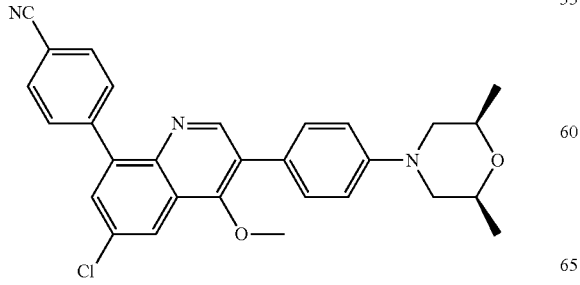

-continued

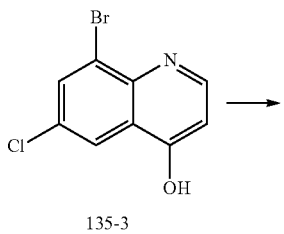

135-3

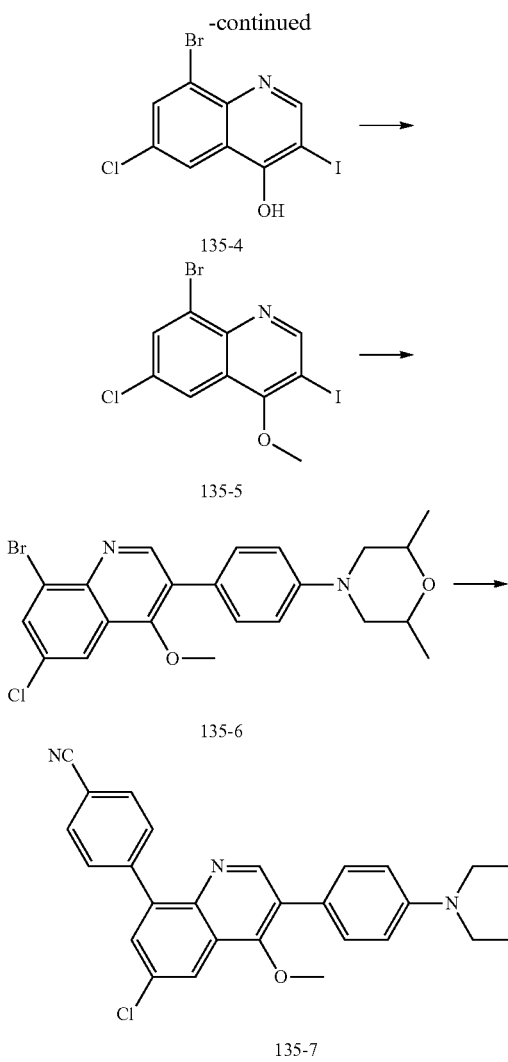

chromatography to deliver 2.2 g product as red solid (yield 47%). MS ESI calcd for $C_{10}H_6BrClINO$ [M+H]$^+$ 397, found 397.

Step 5: Pd(dppf)Cl$_2$ (40 mg, 0.05 mmol) and sodium carbonate (107 mg, 1.0 mmol) were added into a solution of compound 135-5 (200 mg, 0.5 mmol) and 2,6-dimethyl-4-(4-(4,4,5,5-tetramethyl-1,3,2-dioxaborolan-2-yl)phenyl) morpholine (160 mg, 0.5 mmol) in THF/H$_2$O (6 mL, 5:1). The reaction mixture was stirred at 70° C. overnight, then poured into H$_2$O, the mixture was extracted with EtOAc, dried over sodium sulfate, concentrated to deliver compound 135-6 as yellow solid (200 mg, yield 40%). MS ESI calcd for $C_{22}H_{22}BrClN_2O_2$ [M+H]$^+$ 461, found 461.

Step 6: Pd(dppf)Cl$_2$ (37 mg, 0.05 mmol) and sodium carbonate (92 mg, 0.86 mmol) were added into a solution of compound 135-6 (200 mg, 0.43 mmol) and 4-cyanophenyl-boronic acid (63.7 mg, 0.43 mmol) in THF/H$_2$O (6 mL, 5:1). After stirred at 70° C. for 3 h, the mixture was poured into H$_2$O, extracted with EtOAc, dried over sodium sulfate, concentrated to deliver the crude product which was purified by preparative HPLC to deliver the title compound (55 mg, yield 26%) as yellow solid. $^1$H NMR (400 MHz, CDCl$_3$) δ 8.84 (s, 1H), 8.27 (d, 1H, J=2.4 Hz), 7.78 (dd, 4H, J=8.4 Hz, J=10.8 Hz), 7.63 (d, 1H, J=2.0 Hz), 7.54 (d, 2H, J=8.8 Hz), 7.02 (d, 2H, J=8.4 Hz), 3.75-3.85 (m, 2H), 3.68 (s, 3H), 3.56 (d, 2H, J=10.8 Hz), 2.50 (t, 2H, J=11.2 Hz), 1.28 (d, 6H, J=6.4 Hz). MS ESI calcd for $C_{29}H_{26}ClN_3O_2$ [M+H]$^+$ 484, found 484.

Embodiment 136

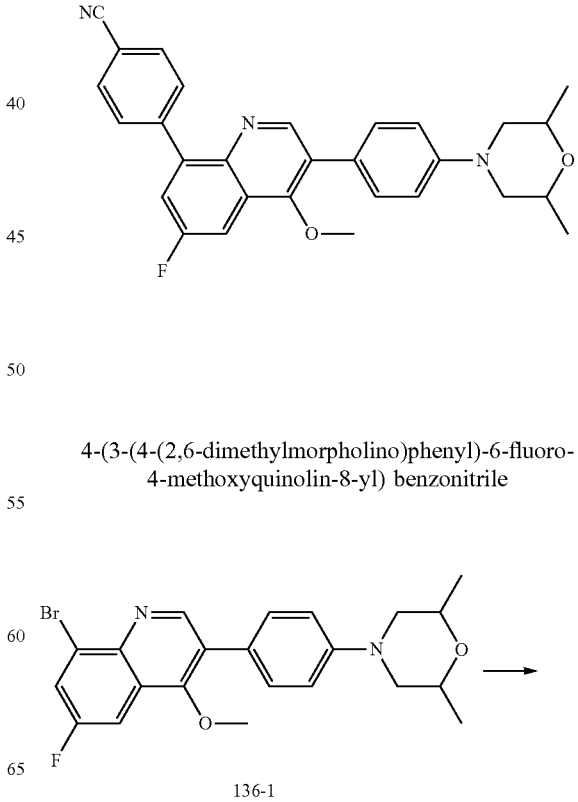

4-(3-(4-(2,6-dimethylmorpholino)phenyl)-6-fluoro-4-methoxyquinolin-8-yl) benzonitrile Step 1: A mixture of 2,2-dimethyl-1,3-dioxane-4,6-dione (19.2 g, 133 mmol) and trimethoxymethane (70 mL, 680 mmol) was refluxed for 2.5 h, then the compound 135-1 (20 g, 97 mmol) was added into the solution at 100° C. and stirred overnight, the solid was collected after filtration to give compound 135-2 (35.6 g, yield 98%) as yellow solid. MS ESI calcd for $C_{13}H_{13}BrClNO_4$ [M+H]$^+$ 362, found 362.

Step 2: A mixture of compound 135-2 (35.6 g, 100 mmol) and compound 135-Ph$_2$O (170 g, 1 mol) was heated to 250° C. for 0.5 h, then cooled to room temperature, the solid was collected after filtration to give the product as brown solid (12.2 g, yield 48%). MS ESI calcd for $C_9H_5BrClNO$ [M+H]$^+$ 258, found 258.

Step 3: To a solution of compound 135-3 (3.56 g, 14 mmol) and NIS (3.1 g, 14 mmol) in DMF (10 mL), the mixture was stirred at room temperature for 2 h, the solid was collected after filtration to give 4.2 g product as yellow solid (yield 80%). MS ESI calcd for $C_9H_4BrClINO$ [M+H]$^+$ 384, found 384.

Step 4: MeI (2.0 g, 14 mmol) and Ag$_2$CO$_3$ (6.6 g, 24 mmol) were added into a solution of compound 135-4 (4.5 g, 12 mmol) in DMF (20 mL), then the mixture was stirred at 70° C. for 2 h, after filtration, the mixture was extracted with EtOAc, dried over sodium sulfate, concentrated to deliver 4.8 g crude product, which was purified by column -continued

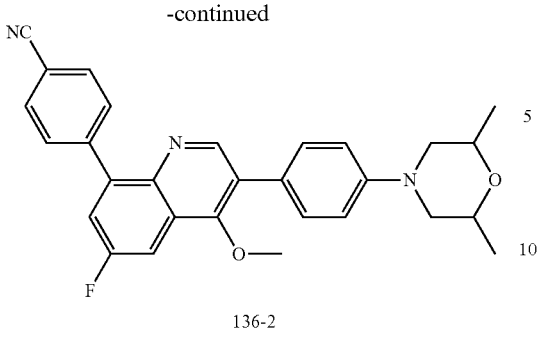

136-2

Pd(dppf)Cl₂ (33 mg, 0.045 mmol) and sodium carbonate (96 mg, 0.9 mmol) were added into a solution of compound 136-1 (200 mg, 0.45 mmol) and 4-cyanophenylboronic acid (66 mg, 0.45 mmol) in THF/H₂O (6 mL, 5:1). The reaction mixture was stirred at 70° C. overnight, then poured into H₂O, extracted with EtOAc, dried over sodium sulfate, concentrated to deliver the crude product which was purified by preparative HPLC to deliver the title compound (45 mg, yield 21.4%) as yellow solid. ¹H NMR (400 MHz, CDCl₃) δ 8.82 (s, 1H), 7.65-7.70 (m, 1H), 7.70-7.80 (m, 4H), 7.50-7.60 (m, 2H), 7.47 (dd, 1H, J=2.8 Hz, J=8.8 Hz), 7.03 (brs, 2H), 3.85 (brs, 2H), 3.68 (s, 3H), 3.56 (d, 2H, J=10.8 Hz), 2.53 (t, 2H, J=10.4 Hz), 1.29 (d, 6H, J=6.4 Hz). MS ESI calcd for C₂₉H₂₆FN₃O₂ [M+H]⁺ 468 found 468.

The compounds listed in table 11 were synthesized by compound 136-1 and corresponding boric acids.

Embodiment 139

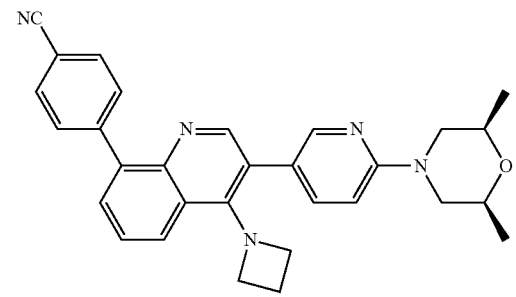

4-(4-(azetidin-1-yl)-3-(6-((2S,6R)-2,6-dimethylmorpholino)pyridin-3-yl)quinolin-8-yl) benzonitrile

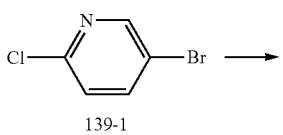

139-1

| Embodiment | Structure | NMR |
|---|---|---|
| 137 | 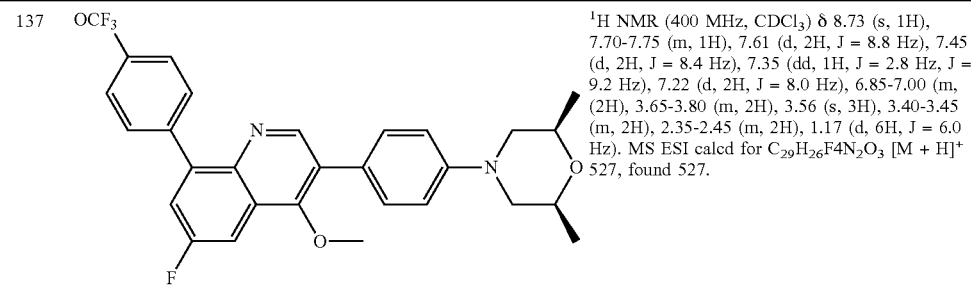 | ¹H NMR (400 MHz, CDCl₃) δ 8.73 (s, 1H), 7.70-7.75 (m, 1H), 7.61 (d, 2H, J = 8.8 Hz), 7.45 (d, 2H, J = 8.4 Hz), 7.35 (dd, 1H, J = 2.8 Hz, J = 9.2 Hz), 7.22 (d, 2H, J = 8.0 Hz), 6.85-7.00 (m, 2H), 3.65-3.80 (m, 2H), 3.56 (s, 3H), 3.40-3.45 (m, 2H), 2.35-2.45 (m, 2H), 1.17 (d, 6H, J = 6.0 Hz). MS ESI calcd for C₂₉H₂₆F₄N₂O₃ [M + H]⁺ 527, found 527. |
| 138 | 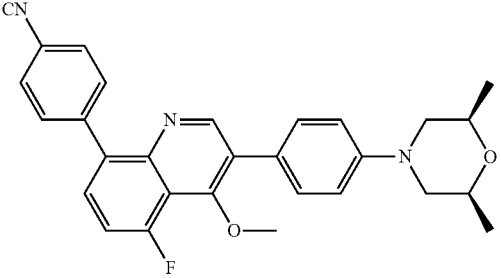 | ¹H NMR (400 MHz, CDCl₃) δ 8.83 (s, 1H), 7.85-7.90 (m, 1H), 7.72-7.78 (m, 4H), 7.50-7.58 (m, 2H), 7.47 (dd, 1H, J = 2.8 Hz, J = 8.8 Hz), 7.05 (m, 2H), 3.75-3.90 (m, 2H), 3.69 (s, 3H), 3.56 (d, 2H, J = 10.8 Hz), 2.53 (t, 2H, J = 10.4 Hz), 1.29 (d, 6H, J = 6.4 Hz). MS ESI calcd for C₂₉H₂₆FN₃O₂ [M + H]⁺ 468, found 468. |

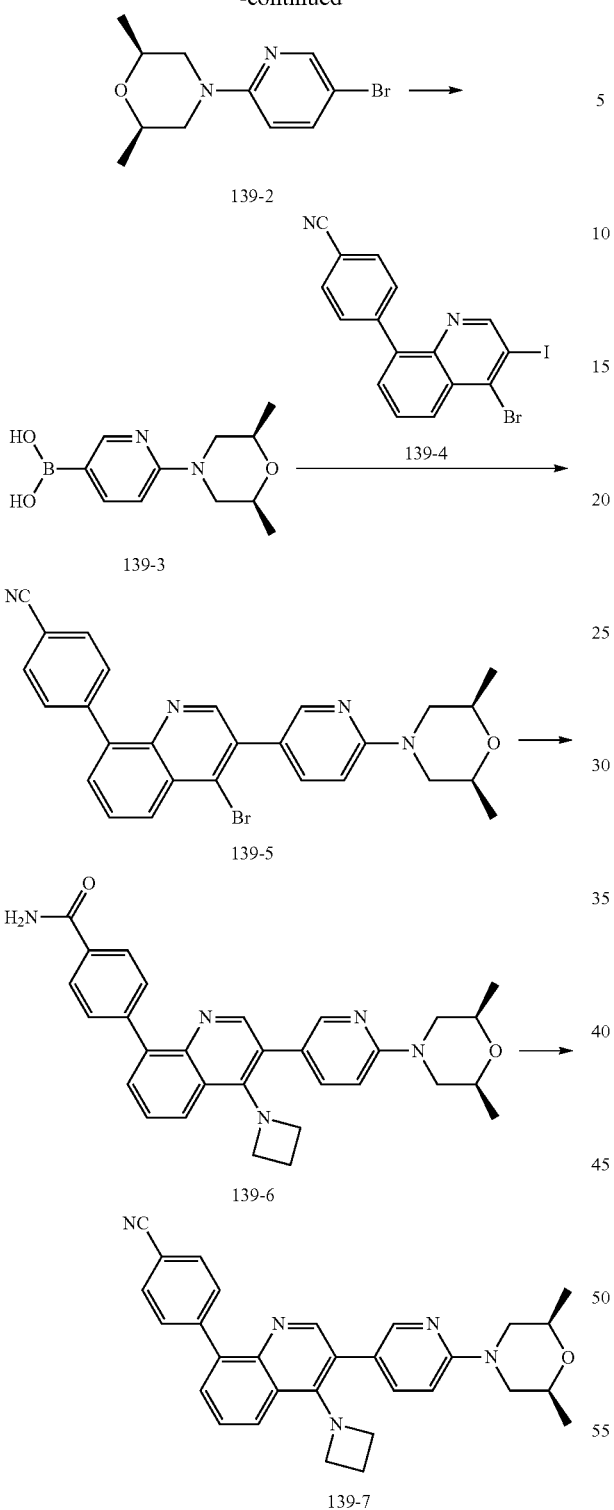

(EtOAc:PE=1:5 to 1:1) to deliver compound 139-2 (15.4 g, yield 57%) as yellow solid. MS ESI calcd for $C_{11}H_{15}BrN_2O$ [M+H]$^+$ 271, found 271.

Step 2: Pd(dppf)Cl$_2$ (732 mg, 1 mmol) and AcOK (4.0 g, 40 mmol) were added into a solution of compound 139-2 (5.4 g, 20 mmol) and bis(pinacolato)diboron (7.6 g, 30 mmol) in 1,4-dioxane (100 mL), the mixture was stirred at 120° C. for 6 h. Then the solvent was removed, the residue was purified by column chromatography (EtOAc:PE=1:10 to 1:2) to deliver compound 139-3 (5.0 g, yield 98%) as white solid. MS ESI calcd for $C_{11}H_{17}BN_2O_3$ [M+H]$^+$ 237, found 237.

Step 3: A mixture of sodium carbonate (214 mg, 4 mmol) was added into a solution of compound 139-3 (236 mg, 0.7 mmol) and compound 139-4 (300 mg, 2 mmol) in DMF/H$_2$O/THF (14:1:5 mL), and the mixture was stirred at −80° C. for 2 h. After poured in H$_2$O, the reaction mixture was extracted with EtOAc, dried over sodium sulfate, concentrated to deliver the crude product which was purified by column chromatography (PE:EtOAc=5:1) to deliver compound 139-5 (200 mg, yield 57%) as white solid. MS ESI calcd for $C_{27}H_{23}BrN_4O$ [M+H]$^+$ 499, found 499.

Step 4: Xantphos (350 mg, 0.6 mmol), Pd$_2$(dba)$_3$ (275 mg, 0.3 mmol) and potassium tert-butoxide (1.3 g, 12 mmol) were added into a solution of compound 139-2 (1.5 g, 3 mmol) and azetidine (560 mg, 6 mmol) in toluene (20 mL), the reaction mixture was stirred at 110° C. for 3 h. After poured in H$_2$O, the reaction mixture was extracted with EtOAc, dried over sodium sulfate, concentrated to deliver the crude product which was purified by column chromatography to deliver the desired product compound 139-6 as yellow solid (500 mg, yield 30%). MS ESI calcd for $C_{30}H_{31}N_5O_2$ [M+H]$^+$ 494, found 494.

Step 5: TFAA (4 mL) and DIPEA (4 mL) were added into a solution of compound 139-6 (1.5 g, 3 mmol) in DCM (20 mL), the reaction mixture was stirred at room temperature for 30 min, then poured in H$_2$O, extracted with EtOAc, dried over sodium sulfate, concentrated to deliver the crude product which was transferred to be purified by preparative HPLC to deliver the title compound as yellow solid (500 mg, yield 30%). $^1$H NMR (400 MHz, CDCl$_3$) δ 8.29 (s, 1H), 8.19 (s, 1H), 8.05 (d, 1H, J=8.0 Hz), 7.93 (brs, 1H), 7.80 (d, 2H, J=7.6 Hz), 7.50-7.70 (m, 4H), 6.98 (brs, 1H), 4.70 (brs, 3H), 4.17 (d, 3H, J=12.4 Hz), 3.65-3.80 (m, 2H), 2.78 (t, 2H, J=11.6 Hz), 2.47 (brs, 2H), 1.30 (d, 6H, J=6.0 Hz). MS ESI calcd for $C_{30}H_{29}N_5O$ [M+H]$^+$ 476 found 476.

Embodiment 140

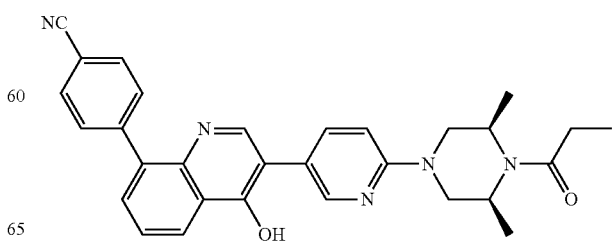

Step 1: 2,6-dimethylmorpholine (18 g, 0.15 mol) and K$_2$CO$_3$ (27.6 g, 0.2 mol) were added into a solution of compound 139-1 (19.2 g, 0.1 mol) in DMF (200 mL), the reaction mixture as stirred at 120° C. for 4 h. After poured into H$_2$O, the reaction mixture was extracted with EtOAc, dried over sodium sulfate, concentrated to deliver the crude product which was purified by column chromatography

187

4-(3-(6-((3S,5R)-3,5-dimethyl-4-propionylpiperazin-1-yl)pyridin-3-yl)-4-hydroxyquinolin-8-yl)benzonitrile

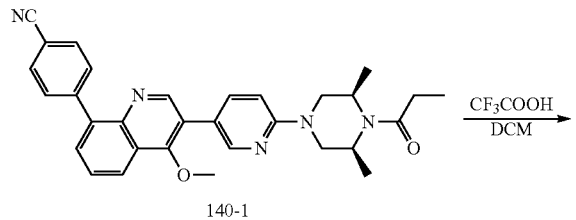

140-1

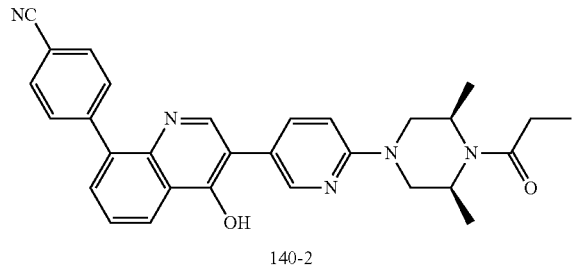

140-2

CF₃COOH (114 mg, 1 mmol) was added into a solution of compound 140-1 (100 mg, 0.2 mmol) in DCM (5 mL). The reaction mixture was stirred at 50° C. for 2 h, the reaction was complete as detected by LC-MS. The reaction mixture was poured in H₂O, extracted with EtOAc (30×3 mL), the organic phase was dried over sodium sulfate. After concentration, the residue was purified by preparative HPLC to deliver the title compound (30 mg) as white solid product. MS ESI calcd for $C_{30}H_{29}N_5O_2$ [M+H]⁺ 492 found 492.

Embodiment 141

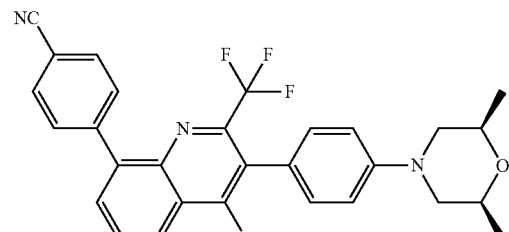

4-(3-(4-((2S,6R)-2,6-dimethylmorpholino)phenyl)-4-methoxy-2-(trifluoromethyl) quinolin-8-yl)benzonitrile

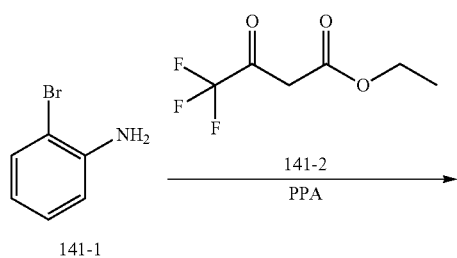

141-1

188

-continued

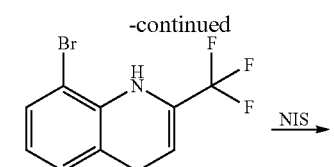

141-3

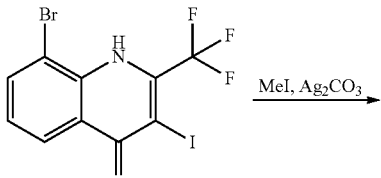

141-4

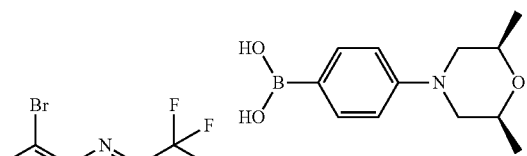

141-5

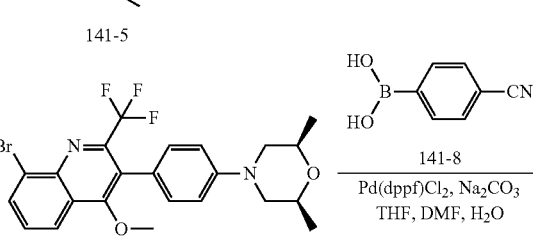

141-7

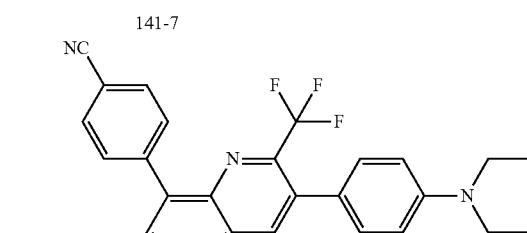

141-9

Step 1: Compound 141-1 (10 g, 58.5 mmol) was added dropwise into a mixture of compound 140-2 (10.7 g, 58.5 mmol) and PPA (40 g) at 100° C., the period of addition was no less than 15 min. After the addition, the reaction mixture was heated to 150° C. and stirred for 12 h. After cooling, the reaction mixture was diluted with sodium hydroxide (160 mL, 10 wt. %). The obtained precipitate was filtrated, the filtrate was acidified with conc. hydrochloric acid. The obtained precipitate was filtrated, recrystallized with ethanol to deliver compound 141-3 (10.5 g, yield 62%) as white solid. MS ESI calcd for $C_{10}H_5BrF_3NO$ [M+H]⁺ 292, found 292.

Step 2: NIS (8.1 g, 36 mmol) was added into a solution of compound 141-3 (10.5 g, 36 mmol) in DMF (100 mL) in portions. The reaction mixture was stirred at room temperature for 1 h. Then the reaction mixture was poured into H₂O (1 L) and filtrated, the filtrate cake was dissolved in EtOAc, dried over sodium sulfate, concentrated to deliver compound 141-4 (14.3 g, yield 95%) as yellow solid. MS ESI calcd for $C_{10}H_4BrF_3INO$ [M+H]$^+$ 418, found 418.

Step 3: MeI (0.22 mL, 3.6 mmol) was added dropwise into a suspension of compound 141-4 (1 g, 2.4 mmol) and $Ag_2CO_3$ (1.5 g, 4.8 mmol) in toluene (10 mL). Then the reaction mixture was stirred at 70° C. for 2 h. The reaction mixture was poured into $H_2O$, extracted with EtOAc. The combined extraction liquid was washed with brines, dried over $Na_2SO_4$ and concentrated to dry, finally purified by column chromatography (PE:EtOAc=10:1) to deliver compound 141-5 (550 mg, yield 55%) as yellow-brown solid. MS ESI calcd for $C_{11}H_6BrF_3INO$ [M+H]$^+$ 432, found 432.

Step 4: A mixture of compound 141-5 (550 mg, 1.27 mmol), compound 140-6 (299 mg, 1.27 mmol), Pd(dppf)Cl$_2$ (93 mg, 0.127 mmol) and Na$_2$CO$_3$ (269 mg, 2.54 mmol) was added into a mixed solvent of THF (5 mL) and H$_2$O (1 mL), under nitrogen gas atmosphere, the reaction mixture was heated to 60° C. and stirred overnight. The reaction mixture was poured into H$_2$O, extracted with EtOAc. The combined extraction liquid was washed with brines, dried over Na$_2$SO$_4$ and concentrated to dry to deliver compound 141-7 (170 mg, yield 27%) as yellow-brown solid. MS ESI calcd for $C_{23}H_{22}BrF_3N_2O_2$ [M+H]$^+$ 495, found 495.

Step 5: A mixture of compound 141-7 (170 mg, 0.34 mmol), compound 140-8 (60.6 mg, 0.41 mmol), Pd(dppf)Cl$_2$ (25 mg, 0.034 mmol) and Na$_2$CO$_3$ (72 mg, 0.68 mmol) was added into a mixed solvent of THF (10 mL), DMF (2 mL) and H$_2$O (2 mL), under nitrogen gas atmosphere, the reaction mixture was heated to 110° C. and stirred overnight. The organic phase was separated and washed with brines, dried over Na$_2$SO$_4$ and concentrated to dry, finally purified by preparative HPLC to deliver the title compound (60 mg, yield 34%) as white solid. $^1$H NMR (400 MHz, CDCl$_3$) δ 8.26 (d, J=8.0 Hz, 1H), 7.82-7.95 (m, 3H), 7.70-7.80 (m, 3H), 7.35-7.50 (m, 4H), 3.95-4.20 (m, 3H), 3.65-3.80 (m, 2H), 3.63 (s, 3H), 2.76-2.90 (m, 2H), 1.33 (s, 3H), 1.32 (s, 3H). MS ESI calcd for $C_{30}H_{26}F_3N_3O_2$ [M+H]$^+$ 518, found 518.

Embodiment 142

4-(2-(4-((2R,6S)-2,6-dimethylmorpholino)phenyl)-4-methoxyquinolin-5-yl) benzonitrile

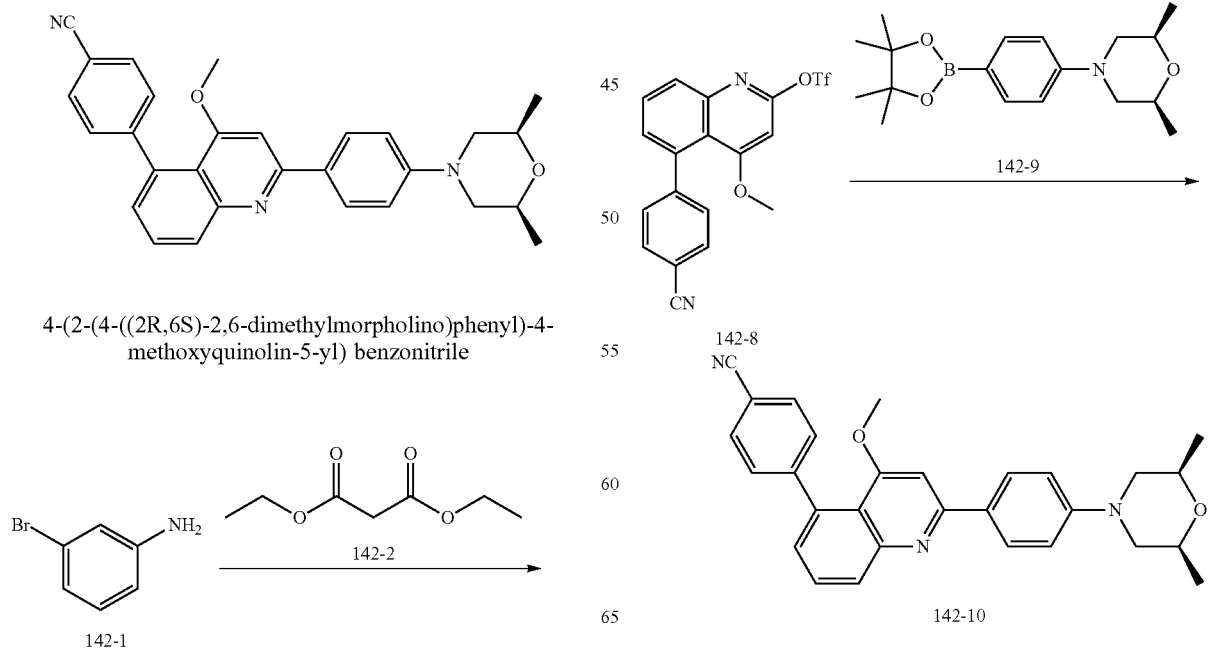

Step 1: Compound 142-1 (3.0 g, 17.4 mmol) and compound 142-2 (1.4 g, 8.7 mmol) were heated to 180° C. under microwave and stirred for 3 h. After cooling, the obtained solid was washed with EtOAc to deliver compound 142-3 (2.4 g, yield 22.2%) as yellow-brown solid. MS ESI calcd for $C_{15}H_{12}Br_2N_2O_2$ $[M+H]^+$ 411, found 411.

Step 2: A solution of compound 142-3 (3.5 g, 8.46 mmol) and $P_2O_5$ (2.4 g, 16.9 mmol) in $CH_3SO_3H$ (15 mL) was heated to 160° C. and stirred for 3 h. The reaction mixture was poured into ice. The solid obtained from filtration was washed with $H_2O$. Then the solid was dissolved into 1 M NaOH solution. The undissolved substance was filtrated. The aqueous phase was adjusted to pH to 3 with conc. hydrochloric acid. The precipitate was filtrated and washed with small amounts of $H_2O$, finally dried under reduced pressure to deliver compound 142-4 (1.85 g, yield 91%) as white solid. MS ESI calcd for $C_9H_6BrNO_2$ $[M+H]^+$ 240, found 240.

Step 3: A mixture of compound 142-4 (1.84 g, 7.62 mmol) and $K_2CO_3$ (2.11 g, 15.24 mmol) was added into acetone (300 mL). Dimethyl sulfate (1.152 g, 9.15 mmol) was added dropwise into the mixture while stirring at room temperature. After addition, the reaction mixture was heated to 50° C. and stirred for 2 h. The reaction mixture was concentrated to dry, then adjusted to pH to 4 with 1 M HCl aqueous solution. The precipitate was filtrated and washed with n-hexane to deliver a mixture of compound 142-5 (0.84 g, yield 43%). The mixture was purified by preparative HPLC to deliver compound 142-5 (420 mg) as white solid. MS ESI calcd for $C_{10}H_8BrNO_2$ $[M+H]^+$ 254, found 254.

Step 4: A mixture of compound 142-5 (300 mg, 1.18 mmol), compound 142-6 (208 mg, 1.41 mmol), $Na_2CO_3$ (313 mg, 2.95 mmol) and $Pd(dppf)Cl_2$ (86 mg, 0.118 mmol) was added into a mixed solvent of $CH_3CN$ (5 mL) and $H_2O$ (1 mL). Then under nitrogen gas atmosphere, the reaction mixture was heated to 80° C. and stirred for 8 h. The reactants was filtrated, the filtrate was concentrated to dry, finally purified by column chromatography to deliver compound 142-7 (223 mg, yield 69%) as yellow-brown solid. MS ESI calcd for $C_{17}H_{12}N_2O_2$ $[M+H]^+$ 277, found 277.

Step 5: Trifluoromethanesulfonic anhydride (644 mg, 2.28 mmol) was added dropwise into a solution of compound 142-7 (350 mg, 1.27 mmol) and pyridine (201 mg, 2.54 mmol) in DCM (15 mL). Then the reaction mixture was stirred overnight. The reaction mixture was concentrated to dry, finally purified by column chromatography to deliver compound 142-8 (254 mg, yield 49%) as white solid. MS ESI calcd for $C_{18}H_{11}F_3N_2O_4S$ $[M+H]^+$ 409, found 409.

Step 6: A mixture of compound 142-8 (100 mg, 0.245 mmol), compound 142-9 (116 mg, 0.367 mmol), $Na_2CO_3$ (78 mg, 0.735 mmol) and $Pd(dppf)Cl_2$ (36 mg, 0.049 mmol) was added into a mixed solvent of $CH_3CN$ (5 mL) and $H_2O$ (1 mL). Under nitrogen gas atmosphere, the reaction mixture was heated to 80° C. and stirred for 3 h. The reactants was filtrated, the filtrate was concentrated to dry, finally purified by preparative HPLC to deliver the title compound (95 mg, yield 86%) as white solid. $^1$H NMR (400 MHz, CDCl$_3$) δ 8.18 (d, J=7.6 Hz, 1H), 8.09 (d, J=8.8 Hz, 2H), 7.62-7.72 (m, 3H), 7.40-7.50 (m, 2H), 7.19 (d, J=6.4 Hz, 1H), 7.09 (s, 1H), 7.03 (d, J=8.8 Hz, 2H), 3.75-3.83 (m, 2H), 3.65 (s, 3H), 3.55-3.64 (m, 2H), 2.45-2.57 (m, 2H), 1.25-1.30 (m, 6H). MS ESI calcd for $C_{29}H_{27}N_3O_2$ $[M+H]^+$ 450, found 450.

Embodiment 143

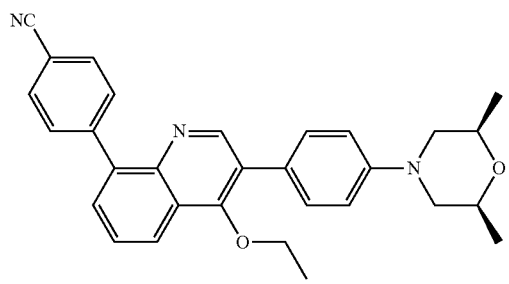 [SMILES: CCOc1c(-c2ccc(N3C[C@@H](C)O[C@@H](C)C3)cc2)cnc2c(-c3ccc(C#N)cc3)cccc12]

4-(3-(4-((2S,6R)-2,6-dimethylmorpholino)phenyl)-4-ethoxyquinolin-8-yl)benzonitrile

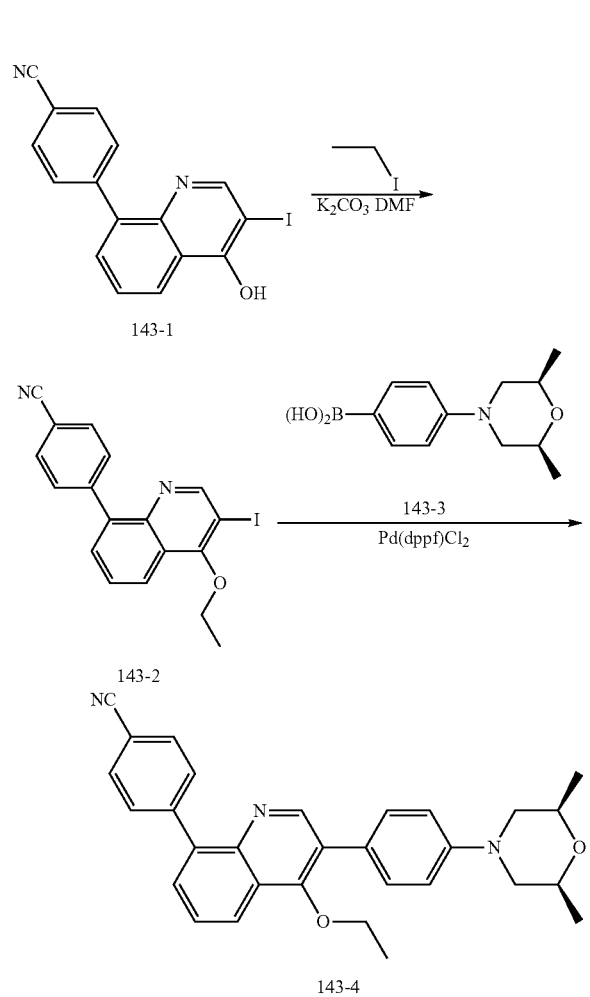

Step 1: $K_2CO_3$ (745 mg, 5.4 mmol) and ethyl iodide were added into a solution of compound 143-1 in DMF (20 mL), the reaction mixture was stirred at 90° C. for 2 h. After the reaction was complete, $H_2O$ was added, then the reaction mixture was extracted with EtOAc. The combined organic phase was washed with brines, dried over $Na_2SO_4$, and concentrated under vacuum to deliver the desired compound 2 (0.9 g, 83%) as solid. MS ESI calcd for $C_{18}H_{13}IN_2O$ $[M+H]^+$ 401, found 401.

Step 2: Compound 143-2 (200 mg, 0.5 mmol), compound 143-3 (176 mg, 0.74 mmol), Pd(dppf)Cl$_2$ (36 mg, 0.05 mmol) and Na$_2$CO$_3$ (106 mg, 1 mmol) were suspended in a mixed solvent of THF/H$_2$O (10:1, 11 mL), then under nitrogen gas atmosphere, the reaction mixture was stirred at 90° C. for 12 h. After cooling, the reaction mixture was diluted with EtOAc, then washed with brines, dried over Na$_2$SO$_4$, concentrated under reduced pressure, the residue was purified by RP-HPLC (acetonitrile/H$_2$O with 0.05% ammonium hydroxide modifier) to deliver the title compound (150 mg, 70%) as white solid. $^1$H NMR (400 MHz, CDCl$_3$) δ 8.89 (s, 1H), 8.51-8.49 (m, 1H), 7.82 (s, 4H), 7.64 (d, J=8.0 Hz, 2H), 7.49 (d, J=7.6 Hz, 2H), 7.08 (d, J=7.6 Hz, 2H), 4.08-4.03 (m, 2H), 3.86 (br. s., 2H), 3.58 (d, J=12 Hz, 2H), 2.56 (t, J=11.2 Hz, 2H), 1.37 (t, J=7.2 Hz, 3H), 1.0 (d, J=6.4 Hz, 6H). MS ESI calcd for C$_{30}$H$_{29}$N$_3$O$_2$ [M+H]$^+$ 464, found 464.

The compounds listed in table 12 were synthesized by compound 143-1 and corresponding haloalkanes.

Embodiment 147

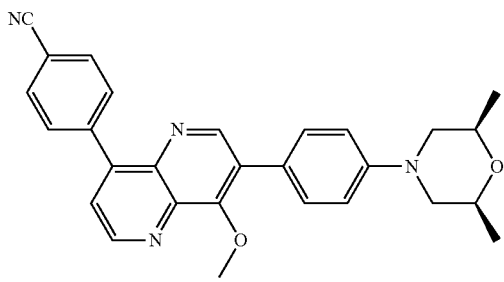

| Embodiment | Structure | NMR |
|---|---|---|
| 144 | 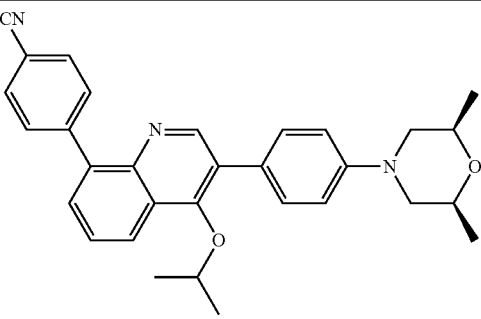 | $^1$H NMR (400 MHz, CDCl$_3$) δ 8.88 (s, 1H), 8.52(dd, J = 7.2, 2.4 Hz, 1H), 7.87-7.82 (m, 4H), 7.63 (d, J = 8 Hz, 2H), 7.52 (d, J = 8.8 Hz, 2H), 7.09 (d, J = 8.8 Hz, 2H), 4.61-4.57 (m, 1H), 3.88-3.84 (m, 2H), 3.58 (d, J = 11.6 Hz, 2H), 2.57 (t, J = 10.8 Hz, 2H), 1.31-1.23 (m, 12H). MS ESI calcd for C$_{31}$H$_{31}$N$_3$O$_2$ [M + H]$^+$ 478, found 478. |
| 145 | 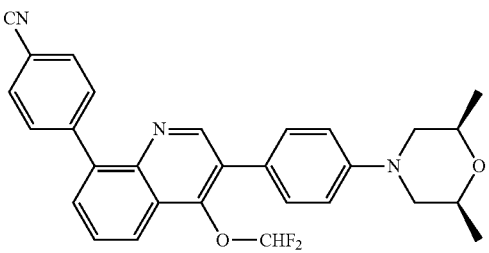 [SMILES: C[C@@H]1CN(c2ccc(-c3cnc4c(-c5ccc(C#N)cc5)cccc4c3OC(F)F)cc2)C[C@H](C)O1] | $^1$H NMR (400 MHz, CDCl$_3$) δ 8.43 (d, J = 7.83 Hz, 1H), 7.92 (d, J = 7.83 Hz, 3H), 7.70 (d, J = 8.2 Hz, 3H), 7.66-7.58 (m, 2H), 7.55-7.48 (m, 2H), 7.38-7.18 (m, 1H), 2.74 (br. s., 1 H), 1.25 (d, J = 6.3 Hz, 6H). MS ESI calcd for C$_{29}$H$_{25}$F$_2$N$_3$O$_2$ [M + H]$^+$ 486, found 486. |
| 146 | 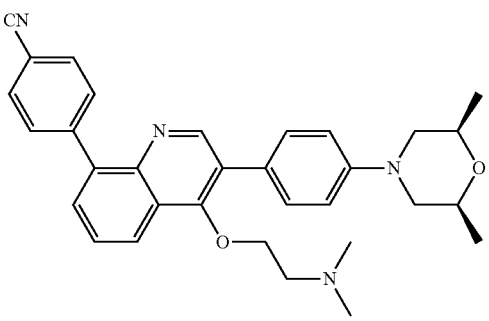 [SMILES: C[C@@H]1CN(c2ccc(-c3cnc4c(-c5ccc(C#N)cc5)cccc4c3OCCN(C)C)cc2)C[C@H](C)O1] | $^1$H NMR (400 MHz, CDCl$_3$) δ 8.88 (s, 1H), 8.32 (s, 1H), 7.77 (d, J = 6.8 Hz, 6H), 7.52 (d, J = 6 Hz, 2H), 7.12 (d, J = 6.8 Hz, 2H), 4.19 (s, 2H), 3.88 (s, 2H), 3.58 (d, J = 11.2 Hz, 2H), 3.56 (s, 2H), 2.91 (s, 6 H), 2.57 (t, J = 10.4 Hz, 2H), 1.30 (d, J = 5.6 Hz, 6H). MS ESI calcd for C$_{32}$H$_{34}$N$_4$O$_2$ [M + H]$^+$ 507, found 507. |

4-(7-(4-((2S,6R)-2,6-dimethylmorpholino)phenyl)-8-methoxy-1,5-naphthyridin-4-yl) benzonitrile

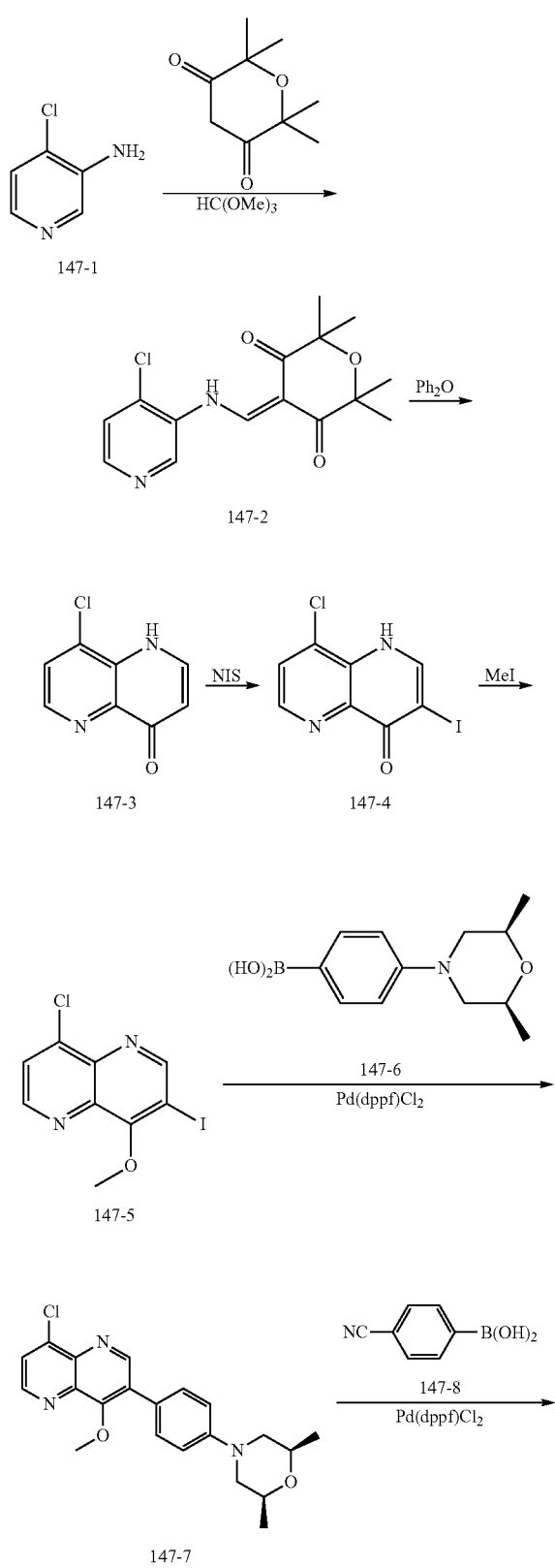

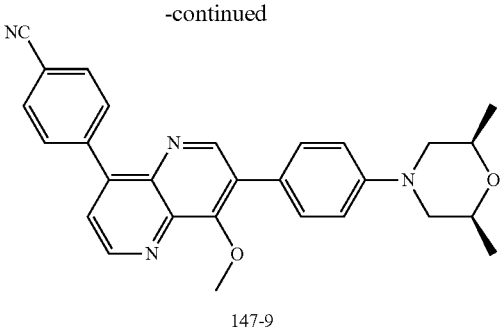

Step 1: 2,2,6,6-tetramethyl-2H-pyran-3,5(4H,6H)-dione (13.8 g, 96 mmol) was added into HC(OMe)₃ (50 mL, 288 mmol). After the mixture was stirred at 80° C. for 3 h, compound 147-1 (10 g, 76.9 mmol) was added, the mixture was stirred for further 5 h. After detected by LC-MS, the mixture was concentrated under reduced pressure, the crude product was washed with MeOH to deliver compound 147-2 (15 g, yield 57%). MS ESI calcd for $C_{15}H_{17}ClN_2O_3$ [M+H]⁺ 309, found 309.

Step 2: Compound 147-2 (13 g, 46 mmol) was added into preheated Ph₂O (250° C.) (500 mL) in portions. After stirred for 5 min, the mixture was detected by LC-MS. After the reaction mixture was cooled to room temperature, petroleum ether was added to filtrate, the filtrate was concentrated under reduced pressure to deliver compound 147-3 (4 g, yield 48%). MS ESI calcd for $C_8H_5ClN_2O$ [M+H]⁺ 309, found 309.

Step 3: A solution of compound 147-3 (3 g, 16.7 mmol) and NIS (4.1 g, 18.3 mmol) in DMF (20 mL) was stirred at room temperature for 16 h. The reaction mixture was filtrated, and the filtrate was concentrated under reduce pressure to deliver 147-4 (2.5 g, yield 49%). MS ESI calcd for $C_8H_4ClIN_2O$ [M+H]⁺ 307, found 307.

Step 4: A solution of compound 147-4 (2.5 g, 8.2 mmol), MeI (1.75 g, 12.3 mmol) and Ag₂CO₃ (4.5 g, 16.4 mmol) in DMF (20 mL) was stirred at 90° C. for 3 h. The reaction mixture was detected by LC-MS. The mixture was poured into H₂O, the aqueous phase was extracted with EtOAc. The combined organic phase was washed with brines, dried over Na₂SO₄, concentrated under reduced pressure. The crude product was purified by silica gel chromatography (PE:EtOAc=10:1) to deliver compound 147-5 (300 mg, yield 12%). MS ESI calcd for $C_9H_6ClIN_2O$ [M+H]⁺ 321, found 321.

Step 5: Compound 147-5 (320 mg, 1 mmol), compound 147-6 (350 mg, 1.1 mmol), Pd(dppf)Cl₂ (74 mg, 0.1 mmol) and Na₂CO₃ (212 mg, 2 mmol) were dissolved in a mixed solvent of THF/H₂O (10:2 mL), and stirred at 70° C. for 16 h. The reaction mixture was detected by LC-MS. The mixture was poured into H₂O, the aqueous phase was extracted with EtOAc. The combined organic phase was washed with brines, dried over Na₂SO₄, concentrated under reduced pressure. The crude product was purified by silica gel chromatography (PE:EtOAc=2:1) to deliver compound 147-7 (200 mg, yield 52%). MS ESI calcd for $C_{21}H_{22}ClN_3O_2$ [M+H]⁺ 384, found 384.

Step 6: Compound 147-7 (200 mg, 0.52 mmol), compound 147-8 (84 mg, 0.57 mmol), Pd(dppf)Cl₂ (38 mg, 0.052 mmol) and Na₂CO₃ (110 mg, 1.04 mmol) were dissolved in a mixed solvent of THF/H₂O/DMF (10:2:2 mL), and the mixture was stirred at 90° C. for 4 h. The reaction mixture was detected by LC-MS. The mixture was poured into H₂O, the aqueous phase was extracted with EtOAc. The combined organic phase was dried over Na₂SO₄, concentrated under reduced pressure. The crude product was purified by preparative HPLC to deliver the title compound (80 mg, yield 34%) as white solid. ¹H NMR (400 MHz, CDCl₃) δ 9.05 (d, J=4.8 Hz, 1H), 8.95 (s, 1H), 7.89-7.81 (m, 4H), 7.59 (t, J=4.4 Hz, 3H), 7.04 (d, J=8.8 Hz, 2H), 4.09 (s, 3H), 3.85-3.82 (m, 2H), 3.58 (d, J=11.2 Hz, 2H), 2.51 (t, J=11.2 Hz, 2H), 1.30-1.25 (m, 6H). MS ESI calcd for C₂₈H₂₆N₄O₂ [M+H]⁺ 451, found 451.

Embodiment 148

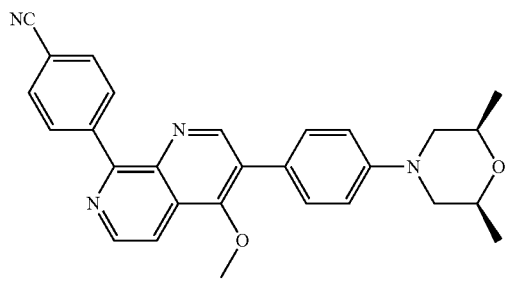 [SMILES: COc1c(-c2ccc(N3C[C@@H](C)O[C@@H](C)C3)cc2)cnc2c(-c3ccc(C#N)cc3)nccc12]

4-(3-(4-((2S,6R)-2,6-dimethylmorpholino)phenyl)-4-methoxy-1,7-naphthyridin-8-yl) benzonitrile

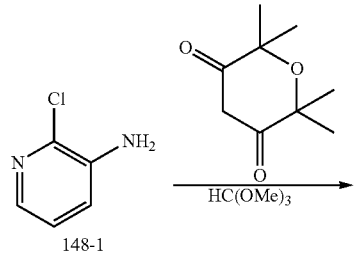

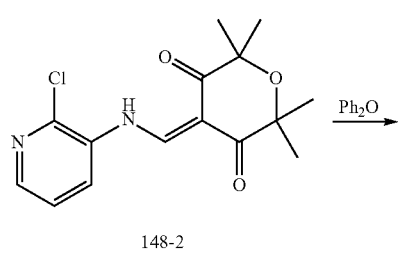

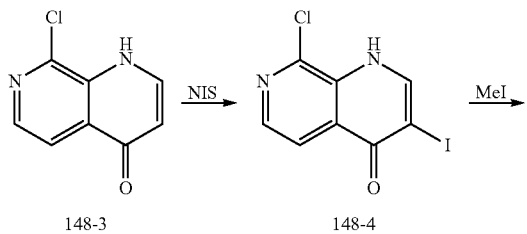

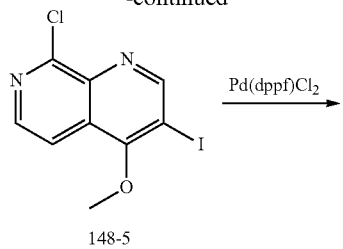

148-5

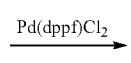

148-6

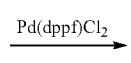

148-7

The title compound was synthesized according to the above-mentioned method as white solid. ¹H NMR (400 MHz, CDCl₃) δ 9.05 (s, 1H), 8.82 (d, J=5.2 Hz, 1H), 8.32 (d, J=5.6 Hz, 1H), 8.14 (d, J=7.6 Hz, 2H), 7.87 (d, J=8 Hz, 2H), 7.62 (d, J=8 Hz, 2H), 7.16 (d, J=8 Hz, 2H), 3.89 (s, 2H), 3.77 (s, 3H), 3.62 (d, J=12 Hz, 2H), 2.61 (d, J=10.8 Hz, 2H), 1.31 (d, J=6 Hz, 6H). MS ESI calcd for C₂₈H₂₆N₄O₂ [M+H]⁺ 451, found 451.

Embodiment 149

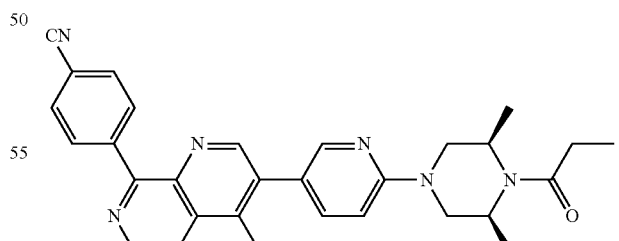

4-(3-(6-((3S,5R)-3,5-dimethyl-4-propionylpiperazizin-1-yl)pyridin-3-yl)-4-methoxy-1,7-naphthyridin-8-yl)benzonitrile The title compound was synthesized according to the above-mentioned method as white solid. ¹H NMR (400

MHz, METHANOL-d$_4$) δ 8.96 (s, 1H), 8.69 (d, J=5.6 Hz, 1H), 8.46 (d, J=2.4 Hz, 1H), 8.18 (dd, J=11.6, 8.4 Hz, 3H), 7.95 (dd, J=8.8, 2.4 Hz, 2H), 7.87 (d, J=8.4 Hz, 2H), 7.06 (d, J=8.8 Hz, 1H), 4.31-4.42 (m, 3H), 3.81 (s, 3H), 3.16 (d, J=11.6 Hz, 2H), 2.50 (m, 2H), 1.31 (s, 6H), 1.15 (t, J=7.6 Hz, 3H). MS ESI calcd for C$_{30}$H$_{30}$N$_6$O$_2$ [M+H]$^+$ 507, found 507.

Embodiment 150

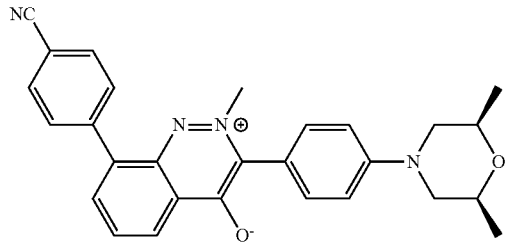 [SMILES: C[C@@H]1CN(c2ccc(-c3c([O-])c4cccc(-c5ccc(C#N)cc5)c4n[n+]3C)cc2)C[C@H](C)O1]

8-(4-cyanophenyl)-3-(4-((2R,6S)-2,6-dimethylmorpholino)phenyl)-2-methylcinnolin-2-ium-4-olate

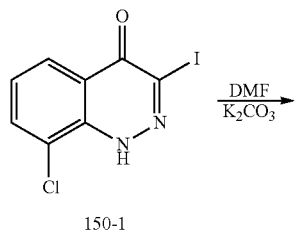

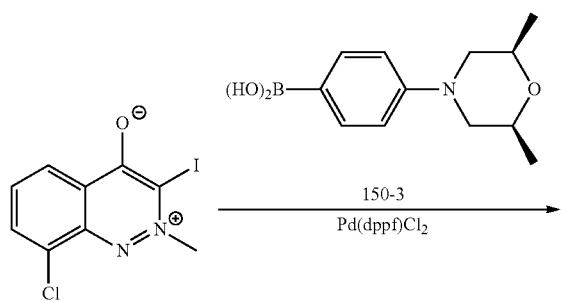

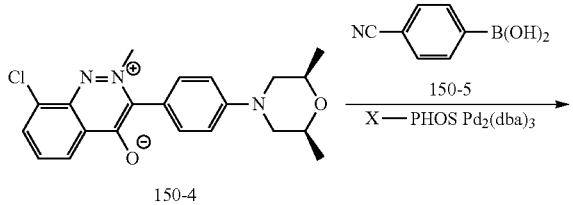

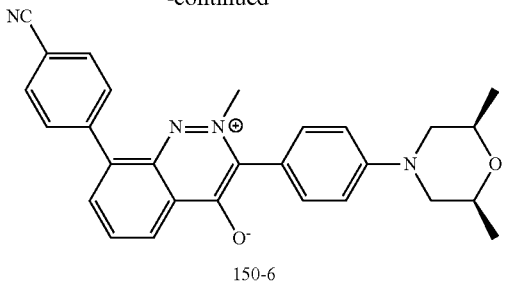

Step 1: K$_2$CO$_3$ (1.9 g, 13.7 mmol) and methyl iodide were added into a solution of compound 150-1 (2.3 g, 6.84 mmol) in DMF (20 mL). The reaction mixture was stirred at 90° C. for 4 h. After the reaction was complete as detected by LC-MS, H$_2$O was added and then the reaction mixture was extracted with EtOAc. The combined organic phase was washed with brines, dried over Na$_2$SO$_4$, and concentrated under vacuum. The residue was purified by silica gel chromatography (PE/EtOAc=3:1) to deliver the desired compound 2 (1.5 g, 68%) as solid. MS ESI calcd for C$_9$H$_6$ClIN$_2$O [M+H]$^+$ 321, found 321.

Step 2: Compound 150-2 (321 mg, 1 mmol), compound 150-3 (282 mg, 1.2 mmol), Pd(dppf)Cl$_2$ (73.2 mg, 0.1 mmol) and Na$_2$CO$_3$ (212 mg, 2 mmol) were suspended in a mixed solvent of THF/H$_2$O (10:1 mL), under nitrogen gas atmosphere, the reaction mixture was stirred at 90° C. overnight. After the reaction was complete as detected by LC-MS, H$_2$O was added and then the reaction mixture was extracted with EtOAc. The combined organic phase was washed with brines, dried over Na$_2$SO$_4$, and concentrated under vacuum to deliver the crude product 4 (320 mg, 83.6%). MS ESI calcd for C$_{21}$H$_{22}$ClN$_3$O$_2$ [M+H]$^+$ 384, found 384.

Step 3: Compound 150-4 (320 mg, 0.84 mmol), compound 150-5 (184 mg, 1.25 mmol), Pd$_2$(dba)$_3$ (77 mg, 0.08 mmol), Xantphos (86 mg, 0.16 mmol) and Na$_2$CO$_3$ (178 mg, 1.68 mmol) were suspended in a mixed solvent of 1,4-dioxane/H$_2$O (10:1 mL), under nitrogen gas atmosphere, the reaction mixture was heated to 120° C. and refluxed for 3 h. After the reaction was complete, the mixture was filtrated with diatomite, the filtrate was evaporated, extracted with EtOAc. The combined EtOAc phase was washed with brines, dried over Na$_2$SO$_4$, and concentrated under reduced pressure. The residue was purified by preparative HPLC to deliver the title compound (80 mg, 20%). $^1$H NMR (400 MHz, CDCl$_3$) δ 8.48 (d, J=8 Hz, 1H), 7.80-7.69 (m, 6H), 7.89-7.81 (m, 4H), 7.36 (d, J=8.8 Hz, 2H), 7.15 (d, J=8.4 Hz, 2H), 4.19 (s, 3H), 3.90-3.86 (m, 2H), 3.60 (d, J=11.6 Hz, 2H), 2.61 (t, J=10.8 Hz, 2H), 1.29 (d, J=6.4 Hz, 6H). MS ESI calcd for C$_{28}$H$_{26}$N$_4$O$_2$ [M+H]$^+$ 451, found 451.

Embodiment 151

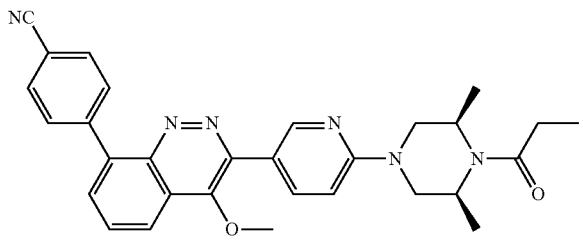

4-(3-(6-(3,5-dimethyl-4-propionylpiperazin-1-yl)pyridin-3-yl)-4-methoxycinnolin-8-yl)benzonitrile

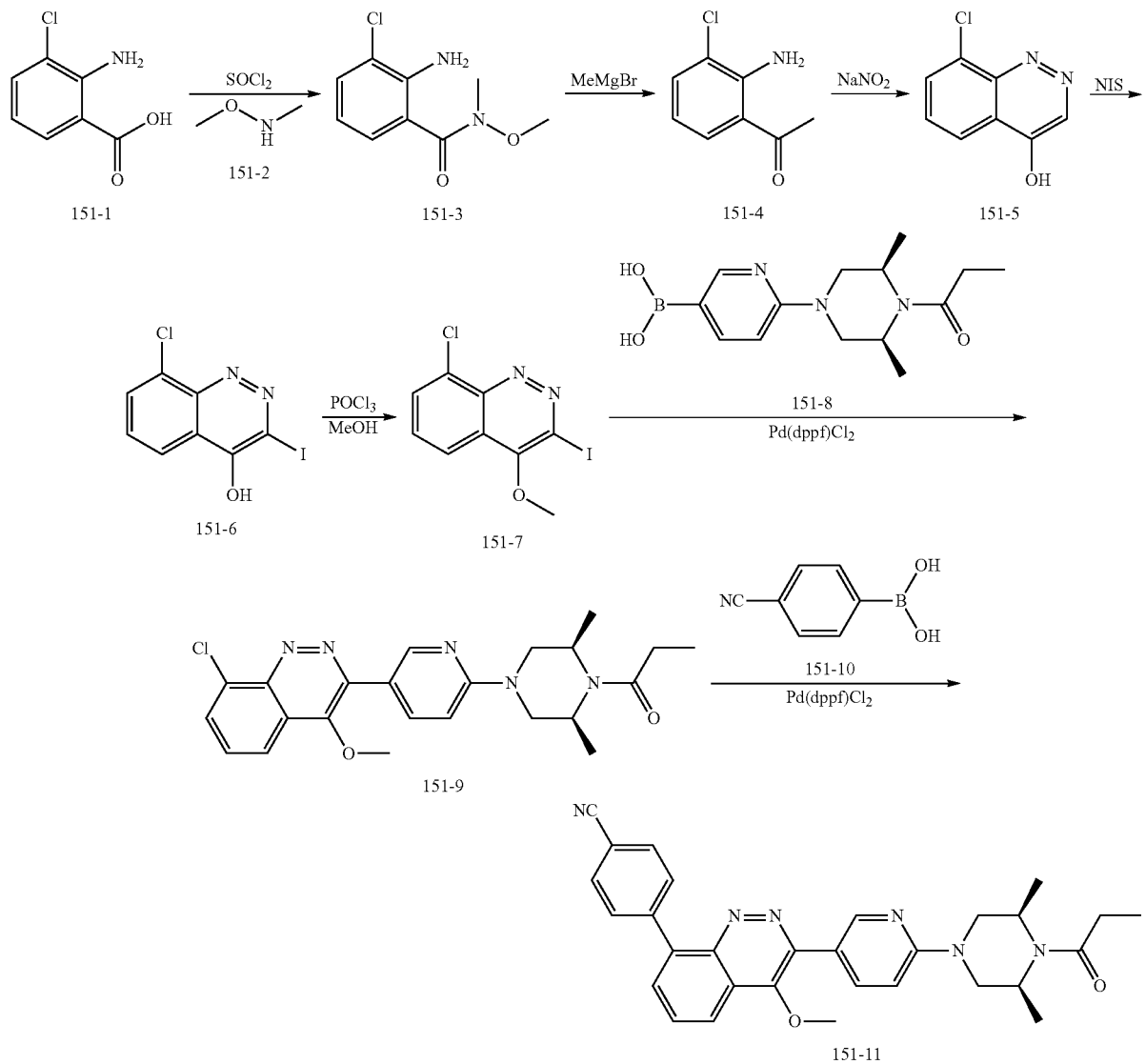

Step 1: Compound 151-1 (51 g, 0.3 mol), thionyl chloride (200 mL) were heated to reflux for 2 h, then thionyl chloride was evaporated, the residue was dissolved in DCM, a solution of compound 151-2 (42.3 g, 0.45 mol), DIPEA (116 g, 0.9 mol) in DCM was added, the reaction mixture reacted at room temperature for 1 h, then poured into H$_2$O, the mixture was washed with H$_2$O and brines respectively, the organic phase was dried and concentrated, the residue was purified by column chromatography to deliver compound 151-3 (26 g, yield 40%) as yellow oil. MS ESI calcd for C$_9$H$_{11}$ClN$_2$O$_2$ [M+H]$^+$ 215, found 215.

Step 2: Compound 151-3 (26 g, 0.12 mol) was dissolved in THF (300 mL), MeMgBr (120 mL, 3M in Et$_2$O) was added slowly into the solution at 0° C. After the addition, the reaction mixture was kept at 0° C. for 2 h, and then poured into ammonium chloride aqueous solution, extracted with EtOAc, the extraction liquid was washed with brines, dried over anhydrous sodium sulfate, and concentrated under vacuum. The residue was purified by column chromatography to deliver compound 151-4 (10.5 g, yield 51.4%) as yellow solid. MS ESI calcd for C$_8$H$_8$ClNO [M+H]$^+$ 169, found 169.

Step 3: Compound 151-4 (1.69 g, 10 mmol) was added into H$_2$O (10 mL), conc. hydrochloric acid (17 mL) was added at 0° C., then a solution of sodium nitrite (2.1 g, 30 mmol) in H$_2$O (10 mL) was added dropwise at −5 to 0° C. After the addition, the reaction mixture reacted at 0° C. for 1 h, then heated to 80° C. and reacted for 6 h, then cooled in an ice bath. The mixture was filtrated, dried to deliver 1.2 g compound 151-5, yield 67% as yellow solid. MS ESI calcd for C$_8$H$_5$ClN$_2$O [M+H]$^+$ 181, found 181.

Step 4: NIS (1.5 g, 0.67 mmol) was added into a solution of compound 151-5 (1.2 g, 0.67 mmol) in DMF (10 mL), the reaction mixture was stirred at room temperature for 2 h, the the solution was poured into H$_2$O, filtrated, the filtrate cake was dried to deliver 1.5 g compound 151-6, yield 75% as yellow solid. MS ESI calcd for C$_8$H$_4$ClIN$_2$O [M+H]$^+$ 307, found 307.

Step 5: Compound 151-6 (1.2 g, 0.67 mmol), phosphorus oxychloride (5 mL) were heated to 120° C. and stirred for 2 h, then the reaction mixture was cooled and poured into methanol, H$_2$O and EtOAc were added respectively, the organic phase was separated, dried and concentrated to deliver 1.0 g compound 151-7, yield 62.5% as yellow solid. MS ESI calcd for C$_9$H$_6$ClIN$_2$O [M+H]$^+$ 321, found 321.

Step 6: Compound 151-7 (320 mg, 1.0 mmol), compound 151-8 (292 mg, 1.0 mmol), Pd(dppf)Cl$_2$ (73 mg, 0.1 mmol) and sodium carbonate (212 mg, 2.0 mmol) were added into a solution of THF/H$_2$O/DMF (10:1:1, 12 mL), under nitrogen gas atmosphere, the reaction mixture was stirred at 80° C. overnight. The mixture was filtrated with diatomite, the filtrate was washed with H$_2$O (10 mL) and extracted with EtOAc (20 mL), the extraction liquid was washed with brines, and dried over anhydrous sodium sulfate, concentrated under vacuum. The residue was purified by column chromatography to deliver compound 151-9 (200 mg, yield 68%) as yellow solid. MS ESI calcd for C$_{23}$H$_{26}$ClN$_5$O$_2$ [M+H]$^+$ 441, found 441.

Step 7: The title compound (10 mg, yield 9%) was synthesized according to the above-mentioned method as white solid. $^1$H NMR (400 MHz, CDCl$_3$) δ 9.04-9.05 (d, J=2.0 Hz, 1H), 8.42-8.43 (d, J=6.8 Hz, 1H), 8.28-8.30 (d, J=8.8 Hz, 1H), 7.91-7.93 (d, J=8.4 Hz, 2H), 7.55-7.85 (m, 4H) 6.86-6.88 (d, J=8.8 Hz, 1H) 4.08-4.13 (m, 2H), 3.90 (s, 3H) 3.17-3.21 (d d, J=4.0 Hz 2H), 2.25-2.28 (m, 2H) 2.03-2.06 (m, 1H) 1.19-1.28 (m, 9H) 0.98-0.99 (d, J=6.4 Hz 2H). MS ESI calcd for C$_{30}$H$_{30}$N$_6$O$_2$ [M+H]$^+$ 507, found 507.

Embodiment 152

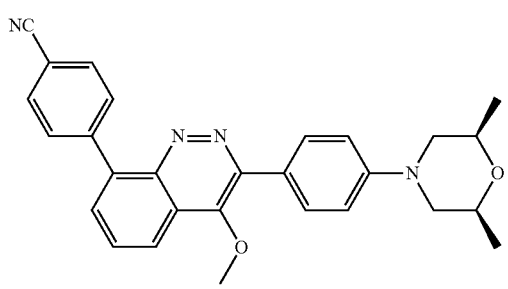 [SMILES: COc1c(-c2ccc(N3C[C@@H](C)O[C@@H](C)C3)cc2)nnc2c(-c3ccc(C#N)cc3)cccc12]

4-(3-(4-((2R,6S)-2,6-dimethylmorpholino)phenyl)-4-methoxycinnolin-8-yl) benzonitrile

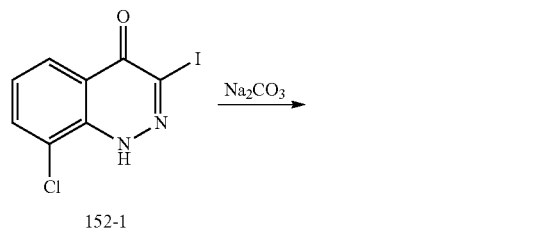

152-1

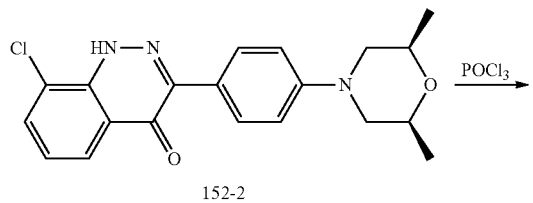

152-2

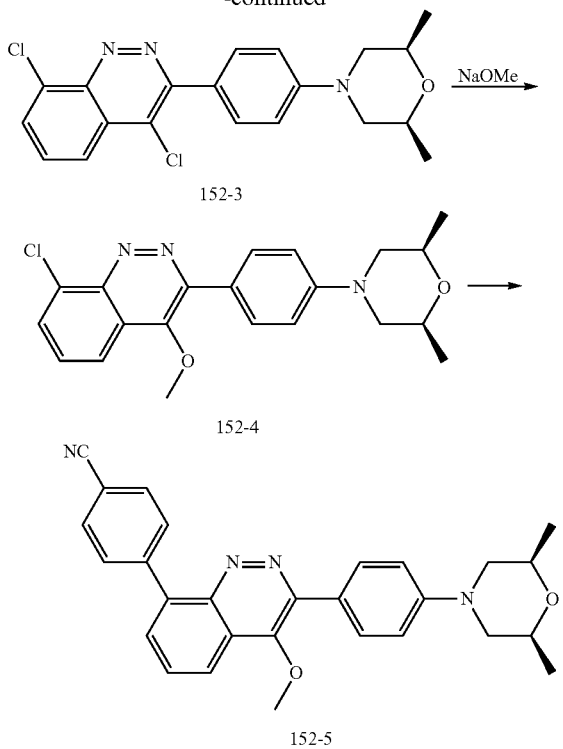

152-3

152-4

152-5

Step 1: Compound 152-1 (1.2 g, 4 mmol), sodium carbonate (4.3 g, 40.2 mmol), Pd(dppf)Cl$_2$ (200 mg, 02 mmol) were added into a solution of 4-((2R,6S)-2,6-dimethylmorpholinyl)benzoboric acid (1.15 g, 5 mmol) in a mixed solvent of THF/H$_2$O (20:4 mL), and stirred at 70° C. overnight. After the reaction was complete as detected by LC-MS, H$_2$O was added, then extracted with EtOAc. The combined organic phase was washed with brines, dried over sodium sulfate, concentrated under vacuum. The residue was purified by silica gel chromatography (PE:EtOAc=5:1-2:1) to deliver compound 152-2 (0.62 g, yield 44%). MS ESI calcd for C$_{20}$H$_{20}$ClN$_3$O$_2$ [M+H]$^+$ 370, found 370.

Step 2: A solution of compound 152-2 (3.7 g, 10 mmol) in POCl$_3$ (35 mL) was heated at 110° C. for 6 h. The solvent was removed under vacuum. The residue was quenched with H$_2$O. The solution was partitioned between EtOAc and H$_2$O, the organic phase were combined, washed with brines, dried over anhydrous sodium sulfate, filtrated and concentrated under vacuum. The residue was purified by silica gel chromatography (PE:EtOAc=2:1) to deliver compound 152-3 (0.78 g, yield 21%). MS ESI calcd for C$_{20}$H$_{19}$Cl$_2$N$_3$O [M+H]$^+$ 389, found 389.

Step 3: NaOMe (0.055 g, 1 mmol) was added into a solution of compound 152-3 (0.19 g, 0.5 mmol) in MeOH (10 mL) at −10° C. in 10 min in portions. The reaction mixture was stirred at 20° C. for 1 h, then stirred at 50° C. for 3 h. After the reaction was complete, H$_2$O (100 mL) was added, then the reaction mixture was extracted with EtOAc. The combined organic phase was washed with brines, dried over sodium sulfate, and concentrated under vacuum to deliver compound 152-4 (0.11 g, 58%) as brown solid which was used in the nest step directly. MS ESI calcd for C$_{21}$H$_{22}$ClN$_3$O$_2$ [M+H]$^+$ 384, found 384.

Step 4: Compound 152-4 (40 mg, 0.1 mmol), 4-cyanophenyl boronic acid (30 mg, 0.2 mmol), Pd$_2$(dba)$_3$ (9 mg, 0.01 mmol), Xantphos (10 mg, 0.02 mmol) and sodium carbonate (4.3 g, 40.2 mmol) were dissolved in a mixed solvent of dioxane/H₂O (5:1 mL), under nitrogen gas atmosphere, the reaction mixture was stirred at 110° C. for 6 h. The mixture was diluted with H₂O (10 mL), extracted with EtOAc. The combined organic phase was washed with brines, dried over anhydrous sodium sulfate, and concentrated under reduced pressure. The residue was purified by preparative HPLC to deliver the title compound as white solid (yield 32%). ¹H NMR (400 MHz, CDCl₃) δ 8.23 (d, J=8 Hz, 1H), 8.06 (d, J=8.4 Hz, 2H), 7.85 (d, J=8 Hz, 2H), 7.77-7.69 (m, 4H), 6.99 (d, J=8.8 Hz, 2H), 3.74 (s, 5H), 3.57 (d, J=12 Hz, 2H), 2.47 (t, J=10.8 Hz, 2H), 1.23 (d, J=6.4 Hz, 6H). MS ESI calcd for C₂₈H₂₆N₄O₂ [M+H]⁺ 451, found 451.

Embodiment 153

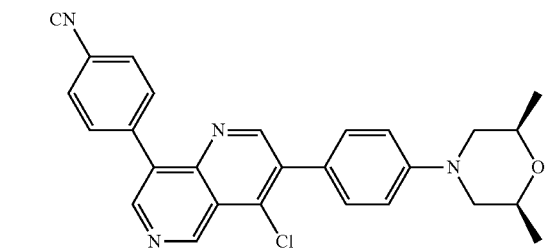

4-(4-chloro-3-(4-((2S,6R)-2,6-dimethylmorpholino)phenyl)-1,6-naphthyridin-8-yl) benzonitrile

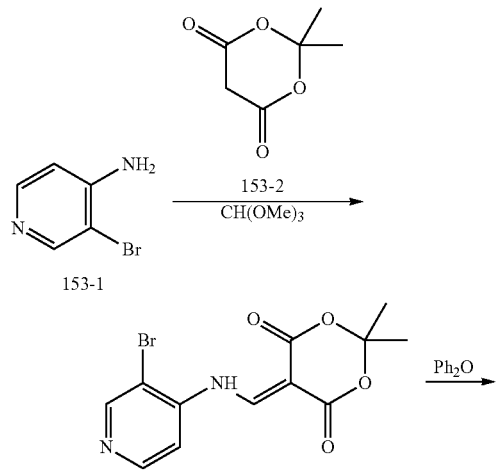

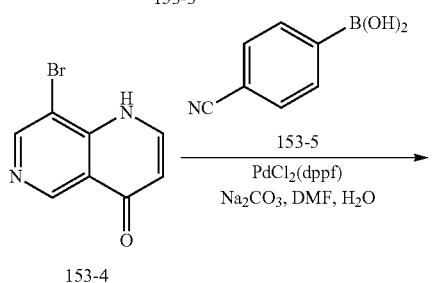

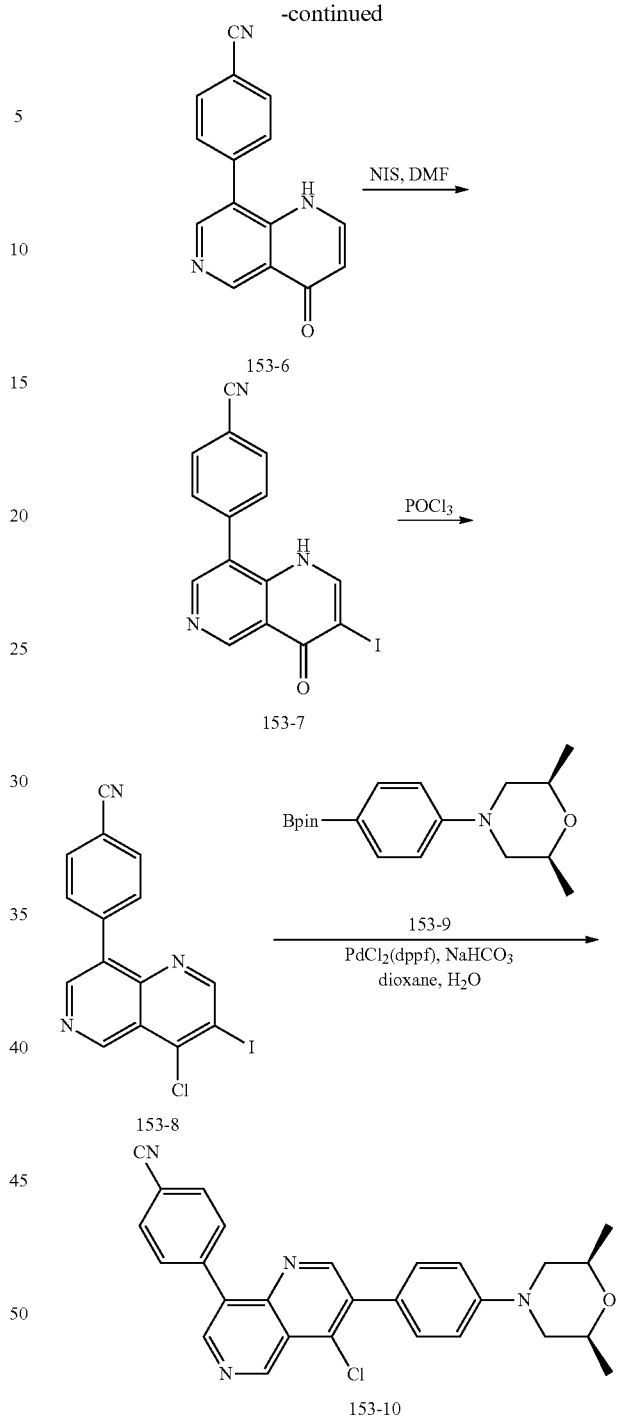

Step 1: A solution of compound 153-2 (21 g, 0.146 mol) in CH(OMe)₃ (50 mL) was stirred at 60° C. for 0.5 h. The reaction mixture was cooled to room temperature, compound 153-1 (21.05 g, 0.122 mol) was added. The mixture was refluxed at 100° C. for 2 h. TLC (PE:EtOAc=1:1) showed that the starting material was completely consumed. The reaction mixture was cooled to 0° C. and filtrated. The filtrate cake was grinded with MeOH to deliver compound 153-2 (24 g, 62%) as dark-yellow solid. ¹H NMR (400 MHz, DMSO-d₆) δ 11.48 (brs, 1H), 8.96-8.81 (m, 1H), 8.77 (s, 1H), 8.51 (d, J=5.29 Hz, 1H), 7.90 (d, J=5.29 Hz, 1H), 7.37

(t, J=7.9 Hz, 1H), 7.15-6.90 (m, 1H), 1.68 (s, 6H). MS ESI calcd for C$_{12}$H$_{11}$BrN$_2$O$_4$ [M+H]$^+$ 326, 328, found 326, 328.

Step 2: A solution of compound 153-2 (0.4 g, 1.223 mol) in PH$_2$O (3 mL) was refluxed at 220° C. for 0.5 h. TLC showed that the starting material was completely consumed. The reaction mixture was cooled to room temperature and hexane was added. The mixture was filtrated, and the filtrate cake was washed with hexane to deliver compound 153-4 (200 mg, 72%) as dark-yellow solid. MS ESI calcd for C$_8$H$_5$BrN$_2$O [M+H]$^+$ 224 and 226, found 224 and 226.

Step 3: Sodium carbonate (780 mg, 7.365 mmol) was added into a solution of compound 153-4 (550 mg, 2.455 mmol) and compound 153-5 (397 mg, 2.701 mmol) (397 mg, 2.701 mmol) in a mixed solvent of DMF (5 mL) and H$_2$O (1 mL) at room temperature. The reaction mixture was swept with nitrogen gas for 3 times, PdCl$_2$(dppf) (90 mg, 0.123 mmol) was added. Then the reaction mixture was swept with nitrogen gas for 3 times again and stirred at reflux overnight. TLC (EtOAc) showed that the starting material was completely consumed. The reaction mixture was filtered with diatomite mat. The filtrate was concentrated to dry to deliver the crude product which was purified by silica gel chromatography (EtOAc:MeOH=100:4) to deliver compound 153-6 (310 mg, 35%) as beige solid. MS ESI calcd for C$_{15}$H$_9$N$_3$O [M+H]$^+$ 248, found 248.

Step 4: NIS (200 mg, 0.887 mmol) was added into a solution of compound 153-6 (210 mg, 0.85 mmol) in DMF (2 mL) in portions at 0° C. The reaction mixture was stirred at room temperature overnight. TLC (EtOAc) showed that most of the starting material was consumed. The reaction mixture was filtrated, the filtrate was concentrated to deliver compound 153-7 (250 mg, 79%) as white sold. MS ESI calcd for C$_{15}$H$_8$IN$_3$O [M+H]$^+$ 374, found 374.

Step 5: A solution of compound 153-7 (310 mg, 0.831 mmol) in POCl$_3$ (10 mL) was stirred at reflux for 4 h. TLC showed that the starting material was completely consumed. The reaction mixture was concentrated to dry and diluted with EtOAc. The obtained solution was basified with NaHCO$_3$ (aq) at 0° C. The mixture was partitioned between EtOAc and H$_2$O. The organic phase was concentrated to dry to deliver a crude product which was purified by silica gel chromatography (PE:EtOAc=1:1) to deliver compound 153-8 (290 mg, 90%) as white solid. MS ESI calcd for C$_{15}$H$_7$ClIN$_3$ [M+H]$^+$ 392, found 392.

Step 6: Compound 153-8 (27 mg, 0.691 mmol) and compound 153-9 (262 mg, 0.828 mmol) were dissolved in a mixed solvent of dioxane (3 mL) and H$_2$O (0.6 mL), sodium bicarbonate (145 mg, 1.727 mmol) was added. The reaction mixture was swept with nitrogen gas for 3 times, Pd (dppf) Cl$_2$ (50 mg, 0.069 mmol) was added, then the reaction mixture was swept with nitrogen gas for 3 times again, and stirred at 80° C. for 2 h. TLC (PE:EtOAc=3:1) showed that the starting material was completely consumed. The reaction mixture was filtered with diatomite mat. The filtrate was concentrated to dry to deliver a crude product which was purified by silica gel chromatography (PE:EtOAc=2:1) to deliver the title compound (120 mg, 30%) as yellow solid. $^1$H NMR (400 MHz, CDCl$_3$) δ 9.85 (s, 1H), 9.08 (s, 1H), 8.87 (s, 1H), 7.90-7.83 (m, 5H), 7.52 (d, J=8.53 Hz, 2H), 7.09 (d, J=7.78 Hz, 2H), 3.87 (br. s., 2H), 3.62 (d, J=11.29 Hz, 2H), 2.57 (t, J=11.17 Hz, 2H), 1.32 (d, J=6.27 Hz, 6H). MS ESI calcd for C$_{27}$H$_{23}$ClN$_4$O [M+H]$^+$ 455, found 455.

Embodiment 154

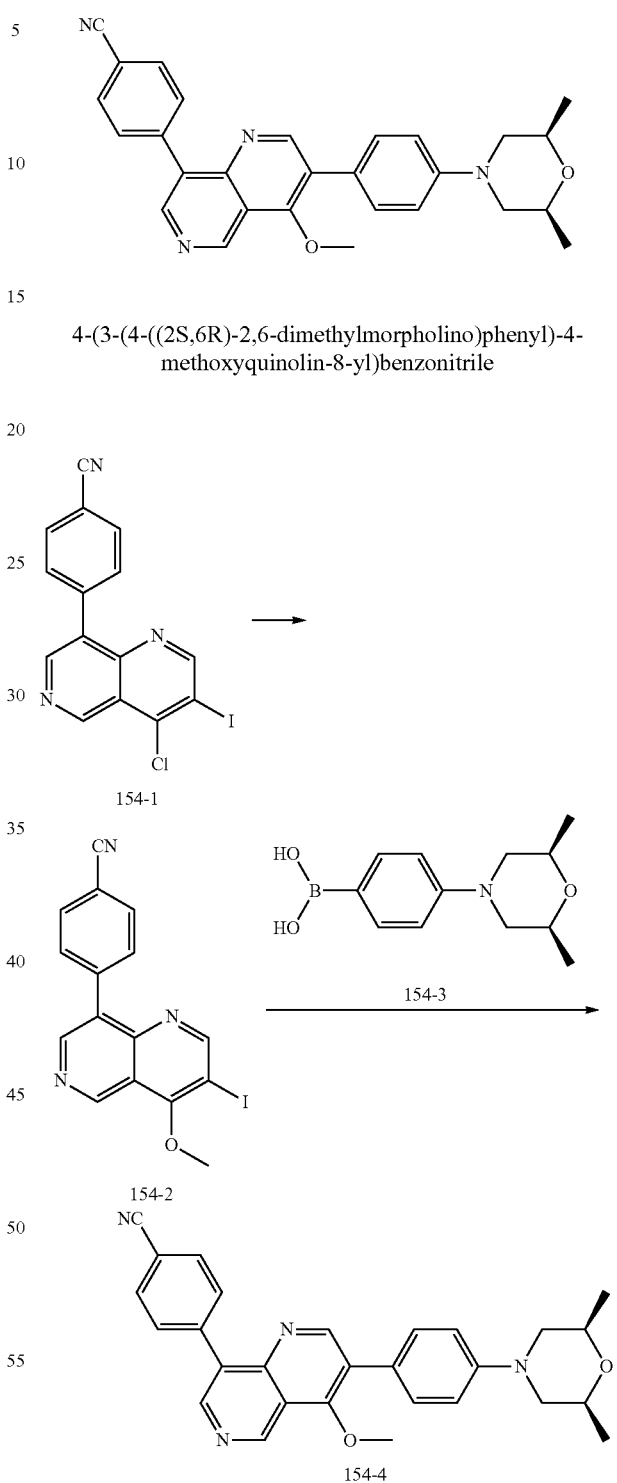

4-(3-(4-((2S,6R)-2,6-dimethylmorpholino)phenyl)-4-methoxyquinolin-8-yl)benzonitrile Step 1: NaOMe (32 mg, 6 mmol) was added into a solution of compound 154-1 (120 mg, 3 mmol) in MeOH (15 mL), and the mixture was stirred at 45° C. for 16 h. After LC-MS showed that the starting material was completely consumed, the solution was concentrated under vacuum and partitioned between EtOAc and H$_2$O. The organic phases were combined and washed with brines, dried over anhydrous sodium sulfate, filtrated and concentrated under reduced pressure to deliver compound 154-2 (0.1 g, 83%) as white solid. MS ESI calcd for $C_{16}H_{10}IN_3O$ [M+H]$^+$ 387, found 387.

Step 2: Compound 154-2 (100 mg, 0.28 mmol), compound 154-3 (91 mg, 0.39 mmol), Pd(dppf)Cl$_2$ (22 mg, 0.032 mmol) and sodium carbonate (45 mg, 0.52 mmol) were dissolved in a mixed solvent of THF (20 mL) and H$_2$O (3 mL), and the mixture was stirred at 80° C. overnight. After LC-MS showed that the starting material was completely consumed, the solution was partitioned between EtOAc and H$_2$O. The organic phases were combined and washed with brines, dried over anhydrous sodium sulfate, filtrated and concentrated under vacuum. The residue was purified by preparative HPLC to deliver the title compound (30 mg, 25%). $^1$H NMR (400 MHz, CDCl3) δ 9.71 (s, 1H), 9.03 (s, 1H), 8.76 (s, 1H), 7.87 (d, J=8 Hz, 2H), 7.81 (d, J=8 Hz, 2H), 7.53 (d, J=8.4 Hz, 2H), 7.04 (d, J=8.8 Hz, 2H), 3.86-3.82 (m, 5H), 3.59 (d, J=10.8 Hz, 2H), 2.52 (t, J=11.2 Hz, 2H), 1.30 (d, J=6.4 Hz, 6H). MS ESI calcd for $C_{28}H_{26}N_4O_2$ [M+H]$^+$ 451, found 451.

Embodiment 155

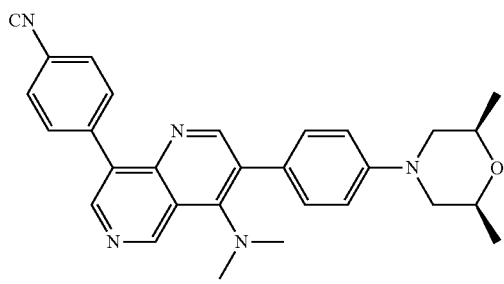

4-(4-(dimethylamino)-3-(4-((2S,6R)-2,6-dimethylmorpholino)phenyl)-1,6-naphthyridin-8-yl)benzonitrile

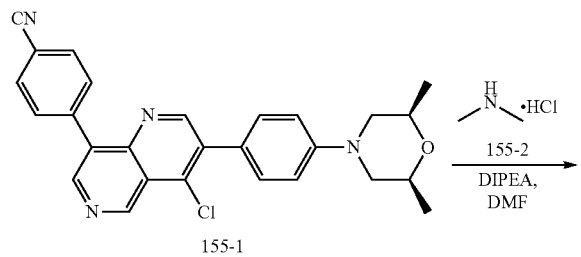

Compound 155-2 (146 mg, 1.79 mmol) and DIPEA (282 mg, 2.186 mmol) were added into a solution of compound 155-1 (80 mg, 0.176 mmol) in DMF (2 mL). The mixture was stirred at 120° C. overnight. TLC (PE:EtOAc=1:1) showed that the starting material was completely consumed. The mixture was concentrated to give a crude product which was purified by silica gel chromatography (PE:EtOAc=1:1) to deliver the title compound (35 mg, 43%) as yellow solid. $^1$H NMR (400 MHz, CDCl$_3$) δ 9.62 (br. s., 1H), 8.77 (s, 1H), 8.61 (s, 1H), 7.91 (d, J=7.06 Hz, 2H), 7.84-7.69 (m, 5H), 7.40 (d, J=7.06 Hz, 2H), 4.58 (br. s., 2H), 3.51 (d, J=11.47 Hz, 2H), 3.01 (s, 6H), 2.91 (t, J=11.25 Hz, 2H), 2.55 (s, 1H), 1.94 (s, 1H), 1.25 (d, J=6.62 Hz, 6H). MS ESI calcd for $C_{29}H_{29}N_5O$ [M+H]$^+$ 464, found 464.

Embodiment 156

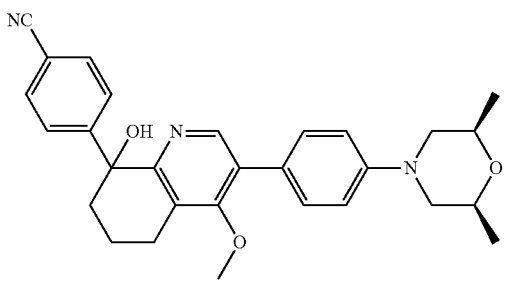 [SMILES: COc1c(-c2ccc(N3C[C@@H](C)O[C@@H](C)C3)cc2)cnc2c1CCCC2(O)c1ccc(C#N)cc1]

4-(3-(4-((2S,6R)-2,6-dimethylmorpholino)phenyl)-8-hydroxy-4-methoxy-5,6,7,8-tetra hydroquinolin-8-yl)benzonitrile

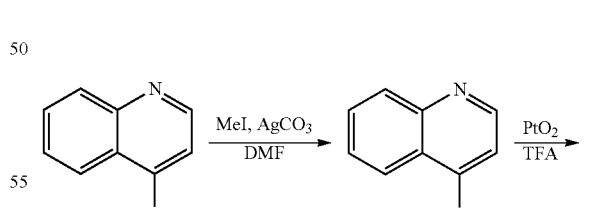

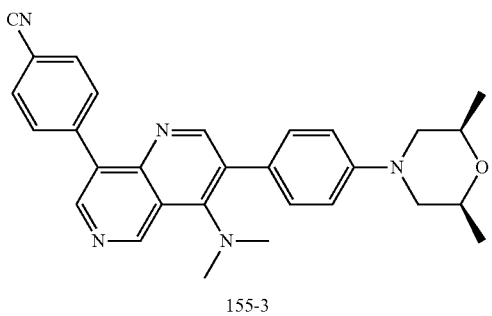

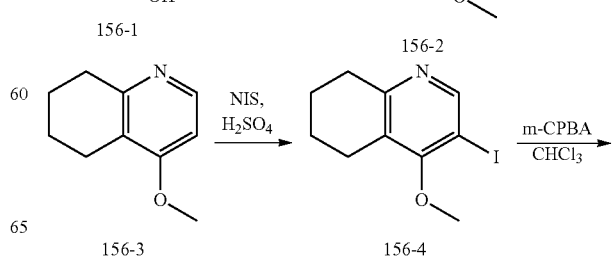

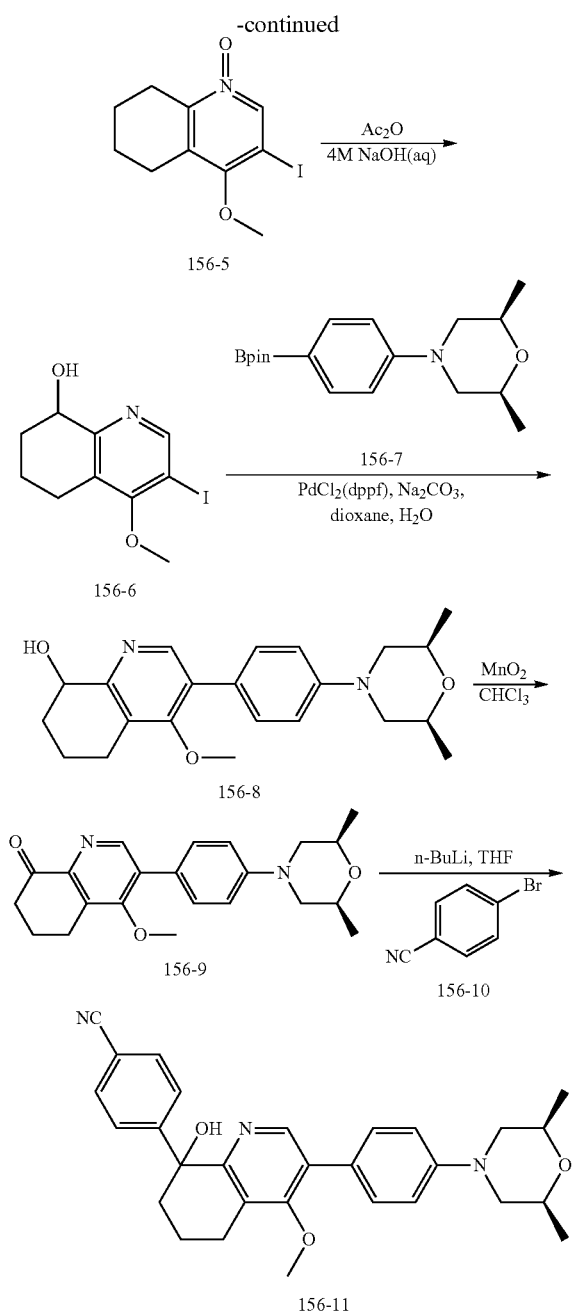

Step 1: Ag$_2$CO$_3$ (55.55 g, 0.201 mol) was added into a solution of compound 156-1 (14.62 g, 0.101 mol) in DMF (150 mL). The reaction mixture was swept with nitrogen gas and MeI (12.88 g, 0.091 mol) was added. Then the reaction mixture was stirred at 80° C. overnight. TLC (EtOAc) showed that the starting material was completely consumed. The mixture was filtrated, the filtrate was partitioned between EtOAc and H$_2$O. The organic phase was concentrated to give a crude product which was purified by silica gel chromatography (PE:EtOAc=2:1) to deliver compound 156-2 (10 g, 56%) as colorless oil. $^1$H NMR (400 MHz, CDCl$_3$) δ 8.72 (d, J=3.53 Hz, 1H), 8.17 (d, J=7.94 Hz, 1H), 8.02 (d, J=8.38 Hz, 1H), 7.71-7.62 (m, 1H), 7.52-7.42 (m, 1H), 6.75-6.59 (m, 1H), 3.99 (d, J=1.76 Hz, 4H). MS ESI calcd for C$_{10}$H$_9$NO [M+H]$^+$ 160, found 160.

Step 2: Under nitrogen gas atmosphere, PtO$_2$ (1 g) was added into a solution of compound 156-2 (5 g, 0.031 mol) in TFA (45 mL). The mixture was stirred under a hydrogen gas pressure of 50 psi at room temperature. TLC (PE: EtOAc=1:1) showed that the starting material was completely consumed. The mixture was filtrated, the filtrate was concentrated under vacuum. The residue was dissolved into H$_2$O, basified to pH=9 with 8 N NaOH (aq.) at 0° C., the aqueous phase was extracted with DCM, the organic phase was washed with brines, dried over anhydrous sodium sulfate and concentrated to deliver compound 156-3 (4 g, 80%) as yellow oil, which was used in the next step directly. $^1$H NMR (400 MHz, CDCl$_3$) δ 8.18 (d, J=5.73 Hz, 1H), 6.50 (d, J=5.73 Hz, 1H), 3.75 (s, 3H), 2.78 (t, J=6.17 Hz, 2H), 2.53 (t, J=6.17 Hz, 2H), 1.79-1.62 (m, 5H). MS ESI calcd for C$_{10}$H$_{13}$NO [M+H]$^+$ 164, found 164.

Step 3: NIS (9.6 g, 0.043 mol) was added into a solution of compound 156-3 (5.8 g, 0.0356 mol) in sulphuric acid (30 mL) at 0° C. in portions, the mixture was stirred at room temperature for 0.5 h, then heated to 60° C. and stirred for 2 h. TLC (PE:EtOAc=1:1) showed that the starting material was completely consumed. The mixture was poured into ice-water, and basified to pH=9 with 8 N NaOH (aq). Then the aqueous phase was extracted with DCM. The organic phase was washed with sat. NaHCO$_3$ (aq) and brines, concentrated to deliver a crude product, which was purified by silica gel chromatography (PE:EtOAc=15:1) to deliver compound 156-4 sat. NaHCO$_3$ (aq) as brown solid. $^1$H NMR (400 MHz, CDCl$_3$) δ 8.55 (brs, 1H), 3.80-3.73 (m, 2H), 2.84-2.77 (m, 2H), 2.76-2.70 (m, 2H), 1.85-1.69 (m, 4H). MS ESI calcd for C$_{10}$H$_{12}$INO [M+H]$^+$ 290, found 290.

Step 4: m-CPBA (2.6 g, 0.015 mol) was added into a solution of compound 156-4 (1.44 g, 0.005 mol) in CHCl$_3$ (10 mL) at 0° C. in portions, the mixture was stirred at 40° C. for 2 h. The mixture was quenched with H$_2$O, adjusted to pH to 14 with 8 N NaOH (aq). Then the aqueous phase was extracted with DCM. The organic phase was washed with sat. NaHCO$_3$ (aq) and brines, concentrated to deliver compound 156-5 (1.3 g, 88%) as yellow solid, which was used for the next step directly. MS ESI calcd for C$_{10}$H$_{12}$INO$_2$ [M+H]$^+$ 306, found 306.

Step 5: A solution of compound 156-5 (1.3 g, 0.0043 mmol) in Ac$_2$O (6 mL) was stirred at 90° C. for 2 h. The mixture was concentrated and 4 N NaOH (aq) (4.3 mL, 0.017 mol) was added. The mixture was stirred at 80° C. for 2 h. Then the aqueous phase was extracted with DCM. The organic phase was concentrated to deliver a crude product, which was purified by silica gel chromatography (PE:EtOAc=3:1) to deliver compound 156-6 (0.82 g, 33%) as yellow solid. $^1$H NMR (400 MHz, CDCl$_3$) δ 8.61 (s, 1H), 4.59 (brs, 1H), 3.79 (s, 3H), 3.67 (br. s., 1H), 2.77 (br. s., 2H), 2.19 (br. s., 1H), 1.94 (br. s., 1H), 1.71 (br. s., 2H). MS ESI calcd for C$_{10}$H$_{12}$INO$_2$ [M+H]$^+$ 306, found 306.

Step 6: Sodium carbonate (0.69 g, 0.0065 mol) was added into a solution of compound 156-6 (0.8 g, 0.0026 mol) and compound 156-7 in a mixed solvent of dioxane (8 mL) and H$_2$O (2 mL). The mixture was swept with nitrogen gas and Pd (dppf)Cl$_2$ (0.19 g, 0.26 mmol) was added. Then the mixture was stirred at 100° C. and refluxed for 2 h. The mixture was filtrated with diatomite mat, the filtrate was concentrated to give a crude product, which was purified by silica gel chromatography (PE:EtOAc=1:2) to deliver compound 156-8 (0.66 g, 68%) as yellow solid. $^1$H NMR (400 MHz, CDCl$_3$) δ 8.28 (s, 1H), 7.37 (d, J=8.82 Hz, 2H), 6.91 (d, J=8.82 Hz, 2H), 4.65 (t, J=6.84 Hz, 1H), 3.88 (s, 1H), 3.79-3.68 (m, 2H), 3.47 (d, J=11.03 Hz, 2H), 3.39 (s, 3H), 2.82-2.63 (m, 2H), 2.41 (t, J=11.03 Hz, 2H), 2.27-2.14 (m, 1H), 2.01-1.91 (m, 1H), 1.73 (t, J=8.16 Hz, 2H), 1.22 (d, J=6.17 Hz, 7H). MS ESI calcd for $C_{22}H_{28}N_2O_3$ [M+H]$^+$ 369, found 369.

Step 7: MnO$_2$ (1.56 g, 0.018 mol) was added into a solution of compound 156-8 (0.66 g, 0.0018 mol) in CHCl$_3$ (10 mL). The mixture was stirred at reflux overnight. The mixture was filtrated with diatomite mat, the filtrate was concentrated to give a crude product, which was purified by silica gel chromatography (PE:EtOAc=1:2) to deliver compound 156-9 (0.57 g, 86%) as yellow solid. MS ESI calcd for $C_{22}H_{26}N_2O_3$ [M+H]$^+$ 367, found 367.

Step 8: Under nitrogen gas atmosphere, n-BuLi (0.3 mL, 0.75 mmol) was added dropwise into a solution of compound 156-10 (124 mg, 0.682 mmol) in THF (2 mL) at –65° C. The mixture was stirred at –65° C. for 0.5 h, then a solution of compound 156-9 (200 mg, 0.546 mmol) in THF (1 mL) was added dropwise. The mixture was stirred at –65° C. for 1 h, and stirred at 0° C. for another 1 h. TLC showed that the starting material was completely consumed. The reaction mixture was quenched with sat. NaHCO$_3$ (aq) and diluted with EtOAc. The organic phase was concentrated to give a crude product, which was purified by silica gel chromatography (PE:EtOAc=3:1) to deliver the title compound (65 mg, 30%) as yellow solid. $^1$H NMR (400 MHz, CDCl$_3$) δ 8.28 (s, 1H), 7.51 (d, J=8.38 Hz, 2H), 7.39 (d, J=8.82 Hz, 2H), 7.27 (d, J=8.38 Hz, 2H), 6.92 (d, J=8.82 Hz, 2H), 4.08 (s, 1H), 3.76 (ddd, J=10.14, 6.17, 2.21 Hz, 2H), 3.49 (s, 1H), 3.46 (s, 4H), 2.91-2.74 (m, 2H), 2.42 (t, J=11.25 Hz, 2H), 2.21-2.11 (m, 2H), 1.85 (brs, 1H), 1.55 (brs, 1H), 1.22 (d, J=6.17 Hz, 6H). MS ESI calcd for $C_{29}H_{31}N_3O_3$ [M+H]$^+$ 470, found 470.

Embodiment 157

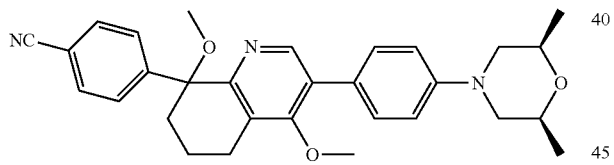

4-(3-(4-((2S,6R)-2,6-dimethylmorpholino)phenyl)-4,8-dimethoxy-5,6,7,8-tetrahydroquinolin-8-yl)benzonitrile

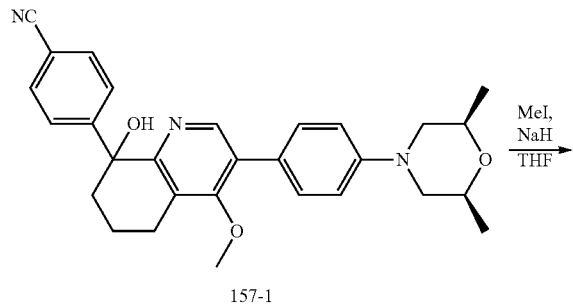

157-1

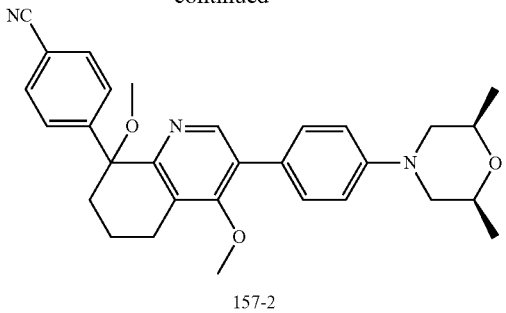

157-2

NaH (27.3 mg, 0.682 mmol) was added into a solution of compound 157-1 (80 mg, 0.171 mmol) in THF (3 mL) at 0° C., the suspension was stirred at 0° C. for 10 min. A solution of MeI (29 mg, 0.204 mmol) in THF (1 mL) was added. The mixture was stirred at room temperature overnight. TLC showed that compound 157-1 was completely consumed. The mixture was concentrated to give a crude product which was purified by pre TLC (PE:EtOAc=3:1) to deliver the title compound (40 mg, 40%) as white solid. $^1$H NMR (400 MHz, CDCl$_3$) δ 8.43 (s, 1H), 7.63 (d, J=8.28 Hz, 2H), 7.56-7.49 (m, 2H), 7.41 (d, J=8.28 Hz, 2H), 7.02 (d, J=8.78 Hz, 2H), 3.90-3.79 (m, 2H), 3.59 (br. s., 1H), 3.57-3.51 (m, 4H), 3.27 (s, 3H), 3.10-3.00 (m, 1H), 2.87-2.76 (m, 1H), 2.51 (t, J=11.17 Hz, 2H), 2.33 (dd, J=13.30, 4.02 Hz, 1H), 2.14 (br. s., 1H), 2.00-1.90 (m, 1H), 1.84 (d, J=6.78 Hz, 1H), 1.31 (d, J=6.27 Hz, 6H). MS ESI calcd for $C_{30}H_{33}N_3O_3$ [M+H]$^+$ 484, found 484.

Embodiment 158

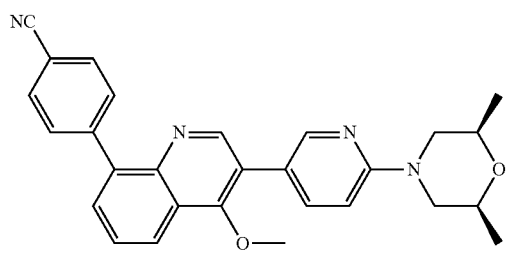

4-(3-(6-((2S,6R)-2,6-dimethylmorpholino)pyridin-3-yl)-4-methoxyquinolin-8-yl) benzonitrile

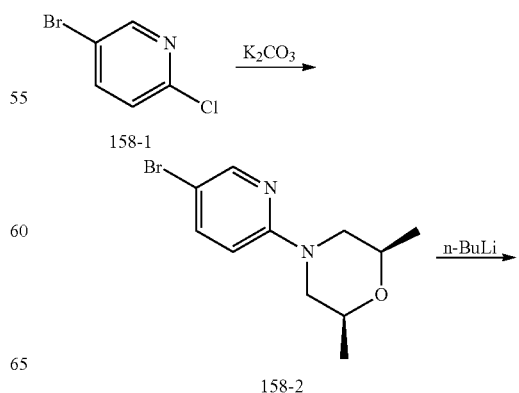

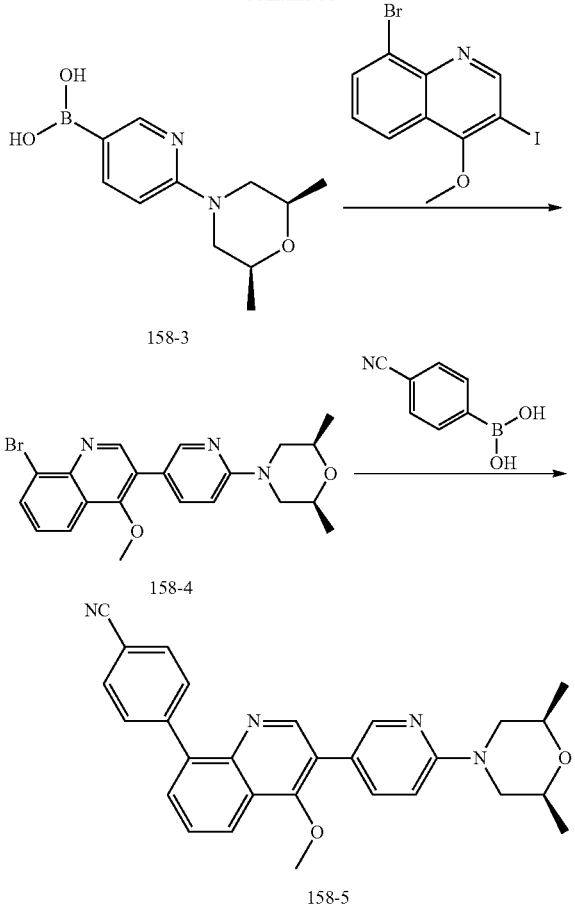

product was purified by silica gel column chromatography to deliver compound 158-2 (6 g, yield 84.9%) as yellow oil. MS ESI calcd for $C_{11}H_{15}BrN_2O$ [M+H]+ 271, found 271.

Step 2: n-BuLi (8.3 mL, 20.6 mmol) was added into a solution of compound 158-2 (3.7 g, 13.7 mmol) in THF (30 mL), under nitrogen gas atmosphere, the reaction mixture was stirred at −78° C. for 30 min. Triisopropyl borate (7.8 g, 41.2 mmol) was added into the reaction mixture, then stirred at −78° C. for 3 h. The mixture was poured into $H_2O$, extracted with EtOAc, dried over sodium sulfate and filtrated, concentrated under reduced pressure, the residue was purified by silica gel column chromatography to deliver compound 158-3 (1.3 g, yield 40.2%) as brown solid. MS ESI calcd for $C_{11}H_{17}BN_2O_3$ [M+H]+ 237, found 237.

Step 3: Compound 158-3 (324 mg, 1.37 mmol), Pd(dppf)Cl$_2$ (100.3 mg, 1.37 mmol) and sodium carbonate (290 mg, 2.74 mmol) were added into a solution of 8-bromo-3-iodo-4-methoxylquinoline (500 mg, 1.37 mmol) in a mixed solvent of THF (4 mL), $H_2O$ (1 mL) and DMF (1 mL), the reaction mixture was stirred at 60° C. for 3 h. Then the reaction mixture was poured into $H_2O$, extracted with EtOAc, dried over anhydrous sodium sulfate, filtrated and concentrated under reduced pressure to deliver a crude product 158-4 (400 mg, yield 68.4%) as brown solid. MS ESI calcd for $C_{21}H_{22}BrN_3O_2$ [M+H]+ 428, found 428.

Step 4: 4-cyanophenylboronic acid (206 mg, 1.4 mmol), Pd(dppf)Cl$_2$ (34 mg, 0.0466 mmol) and sodium carbonate (100 mg, 0.932 mmol) were added into a solution of compound 158-4 (200 mg, 0.466 mmol) in a mixed solvent of THF (3 mL), $H_2O$ (0.5 mL) and DMF (0.5 mL). The reaction mixture was stirred at 70° C. for 4 h. Then the mixture was poured into $H_2O$ and extracted with EtOAc, the organic phase was dried over anhydrous sodium sulfate, filtrated and concentrated under reduced pressure, the crude product was purified by preparative HPLC to deliver the title compound (100 mg, yield 47.8%) as white solid. $^1$H NMR (400 MHz, CDCl$_3$) δ 8.89 (s, 1H), 8.50 (s, 1H), 8.31 (d, J=7.2 Hz, 1H), 7.78-7.87 (m, 5H), 7.66-7.71 (m, 2H), 6.78 (d, J=8.8 Hz, 1H), 4.15 (d, J=12 Hz, 2H), 3.76 (s, 5H), 2.63 (t, J=11.6 Hz, 2H), 1.31 (d, J=6.4 Hz, 7H). MS ESI calcd for $C_{28}H_{26}N_4O_2$ [M+H]+ 451, found 451.

The compounds listed in table 13 were synthesized by compound 158-4 and corresponding boric acids.

Step 1: (2S, 6R)-2,6-dimethylmorpholine (4.0 g, 34.8 mmol) and potassium carbonate (8.0 g, 58 mmol) were added into a solution of 5-bromo-2-chloro-pyridine (5.0 g, 26.2 mmol) in DMF (18 mL). The reaction mixture was stirred at 90° C. for 6 h and filtrated, the filtrate cake was washed with EtOAc. The filtrate was concentrated, the crude

| Embodiment | Structure | NMR |
|---|---|---|
| 159 | CF$_3$ (structure) | $^1$H NMR (400 MHz, CDCl$_3$) δ 8.88 (s, 1H), 8.49 (s, 1H), 8.27(d, J = 6.8 Hz, 1H), 7.65-7.81 (m, 7H), 6.78 (d, J = 8.8 Hz, 1H), 4.15 (d, J = 12.4 Hz, 2H), 3.75 (s, 5H), 2.63 (t, J = 11.6 Hz, 2H), 1.29 (d, J = 6.4 Hz, 7H). MS ESI calcd for $C_{28}H_{26}F_3N_3O_2$ [M + H]+ 494, found 494. |
| 160 | OCF$_3$ (structure) | $^1$H NMR (400 MHz, CDCl$_3$) δ 8.88 (s, 1H), 8.49 (s, 1H), 8.24(d, J = 8.0 Hz, 1H), 7.61-7.85 (m, 5H), 7.32-7.34 (m, 2H), 6.78 (d, J = 8.4 Hz, 1H), 4.15 (d, J = 12.4 Hz, 2H), 3.75 (s, 5H), 2.63 (t, J = 11.4 Hz, 2H), 1.29 (d, J = 6.4 Hz, 7H). MS ESI calcd for $C_{28}H_{26}F_3N_3O_3$ [M + H]+ 510, found 510. |

| Embodiment | Structure | NMR |
|---|---|---|
| 161 | 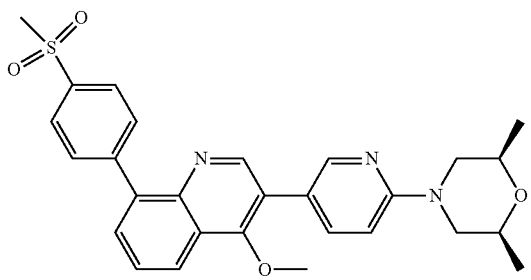 [SMILES: COc1c(-c2ccc(N3C[C@@H](C)O[C@@H](C)C3)nc2)cnc2c(-c3ccc(S(C)(=O)=O)cc3)cccc12] | $^1$H NMR (400 MHz, CDCl$_3$) δ 8.88 (s, 1H), 8.50 (s, 1H), 8.30(d, J = 8.4 Hz, 1H), 8.05-8.07 (m, 2H), 7.89-7.92 (m, 3H), 7.67-7.75 (m, 3H), 3.77 (s, 6H), 3.12 (s, 4H), 1.30 (d, J = 6.4 Hz, 9H). MS ESI Calcd for C$_{28}$H$_{29}$N$_3$O$_4$S [M + H]$^+$ 504, found 504. |
| 162 | 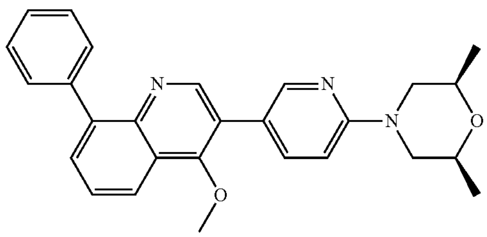 [SMILES: COc1c(-c2ccc(N3C[C@@H](C)O[C@@H](C)C3)nc2)cnc2c(-c3ccccc3)cccc12] | $^1$H NMR (400 MHz, CDCl$_3$) δ 8.83 (s, 1H), 8.50 (s, 1H), 8.31(d, J = 7.2 Hz, 1H), 7.75-7.87 (m, 1H), 7.75-7.87 (m, 4H), 7.61-7.65 (m, 3H), 7.34-7.44 (m, 3H), 6.70 (d, J = 9.2 Hz, 1H), 4.15 (d, J = 12 Hz, 2H), 3.68 (s, 5H), 2.53 (t, J = 11.6 Hz, 2H), 1.23 (d, J = 6.0 Hz, 6H). MS ESI calcd for C$_{27}$H$_{27}$N$_3$O$_2$ [M + H]$^+$ 426, found 426. |
| 163 | 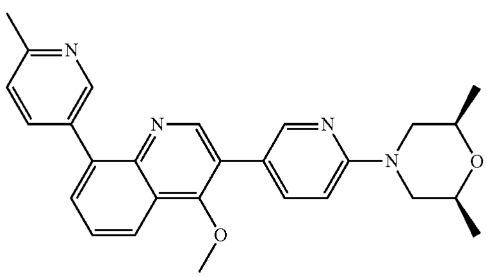 [SMILES: COc1c(-c2ccc(N3C[C@@H](C)O[C@@H](C)C3)nc2)cnc2c(-c3ccc(C)nc3)cccc12] | $^1$H NMR (400 MHz, CDCl$_3$) δ 8.87 (s, 1H), 8.80 (s, 1H), 8.50 (s,1H), 8.25-8.28(m, 1H), 8.02-8.05 (m, 1H), 7.84-7.86 (m, 1H), 7.66-7.71 (m, 3H), 7.29-7.31 (m, 1H), 6.78 (d, J = 8.8 Hz, 1H), 4.15 (d, J = 11.6 Hz, 2H), 3.76 (s, 5H), 2.59-2.65 (m, 5H), 1.29 (d, J = 6.4 Hz, 6H). MS ESI calcd for C$_{27}$H$_{28}$N$_4$O$_2$ [M + H]$^+$ 441, found 441. |
| 164 | 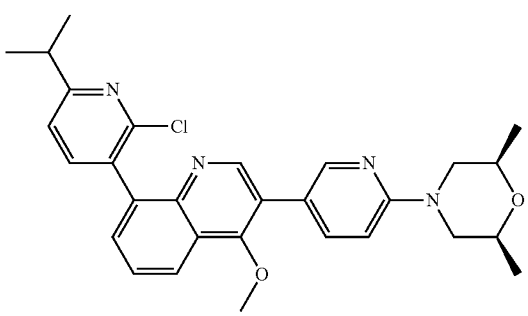 [SMILES: COc1c(-c2ccc(N3C[C@@H](C)O[C@@H](C)C3)nc2)cnc2c(-c3ccc(C(C)C)nc3Cl)cccc12] | $^1$H NMR (400 MHz, CDCl$_3$) δ 8.85 (s, 1H), 8.48 (s, 1H), 8.30(d, J = 8.0 Hz, 1H), 7.83-7.85 (m, 1H), 7.62-7.71 (m, 3H), 7.23-7.25 (m, 1H), 6.78 (d, J = 8.8 Hz, 1H), 4.13 (d, J = 12 Hz, 2H), 3.76 (s, 5H), 3.14 (t, J = 7.0 Hz, 1H), 2.61 (t, J = 11.6 Hz, 2H), 1.31 (d, J = 6.8 Hz, 6H), 1.28 (d, J = 6.4 Hz, 6H). MS ESI calcd for C$_{29}$H$_{31}$ClN$_4$O$_2$ [M + H]$^+$ 503, found 503. |
| 165 | 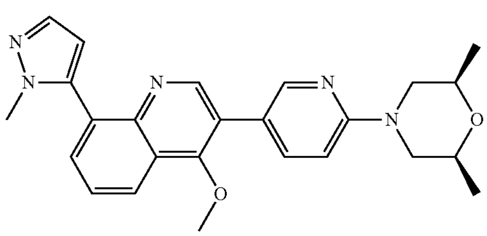 | $^1$H NMR (400 MHz, CDCl$_3$) δ 8.82 (s, 1H), 8.42 (s, 1H), 8.25-8.27(m, 1H), 7.76-7.77 (m, 1H), 7.55-7.64 (m, 3H), 6.70 (d, J = 8.8 Hz, 1H), 6.35 (s, 1H), 4.10 (d, J = 11.6 Hz, 2H), 3.68-3.75 (m, 8H), 2.56(t, J = 11.8 Hz, 2H), 1.23 (d, J = 6.0 Hz, 7H). MS ESI calcd for C$_{25}$H$_{27}$N$_5$O$_2$ [M + H]$^+$ 430, found 430. |

Embodiment 166

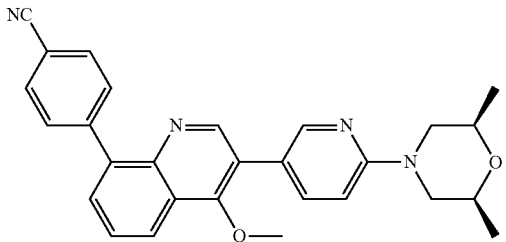

4-(3-(6-((2S,6R)-2,6-dimethylmorpholino)-2-methylpyridin-3-yl)-4-methoxyquinolin-8-yl)benzonitrile

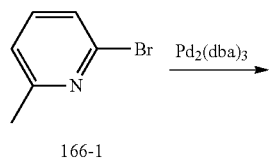

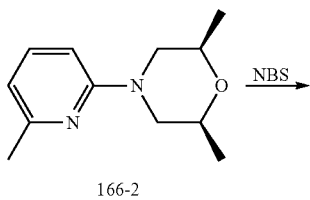

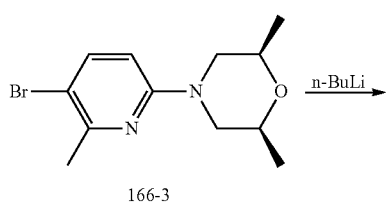

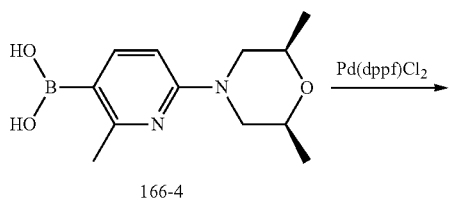

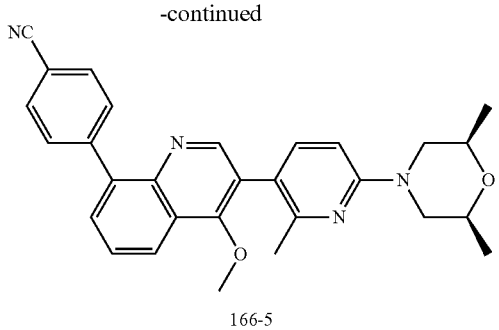

166-5

Step 1: Xantphos (1.7 g, 3.48 mmol), (2S,6R)-2,6-dimethylmorpholine (6 g, 52.2 mmol), potassium tert-butoxide (3.9 g, 34.8 mmol), Pd$_2$(dba)$_3$ (1.6 g, 1.74 mmol) were added into a solution of 2-bromo-6-methyl pyridine (3 g, 17.4 mmol) in toluene (50 mL) respectively. The reaction mixture was stirred at 110° C. for 2 h, then poured into H$_2$O, extracted with EtOAc (50 mL×3), the organic phase was washed with brines, filtrated and dried over sodium sulfate. After concentration, the residue was purified by silica gel column chromatography to deliver compound 166-2 (2.4 g, yield 66.7%) as white solid. MS ESI calcd for C$_{12}$H$_{18}$N$_2$O [M+H]$^+$ 207, found 207.

Step 2: NBS (1.65 g, 9.3 mmol) was added into a solution of compound 166-2 (2.4 g, 11.6 mmol) in DMF (30 mL). The reaction mixture was stirred at room temperature for 6 h, poured into H$_2$O, extracted with EtOAc (30×3 mL), the organic phase was dried over sodium sulfate, after concentration, the crude product was purified by silica gel column chromatography to deliver compound 166-3 (0.86 g, yield 25.9%) as white solid. MS ESI calcd for C$_{12}$H$_{17}$BrN$_2$O [M+H]$^+$ 285, found 285.

Step 3: A solution of n-BuLi (1.8 mL, 4.5 mmol) was added into a solution of compound 166-3 (0.86 g, 3 mmol) in THF (20 mL) at −78° C. The reaction mixture was stirred at −78° C. for 30 min. Then triisopropyl borate (846 mg, 4.5 mmol) was added. Then the reaction mixture was poured into H$_2$O, extracted with EtOAc (50 mL×3), the organic phase was dried over sodium sulfate, filtrated and concentrated to deliver a crude product 166-4 (375 mg) as white solid. MS ESI calcd for C$_{12}$H$_{19}$BN$_2$O$_3$ [M+H]$^+$ 251, found 251.

Step 4: (6-((2S,6R)-2,6-dimethylmorpholino)-2-methylpyridin-3-yl)boric acid (375 mg, 1.5 mmol), 4-(3-bromo-4-methoxyquinolin-8-yl)benzonitrile (340 mg, 1 mmol) and sodium carbonate (212 mg, 2 mmol) were dissolved in DMF (3 mL), H$_2$O (3 mL) and THF (15 mL), Pd(dppf)Cl$_2$ (73 mg, 0.1 mmol) was added into the solution, then the reaction mixture was stirred at 70° C. for 2 h. Then the reaction mixture was poured into H$_2$O, extracted with EtOAc, the organic phase was washed with brines, dried over sodium sulfate. The crude product was purified by preparative HPLC to deliver the title compound (55 mg, yield 8%) as white solid. $^1$H NMR (400 MHz, CDCl$_3$) δ 8.64 (s, 1H), 8.29 (d, J=8.0 Hz, 1H), 7.93-7.95 (m, 2H), 7.84-7.89 (m, 3H), 7.52-7.54 (m, 1H), 7.45-7.50 (m, 1H), 6.82 (d, J=8.4 Hz, 1H), 4.23 (d, J=12 Hz, 2H), 3.63-3.65 (m, 5H), 2.62-2.66 (m, 2H), 2.22 (s, 2H), 1.19 (d, J=6.0 Hz, 7H). MS ESI calcd for C$_{29}$H$_{28}$N$_4$O$_2$ [M+H]$^+$ 465, found 465.

The compound listed in table 14 was synthesized by corresponding aryl halide.

| Embodiment | Structure | NMR |
|---|---|---|
| 167 | 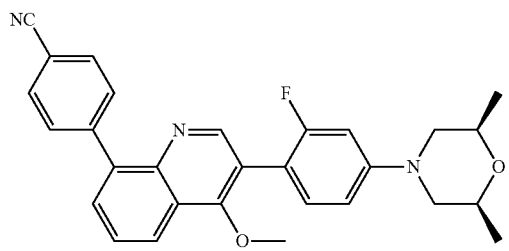 | $^1$H NMR (400 MHz, CDCl$_3$) δ 8.64 (s, 1H), 8.32 (d, J = 8.0 Hz, 1H), 8.12(s, 1H), 7.65-7.84 (m, 6H), 6.64 (s, 1H), 4.15 (d, J = 12.8 Hz, 2H), 3.74-3.78 (m, 2H), 3.68 (s, 3H), 2.61 (s, 1H), 2.18(s, 3H), 1.29 (d, J = 6.0 Hz, 6H). MS ESI calcd for C$_{29}$H$_{28}$N$_4$O$_2$ [M + H]$^+$ 465, found 465. |

Embodiment 168

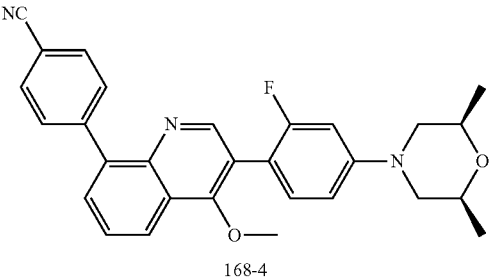

4-(3-(4-((2S,6R)-2,6-dimethylmorpholino)-2-fluorophenyl)-4-methoxyquinolin-8-yl) benzonitrile

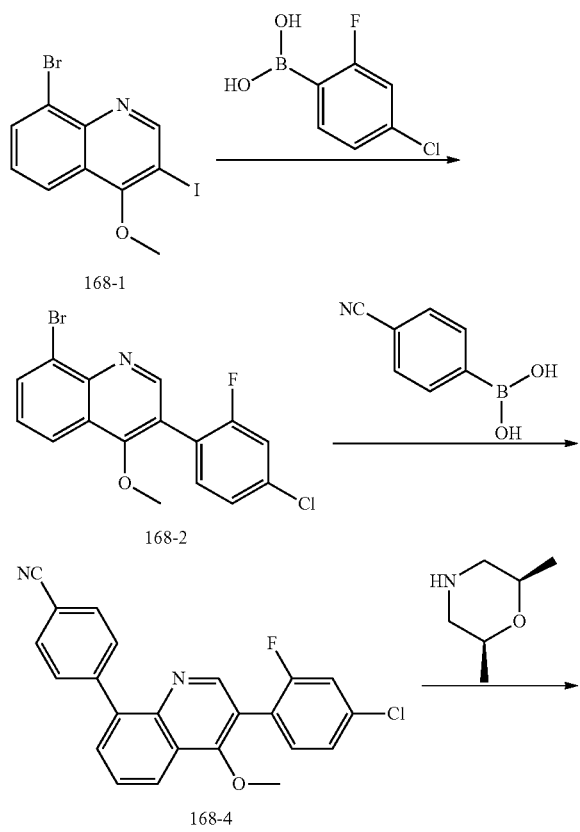

Step 1: (4-chloro-2-fluorophenyl)boric acid (0.87 g, 5 mmol) was added into a solution of compound 168-1 (1.8 g, 5 mmol) in THF/H$_2$O/DMF (15/3/3 mL), Pd(dppf)Cl$_2$ (350 mg, 0.5 mmol) and sodium carbonate (1.1 g, 10 mmol) were added at room temperature. The reaction mixture was stirred at 70° C. for 4 h. The reaction mixture was poured into H$_2$O, extracted with EtOAc, the organic phase was dried over sodium sulfate and concentrated. The residue was purified by silica gel column chromatography eluting with PE/EtOAc (15/1) to deliver compound 168-2 (1.158 g, yield 63.3%) as brown solid. MS ESI calcd for C$_{16}$H$_{10}$BrClFNO [M+H]$^+$366, found 366.

Step 2: 4-cyanophenylboric acid (0.2 g, 1.4 mmol), Pd(dppf)Cl$_2$ (73 mg, 0.1 mmol) and sodium carbonate (0.4 g) were added into a solution of compound 168-2 (0.4 g, 1 mmol) in THF/H$_2$O/DMF (5/1/1 mL) at room temperature. The reaction was stirred at 70° C. for 5 h. The reaction mixture was poured into H$_2$O, extracted with EtOAc, the organic phase was dried over sodium sulfate and concentrated. The residue was purified by silica gel column chromatography eluting with PE/EtOAc (10/1) to deliver compound 168-3 (158 mg, yield 43.2%) as brown solid. MS ESI calcd for C$_{23}$H$_{14}$ClFN$_2$O [M+H]$^+$ 389, found 389.

Step 3: The title compound (100 mg, yield 55.6%) was synthesized according to the above-mentioned method as white solid. $^1$H NMR (400 MHz, CDCl$_3$) δ 8.78 (s, 1H), 8.34 (d, J=6.8 Hz, 1H), 7.85-7.60 (m, 6H), 7.37 (t, J=6.4 Hz, 1H), 6.82-6.71 (m, 2H), 3.90-3.75 (m, 2H), 3.75 (s, 3H), 2.53 (t, J=11.2 Hz, 2H), 1.31 (d, J=6.8 Hz, 6H). MS ESI calcd for C$_{29}$H$_{26}$FN$_3$O$_2$ [M+H]$^+$ 468, found 468.

The compounds listed in table 15 were synthesized by compound 168-1 and corresponding boric acids.

| Embodiment | Structure | NMR |
|---|---|---|
| 169 | 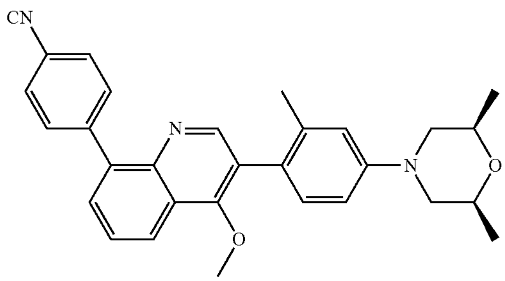 | ¹H NMR (400 MHz, CDCl₃) δ 8.66 (s, 1H), 8.35 (d, J = 7.6 Hz, 1H), 7.85-7.60 (m, 6H), 7.21 (d, J = 8.0 Hz, 1H), 6.90-6.80 (m, 2H), 3.65-3.50 (m, 5H), 2.49 (t, J = 11.2 Hz, 2H), 2.20 (s, 3H), 1.29 (d, J = 6.4 Hz, 6H). MS ESI calcd for C₃₀H₂₉N₃O₂ [M + H]⁺ 464, found 464. |
| 170 | 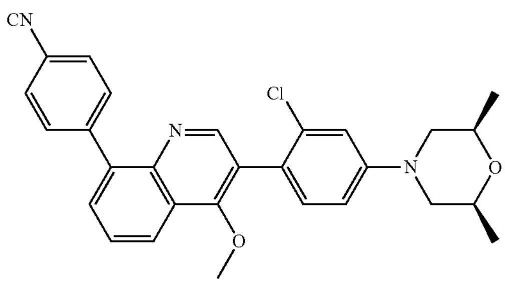 | ¹H NMR (400 MHz, CDCl₃) δ 8.67 (s, 1H), 8.36-8.34 (m, 1H), 7.79-7.77 (m, 2H), 7.73-7.62 (m, 2H), 7.30-7.28 (m, 2H), 7.04-7.03 (m, 1H), 6.92-6.89 (m, 1H), 3.83-3.81 (m, 1H), 3.70 (s, 3H), 3.55-3.52 (m, 2H), 2.55-2.50 (m, 2H). 1.30 (d, J = 6.4 Hz, 6H). MS ESI calcd for C₂₉H₂₆ClN₃O₂ [M + H]⁺ 484, found 484. |
| 171 | 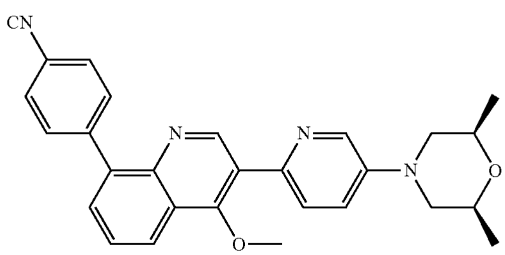 | ¹H NMR (400 MHz, CDCl₃) δ 9.22 (s, 1H), 8.45 (d, J = 2.8 Hz, 1H), 8.40-8.30 (m, 1H), 7.37 (t, J = 6.4 Hz, 1H), 7.85-7.60 (m, 7H), 7.35-7.25 (m, 1H), 3.90-3.75 (m, 5H), 3.62-3.50 (m, 2H), 2.53 (t, J = 11.2 Hz, 2H), 1.30 (d, J = 6.0 Hz, 6H). MS ESI Calcd for C₂₈H₂₆N₄O₂ [M + H]⁺ 451, found 451. |
| 172 | 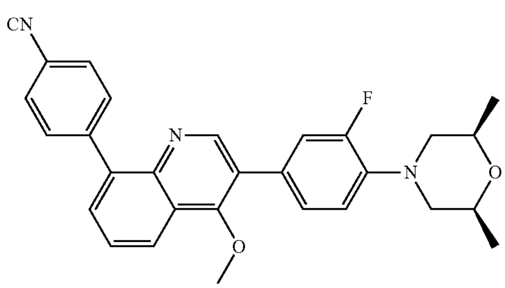 | ¹H NMR (400 MHz, CDCl₃) δ 8.67 (s, 1H), 8.32 (d, J = 8.4 Hz, 1H), 7.85-7.60 (m, 5H), 7.40-7.30 (m, 3H), 7.10-7.00 (m, 1H), 3.95-3.85 (m, 2H), 3.89 (s, 3H), 3.42-3.30 (m, 2H), 2.53 (t, J = 11.2 Hz, 2H), 1.25 (d, J = 6.4 Hz, 6H). MS ESI Calcd for C₂₉H₂₆FN₃O₂ [M + H]⁺ 468, found 468. |
| 173 | 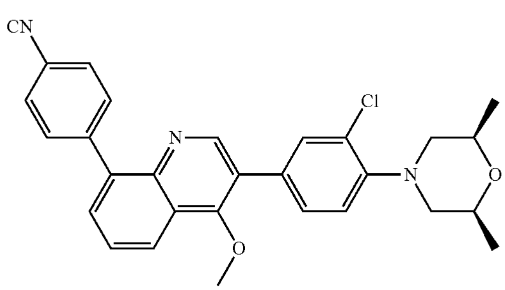 | ¹H NMR (400 MHz, CDCl₃) δ 8.74 (s, 1H), 8.25-8.15 (m, 1H), 7.75-7.50 (m, 7H), 7.40-7.33 (m, 1H), 7.10-7.00 (m, 1H), 3.90-3.875 (m, 2H), 3.61 (s, 3H), 3.25-3.15 (m, 2H), 2.39 (t, J = 11.2 Hz, 2H), 1.13 (d, J = 6.4 Hz, 6H). MS ESI Calcd for C₂₉H₂₆ClN₃O₂ [M + H]⁺ 484, found 484. |

| Embodiment | Structure | NMR |
|---|---|---|
| 174 | 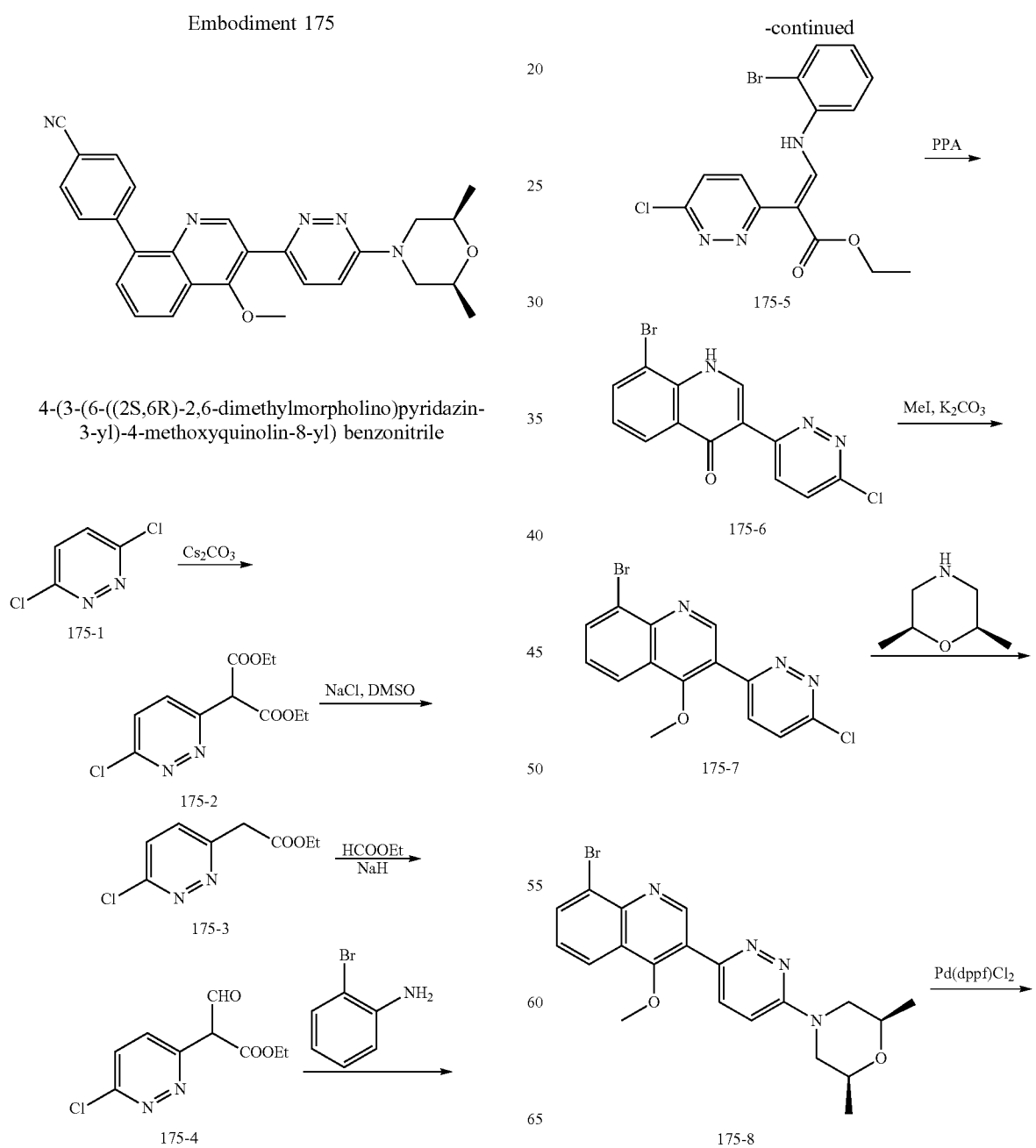 | $^{1}$H NMR (400 MHz, CDCl$_3$) δ 8.34 (d, J = 8.4 Hz, 1H), 7.85-7.60 (m, 7H), 7.50-7.40 (m, 2H), 7.12-7.05 (m, 1H), 3.95-3.85 (m, 2H), 3.72 (s, 3H), 3.03 (d, J = 11.6 Hz, 2H), 2.51 (t, J = 10.8 Hz, 2H), 2.39 (s, 3H), 1.24 (d, J = 6.4 Hz, 6H). MS ESI calcd for C$_{30}$H$_{29}$N$_3$O$_2$ [M + H]$^+$ 464, found 464. |
Embodiment 175
4-(3-(6-((2S,6R)-2,6-dimethylmorpholino)pyridazin-3-yl)-4-methoxyquinolin-8-yl) benzonitrile

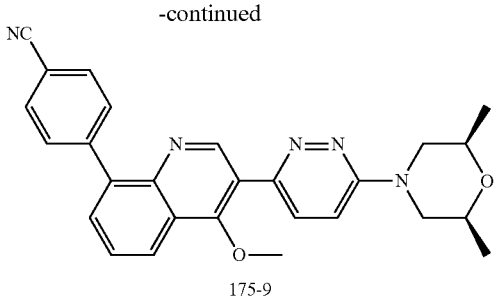

175-9

Step 1: Cesium carbonate (176 g, 540 mmol) was added into a solution of compound 175-1 (40 g, 270 mmol) and diethyl malonate (61 mL, 410 mmol) in DMSO (80 mL) at room temperature. The reaction mixture was stirred at 110° C. for 1 h. The reaction mixture was poured into $H_2O$, extracted with EtOAc. The organic phase was dried over sodium sulfate and concentrated under reduced pressure. The crude product was purified by silica gel chromatography (PE:EtOAc=10:1) to deliver compound 175-2 (52 g, yield 71%) as colorless oil. MS ESI calcd for $C_{11}H_{13}ClN_2O_4$ $[M+H]^+$ 273, found 273.

Step 2: Compound 2 (52 g, 190 mmol), NaCl (45 g, 760 mmol) and $H_2O$ (5 mL) were added into DMSO (300 mL), the reaction mixture was stirred at 150 to 160° C. for 2 h. The reaction mixture was poured into $H_2O$, extracted with EtOAc. The organic phase was concentrated under reduced pressure. The crude product was purified by silica gel chromatography (PE:EtOAc=5:1) to deliver compound 175-3 (30 g, yield 79%) as colorless oil. MS ESI calcd for $C_8H_9ClN_2O_2$ $[M+H]^+$ 201, found 201.

Step 3: Under nitrogen gas atmosphere, NaH (8.4 g, 350 mmol) was added into a solution of compound 175-3 (20 g, 100 mmol) in $HCO_2Et$ (200 mL) at 0° C. The reaction mixture was stirred at room temperature for 2 h. Then the reaction mixture was poured into 5% HCl aqueous solution, extracted with EtOAc. The organic phase was washed with $Na_2CO_3$ aqueous solution and dried over sodium sulfate. The crude product was purified by silica gel chromatography (PE:EtOAc=8:1) to deliver compound 175-4 (6 g, yield 26%) as colorless oil. ESI calcd for $C_9H_9ClN_2O_3$ $[M+H]^+$ 229, found 229.

Step 4: A solution of compound 175-4 (5 g, 22 mmol) and 2-bromophenylamine (3.8 g, 22 mmol) in EtOH (100 mL) was stirred at 70° C. for 20 h. The reaction mixture was cooled to room temperature. The crude product was collected by filtration to deliver compound 175-5 (5 g, yield 57%) as yellow solid. MS ESI calcd for $C_{15}H_{13}BrClN_3O_2$ $[M+H]^+$ 382, found 382.

Step 5: Compound 175-5 (4.4 g, 11.5 mmol) was dissolved in PPA (50 mL). The reaction mixture was stirred at room temperature for 12 h. The reaction mixture was poured into ice water. The product was collected by filtration to deliver compound 175-6 (3 g, yield 77%) as yellow solid. MS ESI calcd for $C_{13}H_7BrClN_3O$ $[M+H]^+$ 335, found 335.

Step 6: A solution of compound 175-6 (1.4 g, 4.2 mmol), $CH_3I$ (887 mg, 6.2 mmol) and $Ag_2CO_3$ (2.3 g, 8.4 mmol) in DMF (20 mL) was stirred at 70° C. for 4 h. The reaction mixture was poured into $H_2O$, extracted with DCM. The organic phase was washed with brines, dried over sodium sulfate and concentrated under reduced pressure. The crude product was purified by silica gel chromatography (PE: EtOAc=1:1) to deliver compound 175-7 (540 mg, yield 37%) as yellow solid. MS ESI calcd for $C_{14}H_9BrClN_3O$ $[M+H]^+$ 350, calcd for 350.

Step 7: A solution of compound 175-7 (540 mg, 1.55 mmol) in (2S,6R)-2,6-dimethylmorpholine (1 mL) was stirred at 120° C. for 2 h. The reaction mixture was poured into $H_2O$, extracted with DCM. The combined organic phase was washed with brines, dried over sodium sulfate and concentrated under reduced pressure to deliver compound 175-8 (663 mg, 100%) as yellow solid. The crude product was used in the next step directly without further purification. MS ESI calcd for $C_{20}H_{21}BrN_4O_2$ $[M+H]^+$ 429, found 429.

Step 8: A solution of Pd(dppf)Cl$_2$ (117 mg, 0.16 mmol) and sodium carbonate (329 mg, 3.1 mmol) in THF/$H_2O$/DMF (10/2/2) was added into a solution of compound 175-8 (663 mg, 1.55 mmol), 4-cyanophenyl boric acid (251 mg, 1.7 mmol), stirred at 90° C. for 3 h. The reaction mixture was filtrated, and partitioned between EtOAc and $H_2O$, the organic phase was dried and concentrated. The crude product was purified by preparative HPLC to deliver the title compound (90 mg, yield 13%) as yellow solid. $^1$H NMR (400 MHz, Methanol-$d_4$) δ 8.96 (s, 1H), 8.65 (d, J=9.6 Hz, 1H), 8.56 (d, J=10.0 Hz, 1H), 8.06 (d, J=8.4 Hz, 1H), 7.92 (d, J=8.4 Hz, 1H), 7.81-7.61 (m, 6H), 4.29 (d, J=12.8 Hz, 2H), 3.81-3.71 (m, 2H), 3.30 (s, 3H), 2.81 (t, J=12.0 Hz, 2H), 1.28 (d, J=5.6 Hz, 6H). MS ESI calcd for $C_{27}H_{25}N_5O_2$ $[M+H]^+$ 452, found 452.

Embodiment 176

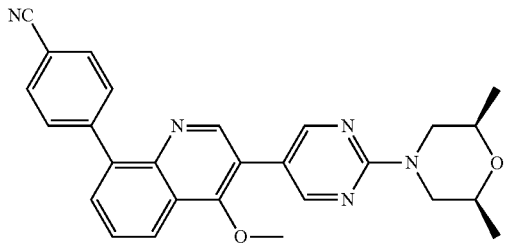

4-(3-(2-((2S,6R)-2,6-dimethylmorpholino)pyrimidin-5-yl)-4-methoxyquinolin-8-yl) benzonitrile

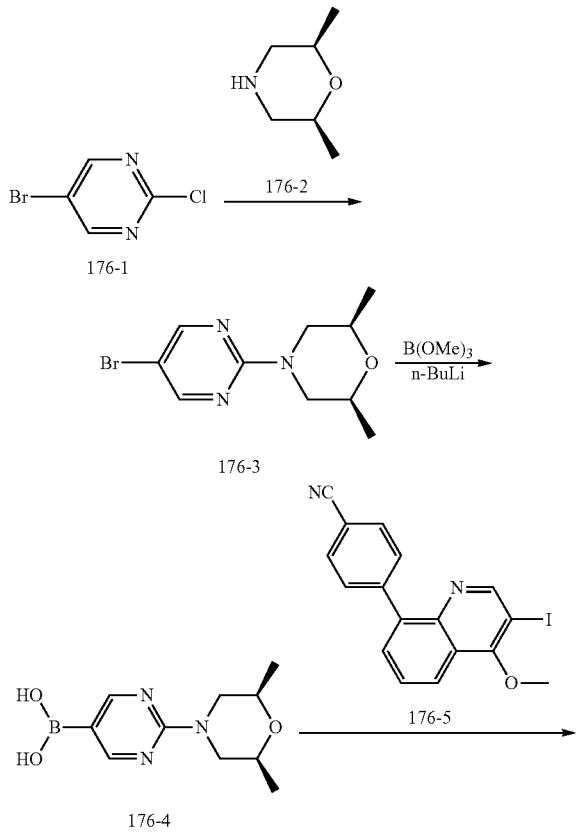

229

-continued

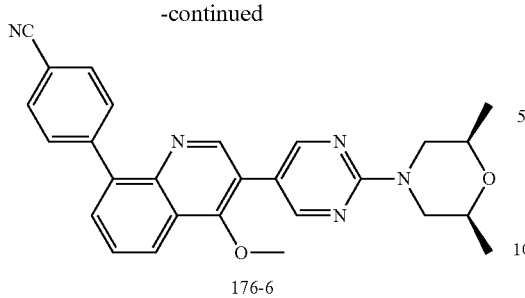

176-6

Step 1: Compound 176-1 (3 g, 15.5 mmol) was dissolved in compound 176-2 (1.8 g, 15.5 mmol), then stirred for 2 h at 100° C. The solution was partitioned between EtOAc and H$_2$O, the organic phase was washed with brines, dried over anhydrous sodium sulfate, filtrated and concentrated under reduced pressure to deliver compound 176-3 (3.1 g, 74%) as white solid. MS ESI calcd for C$_{10}$H$_{14}$BrN$_3$O [M+H]$^+$ 272, found 272.

Step 2: Compound 176-3 (4.2 g, 15.4 mmol) was dissolved in THF (40 mL), n-BuLi (9.2 mL, 23.1 mmol) was added dropwise into the solution at −78° C. The mixture was stirred for 30 min, then B(OMe)$_3$ (4.8 g, 46.2 mmol) was added dropwise. Then the reaction mixture was warmed to 0° C. and stirred for 3 h. The reaction mixture was partitioned between EtOAc and H$_2$O, the organic phase was separated, combined, washed with brines, dried over anhydrous sodium sulfate, filtrated and concentrated to deliver compound 176-4 (2.6 g, 72%) as brown solid. MS ESI calcd for C$_{10}$H$_{16}$BN$_3$O$_3$ [M+H]$^+$ 237, found 237.

Step 3: The title compound was synthesized according to the above-mentioned method (23 mg, 10%) as brown solid. $^1$H NMR (400 MHz, CDCl$_3$) δ 8.83 (s, 1H), 8.65 (s, 2H), 8.27 (d, J=7.2 Hz, 1H), 7.85-7.60 (m, 6H), 4.63 (d, J=12.8 Hz, 2H), 3.80 (s, 3H), 3.75-3.61 (m, 2H), 2.68 (t, J=12.0 Hz, 2H), 1.27 (d, J=6.0 Hz, 6H). MS ESI calcd for C$_{27}$H$_{25}$N$_5$O$_2$ [M+H]$^+$ 452, found 452.

The compound listed in table 16 was synthesized by corresponding aryl halide.

230

4-(3-(5-((2S,6R)-2,6-dimethylmorpholine-4-carbonyl)thiophen-2-yl)-4-methoxyquinolin-8-yl)benzonitrile

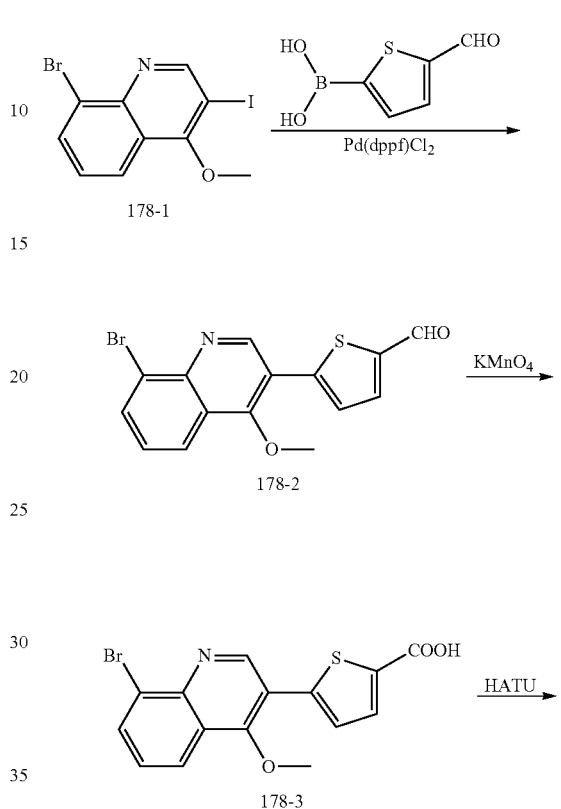

| Embodiment | Structure | LC-MS & NMR |
|---|---|---|
| 177 | 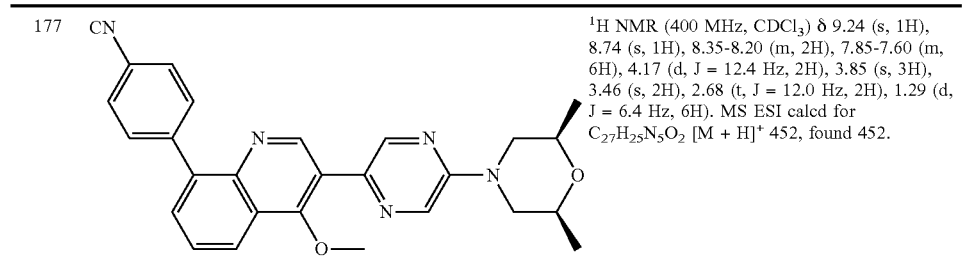 | $^1$H NMR (400 MHz, CDCl$_3$) δ 9.24 (s, 1H), 8.74 (s, 1H), 8.35-8.20 (m, 2H), 7.85-7.60 (m, 6H), 4.17 (d, J = 12.4 Hz, 2H), 3.85 (s, 3H), 3.46 (s, 2H), 2.68 (t, J = 12.0 Hz, 2H), 1.29 (d, J = 6.4 Hz, 6H). MS ESI calcd for C$_{27}$H$_{25}$N$_5$O$_2$ [M + H]$^+$ 452, found 452. |

Embodiment 178

-continued

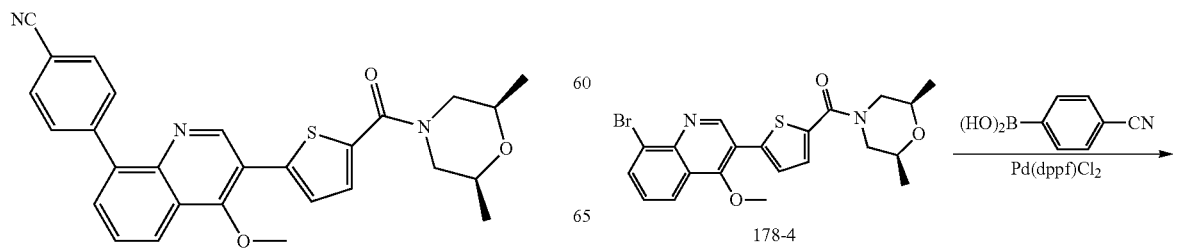

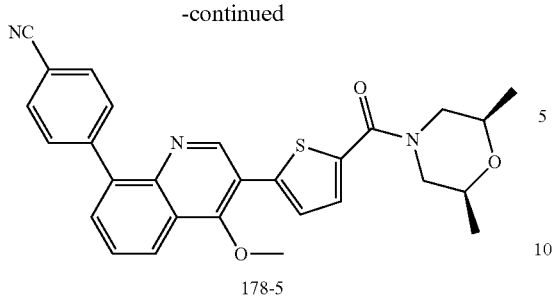

178-5

Step 1: Pd(dppf)Cl₂ (102 mg, 0.14 mmol) was added into a solution of compound 178-1 (500 mg, 1.4 mmol), (5-formylthiophene-2-yl)boric acid (270 mg, 1.7 mmol) and sodium carbonate (300 mg, 2.8 mmol) in DMF (2 mL)/H₂O (2 mL)/THF (10 mL). The mixture was stirred at 70° C. for 2 h. The mixture was poured into H₂O, extracted with EtOAc, the organic phase was washed with brines, dried over sodium sulfate, concentrated. The residue was purified by column chromatography (PE/EtOAc=5:1) to deliver compound 178-2 (438 mg, 91.6%) as brown solid. MS ESI calcd for $C_{15}H_{10}BrNO_2S$ [M+H]⁺ 348, found 348.

Step 2: Sodium dihydrogen phosphate (300 mg, 2.5 mmol) was added into a solution of compound 178-2 (438 mg, 1.25 mmol) and potassium hypermanganate (200 mg, 1.25 mmol) in acetone (15 mL). The mixture was stirred at room temperature for 4 h. The brown MnO₂ precipitate was filtered, acetone was removed under vacuum, the mixture was acidified with 1 N HCl and extracted with EtOAc. The organic phase was dried over anhydrous sodium sulfate, concentrated to deliver compound 178-3 (350 mg, 76.4%) as brown solid. MS ESI calcd for $C_{15}H_{10}BrNO_3S$ [M+H]⁺ 364, found 364.

Step 3: To a solution of compound 178-3 (350 mg, 1 mmol), HATU (384 mg, 1 mmol) and (2S, 6R)-2,6-dimethylmorpholine (138 mg, 1.2 mmol) in DMF (10 mL) was added DIPA (387 mg, 3 mmol). The mixture was stirred at room temperature overnight. The reaction mixture was poured into H₂O, extracted with EtOAc, the organic phase was dried over sodium sulfate and concentrated. The residue was purified by column chromatography (PE/EtOAc=2:1) to deliver compound 178-4 (265 mg, 59.8%) as brown solid. MS ESI calcd for $C_{21}H_{21}BrN_2O_3S$ [M+H]⁺ 461, found 461.

Step 4: Pd(dppf)Cl₂ (45 mg, 0.06 mmol) was added into a solution of compound 178-4 (265 mg, 0.6 mmol), 4-cyanophenylboric acid (106 mg, 0.72 mmol) and sodium carbonate (127 mg, 1.2 mmol) in DMF (2 mL)/H₂O (solvent 2 mL)/THF (10 mL). The mixture was stirred at 70° C. for 2 h. The reaction mixture was poured into H₂O, extracted with EtOAc, the organic phase was washed with brines, dried over sodium sulfate and concentrated. The residue was purified by preparative HPLC to deliver the title compound (32 mg, yield 11%) as white solid. ¹H NMR (400 MHz, CDCl₃) δ 9.20 (s, 1H), 8.26-8.24 (m, 1H), 7.83-7.78 (m, 4H), 7.74-7.68 (m, 2H), 7.56-7.55 (m, 1H), 7.35-7.34 (m, 1H), 4.03 (s, 3H), 3.67 (s, 1H), 1.24 (d, 6H). MS ESI calcd for $C_{28}H_{25}N_3O_3S$ [M+H]⁺ 484, found 484.

Embodiment 179

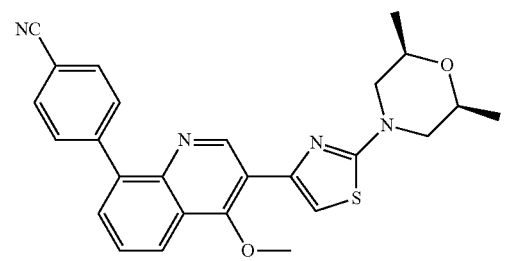 [SMILES: COc1c(-c2csc(N3C[C@@H](C)O[C@@H](C)C3)n2)cnc2c(-c3ccc(C#N)cc3)cccc12]

4-(3-(2-(2,6-dimethylmorpholin-4-yl)thiazol-4-yl)-4-methoxyquinolin-8-yl) benzonitrile

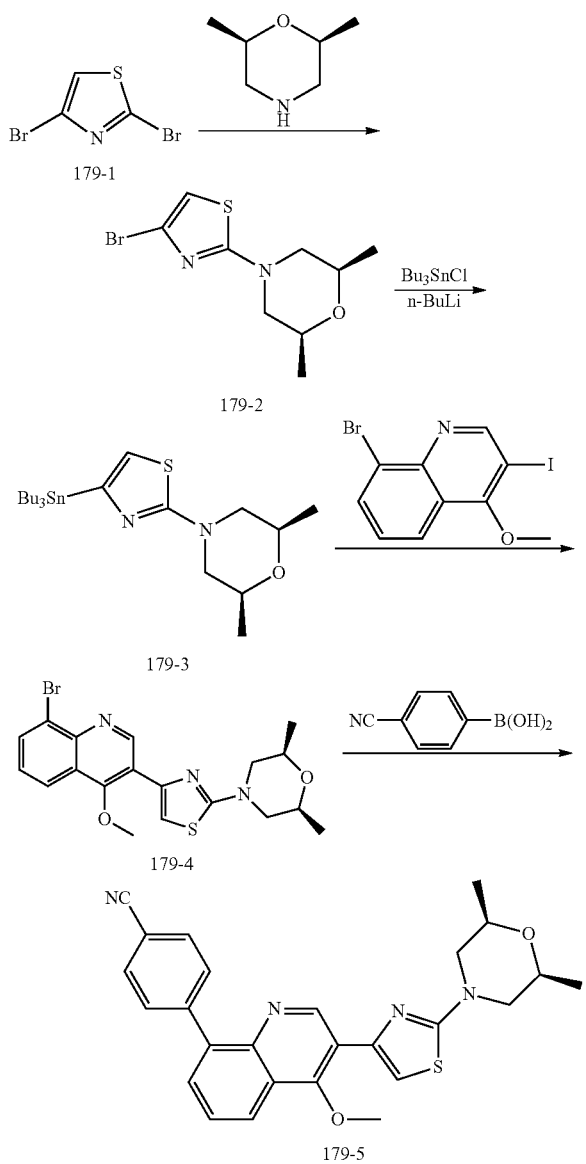

Step 1: K₂CO₃ (5.7 g, 41 mmol) was added into a solution of compound 179-1 (5.0 g, 20.5 mmol) and (2S, 6R)-2,6-dimethylmorpholine (3.55 g, 30.9 mmol) in DMF (60 mL). The mixture was stirred at 70° C. overnight. The reaction mixture was cooled to room temperature, then poured into H₂O, extracted with EtOAc, dried over sodium sulfate and concentrated. The residue was purified by column chromatography to deliver compound 179-2 (5.56 g, yield 99%) as yellow oil. MS ESI calcd for C₉H₁₃BrN₂OS [M+H]⁺ 277, found 277.

Step 2: n-BuLi (0.8 mL, 2.5M in THF solution) was added into a solution of compound 179-2 (500 mg, 1.8 mmol) in THF (10 mL) at −78° C., the mixture was stirred at −78° C. for 1 h, then SnBu₃Cl (650 mg, 2 mmol) was added at −78° C. and stirred at −78° C. for 1 h. The reaction mixture was poured into H₂O, extracted with EtOAc, dried over sodium sulfate, concentrated to deliver compound 179-3 (0.7 g, yield 79%) as colorless oil. MS ESI calcd for C₂₁H₄₀N₂OSSn [M+H]⁺ 489, found 489.

Step 3: Pd(PPh₃)₄ (80 mg, 0.08 mmol) was added into a solution of compound 179-3 (500 mg, 1.2 mmol) and 8-bromo-3-iodo-4-methoxyquinoline (230 mg, 0.6 mmol) in toluene (10 mL). The mixture was stirred at 110° C. overnight. The reaction mixture was partitioned between H₂O and EtOAc. The organic phase was dried over sodium sulfate, concentrated to deliver compound 179-4 (50 mg, yield 12%) as yellow solid. MS ESI calcd for C₁₉H₂₀BrN₃O₂S [M+H]⁺ 433, found 433.

Step 4: Pd(dppf)Cl₂ (25 mg, 0.03 mmol) and sodium carbonate (50 mg, 0.5 mmol) were added into a solution of compound 179-4 (50 mg, 0.14 mmol) and 4-cyanophenyl boric acid (48 mg, 0.14 mmol) in THF/H₂O/DMF (42 mL, 61 seconds past five). The mixture was stirred at 70° C. overnight. The reaction mixture was poured into H₂O, extracted with EtOAc, the organic phase was dried over sodium sulfate and concentrated. The residue was purified by preparative HPLC to deliver the title compound (6 mg, yield 10%) as yellow solid. ¹H NMR (400 MHz, CDCl3) δ 9.45 (s, 1H), 8.15-8.10 (m, 1H), 7.75-7.50 (m, 6H), 7.20 (s, 1H), 3.85 (s, 3H), 3.75-3.60 (m, 4H), 2.68 (t, J=10.8 Hz, 2H), 1.15 (d, J=6.4 Hz, 6H). MS ESI calcd for C₂₆H₂₄N₄O₂S [M+H]⁺ 457, found 457.

Embodiment 180

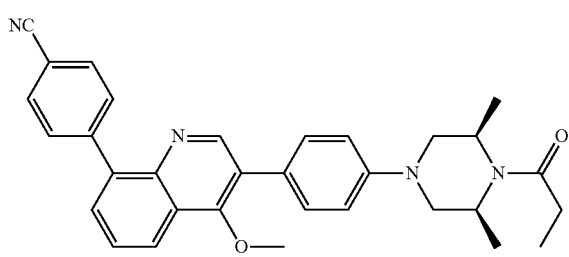 [SMILES: CCC(=O)N1[C@H](C)CN(c2ccc(-c3cnc4c(-c5ccc(C#N)cc5)cccc4c3OC)cc2)C[C@@H]1C]

4-(3-(4-((3S, 5R)-3, 5-dimethyl-4-propionylpiperazin-1-yl)phenyl)-4-methoxyquinolin-8-yl)benzonitrile

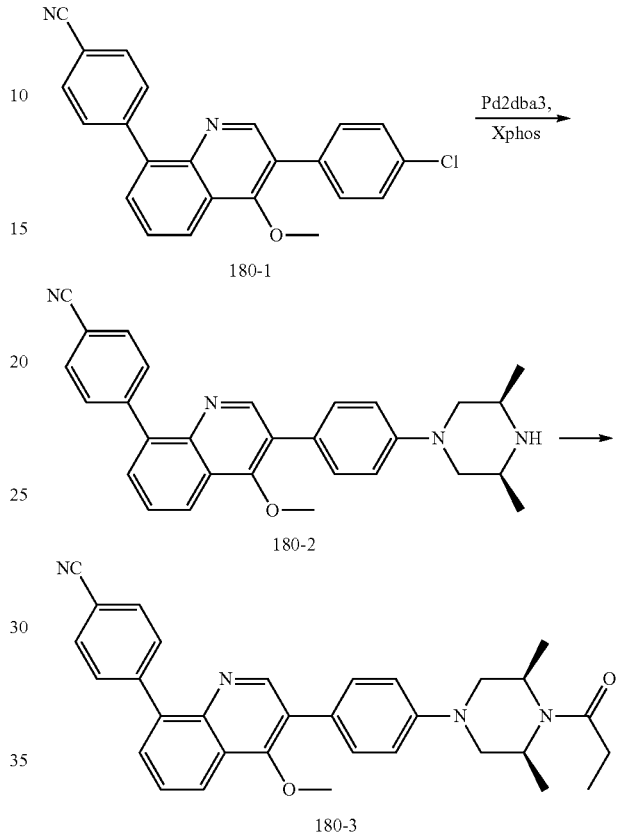

Step 1: Pd₂(dba)₃ (330 mg, 0.3 mmol), Xantphos (350 mg, 0.7 mmol) and KOᵗBu (1.6 g, 15 mmol) were added into a solution of compound 180-1 (2.0 g, 5.4 mmol) and (2S,6R)-2,6-dimethylpiperazine (0.8 g, 7 mmol) in toluene (30 mL). Under nitrogen gas atmosphere, the reaction mixture was stirred at 120° C. for 5 h, then poured into H₂O. The mixture was extracted with ether (3×30 mL), the organic phase was dried over sodium sulfate. The residue was purified by column chromatography to deliver compound 180-2 (1.7 g, yield 70%) as yellow solid. MS ESI calcd for C₂₉H₂₈N₄O [M+H]⁺ 449, found 449.

Step 2: Propionyl chloride (130 mg, 0.1 mmol) was added into a solution of compound 180-2 (90 mg, 0.2 mmol) and TEA (200 mg, 2 mmol) in DCM (10 mL) at room temperature. The reaction mixture was stirred for 1 h and then poured into H₂O, extracted with DCM (2×10 mL), the organic phase was dried over sodium sulfate. The residue was purified by preparative HPLC to deliver the title compound (50 mg, yield 40%) as white solid. ¹H NMR (400 MHz, CDCl₃) δ 8.89 (s, 1H), 8.47-8.45 (m, 2H), 7.97-7.81 (m, 4H), 7.62 (d, J=3.6 Hz, 2H), 7.46 (d, J=4.8 Hz, 2H), 7.02 (d, J=8.8 Hz, 2H), 3.89 (s, 3H), 3.56 (d, J=12.4 Hz, 2H), 3.00 (d, J=9.6 Hz, 2H), 2.51-2.38 (m, 2H), 1.49-1.36 (m, 6H), 1.19 (t, J=7.6 Hz, 3H). MS ESI calcd for C₃₂H₃₂N₄O₂ [M+H]⁺ 505, found 505.

The compounds listed in table 17 were synthesized by compound 180-2 and corresponding acyl chlorides.

| Embodiment | Structure | NMR |
|---|---|---|
| 181 | 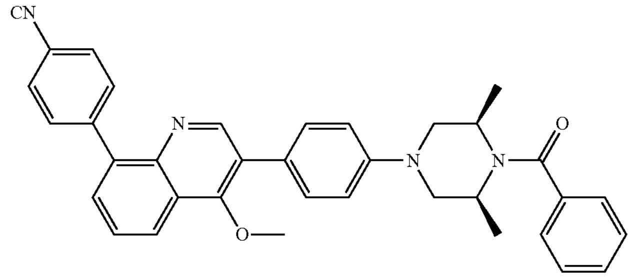 | ¹H NMR (400 MHz, CDCl₃) δ 8.72 (s, 1H), 7.94 (d, J = 8.4 Hz, 1H), 7.80 (d, J = 4.8 Hz, 4H), 7.53 (d, J = 4.8 Hz, 2H), 7.47-7.40 (m, 7H), 7.16 (d, J = 8.8 Hz, 2H), 4.32-4.52 (m, 2H), 3.90 (s, 3H), 3.68 (d, J = 12.0 Hz, 2H), 3.07 (dd, J = 3.2 Hz, J = 12.0 Hz, 2H), 1.44 (d, J = 6.4 Hz, 6H). MS ESI calcd for C₃₆H₃₂N₄O₂ [M + H]⁺ 553, found 553. |
| 182 | 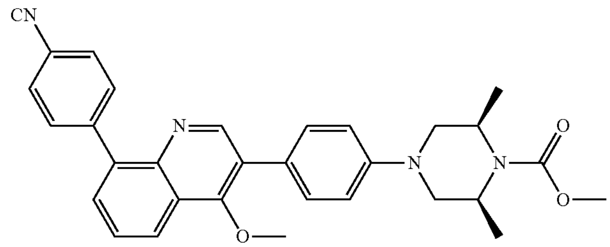 | ¹H NMR (400 MHz, CDCl₃) δ 8.87 (s, 1H), 8.51-8.49 (m, 1H), 7.87-7.78 (m, 4H), 7.62 (d, J = 7.6 Hz, 2H), 7.44 (d, J = 7.6 Hz, 2H), 7.02 (d, J = 8.4 Hz, 2H), 4.35 (d, J = 5.6 Hz, 2H), 3.94 (s, 3H), 3.79 (s, 3H), 3.54 (d, J = 12 Hz, 2H), 3.03-3.00 (m, 1H), 1.39-1.37 (m, 6H). MS ESI calcd for C₃₁H₃₀N₄O₃ [M + H]⁺ 507, found 507. |
| 183 | 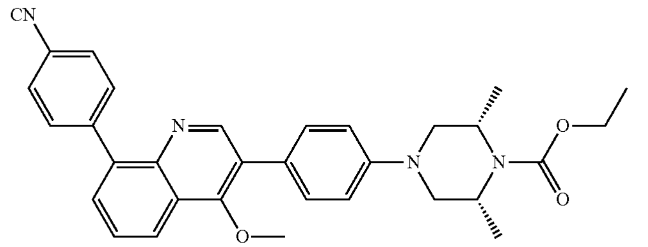 | ¹H NMR (400 MHz, CDCl₃) δ 8.90 (s, 1H), 8.48-8.46 (m, 1H), 7.83-7.81(m, 4H), 7.63 (d, J =8.0 Hz, 2H), 7.46 (d, J = 8.8 Hz, 2H), 7.02 (d, J = 8.4 Hz, 2H), 4.35 (d, J = 5.6 Hz, 2H), 4.22-4.17 (m, 2H), 3.91 (s, 3H), 3.54 (d, J = 12 Hz, 2H), 3.03-3.00 (m, 1H), 1.39-1.37 (m, 6H), 1.30 (t, J = 7.2 Hz, 3H). MS ESI calcd for C₃₂H₃₂N₄O₃ [M + H]⁺ 521, found 521. |
| 184 | 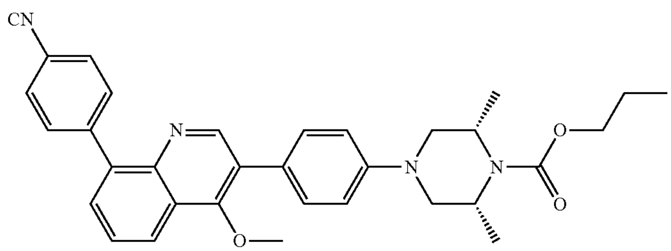 | ¹H NMR (400 MHz, CDCl₃) δ 8.91 (s, 1H), 8.48-8.46 (m, 1H), 7.83-7.80 (m, 4H), 7.64 (d, J =8.0 Hz, 2H), 7.47 (d, J = 8.4 Hz, 2H), 7.02 (d, J = 8.4 Hz, 2H), 4.36 (t, J = 5.6 Hz, 2H), 4.10 (t, J = 6.0 Hz, 2H), 3.90 (s, 3H), 3.54 (d, J = 12 Hz, 2H), 3.03-3.00 (m, 2H), 1.69-1.65 (m, 2H), 1.40-1.38 (m, 6H), 0.98 (t, J = 7.2 Hz, 3H). MS ESI Calcd for C₃₃H₃₄N₄O₃ [M + H]⁺ 535, found 535. |
| 185 | 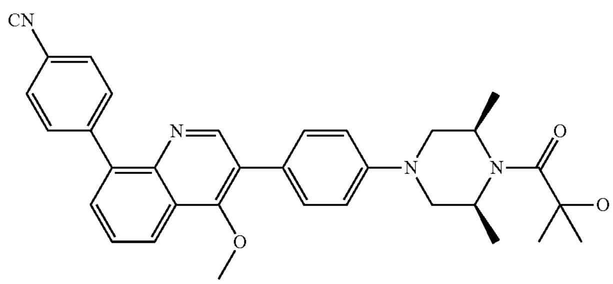 | ¹H NMR (400 MHz, CDCl₃) δ 8.94 (s, 1H), 8.43 (t, J = 4.0 Hz 1H), 7.79 (d, J = 8.0 Hz, 2H), 7.71 (d, J = 4.0 Hz, 2H), 7.70 (d, J = 8.0 Hz, 2H), 7.53 (d, J = 8.0 Hz, 2H), 7.02 (d, J = 8.0 Hz, 1H), 3.83 (s, 3H), 3.56 (d, J = 10.8 Hz, 2H), 3.04 (d, J = 10.8 Hz, 2H), 1.9-2.0 (m, 8H), 1.56 (s, 6H). MS ESI calcd for C₃₃H₃₄N₄O₃ [M + H]⁺ 535, found 535. |
| 186 | 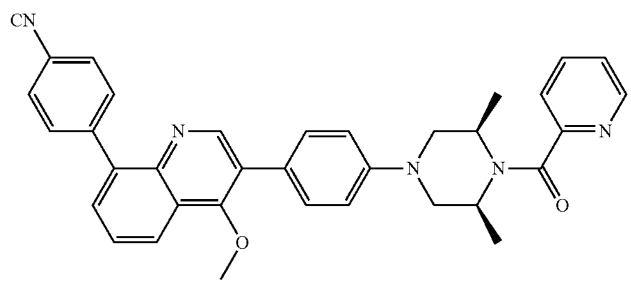 | ¹H NMR (400 MHz, CDCl₃) δ 8.88 (s, 1H), 8.61(d, J = 4.4 Hz, 2H), 8.34-8.30 (m, 1H), 7.85-7.75 (m, 5H), 7.67-7.55 (m, 5H),7.30-7.27 (m, 1H), 7.02 (d, J = 8.4 Hz, 2H), 3.73 (s, 3H), 3.55 (brs, 2H), 3.14-3.09 (m, 2H), 1.24 (s, 6H). MS ESI Calcd for C₃₅H₃₁N₅O₂ [M + H]⁺ 554, found 554. |

| Embodiment | Structure | NMR |
|---|---|---|
| 187 | 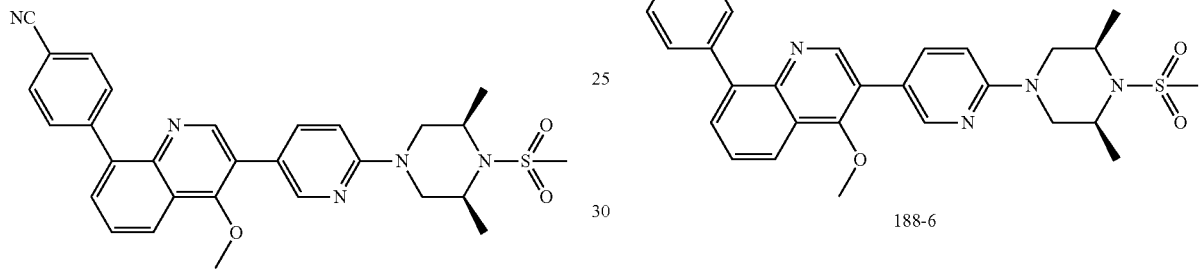 | $^1$H NMR (400 MHz, CDCl$_3$) δ 8.88 (s, 1H), 8.34-8.30 (m, 1H), 7.83-7.75 (m, 5H), 7.70-7.55 (m, 5H),7.33-7.29 (m, 1H), 7.06 (d, J = 8.4 Hz, 2H), 6.25 (brs, 1H), 3.73 (s, 3H), 3.55 (brs, 2H), 3.08 (brs, 2H), 1.45 (s, 6H). MS ESI calcd for C$_{33}$H$_{30}$N$_6$O$_2$ [M + H]$^+$ 543, found 543. |

Embodiment 188

4-(3-(6-(4-methylsulfonyl-3,5-dimethylpiperazin-1-yl)pyridin-3-yl)-4-methoxyquinolin-8-yl)benzonitrile

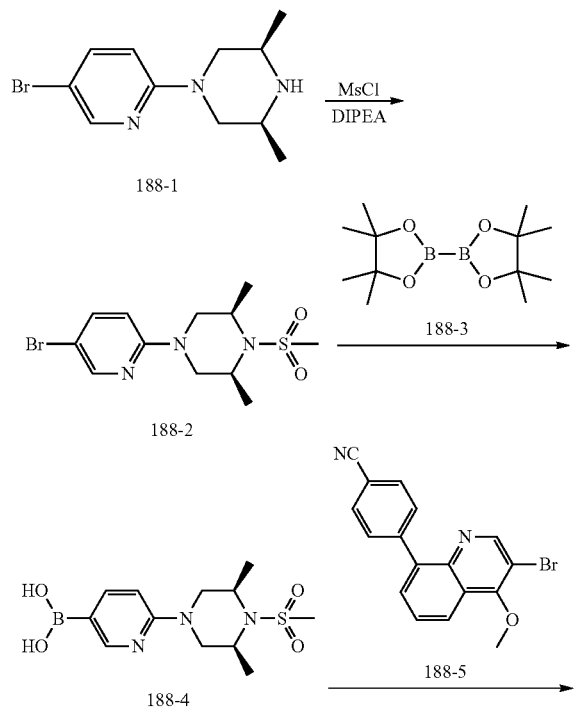

Step 1: MsCl (290 mg, 2.4 mmol) was added dropwise into a solution of compound 188-1 (540 mg, 2 mmol) and DIPEA (774 mg, 6 mmol) in DCM (10 mL), the reaction mixture was stirred at room temperature for 30 min, and monitored by LCMS till the reaction was complete. The mixture was poured into H$_2$O, extracted with EtOAc, the organic phase was dried over anhydrous sodium sulfate, concentrated to give a crude product, which was purified by silica gel column chromatography (MeOH:EtOAc=5:1) to deliver compound 188-2 (500 mg, yield 72%) as white solid. MS ESI calcd for C$_{12}$H$_{18}$BrN$_3$O$_2$S[M+H]$^+$ 350, found 350.

Step 2: Pd(dppf)Cl$_2$ (102 mg, 0.14 mmol) was added into a solution of compound 188-2 (500 mg, 1.4 mmol), 188-3 (432 mg, 1.7 mmol) and AcOK (300 mg, 2.8 mmol) in dioxane (10 mL), the reaction mixture was stirred at 70° C. for 2 h, and monitored by LCMS till the reaction was complete. Then the mixture was poured into H$_2$O, extracted with EtOAc, the organic phase was dried over anhydrous sodium sulfate, concentrated to give a crude product, which was purified by silica gel column chromatography (PE:EtOAc=1:1) to deliver compound 188-4 (460 mg, yield 100%) as yellow solid. MS ESI calcd for C$_{12}$H$_{20}$BN$_3$O$_4$S [M+H]$^+$ 314, found 314.

Step 3: The title compound (120 mg, 23%) was synthesized according to the above-mentioned method as yellow solid. $^1$H NMR (400 MHz, CDCl$_3$) δ 8.90 (s, 1H), 8.50 (d, J=2.0 Hz, 1H), 8.33 (d, J=6.8 Hz, 1H), 7.90-7.73 (m, 7H), 6.82 (d, J=8.8 Hz, 1H), 4.28-4.22 (m, 4H), 3.80 (s, 3H), 3.29 (dd, J=4.4, 12.8 Hz 2H), 2.96 (s, 3H), 1.51 (d, J=7.2 Hz, 6H). MS ESI calcd for C$_{29}$H$_{29}$N$_5$O$_3$S[M+H]$^+$ 528, found 528.

Embodiment 189
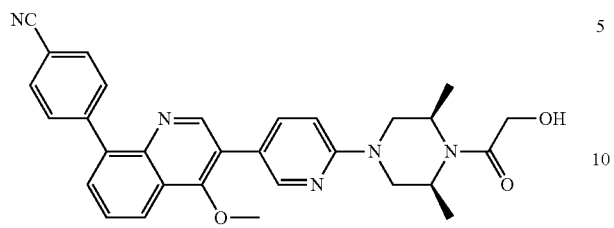
4-(3-(6-(4-(2-hydroxyacetyl)-3,5-dimethylpiperazin-1-yl)pyridin-3-yl)-4-methoxyquinolin-8-yl)benzonitrile
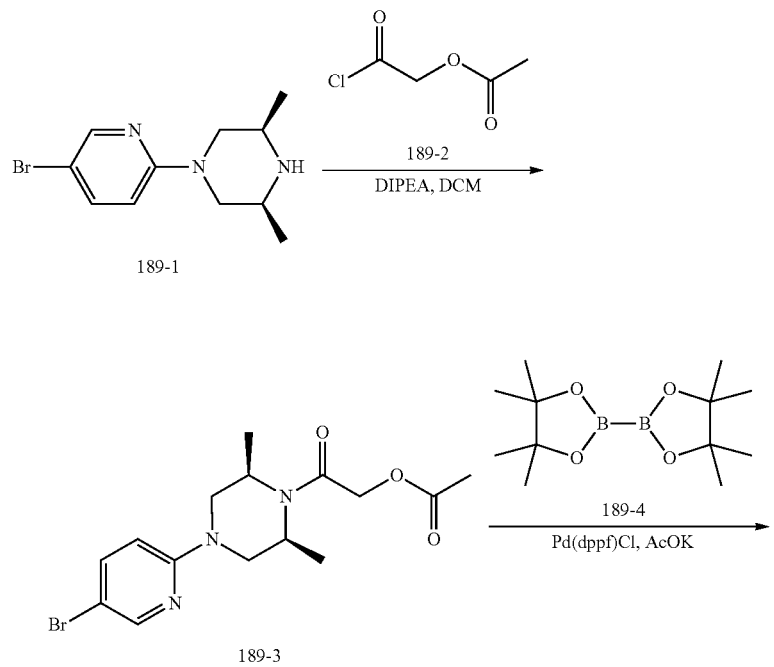
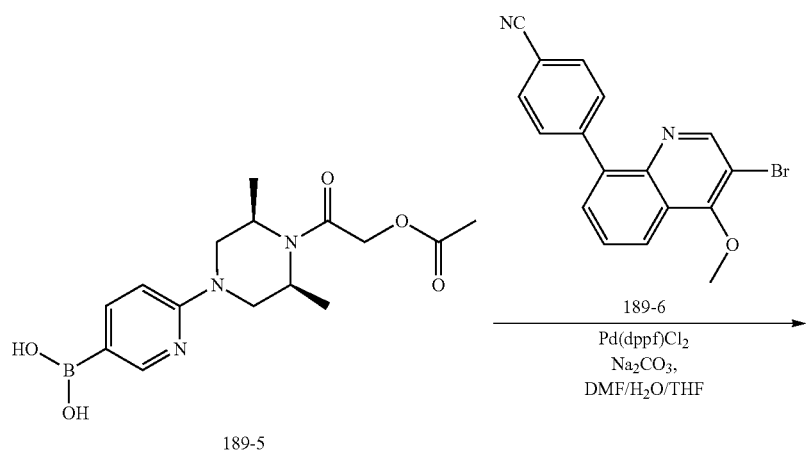

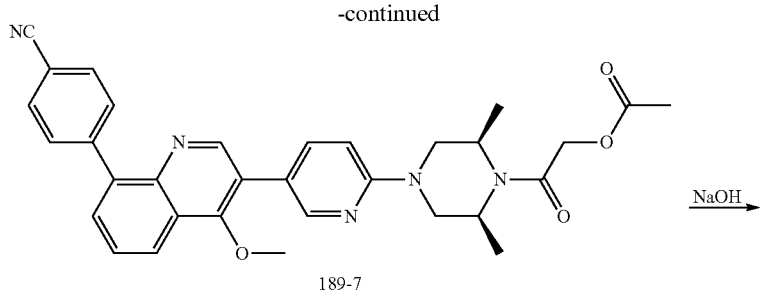

189-7

189-8

Step 1: Compound 189-2 (227 mg, 1.7 mmol) was added into a solution of compound 189-1 (300 mg, 1.1 mmol) and DIPEA (430 mg, 3.3 mmol) in DCM (30 mL), the reaction mixture was stirred at 0° C. for 30 min, and monitored by LCMS till the reaction was complete. Then the mixture was poured into H$_2$O, extracted with EtOAc, the organic phase was dried over anhydrous sodium sulfate, concentrated to give a crude product, which was purified by silica gel column chromatography (PE:EtOAc=5:1) to deliver compound 189-3 (260 mg, yield 63%) as red oil. MS ESI calcd for C$_{15}$H$_{20}$BrN$_3$O$_3$[M+H]$^+$ 370, found 370.

Step 2: Pd(dppf)Cl$_2$ (102 mg, 0.14 mmol) was added into a solution of compound 189-3 (260 mg, 0.7 mmol), 189-4 (213 mg, 0.84 mmol) and AcOK (205 mg, 2.1 mmol) in dioxane (6 mL), the reaction mixture was stirred at 100° C. for 2 h, and monitored by LCMS till the reaction was complete. Then the mixture was poured into H$_2$O, extracted with EtOAc, the organic phase was dried over anhydrous sodium sulfate, concentrated to give a crude product, which was purified by silica gel column chromatography (PE: EtOAc=1:1) to deliver compound 189-5 (170 mg, yield 70%). MS ESI calcd for C$_{15}$H$_{22}$BN$_3$O$_5$ [M+H]$^+$ 336, found 336.

Step 3: compound 189-7 (60 mg, 22%) was synthesized according to the above-mentioned method as white solid. MS ESI calcd for C$_{32}$H$_{31}$N$_5$O$_4$ [M+H]$^+$ 550, found 550.

Step 4: NaOH (132 mg, 3.3 mmol) was added into a solution of compound 189-7 (60 mg, 0.11 mmol) in MeOH (2 mL)/THF (2 mL)/H$_2$O (2 mL), the reaction system was stirred at room temperature for 2 h. The reaction mixture was monitored by LC-MS till the reaction was complete. The mixture was poured into H$_2$O, washed with EtOAc, the aqueous phase was acidified to pH=4 with 1N HCl, then extracted with EtOAc, the organic phase was dried over anhydrous sodium sulfate, concentrated to give a crude product, which was further purified by TLC (DCM: MeOH=20:1) to deliver the title compound (10 mg) as white solid. $^1$H NMR (400 MHz, CDCl$_3$) δ 8.91 (s, 1H), 8.51 (s, 1H), 8.35-8.33 (m, 1H), 7.86-7.70 (m, 7H), 6.87 (d, J=8.8 Hz, 1H), 3.80 (s, 3H), 1.67 (s, 3H), 1.44 (m, 6H). MS ESI calcd for C$_{30}$H$_{29}$N$_5$O$_3$[M+H]$^+$ 508, found 508.

Embodiment 190

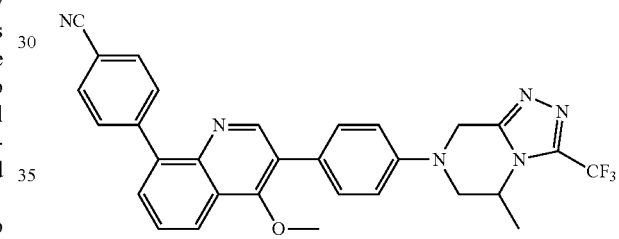

4-(4-methoxy-3-(4-(5-methyl-3-(trifluoromethyl)-5, 6-dihydro-[1,2,4]triazolo[4,3-a]pyrazin-7(8H)-yl) phenyl)quinolin-8-yl)benzonitrile

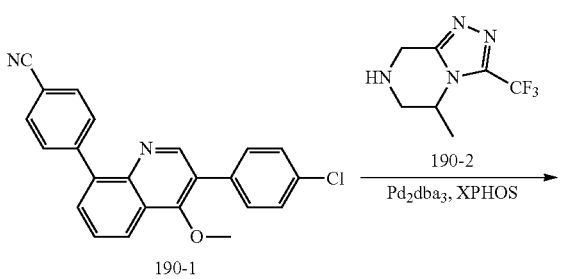

190-1

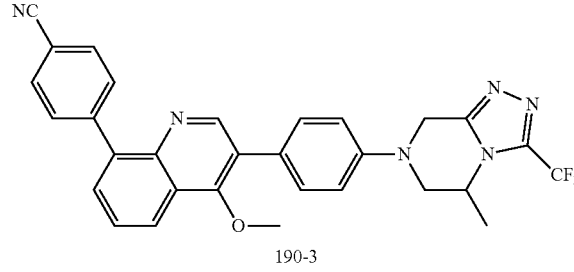

190-3

Pd$_2$(dba)$_3$ (45 mg, 0.05 mmol), Xantphos (50 mg, 0.1 mmol) and KO$^t$Bu (0.23 g, 2 mmol) were added into a solution of compound 190-1 (0.185 g, 0.5 mmol) and 190-2 (0.12 g, 0.6 mmol) in toluene (30 mL), under nitrogen gas atmosphere, the reaction mixture was stirred at 120° C. for 5 h, then poured into H$_2$O, the mixture was extracted with ether (3×30 mL), the organic phase was dried over sodium sulfate, the residue was purified by preparative HPLC to deliver the title compound (70 mg, yield 30%) as white solid. $^1$H NMR (400 MHz, CDCl$_3$) δ 8.88 (s, 1H), 8.40 (t, J=4.8 Hz, 1H), 7.75-7.74 (m, 4H), 7.62-7.52 (m, 4H), 7.04 (d, J=8.4 Hz, 2H), 4.93 (d, J=16 Hz, 1H), 4.69 (s, 1H), 4.45 (d, J=12.0 Hz, 1H), 3.88-3.81 (m, 5H), 1.64 (d, J=9.8 Hz, 3H). MS ESI calcd for C$_{30}$H$_{23}$F$_3$N$_6$O [M+H]$^+$ 541, found 541.

Embodiment 191

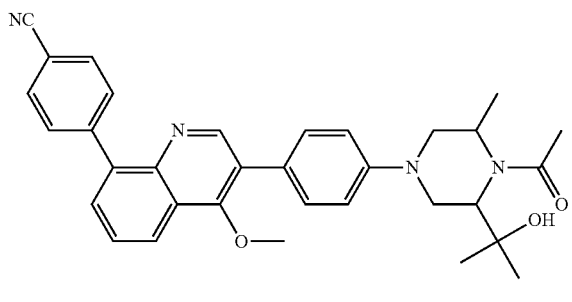 [SMILES: COc1c(-c2ccc(N3CC(C)N(C(C)=O)C(C(C)(C)O)C3)cc2)cnc2c(-c3ccc(C#N)cc3)cccc12]

4-(3-(4-(4-acetyl-3-(2-hydroxypropan-2-yl)-5-methylpiperazin-1-yl)phenyl)-4-methoxyquinolin-8-yl)benzonitrile

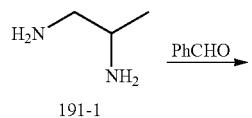

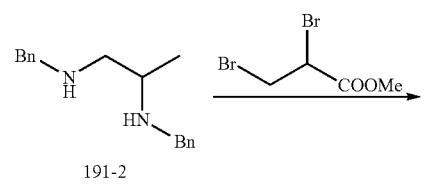

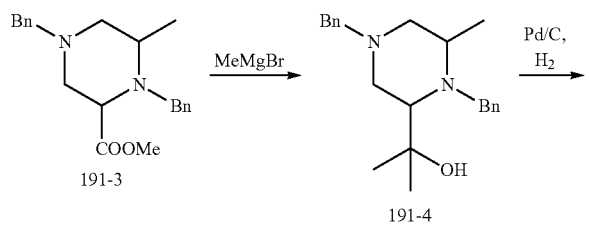

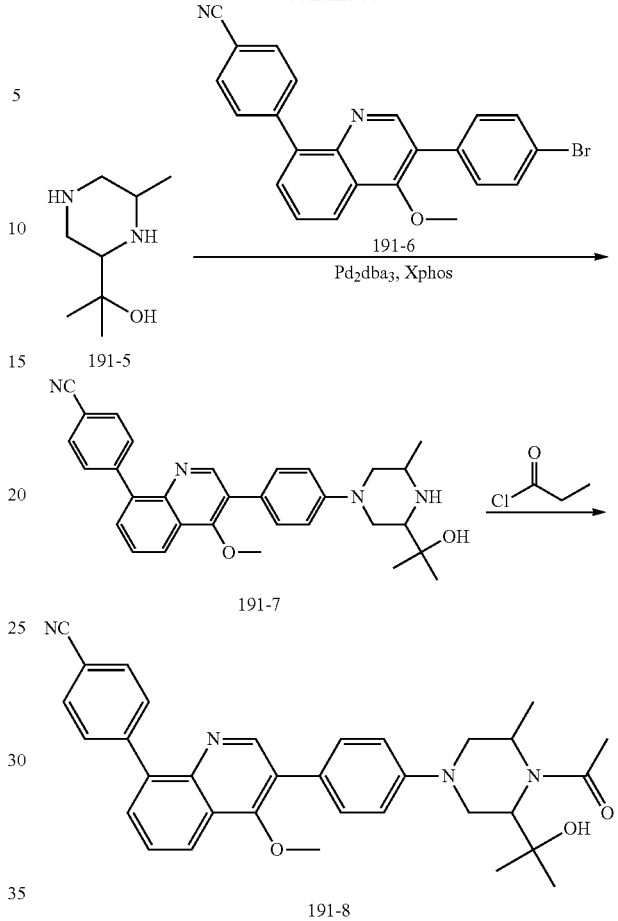

Step 1: Benzaldehyde (29 g, 270 mmol) was added into a solution of compound 191-1 (10 g, 135 mmol) in methanol (100 mL) at 0° C., the reaction mixture was stirred at room temperature for 2 h and then cooled to 0° C. again, sodium borohydride (10 g, 270 mmol) was added in portions. The mixture was stirred at room temperature for 16 h, and concentrated under reduced pressure. The residue was diluted with H$_2$O and DCM and filtrated. The organic phase was collected and washed with brines, dried over sodium sulfate and concentrated. The crude product was purified by column chromatography to deliver compound 191-2 (14 g, yield 40%) as colorless oil. MS ESI calcd for C$_{17}$H$_{22}$N$_2$ [M+H]$^+$ 255, found 255.

Step 2: DIPEA (33 mL, 239 mmol) was added into a solution of 2,3-dibromomethyl propionate (16.5 mL, 55 mmol) and compound 191-2 (14 g, 55 mmol) in toluene (50 mL), the mixture was stirred at room temperature overnight, then diluted with EtOAc and washed with brines. The organic phase was collected and concentrated. The crude product was purified by column chromatography to deliver compound 191-3 (12.5 g, yield 66%) as yellow liquid. MS ESI calcd for C$_{21}$H$_{26}$N$_2$O$_2$ [M+H]$^+$ 339, found 339.

Step 3: Methyl magnesium bromide (48 mL, 143 mmol) was added dropwise into a solution of compound 191-3 (5.6 g, 15.9 mmol) in THF (50 mL). The reaction mixture was stirred at room temperature for 1 h. The mixture was poured into saturated ammonium chloride, the aqueous phase was extracted with EtOAc. The organic phase was washed with brines, dried over sodium sulfate, concentrated under reduced pressure to deliver compound 191-4 (3.3 g, yield 61%), which was used for the next step directly. MS ESI calcd for $C_{22}H_{30}N_2O$ [M+H]$^+$ 339, found 339.

Step 4: Under hydrogen gas atmosphere (50 psi), a solution of compound 191-4 (3.3 g, 9.8 mmol) and Pd/C (330 mg) in methanol (50 mL) was stirred at room temperature for 24 h. The reaction mixture was filtrated and concentrated to deliver compound 191-5 (1.4 g, yield 82%) as light yellow oil. MS ESI calcd for $C_8H_{18}N_2O$ [M+H]$^+$ 159, found 159.

Step 5: Compound 191-7 (120 mg, yield 25%) was synthesized according to the above-mentioned method as light yellow oil. MS ESI calcd for $C_{31}H_{32}N_4O_2$ [M+H]$^+$ 493, found 493.

Step 6: The title compound (13 mg, yield 12%) was synthesized according to the above-mentioned method as white solid. $^1$H NMR (400 MHz, CDCl$_3$) δ 8.89 (s, 1H), 8.34-8.31 (m, 1H), 7.84-7.77 (m, 4H), 7.69-7.65 (m, 2H), 7.58 (d, J=8.4 Hz, 2H), 6.86 (d, J=8.4 Hz, 2H), 4.41-4.31 (m, 1H), 4.11-4.01 (m, 1H), 3.91-3.81 (m, 2H), 3.72 (s, 3H), 3.71-3.62 (m, 1H), 3.32-3.21 (m, 1H), 2.23 (s, 3H), 1.35 (d, J=7.6 Hz, 3H), 1.29 (s, 6H). MS ESI calcd for $C_{33}H_{34}N_4O_3$ [M+H]$^+$ 535, found 535.

Embodiment 192

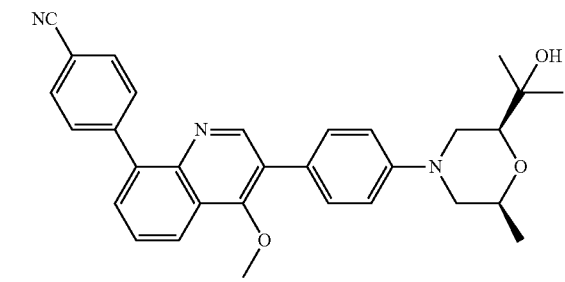 [SMILES: COc1c(-c2ccc(N3C[C@@H](C(C)(C)O)O[C@@H](C)C3)cc2)cnc2c(-c3ccc(C#N)cc3)cccc12]

4-(3-(4-((2S, 6S)-2-(2-hydroxypropan-2-yl)-6-methylmorpholino)phenyl)-4-methoxyquinolin-8-yl)benzonitrile

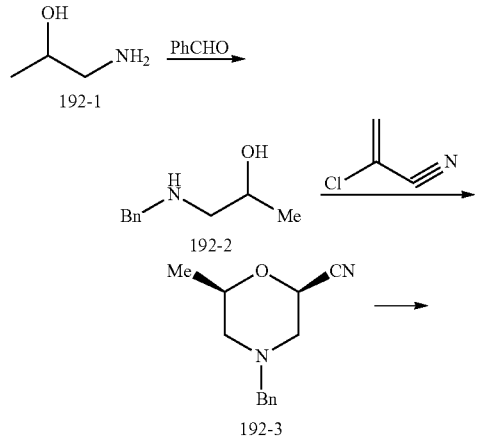

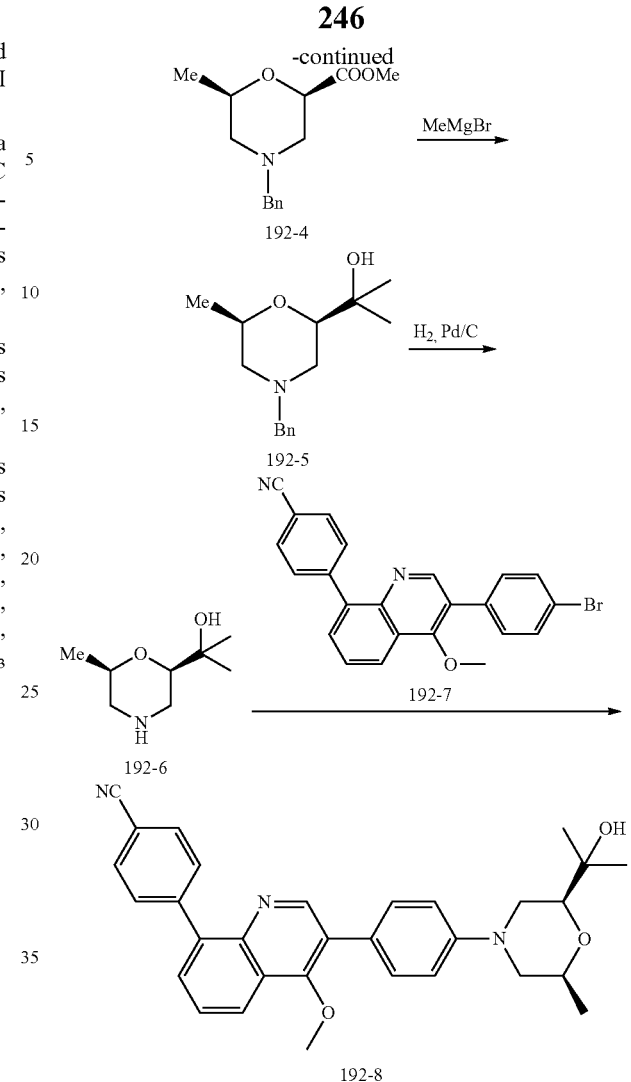

Step 1: A solution of compound 192-1 (2 g, 26.67 mmol), benzaldehyde (2.8 mL, 29 mmol) and magnesium sulfate (8 g) in DCM (70 mL) was stirred at room temperature for 16 h. The reaction mixture was filtrated, and the filtrate was concentrated to dry. The crude product was dissolved in MeOH (70 mL) and sodium borohydride (1 g, 26.6 mmol) was added, the mixture was stirred at room temperature for 5 h. The mixture was concentrated to dry and extracted with 1N diluted HCl and EtOAc. The aqueous phase was basified to pH=11 with NaOH (2M) and extracted with DCM. The organic phase was dried over anhydrous sodium sulfate, concentrated to deliver crude compound 192-2 (3.17 g, 72%), which was used for the next step without further purification. MS ESI calcd for $C_{10}H_{15}NO$ [M+H]$^+$ 166, found 166.

Step 2: A solution of compound 192-2 (15 g, 91 mmol) and 2-chloroacrylonitrile (9.5 g, 109 mmol) in THF (300 mL) was stirred at room temperature for 36 h, KO$^t$Bu (15.3 g, 136.5 mmol) was added into the reaction system, the mixture was heated to 70° C. and stirred for further 2 h. The reaction mixture was extracted with EtOAc and H$_2$O. The organic phase was concentrated, the residue was purified by column chromatography to deliver compound 192-4 (3.5 g, yield 16%) as colorless oil. MS ESI calcd for $C_{13}H_{16}N_2O$ [M+H]$^+$ 217, found 217.

Step 3: A solution of compound 192-3 (1 g, 4.63 mmol) and conc. sulfuric acid (2.5 mL) in MeOH (15 mL) was stirred at 100° C. overnight. After the reaction mixture was cooled, saturated sodium bicarbonate (20 mL) was added, then extracted with EtOAc (100 mL). The organic phase was dried over anhydrous sodium sulfate and concentrated. The crude product was purified by chromatography to deliver compound 192-4 (460 mg, yield 40%) as light yellow oil. MS ESI calcd for $C_{14}H_{19}NO_3$ [M+H]$^+$ 250, found 250.

Step 4: Methyl magnesium bromide (1.4 mL, 4.16 mmol) was added into a solution of compound 192-4 (260 mg, 1.04 mmol) in THF (4 mL) at room temperature and stirred for 1 h. The reaction mixture was quenched with saturated ammonium chloride (1 mL). The mixture was dried over anhydrous sodium sulfate and concentrated to deliver compound 192-5 (200 mg, yield 77%), which was used for the next step directly. MS ESI calcd for $C_{15}H_{23}NO_2$ [M+H]$^+$ 250, found 250.

Step 5: A solution of compound 192-5 (280 mg, 1.12 mmol) and Pd/C (100 mg) in EtOH (10 mL) was heated to 75° C. under a hydrogen gas pressure of 50 psi and stirred for 2 h. The reaction mixture was cooled to room temperature and filtrated, the filtrate was concentrated to deliver compound 192-6 (170 mg, yield 95%) as colorless oil. MS ESI calcd for $C_8H_{17}NO_2$ [M+H]$^+$ 160, found 160.

Step 6: The title compound (50 mg, yield 28%) was synthesized according to the above-mentioned method as white solid. $^1$H NMR (400 MHz, CDCl$_3$) δ ppm 8.90 (s, 1H) 8.36-8.32 (m, 1H) 7.85-7.78 (m, 4H) 7.70-7.65 (m, 2H) 7.60-7.58 (d, J=8, 2H) 7.07-7.05 (d, J=8, 2H) 3.87-3.76 (m, 1H) 3.72 (s, 3H) 3.642-3.52 (m, 3H) 2.73-2.68 (m, 1H) 2.55-2.49 (m, 2H) 1.32-1.28 (m, 9H). MS ESI calcd for $C_{31}H_{31}N_3O_3$ [M+H]$^+$ 494, found 494.

Embodiment 193

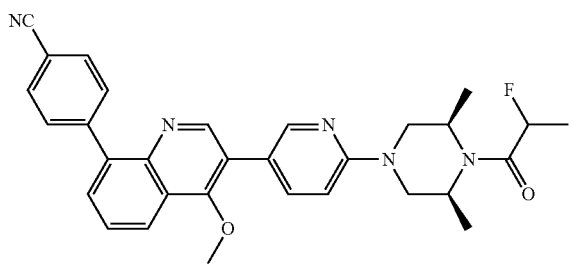 [SMILES: COc1c(-c2ccc(N3C[C@@H](C)N(C(=O)C(C)F)[C@@H](C)C3)nc2)cnc2c(-c3ccc(C#N)cc3)cccc12]

4-(3-(6-((3S, 5R)-4-(2-fluoropropanoyl)-3, 5-dimethylpiperazin-1-yl)pyridin-3-yl)-4-methoxyquinolin-8-yl)benzonitrile

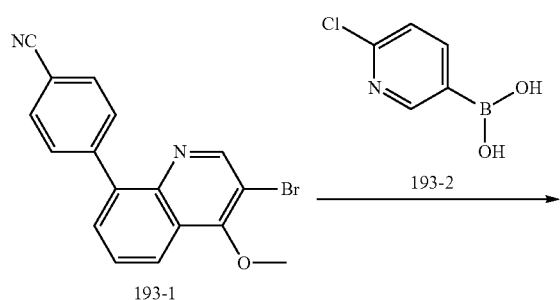

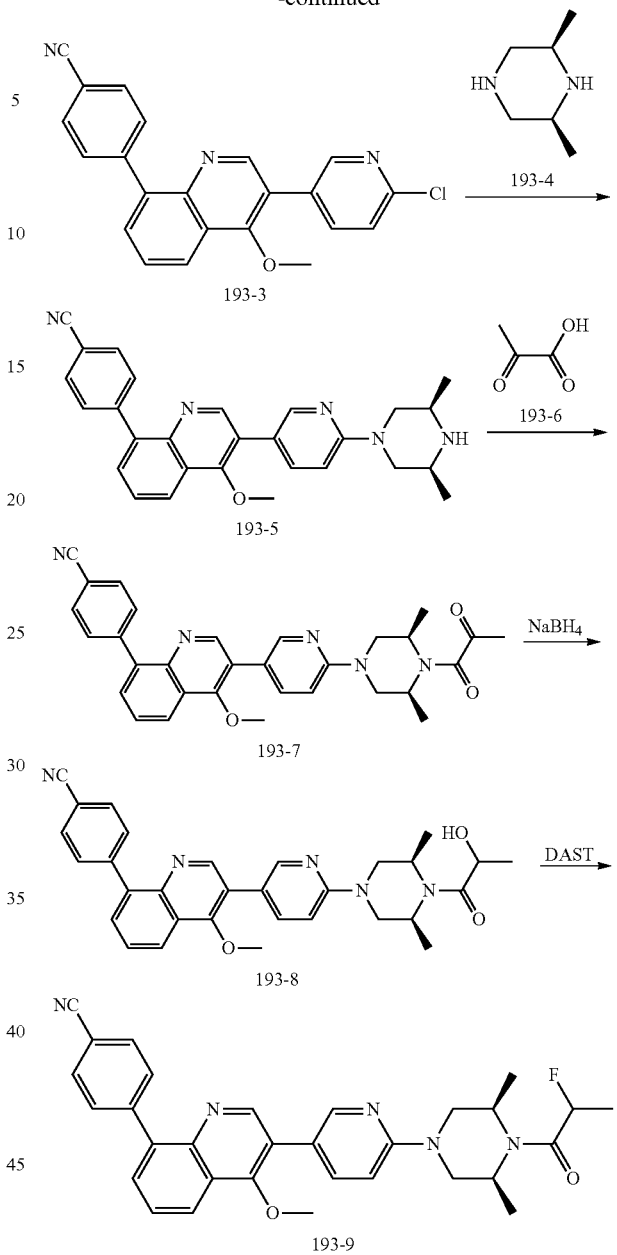

Step 1: Under nitrogen gas atmosphere, Pd (dppf)Cl$_2$ (1.7 g, 2 mmol) was added into a solution of compound 193-1 (8.0 g, 23.6 mmol), compound 193-2 (4.5 g, 28.3 mmol) and sodium carbonate (6.3 g, 59 mmol) in THF (160 mL) and H$_2$O (32 mL). The reaction mixture was heated to 80° C. and stirred for 16 h. The reaction mixture was cooled and extracted with EtOAc, the organic phase was dried over sodium sulfate and concentrated, the residue was purified by column chromatography to deliver pure compound 193-3 (8.51 g, yield 97%) as yellow solid. MS ESI calcd for $C_{22}H_{14}ClN_3O$ [M+H]$^+$ 372, found 372.

Step 2: Under nitrogen gas atmosphere, Pd$_2$(dba)$_3$ (2.1 g, 2.3 mmol) was added into a solution of compound 193-3 (8.51 g, 23 mmol), compound 193-4 (2.88 g, 25 mmol), NaO$^t$Bu (5.51 g, 57 mmol) and Xantphos (2.65 g, 4.6 mmol) in toluene (100 mL). The reaction mixture was heated to 130° C. for 16 h. The mixture was cooled, and extracted with EtOAc, the organic phase was dried over sodium sulfate and concentrated, the residue was purified by column chromatography to deliver compound 193-5 (4 g, yield 39%) as yellow solid. MS ESI calcd for $C_{28}H_{27}N_5O$ [M+H]$^+$ 450, found 450.

Step 3: Compound 193-6 (294 m g, 3.34 mmol) and pyridine (440 mg, 5.57 mmol) were added into a solution of compound 193-5 (1 g, 2.23 mmol) and HATU (1.35 g, 3.56 mmol) in DCM (15 mL), the reaction mixture was stirred at reflux overnight. The residue was extracted with EtOAc and H$_2$O, the organic phase was dried over sodium sulfate and concentrated, the crude product was purified by column chromatography to deliver compound 193-7 (226 mg, yield 20%) as light yellow solid. MS ESI calcd for $C_{31}H_{29}N_5O_3$ [M+H]$^+$ 520, found 520.

Step 4: NaBH$_4$ (33 mg, 0.87 mmol) was added into a solution of compound 193-7 (226 mg, 0.44 mmol) in THF (10 mL). The reaction mixture was stirred at room temperature for 1 h, quenched with H$_2$O (2 drops). The mixture was dried over sodium sulfate and concentrated to dry. The residue was purified by preparative HPLC to deliver compound 193-8 (220 mg, yield 97%) as white solid. $^1$H NMR (400 MHz, CDCl$_3$) δ 8.90 (s, 1H), 8.50 (d, J=4.0 Hz, 1H), 8.31 (s, 1H), 7.90-7.79 (m, 5H), 7.72-7.68 (m, 2H), 6.87-6.85 (d, J=8.0 Hz, 1H), 4.75-4.74 (m, 1H), 4.46-4.43 (m, 2H), 4.22-4.19 (m, 1H), 4.02-4.00 (m, 1H), 3.83-3.81 (m, 1H), 3.79 (s, 3H), 3.20-3.12 (m, 2H), 1.53-1.47 (m, 3H), 1.43-1.40 (m, 6H). MS ESI calcd for $C_{31}H_{31}N_5O_3$ [M+H]$^+$ 522, found 522.

Step 5: DAST (740 mg, 4.6 mmol) was added into a solution of compound 193-8 (120 mg, 0.23 mmol) in DCM (10 mL) at 0° C. The reaction mixture was stirred at room temperature for 1 h, the mixture was diluted with DCM and washed with saturated sodium bicarbonate for 3 times, the organic phase was dried and concentrated, the residue was purified by preparative TLC to deliver the title compound (41 mg, yield 33%) as white solid. $^1$H NMR (400 MHz, CDCl$_3$) δ 8.94 (s, 1H), 8.55 (s, 1H), 8.37 (d, J=8.0 Hz, 1H), 7.94-7.83 (m, 5H), 7.76-7.72 (m, 2H), 6.90 (d, J=8.4 Hz, 1H), 5.46-5.35 (m, 1H), 4.84 (brs, 1H), 4.51-4.21 (m, 3H), 3.83 (s, 3H), 3.36-3.19 (m, 2H), 1.72-1.64 (m, 3H), 1.53-1.45 (m, 6H). MS ESI calcd for $C_{31}H_{30}FN_5O_2$ [M+H]$^+$ 524, found 524.

The compounds listed in table 18 were synthesized by compound 193-5 and corresponding acids.

| Embodiment | Structure | NMR |
|---|---|---|
| 194 | [structure: 8-(4-cyanophenyl)-4-methoxyquinoline-3-yl linked to pyridine-piperazine with 2,6-dimethyl groups and CF$_2$H-C(=O) acyl] | $^1$H NMR (400 MHz, CDCl$_3$) δ 8.90 (s, 1H), 8.53-8.49 (m, 1H), 8.32 (d, J = 8.0 Hz, 1H), 7.89-7.79 (m, 5H), 7.72-7.68 (m, 2H), 6.83 (d, J = 8.0 Hz, 1H), 4.70 (s, 2H), 4.27-4.21 (m, 2H), 3.78(s, 3H), 3.35-3.20 (m, 2H), 1.95-1.85(m, 3H), 1.49(d, J = 6.4 Hz, 3H), 1.41(d, J = 6.4 Hz, 3H). MS ESI calcd for $C_{31}H_{29}F_2N_5O_2$ [M + H]$^+$ 542, found 542. |
| 195 | [structure: 8-(4-cyanophenyl)-4-methoxyquinoline-3-yl linked to pyridine-piperazine with 2,6-dimethyl groups and CH(OMe)CH$_3$-C(=O) acyl] | $^1$H NMR (400 MHz, CDCl$_3$) δ 8.90 (s, 1H), 8.50 (d, J = 4.0 Hz, 1H), 8.31 (s, 1H), 7.90-7.79 (m, 5H), 7.72-7.68 (m, 2H), 6.87-6.85 (d, J = 8.0 Hz, 1H), 4.75-4.74 (m, 1H), 4.46-4.43(m, 2H), 4.22-4.19(m, 1H), 4.02-4.00(m, 1H), 3.83-3.81(m, 1H), 3.79 (s, 3H), 3.20-3.12 (m, 2H), 1.53-1.47(m, 3H), 1.43-1.40(m, 6H). MS ESI calcd for $C_{31}H_{31}N_5O_3$ [M + H]$^+$ 522, found 522. |
| 196 | [structure: 8-(4-cyanophenyl)-4-methoxyquinoline-3-yl linked to pyridine-piperazine with 2,6-dimethyl groups and methyl carbamate] | $^1$H NMR (400 MHz, CDCl$_3$) δ 8.95 (s, 1H), 8.50 (d, J = 4.0 Hz, 1H), 8.33 (d, J = 8.0 Hz, 1H), 7.85-7.75 (m, 5H) 7.71-7.67 (m, 2H) 6.82 (d, J = 8.4 Hz, 1H), 4.40-4.37 (m, 2H), 4.23-4.20(m, 2H), 3.78 (s, 3H), 3.76 (s, 3H), 3.22-3.17(m, 2H) 1.36 (d, J = 6.8 Hz, 6H). MS ESI calcd for $C_{30}H_{29}N_5O_3$ [M + H]$^+$ 508, found 508. |
| 197 | [structure: 8-(4-cyanophenyl)-4-methoxyquinoline-3-yl linked to pyridine-piperazine with 2,6-dimethyl groups and CH$_2$CF$_3$-C(=O) acyl] | $^1$H NMR (400 MHz, CDCl$_3$) δ 8.89 (s, 1H), 8.50 (s, 1H), 8.33 (d, J = 8.0 Hz, 1H), 7.90-7.78 (m, 5H), 7.74-7.66 (m, 2H), 6.85 (d, J = 8.4 Hz, 1H), 3.79 (s, 1H), 3.21-3.16 (m, 2H), 1.43-1.26 (brs, 6 H). MS ESI calcd for $C_{31}H_{28}F_3N_5O_2$ [M + H]$^+$ 560, found 560. |

| Embodiment | Structure | NMR |
|---|---|---|
| 198 | 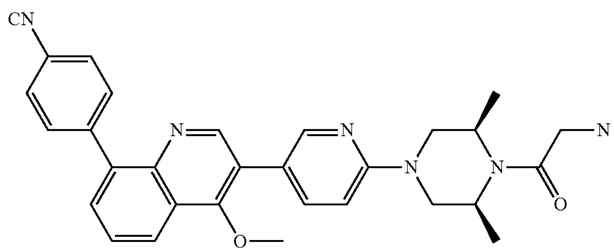 | $^1$H NMR (400 MHz, CDCl$_3$) δ 8.88 (s, 1H), 8.48 (s, 1H), 8.30 (d, J = 8.0 Hz, 1H), 7.87-7.77 (m, 5H), 7.72-7.64 (m, 2H), 6.83 (d, J = 8.4 Hz, 1H), 3.77 (s, 3H), 3.20-3.17 (m, 2H), 1.36 (brs, 6 H). MS ESI calcd for C$_{30}$H$_{30}$N$_6$O$_2$ [M + H]$^+$ 507, found 507. |
| 199 | 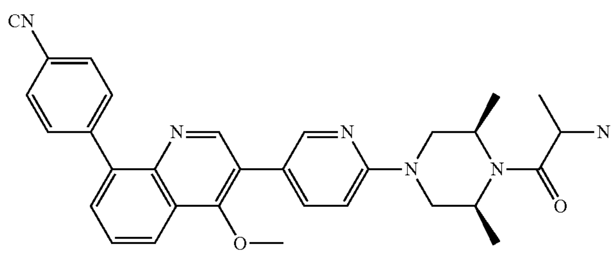 | $^1$H NMR (400 MHz, CDCl$_3$) δ 8.82 (s, 1H), 8.49 (s, 1H), 8.38 (d, J = 8.0 Hz, 1 H), 7.98 (d, J = 6.8 Hz, 1 H), 7.87-7.74 (m, 6 H), 7.11 (d, J = 8.8 Hz, 1 H), 4.65-4.30 (m, 4H), 3.81 (s, 1H), 3.25-3.16 (m, 2H), 1.56-1.47 (m, 6 H), 1.39 (d, J = 6.8 Hz, 3 H). MS ESI calcd for C$_{31}$H$_{32}$N$_6$O$_2$ [M + H]$^+$ 521, found 521. |
| 200 | 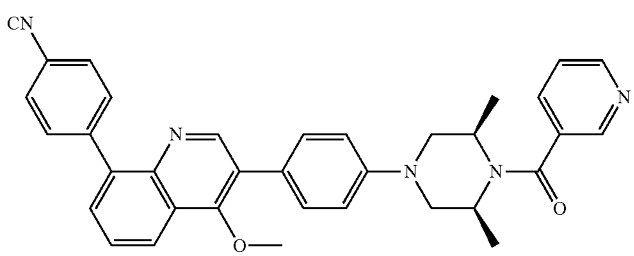 | $^1$H NMR (400 MHz, CDCl$_3$) δ 8.88 (s, 1H), 8.69 (s, 1H), 8.38 (d, J = 8.0 Hz, 1H), 7.87-7.74 (m, 5 H), 7.70-7.54 (m, 4 H), 7.45-7.40 (m, 1 H), 7.04 (d, J = 8.4 Hz, 2 H), 4.49 (brs, 2H), 3.71 (s, 3H), 3.59-3.51 (m, 2H), 3.21-3.11 (m, 2H), 1.26 (d, J = 6.8 Hz, 6 H). MS ESI calcd for C$_{35}$H$_{31}$N$_5$O$_2$ [M + H]$^+$ 554, found 554. |
| 201 | 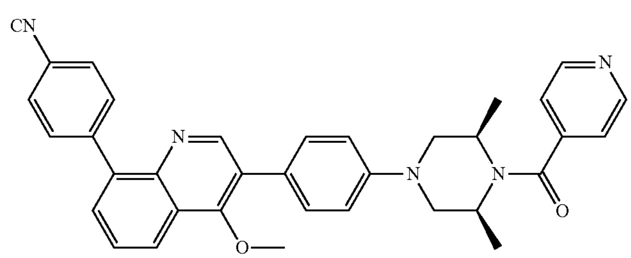 | $^1$H NMR (400 MHz, CDCl$_3$) δ 8.90 (s, 1H), 8.79-8.77 (m, 2H), 8.34 (d, J = 8.0 Hz, 1 H), 7.87-7.75 (m, 5 H), 7.70-7.55 (m, 4 H), 7.35-7.33 (m, 2 H), 7.06 (d, J = 8.4 Hz, 2 H), 3.76 (s, 3H), 3.59-3.56 (m, 2H), 3.11-3.01 (m, 2H), 1.52 (d, J = 6.8 Hz, 6 H). MS ESI Calcd for C$_{35}$H$_{31}$N$_5$O$_2$ [M + H]$^+$ 554, found 554. |
| 202 | 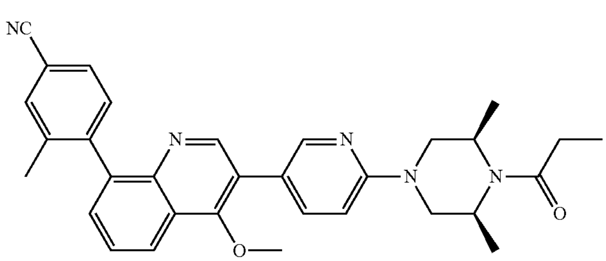 | $^1$H NMR (400 MHz, CDCl$_3$) δ 8.83 (s, 1H), 8.47 (s, 1H), 8.30-8.32 (d, J = 7.6 Hz, 1H), 7.83-7.84 (d, J = 2.0 Hz, 1H), 7.53-7.65 (m, 4H) 7.39-7.40 (d, J = 7.2 Hz, 1H) 6.81-6.83 (d, J = 8.8 Hz, 1H) 4.65-4.85 (m, 2H), 4.08-4.18 (m, 2H) 3.79(s, 3H) 3.12-3.16 (d d, J = 4.0 Hz 2H), 2.41-2.43 (m, 2H) 2.12(s, 3H) 1.37-1.38 (d, J = 6.0 Hz 6H) 1.19-1.26 (m, 3H). MS ESI calcd for C$_{32}$H$_{33}$N$_5$O$_2$ [M + H]$^+$ 520, found 520. |
| 203 | 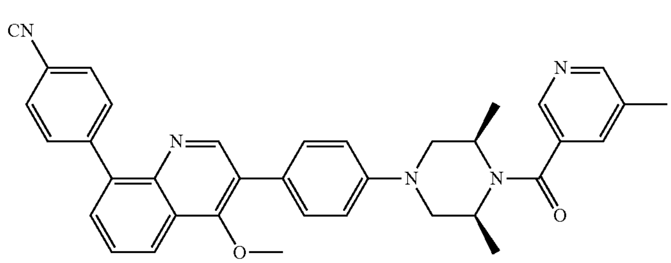 | $^1$H NMR (400 MHz, CDCl$_3$) δ 8.89 (s, 1H), 8.59-8.56 (m, 2H), 8.36 (d, J = 8.0 Hz, 1 H), 7.87-7.75 (m, 4 H), 7.70-7.58 (m, 5 H), 7.05 (d, J = 8.4 Hz, 2 H), 4.50 (brs, 2H), 3.74 (s, 3H), 3.59-3.54 (m, 2H), 3.13-3.00 (m, 2H), 2.41 (s, 3H), 1.51 (d, J = 6.8 Hz, 6 H). MS ESI Calcd for C$_{36}$H$_{33}$N$_5$O$_2$ [M + H]$^+$ 568, found 568. |

| Embodiment | Structure | NMR |
|---|---|---|
| 204 | 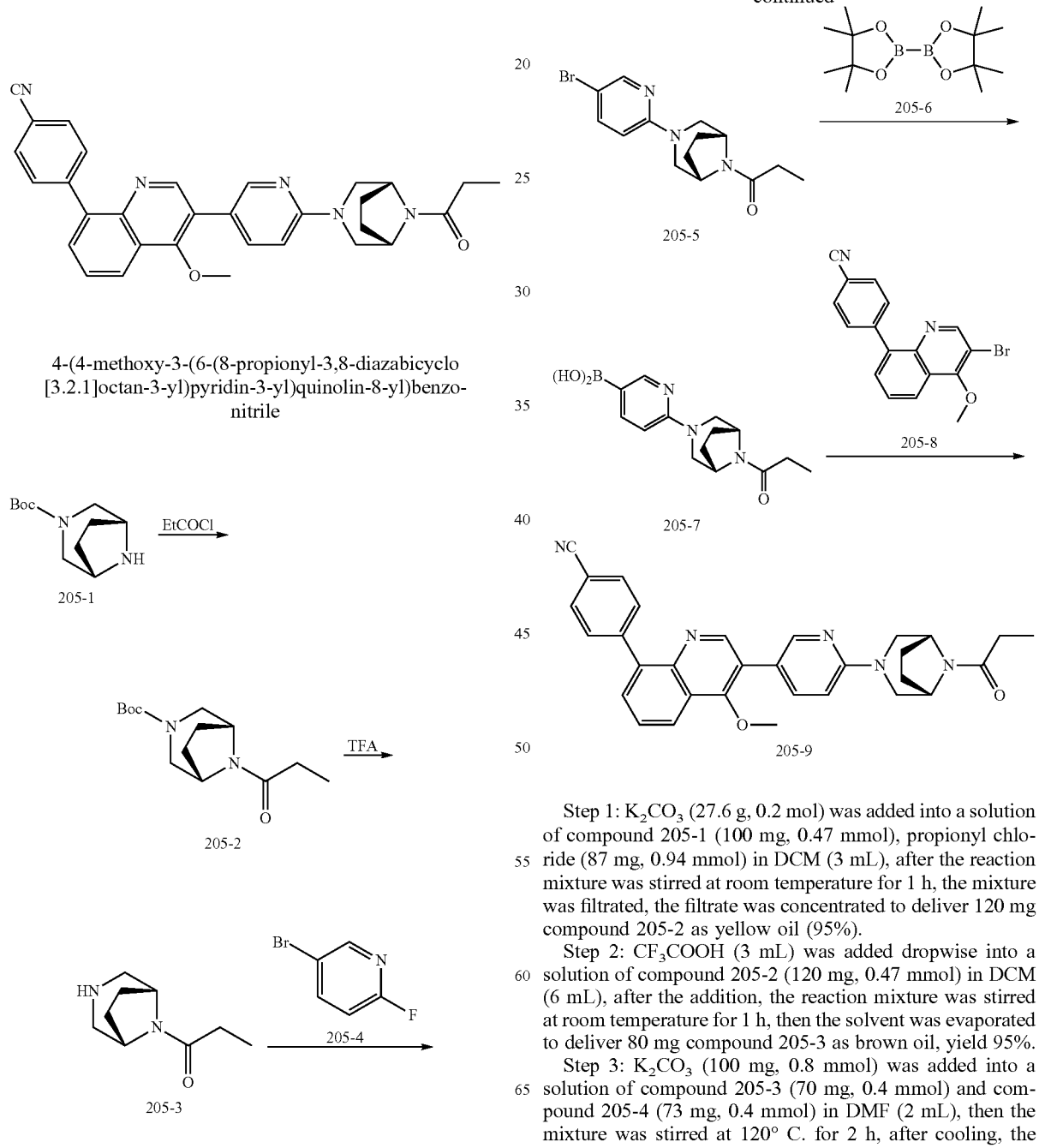 | $^1$H NMR (400 MHz, CDCl$_3$) δ 8.89 (s, 1H), 8.48 (d, J = 8.0 Hz, 1H), 8.30-8.33 (m, 1H), 7.78-7.85 (m, 5H), 7.67-7.71 (m, 2H), 6.83 (d, J = 8.8 Hz, 1H), 4.85-4.80 (m, 2H), 4.15-4.10 (m, 2H), 3.78 (s, 3H), 3.13-3.17 (m, 2H), 2.46-2.41 (m, 2H), 1.38 (s, 6H), 1.21 (d, J = 7.4 Hz, 3H). MS ESI calcd for C$_{31}$H$_{31}$N$_5$O$_2$ [M + H]$^+$ 506, found 506. |

Embodiment 205

4-(4-methoxy-3-(6-(8-propionyl-3,8-diazabicyclo[3.2.1]octan-3-yl)pyridin-3-yl)quinolin-8-yl)benzonitrile Step 1: K$_2$CO$_3$ (27.6 g, 0.2 mol) was added into a solution of compound 205-1 (100 mg, 0.47 mmol), propionyl chloride (87 mg, 0.94 mmol) in DCM (3 mL), after the reaction mixture was stirred at room temperature for 1 h, the mixture was filtrated, the filtrate was concentrated to deliver 120 mg compound 205-2 as yellow oil (95%).

Step 2: CF$_3$COOH (3 mL) was added dropwise into a solution of compound 205-2 (120 mg, 0.47 mmol) in DCM (6 mL), after the addition, the reaction mixture was stirred at room temperature for 1 h, then the solvent was evaporated to deliver 80 mg compound 205-3 as brown oil, yield 95%.

Step 3: K$_2$CO$_3$ (100 mg, 0.8 mmol) was added into a solution of compound 205-3 (70 mg, 0.4 mmol) and compound 205-4 (73 mg, 0.4 mmol) in DMF (2 mL), then the mixture was stirred at 120° C. for 2 h, after cooling, the reaction mixture was poured into H₂O, and extracted with EtOAc (10 mL), the extraction liquid was washed with brines, dried over anhydrous sodium sulfate and concentrated under vacuum to deliver 40 mg compound 205-5 as white solid, yield 31%. MS ESI calcd for $C_{14}H_{18}BrN_3O$ [M+H]⁺ 325, found 325.

Step 4: Compound 205-5 (33 mg, 0.1 mmol), compound 205-6 (50 mg, 0.2 mmol), Pd(dppf)Cl₂ (8 mg, 0.01 mmol) and potassium acetate (20 mg, 0.2 mmol) were added into 1,4-dioxane (2 mL), under nitrogen gas atmosphere, the reaction mixture was stirred at 110° C. for 2 h. The mixture was filtered with diatomite, the filtrate was concentrated under vacuum. The residue was purified by column chromatography to deliver compound 205-7 (20 mg, yield 95%) as white solid. MS ESI calcd for $C_{14}H_{20}BN_3O_3$ [M+H]⁺ 290, found 290.

Step 5: The title compound (10 mg, yield 20%) was synthesized according to the above-mentioned method as white solid. ¹H NMR (400 MHz, CDCl₃) δ 8.89 (s, 1H), 8.49-8.50 (d, J=2.4 Hz, 1H), 8.31-8.33 (m, 1H) 7.78-7.86 (m, 5H) 7.68-7.72 (m, 2H) 6.73-6.75 (d, J=8.8 Hz, 1H) 4.93-4.95 (d, J=5.2 Hz, 2H), 4.36-4.38 (d, J=6.0 Hz, 2H), 4.24-4.27 (m, 2H) 3.92-3.94 (m, 2H) 3.78 (s, 3H) 3.12-3.25 (d d, J=10.8 Hz 2H) 2.38-2.47 (m, 2H) 1.95-2.03 (m, 4H) 1.22-1.25 (t, J=14.8 Hz 3H). MS ESI calcd for $C_{31}H_{29}N_5O_2$ [M+H]⁺ 504, found 504.

Embodiment 206

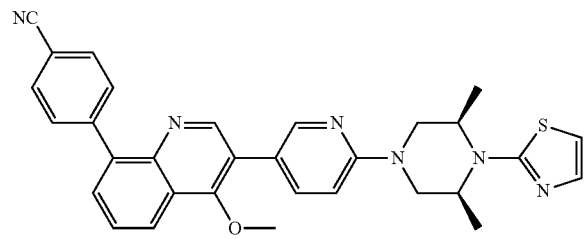 [SMILES: COc1c(-c2ccc(N3C[C@@H](C)N(c4nccs4)[C@@H](C)C3)nc2)cnc2c(-c3ccc(C#N)cc3)cccc12]

4-(3-(6-((3S,5R)-3,5-dimethyl-4-(thiazol-2-yl)piper-azin-1-yl)pyridin-3-yl)-4-methoxyquinolin-8-yl)benzonitrile

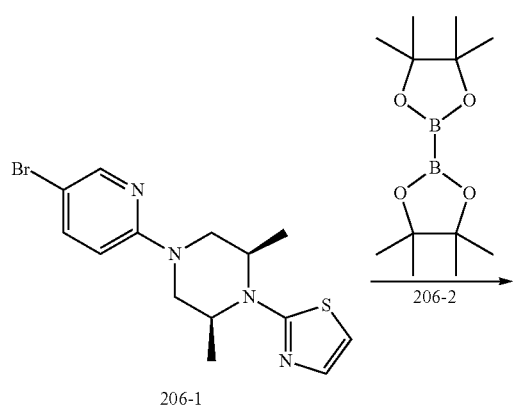

206-1

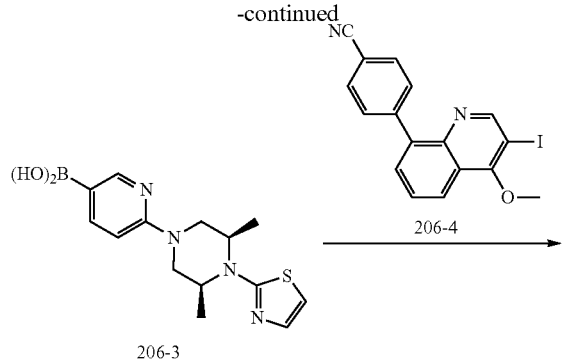

206-3

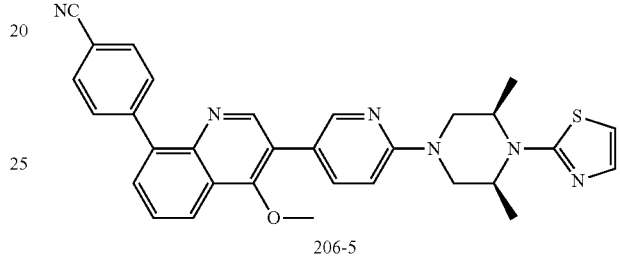

206-5

Step 1: Under nitrogen gas atmosphere, Pd(dppf)₂Cl₂ (50 mg, 0.07 mmol) and KOAc (150 mg, 1.42 mmol) were added into a solution of compound 206-1 (250 mg, 0.71 mmol) and compound 206-2 (216 mg, 0.85 mmol) in dioxane (5 mL). The reaction mixture was stirred at 120° C. for 4 h, and used for the next step directly.

Step 2: The title compound (30 mg, yield 12%) was synthesized according to the above-mentioned method as white solid. ¹H NMR (400 MHz, CDCl₃) δ 8.86 (s, 1H), 8.49 (s, 1H), 8.33 (d, J=8.0 Hz, 1H), 7.85-7.55 (m, 7H), 7.23 (d, J=4.0 Hz, 1H), 6.87 (d, J=8.8 Hz, 1H), 6.57 (d, J=4.0 Hz, 1H), 4.33-4.28 (m, 4H), 3.78 (s, 3H), 3.35-3.30 (m, 2H), 1.43 (d, J=6.8 Hz, 6H). MS ESI calcd for $C_{31}H_{28}N_6OS$ [M+H]⁺ 533, found 533.

Embodiment 207

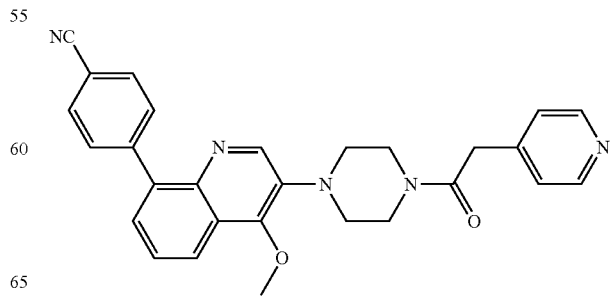

4-(4-methoxy-3-(4-(2-(pyridin-4-yl)acetyl)piperazin-1-yl)quinolin-8-yl)benzonitrile

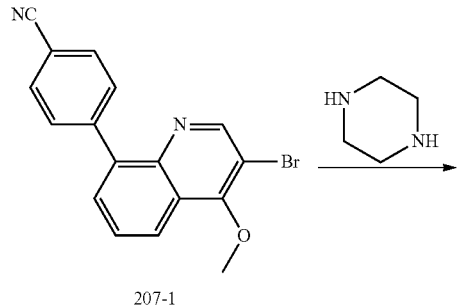

207-1

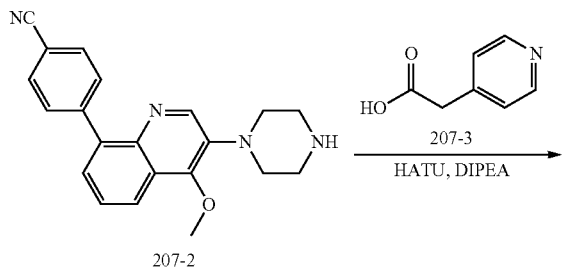

207-2

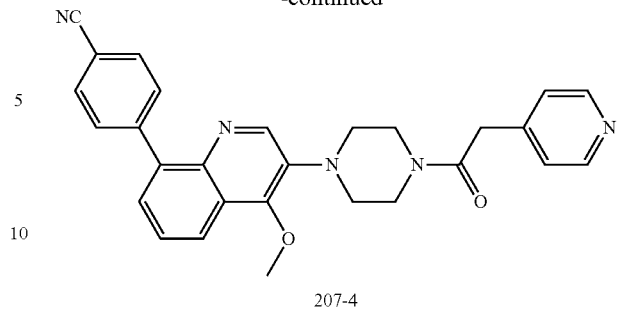

207-4

Step 1: Under nitrogen gas atmosphere, sodium tert-butoxide (900 mg, 9 mmol), Pd$_2$(dba)$_3$ (270 mg, 0.3 mmol) and Xantphos (350 mg, 0.6 mmol) were added into a solution of compound 207-1 (1 g, 3 mmol) and piperazine (270 mg, 3 mmol) in toluene (15 mL). The reaction mixture was stirred at 130° C. for 3 h. The mixture was concentrated under vacuum, the crude product was purified by column chromatography (EtOAc/methanol=1:1) to deliver compound 207-2 (420 mg, yield 42%) as yellow solid. MS ESI calcd for C$_{21}$H$_2$ON$_4$O [M+H]$^+$ 345, found 345.

Step 2: DIPEA (260 mg, 2 mmol) and HATU (380 mg, 1 mmol) were added into a solution of compound 207-2 (69 mg, 0.2 mmol), compound 207-3 (144 mg, 1 mmol) in DMF. The mixture was stirred at room temperature for 30 min, purified by preparative HPLC to deliver the title compound (20 mg, 21%) as white solid. $^1$H NMR (400 MHz, CDCl$_3$) δ 8.68 (s, 1H), 8.59 (d, J=8.0 Hz, 2H), 7.75-7.73 (m, 4H), 7.61-7.59 (m, 2H), 7.24-7.22 (m, 2H), 4.09 (s, 3H), 3.88-3.85 (m, 2H), 3.80 (s, 2H), 3.68-3.65 (m, 2H), 3.28-3.25 (m, 2H), 3.18-3.15 (m, 2H). MS ESI calcd for C$_{28}$H$_{25}$N$_5$O$_2$ [M+H]$^+$ 464, found 464.

The compounds listed in table 19 were synthesized by compound 207-2 and corresponding acids.

| Embodiment | Structure | NMR |
|---|---|---|
| 208 | (structure) | $^1$H NMR (400 MHz, CDCl$_3$) δ 8.74 (s, 1H), 8.20-8.17 (m, 1H), 7.76-7.73 (m, 4H), 7.58-7.54 (m, 2H), 4.11 (s, 3 H), 3.23 (t, J = 4.4Hz, 4H), 3.10 (t, J = 4.4Hz, 4H). MS ESI Calcd for C$_{21}$H$_{20}$N$_4$O [M + H]$^+$ 345, found 345. |
| 209 | (structure) | $^1$H NMR (400 MHz, CDCl$_3$) δ 8.73 (s, 1H), 8.51 (d, J = 8.0 Hz, 2H), 8.38 (d, J = 8.0 Hz, 1H), 8.01 (d, J = 8.0 Hz, 2H), 7.89 (d, J = 8.4 Hz, 2H), 7.80-7.74 (m, 4H), 4.36 (s, 3 H), 3.91 (t, J = 4.4 Hz, 4 H), 3.37 (t, J = 4.4 Hz, 4 H). MS ESI calcd for C$_{27}$H$_{24}$N$_6$O2 [M + H]$^+$ 465, found 465. |

| Embodiment | Structure | NMR |
|---|---|---|
| 210 | 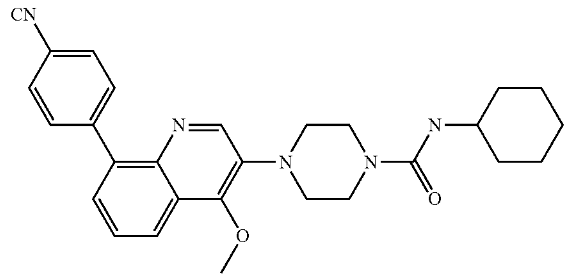 | $^1$H NMR (400 MHz, MeOD) δ 8.67 (s, 1H), 8.44-8.42 (m, 1H), 7.92 (d, J = 8.0 Hz, 2H), 7.84 (d, J = 8.0 Hz, 2H), 7.81-7.74 (m, 2H), 4.40 (s, 3 H), 3.66 (t, J = 4.4 Hz, 4 H), 3.29 (t, J = 4.4 Hz, 4 H), 1.97-1.91 (m, 2 H), 1.76-1.69 (m, 2 H), 1.60-1.50 (m, 1H), 0.91-0.67(m, 6 H). MS ESI calcd for $C_{28}H_{31}N_5O_2$ [M + H]$^+$ 470, found 470. |
| 211 | 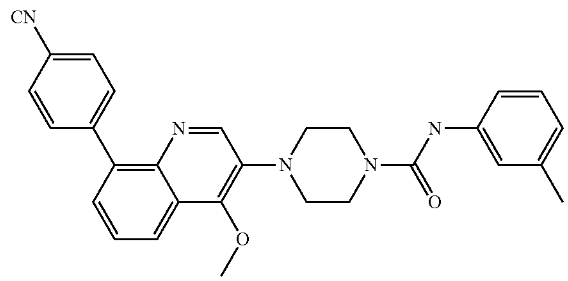 | $^1$H NMR (400 MHz, MeOD) δ 8.74 (s, 1H), 8.54-8.52 (m, 1H), 8.00 (d, J = 8.0 Hz, 2H), 7.92 (d, J = 8.0 Hz, 2H), 7.81-7.74 (m, 2H), 7.23 (s, 1H), 7.17 (d, J = 8.4 Hz, 2H), 6.91-6.88 (m, 1H), 4.52 (s, 3 H), 3.84 (t, J = 4.4 Hz, 4 H), 3.29 (t, J = 4.4 Hz, 4 H), 2.32(s, 3 H). MS ESI calcd for $C_{29}H_{27}N_5O_2$ [M + H]$^+$ 478, found 478. |
| 212 | 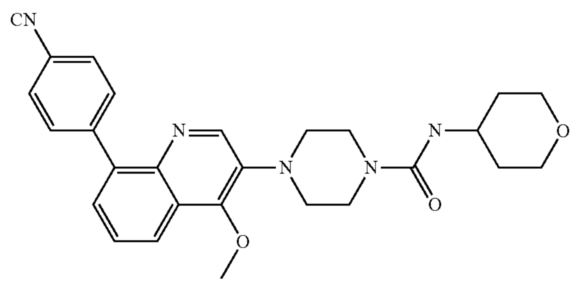 | $^1$H NMR (400 MHz, CDCl$_3$) δ 8.72 (s, 1H), 8.21 (d, J = 8.0 Hz, 2H), 7.78-7.73 (m, 4H), 7.59-7.53 (m, 2H), 4.38-4.36 (m, 1H), 4.09(s, 3H), 3.98-3.85(m, 3 H), 3.65-3.55(m, 6 H), 3.39-3.30(m, 4 H), 1.97-1.94(m, 2 H), 1.47-1.44(m, 2 H). MS ESI calcd for $C_{27}H_{29}N_5O_3$ [M + H]$^+$ 472, found 472. |
| 213 | 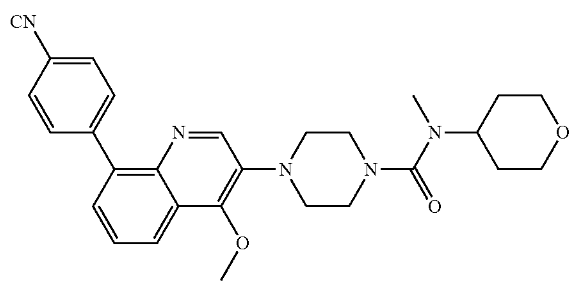 | $^1$H NMR (400 MHz, CDCl$_3$) δ 8.67 (s, 1H), 8.16 (d, J = 8.0 Hz, 2H), 7.73-7.70 (m, 4H), 7.57-7.51 (m, 2H), 4.01 (s, 3H), 3.99-3.89 (m, 3 H), 3.47-3.41 (m, 6 H), 3.30-3.27 (m, 4 H), 3.22 (s, 3H), 1.85-1.77 (m, 2 H), 1.67-1.54 (m, 2 H). MS ESI calcd for $C_{28}H_{31}N_5O_3$ [M + H]$^+$ 486, found 486. |
| 214 | 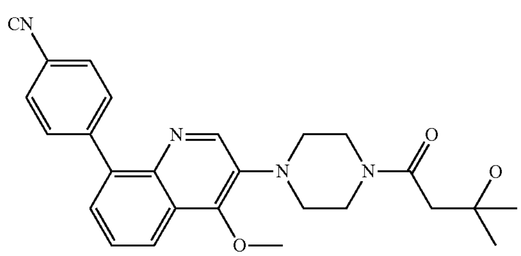 | $^1$H NMR (400 MHz, CDCl$_3$) δ 8.70 (s, 1H), 8.20-8.17 (m, 1H), 7.76-7.70 (m, 4H), 7.59-7.56 (m, 2H), 5.02 (brs, 1H), 4.14 (s, 3 H), 3.87-3.85 (m, 2H), 3.76-3.68 (m, 2 H), 3.27-3.241 (m, 4 H), 2.51 (s, 2H), 1.37 (s, 6H). MS ESI calcd for $C_{26}H_{28}N_4O_3$ [M + H]$^+$ 445, found 445. |

-continued

| Embodiment | Structure | NMR |
|---|---|---|
| 215 | 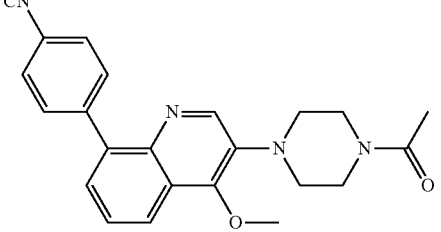 | $^1$H NMR (400 MHz, CDCl$_3$) δ 8.70 (s, 1H), 8.21-8.18 (m, 1H), 7.78-7.74 (m, 4H), 7.59-7.56 (m, 2H), 4.11 (s, 3 H), 3.85-3.83 (m, 2H), 3.69-3.67 (m, 2H), 3.29-3.25 (m, 4H), 2.16 (s, 2 H). MS ESI calcd for C$_{23}$H$_{22}$N$_4$O$_2$ [M + H]$^+$ 387, found 387. |
| 216 | 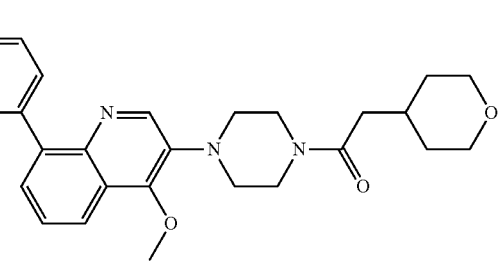 | $^1$H NMR (400 MHz, CDCl$_3$) δ 8.65 (s, 1H), 8.11-8.16 (m, 1H), 7.52-7.68(m, 4H), 7.52-7.56(m, 2H), 4.06(s, 3H), 3.88-3.91 (m, 2H),3.80 (s, 2H), 3.65 (s, 2H), 2.25-2.27 (m, 2H), 2.05-2.07(m, 1H),1.63-1.66 (m, 2H), 1.27-1.34(m,2H). MS ESI calcd for C$_{28}$H$_{30}$N$_4$O$_3$ [M + H]$^+$ 471, found 471. |

Embodiment 217

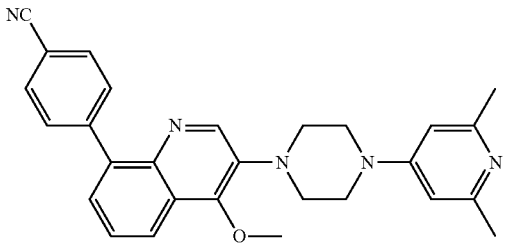 [SMILES: COc1c(N2CCN(c3cc(C)nc(C)c3)CC2)cnc2c(-c3ccc(C#N)cc3)cccc12]

4-(3-(4-(2,6-dimethylpyridin-4-yl)piperazin-1-yl)-4-methoxyquinolin-8-yl)benzonitrile

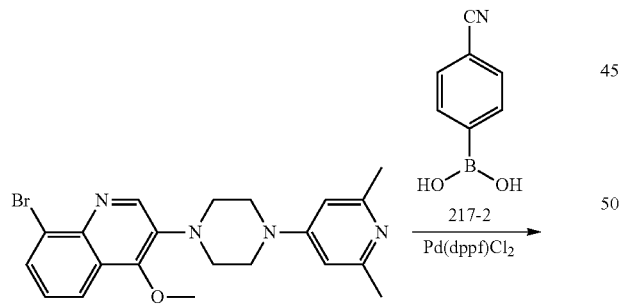

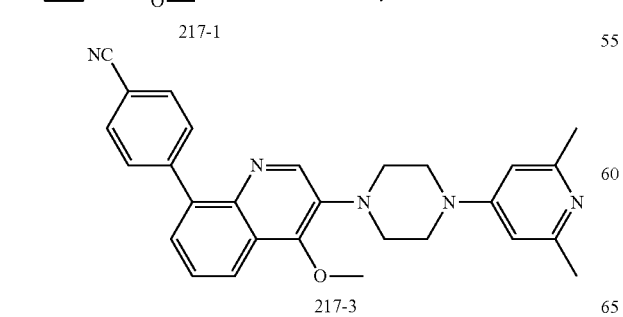

Compound 217-1 (490 mg, 1.1 mmol), compound 217-2 (253 mg, 1.7 mmol), Pd(dppf)Cl$_2$ (81 mg, 0.11 mmol) and Na$_2$CO$_3$ (233 mg, 2.2 mmol) were added into THF/H$_2$O (10:1, 11 mL), under nitrogen gas atmosphere, the mixture was stirred at 80° C. overnight. The mixture was filtrated with diatomite, the filtrate was washed with H$_2$O (50 mL) and extracted with EtOAc (100 mL), the extraction liquid was washed with brines and dried over anhydrous sodium sulfate and concentrated under vacuum. The residue was purified by preparative HPLC to deliver the title compound (200 mg, yield 45%) as white solid. $^1$H NMR (400 MHz, CDCl$_3$) δ 8.93 (s, 1H), 8.31 (d, J=8.0 Hz, 1H), 7.76-7.74 (m, 6H), 7.48-7.38 (m, 1H), 6.60 (s, 2H), 4.27 (s, 3H), 3.83 (s, 4H), 3.41 (s, 4H), 2.51 (s, 6H). MS ESI calcd for C$_{28}$H$_{27}$N$_5$O [M+H]$^+$ 450, found 450.

Embodiment 218

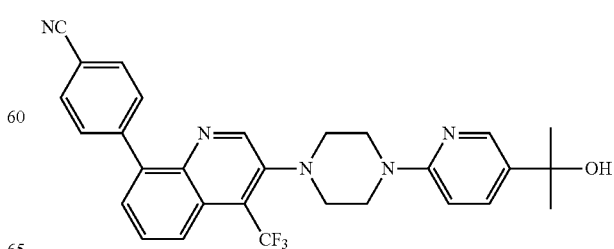

4-(3-(4-(5-(2-hydroxypropan-2-yl)pyridin-2-yl)piperazin-1-yl)-4-(trifluoromethyl) quinolin-8-yl)benzonitrile

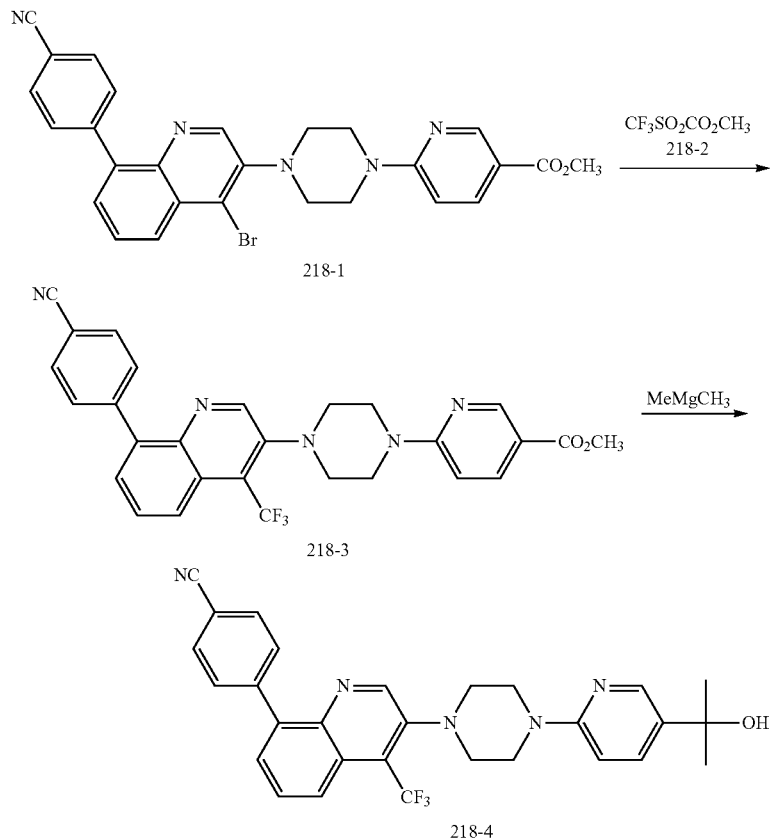

Step 1: CuI (155 mg, 0.82 mmol) and KF (32 mg, 0.55 mmol) were added into a solution of compound 218-1 (300 mg, 0.55 mmol) and compound 218-2 (210 mg, 1.1 mmol) in DMF (10 mL). The suspension was stirred at 110° C. for 3 h, then poured into $H_2O$, extracted with EtOAc, dried over sodium sulfate and concentrated. The crude product was purified by column chromatography to deliver compound 218-3 as yellow solid (200 mg, yield 70%). MS ESI calcd for $C_{28}H_{22}F_3N_5O_2$ [M+H]$^+$ 518, found 518.

Step 2: MeMgBr solution (3 M, 0.13 mL, 0.38 mmol) was added into a solution of compound 218-3 (200 mg, 0.38 mmol) in THF (20 mL) at 0° C. The mixture was stirred at 0° C. for 2 h, then poured into saturated ammonium chloride, extracted with EtOAc, dried over sodium sulfate and concentrated. The crude product was purified by preparative HPLC to deliver the title compound (30 mg, yield 15%) as yellow solid. $^1$H NMR (400 MHz, CDCl3) δ 8.96 (s, 1H), 8.36 (s, 1H), 8.22 (d, J=8.0 Hz, 1H), 7.75-7.53 (m, 7H), 6.75-6.70 (m, 1H), 3.77 (t, J=4.4 Hz, 4H), 3.40 (t, J=4.4 Hz, 4H), 1.56 (s, 6H). MS ESI calcd for $C_{29}H_{26}F_3N_5O$ [M+H]$^+$ 518, found 518.

Embodiment 219

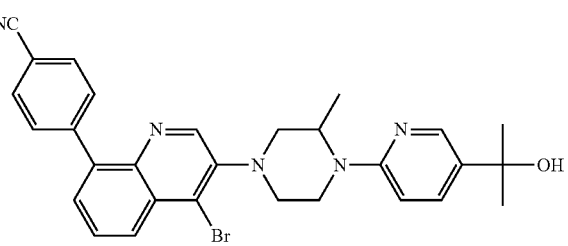

4-(4-bromo-3-(4-(5-(2-hydroxypropan-2-yl)pyridin-2-yl)-3-methylpiperazin-1-yl) quinolin-8-yl)benzonitrile

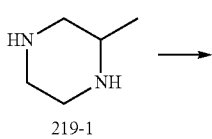

219-1

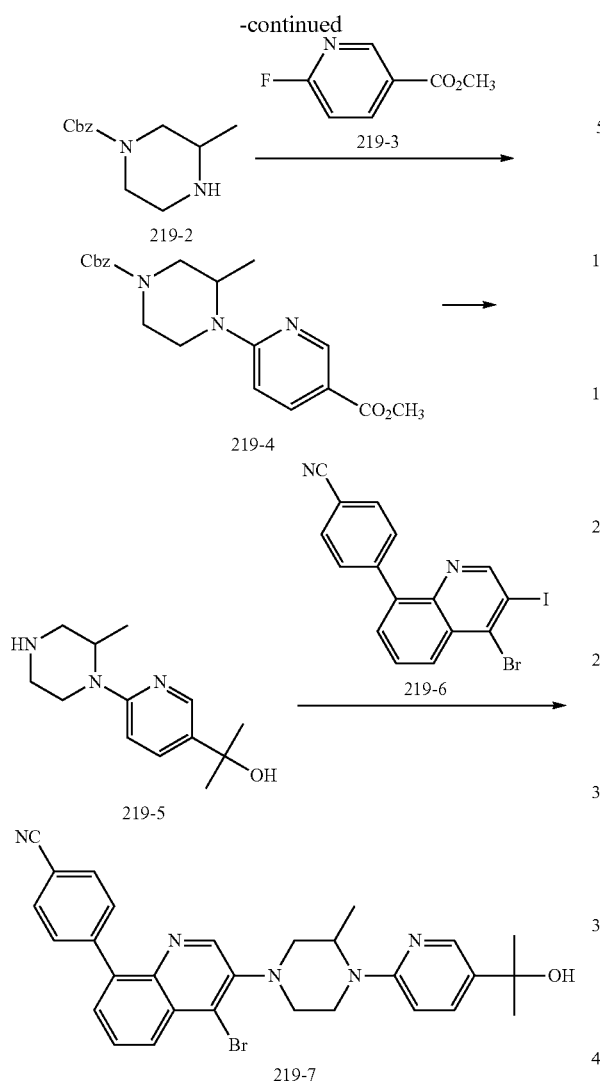

Step 4: The title compound (120 mg, yield 23%) was synthesized according to the above-mentioned method as white solid. $^1$H NMR (400 MHz, CDCl$_3$) δ 8.74 (s, 1H), 8.39-8.34 (m, 2H), 7.76-7.63 (m, 5H), 6.67-6.61 (m, 1H), 4.65 (brs, 1H), 4.22-4.19 (m, 1H), 3.62-3.32 (m, 4H), 3.20-3.01 (m, 4H), 1.60 (s, 6H), 1.47 (d, J=6.4 Hz, 3H). MS ESI calcd for C$_{29}$H$_{28}$BrN$_5$O [M+H]$^+$ 542, found 542.

Embodiment 220

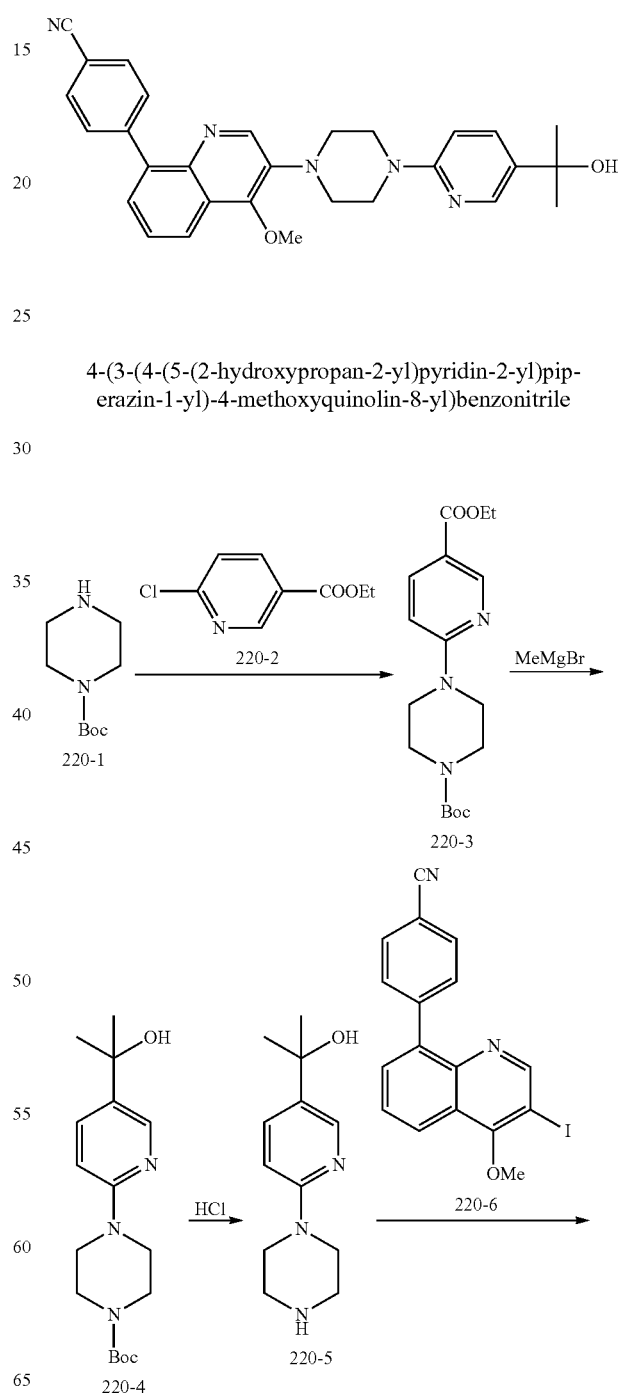

4-(3-(4-(5-(2-hydroxypropan-2-yl)pyridin-2-yl)piperazin-1-yl)-4-methoxyquinolin-8-yl)benzonitrile Step 1: CbzCl (17 g, 0.1 mol) was added into a solution of compound 219-1 (30 g, 0.3 mol) and DIPEA (40 g, 0.3 mol) in DCM (200 mL) at 0° C., then the mixture was stirred at room temperature for 3 h and the solvent was removed, the crude product was purified by column chromatography to deliver compound 2 (11 g, yield 47%) as yellow oil. MS ESI calcd for C$_{13}$H$_{18}$N$_2$O$_2$ [M+H]$^+$ 235, found 235.

Step 2: K$_2$CO$_3$ (4 g, 0.029 mol) was added into a solution of compound 219-2 (2.25 g, 14.5 mmol) and compound 219-3 (3.41 g, 14.5 mmol) in DMF (10 mL). The mixture was stirred at 160° C. for 4 h, then poured into H$_2$O. The mixture was extracted with EtOAc, dried over anhydrous sodium sulfate and concentrated, the crude product was purified by column chromatography to deliver compound 219-4 (2.8 g, yield 52%). MS ESI calcd for C$_{20}$H$_{23}$N$_3$O$_4$ [M+H]$^+$ 370, found 370.

Step 3: MeMgBr solution (3.3 mL, 11 mmol) was added slowly into a solution of compound 219-4 (370 mg, 1 mmol) in THF (10 mL) at 0° C. The mixture was stirred at 0° C. for 1 h, then heated to 80° C. and stirred for 2 h, then poured into a saturated ammonium chloride solution, the mixture was extracted with EtOAc, dried over anhydrous sodium sulfate and concentrated to deliver compound 219-5 (100 mg, yield 42%) as white solid. MS ESI calcd for C$_{13}$H$_{21}$N$_3$O [M+H]$^+$ 236, found 236.

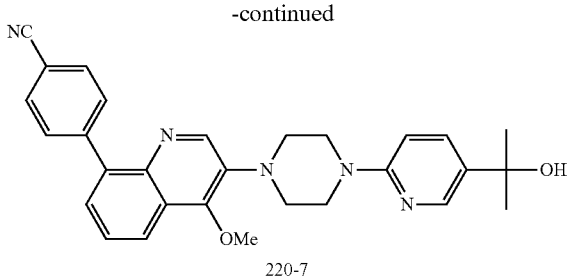

220-7

Step 1: A solution of compound 220-1 (5 g, 36.9 mmol), compound 220-2 (5.34 g, 28.8 mmol) and DIPEA (7 mL, 40 mmol) in DME (30 mL) was heated to 130° C. overnight in an autoclave. The mixture was diluted with EtOAc (200 mL), washed with 10% NaOH aqueous solution twice, citric acid and brines once respectively. The organic phase was dried over sodium sulfate and concentrated, the crude product was purified by silica gel column chromatography to deliver compound 220-3 (7.7 g, yield 85%) as yellow solid. $^1$H NMR (400 MHz, CDCl$_3$) δ 8.81 (s, 1H) 8.04 (d, J=12.0 Hz, 1H) 6.59 (d, J=8.0 Hz, 1H) 4.37-4.31 (m, 2H) 3.70-3.67 (m, 4H) 3.56-3.54 (m, 4H) 1.49 (s, 9H) 1.39-1.36 (m, 3H). MS ESI calcd for $C_{17}H_{25}N_3O_4$ [M+H]$^+$ 336, found 336.

Step 2: MeMgBr solution (24 mL, 71.6 mmol) was added dropwise into a solution of compound 220-3 (6 g, 17.9 mmol) in THF (80 mL) and the mixture was stirred at room temperature for 3 h. The reaction mixture was quenched with saturated ammonium chloride (10 mL) and extracted with EtOAc (200 mL). The organic phase was dried over sodium sulfate and concentrated. The crude product was purified by column chromatography to deliver pure compound 220-4 (4.3 g, yield 74%) as yellow solid. $^1$H NMR (400 MHz, CDCl$_3$) δ 8.30 (s, 1H) 7.68-7.60 (m, 1H) 6.64 (d, J=8.0 Hz, 1H) 3.54-3.52 (m, 8H) 1.57 (s, 6H) 1.49 (s, 9H). MS ESI calcd for $C_{17}H_{27}N_3O_3$ [M+H]$^+$ 322, found 322.

Step 3: CF$_3$COOH (15 mL) was added into a solution of compound 220-4 (3 g, 9.33 mmol) in DCM (30 mL). Then the mixture was stirred at room temperature for 30 min. NaOH (6 M) was added to basify the mixture to pH=9, then the mixture was extracted with CHCl$_3$ for 3 times. The combined organic phase was dried over sodium sulfate and concentrated. The crude product was purified by column chromatography to deliver compound 220-5 (1.6 g, yield 75%) as light yellow solid. $^1$H NMR (400 MHz, CDCl$_3$) δ 8.22 (s, 1H) 7.71-7.68 (m, 1H) 6.80-6.75 (m, 1H) 3.47-3.40 (m, 4H) 2.94-2.88 (m, 4H), 1.51 (s, 6H). MS ESI calcd for $C_{12}H_{19}N_3O$ [M+H]$^+$ 222, found 222.

Step 4: The title compound (21 mg, yield 11%) was synthesized according to the above-mentioned method as white solid. $^1$H NMR (400 MHz, CDCl$_3$) δ 8.79 (s, 1H) 8.36-8.35 (m, 1H) 8.24-8.22 (m, 1H) 7.81-7.78 (m, 4H) 7.76-7.70 (m, 1H) 7.60-7.59 (m, 2H) 6.75-6.73 (m, 1H) 4.16 (s, 3H) 3.78-3.76 (m, 4H) 3.42-3.39 (m, 4H) 1.67 (s, 1H) 1.60 (s, 6H). MS ESI calcd for $C_{29}H_{29}N_5O_2$ [M+H]$^+$ 480, found 480.

The compounds listed in table 20 were synthesized by compound 220-6 and corresponding amines.

| Embodiment | Structure | NMR |
|---|---|---|
| 221 | 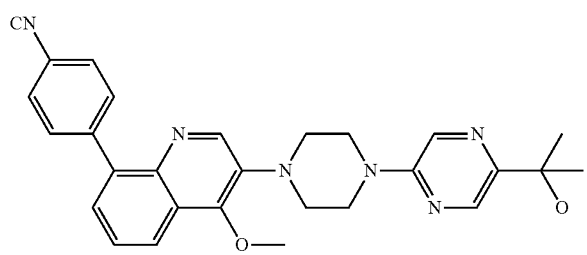 | $^1$H NMR (400 MHz, CDCl$_3$) δ 9.05 (s, 1H), 8.81 (s, 1H), 8.43 (d, J = 8.0 Hz, 1H), 8.16 (s, 1H), 7.81-7.64 (m, 6H), 4.32 (s, 3 H), 4.01 (s, 4 H), 3.41 (s, 4 H), 2.62(s, 6 H). MS ESI calcd for $C_{28}H_{28}N_6O_2$ [M + H]$^+$ 481, found 481. |
| 222 | 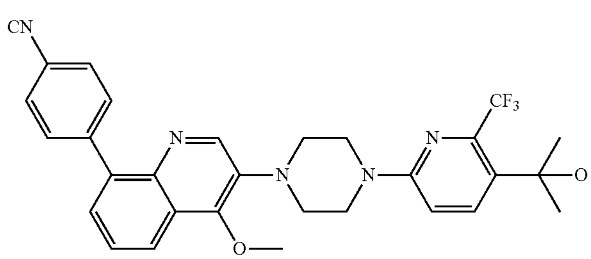 | $^1$H NMR (400 MHz, CDCl$_3$) δ 8.76 (s, 1H), 8.31-8.17 (m, 2H), 7.91-7.80 (m, 4H), 7.58 (d, J = 8.0 Hz, 2H), 6.81 (d, J = 8.0 Hz, 1H), 4.14 (s, 3 H), 3.80 (s, 4 H), 3.34 (s, 4 H), 1.65 (s, 6 H). MS ESI calcd for $C_{30}H_{28}F_3N_5O_2$ [M + H]$^+$ 548, found 548. |
| 223 | 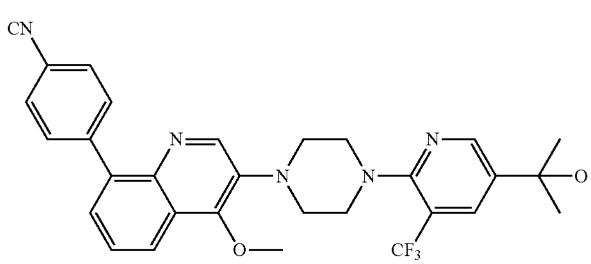 | $^1$H NMR (400 MHz, CDCl$_3$) δ 8.75 (s, 1H), 8.50 (s, 1H), 8.21-8.17 (m, 1H), 8.00 (s, 1H), 7.75-7.60 (m, 4H), 7.52-7.48 (m, 2H), 4.07 (s, 3 H), 3.57-3.41 (m, 8 H), 1.55 (s, 6 H). MS ESI Calcd for $C_{30}H_{28}F_3N_5O_2$ [M + H]$^+$ 548, found 548. |

| Embodiment | Structure | NMR |
|---|---|---|
| 224 | 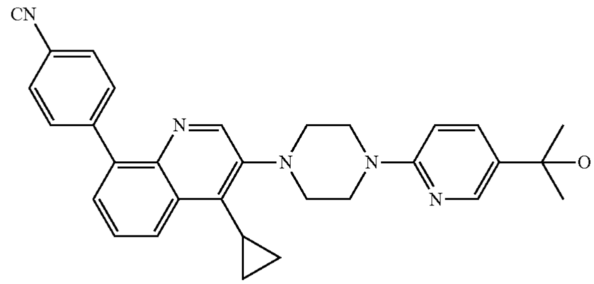 | $^1$H NMR (400 MHz, CDCl$_3$) δ 8.76 (s, 1H), 8.52 (d, J = 8.0 Hz, 1H), 8.35 (d, J = 7.2 Hz, 1H), 7.62-7.53 (m, 7H), 6.75 (d, J = 8.0 Hz, 1H), 3.75 (t, J = 4.4 Hz, 4 H), 3.41 (t, J = 4.4 Hz, 4 H), 2.07-2.01 (m, 1H), 1.97-1.91 (m, 2H), 1.59 (s, 6H), 1.42-1.35 (m, 2H). MS ESI Calcd for C$_{31}$H$_{31}$N$_5$O [M + H]$^+$ 490, found 490. |
| 225 | 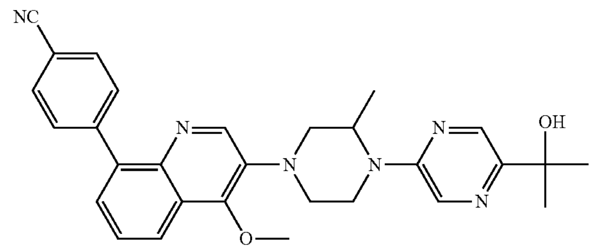 [SMILES: COc1c(N2CCN(c3cnc(C(C)(C)O)cn3)C(C)C2)cnc2c(-c3ccc(C#N)cc3)cccc12] | MS ESI calcd for C$_{29}$H$_{30}$N$_6$O$_2$[M + H]$^+$ 495, found 495. |
| 226 | 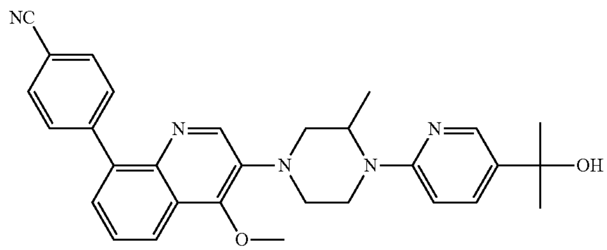 [SMILES: COc1c(N2CCN(c3ccc(C(C)(C)O)cn3)C(C)C2)cnc2c(-c3ccc(C#N)cc3)cccc12] | $^1$H NMR (400 MHz, CDCl$_3$) δ 8.72 (s, 1H), 8.35 (s, 1H), 8.27-8.25 (m, 1H), 7.81-7.64 (m, 5H), 7.61-7.57 (m, 2H), 6.77-6.72 (m, 1H), 4.68 (brs, 1H), 4.22-4.18 (m, 1H), 4.14(s, 3H), 3.72-3.70 (m, 1H), 3.63-3.61 (m, 1H), 3.50-3.48 (m, 1H), 3.30-3.28 (m, 1H), 3.02-2.99 (m, 1H), 1.59 (s, 6 H), 1.35 (d, J = 6.0 Hz, 3H). MS ESI Calcd for C$_{30}$H$_{31}$N$_5$O$_2$ [M + H]$^+$ 494, found 494. |

Embodiment 227

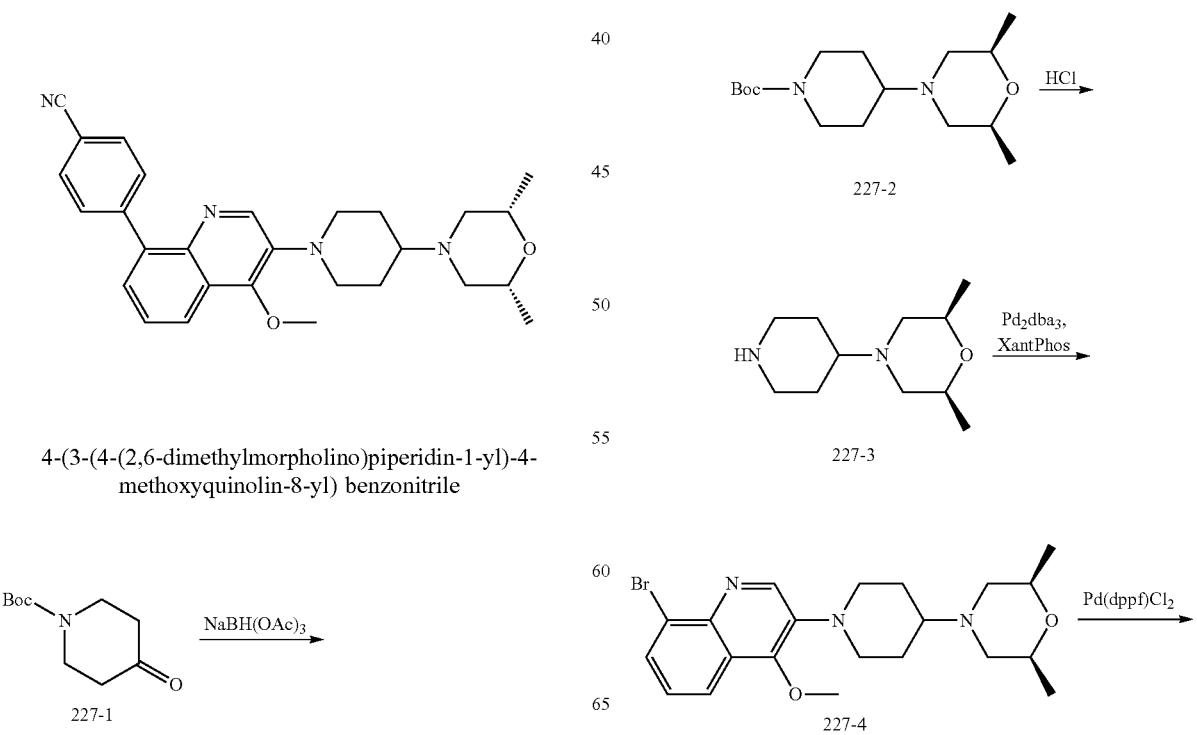

4-(3-(4-(2,6-dimethylmorpholino)piperidin-1-yl)-4-methoxyquinolin-8-yl) benzonitrile -continued

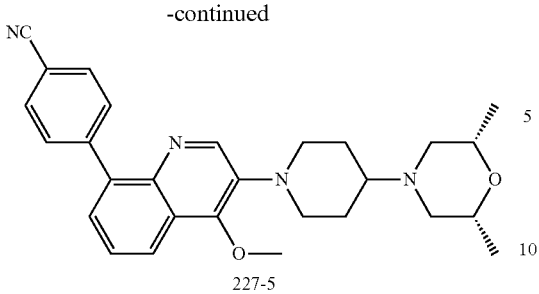

227-5

Step 1: A solution of compound 227-1 (2.0 g, 10 mmol) and cis-2,6-dimethylmorpholine (1.25 g, 11 mmol) in DCM (40 mL) was stirred at 0° C. for 1 h, then sodium triacetoxyborohydride (5.3 g, 25 mmol) was added at 20° C. and the mixture was stirred at 20° C. for 5 h. Then the reaction mixture was quenched with saturated sodium carbonate aqueous solution, extracted with DCM (30×2 mL). The organic phases were combined and dried over sodium sulfate and concentrated under reduced pressure. The residue was purified by silica gel column chromatography (PE/EtOAc=5:1-1:1) to deliver compound 227-2 (1.5 g, 50%) as white solid. MS ESI calcd for $C_{16}H_{30}N_2O_3$ [M+H]$^+$ 299, found 299.

Step 2: HCl (4 M methanol solution, 10 mL) was added into a solution of compound 227-2 (3.0 g, 10 mmol) in methanol (20 mL). The obtained solution was stirred at 20° C. for 4 h, then concentrated under reduced pressure. The obtained yellow solid was used for the next step directly without further purification (1.9 g, 99%). MS ESI calcd for $C_{11}H_{22}N_2O$ [M+H]$^+$ 199, found 199.

Step 3: Under nitrogen gas atmosphere, Pd$_2$(dba)$_3$ (180 mg, 0.2 mmol), Xantphos (290 mg, 0.5 mmol) and sodium tert-butoxide (1.0 g, 10 mmol) were added into a solution of compound 227-3 (1.0 g, 5.0 mmol) and 8-bromo-3-iodo-4-methoxyquinoline (1.4 g, 4 mmol) in toluene (30 mL), the reaction mixture was stirred at 120° C. for 5 h, then poured into H$_2$O, and extracted with ether (3×3 mL), the organic phases were combined and dried over sodium sulfate and concentrated under reduced pressure, the residue was purified by silica gel column chromatography (PE/EtOAc=1:1-1:2) to deliver compound 227-4 (0.36 g, 50%) as yellow solid. MS ESI calcd for $C_{21}H_{28}BrN_3O_2$ [M+H]$^+$ 435, found 435.

Step 4: The title compound (0.1 g, 40%) was synthesized according to the above-mentioned method as white solid. $^1$H NMR (400 MHz, CDCl$_3$) δ 8.75 (s, 1H), 8.23-8.15 (m, 1H), 7.79-7.74 (m, 4H), 7.58-7.46 (m, 2H), 4.11 (s, 3H), 3.72-3.65 (m, 4H), 2.90-2.84 (m, 4H), 2.35-2.28 (m, 1H), 2.20-2.10 (m, 2H), 1.90-1.80 (m, 2H), 1.77-1.67 (m, 2H), 1.21 (d, J=5.6 Hz, 6H). MS ESI calcd for $C_{28}H_{32}N_4O_2$ [M+H]$^+$ 457, found 457.

Embodiment 228

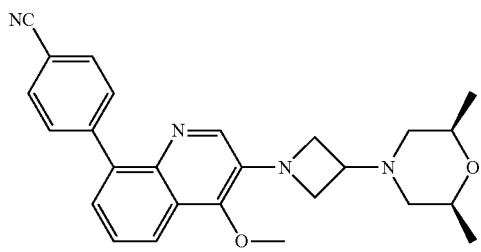 [SMILES: COc1c(N2CC(N3C[C@@H](C)O[C@@H](C)C3)C2)cnc2c(-c3ccc(C#N)cc3)cccc12]

4-(3-(3-(2,6-dimethylmorpholino-4-yl)azetidin-1-yl)-4-methoxyquinolin-8-yl) benzonitrile

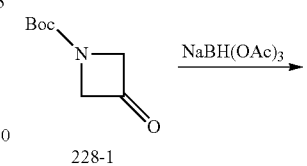

228-1

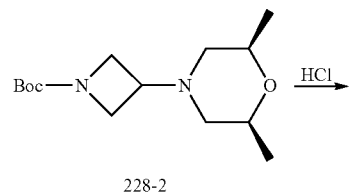

228-2

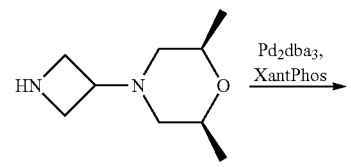

228-3

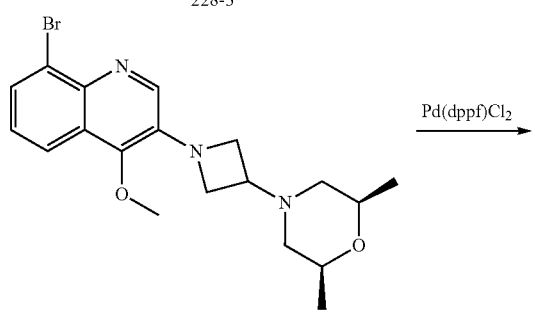

228-4

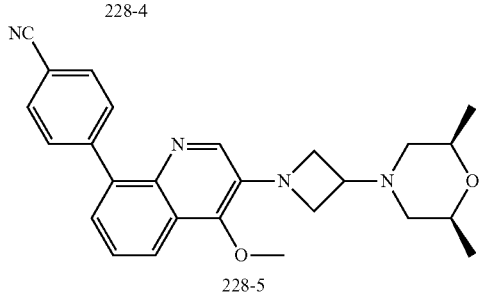

228-5

Step 1: A solution of compound 228-1 (1.7 g, 10 mmol) and cis-2,6-dimethylmorpholine (1.4 g, 12 mmol) in DCM (30 mL) was stirred at 0° C. for 1 h, then sodium triacetoxyborohydride (6.0 g, 30 mmol) was added at 20° C. and the mixture was stirred at 20° C. for 5 h. Then the reaction mixture was quenched with saturated sodium carbonate aqueous solution, extracted with DCM (30×2 mL). The organic phases were combined and dried over sodium sulfate and concentrated under reduced pressure. The residue was purified by silica gel column chromatography (PE/EtOAc=5:1-1:1) to deliver compound 228-2 (1.8 g, 67%) as white solid. MS ESI calcd for $C_{14}H_{26}N_2O_3$ [M+H]$^+$ 271, found 271.

Step 2: HCl (4 M methanol solution, 10 mL) was added into a solution of compound 228-2 (2.6 g, 10 mmol) in methanol (20 mL). The obtained solution was stirred at 20° C. for 4 h, then concentrated under reduced pressure. The obtained yellow solid was used for the next step directly without further purification (1.6 g, 99%). MS ESI calcd for $C_9H_{18}N_2O$ [M+H]$^+$ 171, found 171.

Step 3: Under nitrogen gas atmosphere, Pd$_2$(dba)$_3$ (90 mg, 0.1 mmol), Xantphos (120 mg, 0.2 mmol) and sodium tert-butoxide (0.6 g, 6 mmol) were added into a solution of compound 228-3 (1.1 g, 3 mmol) and 8-bromo-3-iodo-4-methoxylquinoline (0.55 g, 3.3 mmol) in toluene (10 mL), the reaction mixture was stirred at 120° C. for 5 h, then poured into H$_2$O, and extracted with ether (3×3 mL), the organic phases were combined and dried over anhydrous sodium sulfate and concentrated under reduced pressure, the residue was purified by silica gel column chromatography (PE/EtOAc=1:1-1:2) to deliver compound 228-4 (0.57 g, 47%) as yellow solid. MS ESI calcd for $C_{19}H_{24}BrN_3O_2$ [M+H]$^+$ 407, found 407.

Step 4: The title compound (0.045 g, 10%) was synthesized according to the above-mentioned method as white solid. $^1$H NMR (400 MHz, CDCl$_3$) δ 8.50 (s, 1H), 8.09 (d, J=8.0 Hz, 1H), 7.80-7.65 (m, 6H), 4.56 (brs, 2H), 4.41 (brs, 2H), 4.06 (brs, 2H), 3.94 (s, 3H), 3.91 (brs, 1H), 3.49 (d, J=7.6 Hz, 2H), 2.34 (t, J=11.6 Hz, 2H), 1.26 (d, J=6.0 Hz, 6H). MS ESI calcd for $C_{26}H_{28}N_4O_2$ [M+H]$^+$ 429, found 429.

Embodiment 229

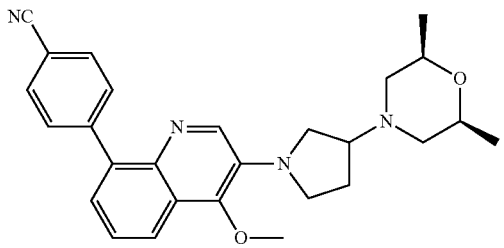 [SMILES: COc1c(N2CCC(N3C[C@@H](C)O[C@@H](C)C3)C2)cnc2c(-c3ccc(C#N)cc3)cccc12]

4-(3-(3-(2,6-dimethylmorpholino)pyrrolidin-1-yl)-4-methoxyquinolin-8-yl) benzonitrile

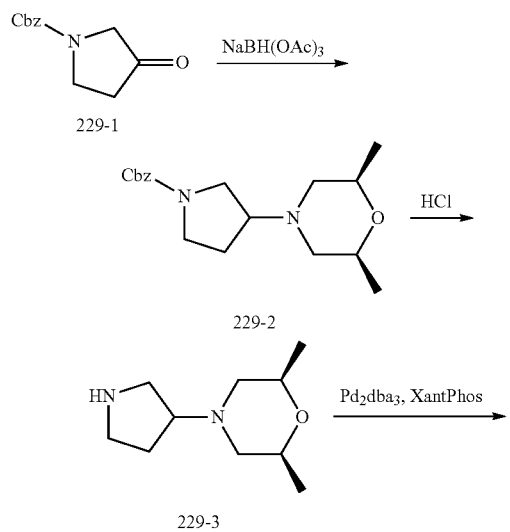

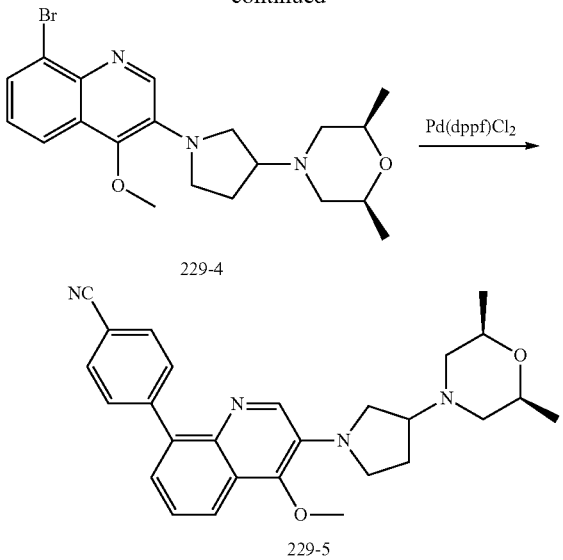

Step 1: A solution of compound 229-1 (2.0 g, 10 mmol) and cis-2,6-dimethylmorpholine (1.25 g, 11 mmol) in DCM (40 mL) was stirred at 0° C. for 1 h, then sodium triacetoxyborohydride (6.0 g, 30 mmol) was added at 20° C. and the mixture was stirred at 20° C. for 5 h. Then the reaction mixture was quenched with saturated sodium carbonate aqueous solution, extracted with DCM (30×2 mL). The organic phases were combined and dried over sodium sulfate and concentrated under reduced pressure. The residue was purified by silica gel column chromatography (PE/EtOAc=5:1-1:1) to deliver compound 229-2 (1.5 g, 60%) as white solid. MS ESI calcd for $C_{18}H_{26}N_2O_3$ [M+H]$^+$ 319, found 319.

Step 2: Pd/C (100 mg) was added into a solution of compound 229-2 (0.65 g, 2 mmol) in methanol (10 mL) and the mixture was hydrogenated under 30 psi at 20° C. for 4 h. Then the mixture was filtrated and concentrated under reduced pressure. The obtained yellow solid was used for the next step directly without further purification (0.37 g, 99%). MS ESI calcd for $C_{10}H_{20}N_2O$ [M+H]$^+$ 185, found 185.

Step 3: Under nitrogen gas atmosphere, Pd$_2$(dba)$_3$ (90 mg, 0.1 mmol), Xantphos (120 mg, 0.2 mmol) and sodium tert-butoxide (0.4 g, 3 mmol) were added into a solution of compound 229-3 (0.4 g, 1.1 mmol) and 8-bromo-3-iodo-4-methoxyquinoline (0.2 g, 1.1 mmol) in toluene (10 mL), the reaction mixture was stirred at 120° C. for 5 h, then poured into H$_2$O, and extracted with ether (3×3 mL), the organic phases were combined and dried over sodium sulfate and concentrated under reduced pressure, the residue was purified by silica gel column chromatography (PE/EtOAc=1:1-1:2) to deliver compound 229-4 (0.36 g, 42%) as yellow solid. MS ESI calcd for $C_{20}H_{26}BrN_3O_2$ [M+H]$^+$ 421, found 421.

Step 4: The title compound (0.13 g, 60%) was synthesized according to the above-mentioned method as white solid. $^1$H NMR (400 MHz, CDCl$_3$) δ 8.68 (s, 1H), 8.14-8.12 (m, 1H), 7.72-7.65 (m, 4H), 7.49-7.47 (m, 2H), 4.04 (s, 3H), 3.64-3.60 (m, 4H), 2.82-2.78 (m, 4H), 2.24-2.20 (m, 1H), 2.00-1.92 (m, 2H), 1.86-1.72 (m, 2H), 1.68-1.56 (m, 2H), 1.16 (d, J=6.0 Hz, 6H). MS ESI calcd for $C_{27}H_{30}N_4O_2$ [M+H]$^+$ 443, found 443.

Embodiment 230

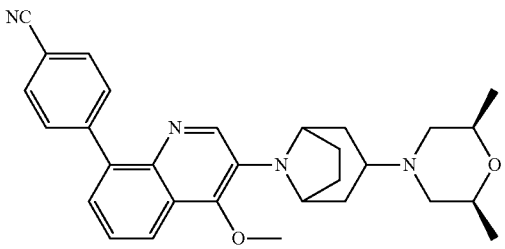 [SMILES: COc1c(N2C3CCC2CC(N2C[C@@H](C)O[C@@H](C)C2)C3)cnc2c(-c3ccc(C#N)cc3)cccc12]

4-(3-(3-(2,6-dimethylmorpholino-4-yl)-8-azabicyclo[3.2.1]octan-8-yl)-4-methoxyquinolin-8-yl)benzonitrile

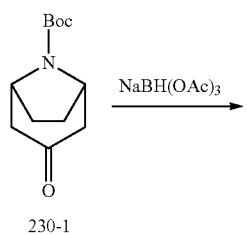

230-1

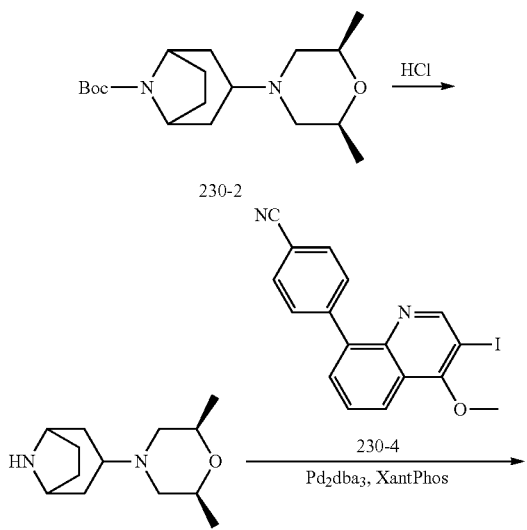

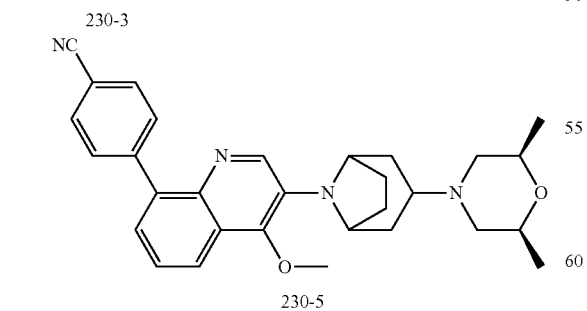

230-5

Step 1: Sodium triacetoxyborohydride (6.3 g, 30 mmol) was added into a solution of compound 230-1 (4.5 g, 20 mmol) and cis-2,6-dimethyl morpholine (2.5 g, 22 mmol) in DCM (60 mL) at 0° C. and the mixture was stirred at 25° C. for 12 h. Then the mixture was poured into H₂O, and extracted with EtOAc. The organic phases were combined, dried over sodium sulfate and concentrated under reduced pressure. The residue was purified by silica gel column chromatography (PE/EtOAc=10:1) to deliver compound 230-2 (1.1 g, 17%) as white solid. MS ESI calcd for $C_{18}H_{32}N_2O_3$ [M+H]⁺ 325, found 325.

Step 2: HCl (4 M methanol solution, 10 mL) was added into a solution of compound 230-2 (324 mg, 1 mmol) in methanol (5 mL). The obtained solution was stirred at 25° C. for 2 h, then concentrated under reduced pressure. The obtained yellow solid was used for the next step directly without further purification (224 mg, 100%). MS ESI calcd for $C_{13}H_{24}N_2O$ [M+H]⁺ 225, found 225.

Step 3: The title compound (40 mg, 8.3%) was synthesized according to the above-mentioned method as white solid. ¹H NMR (400 MHz, CDCl₃) δ 8.71 (s, 1H), 8.24-8.21 (m, 1H), 7.82-7.75 (m, 4H), 7.59-7.57 (m, 2H), 4.75-4.60 (m, 2H), 3.97 (s, 3H), 3.74-3.68 (m, 3H), 3.52 (d, J=12.0 Hz, 2H), 2.62-2.50 (m, 2H), 2.20-2.18 (m, 4H), 2.00-1.89 (m, 2H), 1.21 (d, J=6.4 Hz, 6H). MS ESI calcd for $C_{30}H_{34}N_4O_2$ [M+H]⁺ 483, found 483.

Embodiment 231

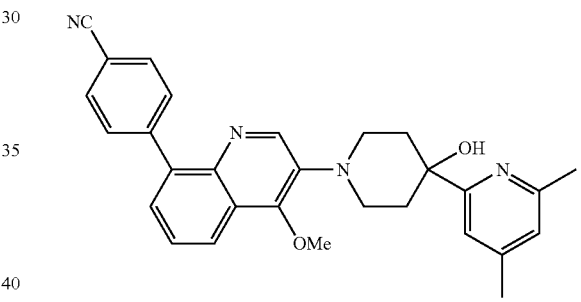

4-(3-(4'-hydroxy-4,6-dimethyl-3',4',5',6'-tetrahydro-2'H-[2,4']bipyridyl-1'-yl)-4-methoxyquinolin-8-yl)benzonitrile

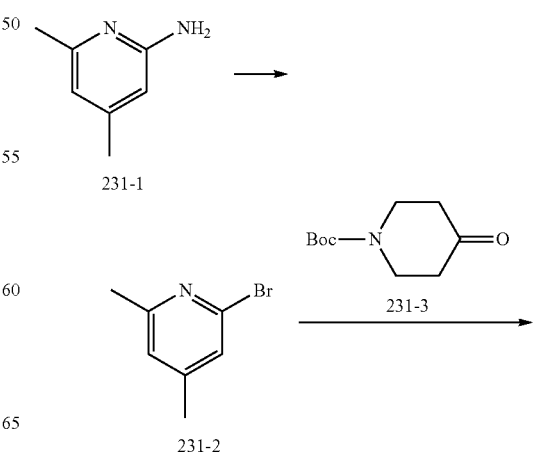

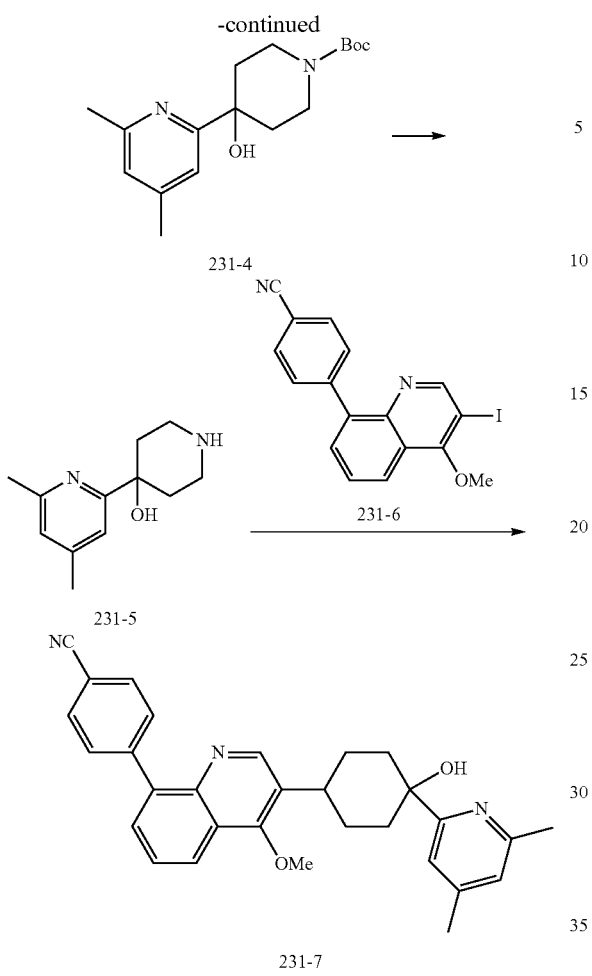

The reaction mixture was stirred at room temperature for 30 min. Then the reaction mixture was basified with 6 N NaOH to pH=9, extracted with CHCl₃ (70×3 mL). The organic phases were combined, dried over sodium sulfate and concentrated under reduced pressure to deliver crude compound 231-5 (1.197 g, 89%) as yellow solid, which was used for the next step directly without further purification. MS ESI calcd for $C_{12}H_{18}N_2O$ [M+H]⁺ 207, found 207.

Step 4: The title compound (18 mg, 9.5%) was synthesized according to the above-mentioned method as white solid. ¹H NMR (400 MHz, CDCl₃) δ 8.89 (s, 1H), 8.24-8.21 (m, 1H), 7.83-7.76 (m, 4H), 7.60-7.56 (m, 2H), 7.01 (s, 1H), 6.94 (s, 1H), 5.74 (s, 1H), 4.19 (s, 3H), 3.63-3.49 (m, 4H), 2.54 (s, 3H), 2.37 (s, 3H), 2.28-2.21 (m, 2H), 1.79-1.76 (m, 2H). MS ESI calcd for $C_{29}H_{28}N_4O_2$ [M+H]⁺ 465, found 465.

Embodiment 232

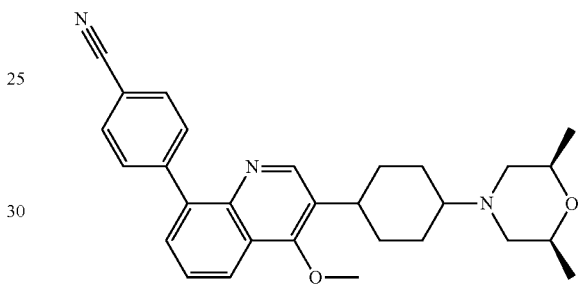

4-(3-(4-(2,6-dimethylmorpholino-4-yl)cyclohexyl)-4-methoxyquinolin-8-yl) benzonitrile Step 1: Br₂ (36.8 g, 0.23 mmol) was added into a solution of compound 231-1 (10 g, 82 mmol) in HBr (41 mL), and the mixture was stirred at −10° C. for 10 min. Then NaNO₂ (14.1 g, 210 mmol) was added while the reaction temperature was kept no more than 0° C. The reaction mixture was stirred for 30 min. Then NaOH solution (35 g dissolved in 35 mL H₂O) was added, and the mixture was extracted with EtOAc. The organic phases were combined, dried over anhydrous sodium sulfate and concentrated under reduced pressure. The residue was purified by silica gel column chromatography (PE/EtOAc=10:1) to deliver compound 231-2 (3.36 g, 22%) as light yellow oil. MS ESI calcd for $C_7H_8BrN$ [M+H]⁺ 187, found 187.

Step 2: n-BuLi (8 mL, 19.91 mmol) was added into a solution of compound 231-2 (3.36 g, 18.1 mmol) in THF (70 mL) at −70° C. and stirred for 1 h. Then compound 231-3 (4.32 g, 21.71 mmol) was added at −70° C. The reaction mixture was warmed to room temperature slowly and stirred at room temperature for 2 h. Then the reaction mixture was quenched with saturated ammonium chloride aqueous solution (2 mL) and extracted with EtOAc (200 mL). The organic phases were combined, dried over anhydrous sodium sulfate and concentrated under reduced pressure. The residue was purified by silica gel column chromatography (PE/EtOAc=5:1) to deliver compound 231-4 (3.11 g, 56%) as light yellow oil. MS ESI calcd for $C_{17}H_{26}N_2O_3$ [M+H]⁺ 307, found 307.

Step 3: CF₃COOH (6 mL) was added dropwise into a solution of compound 231-4 (2 g, 6.5 mL) in DCM (30 mL).

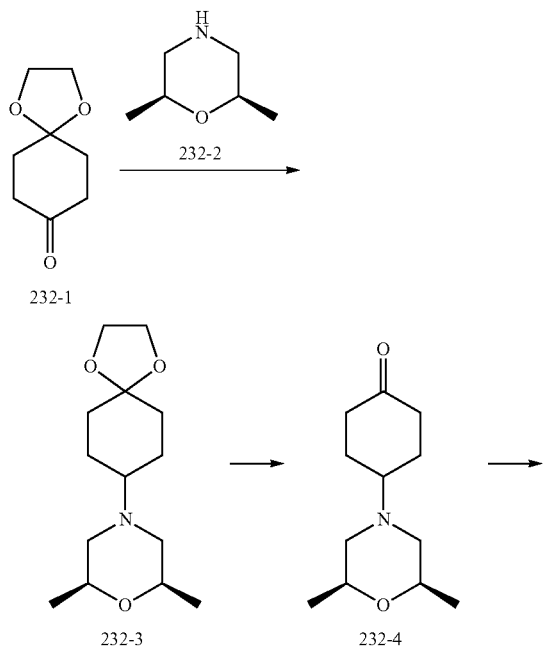

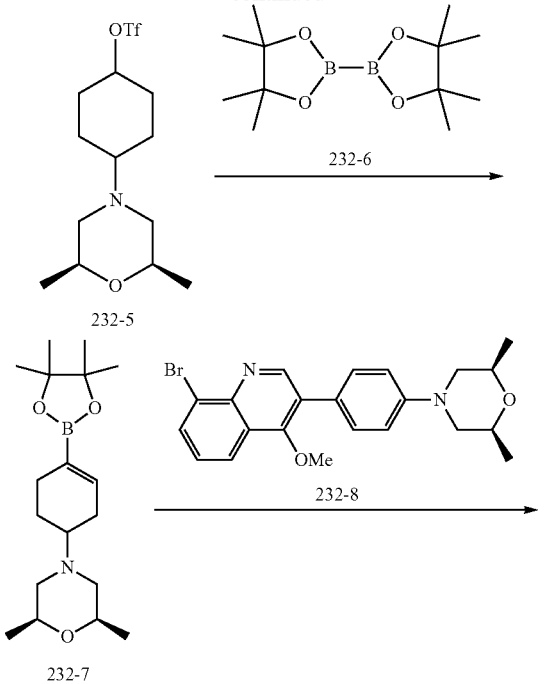

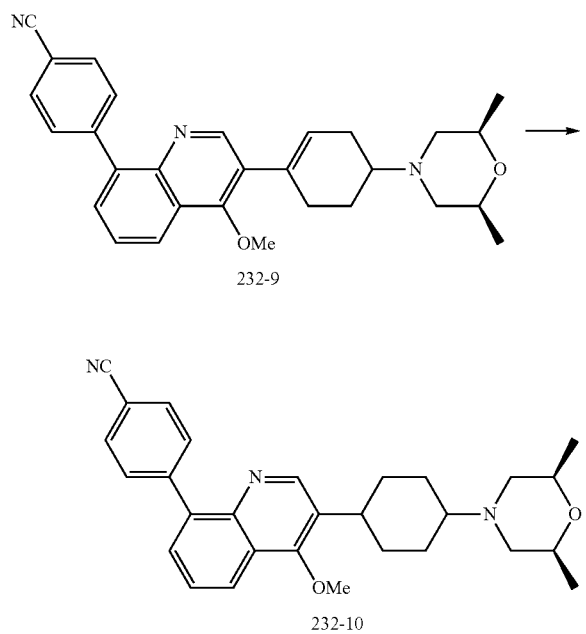 [SMILES: COc1c(C2=CCC(N3C[C@@H](C)O[C@@H](C)C3)CC2)cnc2c(-c3ccc(C#N)cc3)cccc12 ; COc1c(C2CCC(N3C[C@@H](C)O[C@@H](C)C3)CC2)cnc2c(-c3ccc(C#N)cc3)cccc12]

Step 1: Sodium triacetoxyborohydride (54.3 g, 0.26 mol) was added into a solution of compound 232-1 (20 g, 0.13 mol), cis-2,6-dimethyl morpholine (14.74 g, 0.13 mol) and acetic acid (7.69 mg, 0.13 mol) in 1,2-dichloroethane (400 mL) at 0° C. and the mixture was stirred at 25° C. for 16 h. Then 10% NaOH aqueous solution (200 mL) was slowly added dropwise (in 20 min) to quench the reaction, then the mixture was extracted with EtOAc. The organic phases were combined, dried over sodium sulfate and concentrated under reduced pressure to deliver compound 232-3 (30 g, 92%) as white solid. MS ESI calcd for $C_{14}H_{25}NO_3$ [M+H]$^+$ 256, found 256.

Step 2: 7 N HCl aqueous solution (40 mL) was added into a solution of compound 232-3 (10 g, 39.2 mmol) in THF (200 mL), and the mixture was stirred at 25° C. for 16 h. Then 2 N NaOH aqueous solution (500 mL) was added to quench the reaction, then the mixture was extracted with EtOAc (1×) and DCM (3×). The organic phases were combined, dried over sodium sulfate and concentrated under reduced pressure to deliver crude compound 232-4 (8 g, 96%) as white solid. MS ESI calcd for $C_{21}H_{12}NO_2$ [M+H]$^+$ 212, found 212.

Step 3: LiHMDS (17 mL, 17 mmol) was added into a solution of compound 232-4 (3 g, 14.2 mmol) in THF (50 mL) at 0° C., then the reaction mixture was stirred for 30 min. Then N,N-bis(trifluoromethylsulfonyl)aniline (5.58 g, 15.6 mmol) was added, and the reaction mixture was stirred at 25° C. for 6 h. The reaction mixture was poured into $H_2O$ and extracted with EtOAc. The organic phases were combined, dried over sodium sulfate and concentrated under reduced pressure. The residue was purified by silica gel column chromatography (PE/EtOAc=5:1) to deliver compound 232-5 (2.3 g, 47%) as white solid. MS ESI calcd for $C_{13}H_{20}F_3NO_4S$ [M+H]$^+$ 344, found 344.

Step 4: Under nitrogen gas atmosphere, Pd(dppf)Cl$_2$ (0.4 mg, 0.11 mmol) and KOAc (0.65 g, 6.6 mmol) were added into a solution of compound 232-5 (0.76 g, 2.2 mmol) and compound 232-6 (0.67 g, 2.6 mmol) in 1,4-dioxane (15 mL). The reaction mixture was stirred at 100° C. for 15 h, then poured into $H_2O$ and extracted with EtOAc (50×2 mL). The organic phases were combined, dried over sodium sulfate and concentrated under reduced pressure. The residue was purified by silica gel column chromatography (PE/EtOAc=5:1) to deliver compound 232-7 (0.35 g, 49%) as yellow solid. MS ESI calcd for $C_{18}H_{32}BNO_3$ [M+H]$^+$ 322, found 322.

Step 5: Under nitrogen gas atmosphere, Pd(dppf)Cl$_2$ (113.8 mg, 0.16 mmol) and Na$_2$CO$_3$ (412 mg, 3.89 mmol) were added into a solution of compound 232-7 (600 mg, 1.87 mmol) and compound 232-8 (601 mg, 1.56 mmol) in THF (10 mL) and H$_2$O (2 mL). The reaction mixture was stirred at 80° C. for 4 h, then extracted with EtOAc (50×2 mL). The organic phases were combined, dried over sodium sulfate and concentrated under reduced pressure. The residue was purified by silica gel column chromatography (PE/EtOAc=5:1) to deliver compound 232-7 (400 mg, 48%) as white solid. MS ESI calcd for $C_{29}H_{31}N_3O_2$ [M+H]$^+$ 454, found 454.

Step 6: Pd/C (100 mg) was added into a solution of compound 232-9 (100 mg, 0.22 mmol) in EtOAc (20 mL), and the reaction mixture was hydrogenated under hydrogen balloon at 20° C. for 50 h. Then the mixture was filtrated and concentrated under reduced pressure. The obtained yellow solid was purified by preparative HPLC to deliver the title compound (27 mg, 54%) as white solid. $^1$H NMR (400 MHz, DMSO) δ 8.99 (s, 1H), 8.17-8.15 (J=8 Hz, d, 1H), 7.94-7.92 (d, J=12 Hz, 2H), 7.85-7.83 (d, J=8 Hz, 2H), 7.80-7.78 (J=8 Hz, d, 1H), 7.74-7.72 (J=8 Hz, d, 1H), 3.98 (s, 3H) 3.54 (s, 2H), 3.18-3.17 (J=4 Hz, d, 1H), 3.54 (s, 1H), 2.76-2.74 (J=8 Hz, d, 2H), 1.95-1.71 (m, 8H), 1.49-1.44 (m, 2H), 1.07-1.05 (J=8 Hz, d, 6H). MS ESI calcd for $C_{29}H_{33}N_3O_2$ [M+H]$^+$ 465, found 465.

Embodiment 233

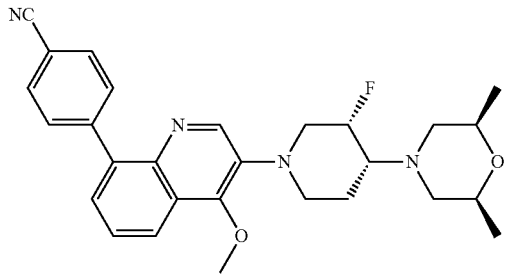 [SMILES: COc1c(N2CC[C@@H](N3C[C@@H](C)O[C@@H](C)C3)[C@@H](F)C2)cnc2c(-c3ccc(C#N)cc3)cccc12]

4-(3-(4-(2,6-dimethylmorpholino-4-yl)-3-fluoropiperidin-1-yl)-4-methoxyquinolin-8-yl)benzonitrile

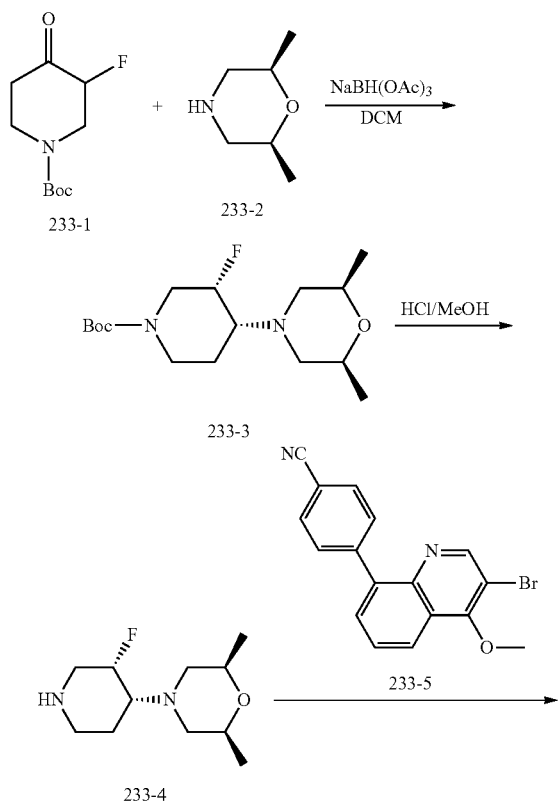

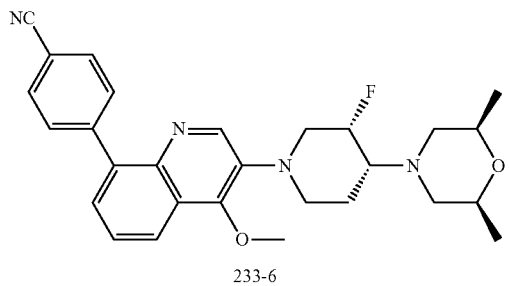

233-6

Step 1: A solution of compound 1 (3.0 g, 13.8 mmol) and cis-2,6-dimethylmorpholine (1.7 g, 15.2 mmol) in DCM (15 mL) was stirred at 20° C. for 0.5 h, then sodium triacetoxyborohydride (4.4 g, 20.7 mmol) was added at 20° C. and the reaction mixture was stirred at 20° C. for 15 h. Then the reaction mixture was quenched with saturated sodium carbonate aqueous solution (50 mL), extracted with DCM (50 mL). The organic phases were combined, dried over anhydrous sodium sulfate and concentrated under reduced pressure. The residue was purified by silica gel column chromatography (PE/EtOAc=8:1-1:1) to deliver compound 233-3 (1.2 g, 27%) as white solid. MS ESI calcd for $C_{16}H_{29}FN_2O_3$ [M+H]$^+$ 317, found 317.

Step 2: HCl (4 M methanol solution, 60 mL) was added into a solution of compound 233-3 (1.2 g, 3.8 mmol) in methanol (10 mL). The obtained solution was stirred at 20° C. for 0.5 h, then concentrated under reduced pressure. The obtained yellow solid was used for the next step directly without further purification (0.6 g, 75%). MS ESI calcd for $C_{11}H_{21}FN_2O$ [M+H]$^+$ 217, found 217.

Step 3: The title compound (27 mg, 15%) was synthesized according to the above-mentioned method as white solid. $^1$H NMR (400 MHz, CDCl$_3$) δ 8.73 (s, 1H), 8.24-8.21 (m, 1H), 7.80-7.75 (m, 4H), 7.59-7.58 (d, J=4 Hz, 2H), 4.15 (s, 3H), 4.03-4.00 (m, 1H), 3.74-3.71 (m, 3H), 3.07-2.92 (m, 4H), 2.25-1.94 (m, 6H), 1.21-1.19 (d, J=8 Hz, 6H). MS ESI calcd for $C_{28}H_{31}FN_4O_2$ [M+H]$^+$ 475, found 475.

The compound listed in table 21 was synthesized by compound 233-5 and corresponding amine.

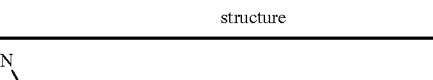

| Embodiment | structure | NMR |
|---|---|---|
| 234 | 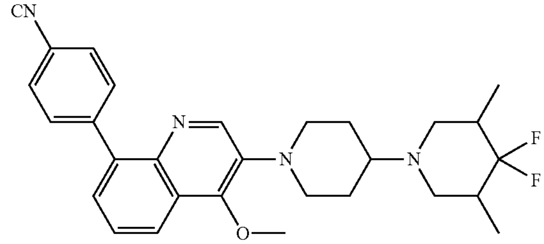 | $^1$H NMR (400 MHz, CDCl$_3$) δ ppm 8.76 (s, 1H) 8.23-8.19 (m, 1H) 7.81-7.77 (m, 4H) 7.58-7.56 (m, 2H) 4.12 (s, 3H) 3.72-3.69 (m, 2H) 2.90-2.85 (m, 4H) 2.49-2.24(m, 1H) 2.21-1.98(m, 6H) 1.78-1.74 (m, 2H) 1.05-1.03 (d, j = 8, 6H). |

Embodiment 235

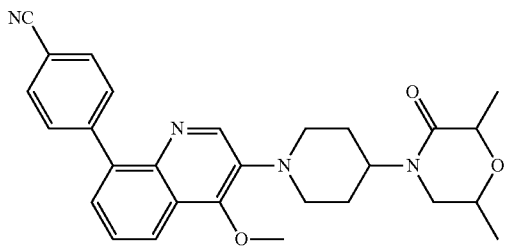 [SMILES: COc1c(N2CCC(N3CC(C)OC(C)C3=O)CC2)cnc2c(-c3ccc(C#N)cc3)cccc12]

4-(3-(4-(2,6-dimethyl-3-oxo-morpholino-4-yl)piperidin-1-yl)-4-methoxyquinolin-8-yl) benzonitrile

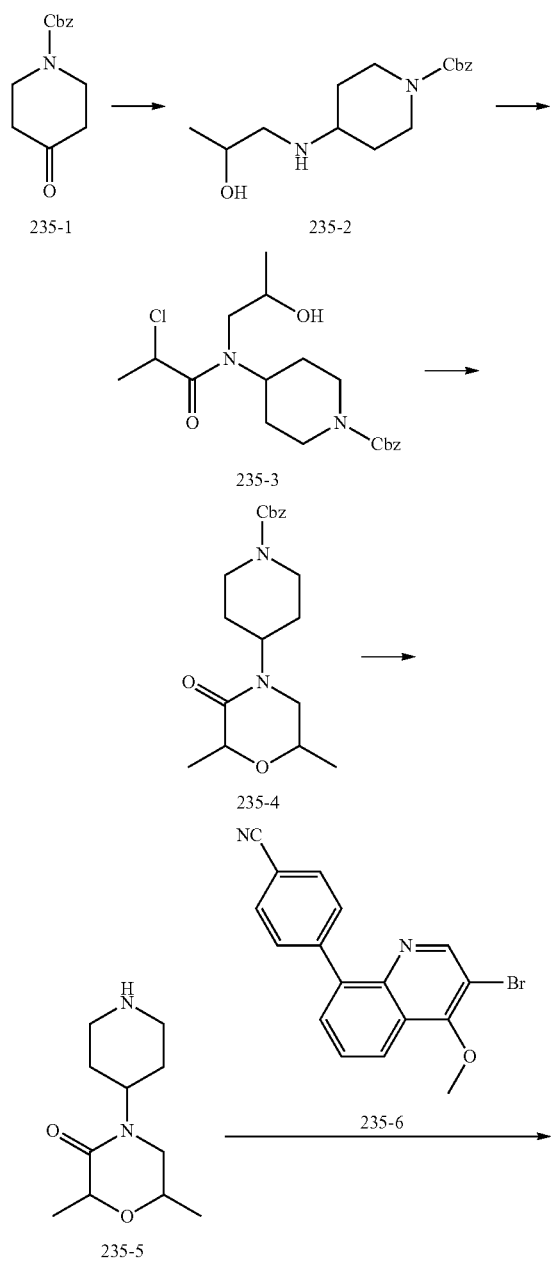

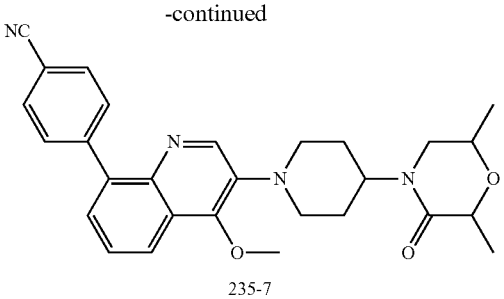

Step 1: A solution of compound 235-1 (15 g, 64 mmol), compound 235-A (12 mL, 192 mmol) and acetic acid (11.04 mL, 192 mmol) in methanol (200 mL) was stirred at 20° C. for 1 h, then NaBH$_3$CN (12.11 g, 192 mmol) was added in a whole and the mixture was stirred at 25° C. overnight. After the reaction was complete as detected by LCMS, the reaction mixture was extracted with DCM and washed with saturated sodium bicarbonate aqueous solution. The organic phases were combined, dried over sodium sulfate and concentrated under reduced pressure to deliver compound 235-2 (15.6 g, 83%) as yellow oil. MS ESI calcd for $C_{16}H_{24}N_2O_3$ [M+H]$^+$ 293, found 293.

Step 2: TEA (0.7 g, 7 mmol) and compound 235-B (0.59 g, 4.65 mmol) were added into a solution of compound 235-2 (1.36 g, 4.65 mmol) in DCM (20 mL), the mixture was stirred at room temperature for 2 h. After the reaction was complete as detected by LCMS, the reaction mixture was extracted with DCM. The organic phases were combined, dried over sodium sulfate and concentrated under reduced pressure. The residue was purified by silica gel column chromatography (PE/EtOAc=5:1) to deliver compound 235-3 (1.2 g, 67.4%) as yellow oil. MS ESI calcd for $C_{19}H_{27}ClN_2O_4$ [M+H]$^+$ 383, found 383.

Step 3: Potassium tert-butoxide (225 mg, 2 mmol) was added into a solution of compound 235-3 (760 mg, 2 mmol) in THF (10 mL), the mixture was stirred at room temperature for 2 h. After the reaction was complete as detected by LCMS, the reaction mixture was extracted with EtOAc. The organic phases were combined, dried over sodium sulfate and concentrated under reduced pressure to deliver compound 235-4 (500 mg, 70%) as yellow oil. MS ESI calcd for $C_{19}H_{26}N_2O_4$ [M+H]$^+$ 347, found 347.

Step 4: Pd/C (300 mg) was added into a solution of compound 235-4 (3.0 g, 8.6 mmol) in methanol (10 mL), and the mixture was hydrogenated under 40 psi at room temperature overnight. Then the mixture was filtrated and concentrated under reduced pressure. The obtained colorless oil was used for the next step directly without further purification (1.3 g, 71%). MS ESI calcd for $C_{11}H_{20}N_2O_2$ [M+H]$^+$ 213, found 213.

Step 5: The title compound (20 mg, 1.8%) was synthesized according to the above-mentioned method as yellow solid. $^1$H NMR (400 MHz, CDCl$_3$) δ 8.93 (s, 1H), 8.35-8.32 (m, 1H), 7.83-7.72 (m, 4H), 7.59-7.57 (m, 2H), 4.55-4.50 (m, 1H), 4.49-4.45 (m, 1H), 4.32 (s, 3H), 4.15-4.02 (m, 2H), 3.75-3.52 (m, 2H), 3.22-3.02 (m, 4H), 2.15-2.07 (m, 2H), 2.05-1.92 (m, 2H), 1.48 (d, J=7.2 Hz, 3H). MS ESI calcd for $C_{28}H_{30}N_4O_3$ [M+H]$^+$ 471, found 471.

Embodiment 236

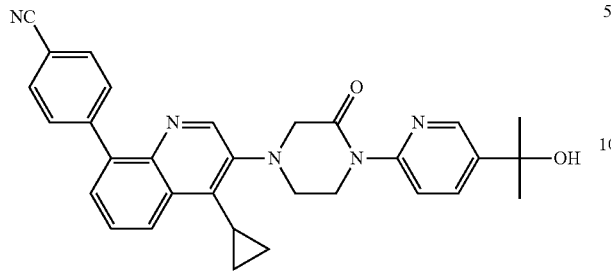

4-(4-cyclopropyl-3-(4-(5-(1-hydroxy-1-methyl-ethyl)pyridin-2-yl)-3-oxo-piperazin-1-yl)quinolin-8-yl)benzonitrile

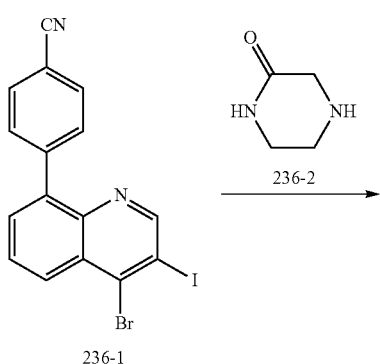

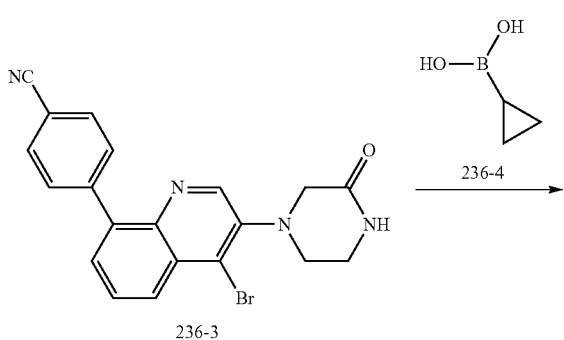

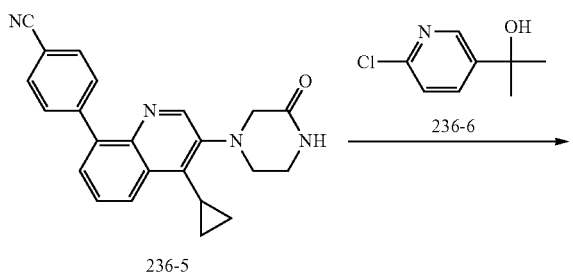

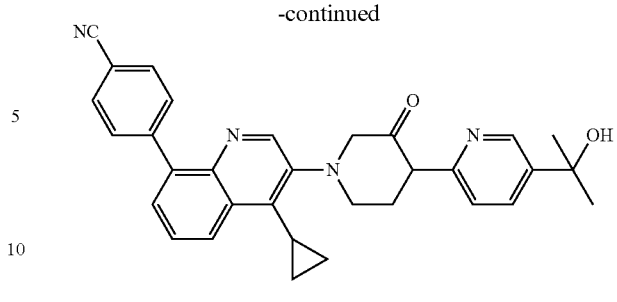

236-7

Step 1: Compound 236-1 (4.35 g, 10 mmol), compound 236-2 (1.0 g, 10 mmol), Pd$_2$(dba)$_3$ (920 mg, 1.0 mmol), Xantphos (1.15 g, 2.0 mmol) and sodium tert-butoxide (2.0 g, 20 mmol) were added into toluene (30 mL), under nitrogen gas atmosphere, the reaction mixture was stirred at 120° C. for 2 h. The mixture was poured into H$_2$O, extracted with EtOAc (100 mL), the extraction liquid was washed with brines, dried over anhydrous sodium sulfate and concentrated under reduced pressure. The residue was purified by silica gel column chromatography to deliver 1.5 g compound 236-3, yield 37.5%, as yellow solid. MS ESI calcd for C$_{20}$H$_{15}$BrN$_4$O [M+H]$^+$ 407, found 407.

Step 2: Compound 236-3 (407 mg, 1.0 mmol), compound 236-4 (870 mg, 10 mmol), n-BuPAd$_2$ (71 mg, 0.2 mmol), palladium acetate (23 mg, 0.1 mmol) and cesium carbonate (650 mg, 2.0 mmol) were added into toluene/H$_2$O (5:1, 12 mL), under nitrogen gas atmosphere, the reaction mixture was stirred at 110° C. for 2 h. The mixture was poured into H$_2$O, extracted with EtOAc (50 mL), the extraction liquid was washed with brines, dried over anhydrous sodium sulfate and concentrated under reduced pressure. The residue was purified by silica gel column chromatography to deliver 230 mg compound 236-5, yield 64%, as yellow solid. MS ESI calcd for C$_{23}$H$_{20}$N$_4$O [M+H]$^+$ 369, found 369.

Step 3: Compound 236-5 (185 mg, 0.5 mmol), compound 236-6 (86 mg, 0.5 mmol), Pd$_2$(dba)$_3$ (46 mg, 0.05 mmol), Xantphos (57.7 mg, 0.1 mmol) and cesium carbonate (325 mg, 1.0 mmol) were added into toluene (10 mL), under nitrogen gas atmosphere, the reaction mixture was stirred at 120° C. for 2 h. The mixture was poured into H$_2$O, extracted with EtOAc (100 mL), the extraction liquid was washed with brines, dried over anhydrous sodium sulfate and concentrated under reduced pressure. The residue was purified by preparative HPLC to deliver the title compound (80 mg, yield 32%) as white solid. $^1$H NMR (400 MHz, CDCl$_3$) δ 8.78 (s, 1H), 8.61-8.62 (d, J=2.0 Hz, 1H), 8.53-8.55 (d, J=7.6 Hz, 1H), 8.01-8.04 (d, J=8.4 Hz, 1H), 7.78-7.80 (m, 4H) 7.61-7.67 (m, 2H) 4.26-4.28 (t, J=10.4 Hz 2H), 4.23 (s, 2H) 3.74-3.76 (t, J=10.8 Hz 2H), 2.11-2.15 (m, 1H) δ 1.65 (s, 6H), 1.34-1.37 (m, 2H) 0.98-1.00 (d, J=6.4 Hz 2H). MS ESI calcd for C$_{31}$H$_{29}$N$_5$O$_2$ [M+H]$^+$ 504, found 504.

Embodiment 237

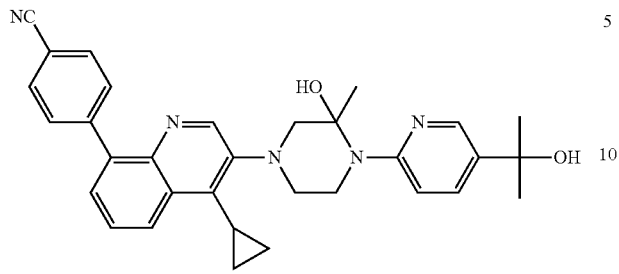

4-(4-cyclopropyl-3-(3-hydroxy-4-(5-(1-hydroxy-1-methyl-ethyl)pyridin-2-yl)-3-methylpiperazin-1-yl)quinolin-8-yl)benzonitrile

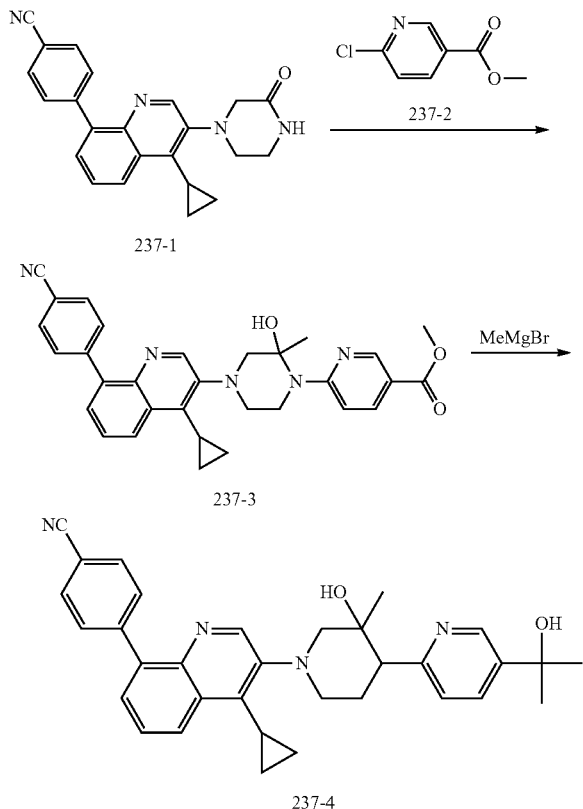

Step 1: Compound 237-1 (150 mg, 0.4 mmol), compound 237-2 (70 mg, 0.4 mmol), Pd$_2$(dba)$_3$ (37 mg, 0.04 mmol), Xantphos (45 mg, 0.08 mmol) and cesium carbonate (260 mg, 0.8 mmol) were added into toluene (2 mL), under nitrogen gas atmosphere, the reaction mixture was stirred at 120° C. for 2 h. The mixture was poured into H$_2$O, extracted with EtOAc (10 mL), the extraction liquid was washed with brines, dried over anhydrous sodium sulfate and concentrated under vacuum. The residue was purified by silica gel column chromatography to deliver 80 mg compound 237-3, yield 39% as yellow solid. MS ESI calcd for C$_{30}$H$_{25}$N$_5$O$_3$ [M+H]$^+$ 504, found 504.

Step 2: Compound 237-3 (50 mg, 0.1 mmol) was dissolved in THF (5 mL), methyl magnesium bromide (0.1 mL, 3 M in Et$_2$O) was added slowly into the solution at −76° C., stirred at this temperature for 1 h, the reaction mixture was poured into an ammonium chloride aqueous solution, extracted with EtOAc (10 mL), the extraction liquid was washed with brines, dried over anhydrous sodium sulfate and concentrated under vacuum. The residue was purified by preparative HPLC to deliver the title compound (10 mg, yield 20%) as white solid. $^1$H NMR (400 MHz, CDCl$_3$) δ 8.76 (s, 1H), 8.66 (s, 1H), 8.38-8.39 (d, J=6.4 Hz, 1H), 7.83-7.85 (d d, J=2.0 Hz, 1H), 7.80-7.83 (m, 4H) 7.54-7.57 (m, 2H) 6.25-6.33 (m, 2H) 4.29 (s, 2H) 3.84 (s, 3H) 3.72-3.75 (t, J=11.2 Hz 2H), 3.47-3.49 (d, J=6.8 Hz, 2H), 2.16 (s, 6H) 1.92-1.95 (m, 1H), 1.22-1.26 (m, 2H) 0.75-0.79 (m, 2H). MS ESI calcd for C$_{32}$H$_{33}$N$_5$O$_2$ [M+H]$^+$ 520, found 520.

Embodiment 238

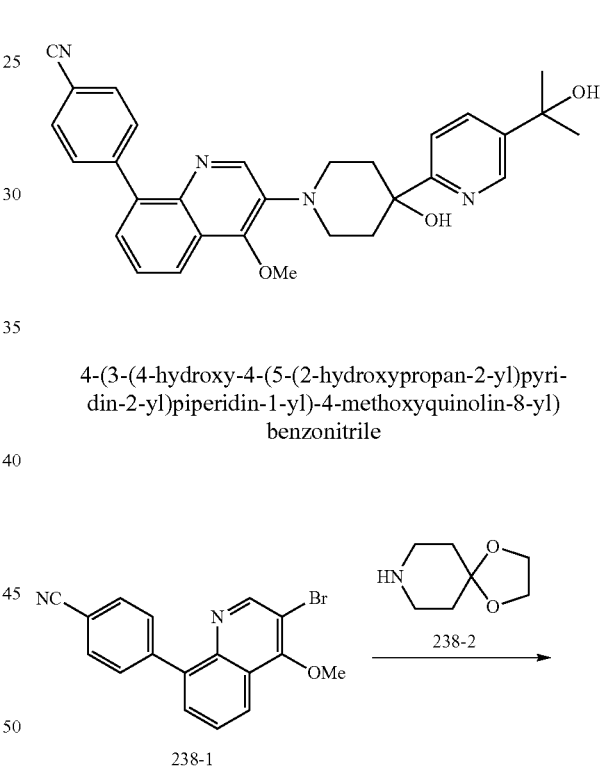

4-(3-(4-hydroxy-4-(5-(2-hydroxypropan-2-yl)pyridin-2-yl)piperidin-1-yl)-4-methoxyquinolin-8-yl)benzonitrile

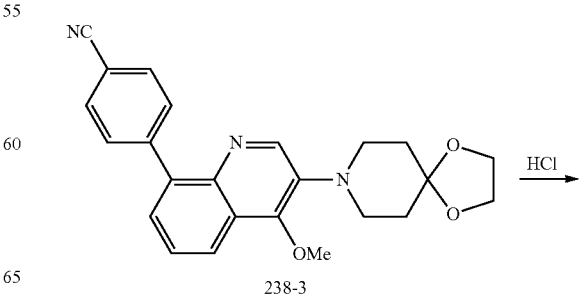

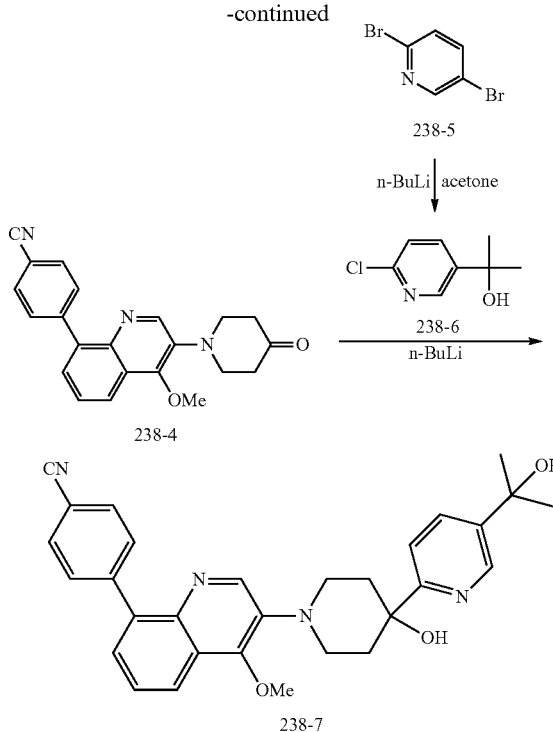

Step 1: Compound 238-2 (930 mg, 6.5 mmol) and sodium tert-butoxide (1.9 g, 19.5 mmol) were added into a solution of compound 238-1 (2.64 g, 7.8 mmol) in toluene (70 mL), then under nitrogen gas atmosphere, Pd$_2$(dba)$_3$ (595 mg, 0.65 mmol) and Xantphos (750 mg, 1.3 mmol) were added, the reaction mixture was heated to 100° C. and stirred for 3 h. The solvent was evaporated, H$_2$O (100 mL) was added, the mixture was extracted with EtOAc (50 mL×3). The organic phase was washed with brines, dried over sodium sulfate and concentrated to give a crude product. The crude product was purified by silica gel column chromatography (PE/EtOAc=5/1) to deliver compound 238-3 (1 g crude) as yellow solid. MS ESI calcd for C$_{24}$H$_{23}$N$_3$O$_3$ [M+H]$^+$ 402, found 402.

Step 2: 2 N HCl (15 mL) was added into a solution of compound 238-3 (1 g crude, 2.5 mmol) in THF (15 mL), the reaction mixture was stirred at room temperature for h. The mixture was quenched with 2 N NaOH aqueous solution, and adjusted to pH=7 to 8. H$_2$O (20 mL) was added, the mixture was extracted with EtOAc (20 mL×2). The organic phase was washed with brines, dried over sodium sulfate and concentrated to deliver compound 238-4 (380 mg crude) as yellow oil. MS ESI calcd for C$_{22}$H$_{19}$N$_3$O$_2$ [M+H]$^+$ 358, found 358.

Step 3: Compound 238-5 was dissolved in THF (150 mL), cooled to −70° C., n-BuLi (5 mL, 12.5 mmol) was added dropwise, after reacting for 30 min, acetone (2 mL, 20 mmol) was added dropwise, then the reaction mixture was stirred at −70° C. for 1 h. The reaction mixture was quenched with saturated ammonium chloride solution, H$_2$O (30 mL) was added, then extracted with EtOAc (30 mL×3). The organic phase was washed with brines, dried over sodium sulfate and concentrated to give a crude product. The crude product was purified by column chromatography (PE/EtOAc=3/1) to deliver compound 238-6 (462 mg, 17.1%) as white solid. MS ESI calcd for C$_8$H$_{10}$BrNO [M+H]$^+$ 216, found 216.

Step 4: Compound 238-6 (30 mg, 0.14 mmol) was dissolved in THF (5 mL), the mixture was cooled to −70° C., n-BuLi (0.12 mL, 0.31 mmol) was added dropwise, after reacting for 30 min, compound 238-4 (50 mg crude, 0.14 mmol) in THF (2 mL) was added dropwise, the reaction mixture was stirred at −70° C. for 1 h. The reaction mixture was quenched with saturated ammonium chloride solution, H$_2$O (10 mL) was added, then extracted with EtOAc (20 mL). The organic phase was washed with brines, dried over sodium sulfate and concentrated to give a crude product. The crude product was purified by prep-HPLC to deliver the title compound (3 mg, 4.3%) as yellow solid. MS ESI calcd for C$_{30}$H$_{30}$N$_4$O$_3$ [M+H]$^+$ 495, found 495.

Embodiment 239

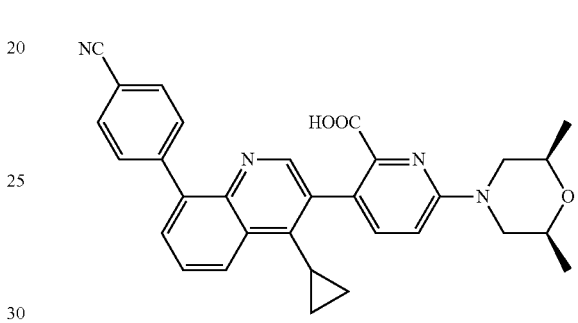

3-(8-(4-cyanophenyl)-4-cyclopropylquinolin-3-yl)-6-(2,6-dimethylmorpholino-4-yl)pyridin-2-carboxylic acid

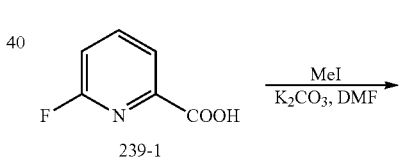

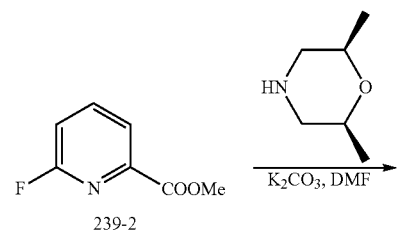

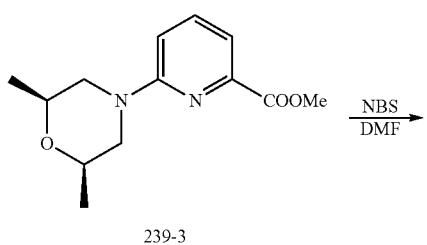

-continued

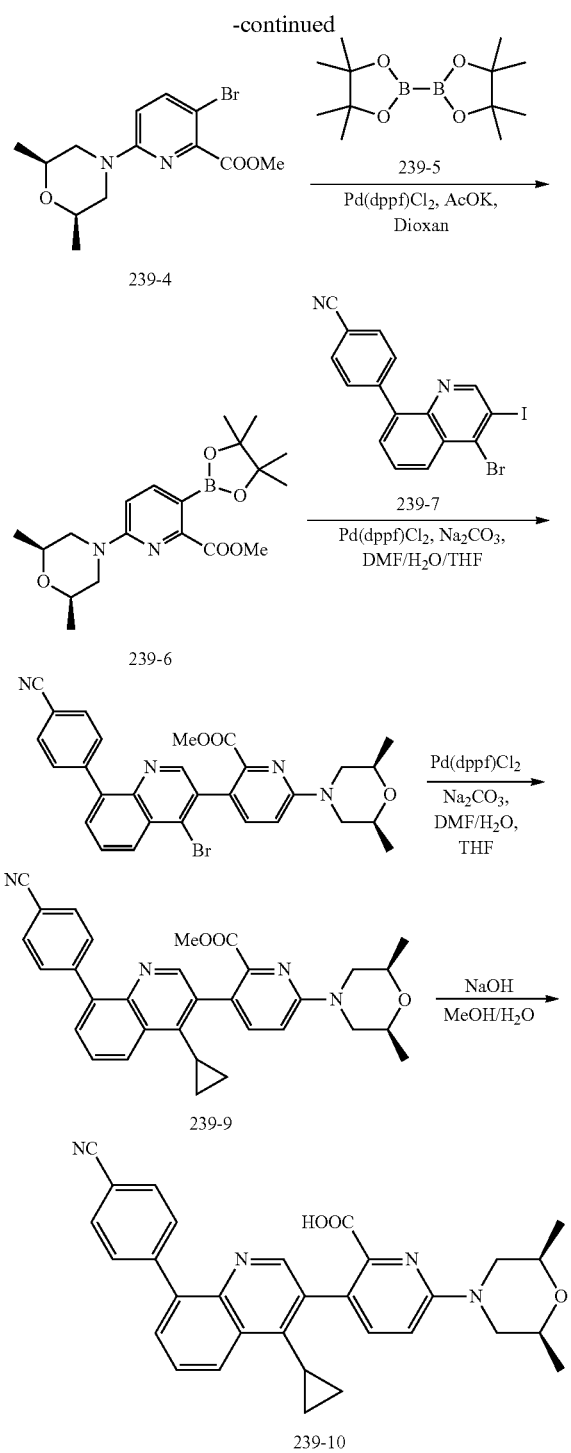

Step 1: Compound 239-1 (5 g, 35 mmol) and $K_2CO_3$ (10 g, 70 mmol) were added into a solution of MeI (5 g, 35 mmol) in DMF (40 mL), the reaction mixture was stirred at 60° C. for 2 h, the reaction was monitored by LCMS till completion. Then 2,6-dimethylmorpholine (6.1 g, 53 mmol) was added into the reaction system, then the mixture was stirred at 110° C. for 2 h, after the reaction was complete as detected by TLC, the mixture was poured into $H_2O$ and extracted with EtOAc, the organic phase was dried over anhydrous sodium sulfate and concentrated to deliver a crude product. The crude product was purified by silica gel column chromatography (MeOH:EtOAc=5:1) to deliver compound 239-3 (3.5 g, yield 40%) as oil. MS ESI calcd for $C_{13}H_{18}N_2O_3[M+H]^+$ 251, found 251.

Step 2: NBS (1.6 g, 9 mmol) was added slowly into a solution of compound 239-3 (5 g, 35 mmol) in DMF (15 mL), the reaction mixture was stirred at room temperature for 6 h, and the reaction was monitored by LCMS till completion. Then the mixture was poured into $H_2O$, and extracted with EtOAc (100×3 mL), the organic phase was dried over anhydrous sodium sulfate and concentrated to deliver a crude product. The crude product was purified by silica gel column chromatography (PE:EtOAc=5:1) to deliver compound 239-4 (3 g, yield 91%) as white solid. MS ESI calcd for $C_{13}H_{17}BrN_2O_3[M+H]^+$ 329, found 329.

Step 3: Compound 239-4 (2 g, 6 mmol), compound 239-5 (1.82 g, 7.2 mmol) and KOAc (1.2 g, 12 mmol) were dissolved in dioxane (50 mL), then under nitrogen gas atmosphere, $Pd(dppf)Cl_2$ (440 mg, 0.6 mmol) was added, the reaction mixture was stirred at 120° C. for 3 h. After the reaction was complete, the mixture was poured into $H_2O$, and extracted with EtOAc. The organic phase was dried over anhydrous sodium sulfate and concentrated to deliver a crude product. The crude product was purified by silica gel column chromatography (PE:EtOAc=5:1) to deliver compound 239-6 (1.3 g, 60%) as yellow solid. MS ESI calcd for $C_{19}H_{29}BN_2O_5[M+H]^+$ 377, found 377.

Step 4: Compound 239-7 (1.74 g, 4 mmol), compound 239-6 (1.5 g, 4 mmol), and $Na_2CO_3$ (848 mg, 8 mmol) were dissolved in DMF (2 mL)/$H_2O$ (2 mL)/THF (10 mL), then $Pd(dppf)Cl_2$ (293 mg, 0.4 mmol) was added into the solution. The reaction system reacted at 70° C. overnight. After the reaction was complete as detected by LC-MS. The mixture was poured into $H_2O$, and extracted with EtOAc. The organic phase was dried over anhydrous sodium sulfate and concentrated to deliver a crude product. The crude product was purified by silica gel column chromatography (PE:EtOAc=2:1) to deliver compound 239-8 (474 mg, 21%) as red solid. MS ESI calcd for $C_{29}H_{25}BrN_4O_3[M+H]^+$ 557, found 557.

Step 5: Compound 239-8 (474 mg, 0.85 mmol), cyclopropyl boric acid (731 mg, 8.5 mmol) and $Na_2CO_3$ (180 mg, 1.7 mmol) were dissolved in DMF (2 mL)/$H_2O$ (2 mL)/THF (10 mL), then $Pd(dppf)Cl_2$ (73 mg, 0.1 mmol) was added into the solution. The reaction system was reacted at 70° C. overnight. After the reaction was complete as detected by LC-MS. The mixture was poured into $H_2O$, and extracted with EtOAc. The organic phase was dried over anhydrous sodium sulfate and concentrated to deliver a crude product. The crude product was purified by silica gel column chromatography (PE:EtOAc=2:1) to deliver compound 239-9 (200 mg, 21%) as red solid. MS ESI calcd for $C_{32}H_{30}N_4O_3$ $[M+H]^+$ 519, found 519.

Step 6: NaOH (80 mg, 2 mmol) was added into a solution of compound 239-9 (200 mg, 0.4 mmol) in MeOH (5 mL)/$H_2O$ (1 mL), the reaction system reacted at room temperature overnight. After the reaction was complete as detected by LC-MS, the crude product was purified by HPLC to deliver the title compound (30 mg, 15%) as yellow solid. $^1$H NMR (400 MHz, $CDCl_3$) δ 8.77 (d, J=8.4 Hz, 1H), 7.86-7.82 (m, 5H), 7.76-7.06 (m, 3H), 7.07 (d, J=8.4 Hz, 1H), 4.10 (d, J=12.0 Hz, 2H), 3.81 (m, 2H), 2.76 (m, 2H), 2.32 (m, 2H), 1.37 (d, J=6.0 Hz, 6H), 1.08 (m, 2H), 0.49 (d, J=5.2 Hz, 2H), MS ESI calcd for $C_{31}H_{28}N_4O_3[M+H]^+$ 505, found 505.

Embodiment 240

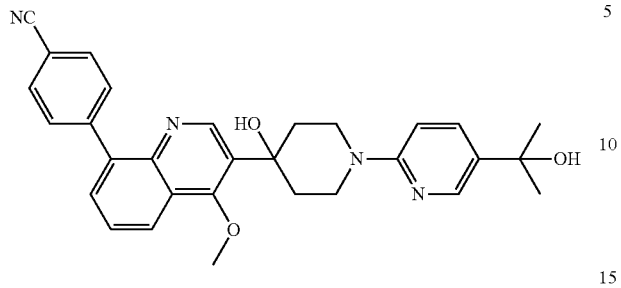

4-(3-(4-hydroxy-5'-(1-hydroxy-1-methyl-ethyl)-3,4,5,6-tetrahydro-2H-[1,2']bipyridyl-4-yl)4-methoxy-quinolin-8-yl)benzonitrile

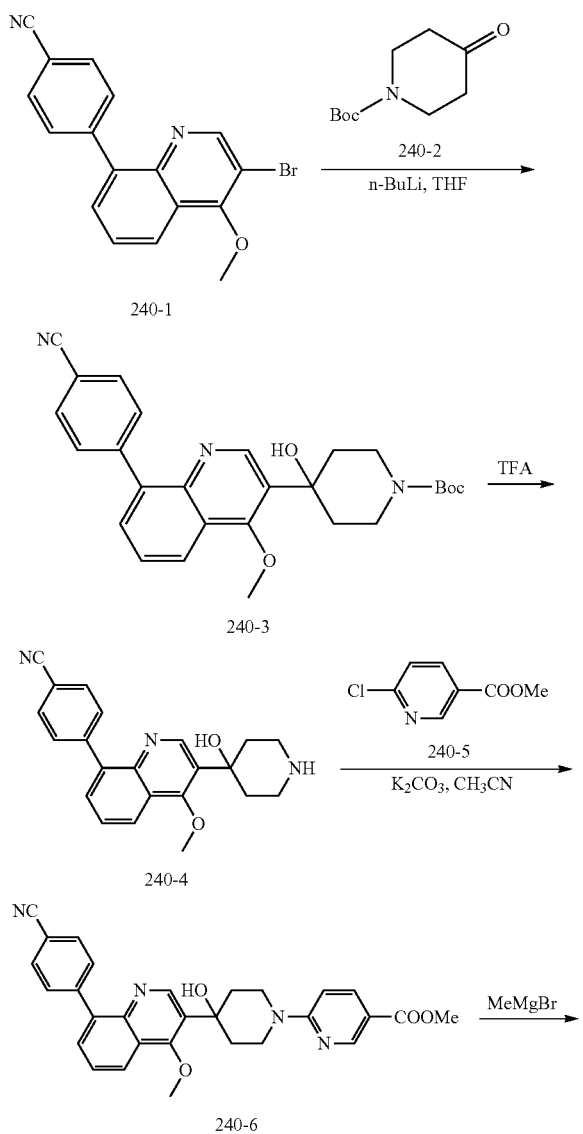

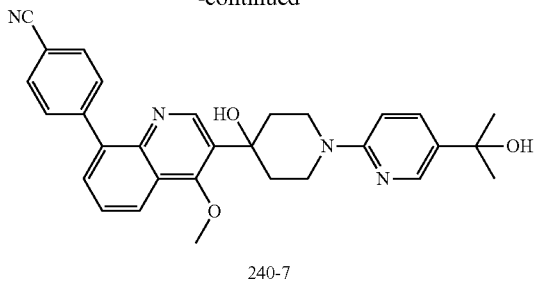

240-7

Step 1: n-BuLi (2.5 M, 1.25 mmol) was added slowly into a solution of compound 240-1 (170 mg, 0.5 mmol) in THF (10 mL) at −78° C., the reaction mixture was stirred at −78° C. for 0.5 h, then 2 (100 mg, 0.5 mmol) was added into the reaction system, the mixture was stirred at −78° C. for 2 h, after the reaction was complete as detected by TLC, the mixture was poured into NH$_4$Cl (aq), extracted with EtOAc, the organic phase was dried over anhydrous sodium sulfate and concentrated to deliver a crude product. The crude product was purified by silica gel column chromatography (MeOH:EtOAc=2:1) to deliver compound 240-3 (100 mg, yield 33%) as oil. MS ESI calcd for C$_{27}$H$_{29}$N$_3$O$_4$[M+H]$^+$ 460, found 460.

Step 2: CF$_3$COOH (2 mL) was added into a solution of compound 240-3 (400 mg, 0.9 mmol) in DCM (4 mL), the reaction mixture was stirred at room temperature for 1 h, the reaction was monitored by TLC till completion. Then the solvent was evaporated to dry, the crude product was used for the next step directly.

Step 3: Compound 240-4 (250 mg, 0.7 mmol), K$_2$CO$_3$ (292 mg, 2.1 mmol) were dissolved in ACN (10 mL), then 240-5 (120 mg, 0.7 mmol) was added, the reaction mixture was stirred at 100° C. for 8 h. After the reaction was complete as detected by LCMS, the filtrate was concentrated to give a crude product. The crude product was purified by silica gel column chromatography (PE:EtOAc=1:1) to deliver compound 240-6 (200 mg, 58%) as white solid. MS ESI calcd for C$_{29}$H$_{26}$N$_4$O$_4$[M+H]$^+$ 495, found 495.

Step 4: MeMgBr (1 mL, 3.0 mmol) was added dropwise slowly into a solution of compound 240-6 (200 mg, 0.4 mmol) in THF (10 mL) at room temperature, the reaction mixture was stirred at room temperature for 30 min. After the reaction was complete as detected by LC-MS. The mixture was poured into NH$_4$Cl (aq), and extracted with EtOAc (100×3 mL). The organic phase was dried over anhydrous sodium sulfate and concentrated to deliver a crude product. The crude product was purified by HPLC to deliver the title compound (25 mg, 13%) as yellow solid. $^1$H NMR (400 MHz, CDCl$_3$) δ 8.95 (s, 1H), 8.35 (d, J=3.2 Hz, 1H), 8.15 (dd, J=1.2, 8.0 Hz, 1H), 7.79 (s, 4H), 7.74-7.68 (m, 3H), 6.76 (d, J=7.2 Hz, 1H), 4.29-4.26 (m, 2H), 4.20 (s, 3H), 3.86 (s, 1H), 3.51 (t, J=12 Hz, 2H), 2.40-2.33 (m, 2H), 2.09-2.03 (m, 2H), 1.61 (s, 6H). MS ESI calcd for C$_{30}$H$_{30}$N$_4$O$_3$[M+H]$^+$ 495, found 495.

Embodiment 241

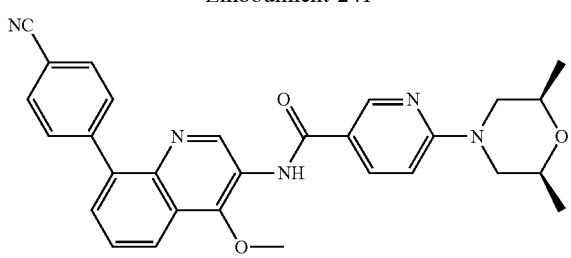

N-(8-(4-cyanophenyl)-4-methoxyquinolin-3-yl)-6-(2,6-dimethylmorpholino-4-yl) nicotinamide

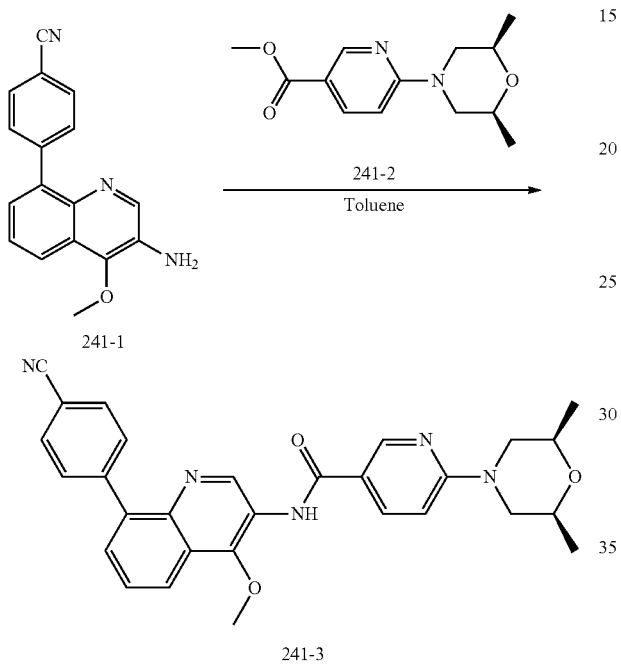

Compound 241-1 (100 mg, 0.36 mmol), compound 241-2 (100 mg, 0.4 mmol), trimethyl aluminum solution (0.9 mL, 0.9 mmol) were dissolved in toluene (2 mL), the reaction mixture was stirred at 800° C. for 12 h. The reaction mixture was cooled to room temperature, H$_2$O was added, the solution was extracted with EtOAc (50 mL×2), the organic phase was washed with H$_2$O, brines respectively, dried over over anhydrous sodium sulfate, filtrated and concentrated under reduced pressure, the crude product was purified by silica gel column chromatography to deliver the title compound (80 mg, yield 44%) as white solid. $^1$H NMR (400 MHz, CD$_3$OD) δ ppm 8.89 (s, 1H), 8.84 (s, 1H), 8.33-8.36 (d, J=8.4 Hz, 1H), 8.17 (d, J=8.8 Hz, 1H), 7.71-7.85 (m, 5H), 6.94 (d, J=9.2 Hz, 1H), 5.51 (s, 1H), 4.35 (d, J=13.2 Hz, 2H), 4.16 (s, 3H), 2.66 (t, J=12.8 Hz, 2H), 1.28 (d, J=6.4 Hz, 6H). MS ESI calcd for C$_{29}$H$_{27}$N$_5$O$_3$ [M+H]$^+$ 494, found 494.

Embodiment 242

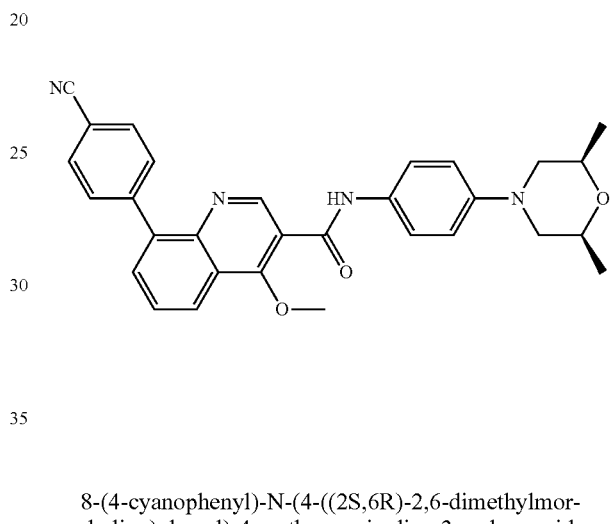

8-(4-cyanophenyl)-N-(4-((2S,6R)-2,6-dimethylmorpholino)phenyl)-4-methoxyquinoline-3-carboxamide

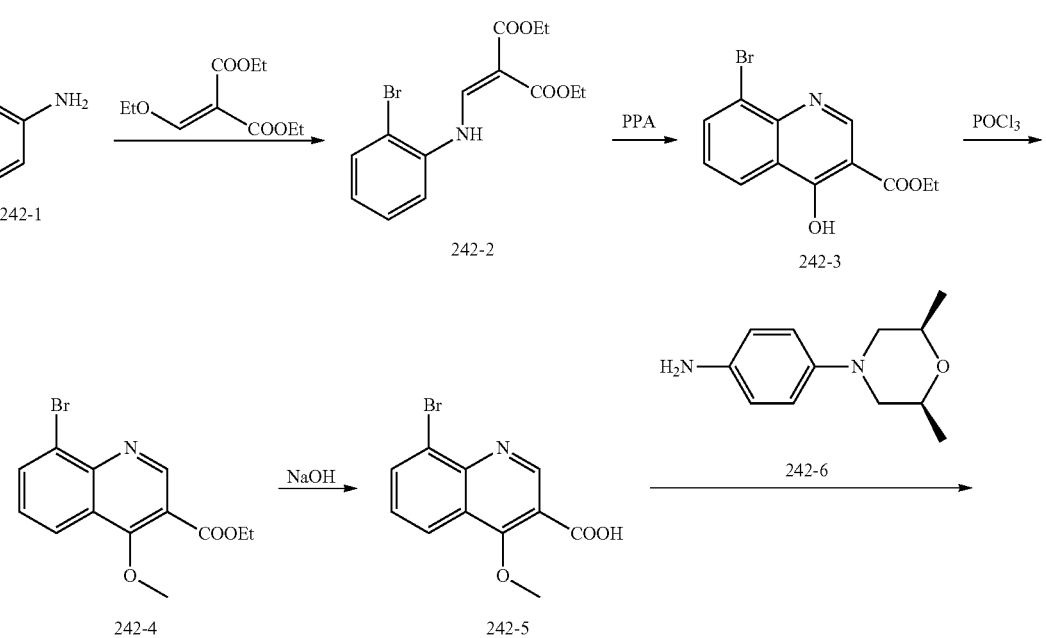

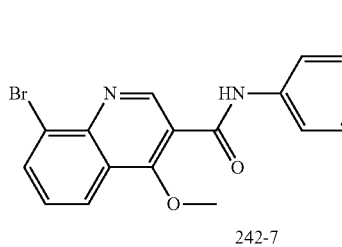

242-7

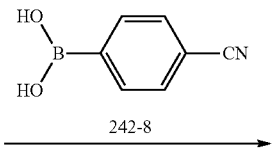

242-8

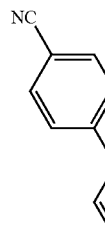

242-9

Step 1: (Diethyl ethoxymethylene)malonate (13 g, 60 mmol), 2-bromoaniline (10.3 g, 60 mmol) were mixed and stirred at 100° C. for 2 h. After cooled to room temperature, the reaction mixture was poured into methanol, recrystallized with methanol to deliver compound 242-2 (14.5 g, yield 70.7%) as yellow solid. MS ESI calcd for $C_{14}H_{16}BrNO_4$ [M+H]$^+$ 342, found 342.

Step 2: Compound 242-2 (10 g, 29.2 mmol) in Ph$_2$O (100 mL) was stirred at reflux for 30 min, then cooled to room temperature, hexane was added, the mixture was filtrated to deliver compound 242-3 (2.8 g, yield 32.6%) as brown solid. MS ESI calcd for $C_{12}H_{10}BrNO_3$ [M+H]$^+$ 295, found 295.

Step 3: Compound 242-3 (500 mg, 1.7 mmol) was dissolved in POCl$_3$ (4 mL), and the mixture was stirred at 110° C. for 1 h. Then the reaction mixture was poured into methanol and sodium carbonate aqueous solution was added. The mixture was extracted with EtOAc, dried over over anhydrous sodium sulfate, filtrated and concentrated under vacuum to deliver compound 242-4 (400 mg, yield 76%) as brown solid. MS ESI calcd for $C_{13}H_{12}BrNO_3$ [M+H]$^+$ 310, found 310.

Step 4: Compound 242-4 (527 mg, 1.7 mmol) was dissolved in methanol (5 mL), H$_2$O (1 mL), NaOH (340 mg, 8.5 mmol) was added, the reaction mixture was stirred at room temperature for 5 h. Then the mixture was poured into H$_2$O, then HCl solution was added to adjust pH=7, the mixture was extracted with EtOAc, dried over over sodium sulfate, filtrated and concentrated under vacuum to deliver compound 242-5 (478 mg, yield 99%) as yellow solid. MS ESI calcd for $C_{11}H_8BrNO_3$ [M+H]$^+$ 282, found 282.

Step 5: Compound 242-5 (478 mg, 1.7 mmol), 4-((2S,6R)-2,6-dimethylmorpholino)aniline 6 (525 mg, 2.55 mmol), TEA (515 mg, 5.1 mmol) were dissolved in DMF (5 mL), HATU (980 mg, 2.55 mmol) was added, the reaction mixture was stirred at room temperature for 2 h. Then the reaction mixture was poured into H$_2$O, extracted with EtOAc, the organic phase was dried over sodium sulfate, filtrated and concentrated under vacuum, the residue was purified by silica gel column chromatography to deliver compound 242-7 (400 mg, yield 50%) as yellow solid. MS ESI calcd for $C_{23}H_{24}BrN_3O_3$ [M+H]$^+$ 470, found 470.

Step 6: The title compound (100 mg, yield 32%) was synthesized according to the above-mentioned method as white solid. $^1$H NMR (400 MHz, CDCl$_3$) δ 9.49 (s, 1H), 9.23 (s, 1H), 8.28 (d, J=8.0 Hz, 1H), 7.74-7.84 (m, 7H), 7.65-7.67 (m, 2H), 7.02 (s, 1H), 4.21 (s, 3H), 3.90 (s, 1H), 3.44-3.49 (m, 3H), 2.48 (s, 2H), 1.28 (d, J=6.0 Hz, 6H). MS ESI calcd for $C_{30}H_{28}N_4O_3$ [M+H]$^+$ 493, found 493.

Embodiment 243

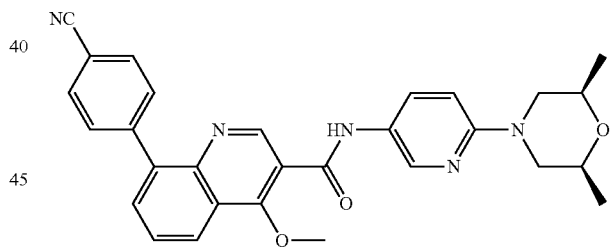

8-(4-cyanophenyl)-N-(6-((2S,6R)-2,6-dimethylmorpholino)pyridin-3-yl)-4-methoxyquinoline-3-carboxamide

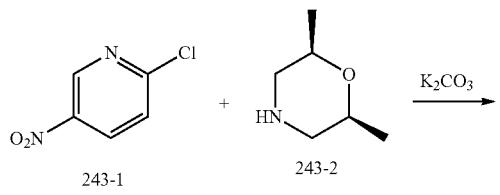

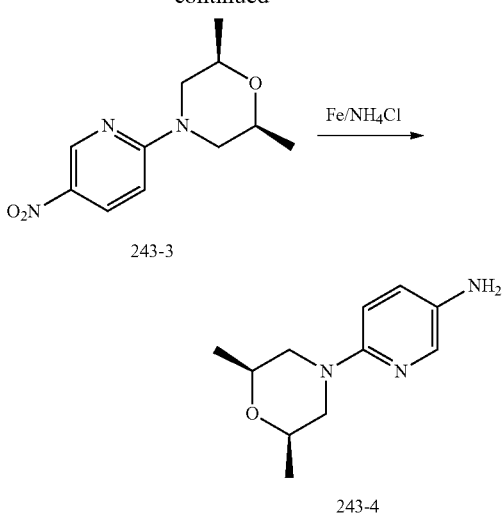

243-3

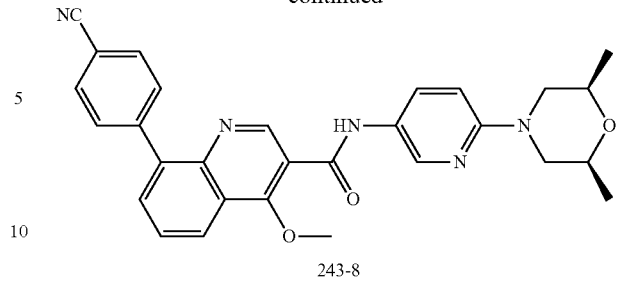

243-8

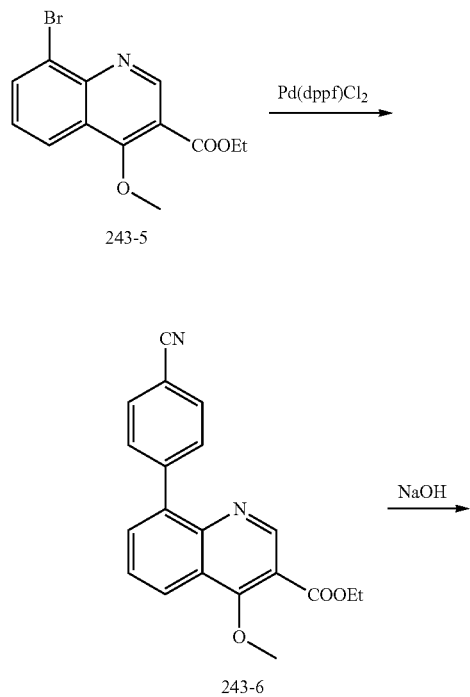

243-4

243-5

243-6

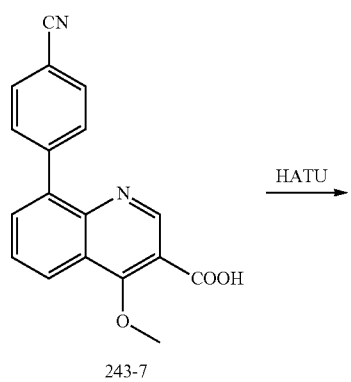

243-7

Step 1: Compound 2-chloro-5-nitropyridine (5 g, 32 mmol) and $K_2CO_3$ (8.8 g, 64 mmol) were dissolved in MeCN (40 mL), (2S,6R)-2,6-dimethylmorpholine (4.4 g, 38.4 mmol) was added. The reaction mixture was stirred at 110° C. for 2 h. Then the reaction mixture was filtrated, the filtrate was concentrated to deliver compound 243-3 (7.3 g) as yellow solid. MS ESI calcd for $C_{11}H_{15}N_3O_3$ [M+H]$^+$ 238, found 238.

Step 2: Compound 243-3 (7.3 g, 31 mmol) and ammonium chloride (16.7 g, 310 mmol) were dissolved in MeOH (80 mL) and $H_2O$ (80 mL), iron powder (20.8 g, 372 mmol) was added. The reaction mixture was stirred at 80° C. for 3 h. Then the mixture was filtrated, the filtrate was concentrated, the residue was dissolved in acetone, filtrated and concentrated under vacuum, the crude product was purified by silica gel column chromatography to deliver compound 243-4 (800 mg) as brown solid. MS ESI calcd for $C_{11}H_{17}N_3O$ [M+H]$^+$ 208, found 208.

Step 3: 4-cyanophenyl boric acid (1.8 g, 12 mmol), compound 243-4 (3.1 g, 10 mmol) and sodium carbonate (2.1 g, 20 mmol) were dissolved in DMF (5 mL), $H_2O$ (5 mL) and THF (25 mL), Pd(dppf)Cl$_2$ (732 mg, 1 mmol) was added. The reaction mixture was stirred at 70° C. for 2 h. Then the mixture was poured into $H_2O$, extracted with EtOAc, the organic phase was washed with brines, dried over over sodium sulfate, filtrated and concentrated, the residue was purified by silica gel column chromatography to deliver compound 243-6 (2.8 g) as white solid. MS ESI calcd for $C_{20}H_{16}N_2O_3$ [M+H]$^+$ 333, found 333.

Step 4: Compound 243-6 (1.8 g, 5.4 mmol) was dissolved in MeOH (10 mL) and $H_2O$ (4 mL), NaOH (1 g, 27 mmol) was added, the reaction mixture was stirred at room temperature for 2 h. Then the mixture was poured into $H_2O$, extracted with EtOAc, the aqueous phase was acidified to pH=4 with 1 N hydrochloric acid, and then extracted with EtOAc, the organic phase was washed with brines, dried over over sodium sulfate, filtrated and concentrated under reduced pressure to deliver compound 243-7 (580 mg) as white solid. MS ESI calcd for $C_{18}H_{12}N_2O_3$ [M+H]$^+$ 305, found 305.

Step 5: Compound 243-7 (200 mg, 0.65 mmol), HATU (494 mg, 1.3 mmol) and compound 243-4 (136 mg, 0.65 mmol) were dissolved in DMF (5 mL), DIPEA (387 mg, 3 mmol) was added. The reaction mixture was stirred at room temperature overnight, the reaction mixture was purified by preparative HPLC to deliver the title compound (100 mg) as white solid. $^1$H NMR (400 MHz, CDCl3) δ 9.49 (s, 1H), 9.23 (s, 1H), 8.27-8.30 (m, 3H), 7.73-7.85 (m, 7H), 6.73-6.75 (m, 1H), 4.21 (s, 3H), 4.05-4.08 (m, 2H), 3.74-3.79 (m, 2H), 2.56-2.61 (m, 2H), 1.29 (d, J=6.0 Hz, 6H). MS ESI calcd for $C_{29}H_{27}N_5O_3$ [M+H]$^+$ 494, found 494.

Embodiment 244

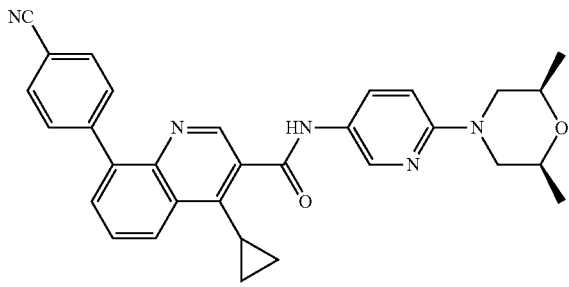 [SMILES: C[C@@H]1CN(c2ccc(NC(=O)c3cnc4c(-c5ccc(C#N)cc5)cccc4c3C3CC3)cn2)C[C@H](C)O1]

8-(4-cyanophenyl)-4-cyclopropyl-N-(6-((2S,6R)-2,6-dimethylmorpholino)pyridin-3-yl) quinoline-3-carboxamide

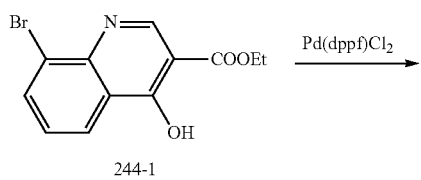

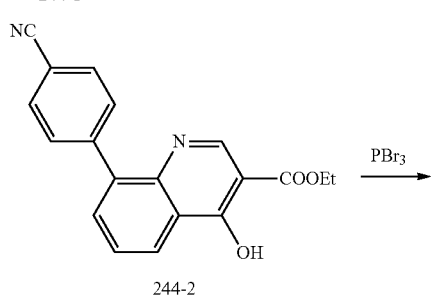

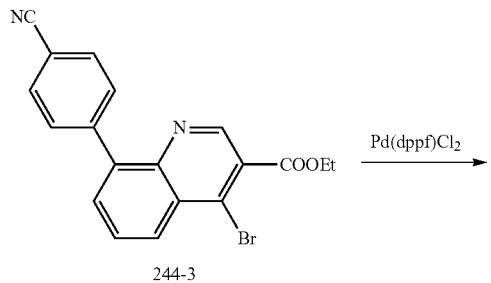

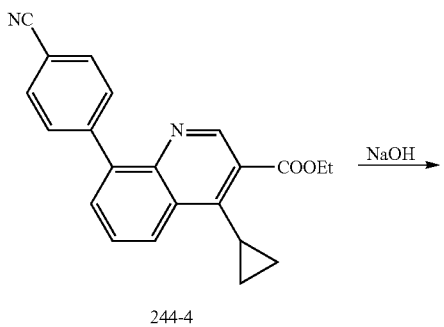

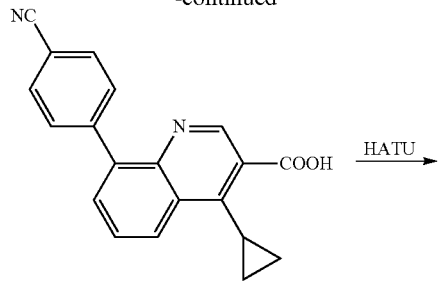

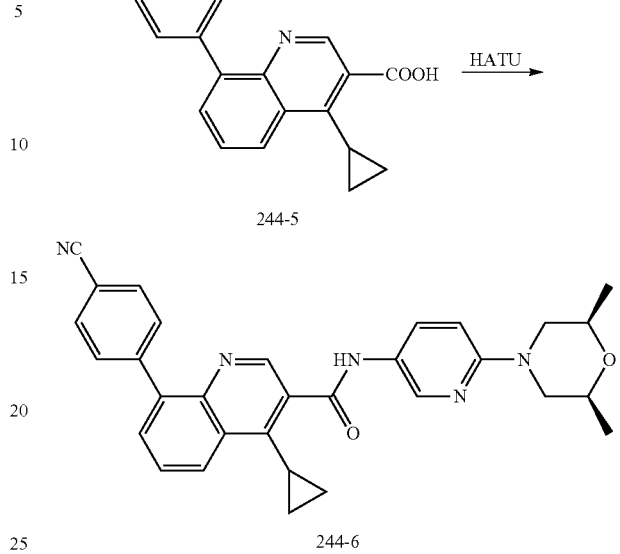

Step 1: 4-cyanophenyl boric acid (2 g, 14.4 mmol), ethyl-8-bromo-4-hydroxyquinolyl-3-carboxylic acid ethyl ester (3.5 g, 12 mmol) and sodium carbonate (2.5 g, 24 mmol) were dissolved in DMF (5 mL), H$_2$O (5 mL) and THF (25 mL), Pd(dppf)Cl$_2$ (878 mg, 1.2 mmol) was added. The reaction mixture was stirred at 70° C. for 2 h. Then the mixture was poured into H$_2$O, filtrated to deliver compound 244-2 (3.2 g) as brown solid. MS ESI calcd for C$_{19}$H$_{14}$N$_2$O$_3$ [M+H]$^+$ 319, found 319.

Step 2: Compound 244-2 (3.2 g, 10 mmol) was dissolved in DMF (40 mL), PBr$_3$ (4 mL, 10 M) was added, the reaction mixture was stirred at room temperature for 1 h. Then the mixture was poured into H$_2$O, the solid was filtrated and washed with H$_2$O, dried in the air to deliver compound 244-3 (3.0 g) as brown solid. MS ESI calcd for C$_{19}$H$_{13}$BrN$_2$O$_2$ [M+H]$^+$ 381, found 381.

Step 3: Cyclopropyl boric acid (6.7 g, 78 mmol), compound 244-3 (3.0 g, 7.8 mmol) and sodium carbonate (1.7 g, 15.6 mmol) were dissolved in DMF (5 mL), H$_2$O (5 mL) and THF (25 mL), Pd(dppf)Cl$_2$ (571 mg, 0.78 mmol) was added. The reaction mixture was stirred at 70° C. for 2 h. Then the mixture was poured into H$_2$O, extracted with EtOAc, the organic phase was washed with brines, dried over sodium sulfate, filtrated and concentrated under reduced pressure, the crude was purified by silica gel column chromatography to deliver compound 244-4 (1.8 g) as yellow solid. MS ESI calcd for C$_{22}$H$_{18}$N$_2$O$_2$ [M+H]$^+$ 343, found 343.

Step 4: Compound 244-4 (1.8 g, 5.4 mmol) was dissolved in MeOH (10 mL) and H$_2$O (4 mL), NaOH (1 g, 27 mmol) was added. The reaction mixture was stirred at room temperature for 2 h. Then the mixture was poured into H$_2$O, extracted with EtOAc, the aqueous phase was acidified with 1N HCl solution, extracted with EtOAc, the organic phase was washed with brines, dried over sodium sulfate, filtrated and concentrated under reduced pressure to deliver compound 244-5 (570 mg) as yellow solid. MS ESI calcd for C$_{20}$H$_{14}$N$_2$O$_2$ [M+H]$^+$ 315, found 315.

Step 5: Compound 244-5 (200 mg, 0.65 mmol), HATU (494 mg, 1.3 mmol) and 6-((2S,6R)-2,6-dimethylmorpholino)pyridine-3-amine (136 mg, 0.65 mmol) were dissolved in DMF (5 mL), DIPEA (387 mg, 3 mmol) was added. The reaction mixture was stirred at room temperature overnight, purified by preparative HPLC (100 mg) to deliver the title compound as white solid. $^1$H NMR (400 MHz, CDCl$_3$) δ 10.2 (s, 1H), 8.95 (s, 1H), 8.61-8.74 (m, 3H), 7.75-7.78 (m, 4H), 7.63-7.65 (m, 2H), 7.08 (d, J=9.2 Hz, 1H), 4.04 (d, J=13.2 Hz, 2H), 3.74 (s, 2H), 2.83-2.89 (m, 2H), 2.64 (s, 1H), 1.27 (d, J=6.0 Hz, 8H), 0.72-0.73 (m, 1H). MS ESI calcd for C$_{31}$H$_{29}$N$_5$O$_2$ [M+H]$^+$ 504, found 504.

Embodiment 245

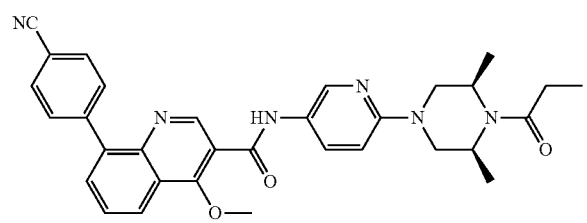 [SMILES: CCC(=O)N1[C@H](C)CN(c2ccc(NC(=O)c3cnc4c(-c5ccc(C#N)cc5)cccc4c3OC)cn2)C[C@@H]1C]

8-(4-cyanophenyl)-N-(6-((3S,5R)-3,5-dimethyl-4-propionylpiperazin-1-yl)pyridin-3-yl)-4-methoxyquinoline-3-carboxamide

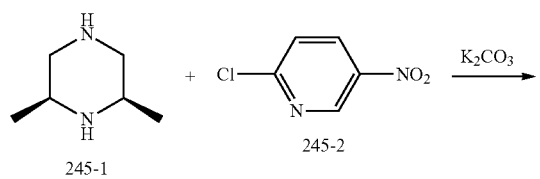

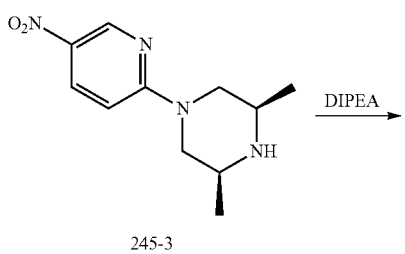

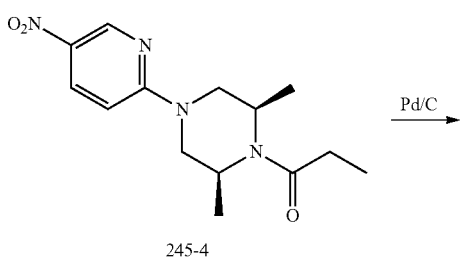

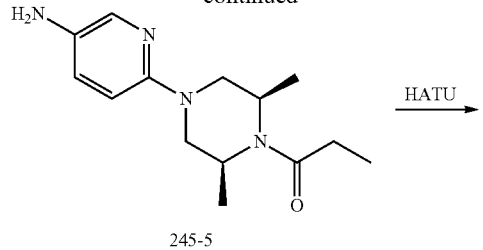

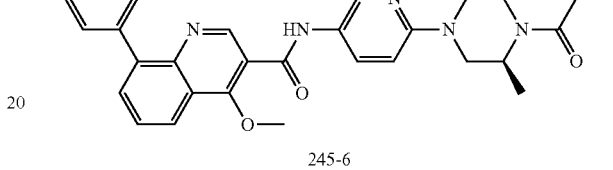

Step 1: 2-chloro-5-nitropyridine (5 g, 32 mmol) and K$_2$CO$_3$ (8.8 g, 64 mmol) were dissolved in acetonitrile (40 mL), compound 245-1 (4.3 g, 38.4 mmol) was added. The reaction mixture was stirred at 80° C. for 1 h, then the reaction mixture was filtrated, concentrated to deliver compound 245-3 (4.5 g) as yellow solid. MS ESI calcd for C$_{11}$H$_{16}$N$_4$O$_2$ [M+H]$^+$ 237, found 237.

Step 2: Compound 245-3 (4.5 g, 19 mmol) and DIPEA (7.4 g, 57 mmol) in DCM (40 mL), propionyl chloride (2.2 g, 23 mmol) was added. The reaction mixture was stirred at 0° C. for 30 min. Then the reaction mixture was poured into H2O, extracted with EtOAc, the organic phase was washed with brines, dried over sodium sulfate, filtrated and concentrated under reduced pressure to deliver compound 245-4 (3.2 g) as yellow solid. MS ESI calcd for C$_{14}$H$_{20}$N$_4$O$_3$ [M+H]$^+$ 293, found 293.

Step 3: Compound 245-4 (3.2 g, 11 mmol) and Pd/C (0.32 g) were dissolved in methanol (500 mL), the reaction mixture was stirred at room temperature under a hydrogen gas pressure of 40 psi overnight. Then the reaction mixture was filtrated, the solvent was concentrated under reduced pressure to deliver crude compound 245-5 (800 mg) as red oil. MS ESI calcd for C$_{14}$H$_{22}$N$_4$O [M+H]$^+$ 263, found 263.

Step 4: A solution of 8-(4-cyanophenyl)-4-methoxyquinoline-3-carboxylic acid (100 mg, 0.33 mmol), HATU (251 mg, 0.66 mmol) and compound 245-5 (86 mg, 0.33 mmol) were dissolved in DMF (5 mL), DIPEA (86 mg, 0.33 mmol) was added. After stirred at room temperature overnight, the reaction mixture was purified by HPLC to deliver the title compound (80 mg) as white solid. $^1$H NMR (400 MHz, CDCl$_3$) δ 9.47 (s, 1H), 9.24 (s, 1H), 8.26-8.28 (m, 3H), 7.72-7.84 (m, 6H), 6.77 (d, J=9.2 Hz, 1H), 4.21 (s, 3H), 3.05-3.10 (m, 2H), 1.34 (s, 6H), 1.19 (t, J=7.4 Hz, 1H). MS ESI calcd for C$_{32}$H$_{32}$N$_6$O$_3$ [M+H]$^+$ 548, found 548.

The compound listed in table 22 was synthesized by compound 245-5 and corresponding acid.

| Embodiment | structure | NMR |
|---|---|---|
| 246 | 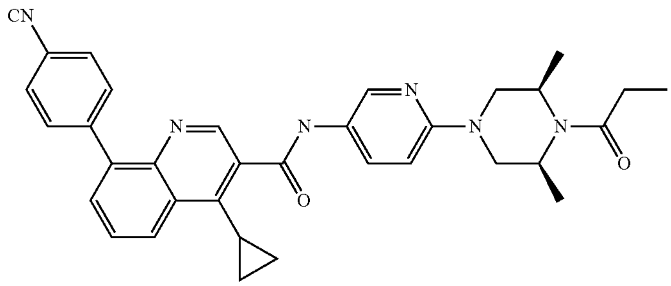 | $^1$H NMR (400 MHz, CDCl$_3$) δ 10.02 (s, 1H), 8.93 (s, 1H), 8.60-8.70 (m, 3H), 7.74-7.78(m, 4H), 7.63-7.65(m, 2H), 7.10(d, J = 9.6 Hz, 1H), 3.78-3.80 (m, 2H), 2.55 (s, 1H), 1.15-1.35 (m, 12H), 0.72-0.74 (m,2H). MS ESI Calcd for C$_{34}$H$_{34}$N$_6$O$_2$ [M + H]$^+$ 559, found 559. |

Embodiment 247

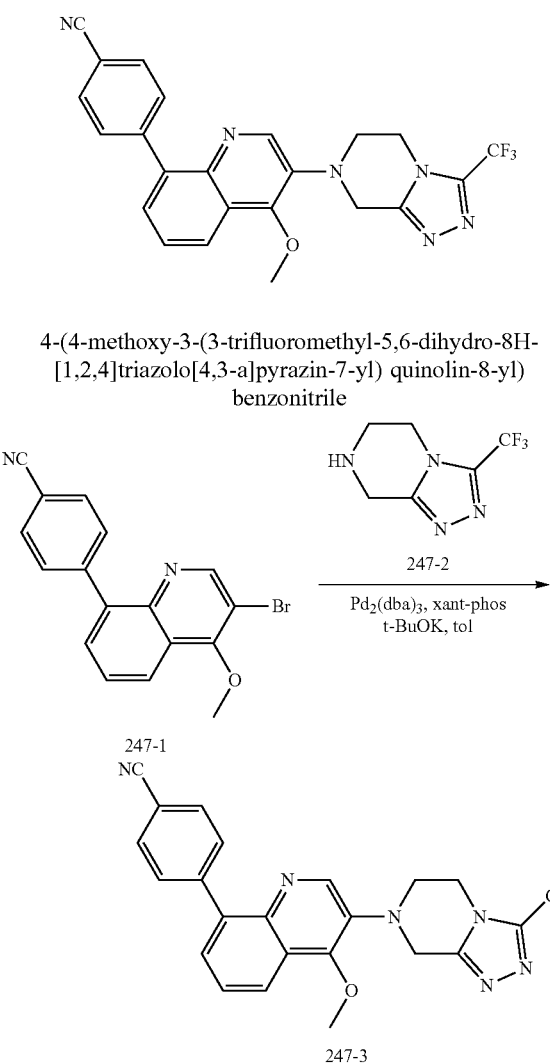

4-(4-methoxy-3-(3-trifluoromethyl-5,6-dihydro-8H-[1,2,4]triazolo[4,3-a]pyrazin-7-yl) quinolin-8-yl) benzonitrile Compound 247-1 (339 mg, 1 mmol), Xantphos (115 mg, 0.2 mmol), 247-2 (192 mg, 1 mmol) and t-BuONa (200 mg, 2 mmol) were dissolved in toluene (10 mL), then under nitrogen gas atmosphere, Pd$_2$(dba)$_3$ (92 mg, 0.1 mmol) was added, the reaction mixture was stirred at 110° C. for 2 h. After the reaction was complete, the mixture was poured into H$_2$O, extracted with EtOAc. The organic phase was dried over anhydrous sodium sulfate, concentrated to give a crude product. The crude product was purified by HPLC to deliver the title compound (30 mg, 7%) as yellow solid. $^1$H NMR (400 MHz, CDCl$_3$) δ 9.48 (s, 1H), 8.45 (d, J=8.0 Hz, 1H), 7.87 (m, 4H), 7.66 (m, 2H), 4.98 (s, 1H), 4.45-4.39 (m, 5H), 4.02 (s, 2H). MS ESI calcd for C$_{23}$H$_{17}$F$_3$N$_6$O[M+H]$^+$ 451, found 451.

Embodiment 248

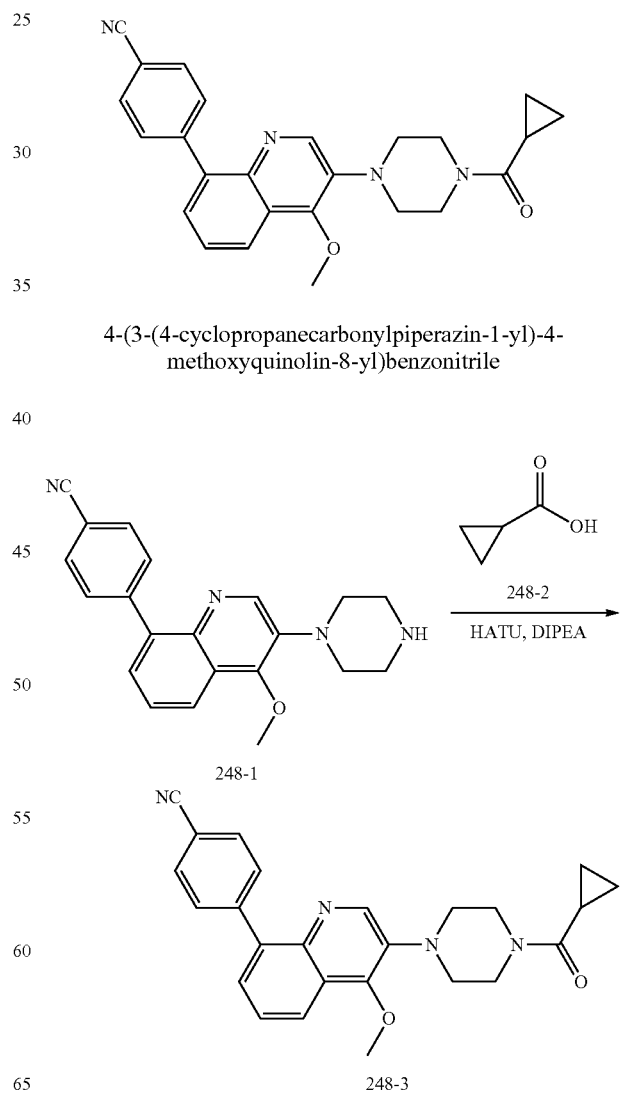

4-(3-(4-cyclopropanecarbonylpiperazin-1-yl)-4-methoxyquinolin-8-yl)benzonitrile

Compound 248-1 (172 mg, 0.5 mmol), HATU (380 mg, 1 mmol) and 248-2 (86 mg, 1 mmol) were dissolved in DMF (4 mL), then DIPEA (194 mg, 1.5 mmol) was added, the reaction mixture was stirred at room temperature overnight. The reaction mixture was monitored by LCMS till completion. The reaction system was purified by HPLC to deliver the title compound (40 mg, 20%) as yellow solid. $^1$H NMR (400 MHz, CDCl$_3$) δ 8.76 (s, 1H), 8.4 (t, J=4.8 Hz, 1H), 7.82-7.79 (m, 4H), 7.63-7.59 (m, 2H), 4.16 (s, 3H), 3.92 (m, 4H), 3.33-3.30 (m, 4H), 1.85-1.80 (m, 1H), 1.08-1.05 (m, 2H), 0.86-0.83 (m, 2H). MS ESI calcd for C$_{25}$H$_{24}$N$_4$O$_2$[M+H]$^+$ 413, found 413.

Embodiment 249

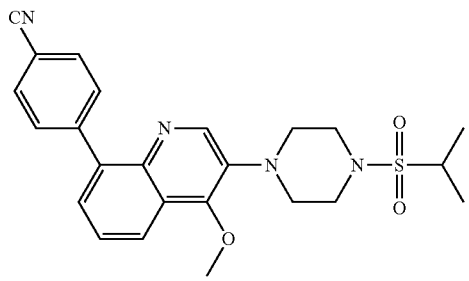 [SMILES: COc1c(N2CCN(S(=O)(=O)C(C)C)CC2)cnc2c(-c3ccc(C#N)cc3)cccc12]

4-(4-methoxy-3-(4-(propane-2-sulfonyl)piperazin-1-yl)-quinolin-8-yl)benzonitrile

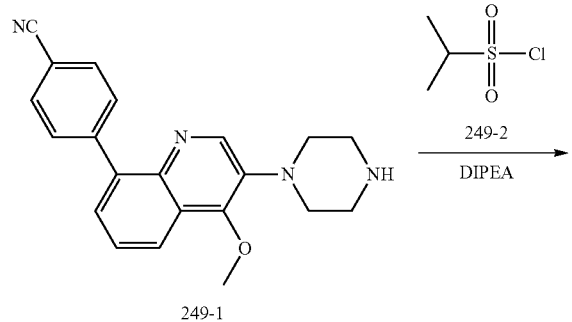

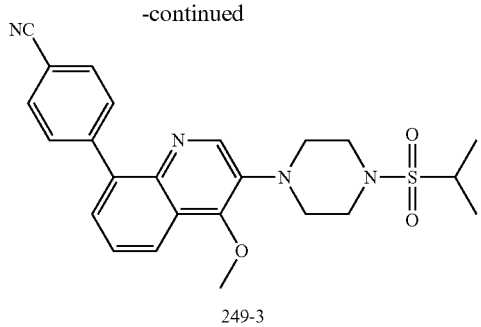

249-3

Compound 249-1 (172 mg, 0.5 mmol) and DIPEA (194 mg, 1.5 mmol) were dissolved in DCM (5 mL), then 2 (142 mg, 1 mmol) was added, the reaction mixture was stirred at room temperature for 30 min. The reaction mixture was monitored by LCMS till completion. The reaction mixture was poured into H$_2$O, extracted with EtOAc. The organic phase was dried over anhydrous sodium sulfate, concentrated to give a crude product. The crude product was purified by HPLC to deliver the title compound (20 mg, 10%) as yellow solid. $^1$H NMR (400 MHz, CDCl$_3$) δ 8.75 (s, 1H), 8.22 (dd, J=4.4, 5.6 Hz, 1H), 7.82-7.77 (m, 4H), 7.63-7.61 (m, 2H), 4.13 (s, 3H), 3.62-3.60 (m, 4H), 3.33-3.30 (m, 4H), 3.31-3.26 (m, 1H), 1.43 (d, J=7.2 Hz, 6H). MS ESI calcd for C$_{24}$H$_{26}$N$_4$O$_3$S[M+H]$^+$ 451, found 451.

Embodiment 250

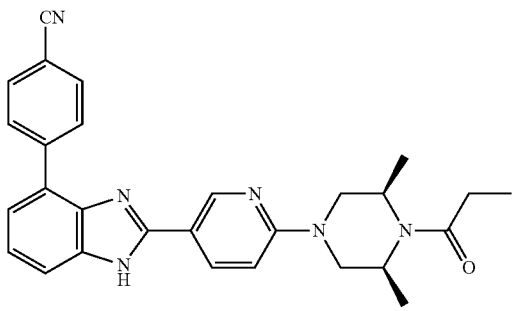

4-(2-(6-(3,5-dimethyl-4-propionylpiperazin-1-yl)pyridin-3-yl)-1H-benzo[d]imidazol-4-yl)benzonitrile

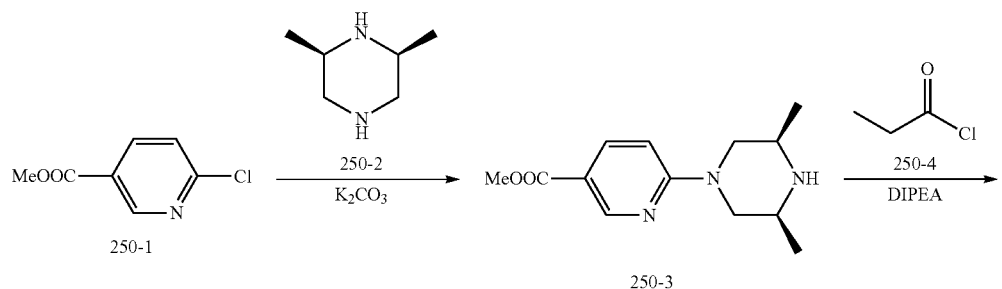

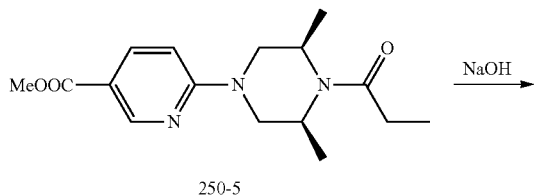
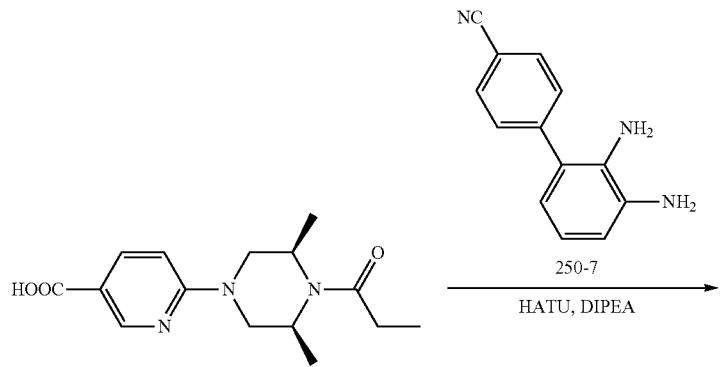
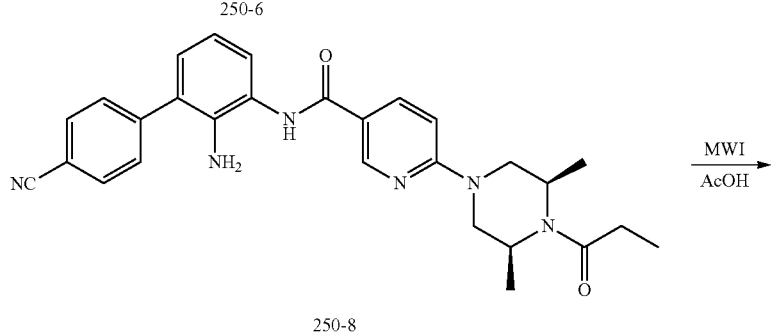
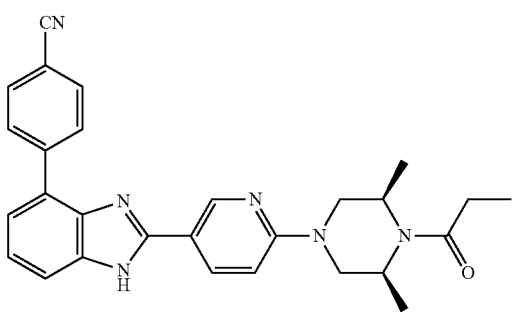 [SMILES: CCC(=O)N1[C@H](C)CN(c2ccc(-c3nc4c(-c5ccc(C#N)cc5)cccc4[nH]3)cn2)C[C@@H]1C]
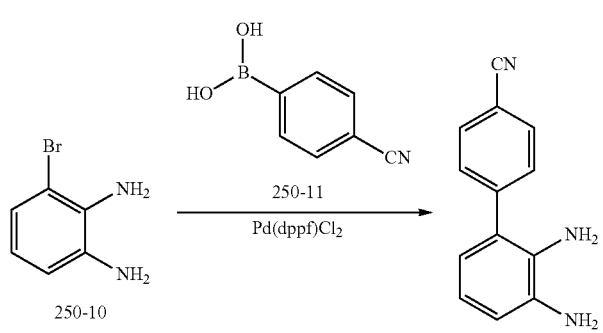

Step 1: Compound 250-2 (1.14 g, 10 mmol) was added into a solution of compound 250-1 (1.71 g, 10 mmol) and K₂CO₃ (2.78 g, 20 mmol) in DMF (20 mL), the reaction mixture was stirred at 110° C. for 2 h, monitored by LCMS till completion. Then the mixture was poured into H₂O, extracted with EtOAc, the organic phase was dried over anhydrous sodium sulfate, concentrated to give a crude product. The crude product was purified by silica gel column chromatography (PE:EtOAc=1:1) to deliver compound 250-3 (2.3 g, yield 92%) as oil. MS ESI calcd for C₁₃H₁₉N₃O₂[M+H]⁺ 250, found 250.

Step 2: 250-4 (1.0 g, 10.8 mmol) was added slowly into a solution of compound 250-3 (2.3 g, 9 mmol) and DIPEA (2.3 g, 18 mmol) in DCM (30 mL), the reaction mixture was stirred at 0° C. for 30 min, monitored by LCMS till completion. Then the mixture was poured into H₂O, extracted with EtOAc (100×3 mL), the organic phase was dried over anhydrous sodium sulfate, concentrated to deliver crude product 250-5 (2.5 g, yield 91%). MS ESI calcd for C₁₆H₂₃N₃O₃[M+H]⁺ 306, found 306.

Step 3: NaOH (1.28 g, 32 mmol) was added into a solution of compound 250-5 (2.5 g, 8 mmol) in MeOH (10 mL)/H₂O (2 mL), the reaction mixture was stirred at 40° C. for 1 h. After the reaction was complete, the mixture was poured into H₂O, washed with EtOAc, the aqueous phase was acidified to pH=4 with 1 N HCl solution, then extracted with EtOAc, the organic phase was dried over anhydrous sodium sulfate, concentrated to deliver crude product 250-6 (1 g, 43%). The crude product was used for the next step directly.

Step 4: Compound 250-10 (374 mg, 2 mmol), compound 250-11 (294 mg, 2 mmol) and Na₂CO₃ (424 mg, 4 mmol) were dissolved in DMF (2 mL)/H₂O (2 mL)/THF (10 mL), then Pd(dppf)Cl₂ (146 mg, 0.2 mmol) was added into the solution. The reaction system was stirred at 70° C. overnight, monitored by LC-MS till completion. The mixture was poured into H₂O, extracted with EtOAc. The organic phase was dried over anhydrous sodium sulfate, concentrated to give a crude product. The crude product was purified by silica gel column chromatography (PE: EtOAc=1:1) to deliver compound 250-7 (200 mg, 50%) as red solid. MS ESI calcd for C₁₃H₁₁N₃[M+H]⁺ 210, found 210.

Step 5: Compound 250-7 (200 mg, 1 mmol), HATU (760 mg, 2 mmol) and 250-6 (291 mg, 1 mmol) were dissolved in DMF (10 mL), then DIPEA (387 mg, 3 mmol) was added into the solution. The reaction system was stirred at room temperature for 1 h, monitored by LC-MS till completion. The mixture was poured into H₂O, extracted with EtOAc. The organic phase was dried over anhydrous sodium sulfate, concentrated to give a crude product. The crude product was purified by silica gel column chromatography (PE: EtOAc=1:1) to deliver compound 250-5 (200 mg, 42%) as brown solid. MS ESI calcd for C₂₈H₃₀N₆O₂[M+H]⁺ 483, found 483.

Step 6: Compound 250-5 (80 mg, 0.16 mmol) was dissolved in AcOH (2 mL), the reaction system reacted under microwave at 180° C. for 40 min. The reaction mixture was monitored by LC-MS till completion. The crude product was purified by HPLC to deliver the title compound (10 mg, 14%) as yellow solid. ¹H NMR (400 MHz, CDCl₃) δ 8.83-8.82 (m, 1H), 8.30-8.26 (m, 3H), 7.78-7.62 (m, 3H), 7.52-7.32 (m, 2H), 6.79-6.75 (m, 1H), 3.23-3.18 (m, 2H), 1.67 (s, 3H), 1.34 (s, 6H), 1.22 (t, J=7.6 Hz, 3H). MS ESI calcd for C₂₈H₂₈N₆O [M+H]⁺ 465, found 465.

Embodiment 251

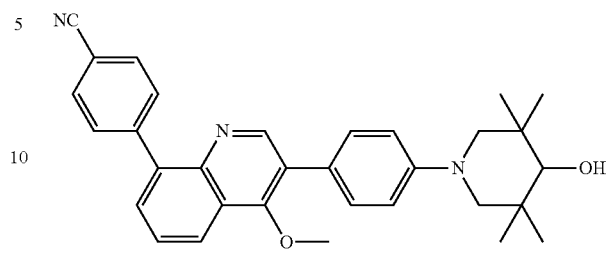

4-(2-(6-(3,5-dimethyl-4-propionylpiperazidin-1-yl) pyridin-3-yl)-1H-benzimidazole-4-yl)benzonitrile

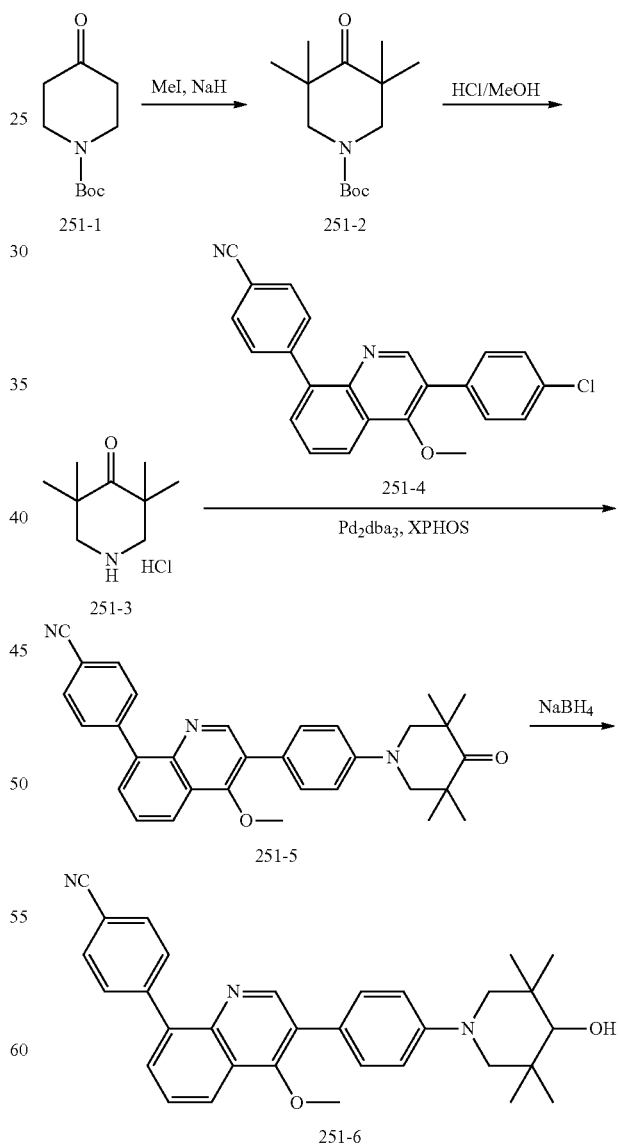

Step 1: Under an ice bath, NaH (6.4 g, 160 mmol) was added into a solution of compound 251-1 (4 g, 20 mmol) in THF (50 mL). The reaction mixture was stirred at room temperature for 0.5 h, then cooled to 0° C. again, MeI (10 mL, 160 mmol) was added dropwise. Then the reaction mixture was warmed to room temperature and stirred for another 2 h. The reaction was detected by TLC. The mixture was quenched with H₂O. The aqueous phase was extracted with EtOAc. The combined organic phase was washed with saturated sodium chloride solution, dried over sodium sulfate, concentrated under reduced pressure to deliver the desired product 251-2 (4.5 g, 88%). MS ESI calcd for C₁₄H₂₅NO₃ [M+H]⁺ 256, found 256.

Step 2: Compound 251-2 (410 mg, 1.6 mmol) was dissolved in HCl/methanol (4 M, 10 mL), and stirred at room temperature for 2 h. After the reaction was complete, the reaction mixture was concentrated under reduced pressure to deliver the desired product 251-3 (330 mg, 86%). MS ESI calcd for C₉H₁₇NO [M+H]⁺ 156, found 156.

Step 3: Compound 251-5 (300 mg, yield 75%) was synthesized as mentioned before. MS ESI calcd for C₃₂H₃₁N₃O₂ [M+H]⁺ 490, found 490.

Step 4: NaBH₄ (57 mg, 1.5 mmol) was added into a solution of compound 251-5 (490 mg, 1 mmol) in THF (10 mL), then stirred at room temperature for 0.5 h. After the reaction was complete as detected by LC-MS, the residue was poured into H₂O. The aqueous phase was extracted with DCM. The combined organic phase was washed with saturated sodium chloride solution, dried over sodium sulfate and concentrated. The crude product was purified by preparative HPLC to deliver the title compound (64 mg, yield 13%) as white solid. ¹H NMR (400 MHz, CDCl₃) δ 8.93 (s, 1H), 8.47-8.44 (m, 1H), 7.83-7.78 (m, 4H), 7.66 (d, J=7.6 Hz, 2H), 7.43 (d, J=8.4 Hz, 2H), 7.00 (d, J=8.8 Hz, 2H), 3.88 (s, 3H), 3.47 (d, J=12.4 Hz, 2H), 3.12 (s, 1H), 2.64 (s, 2H), 1.08 (s, 6H), 1.05 (s, 6H).

Embodiment 252

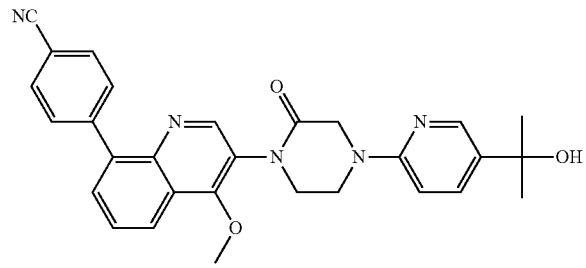 [SMILES: COc1c(N2CCN(c3ccc(C(C)(C)O)cn3)CC2=O)cnc2c(-c3ccc(C#N)cc3)cccc12]

4-(3-(4-(5-(2-hydroxypropan-2-yl)pyridin-2-yl)-2-oxopiperazin-1-yl-4-methoxyquinolin-8-yl))benzonitrile

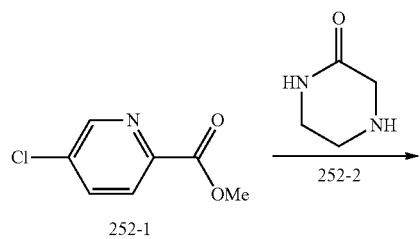

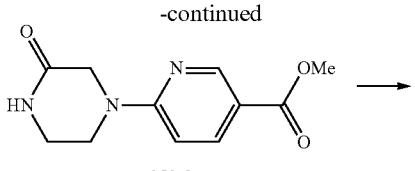

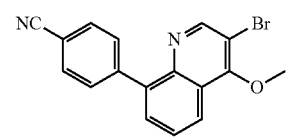

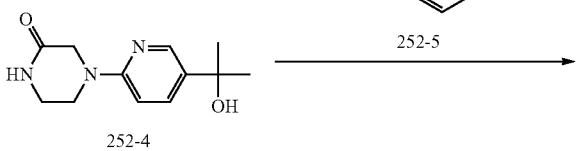

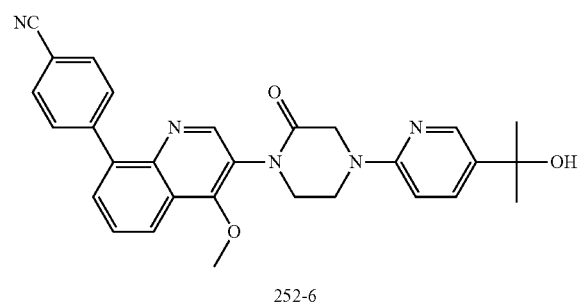

Step 1: K₂CO₃ (13.8 g, 0.1 mol) was added into a solution of compound 252-1 (8.6 g, 50 mmol) and 252-2 (5 g, 50 mmol) in DMF (50 mL), then the mixture was stirred at 120° C. overnight. The mixture was cooled and poured into H₂O. The precipitate was collected after filtration, washed with H₂O and methanol to deliver 6-(3-oxopiperazin-1-yl)nicotinic acid methyl ester (8.5 g, yield 72.6%) as yellow solid. MS ESI calcd for C₁₁H₁₃N₃O₃ [M+H]⁺ 236, found 236.

Step 2: At −78° C., MeMgBr (3 mL, 3 M in THF, 9 mmol) was added into a solution of 252-3 (708 mg, 3 mmol) in THF (50 mL). The mixture was stirred at room temperature for 1 h and poured into saturated NH₄Cl solution. The mixture was extracted with EtOAc, dried over sodium sulfate, concentrated to deliver 252-4 (260 mg, yield 37%) as yellow solid. MS ESI calcd for C₁₂H₁₇N₃O₂ [M+H]⁺ 236, found 236.

Step 3: Under nitrogen gas atmosphere, N1,N1,N3,N3-tetramethylpropane-1,3-diamine (3 mg, 0.03 mmol), CuI (4 mg, 0.02 mmol) and K₂CO₃ (70 mg, 0.6 mmol) were added into a solution of compound 252-4 (100 mg, 0.3 mmol) and 252-5 (72 mg, 0.3 mmol) in toluene (5 mL). The reaction mixture was stirred at 120° C. overnight. After poured into H₂O, the mixture was extracted with EtOAc twice. The organic phase was dried over sodium sulfate and concentrated. The concentration was purified by preparative HPLC to deliver the title compound (10 mg, yield 7%) as yellow solid. MS ESI calcd for C₂₉H₂₇N₅O₃ [M+H]⁺ 494, found 494. ¹HNMR (400 MHz, CDCl₃) δ ppm 8.69 (s, 1H), 8.39-8.40 (d, J=2.0 Hz, 1H), 8.27 (m, 1H), 7.67-7.80 (m, 7H), 6.69-6.71 (d, J=8.8 Hz, 1H), 4.39 (s, 2H), 4.15-4.18 (m, 2H), 4.11 (s, 3H), 3.88 (s, 2H), 1.62 (m, 6H).

Embodiment 253

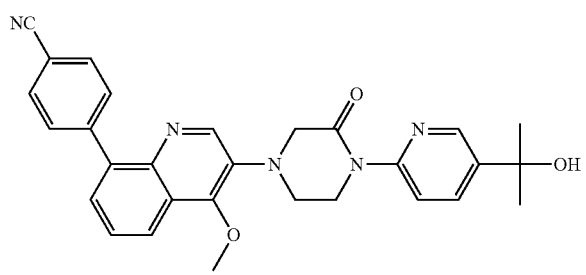 [SMILES: COc1c(N2CCN(c3ccc(C(C)(C)O)cn3)C(=O)C2)cnc2c(-c3ccc(C#N)cc3)cccc12]

4-(3-(4-(5-(2-hydroxypropan-2-yl)pyridin-2-yl)-3-oxopiperazin-1-yl-4-methoxyquinolin-8-yl))benzonitrile

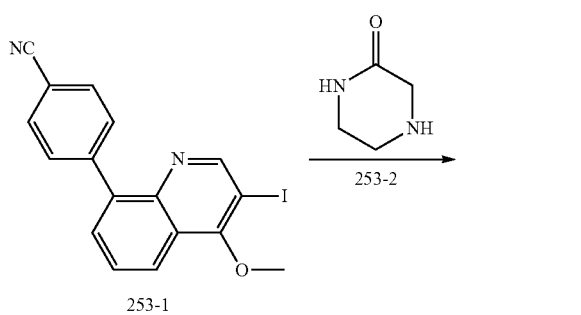

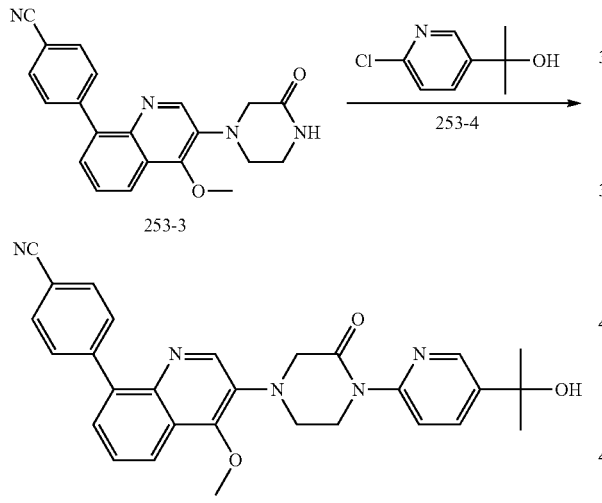

Step 1: Under nitrogen gas atmosphere, Pd$_2$(dba)$_3$ (184 mg, 0.2 mmol), Xantphos (240 mg, 0.4 mmol) and cesium carbonate (1.3 g, 4 mmol) were added into a solution of compound 253-1 (768 mg, 2 mmol) and 253-2 (200 mg, 2 mmol) in toluene (10 mL). The mixture was stirred at 120° C. overnight. After poured into H$_2$O, the mixture was extracted with EtOAc twice. The organic phase was dried over sodium sulfate and concentrated. The concentration was purified by silica gel column chromatography (PE/EtOAc 1:1) to deliver 253-3 (300 mg, yield 44%) as yellow solid. MS ESI calcd for C$_{21}$H$_{18}$N$_4$O$_2$ [M+H]$^+$ 359, found 359.

Step 2: 253-3 (180 mg, 0.5 mmol) and 253-4 (86 mg, 0.5 mmol) were added into toluene (5 mL), Pd$_2$(dba)$_3$ (46 mg, 0.05 mmol), Xantphos (57.7 mg, 0.1 mmol) and cesium carbonate (325 mg, 1 mmol) were added into the obtained solution under nitrogen gas atmosphere. The mixture was stirred at 120° C. overnight. After poured into H$_2$O, the mixture was extracted with EtOAc twice. The organic phase was dried over sodium sulfate and concentrated. The residue was purified by preparative HPLC to deliver the target product (80 mg, yield 12%) as yellow solid. MS ESI calcd for C$_{29}$H$_{27}$N$_5$O$_3$ [M+H]$^+$ 494, found 494. $^1$H NMR (400 MHz, CDCl$_3$) δ ppm 8.69 (s, 1H), 8.39-8.40 (d, J=2.0 Hz, 1H), 8.27 (m, 1H), 7.67-7.80 (m, 7H), 6.69-6.71 (d, J=8.8 Hz, 1H), 4.39 (s, 2H), 4.15-4.18 (m, 2H), 4.11 (s, 3H), 3.88 (s, 2H), 1.64 (m, 6H).

Embodiment 254

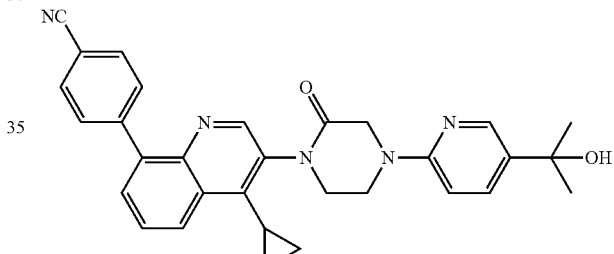

4-(4-cyclopropyl-3-(4-(5-(2-hydroxypropan-2-yl)pyridin-2-yl)-2-oxopiperazin-1-yl) quinolin-8-yl)benzonitrile

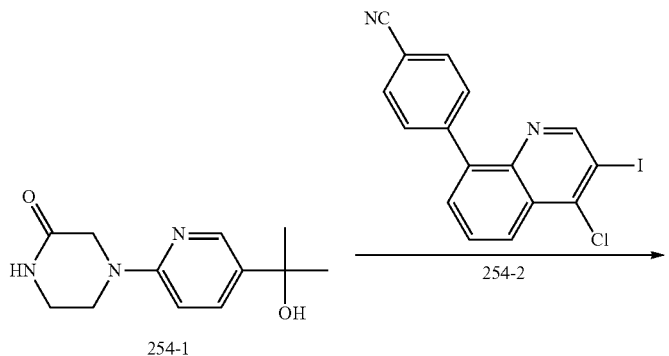

-continued

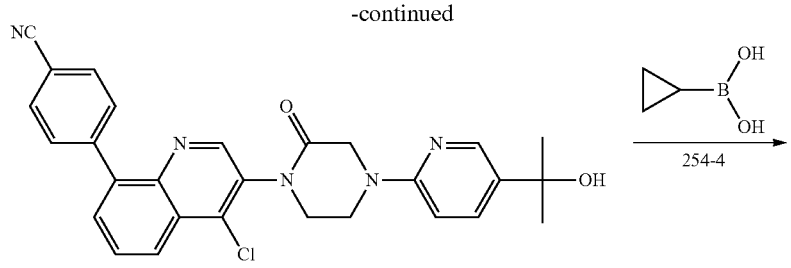

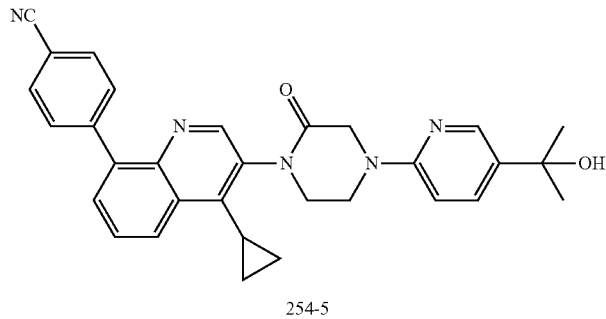

Step 1: 254-1 (472 mg, 2 mmol) and 254-2 (780 mg, 2 mmol), Pd$_2$(dba)$_3$ (180 mg, 0.2 mmol), Xantphos (240 mg, 0.4 mmol) and cesium carbonate (1.3 mg, 4 mmol) were added into toluene (20 mL). The mixture was stirred at 120° C. overnight under nitrogen gas atmosphere. After poured into H$_2$O, the mixture was extracted with EtOAc twice. The organic phase was dried over sodium sulfate and concentrated. The concentration was purified by silica gel column chromatography (PE:EtOAc=1:1) to deliver compound 254-3 (520 mg, yield 52%) as yellow solid. MS ESI calcd for C$_{28}$H$_{24}$ClN$_5$O$_2$ [M+H]$^+$ 498, found 498.

Step 2: 254-3 (150 mg, 0.3 mmol) and cyclopropyl boric acid (262 mg, 3 mmol), n-BuPAd (22 mg, 0.06 mmol), Pd(OAc)$_2$ (7 mg, 0.03 mmol) and cesium carbonate (195 mg, 0.6 mmol) were added into toluene/H$_2$O (5 mL/1 mL). The mixture was stirred at 120° C. overnight under nitrogen gas atmosphere. After poured into H$_2$O, the mixture was extracted with EtOAc twice. The organic phase was dried over sodium sulfate and concentrated. The residue was purified by preparative HPLC to deliver the target compound (50 mg, yield 33%) as yellow solid. MS ESI calcd for C$_{31}$H$_{29}$N$_5$O$_2$ [M+H]$^+$ 504, found 504. $^1$H NMR (400 MHz, CDCL3) δ ppm 8.71 (s, 1H), 8.59-8.61 (d, J=8.0 Hz, 1H), 8.39 (dd, J=2.0 Hz, 1H), 7.68-7.78 (m, 7H), 6.69-6.71 (d, J=8.8 Hz, 1H), 4.31-4.65 (m, 2H), 4.12-4.23 (m, 2H), 3.91-3.96 (m, 2H), 2.13 (m, 1H), 1.62 (s, 6H), 1.18-1.24 (m, 2H), 0.84 (m, 1H), 0.64 (m, 1H).

Embodiment 255

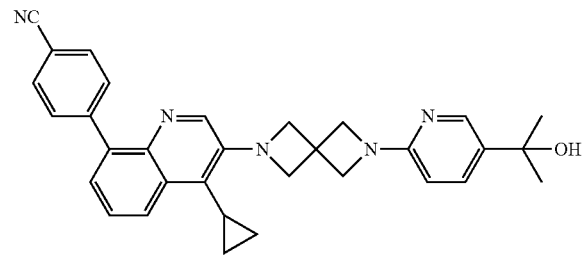 [SMILES: CC(C)(O)c1ccc(N2CC3(C2)CN(c2cnc4c(-c5ccc(C#N)cc5)cccc4c2C2CC2)C3)nc1]

4-(4-cyclopropyl-3-(6-(5-(2-hydroxypropan-2-yl) pyridin-2-yl)-2,6-diazaspiro[3.3]heptan-2-yl)quinolin-8-yl)benzonitrile

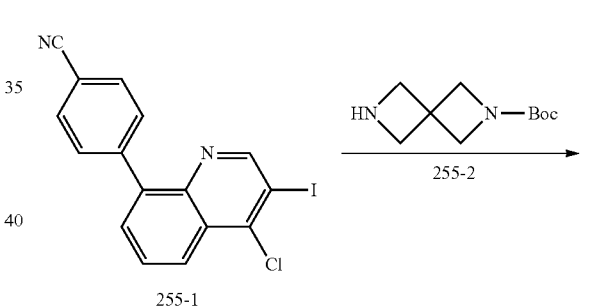

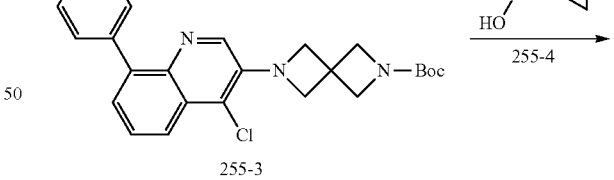

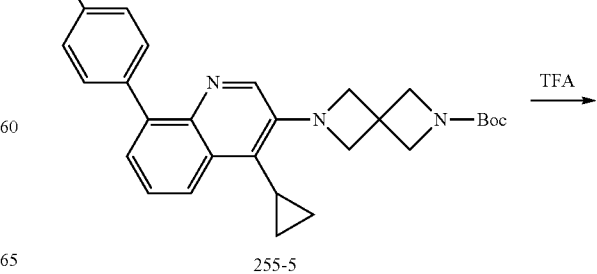

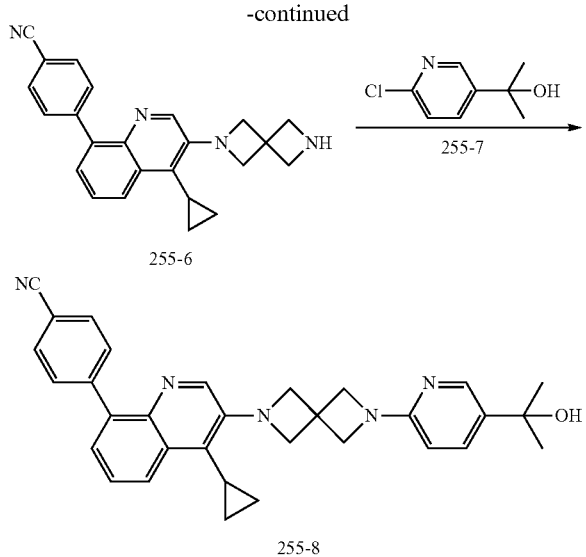

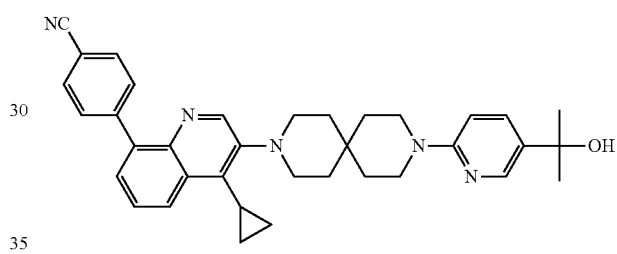

Step 1: Pd₂(dba)₃ (92 mg, 0.1 mmol), Xantphos (120 mg, 0.2 mmol) and cesium carbonate (650 mg, 2 mmol) were added into a solution of 255-1 (390 mg, 1 mmol) and 255-2 (299 mg, 1 mmol) in toluene (10 mL). Under nitrogen gas atmosphere, the mixture was stirred at 120° C. overnight. After poured into H₂O, the mixture was extracted with EtOAc twice. The organic phase was dried over anhydrous sodium sulfate and concentrated. The concentration was purified by silica gel column chromatography (PE/EtOAc=1:1) to deliver 255-3 (400 mg, yield 87%) as yellow solid. MS ESI calcd for $C_{26}H_{25}ClN_4O_2$ [M+H]⁺ 461, found 461.

Step 2: 255-3 (400 mg, 0.87 mmol) and cyclopropyl boric acid (378 mg, 4.35 mmol), n-BuPAd (62 mg, 0.174 mmol), Pd(OAc)₂ (20 mg, 0.09 mmol) and cesium carbonate (565 mg, 1.74 mmol) were added into toluene/H₂O (10 mL/1 mL). Under nitrogen gas atmosphere, the mixture was stirred at 120° C. overnight. After poured into H₂O, the mixture was extracted with EtOAc twice. The organic phase was dried over sodium sulfate and concentrated. The residue was purified by silica gel column chromatography (PE/EtOAc=3:1) to deliver 255-5 (400 mg, yield 98%) as yellow solid. MS ESI calcd for $C_{29}H_{30}N_4O_2$ [M+H]⁺ 467, found 467.

Step 3: 255-5 (400 mg, 0.87 mmol) was dissolved in DCM (10 mL) and TFA (5 mL) was added, the mixture was stirred at room temperature for 2 h. The mixture was concentrated and dried to deliver compound 255-6 (300 mg, yield 94%) as yellow oil. MS ESI calcd for $C_{24}H_{22}N_4$ [M+H]⁺ 367, found 367.

Step 4: 255-6 (184 mg, 0.5 mmol) and 255-7 (86 mg, 0.5 mmol), Pd₂(dba)₃ (46 mg, 0.05 mmol), Xantphos (57.7 mg, 0.1 mmol) and cesium carbonate (325 mg, 1 mmol) were added in toluene (5 mL). Under nitrogen gas atmosphere, the mixture was stirred at 120° C. overnight. After poured into H₂O, the mixture was extracted with EtOAc twice. The organic phase was dried over sodium sulfate and concentrated. The residue was purified by preparative HPLC to deliver the target compound (30 mg, yield 12%) as yellow solid. MS ESI calcd for $C_{32}H_{31}N_5O$ [M+H]⁺ 502, found 502. ¹H NMR (400 MHz, CDCL3) δ ppm 8.30-8.38 (m, 3H), 7.70-7.77 (m, 4H), 7.68 (d, J=2.0 Hz, 1H), 7.56-7.58 (d, J=8.4 Hz, 1H), 6.35-6.37 (d, J=8.8 Hz, 1H), 4.37-4.40 (m, 4H), 4.11-4.13 (m, 4H), 2.05-2.07 (m, 1H), 1.59 (s, 6H), 1.23-1.27 (m, 2H), 0.78-0.79 (m, 2H)

Embodiment 256

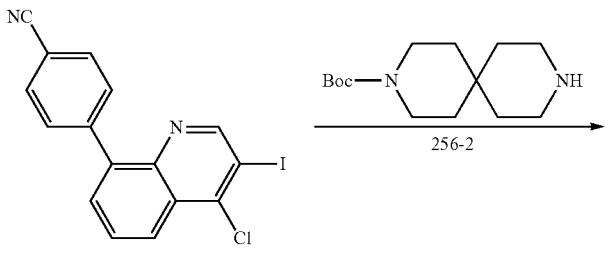

4-(4-cyclopropyl-3-(9-(5-(2-hydroxypropan-2-yl)pyridin-2-yl)-3,9-diazaspiro[5.5]undecan-3-yl)quinolin-8-yl)benzonitrile

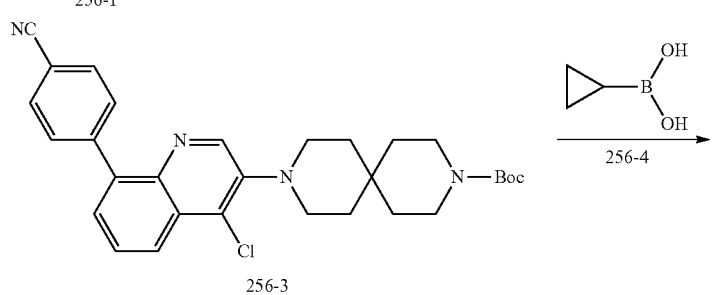

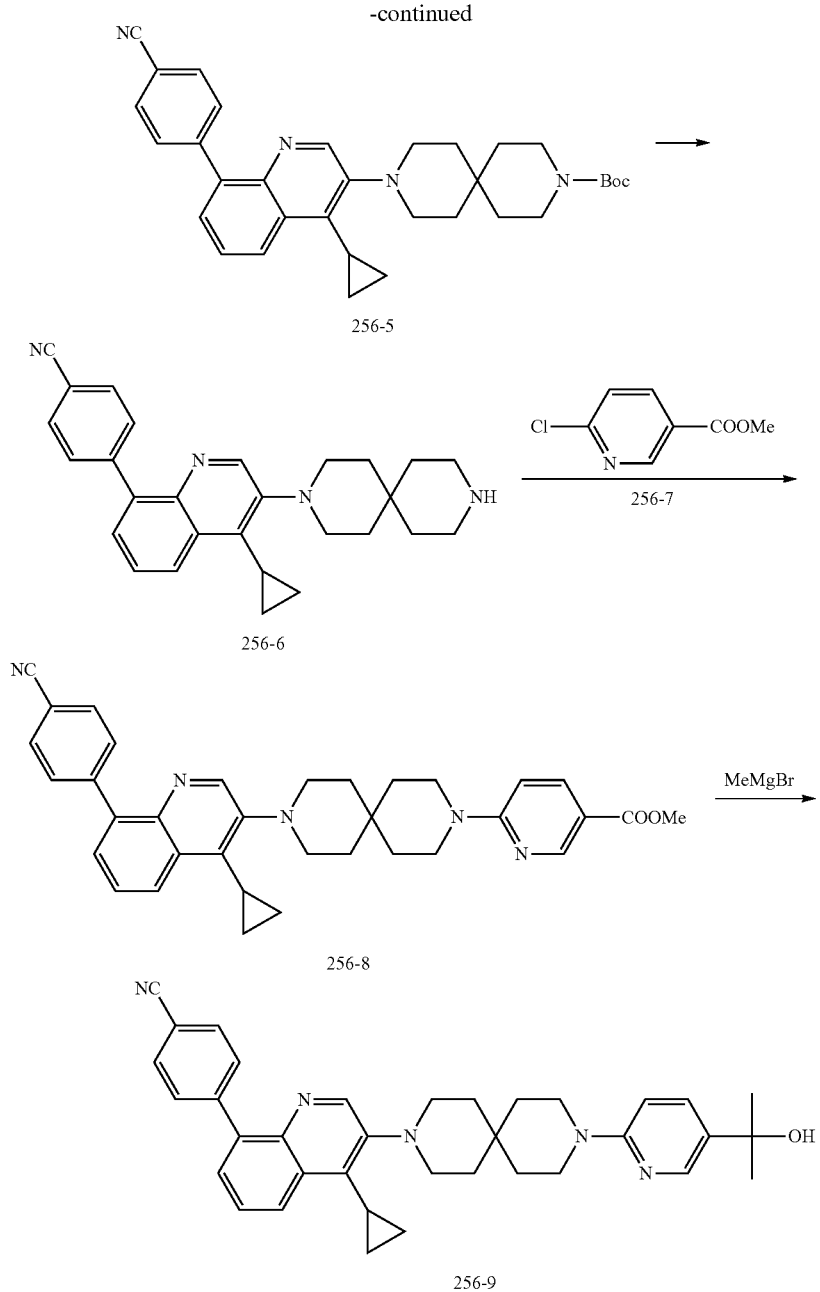

Step 1: 256-1 (780.00 mg, 2.0 mmol) and 256-2 (507.96 mg, 2.0 mmol) were dissolved in toluene (20 mL), under nitrogen gas atmosphere, $Pd_2(dba)_3$ (115.00 mg, 200.00 µmol) was added. The mixture was stirred at room temperature for 10 min, then heated to 110° C. and reacted for 3 h. After cooled to room temperature, the mixture was poured into $H_2O$ (200 mL) and stirred for 20 min. Then the mixture was extracted with EtOAc (400 mL*3). The combined organic phase was washed with $H_2O$ and brines (200 mL*2) respectively, dried over sodium sulfate, filtrated and concentrated under reduced pressure. The residue was purified by thin layer chromatography (PE/EtOAc extract part=5:1) to deliver 256-3 (100 mg, yield 9.67%) as yellow solid. MS ESI calcd for $C_{30}H_{33}ClN_4O_2$ [M+H]$^+$ 517, found 517.

Step 2: 256-3 (100 mg, 193.4 µmol), cyclopropyl boric acid (83.07 mg, 967 mol) were dissolved in toluene (10 mL), under nitrogen gas atmosphere, $Pd(OAc)_2$ (0.20 mg, 38.68 µmol) was added. The mixture was stirred at room temperature for 10 min, then heated to 110° C. and reacted for 1 h. After cooled to room temperature, the mixture was poured into $H_2O$ (50 mL) and stirred for 20 min. Then the mixture was extracted with EtOAc (100 mL*3). The combined organic phase was washed with $H_2O$ and brines (50 mL*2), dried over anhydrous sodium sulfate, filtrated and concentrated under reduced pressure. The residue was purified by silica gel column chromatography (PE/EtOAc=5:1) to deliver 256-5 (80.00 mg, yield 79.14%) as yellow solid. MS ESI calcd for $C_{33}H_{38}N_4O_2$ [M+H]$^+$ 523, found 523.

Step 3: 256-5 (80 mg, 153.06 µmol) was dissolved in DCM (5 mL) and HCl/EtOAc (4 M, 2 mL) was added. Then the mixture was stirred at room temperature for 2 h. The crude product 256-6 obtained after concentration was used for the next step directly. MS ESI calcd for $C_{28}H_{30}N_4$ [M+H]$^+$ 423, found 423.

Step 4: 256-6 (50 mg, 118.33 μmol) and 256-7 (24.36 mg, 142 μmol) were dissolved in acetonitrile (5 mL) and $K_2CO_3$ (163.54 mg, 1.18 mmol) was added. The mixture was stirred at room temperature for 10 min, then heated to 80° C. for 12 h. After cooled to room temperature, the mixture was poured into $H_2O$ (50 mL) and stirred for 20 min, the obtained mixture was extracted with EtOAc (50 mL*3). The organic phases were combined and washed with brines (50 mL), dried over anhydrous sodium sulfate, filtrated and concentrated under vacuum. The residue was purified by thin layer chromatography (PE/EtOAc=5:1) to deliver 256-8 (30 mg, yield 45.46%) as yellow solid. MS ESI calcd for $C_{35}H_{35}N_5O_2$ [M+H]$^+$ 558, found 558.

Step 5: 256-8 (30 mg, 53.79 μmol) was dissolved in THF (5 mL), methyl magnesium bromide (32.07 mg, 268.95 μmol) was added dropwise at room temperature. The mixture was stirred at room temperature for 1 h, then poured into ammonium chloride aqueous solution (50 mL), stirred for 20 min, the obtained mixture was extracted with EtOAc (50 mL×3). The organic phases were combined and washed with brines (20 mL), dried over anhydrous sodium sulfate, filtrated and concentrated under vacuum. The residue was purified by preparative HPLC to deliver the target compound (2 mg, yield 6.67%) as yellow solid. MS ESI calcd for $C_{36}H_{39}N_5O$ [M+H]$^+$ 558, found 558. $^1$HNMR (400 MHz, METHANOL-d$_4$) δ ppm 8.76 (s, 1H), 8.49 (d, J=8 Hz, 1H), 8.31 (d, J=2.0 Hz, 1H), 7.76 (s, 4H), 7.66 (t, J=6.4 Hz, 1H), 7.51-7.58 (m, 2H), 3.50-3.58 (m, 4H), 3.25-3.29 (m, 4H), 2.01-2.05 (m, 2H), 1.63 (s, 6H), 1.23-1.26 (m, 2H).

Embodiment 257

4-(4-cyclopropyl-3-(6-((2S,6R)-2,6-dimethylmorpholino)-2-methylpyridin-3-yl) quinolin-8-yl)benzonitrile

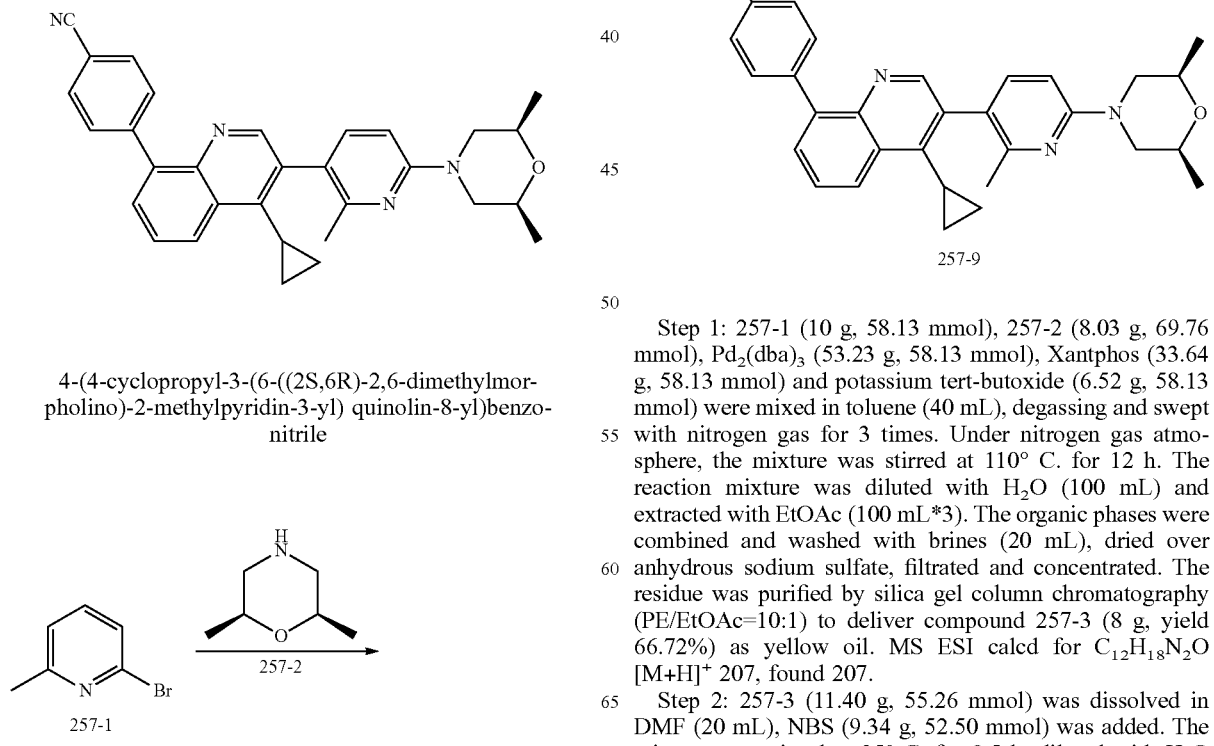

Step 1: 257-1 (10 g, 58.13 mmol), 257-2 (8.03 g, 69.76 mmol), Pd$_2$(dba)$_3$ (53.23 g, 58.13 mmol), Xantphos (33.64 g, 58.13 mmol) and potassium tert-butoxide (6.52 g, 58.13 mmol) were mixed in toluene (40 mL), degassing and swept with nitrogen gas for 3 times. Under nitrogen gas atmosphere, the mixture was stirred at 110° C. for 12 h. The reaction mixture was diluted with $H_2O$ (100 mL) and extracted with EtOAc (100 mL*3). The organic phases were combined and washed with brines (20 mL), dried over anhydrous sodium sulfate, filtrated and concentrated. The residue was purified by silica gel column chromatography (PE/EtOAc=10:1) to deliver compound 257-3 (8 g, yield 66.72%) as yellow oil. MS ESI calcd for $C_{12}H_{18}N_2O$ [M+H]$^+$ 207, found 207.

Step 2: 257-3 (11.40 g, 55.26 mmol) was dissolved in DMF (20 mL), NBS (9.34 g, 52.50 mmol) was added. The mixture was stirred at 25° C. for 0.5 h, diluted with $H_2O$ (100 mL), then extracted with EtOAc (100 mL×3). The combined organic phase was washed with brines (100 mL), dried over anhydrous sodium sulfate, filtrated and concentrated. The residue was purified by silica gel column chromatography (PE/EtOAc=10:1) to deliver compound 257-4 (12 g, yield 76.15%) as white solid. MS ESI calcd for $C_{12}H_{17}BrN_2O$ [M+H]$^+$ 285, found 285.

Step 3: 257-4 (16 g, 56.10 mmol), bis(pinacolato)diboron (21.37 g, 84.15 mmol), Pd(dppf)Cl$_2$ (2.05 g, 2.81 mmol) and KOAc (11.01 g, 112.20 mmol) were mixed in dioxane (50 mL). Under nitrogen gas atmosphere, the mixture was stirred at 100° C. for 2 h. The reaction mixture was diluted with H$_2$O (100 mL) and extracted with EtOAc (100 mL*3). The organic phase was combined and washed with brines (20 mL), dried over sodium sulfate, filtrated and concentrated. The residue was purified by silica gel column chromatography (PE/EtOAc=10:1) to deliver compound 257-5 (10 g, yield 53.65%) as white solid. MS ESI calcd for $C_{18}H_{29}BN_2O_3$ [M+H]$^+$ 333, found 333.

Step 4: Pd(dppf)Cl$_2$ (561.95 mg, 768 μmol) and Na$_2$CO$_3$ (3.26 g, 30.72 mmol) were added into a solution of 257-6 (6 g, 15.36 mmol) and 257-5 (7.65 g, 23.04 mmol) in DMF (5 mL)/H$_2$O (5 mL)/THF (25 mL). The mixture was stirred at 70° C. for 2 h. The reaction mixture was diluted with H$_2$O (100 mL) and extracted with EtOAc (100 mL*3). The combined organic phase was washed with brines (20 mL), dried over sodium sulfate, filtrated and concentrated under reduced pressure. The residue was purified by column chromatography (PE/EtOAc=5:1) to deliver 257-7 (3 g, yield 41.65%) as yellow solid. MS ESI calcd for $C_{28}H_{25}ClN_4O$ [M+H]$^+$ 469, found 469.

Step 5: Bis(adamantyl) butyl phosphine (229.47 mg, 640 μmol), Cs$_2$CO$_3$ (2.09 g, 6.40 mmol) and Pd(OAc)$_2$ (71.84 mg, 320 μmol) were added into a solution of 257-7 (1.50 g, 3.20 mmol) and cyclopropyl boric acid (1.37 g, 16 mmol) in toluene (15 mL). The mixture was stirred at 110° C. for 2 h. The reaction mixture was diluted with H$_2$O (100 mL) and extracted with EtOAc (100 mL*3). The combined organic phase was washed with brines (20 mL), dried over sodium sulfate, filtrated and concentrated. The residue was purified by column chromatography (PE/EtOAc=10:1) to deliver the target product (1 g, yield 65.85%) as light red solid. MS ESI calcd for $C_{31}H_3ON_4O$ [M+H]$^+$ 475, found 475. $^1$HNMR (400 MHz, CDCl$_3$) δ ppm 8.69 (s, 1H), 8.64 (dd, J=3.0, 6.5 Hz, 1H), 7.74-7.90 (m, 4H), 7.67-7.72 (m, 2H), 7.35 (d, J=8.5 Hz, 1H), 6.58 (d, J=8.5 Hz, 1H), 4.06-4.26 (m, 2H), 3.69-3.79 (m, 2H), 2.58 (t, J=11.5 Hz, 2H), 2.29 (s, 3H), 2.09-2.21 (m, 1H), 1.31 (d, J=6.5 Hz, 6H), 0.99 (q, J=5.3, 8.6 Hz, 2H), 0.27-0.54 (m, 2H).

Embodiment 258

4-(3-(6-((2S,6R)-2,6-dimethylmorpholino)pyridin-3-yl)-4-isopropylquinolin-8-yl) benzonitrile

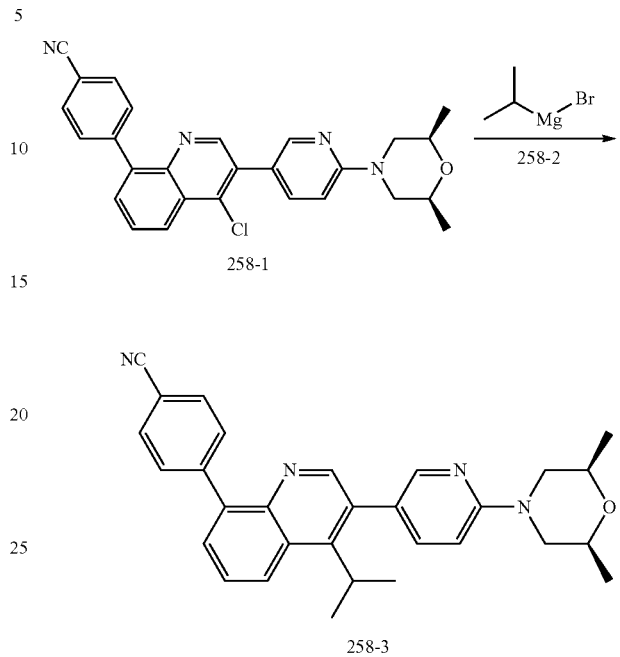

258-1 (227.48 mg, 500 μmol) was dissolved in THF (4 mL) and NMP (1 mL), then at −40° C. isopropyl magnesium bromide (73.65 mg, 500 μmol) was added dropwise. The reaction mixture was warmed to 0° C. and stirred for 10 min, then room temperature for 2 h. The reaction mixture was quenched with ice slowly, then extracted with EtOAc (5 mL×3). The organic phases were combined and washed with brines (100 mL), dried over anhydrous sodium sulfate, filtrated and concentrated. The residue was purified by HPLC to deliver the target compound (20 mg, yield 8.79%) as white solid. MS ESI calcd for $C_{30}H_{30}N_4O$ [M+H]$^+$ 463, found 463. $^1$HNMR (400 MHz, CHLOROFORM-d) δ ppm 8.68 (s, 1H), 8.46-8.48 (t, J=5.02 Hz, 1H), 8.22 (s, 1H), 7.73-7.82 (m, 7H), 7.06-7.08 (d, J=9.2 Hz, 1H), 4.13-4.16 (m, 2H), 3.81-3.84 (m, 2H), 3.65 (m, 1H), 2.91-2.97 (m, 2H), 1.60-1.62 (d, J=7.2 Hz, 6H), 1.33-1.35 (d, J=6.0 Hz, 6H).

Embodiment 259

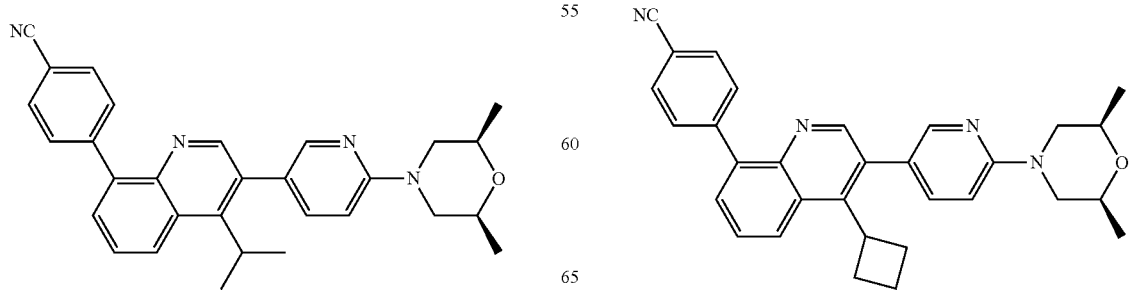

327

4-(4-cyclobutyl-3-(6-((2S,6R)-2,6-dimethylmorpholino)pyridin-3-yl)quinolin-8-yl) benzonitrile

328

4-(4-(1-cyclopenten-1-yl)-6-(3-(-(2S,6R)-2,6-dimethylmorpholino)pyridin-3-yl) quinolin-8-yl)benzonitrile

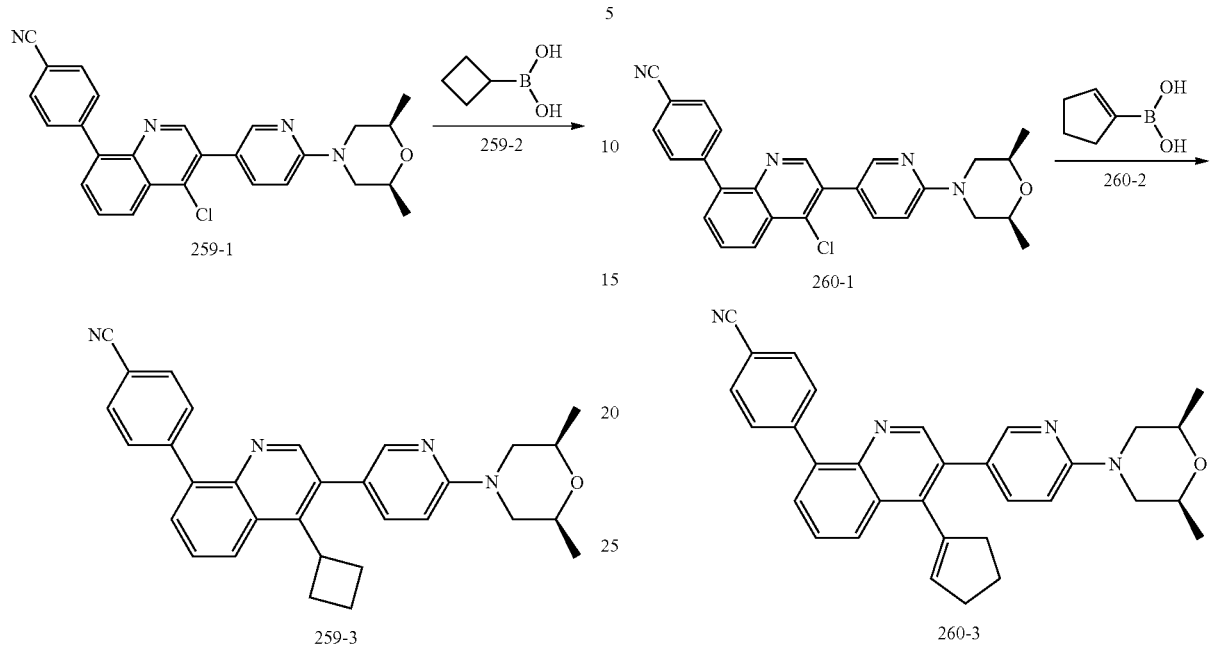

Pd(dppf)Cl$_2$ (36.59 mg, 50 μmol) and Na$_2$CO$_3$ (105.99 mg, 1 mmol) were added into a solution of 259-1 (227.48 mg, 500 μmol), cyclobutyl boric acid (99.92 mg, 1 mmol) in THF/H$_2$O (2 mL). Under nitrogen gas atmosphere, the mixture was heated to 80° C. and reacted for 2 h, then poured into H$_2$O (10 mL). The reaction mixture was extracted with EtOAc (10 mL*3). The organic phase was washed with brines (30 mL), dried over anhydrous MgSO$_4$, concentrated under vacuum. The residue was purified by prep-HPLC to deliver the target product (50 mg, yield 21.07%). MS ESI calcd for C$_{31}$H$_{30}$N$_4$O [M+H]$^+$ 475, found 475. $^1$HNMR (400 MHz, CHLOROFORM-d) δ ppm 8.70 (s, 1H), 8.09-8.23 (m, 2H), 7.79 (d, J=3.01 Hz, 4H), 7.58-7.71 (m, 2H), 7.46-7.57 (m, 1H), 6.63-6.84 (m, 1H), 4.26-4.50 (m, 1H), 4.12 (d, J=12.55 Hz, 2H), 3.76 (d, J=6.53 Hz, 2H), 2.54-2.69 (m, 2H), 2.37 (d, J=8.53 Hz, 2H), 1.84-2.15 (m, 4H), 1.65-1.78 (m, 1H), 1.17-1.38 (m, 8H).

Pd(dppf)Cl$_2$ (80.49 mg, 110 μmol) and Na$_2$CO$_3$ (233.18 mg, 2.20 mmol) were added into a solution of 260-1 (500 mg, 1.10 mmol), 260-2 (256.19 mg, 1.32 mmol) in THF (10 mL). Under nitrogen gas atmosphere, the mixture was heated to 80° C. and reacted for 2 h. The reaction mixture was poured into H$_2$O (10 mL) and extracted with EtOAc (10 mL*3). The organic phase was washed with brines (10 mL), dried over anhydrous magnesium sulfate and concentrated under vacuum. The residue was purified by column chromatography to deliver the target compound (450 mg, yield 84.07%) as yellow solid. MS ESI calcd for C$_{32}$H$_{30}$N$_4$O [M+H]$^+$ 487, found 487. $^1$HNMR (400 MHz, CHLOROFORM-d) δ ppm 8.78-8.91 (m, 1H), 8.31 (d, J=2.26 Hz, 1H), 8.13 (dd, J=8.28, 1.25 Hz, 1H), 7.74-7.88 (m, 5H), 7.60-7.73 (m, 2H), 6.72 (d, J=8.78 Hz, 1H), 5.96 (s, 1H), 4.05-4.29 (m, 2H), 3.72-3.90 (m, 2H), 2.64 (d, J=10.54 Hz, 4H), 2.32-2.47 (m, 1H), 2.01 (t, J=7.28 Hz, 2H), 1.32 (d, J=6.27 Hz, 6H).

Embodiment 260

Embodiment 261

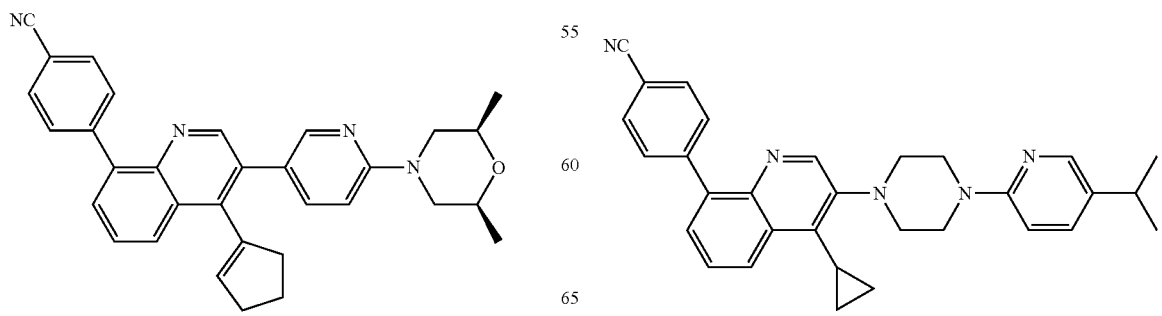

4-(4-((4-cyclopropyl-35-isopropylpyridin-2-yl)-3-)-quinolin-8-yl)benzonitrile

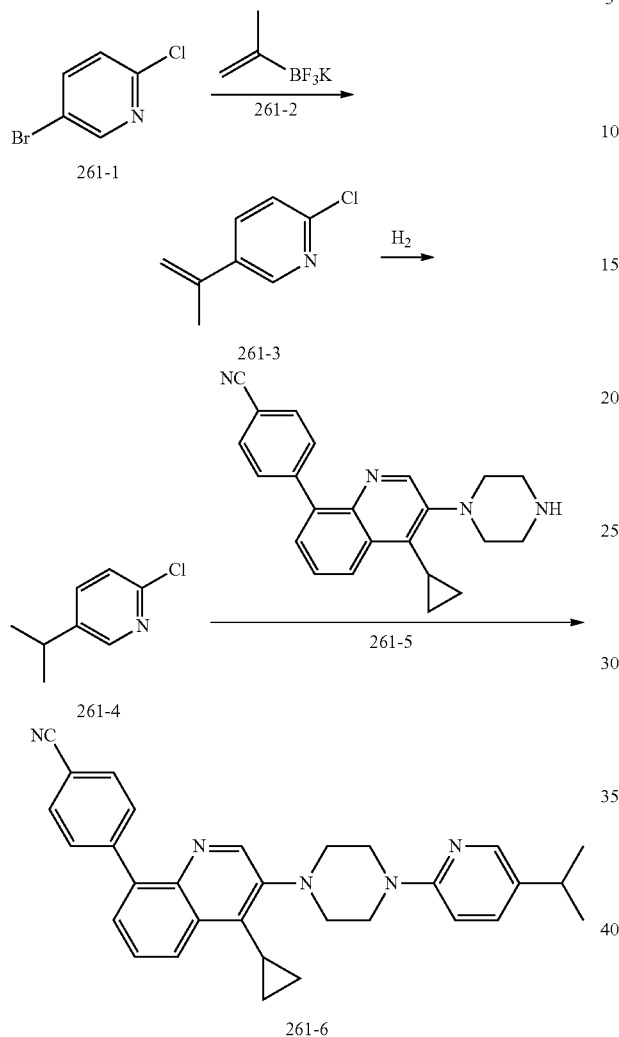

Step 1: Under nitrogen gas atmosphere, Pd(dppf)Cl$_2$ (1.14 g, 1.56 mmol, 0.10 eq) was added into a mixture of 261-1 (3 g, 15.59 mmol, 1 eq), sodium carbonate (3.30 g, 31.18 mmol, 2 eq) and 261-2 (2.77 g, 18.71 mmol, 1.20 eq) in DMF (2 mL)/H$_2$O (2 mL)/THF (10 mL). The mixture was stirred at 70° C. for 12 h, poured into H$_2$O (150 mL). The obtained mixture was extracted with EtOAc (100×3). The combined organic phase was washed with brines (150 mL), dried over anhydrous sodium sulfate, filtrated and concentrated under vacuum. The residue was purified by column chromatography (PE/EtOAc=20:1) to deliver 261-3 (1.50 g, yield 62.60%) as colorless oil. MS ESI calcd for C$_8$H$_8$ClN [M+H]$^+$ 154, found 154.

Step 2: 261-3 (1.50 g, 9.76 mmol, 1 eq) was dissolved in ethanol (30 mL), under nitrogen gas atmosphere, PtO$_2$ (2.22 g, 9.76 mmol, 1 eq) (10%, 0.15 g) was added. The suspension was degassed under vacuum and swept by hydrogen gas for 3 times. The mixture was stirred at 25° C. for 4 h under H$_2$ (30 psi). The reaction mixture was filtrated, the filtrate was concentrated. The crude product was used for the next step directly. MS ESI calcd for C$_8$H$_{10}$ClN [M+H]$^+$ 156, found 156.

Step 3: A mixture of 261-5 (100 mg, 282.13 μmol, 1 eq), cesium carbonate (183.85 mg, 564.26 μmol, 2 eq), Xantphos (32.65 mg, 56.43 μmol, 0.20 eq) and 261-4 (65.86 mg, 423.20 μmol, 1.50 eq) was dissolved in toluene (10 mL), under nitrogen gas atmosphere, Pd$_2$(dba)$_3$ (25.84 mg, 28.21 mmol, 0.10 eq) was added. The mixture was stirred at 110° C. for 2 h, poured into H$_2$O (100 mL). The obtained mixture was extracted with EtOAc (100 mL×3). The organic phases were combined and washed with brines (100 mL), dried over anhydrous sodium sulfate, filtrated and concentrated under vacuum. The residue was purified (acid) by HPLC to deliver the target compound (20 mg, yield 14.97%) as yellow solid. MS ESI calcd for C$_{31}$H$_{31}$N$_5$ [M+H]$^+$ 474, found 474. $^1$H NMR (400 MHz, METHANOL-d$_4$) δ ppm 8.86 (d, J=8.3 Hz, 1H), 8.73 (s, 1H), 8.14 (dd, J=2.0, 9.3 Hz, 1H), 7.95-8.03 (m, 3H), 7.75-7.91 (m, 4H), 7.52 (d, J=9.5 Hz, 1H), 4.04 (brs, 4H), 3.64 (brs, 4H), 1.59 (d, J=7.3 Hz, 2H), 1.32 (d, J=7.0 Hz, 7H), 1.10 (d, J=4.8 Hz, 2H).

Embodiment 262

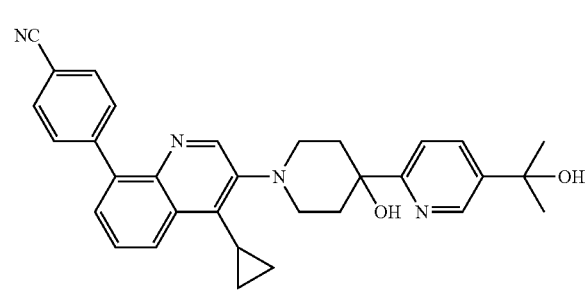 [SMILES: CC(C)(O)c1ccc(C2(O)CCN(c3cnc4c(-c5ccc(C#N)cc5)cccc4c3C3CC3)CC2)nc1]

4-(4-cyclopropyl-3-(4-hydroxy-(5-(2-hydroxypropan-2-yl)pyridin-2-yl)piperidin-1-yl) quinolin-8-yl benzonitrile

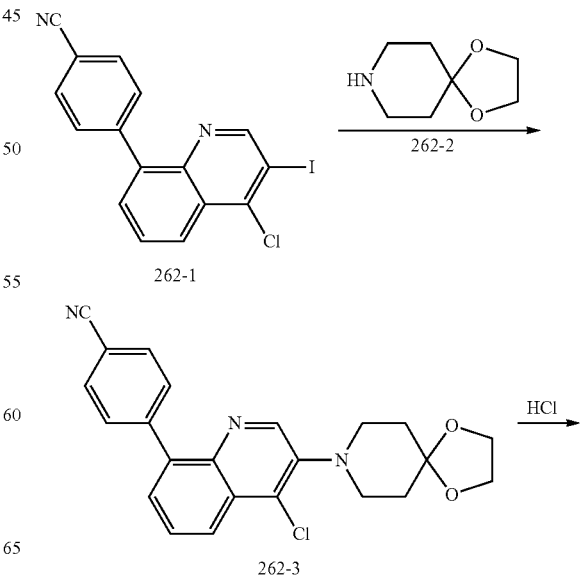

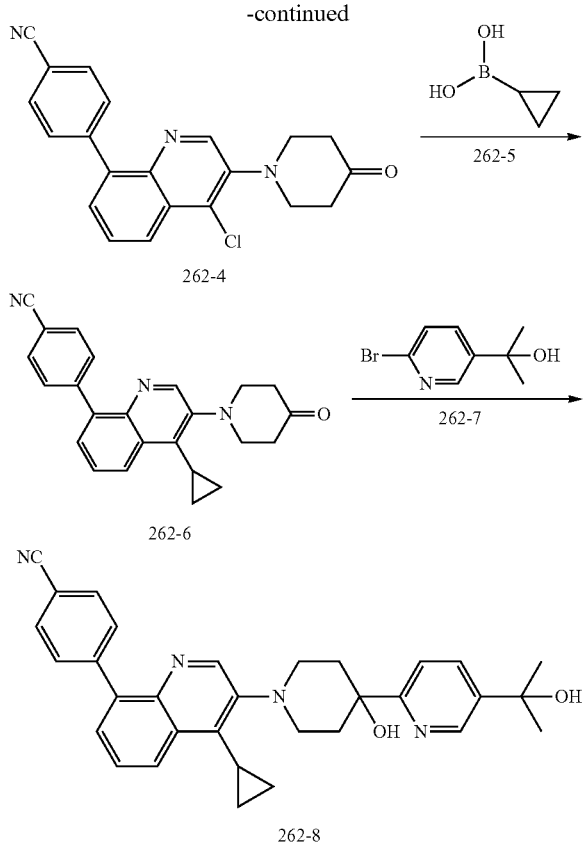

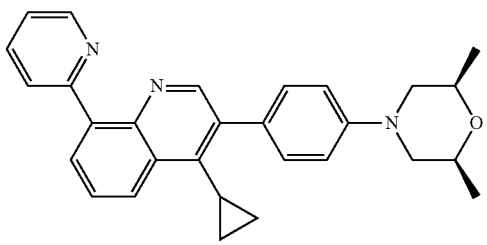 [SMILES: C[C@@H]1CN(c2ccc(-c3cnc4c(-c5ccccn5)cccc4c3C3CC3)cc2)C[C@H](C)O1]

Step 1: Under nitrogen gas atmosphere, Pd$_2$(dba)$_3$ (234.42 mg, 256 µmol, 0.10 eq) was added into a mixture of 262-1 (1 g, 2.56 mmol, 1 eq), Xantphos (296.25 mg, 512 µmol, 0.20 eq), cesium carbonate (1.67 g, 5.12 mmol, 2 eq) and 262-2 (439.85 mg, 3.07 mmol, 1.20 eq) in toluene (20 mL). The mixture was stirred at 110° C. for 2 h, poured into H$_2$O (150 mL). The obtained mixture was extracted with EtOAc (400 mL×3). The organic phases were combined and washed with brines (200 mL), dried over anhydrous sodium sulfate, filtrated and concentrated under vacuum. The residue was purified by column chromatography (PE/EtOAc=3:1) to deliver compound 262-3 (800 mg, yield 76.99%) as yellow solid. MS ESI calcd for C$_{23}$H$_{20}$ClN$_3$O$_2$ [M+H]$^+$ 406, found 406.

Step 2: 262-3 (400 mg, 985.51 µmol, 1 eq) was dissolved in THF (10 mL) and HCl solution (4 M EtOAc, 2 mL) was added. The reaction mixture was stirred at room temperature for 12 h, then heated to 45° C. and stirred for another 1 h. The mixture was poured into H$_2$O (150 mL) and extracted with EtOAc (400 mL×3). The organic phases were combined and washed with brines (20 mL), dried over anhydrous sodium sulfate, filtrated and concentrated under vacuum. The residue was purified by column chromatography (PE/EtOAc=2:1) to deliver 262-4 (320 mg, yield 89.74%) as white solid. MS ESI calcd for C$_{22}$H$_{19}$N$_3$O$_2$ [M+H]$^+$ 358, found 358.

Step 3: Under nitrogen gas atmosphere, bis(adamantyl)butyl phosphine (79.27 mg, 221.10 µmol) was added into a mixture of 262-4 (200 mg, 552.76 µmol, 1 eq) and 262-5 (237.41 mg, 2.76 mmol, 5 eq) in toluene (10 mL). The mixture was stirred at 110° C. for 2 h, poured into H$_2$O (150 mL). The obtained mixture was extracted with EtOA (400 mL×3). The organic phases were combined and washed with brines (200 mL), dried over anhydrous sodium sulfate, filtrated, and concentrated under vacuum. The residue was purified by column chromatography (PE/EtOAc=2:1) to deliver 262-6 (150 mg, yield 73.85%) as white solid. MS ESI calcd for C$_{24}$H$_{21}$N$_3$O [M+H]$^+$ 368, found 368.

Step 4: Under nitrogen gas atmosphere, n-BuLi (52.30 mg, 816.45 µmol, 3 eq) was added dropwise into a solution of 262-7 (70.56 mg, 326.58 µmol, 1.20 eq) dissolved in THF (5 mL) at −78° C. After 1 h, 262-6 (100 mg, 272.15 µmol, 1 eq) was added into the mixture, and the mixture was stirred at −78° C. for further 1 h. The mixture was warmed to 25° C., poured into saturated NH$_4$Cl solution (50 mL), then stirred for 20 min, the obtained mixture was extracted with EtOAc (100 mL×3). The organic phases were combined and washed with brines (50 mL), dried over anhydrous sodium sulfate, filtrated, and concentrated under vacuum. The residue was purified by HPLC to deliver the target compound (3 mg, yield 2.18%) as yellow solid. MS ESI calcd for C$_{32}$H$_{32}$N$_4$O$_2$ [M+H]$^+$ 505, found 505. $^1$HNMR (400 MHz, CDCl$_3$) δ ppm 8.56-9.23 (m, 2H), 7.53-7.95 (m, 10H), 3.68 (brs., 4H), 2.21 (brs, 1H), 1.58 (brs, 11H), 1.06 (brs., 2H).

Embodiment 263

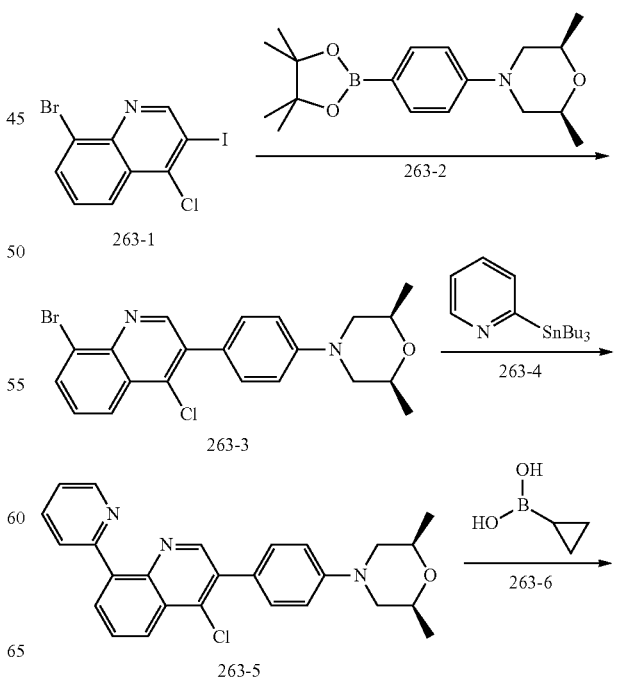

(2S,6R)-4-(5-(4-8-cyclopropyl-(2-pyridinyl)quinolin-3-yl)pyridin-2-yl)-2,6-dimethylmorpholine

333

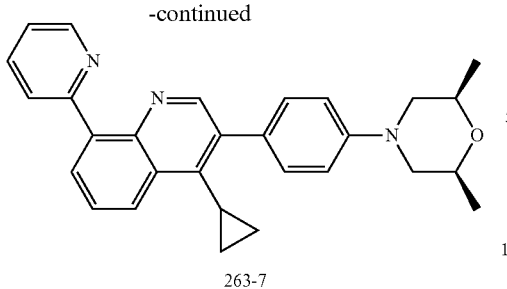

263-7

Step 1: 263-1 (266.27 mg, 722.77 µmol, 1 eq) and 263-2 (230 mg, 722.77 mol, 1 eq) were dissolved in DMF (2 mL)/THF (2 mL). Under nitrogen gas atmosphere, Pd(dppf)Cl$_2$ (52.89 mg, 72.28 µmol, 0.10 eq) was added into the reaction system. The mixture was stirred at 70° C. for 2 h, poured into H$_2$O (100 mL). The mixture was extracted with EtOAc (200 mL×3). The organic phases were combined and washed with brines (100 mL), dried over anhydrous sodium sulfate, filtrated, and concentrated under vacuum. The residue was purified by column chromatography (PE/EtOAc=5:1) to deliver 263-3 (270 mg, yield 86.33%) as white solid. MS ESI calcd for C$_{21}$H$_{20}$BrClN$_2$O [M+H]$^+$ 431, found 431.

Step 2: Under nitrogen gas atmosphere, Pd(PPh$_3$)$_4$ (72.10 mg, 62.39 µmol, 0.10 eq) was added in a solution of 263-3 (270 mg, 623.93 µmol, 1 eq) and 263-4 (229.69 mg, 623.93 µmol, 1 eq) in toluene (10 mL). The mixture was stirred at 110° C. for 2 h, poured into H$_2$O (50 mL). The mixture was extracted with EtOAc (100 mL×3). The organic phases were combined and washed with brines (50 mL), dried over anhydrous sodium sulfate, filtrated and concentrated under vacuum. The residue was purified by column chromatography (PE/EtOAc=2:1) to deliver 263-5 (120 mg, yield 44.63%) as white solid. MS ESI calcd for C$_{26}$H$_{24}$ClN$_3$O [M+H]$^+$ 430, found 430.

Step 3: Under nitrogen gas atmosphere, Pd(OAc)$_2$ and bis(adamantyl) butyl phosphine (66.56 mg, 185.65 µmol, 1 eq) were added into a solution of 263-5 (80 mg, 185.65 µmol, 1 eq) and cyclopropyl boric acid (159.47 mg, 1.86 mmol, 10 eq) in toluene (5 mL). The mixture was stirred at 110° C. for 2 h, then poured into H$_2$O (50 mL). The mixture was extracted with EtOAc (100 mL×3). The organic phases were combined and washed with brines (50 mL), dried over anhydrous sodium sulfate, filtrated, and concentrated under vacuum. The residue was purified by HPLC to deliver the target compound (15 mg, yield 18.51%) as white solid. MS ESI calcd for C$_{29}$H$_{29}$N$_3$O [M+H]$^+$ 436, found 436. $^1$HNMR (400 MHz, METHANOL-d$_4$) δ ppm 9.14 (s, 1H), 9.03-9.13 (m, 2H), 8.75-8.81 (m, 1H), 8.65-8.72 (m, 2H), 8.41-8.51 (m, 1H), 8.35 (s, 1H), 8.03-8.11 (m, 2H), 7.68 (d, J=9.5 Hz, 1H), 4.19-4.29 (m, 2H), 3.89 (dd, J=6.3, 8.5 Hz, 2H), 3.04 (dd, J=11.2, 12.4 Hz, 2H), 2.57-2.75 (m, 1H), 1.28-1.37 (m, 8H), 0.52 (q, J=5.5 Hz, 2H).

Embodiment 264

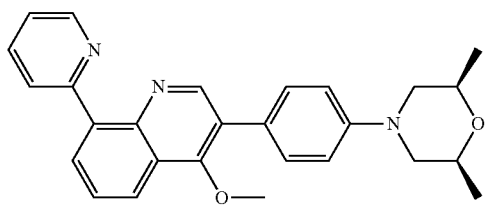 [SMILES: COc1c(-c2ccc(N3C[C@@H](C)O[C@@H](C)C3)cc2)cnc2c(-c3ccccn3)cccc12]

334

(2S,6R)-4-(5-(4-methoxy-8-(pyridin-2-yl)quinolin-3-yl)pyridin-2-yl)-2,6-dimethylmorpholine

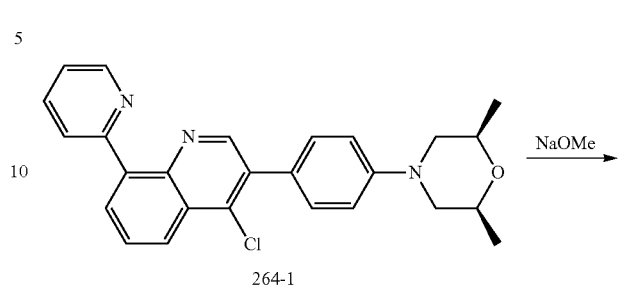

264-1

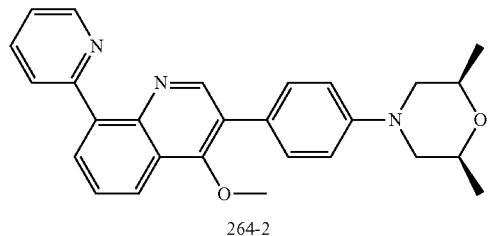

264-2

264-1 (40 mg, 92.82 µmol) was dissolved in methanol (5 mL), then NaOMe (50.14 mg, 928.20 µmol) was added. The mixture was stirred at 25° C. for 48 h, quenched with H$_2$O. After concentration, the residue was purified by prep-HPLC to deliver the target compound (3 mg, yield 7.58%) as white solid. MS ESI calcd for C$_{27}$H$_{27}$N$_3$O$_2$ [M+H]$^+$ 426, found 426. $^1$H NMR (400 MHz, CDCl$_3$) δ ppm 8.91 (s, 1H), 8.79 (d, J=4.5 Hz, 1H), 8.51 (d, J=2.0 Hz, 1H), 8.31 (d, J=8.5 Hz, 1H), 8.08 (dd, J=7.3, 13.8 Hz, 2H), 7.79-7.90 (m, 2H), 7.70 (t, J=7.8 Hz, 1H), 7.28-7.36 (m, 1H), 6.79 (d, J=9.0 Hz, 1H), 4.16 (d, J=12.0 Hz, 2H), 3.68-3.84 (m, 5H), 2.63 (t, J=11.8 Hz, 2H), 1.31 (d, J=6.0 Hz, 6H).

Embodiment 265

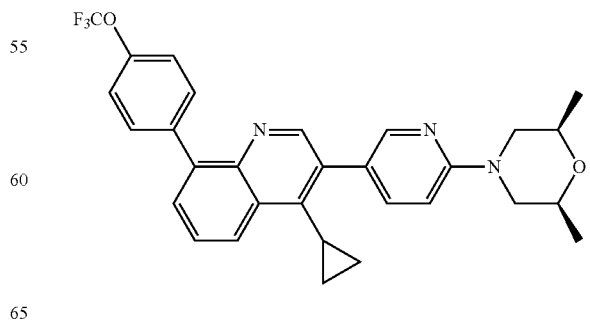

(2S,6R)-4-(5-(4-cyclopropyl-8-(4-(trifluoromethoxy)phenyl)quinolin-3-yl)pyridin-2-yl)-2,6-dimethylmorpholine

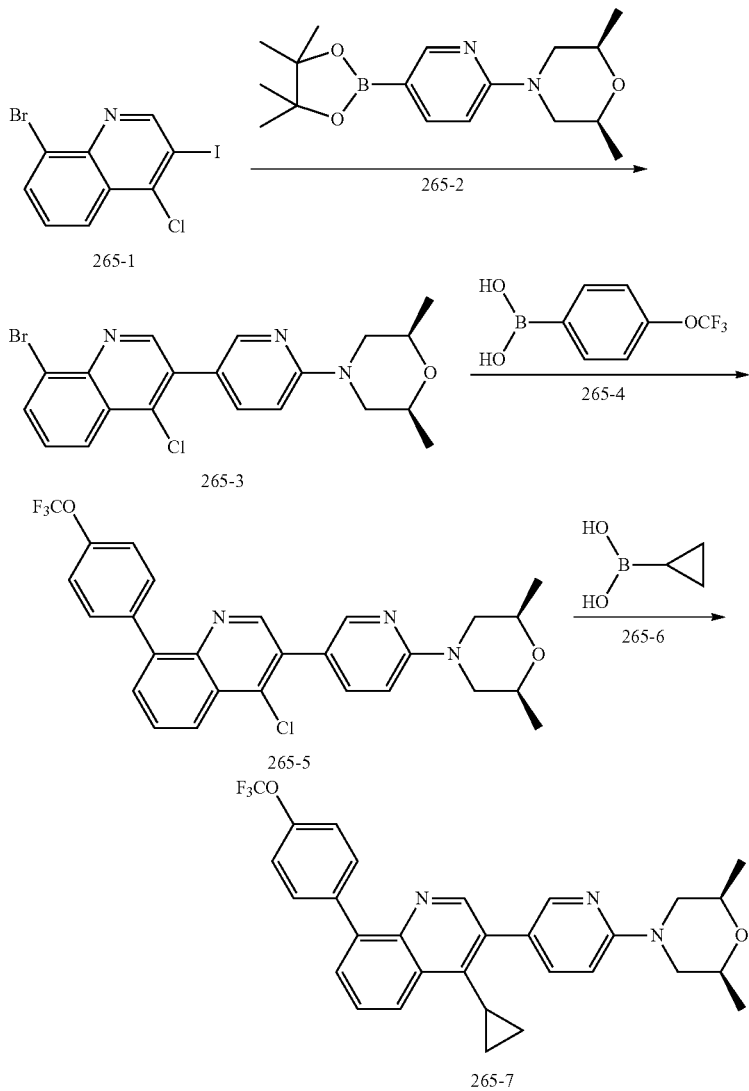

Step 1: Under nitrogen gas atmosphere, a mixture of 265-1 (500 mg, 1.36 mmol, 1 eq), 265-2 (431.89 mg, 1.36 mmol, 1 eq), Pd(dppf)Cl$_2$ (99.51 mg, 136 μmol, 0.10 eq) and Na$_2$CO$_3$ (288.29 mg, 2.72 mmol, 2 eq) in THF (10 mL) was heated to 80° C. and reacted for 2 h. The reaction mixture was poured into H$_2$O (10 mL). The mixture was extracted with EtOAc twice. The organic phase was washed with brines (10 mL), dried over anhydrous MgSO$_4$, concentrated under vacuum. The residue was purified by column chromatography (PE/EtOAc 3:1) to deliver 265-3 (500 mg, yield 84.96%) as yellow solid. MS ESI calcd for C$_{20}$H$_{19}$BrClN$_3$O [M+H]432, found 432.

Step 2: Under nitrogen gas atmosphere, a mixture of 265-3 (500 mg, 1.16 mmol, 1 eq), 265-4 (237.94 mg, 1.16 mmol, 1 eq), Pd(dppf)Cl$_2$ (84.88 mg, 116 μmol, 0.10 eq) and Na$_2$CO$_3$ (245.90 mg, 2.32 mmol, 2 eq) in THF (10 mL) and H$_2$O (2 mL) were heated to 80° C. and reacted for 2 h. The reaction mixture was poured into H$_2$O (10 mL), extracted with EtOAc (10 mL×3). The organic phase was washed with brines (10 mL), dried over anhydrous MgSO$_4$ and concentrated under vacuum. The residue was purified by column chromatography (PE/EtOAc=3:1) to deliver 265-5 (560 mg, 1.09 mmol, 93.93% yield) as yellow solid. MS ESI calcd for C$_{27}$H$_{23}$ClF$_3$N$_3$O$_2$ [M+H]$^+$ 514, found 514.

Step 3: Under nitrogen gas atmosphere, a mixture of 265-5 (100 mg, 194.58 μmol, 1 eq), cyclopropyl boric acid (83.57 mg, 972.90 μmol, 5 eq), Pd(OAc)$_2$ (4.37 mg, 19.46 μmol, 0.10 eq) and bis(adamantyl)butyl phosphine (13.95 mg, 38.92 μmol, 0.20 eq) in toluene (5 mL) was heated to 120° C. and reacted for 2 h. The reaction mixture was poured into H$_2$O (10 mL), extracted with EtOAc (10 mL×3). The organic phase was washed with brines (10 mL), dried over anhydrous Na$_2$SO$_4$ and concentrated under vacuum. The residue was purified by preparative HPLC (TFA) to deliver the target compound (60 mg, yield 59.35%) as white solid. MS ESI calcd for C$_{30}$H$_{28}$F$_3$N$_3$O$_2$ [M+H]$^+$ 520, found 520.

¹H NMR (400 MHz, CHLOROFORM-d) δ ppm 8.87 (s, 1H), 8.63 (dd, J=7.28, 2.51 Hz, 1H), 8.40 (d, J=2.26 Hz, 1H), 7.63-7.80 (m, 5H), 7.36 (d, J=8.28 Hz, 2H), 6.79 (d, J=8.78 Hz, 1H), 4.17 (d, J=11.29 Hz, 2H), 3.81 (dd, J=4.02, 2.26 Hz, 2H), 2.65 (dd, J=12.42, 10.92 Hz, 2H), 2.34 (s, 1H), 1.33 (d, J=6.27 Hz, 6H), 1.13 (d, J=7.53 Hz, 2H), 0.41 (d, J=5.02 Hz, 2H).

Embodiment 266

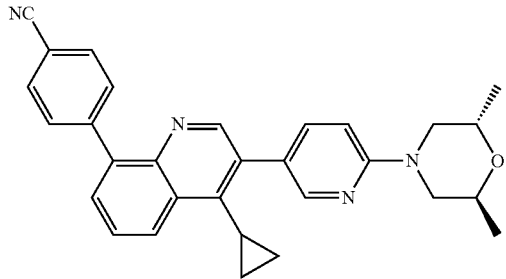 [SMILES: C[C@H]1CN(c2ccc(-c3cnc4c(-c5ccc(C#N)cc5)cccc4c3C3CC3)cn2)C[C@H](C)O1]

4-(4-cyclopropyl-3-(6-((2S,6S)-2,6-dimethylmorpholino)pyridin-3-yl)quinolin-8-yl) benzonitrile

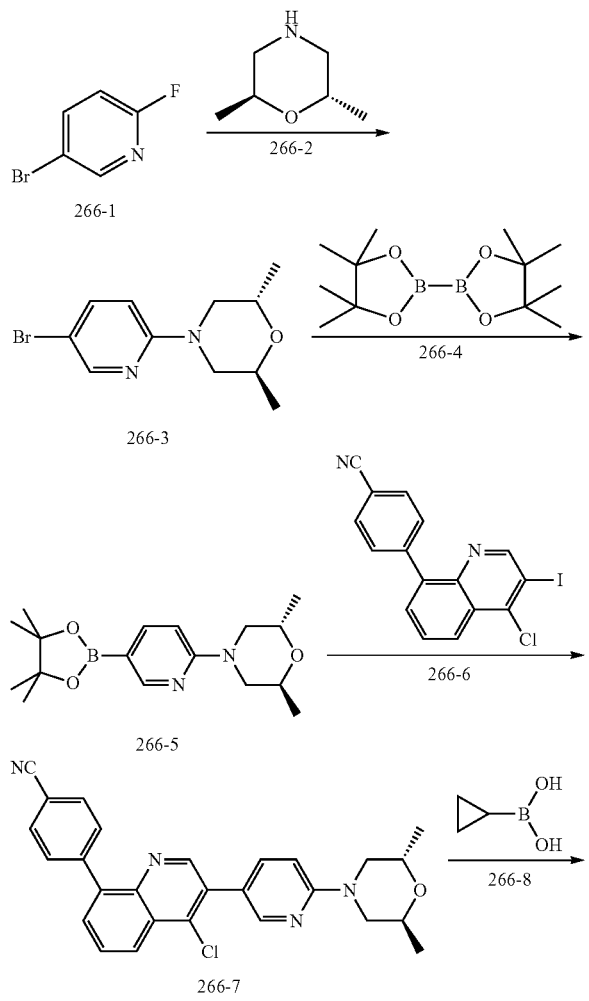

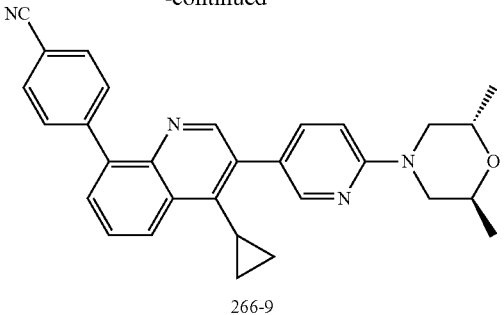

266-9

Step 1: 266-1 (600 mg, 3.41 mmol, 1 eq) and 266-2 (471.28 mg, 4.09 mmol, 1.20 eq) were dissolved in acetonitrile (10 mL), then K₂CO₃ (942.59 mg, 6.82 mmol, 2 eq) was added. The mixture was stirred at 80° C. for 24 h. The mixture was cooled, filtrated and concentrated. The residue was purified by column chromatography (PE/EtOAc=10:1) to deliver 266-3 (450 mg, yield 48.67%) as white solid. MS ESI calcd for $C_{11}H_{15}BrN_2O$ [M+H]⁺ 271, found 271.

Step 2: Under nitrogen gas atmosphere, Pd(dppf)Cl₂ (121.46 mg, 166 μmol, 0.10 eq) was added into a solution of 266-3 (450 mg, 1.66 mmol, 1 eq), KOAc (325.82 mg, 3.32 mmol, 2 eq) and 266-4 (843.08 mg, 3.32 mmol, 2 eq) in dioxane (10 mL). The mixture was stirred at 80° C. for 2 h, poured into H₂O (100 mL). The mixture was extracted with EtOAc (100×3). The organic phases were combined and washed with brines (100 mL), dried over anhydrous sodium sulfate, filtrated, and concentrated under vacuum. The residue was purified by column chromatography (PE/EtOAc=5:1) to deliver 266-5 (200 mg, yield 37.86%) as yellow solid. MS ESI calcd for $C_{17}H_{27}BN_2O_3$ [M+H]⁺ 319, found 319.

Step 3: 266-6 (200 mg, 512.03 μmol, 1 eq) and 266-5 (195.53 mg, 614.44 mol, 1.20 eq) were dissolved in DMF (2 mL)/H₂O (2 mL)/THF (10 mL), under nitrogen gas atmosphere, Pd(dppf)Cl₂ (37.47 mg, 51.20 μmol, 0.10 eq) was added. The mixture was stirred at 70° C. for 2 h, poured into H₂O (150 mL). The mixture was extracted with EtOAc (150 mL×3). The organic phases were combined and washed with brines (100 mL), dried over anhydrous sodium sulfate, filtrated and concentrated under vacuum. The residue was purified by column chromatography (PE/EtOAc=5:1) to deliver 266-7 (150 mg, yield 64.39%) as yellow solid. MS ESI calcd for $C_{27}H_{23}ClN_4O$ [M+H]⁺ 455, found 455.

Step 4: 266-7 (150 mg, 329.71 μmol, 1 eq), cesium carbonate (214.85 mg, 659.42 μmol, 2 eq), bis(adamantyl) butyl phosphine (118.21 mg, 329.71 μmol, 1 eq) and cyclopropyl boric acid (141.61 mg, 1.65 mmol, 5 eq) were dissolved in toluene (10 mL), under nitrogen gas atmosphere, Pd(OAc)₂ (37.01 mg, 164.86 μmol, 0.50 eq) was added. The mixture was stirred at 110° C. for 2 h, poured into H₂O (100 mL). The obtained mixture was extracted with EtOAc (100 mL×3). The organic phases were combined and washed with brines (100 mL), dried over anhydrous sodium sulfate, filtrated, and concentrated under vacuum. The residue was purified by HPLC (acid) to deliver 266-9 (50 mg, yield 32.93%) as yellow solid. MS ESI calcd for $C_{30}H_{28}N_4O$ [M+H]⁺ 461, found 461. ¹H NMR (CDCl₃, 400 MHz): δ ppm 8.83 (s, 1H), 8.65 (t, J=4.8 Hz, 1H), 8.36 (s, 1H), 7.74-7.85 (m, 4H), 7.64-7.73 (m, 3H), 6.74 (d, J=9.0 Hz, 1H), 4.20 (td, J=6.3, 3.5 Hz, 2H), 3.78 (d, J=3.0 Hz, 1H), 3.69-3.74 (m, 1H), 3.33 (dd, J=12.5, 6.5 Hz, 2H), 2.28-2.41 (m, 1H), 1.33 (d, J=6.5 Hz, 6H), 1.13 (d, J=8.0 Hz, 2H), 0.39 (q, J=5.5 Hz, 2H).

Embodiment 267

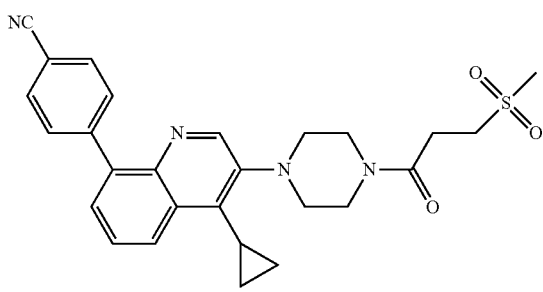 [SMILES: CS(=O)(=O)CCC(=O)N1CCN(c2cnc3c(-c4ccc(C#N)cc4)cccc3c2C2CC2)CC1]

4-(4-cyclopropyl-3-(4-(3-(methylsulfonyl)-3-propanoyl))quinolin-8-yl) benzonitrile

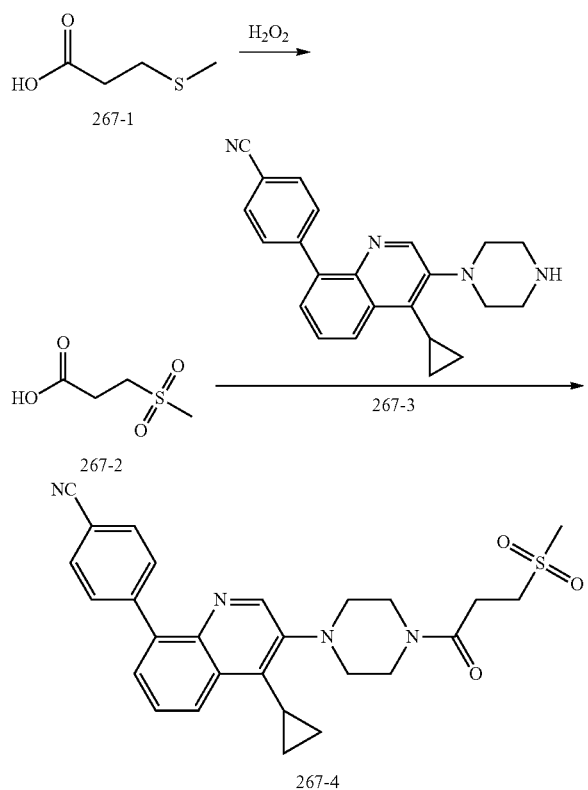

Step 1: 267-1 (3 g, 24.96 mmol, 1 eq) was dissolved in acetic anhydride (20 mL)/acetic acid (20 mL), H$_2$O$_2$ (40%, 2 mL) was added. The mixture was stirred at 25° C. for 12 h. After filtration, the filtrate was concentrated to deliver 267-2 (3 g, yield 78.99%) as white solid. MS ESI calcd for C$_{25}$H$_{25}$ClN$_4$O$_2$ [M+H]$^+$ 449, found 153.

Step 2: 267-3 (1.08 g, 3.05 mmol, 1 eq) and 267-2 (556.94 mg, 3.66 mmol, 1.20 eq) were dissolved in DMF (10 mL), HATU (2.32 g, 6.10 mmol, 2 eq) and DIEA (1.18 g, 9.15 mmol, 3 eq) were added. The mixture was stirred at 25° C. for 0.5 h, then the mixture was partitioned between H$_2$O (100 mL) and EtOAc (100 mL). The EtOAc phase was washed with brines (30×3), dried over Na$_2$SO$_4$, filtrated and concentrated. The residue was purified by column chromatography (PE/EtOAc=3:1) to deliver the target compound (800 mg, yield 53.68%) as yellow solid. MS ESI calcd for C$_{27}$H$_{28}$N$_4$O$_3$S [M+H]$^+$ 489, found 489. $^1$HNMR (400 MHz, CDCl3) δ ppm 8.69 (s, 1H), 8.51 (d, J=8.5 Hz, 1H), 7.76 (s, 4H), 7.56-7.63 (m, 2H), 3.88 (brs, 2H), 3.74 (brs, 2H), 3.48 (t, J=7.0 Hz, 2H), 3.18-3.36 (m, 4H), 3.01 (s, 3H), 2.99 (d, J=7.5 Hz, 2H), 2.00-2.16 (m, 1H), 1.32 (d, J=8.0 Hz, 2H), 0.98 (d, J=4.5 Hz, 2H).

Embodiment 268

4-(4-methoxy-3-(4-(pyrrolidin-1-yl)piperidin-1-yl)quinolin-8-yl)benzonitrile

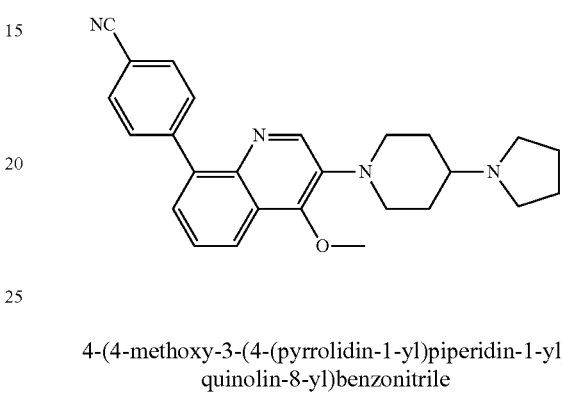

342

4-(4-cyclopropyl-3-((3S,4R)-4-((2S,6R)-2,6-dimethylmorpholino)-3-fluoropiperidin-1-yl)quinolin-8-yl)benzonitrile

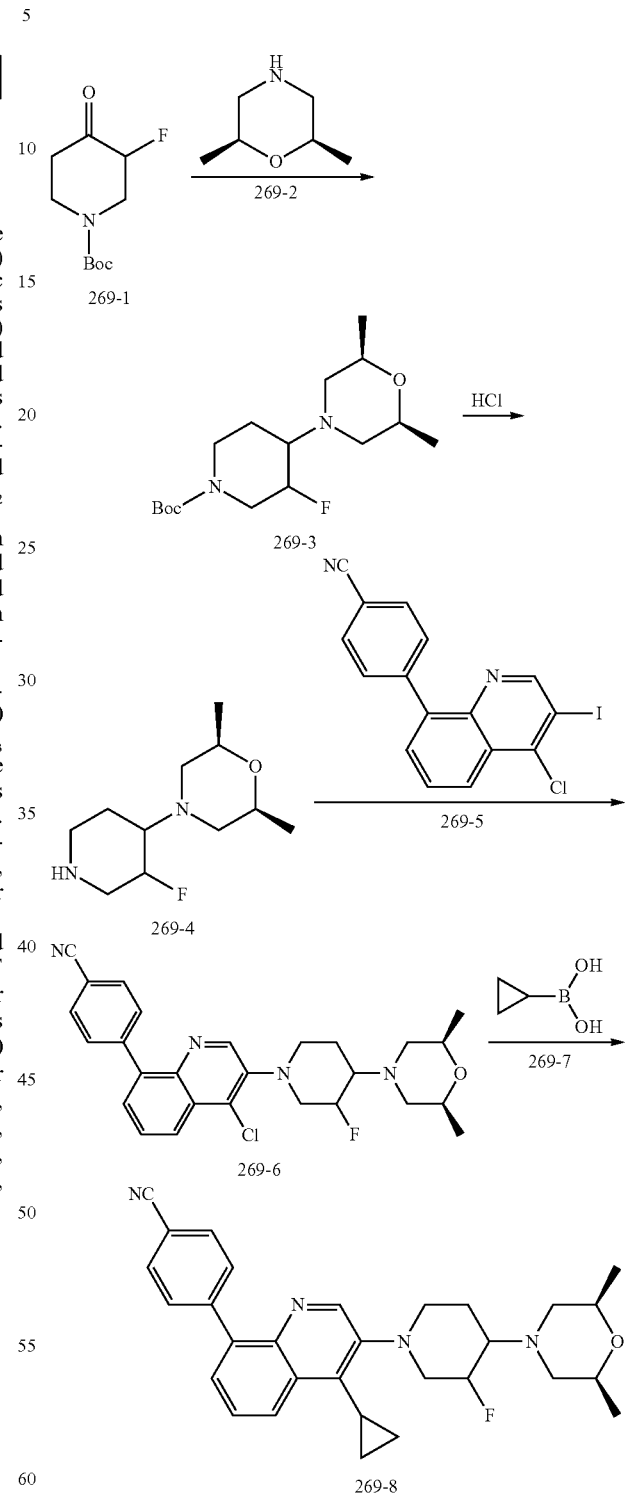

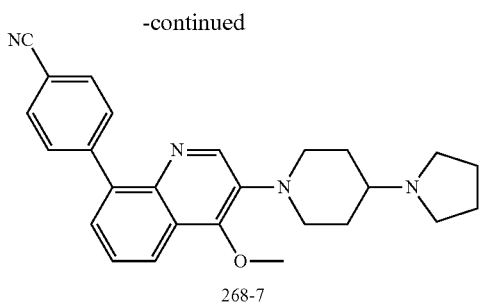

Step 1: 268-1 (10 g, 50.19 mmol, 1 eq) and pyrrolidine (3.57 g, 50.19 mmol, 1 eq) were dissolved in DCM (100 mL) and NaBH(OAc)$_3$ (15.96 g, 75.29 mmol, 1.50 eq) and acetic acid (1.05 g, 17.49 mmol) were added. The mixture was stirred at 25° C. for 16 h, poured into ice-water (W/W=1/1) (100 mL) and stirred for 10 min. The mixture was extracted with DCM (100 mL×3). The organic phases were combined and washed with brines (100 mL), dried over anhydrous sodium sulfate, filtrated, and concentrated under vacuum. The residue was purified by silica gel column chromatography (PE/EtOAc=5:1 to 1:1) to deliver 268-3 (8.50 g, yield 66.58%) as yellow solid. MS ESI calcd for $C_{14}H_{26}N_2O_2$ [M+H]$^+$ 255, found 255.

Step 2: 268-3 (8.50 g, 33.42 mmol, 1 eq) was dissolved in DCM (50 mL) and TFA (50 mL) was added. The obtained compound was stirred at 25° C. for 5 h, concentrated and dried to deliver crude product 268-4 as yellow oil, which was used for the next step directly without further purification. MS ESI calcd for $C_9H_{18}N_2$ [M+H]$^+$ 155, found 155.

Step 3: 268-5 (500 mg, 1.15 mmol, 1 eq) and 268-4 (308.31 mg, 1.15 mmol, 1 eq) were dissolved in toluene (10 mL), Xantphos (133 mg, 229.85 μmol, 0.20 eq), Pd$_2$(dba)$_3$ (105.24 mg, 114.93 μmol, 0.10 eq), and cesium carbonate (1.50 g, 4.60 mmol, 4 eq) were added. The mixture was stirred at 120° C. for 2 h, cooled to 60° C. and concentrated. The concentrate was purified by silica gel column chromatography (PE/EtOAc=10:1 to 1:1) to deliver 268-6 (220 mg, yield 41.46%) as yellow solid. MS ESI calcd for $C_{25}H_{25}BrN_4$ [M+H]$^+$ 461, found 461.

Step 4: KOMe (7.60 mg, 108.37 μmol, 1 eq) was added into a solution of 268-6 (50 mg, 108.37 μmol, 1 eq) in DMF (2 mL) in portions. The compound was stirred at 25° C. for 2 h and concentrated under vacuum. The residue was purified by HPLC (TFA) to deliver the target compound (10 mg, yield 22.37%) as yellow solid. MS ESI calcd for $C_{26}H_{28}N_4O$ [M+H]$^+$ 413, found 413. $^1$HNMR (400 MHz, CHLOROFORM-d) δ ppm 9.07 (brs, 1H), 2.13 Hz, 1H), 8.36 (d, J=7.65, 7.82 (d, J=8.03 Hz, 2H), 7.71-7.78 (m, 2H), 7.65 (d, J=7.78 Hz, 2H), 4.34 (s, 3H), 3.86-4.05 (m, 3H), 3.57-3.72 (m, 2H), 2.95-3.16 (m, 5H), 2.05-2.43 (m, 9H).

Embodiment 269

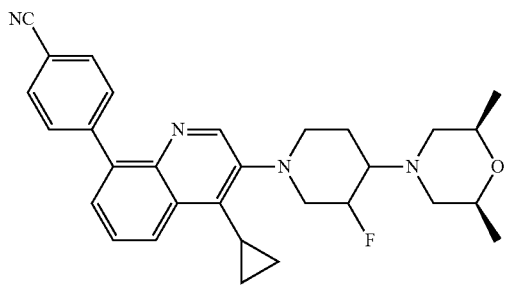 [SMILES: C[C@@H]1CN(C2CCN(c3cnc4c(-c5ccc(C#N)cc5)cccc4c3C3CC3)CC2F)C[C@H](C)O1]

Step 1: 269-1 (3 g, 1.00 mmol) and 269-2 (1.91 g, 1.20 mmol) were dissolved in DCM (15 mL) and stirred at room temperature for 0.5 h, then NaBH(OAc)$_3$ (4.39 g, 16.57 mmol) was added, the mixture was stirred for 17 h. The mixture was poured into H$_2$O (100 mL), extracted with DCM (150 mL*3). The organic phase was washed with brines (150 mL), dried over Na$_2$SO$_4$, filtrated and concentrated under vacuum. The residue was purified by silica gel column chromatography (PE/EtOAc=10:1 to 2:1) to deliver 269-3 (2 g, yield 45.77%) as colorless oil. MS ESI calcd for C$_{16}$H$_{29}$FN$_2$O$_3$ [M+H]$^+$ 317, found 317.

Step 2: 269-3 (720 mg, 2.28 mmol) was dissolved in DCM (10 mL) and HCl/dioxane (4 M, 2 mL) was added. The mixture was stirred at room temperature for 30 min. After concentration, 269-4 was obtained, which was used for the next step directly. MS ESI calcd for C$_{11}$H$_{21}$FN$_2$O [M+H]$^+$ 217, found 217.

Step 3: 269-5 (700 mg, 1.79 mmol), Xantphos (207.15 mg, 358.00 μmol), Cs$_2$CO$_3$ (2.33 g, 7.16 mmol) and 269-4 (464.5 mg, 2.15 mmol) were dissolved in toluene (15 mL) and Pd$_2$(dba)$_3$ (163.91 mg, 179 μmol) was added. The mixture was stirred at 110° C. for 2 h, then poured into H$_2$O (150 mL). The mixture was extracted with EtOAc (200 mL*3). The organic phase was washed with brines (200 mL), dried over anhydrous sodium sulfate, filtrated and concentrated. The residue was purified by column chromatography (PE/EtOAc=8:1 to 1:1) to deliver 269-3 (200 mg, yield 23.33%) as white solid. MS ESI calcd for C$_{27}$H$_{28}$ClFN$_4$O [M+H]$^+$ 479, found 479.

Step 4: 269-6 (50 mg, 104.39 μmol), cesium carbonate (68.02 mg, 208.78 μmol), bis(adamantyl)butyl phosphine (37.43 mg, 104.39 μmol) and 269-7 (44.84 mg, 521.955 μmol) were dissolved in toluene (3 mL), Pd(OAc)$_2$ (11.72 mg, 52.20 μmol) was added. The mixture was stirred at 110° C. for 2 h, then poured into H$_2$O (50 mL). The mixture was extracted with EtOAc (20 mL*3). The organic phase was washed with brines (50 mL), dried over anhydrous sodium sulfate, and concentrated under vacuum. The residue was purified by HPLC to deliver compound (2 mg, yield 3.95%) as yellow solid. MS ESI calcd for C$_{30}$H$_{33}$FN$_4$O [M+H]$^+$ 485, found 485. $^1$HNMR (400 MHz, CDCl$_3$) δ ppm 8.72 (s, 1H), 8.51 (d, J=7.8 Hz, 1H), 7.77 (s, 5H), 7.56-7.62 (m, 2H), 3.73-3.91 (m, 4H), 3.17-3.23 (m, 1H), 2.95-3.12 (m, 3H), 2.28-2.48 (m, 2H), 1.98-2.17 (m, 4H), 1.91 (d, J=9.8 Hz, 1H), 1.22 (d, J=6.0 Hz, 7H), 0.90 (t, J=6.7 Hz, 3H).

Embodiment 270

4-(3-(4-(5-isopropylpyridin-2-yl)-3-)-4-methoxyquinolin-8-yl) benzonitrile

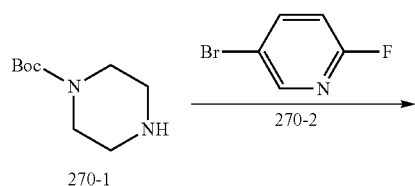

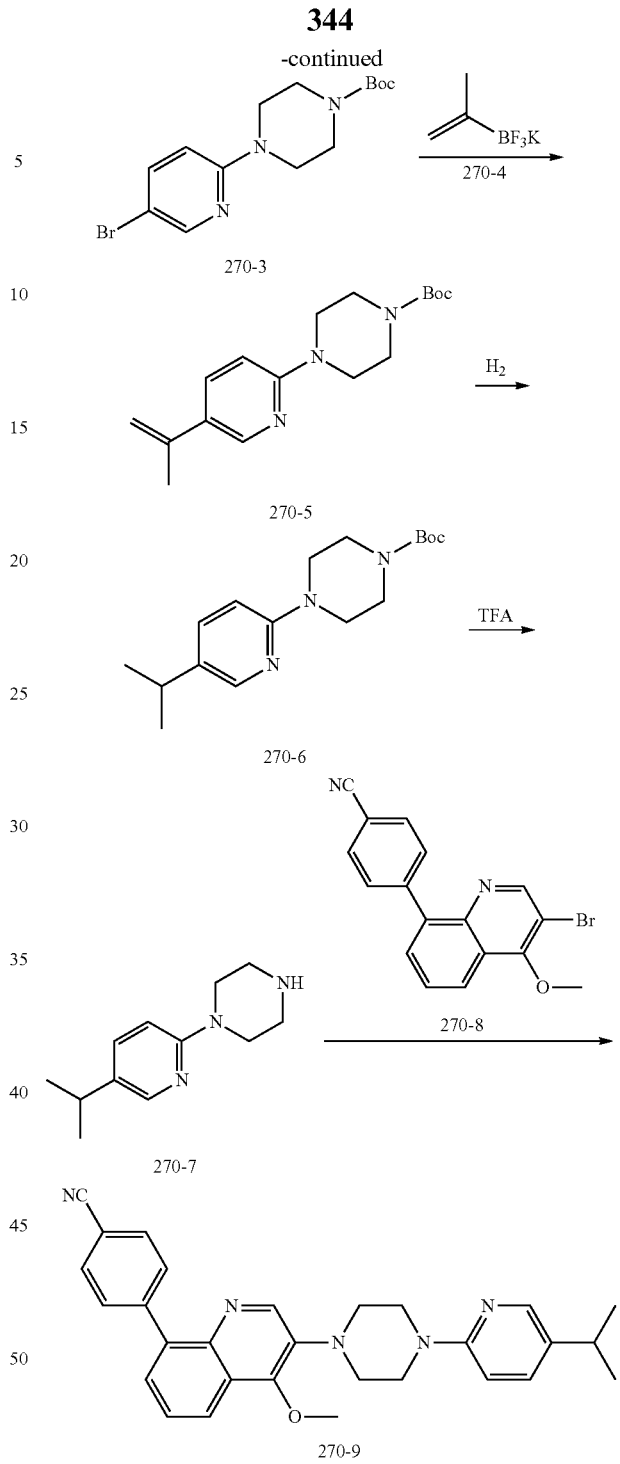

Step 1: K$_2$CO$_3$ (2.76 g, 20 mmol) was added into a mixture of 270-2 (1.76 g, 10 mmol) and 270-1 (2.24 g, 12 mmol) in DMF (20 mL). The mixture was stirred at 110° C. for 12 h, poured into H$_2$O (100 mL). The obtained mixture was extracted with EtOAc (150 mL×3). The organic phases were combined and washed with brines (150 mL), dried over anhydrous sodium sulfate, filtrated, and concentrated under vacuum. The residue was purified by column chromatography (PE/EtOAc=7:1) to deliver 270-3 (3 g, yield 87.66%) as colorless oil. MS ESI calcd for C$_{14}$H$_2$OBrN$_3$O$_2$ [M+H]$^+$ 342, found 342.

Step 2: 270-3 (1.70 g, 4.97 mmol), Na$_2$CO$_3$ (1.05 g, 9.94 mmol) and potassium isopropenyl trifluoroborate (1.49 g, 9.94 mmol) were dissolved in DMF (2 mL), under nitrogen gas atmosphere, Pd(dppf)Cl$_2$ (363.65 mg, 497 μmol) was added. The mixture was stirred at 70° C. for 2 h, then poured into H$_2$O (150 mL). The obtained mixture was extracted with EtOAc (150 mL×3). The organic phases were combined and washed with brines (150 mL), dried over anhydrous sodium sulfate, filtrated and concentrated under vacuum. The residue was purified by column chromatography (PE/EtOAc=10:1) to deliver 270-5 (1 g, yield 66.32%) as colorless oil. MS ESI calcd for C$_{17}$H$_{25}$N$_3$O$_2$ [M+H]$^+$ 304, found 304.

Step 3: 270-5 (1 g, 3.30 mmol) was dissolved in methanol (30 mL)/EtOAc (30 mL) and Pd(OH)$_2$/C (10%, 0.1 g) was added. The suspension was degassed and swept with hydrogen gas for 3 times. The mixture was stirred at 25° C. for 2 h under H$_2$ (40 psi). TLC showed that the starting material was completely consumed. The mixture was filtrated, the filtrate was concentrated. The crude product was used for the next step directly. MS ESI calcd for C$_{17}$H$_{27}$N$_3$O$_2$ [M+H]$^+$ 306, found 306.

Step 4: 270-6 (500 mg, 1.64 mmol) was dissolved in DCM (5 mL) and TFA (2.43 g, 21.32 mmol) was added in portions. The mixture was stirred for 30 min and concentrated. The residue was poured into saturated Na$_2$CO$_3$ solution (100 mL). The obtained mixture was extracted with EtOAc (100 mL×3). The organic phases were combined and washed with brines (100 mL), dried over anhydrous sodium sulfate, filtrated, and concentrated under vacuum. The crude product was used for the next step directly. MS ESI calcd for C$_{12}$H$_{19}$N$_3$ [M+H]$^+$ 206, found 206.

Step 5: Under nitrogen gas atmosphere, Pd$_2$(dba)$_3$ (40.50 mg, 44.22 μmol, 0.10 eq) was added into a solution of 270-8 (150 mg, 442.23 μmol, 1 eq), cesium carbonate (288.17 mg, 884.46 μmol, 2 eq), Xantphos (51.18 mg, 88.45 μmol, 0.20 eq) and 270-7 (108.95 mg, 530.68 μmol, 1.20 eq) in toluene (10 mL). The mixture was stirred at 110° C. for 2 h, poured into H$_2$O (100 mL). The obtained mixture was extracted with EtOAc (150 mL×3). The organic phases were combined and washed with brines (100 mL), dried over anhydrous sodium sulfate, filtrated, and concentrated under vacuum. The residue was purified by HPLC (acid) to deliver the target product (50 mg, yield 24.39%) as yellow solid. MS ESI calcd for C$_{29}$H$_{29}$N$_5$O [M+H]$^+$ 464, found 464. $^1$H NMR (400 MHz, CDCl$_{3 6}$) δ ppm 8.79 (s, 1H), 8.16-8.27 (m, 1H), 8.05-8.14 (m, 1H), 7.74-7.82 (m, 4H), 7.53-7.64 (m, 2H), 7.35-7.45 (m, 1H), 6.72 (dd, J=6.3, 8.3 Hz, 1H), 4.15 (s, 3H), 3.7$_2$ (d, J=4.0 Hz, 4H), 3.34-3.44 (m, 4H), 2.49 (t, J=7.5 Hz, 1H), 1.21-1.31 (m, 5H).

Embodiment 271

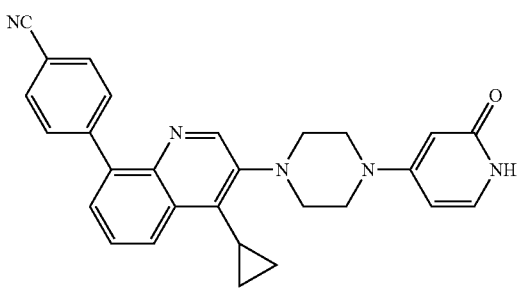 [SMILES: N#Cc1ccc(-c2cccc3c(C4CC4)c(N4CCN(c5cc[nH]c(=O)c5)CC4)cnc23)cc1]

4-(4-cyclopropyl-3-(4-(2-oxo-1,2-dihydropyridin-4-yl)piperazin-1-yl)quinolin-8-yl) benzonitrile

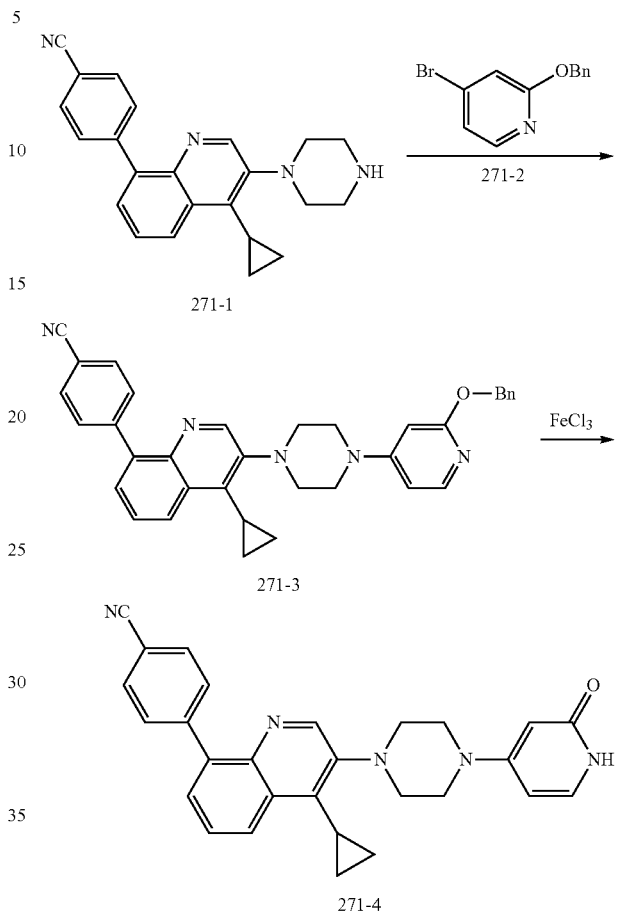

Step 1: Under nitrogen gas atmosphere, Pd$_2$(dba)$_3$ (38.75 mg, 42.32 μmol) was added into a mixture of 271-1 (150 mg, 423.19 μmol), sodium tert-butoxide (81.34 mg, 846.38 μmol), Xantphos (48.97 mg, 84.64 μmol) and 271-2 (134.13 mg, 507.83 μmol) in toluene (10 mL). The mixture was stirred at 110° C. for 2 h, poured into H$_2$O (150 mL). The obtained mixture was extracted with EtOAc (100×3). The organic phases were combined and washed with brines (100 mL), dried over anhydrous sodium sulfate, filtrated, and concentrated under vacuum. The residue was purified by column chromatography (PE/EtOAc=3:1) to deliver 271-3 (150 mg, yield 65.93%) as yellow solid. MS ESI calcd for C$_{35}$H$_{31}$N$_5$O [M+H]$^+$ 538, found 538.

Step 2: FeCl$_3$ (452.52 mg, 2.79 mmol) was added into a mixture of 271-3 (150 mg, 278.99 μmol) in DCM (10 mL) in portions. The reaction mixture was stirred at room temperature for 60 min, then filtrated, extracted with EtOAc (100 mL×3). The organic phases were combined and washed with brines (100 mL), dried over anhydrous sodium sulfate, filtrated, and concentrated under vacuum. The residue was purified by preparative HPLC (acid) to deliver the target compound (50 mg, yield 40.05%) as yellow solid. MS ESI calcd for C$_{28}$H$_{25}$N$_5$O [M+H]$^+$ 448, found 448. $^1$HNMR (400 MHz, METHANOL-d$_4$) δ ppm 8.77 (d, J=7.8 Hz, 1H), 8.67 (s, 1H), 7.93 (d, J=8.3 Hz, 2H), 7.82-7.89 (m, 1H), 7.76-7.83 (m, 3H), 7.72 (d, J=7.5 Hz, 1H), 6.86 (d, J=5.5 Hz, 1H), 6.25

(d, J=2.3 Hz, 1H), 3.91 (brs., 4H), 3.55 (d, J=4.8 Hz, 4H), 1.52 (brs, 1H), 0.99-1.09 (m, 2H), 0.13 (brs, 2H).

Experiment 1: Assay In Vitro

Experimental Objective:

The luciferase (Gli-Luc) reporter gene with Gli response element was transfected into C3H10T1/2 cells, under Shh-N stimulation conditions, determine the Hedgehog signaling pathway inhibitors through the detection of gene expression in cell activity report. In this study, we evaluated the inhibitory effects of compounds on Hedgehog signaling pathway in the IC50 value of the compound as an index.

Experimental Materials:

Cell lines: C3H10T1/2/Gli-Luc stable cell line

C3H10T1/2/Gli-Luc Cell culture medium (DMEM/high glucose HyClone, #SH30022.01B; 10% serum Hyclone, #SV30087; 0.4% Hygromycin B Roche, #13398200)

0.25% Trypsin-EDTA (Gibco, #25200)

PBS ($KH_2PO_4$ 0.24 g, $Na_2HPO_4$ 1.44 g, NaCl 8.0 g, KCl 0.2 g, H2O added to 1 L and adjusted to PH 7.4)

Shh-N, HEK293/SHH-N stable cell culture supernatant

Lysates (Promega, # E1531)

Reaction solution (Promega, # E1501)

384-well plate, Greiner #781074

96-well culture plate, Greiner #655180

96-well microhole plate, Bi Yuntian #FPT019

$CO_2$ incubator, Thermo #3423

Clean bench, AIRTECH #A10051560

Inverted microscope, Nikon #TS100

Centrifuge, Xiangyi #L530

Therom VarioSkan Flash Multifunctional reading instrument

Experimental Procedure and Method:

Inoculate the logarithmic growth phase of C3H10T1/2/Gli-Luc cells into a 96-well culture plate with 20000 cells per well, cells were cultured in a 37° C., 5% $CO_2$ incubator overnight. The next day, the compounds were diluted in the following ways: the positive compound GDC0449 (1 mM) and the compounds (1 mM) to be measured were serially diluted to 7 concentrations by DMSO according to 1:3 and 1:10 respectively, the eighth is for DMSO control, and then diluted with fresh medium 100 times. The medium of the cells cultured overnight was removed, 80 μL fresh culture medium was added per well, then 20 μL gradiently diluted positive compound and compounds to be measured and 100 μL 30 nM Shh-N containing conditioned medium were added, each concentration repeated 2 wells, at the same time, positive and negative reference well were set (i.e. Shh Ctrl: 80 μL fresh medium+20 μL 1% DMSO containing medium+100 μL 30 nM Shh-N containing conditioned medium; Unstimulated Ctrl: 180 μL fresh medium+20 μL 1% DMSO containing medium), cells were cultured in the incubator for further 24 h.

Intracellular luciferase activity detection: take the cells out of 96-well plate, discard the culture medium, the cells were washed with PBS twice, then each well added with 20 μL lysate (Promega E1531), oscillate pyrolysis at room temperature for 30 min. 5 μL cell lysates were transferred to 384-well plate (Greiner 781074), then each well was added with 25 μL luciferase reaction liquid (Promega E1501), after rapid mixed, immediately placed into the VarioSkan Flash multi-function reading instrument to read the relative light units (RLU) value.

Data analysis: using Prism's GraphPad 5 for data analysis. RLU reading to the logarithmic mapping of compound concentration on behalf of luciferase activity, and then curve fitting using the following equation to give $IC_{50}$ value, Y (RLU)=minimum+(maximum−minimum)/(1+10^(log of compound concentration−Log $IC_{50}$)).

TABLE 1

$IC_{50}$ of the inhibitory activities of compounds on the hedgehog pathway or inhibition rates of compounds at a certain concentration

| Compounds obtained in Embodiments | biological activity |
| --- | --- |
| Embodiment 1 | C |
| Embodiment 2 | C |
| Embodiment 3 | C |
| Embodiment 4 | C |
| Embodiment 5 | C |
| Embodiment 6 | D |
| Embodiment 7 | D |
| Embodiment 8 | C |
| Embodiment 9 | E |
| Embodiment 10 | C |
| Embodiment 11 | C |
| Embodiment 12 | D |
| Embodiment 13 | C |
| Embodiment 14 | B |
| Embodiment 15 | C |
| Embodiment 16 | C |
| Embodiment 17 | B |
| Embodiment 18 | C |
| Embodiment 19 | C |
| Embodiment 20 | C |
| Embodiment 21 | C |
| Embodiment 22 | B |
| Embodiment 23 | A |
| Embodiment 24 | B |
| Embodiment 25 | B |
| Embodiment 26 | B |
| Embodiment 27 | A |
| Embodiment 28 | A |
| Embodiment 29 | C |
| Embodiment 30 | C |
| Embodiment 31 | C |
| Embodiment 32 | C |
| Embodiment 33 | C |
| Embodiment 34 | C |
| Embodiment 35 | C |
| Embodiment 36 | C |
| Embodiment 37 | C |
| Embodiment 38 | A |
| Embodiment 39 | A |
| Embodiment 40 | A |
| Embodiment 41 | A |
| Embodiment 42 | C |
| Embodiment 43 | E |
| Embodiment 44 | D |
| Embodiment 45 | E |
| Embodiment 46 | C |
| Embodiment 47 | E |
| Embodiment 48 | E |
| Embodiment 49 | D |
| Embodiment 50 | D |
| Embodiment 51 | C |
| Embodiment 52 | C |
| Embodiment 53 | D |
| Embodiment 54 | E |
| Embodiment 55 | E |
| Embodiment 56 | D |
| Embodiment 57 | D |
| Embodiment 58 | E |
| Embodiment 59 | D |
| Embodiment 60 | C |
| Embodiment 61 | C |
| Embodiment 62 | C |
| Embodiment 63 | E |
| Embodiment 64 | D |
| Embodiment 65 | D |
| Embodiment 66 | D |
| Embodiment 67 | D |
| Embodiment 68 | E |
| Embodiment 69 | D |
| Embodiment 70 | D |
| Embodiment 71 | E |

TABLE 1-continued

IC$_{50}$ of the inhibitory activities of compounds on the hedgehog pathway or inhibition rates of compounds at a certain concentration

| Compounds obtained in Embodiments | biological activity |
| --- | --- |
| Embodiment 72 | E |
| Embodiment 73 | D |
| Embodiment 74 | E |
| Embodiment 75 | E |
| Embodiment 76 | C |
| Embodiment 77 | D |
| Embodiment 78 | C |
| Embodiment 79 | D |
| Embodiment 80 | E |
| Embodiment 81 | E |
| Embodiment 82 | E |
| Embodiment 83 | E |
| Embodiment 84 | E |
| Embodiment 85 | D |
| Embodiment 86 | D |
| Embodiment 87 | C |
| Embodiment 88 | A |
| Embodiment 89 | A |
| Embodiment 90 | B |
| Embodiment 91 | A |
| Embodiment 92 | A |
| Embodiment 93 | A |
| Embodiment 94 | A |
| Embodiment 95 | A |
| Embodiment 96 | C |
| Embodiment 97 | C |
| Embodiment 98 | A |
| Embodiment 99 | A |
| Embodiment 100 | C |
| Embodiment 101 | C |
| Embodiment 102 | B |
| Embodiment 103 | B |
| Embodiment 104 | A |
| Embodiment 105 | A |
| Embodiment 106 | B |
| Embodiment 107 | A |
| Embodiment 108 | C |
| Embodiment 109 | B |
| Embodiment 110 | C |
| Embodiment 111 | C |
| Embodiment 112 | A |
| Embodiment 113 | A |
| Embodiment 114 | E |
| Embodiment 115 | E |
| Embodiment 116 | C |
| Embodiment 117 | E |
| Embodiment 118 | B |
| Embodiment 119 | B |
| Embodiment 120 | D |
| Embodiment 121 | A |
| Embodiment 122 | B |
| Embodiment 123 | A |
| Embodiment 124 | B |
| Embodiment 125 | A |
| Embodiment 126 | C |
| Embodiment 127 | C |
| Embodiment 128 | D |
| Embodiment 129 | B |
| Embodiment 130 | D |
| Embodiment 131 | E |
| Embodiment 132 | A |
| Embodiment 133 | A |
| Embodiment 134 | A |
| Embodiment 135 | C |
| Embodiment 136 | B |
| Embodiment 137 | C |
| Embodiment 138 | A |
| Embodiment 139 | B |
| Embodiment 140 | D |
| Embodiment 141 | C |
| Embodiment 142 | D |
| Embodiment 143 | A |
| Embodiment 144 | C |
| Embodiment 145 | A |
| Embodiment 146 | D |
| Embodiment 147 | C |
| Embodiment 148 | B |
| Embodiment 149 | A |
| Embodiment 150 | D |
| Embodiment 151 | A |
| Embodiment 152 | A |
| Embodiment 153 | C |
| Embodiment 154 | A |
| Embodiment 155 | C |
| Embodiment 156 | D |
| Embodiment 157 | E |
| Embodiment 158 | A |
| Embodiment 159 | A |
| Embodiment 160 | A |
| Embodiment 161 | A |
| Embodiment 162 | A |
| Embodiment 163 | C |
| Embodiment 164 | C |
| Embodiment 165 | C |
| Embodiment 166 | A |
| Embodiment 167 | A |
| Embodiment 168 | A |
| Embodiment 169 | A |
| Embodiment 170 | A |
| Embodiment 171 | A |
| Embodiment 172 | A |
| Embodiment 173 | C |
| Embodiment 174 | C |
| Embodiment 175 | C |
| Embodiment 176 | A |
| Embodiment 177 | A |
| Embodiment 178 | C |
| Embodiment 179 | D |
| Embodiment 180 | A |
| Embodiment 181 | A |
| Embodiment 182 | A |
| Embodiment 183 | B |
| Embodiment 184 | B |
| Embodiment 185 | C |
| Embodiment 186 | A |
| Embodiment 187 | A |
| Embodiment 188 | A |
| Embodiment 189 | A |
| Embodiment 190 | A |
| Embodiment 191 | A |
| Embodiment 192 | A |
| Embodiment 193 | C |
| Embodiment 194 | A |
| Embodiment 195 | B |
| Embodiment 196 | C |
| Embodiment 197 | D |
| Embodiment 198 | B |
| Embodiment 199 | C |
| Embodiment 200 | A |
| Embodiment 201 | A |
| Embodiment 202 | A |
| Embodiment 203 | A |
| Embodiment 204 | A |
| Embodiment 205 | B |
| Embodiment 206 | A |
| Embodiment 207 | C |
| Embodiment 208 | C |
| Embodiment 209 | A |
| Embodiment 210 | A |
| Embodiment 211 | A |
| Embodiment 212 | A |
| Embodiment 213 | A |
| Embodiment 214 | A |
| Embodiment 215 | C |
| Embodiment 216 | C |
| Embodiment 217 | C |
| Embodiment 218 | A |
| Embodiment 219 | A |
| Embodiment 220 | A |
| Embodiment 221 | A |

TABLE 1-continued

IC$_{50}$ of the inhibitory activities of compounds on the hedgehog pathway or inhibition rates of compounds at a certain concentration

| Compounds obtained in Embodiments | biological activity |
|---|---|
| Embodiment 222 | A |
| Embodiment 223 | C |
| Embodiment 224 | A |
| Embodiment 225 | A |
| Embodiment 226 | A |
| Embodiment 227 | A |
| Embodiment 228 | C |
| Embodiment 229 | C |
| Embodiment 230 | C |
| Embodiment 231 | A |
| Embodiment 232 | C |
| Embodiment 233 | A |
| Embodiment 234 | A |
| Embodiment 235 | A |
| Embodiment 236 | A |
| Embodiment 237 | C |
| Embodiment 238 | A |
| Embodiment 239 | C |
| Embodiment 240 | C |
| Embodiment 241 | C |
| Embodiment 242 | A |
| Embodiment 243 | A |
| Embodiment 244 | A |
| Embodiment 245 | C |
| Embodiment 246 | A |
| Embodiment 247 | C |
| Embodiment 248 | A |
| Embodiment 249 | A |
| Embodiment 250 | C |
| Embodiment 251 | A |
| Embodiment 252 | C |
| Embodiment 253 | C |
| Embodiment 254 | A |
| Embodiment 255 | C |
| Embodiment 256 | C |
| Embodiment 257 | A |
| Embodiment 258 | C |
| Embodiment 259 | B |
| Embodiment 260 | C |
| Embodiment 261 | C |
| Embodiment 262 | A |
| Embodiment 263 | A |
| Embodiment 264 | A |
| Embodiment 265 | B |
| Embodiment 266 | A |
| Embodiment 267 | A |
| Embodiment 268 | C |
| Embodiment 269 | A |
| Embodiment 270 | B |
| Embodiment 271 | C |

Note:
A ≤50 nM;
50 nM < B ≤ 100 nM;
100 nM < C ≤ 500 nM;
500 nM < D ≤ 1000 nM;
1000 nM < E ≤ 5000 nM.

Conclusion: the compounds of the present invention have significant inhibition effect on the hedgehog pathway.

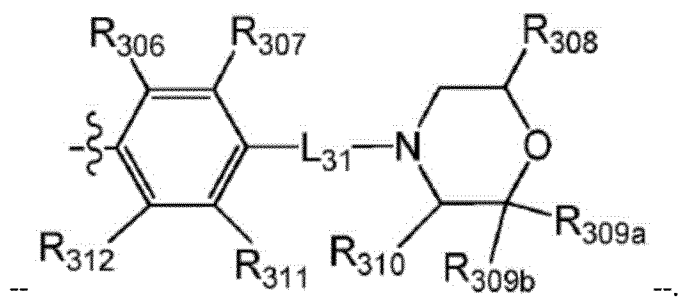

What is claimed is:

1. A compound represented by formula (I), or a pharmaceutically acceptable salt thereof,
wherein, A is selected from

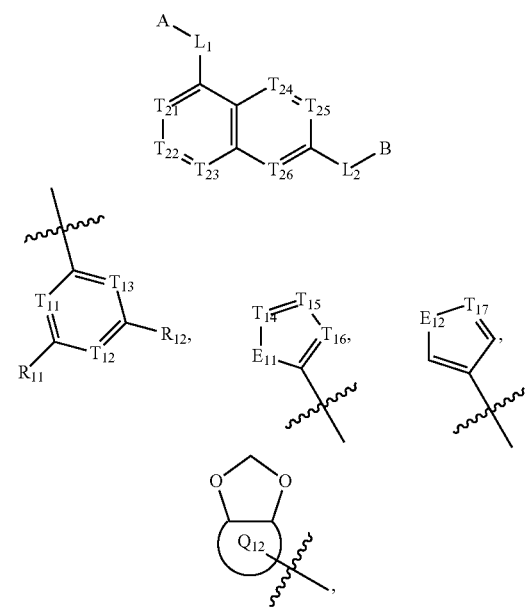

each of $T_{11-17}$ is independently selected from N, $C(R_{13})$;
$L_1$ is a single bond;
$L_2$ is $C(=O)N(R_{15})$ or a single bond;
each of $E_{11-12}$ is independently selected from $N(R_{14})$ or $C(R_{18})(R_{19})$;
each of $R_{11-13}$, $R_{18-19}$ is independently selected from H, F, Cl, Br, I, CN, OH, SH, NH$_2$, an optionally $R_{01}$-substituted $C_{1-6}$ alkyl or heteroalkyl or alkyl-heteroatom group or heteroalkyl-heteroatom group, an optionally $R_{02}$-substituted $C_{3-8}$ cyclic group or heterocyclic group or cycle-heteroatom group or heterocycle-heteroatom group;
each of $R_{14-15}$ is independently selected from H, an optionally $R_{01}$-substituted $C_{1-6}$ alkyl or $C_{3-6}$ cycloalkyl;
each of $Q_{12}$ is independently selected from a phenyl, a pyridyl, a thienyl, a furyl;
$T_{21}$-$T_{23}$ are CH; $T_{24}$ is N; $T_e$ is N or CH; $T_{26}$ is $C(R_{25})$;
each of $R_{25}$ is independently selected from H, F, Cl, Br, I, CN, OH, SH, NH$_2$, an optionally $R_{01}$-substituted $C_{1-6}$ alkyl or heteroalkyl or alkyl-heteroatom group or heteroalkyl-heteroatom group, an optionally $R_{02}$-substituted $C_{3-8}$ cyclic group or heterocyclic group or cycle-heteroatom group or heterocycle-heteroatom group;
B is selected from

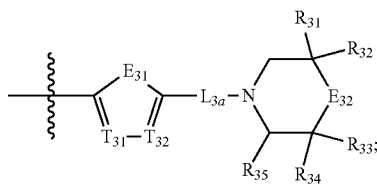

each of $E_{31-32}$, $L_{3a}$ is independently selected from $N(R_{40})$, $N(R_{40})$ $(CH_2)_{1-3}$, $C(=O)N(R_{40})(CH_2)_{1-3}$, $C(=O)N$ (R$_{41}$), S(=O)$_2$ N(R$_{42}$), C=N(R$_{43}$), C(R$_{44}$)(R$_{45}$), S, C(=O)O, C(=O), C=S, S(=O), S(=O)$_2$, O or C(=O)C(R$_{44}$) (R$_{45}$);

each of L$_{3a}$ can also be independently selected from a single bond or C$_{1-5}$ alkyl;

each of E$_{31}$ can also be independently selected from -T$_{39}$=T$_{40}$-;

each of T$_{31-32, 39-40}$ is independently selected from N, C(R$_{46}$);

each of R$_{40-43}$ is independently selected from H, an optionally R$_{01}$-substituted C$_{1-6}$ alkyl or C$_{3-6}$ cycloalkyl, an optionally R$_{01}$-substituted C$_{1-6}$ alkyl acyl or C$_{3-6}$ cycloalkyl acyl, an optionally R$_{01}$-substituted C$_{1-6}$ alkyl sulfonyl or C$_{3-6}$ cycloalkyl sulfonyl, an optionally R$_{01}$-substituted 5-6 membered aryl acyl, an optionally R$_{01}$-substituted 5-6 membered heteroaryl acyl, an optionally R$_{01}$-substituted 5-6 membered aryl sulfonyl, an optionally R$_{01}$-substituted C$_{1-6}$ alkyoxycarbonyl, an optionally R$_{01}$-substituted C$_{1-6}$ alkyl amino carbonyl;

each of R$_{31-35}$, R$_{44-46}$ is independently selected from H, F, Cl, Br, I, CN, OH, SH, NH$_2$, C(=O)OH, an optionally R$_{01}$-substituted C$_{1-6}$ alkyl or heteroalkyl or alkyl-heteroatom group or heteroalkyl-heteroatom group, an optionally R$_{02}$-substituted C$_{0-3}$ alkyl-C$_{3-8}$ cyclic group or heterocyclic group or cycle-heteroatom group or heterocycle-heteroatom group;

each of R$_{01}$, R$_{02}$ is independently selected from F, Cl, Br, I, CN, OH, SH, NH$_2$, R$_{03}$;

R$_{03}$ is selected from a C$_{1-6}$ alkyl amino, a di(C$_{1-6}$ alkyl) amino, a C$_{1-6}$ alkoxy, a C$_{3-8}$ cycloalkyl amino, a C$_{3-8}$ heterocycloalkyl amino, a C$_{3-8}$ cycloalkoxy;

the heteroatom or the heteroatom group is independently selected from C(=O)NR$_{04}$, N(R$_{05}$), C=N(R$_{06}$), O, S, C(=O)O, C(=O), C=S, S(=O), S(=O)$_2$ and/or S(=O)$_2$ N(R$_{07}$);

each of R$_{04-07}$ is independently selected from H, R$_{08}$;

R$_{08}$ is selected from a C$_{1-6}$ alkyl or a C$_{3-8}$ cycloalkyl;

R$_{03}$, R$_{08}$ are optionally substituted by R$_{001}$, R$_{001}$ is selected from OH, N(CH$_3$)$_2$, NH(CH$_3$), NH$_2$, F, Cl, Br, I, CN, a methyl, a methoxy;

a number of R$_{01}$, R$_{02}$, R$_{001}$, the heteroatom or the heteroatom group is independently selected from 0, 1, 2, or 3;

optionally, R$_{31}$ and R$_{32}$, R$_{31}$ and R$_{33}$, R$_{31}$ and R$_{35}$, E$_{33}$ and E$_{34}$ form a linking bond (CH$_2$)$_{1-6}$ together;

optionally, R$_{32}$ and R$_{32}$ connect with each other to form a 5-membered carbocyclic ring or a heterocyclic ring;

optionally, when E$_{32}$ is selected from N(R$_{40}$) or O, R$_{31}$ and R$_{34}$ present a cis-arrangement; when E$_{32}$ is selected from C(R$_{43}$)(R$_{44}$), R$_{31}$ and R$_{34}$ present a trans-arrangement.

2. The compound represented by formula (I), or the pharmaceutically acceptable salt thereof according to claim 1, A is selected from

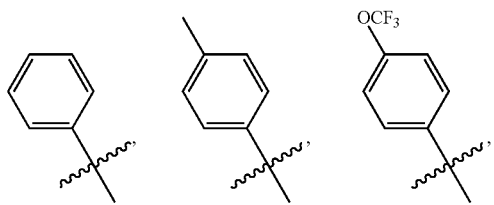

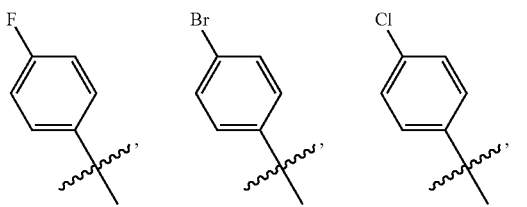

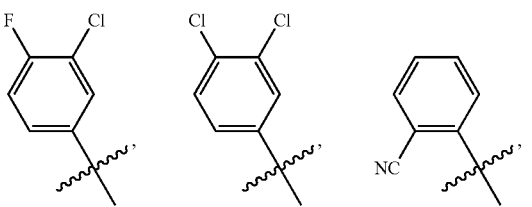

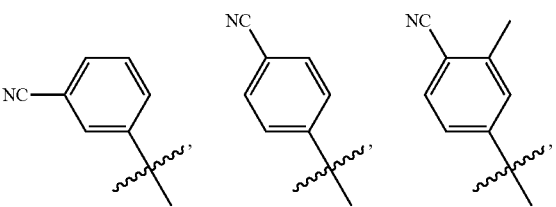

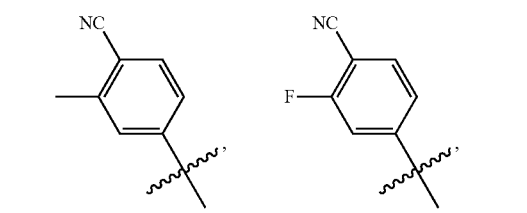

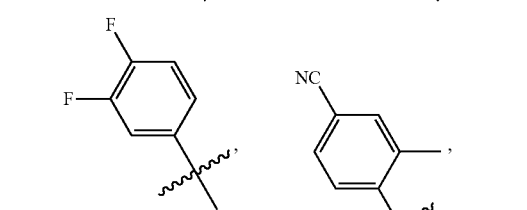

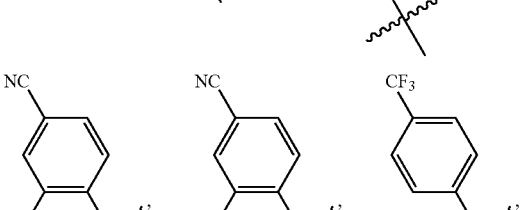

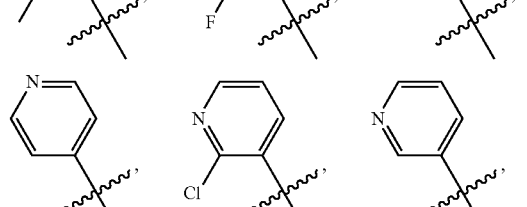

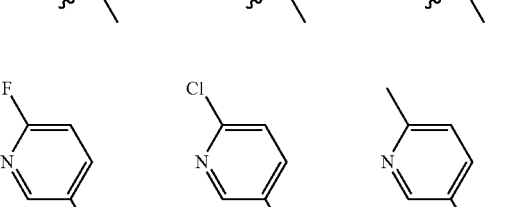

-continued
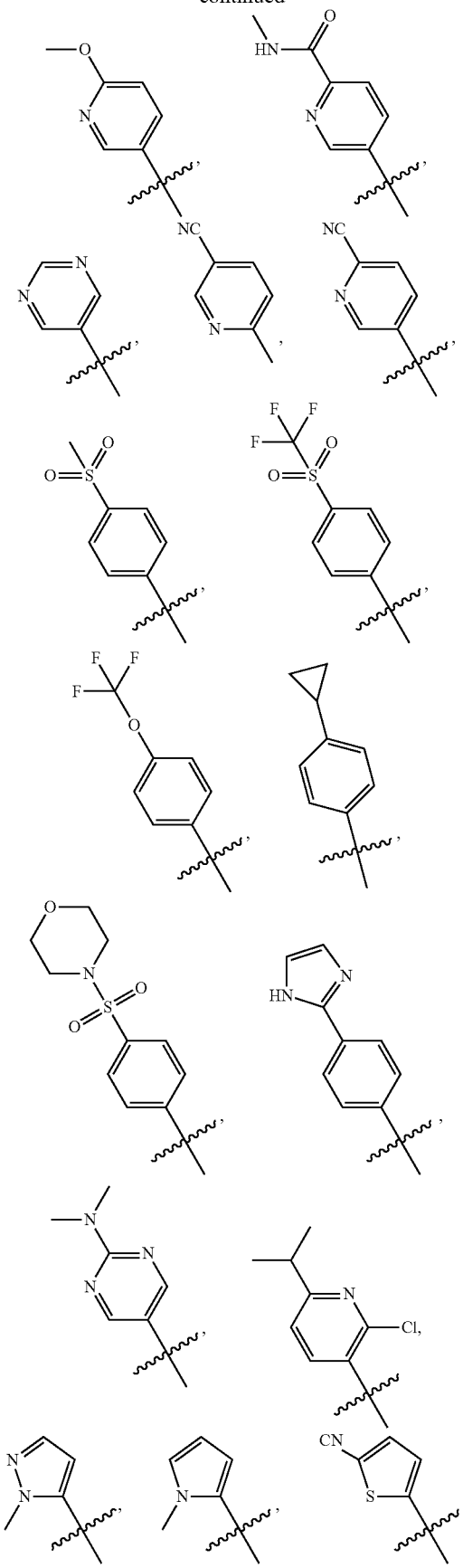
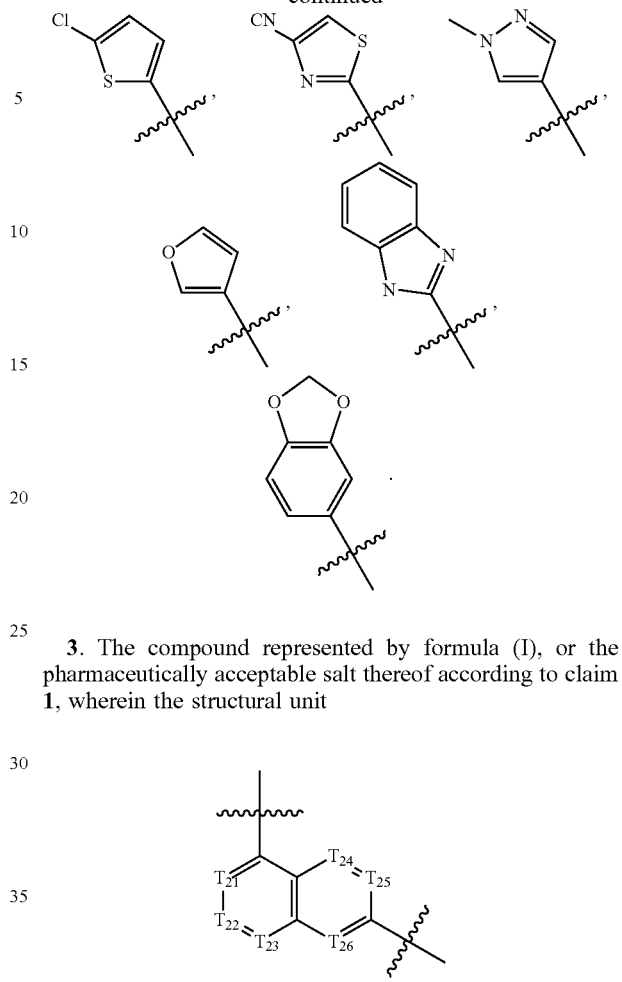
3. The compound represented by formula (I), or the pharmaceutically acceptable salt thereof according to claim 1, wherein the structural unit
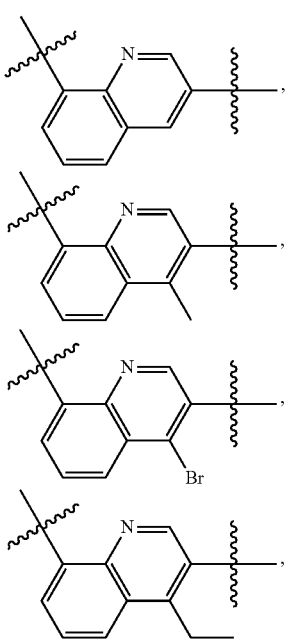
is selected from 357
-continued
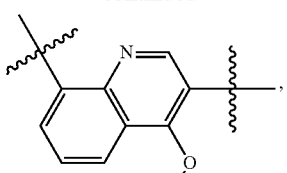,
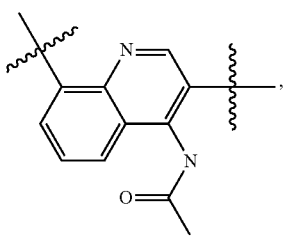,
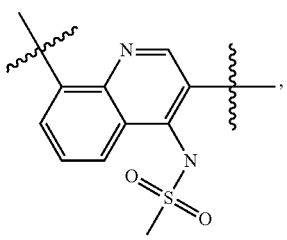,
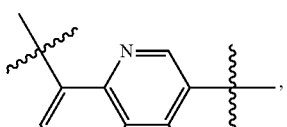,
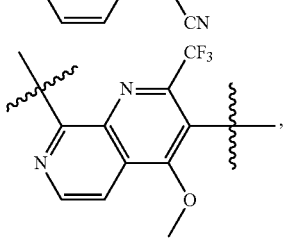,
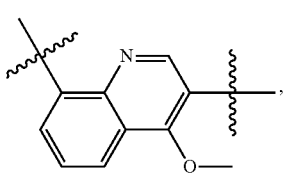,
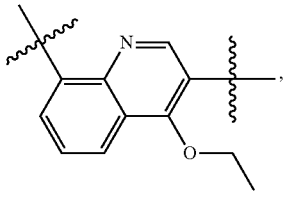,
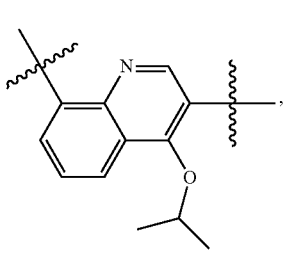,
358
-continued
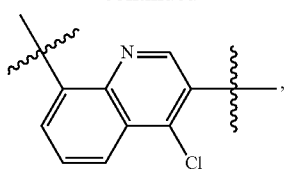,
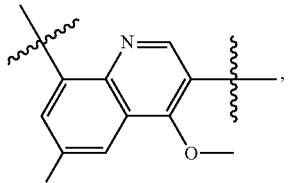,
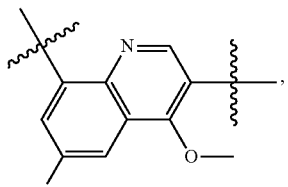,
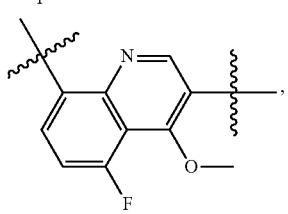,
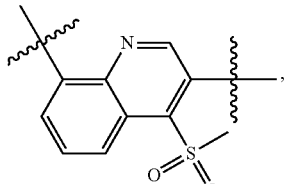,
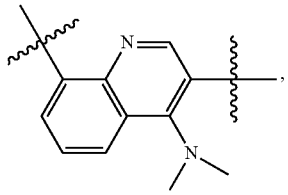,
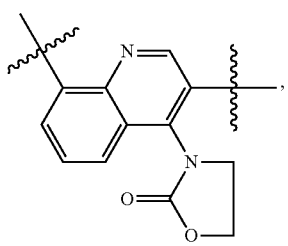,
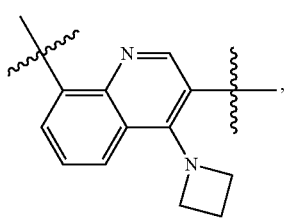,

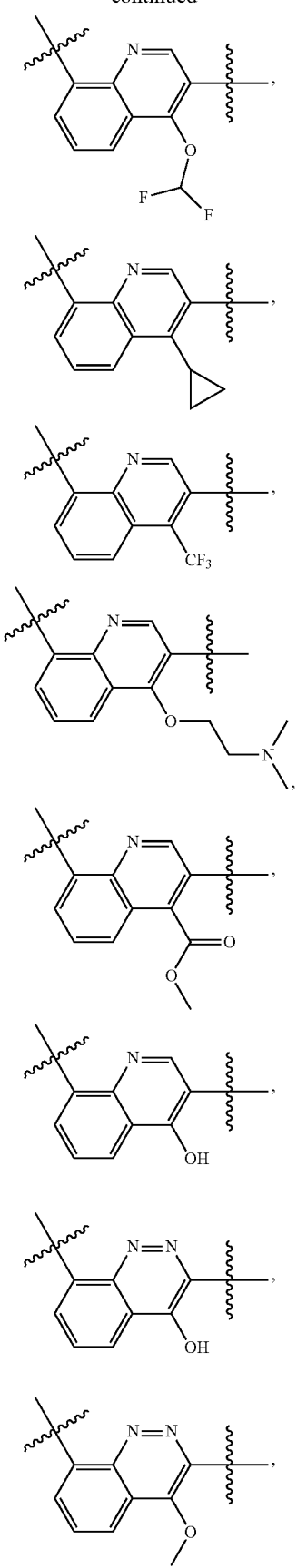

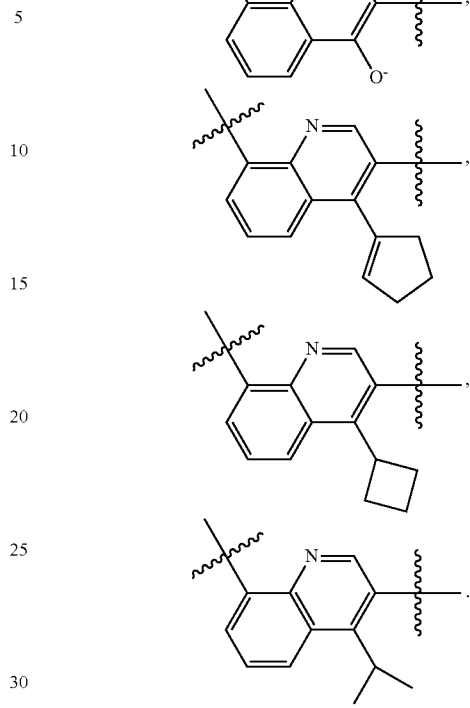

4. The compound represented by formula (I), or the pharmaceutically acceptable salt thereof according to claim 1, wherein B is selected from

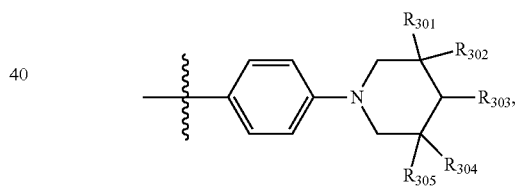

wherein,
  each of $R_{301-305}$ is independently selected from H, OH, $NH_2$, F, Cl, Br, I, CN, an optionally $R_{3001}$-substituted $C_{1-3}$ alkyl or alkoxy or alkyl amino or cyclopropyl;
  $R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
  optionally, the structural unit

in the general structure can be replaced by a pyridyl, a thienyl, a furyl;
  optionally,
  each of $R_{301-305}$ is independently selected from a methyl, H, OH, $NH_2$, F, Cl, Br, I, CN.

5. The compound represented by formula (I), or the pharmaceutically acceptable salt thereof according to claim 1, wherein, B is selected from

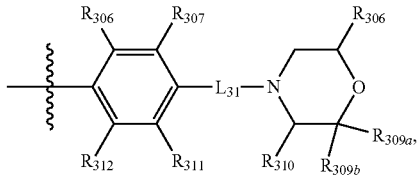

wherein,
each of $R_{306\text{-}308}$, $R_{309a}$, $R_{309b}$, $R_{310\text{-}312}$ is independently selected from H, OH, $NH_2$, F, Cl, Br, I, CN, an optionally $R_{3001}$-substituted $C_{1\text{-}3}$ alkyl or alkoxy or alkyl amino or cyclopropyl;
$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
$L_{31}$ is selected from a single bond, $R_{3002}N(R_{3003})R_{3004}$, O, S, C(=O)O, C(=O), C=S, S(=O) and/or S(=O)$_2$, $R_{3002}$ is selected from a single bond or C(=O);
$R_{3003}$ is selected from H, a $C_{1\text{-}3}$ alkyl or a cyclopropyl;
$R_{3004}$ is selected from $(CH_2)_{0\text{-}3}$;
optionally, $R_{308}$ and $R_{309a}$, $R_{308}$ and $R_{310}$ form a linking bond $(CH_2)_{1\text{-}3}$ together;
$L_{31}$ is selected from a single bond, $NHCH_2CH_2$.

6. The compound represented by formula (I), or the pharmaceutically acceptable salt thereof according to claim 1, wherein, B is selected from

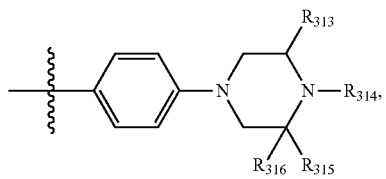

wherein,
each of $R_{313}$, $R_{315}$, $R_{316}$ is independently selected from H, OH, $NH_2$, F, Cl, Br, I, CN, an optionally $R_{3001}$-substituted $C_{1\text{-}3}$ alkyl or alkoxy or alkyl amino or cyclopropyl;
$R_{314}$ is selected from H, OH, $NH_2$, F, Cl, Br, I, CN, an optionally $R_{3001}$-substituted $C_{1\text{-}3}$ alkyl or alkoxy or alkyl amino or cyclopropyl, $(CH_2)_{0\text{-}3}R_{3005}$,

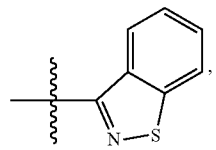

wherein $R_{3005}$ is optionally substituted by $R_{3001}$;
$R_{3005}$ is selected from a $C_{3\text{-}6}$ cycloalkyl, a phenyl, a pyridyl, a thienyl, a furyl, an imidazolyl, an oxazolyl, a thiazolyl, an isothiazolyl, each of the above-mentioned group is optionally fused with a benzene ring;
$R_{3001}$ is selected from OH, $N(CH_3)_2$, $NH(CH_3)$, $NH_2$, F, Cl, Br, I, CN, a methyl, a methoxy, the number of $R_{3001}$ is selected from 1, 2 or 3;
optionally, the

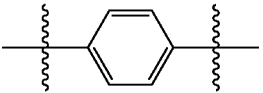 [SMILES: *c1ccc(*)cc1]

in the general structure can be replaced by a pyridyl, a thienyl, a furyl, an imidazolyl, an oxazolyl, a thiazolyl, an isothiazolyl.

7. The compound represented by formula (I), or the pharmaceutically acceptable salt thereof according to claim 1, wherein B is selected from

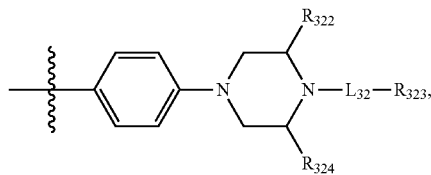

wherein,
$L_{32}$ is selected from $C(R_{3007})(R_{3008})$, O, $CON(R_{3009})$, $N(R_{3010})$, C=N $(R_{3011})$, S, C(=O)O, C(=O), C=S, S(=O) and/or S(=O)$_2$;
$R_{323}$ is selected from a $C_{1\text{-}6}$ alkyl, a $C_{3\text{-}6}$ cycloalkyl, a phenyl, a pyridyl, an imidazolyl, a thienyl, a furyl, an oxazolyl, a thiazolyl, an isothiazolyl, each of the above-mentioned group is optionally substituted by $R_{3012}$;
each of $R_{322}$, $R_{324}$, $R_{3007}$, $R_{3008}$, $R_{3012}$ is independently selected from H, OH, $NH_2$, F, Cl, Br, I, CN, an optionally $R_{3001}$-substituted $C_{1\text{-}3}$ alkyl or alkoxy or alkyl amino or cyclopropyl;
each of $R_{3009\text{-}3011}$ is independently selected from H, an optionally $R_{3001}$-substituted $C_{1\text{-}3}$ alkyl or cyclopropyl;
$R_{3001}$ is selected from OH, $N(CH_3)_2$, $NH(CH_3)$, $NH_2$, F, Cl, Br, I, CN, a methyl, a methoxy;
the number of each of $R_{3001}$, $R_{3012}$ is selected from 1, 2 or 3;
optionally, the

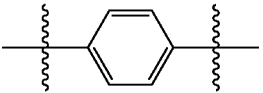 [SMILES: *c1ccc(*)cc1]

in the general structure can be replaced by a pyridyl, a thienyl, a furyl, an imidazolyl, an oxazolyl, a thiazolyl, an isothiazolyl.

8. The compound represented by formula (I), or the pharmaceutically acceptable salt thereof according to claim 1, wherein B is selected from

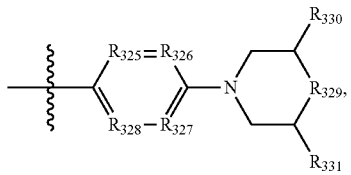

wherein,
one or two of $R_{325\text{-}328}$ is selected from N, the rest are selected from $C(R_{3013})$;
$R_{329}$ is selected from $N(R_{3014})$, O, $C(R_{3015})(R_{3016})$, CON$(R_{3017})$, $N(R_{3018})$, C=N $(R_{3019})$, S, C(=O)O, C(=O), C=S, S(=O) and/or S(=O)$_2$;
$R_{3014}$ is selected from C(=O)$R_{3020}$, S(=O)$_2R_{3020}$, a thiazolyl, an isothiazolyl, a phenyl, a pyridyl, an imidazolyl, a thienyl, a furyl, an oxazolyl
$R_{3020}$ is selected from an optionally $R_{3001}$-substituted $C_{1\text{-}3}$ alkyl or alkoxyl;
each of $R_{3013}$, $R_{3015}$, $R_{3016}$, $R_{330\text{-}331}$ is independently selected from H, OH, NH$_2$, F, Cl, Br, I, CN, C(=O)OH, an optionally $R_{3001}$-substituted $C_{1\text{-}3}$ alkyl or alkoxy or alkyl amino or cyclopropyl;
each of $R_{3017\text{-}3019}$ is independently selected from H, an optionally $R_{3001}$-substituted $C_{1\text{-}3}$ alkyl or cyclopropyl;
$R_{3001}$ is selected from OH, N(CH$_3$)$_2$, NH(CH$_3$), NH$_2$, F, Cl, Br, I, CN, a methyl, a methoxy, the number of $R_{3001}$ is selected from 1, 2 or 3;
optionally, $R_{330}$ and $R_{331}$ form a linking bond (CH$_2$)$_{1\text{-}3}$ together;
optionally, when $R_{329}$ is selected from $N(R_{3014})$ or O, $R_{330}$ and $R_{331}$ present a cis-arrangement; when $R_{329}$ is selected from $C(R_{3015})(R_{3016})$, $R_{330}$ and $R_{331}$ present a trans-arrangement.

9. The compound represented by formula (I), or the pharmaceutically acceptable salt thereof according to claim 1, wherein B is selected from

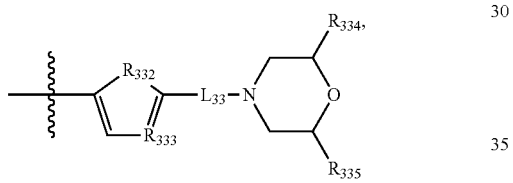

wherein,
$R_{332}$ is selected from S, N($R_{3021}$), O, C($R_{3022}$)($R_{3023}$), CON($R_{3024}$), N($R_{3025}$), C=N ($R_{3026}$), S, C(=O)O, C(=O), C=S, S(=O) and/or S(=O)$_2$;
$L_{33}$ is selected from a single bond, C(=O), S, O, C($R_{3022}$)($R_{3023}$), CON($R_{3024}$), N($R_{3025}$), C=N($R_{3026}$), S, C(=O)O, C=S, S(=O) and/or S(=O)$_2$;
$R_{333}$ is selected from N, C($R_{3027}$);
each of $R_{3027}$, $R_{334}$, $R_{335}$, $R_{3022}$, $R_{3023}$ is independently selected from H, OH, NH$_2$, F, Cl, Br, I, CN, an optionally $R_{3001}$-substituted $C_{1\text{-}3}$ alkyl or alkoxy or alkyl amino or cyclopropyl;
each of $R_{3021}$, $R_{3024\text{-}3026}$ is independently selected from H, an optionally $R_{3001}$-substituted $C_{1\text{-}3}$ alkyl or cyclopropyl;
$R_{3001}$ is selected from OH, N(CH$_3$)$_2$, NH(CH$_3$), NH$_2$, F, Cl, Br, I, CN, a methyl, a methoxy, the number of $R_{3001}$ is selected from 1, 2 or 3.

10. The compound represented by formula (I), or the pharmaceutically acceptable salt thereof according to claim 1, wherein B is selected from the group consisting of

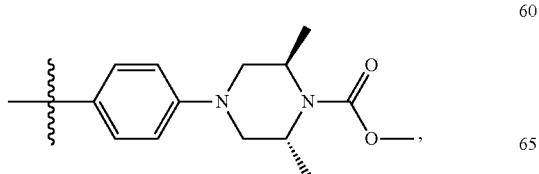

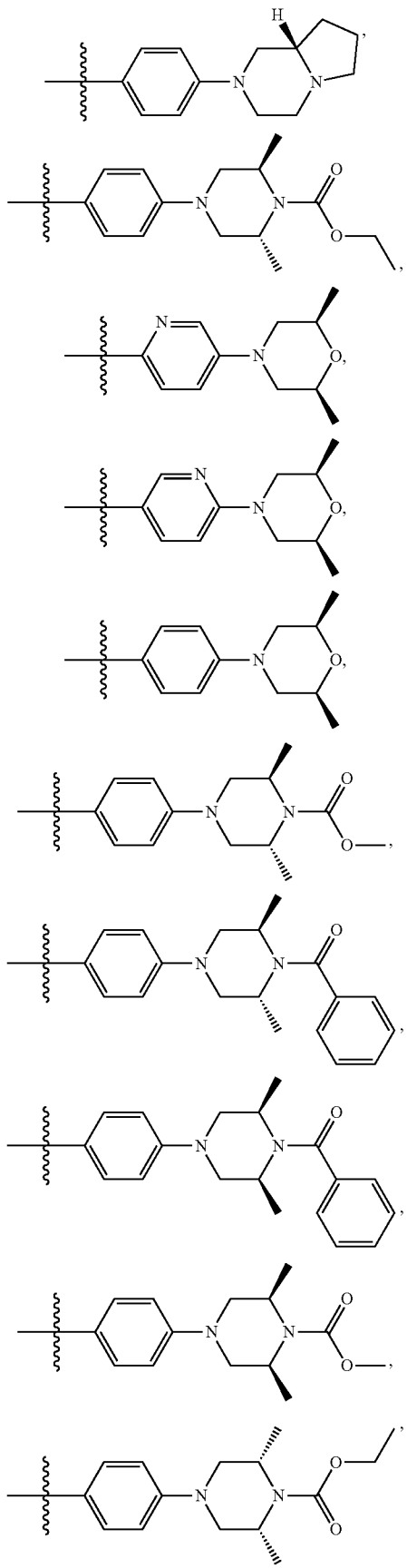

365
-continued
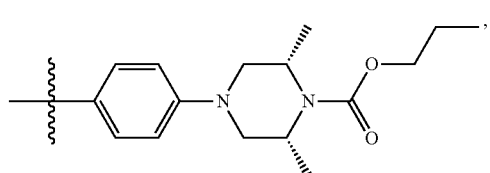
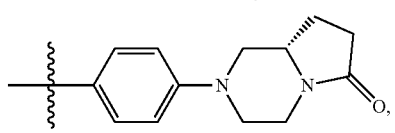
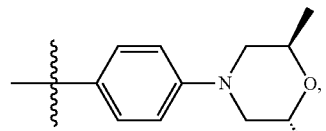
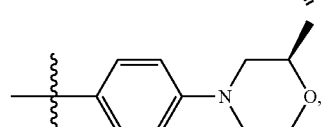
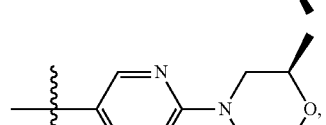
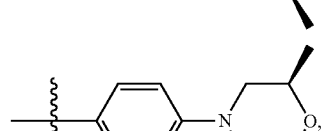
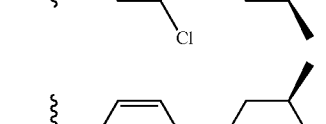
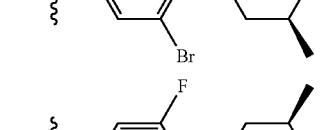
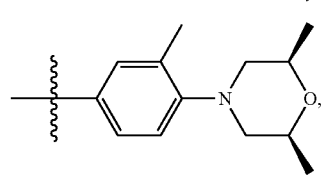
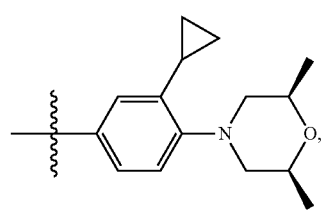
366
-continued
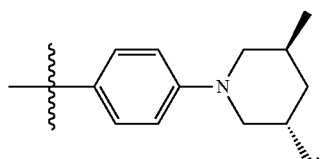
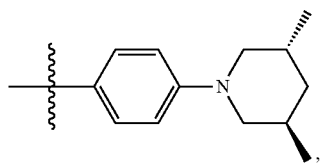
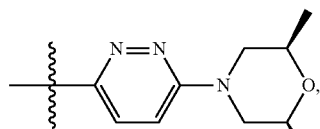
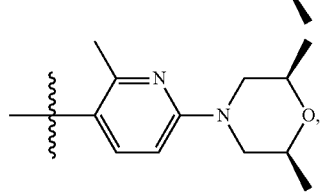
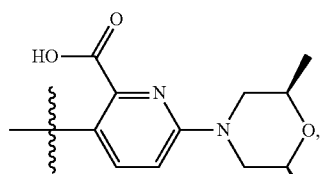
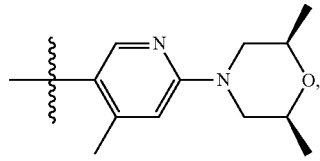
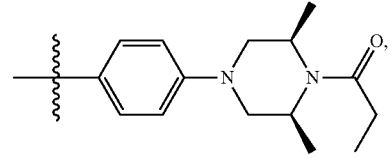
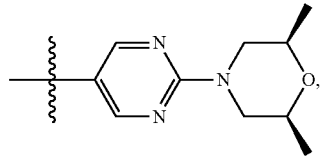
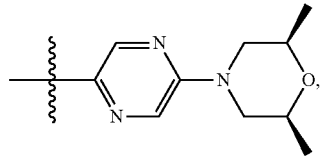

367
-continued
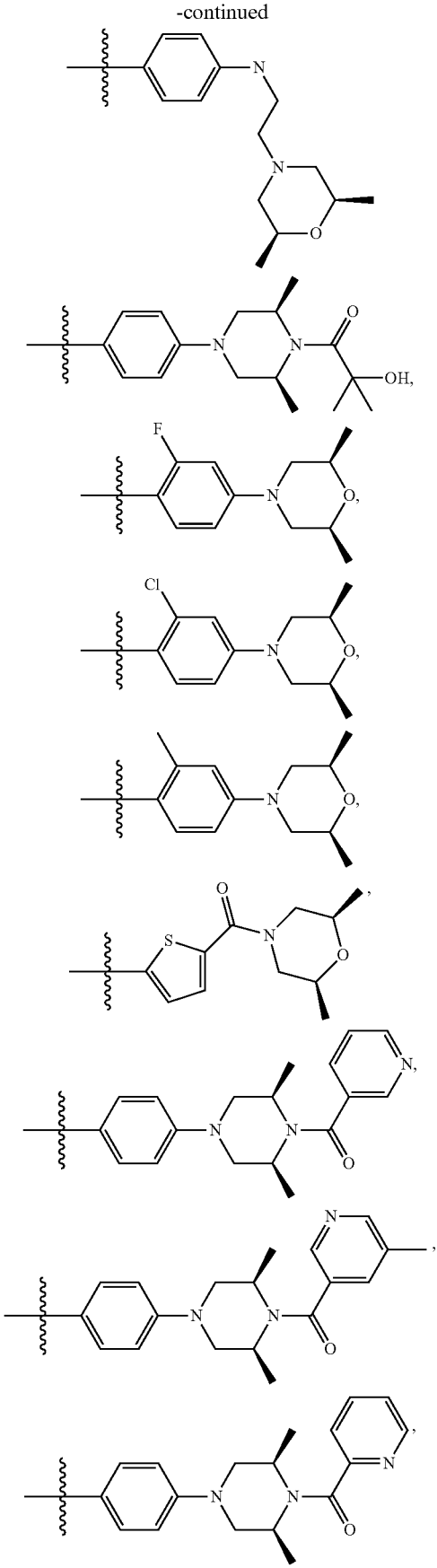
368
-continued
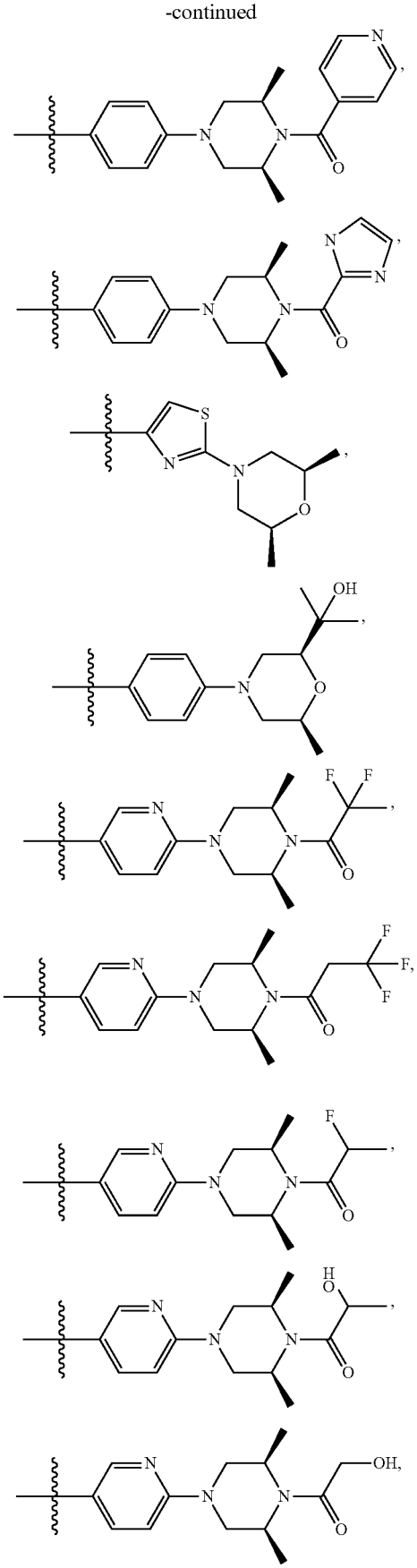

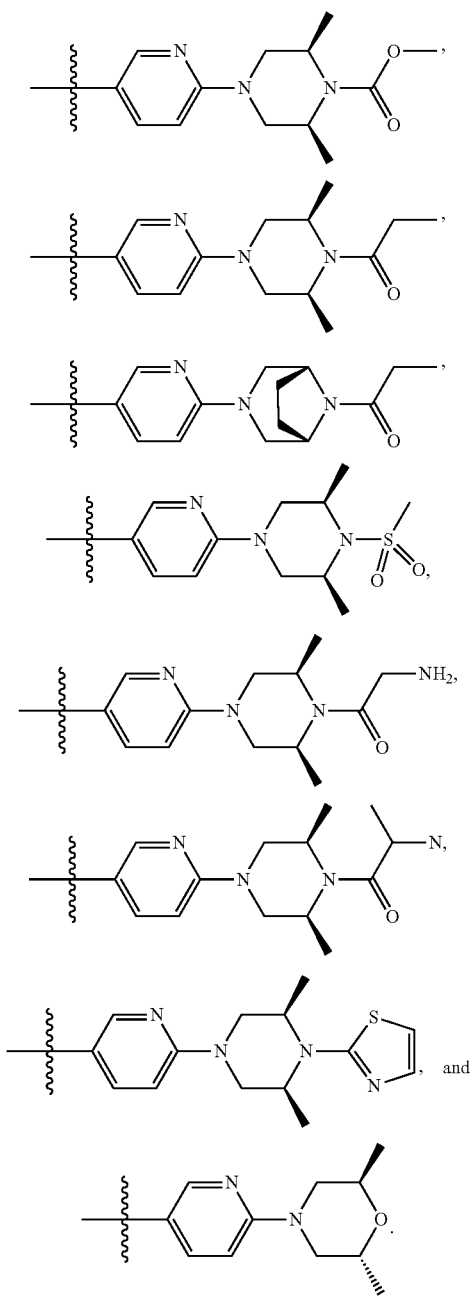
11. A compound represented by formula (I), or the pharmaceutically acceptable salt thereof, which is selected from the group consisting of
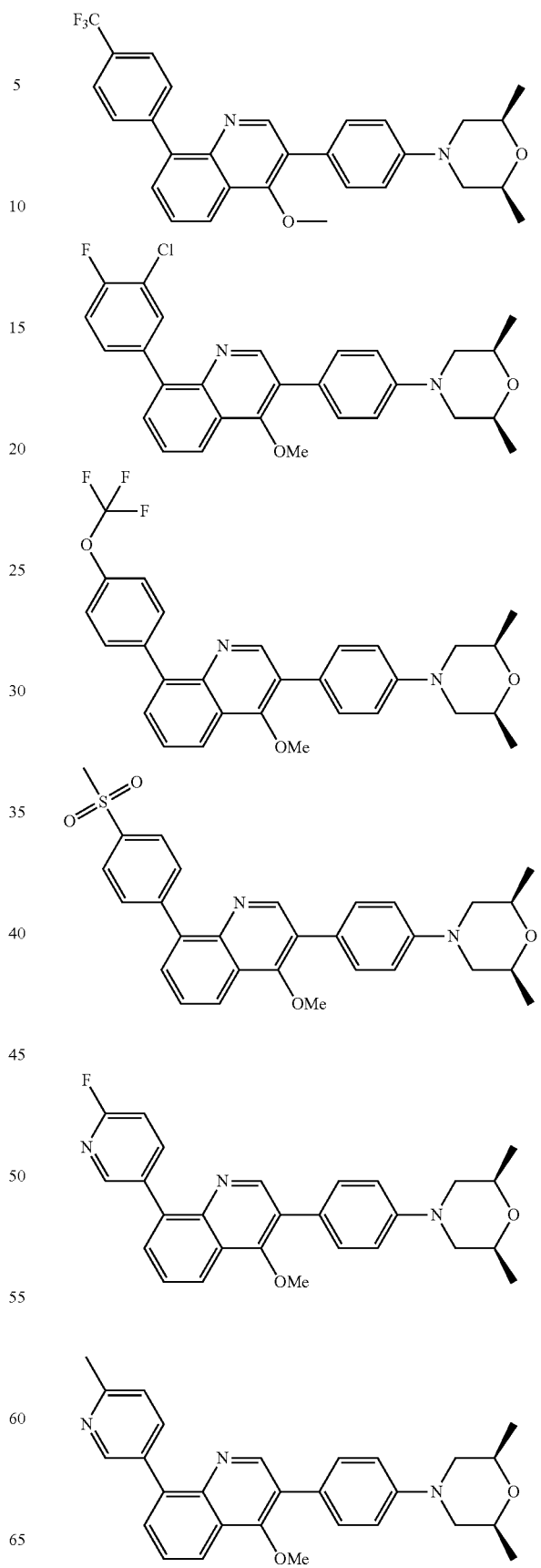

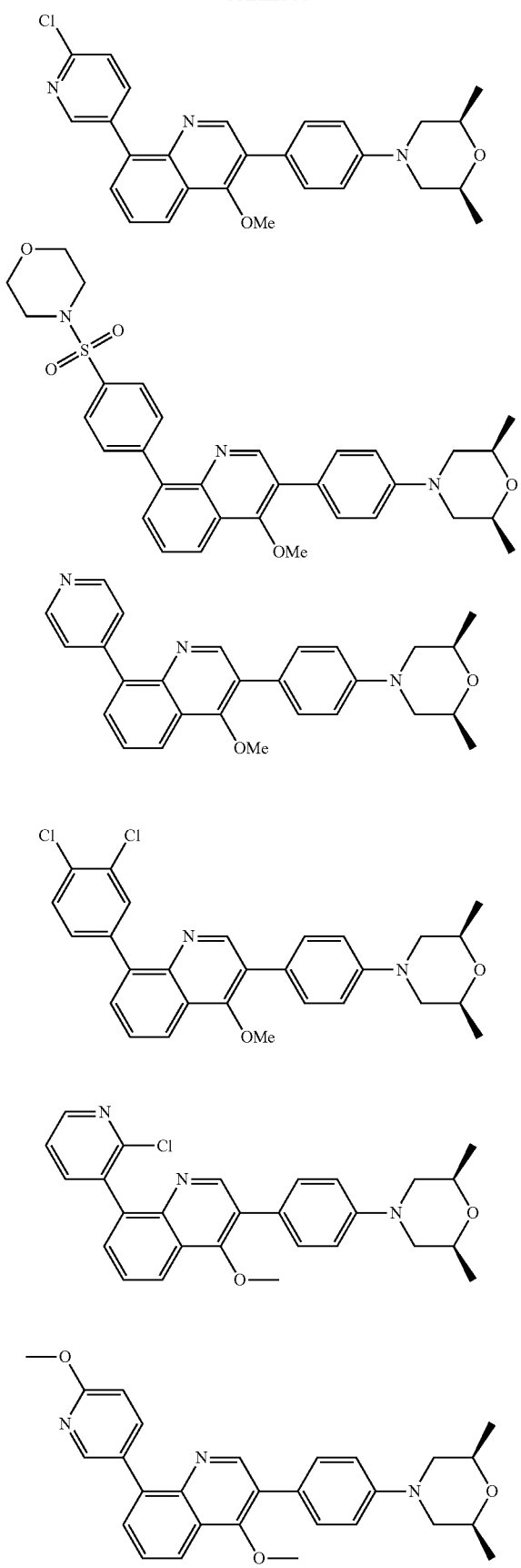
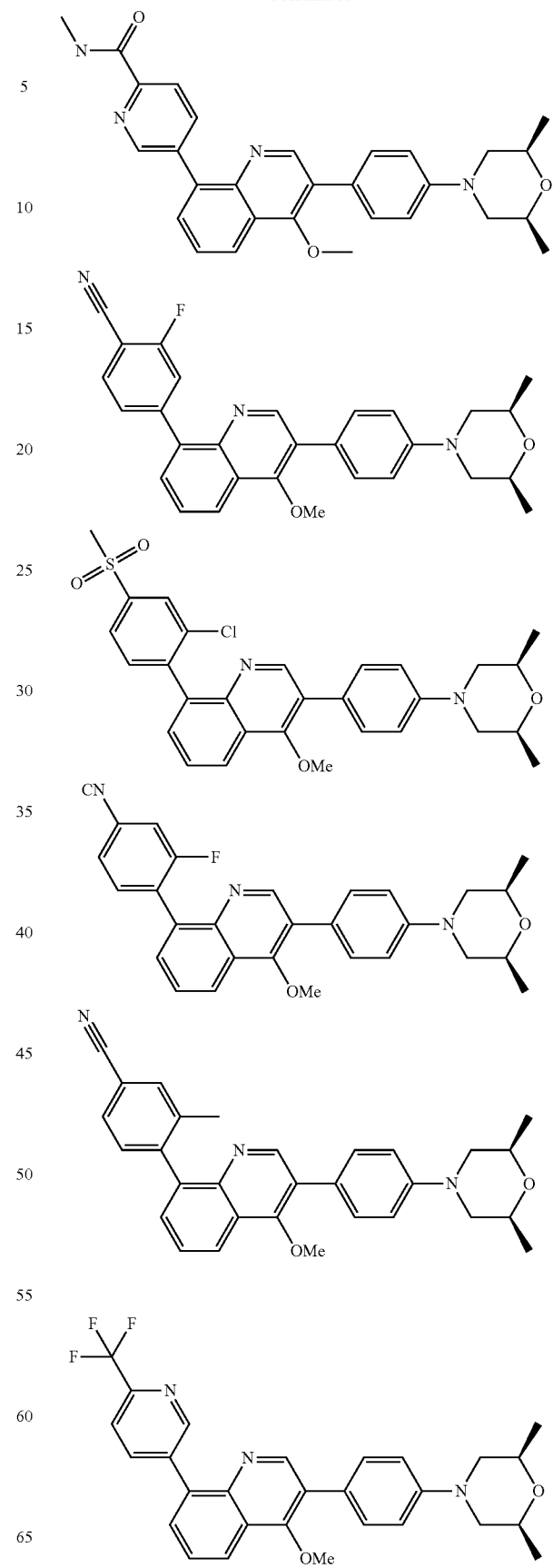

373
-continued
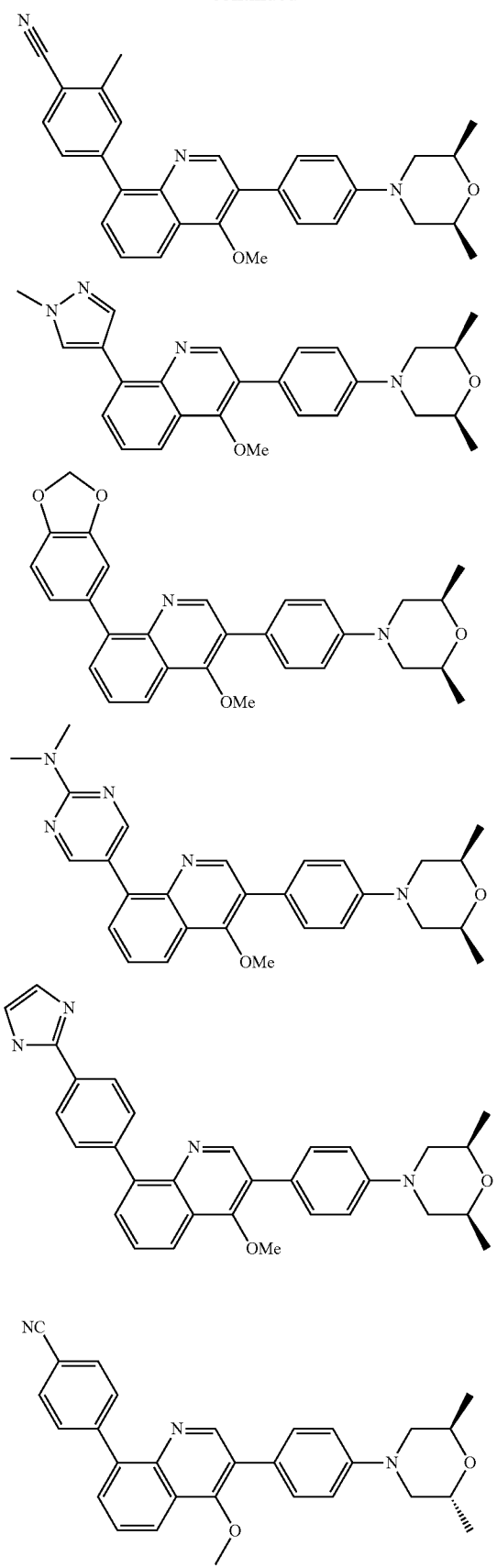
374
-continued
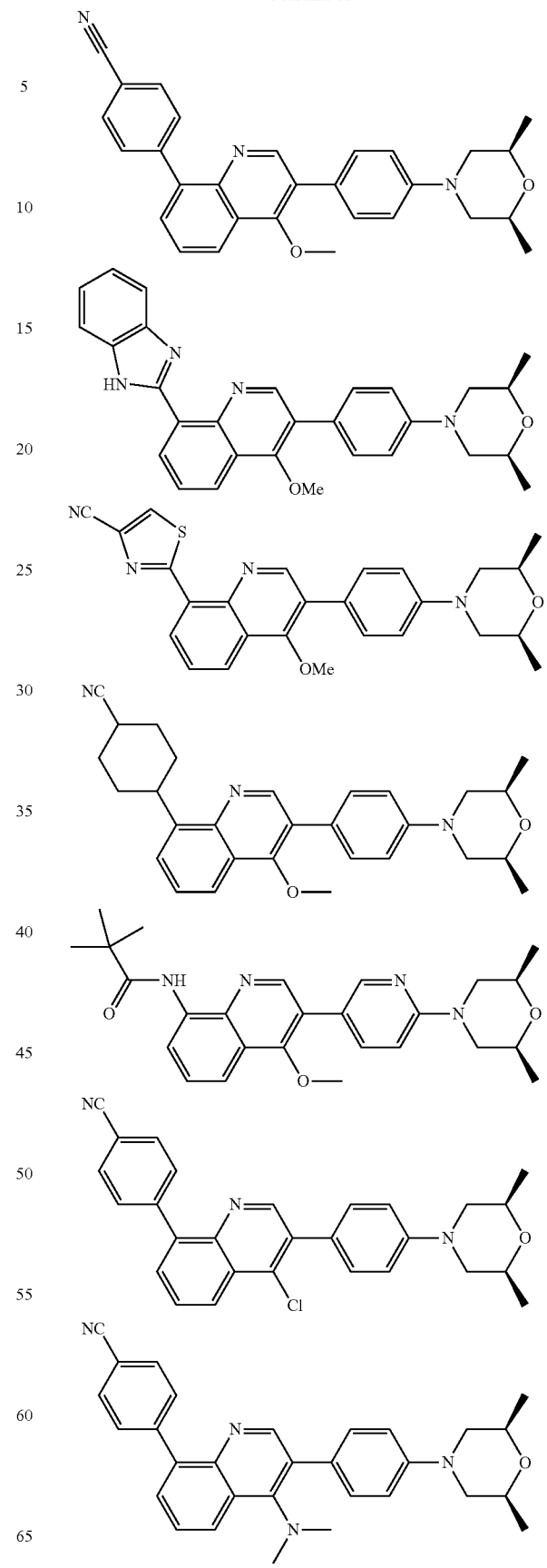

375
-continued
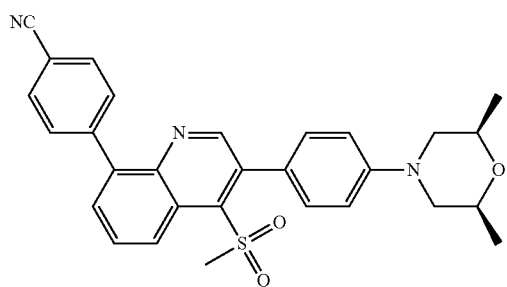
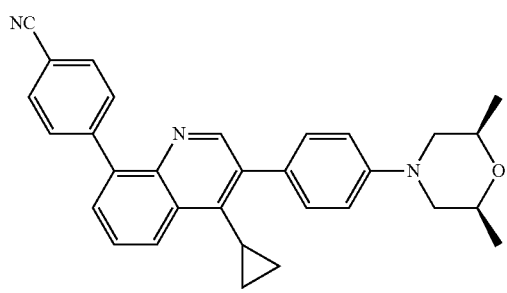
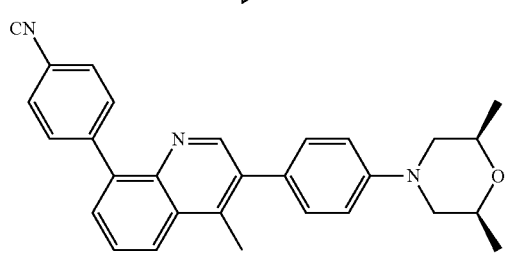
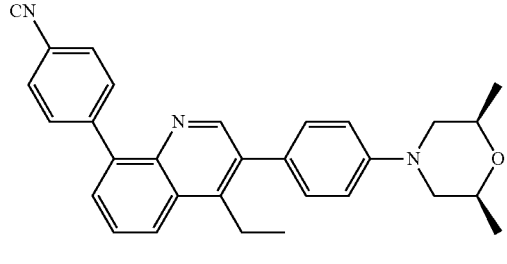
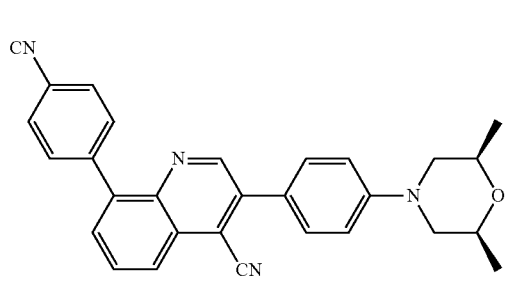
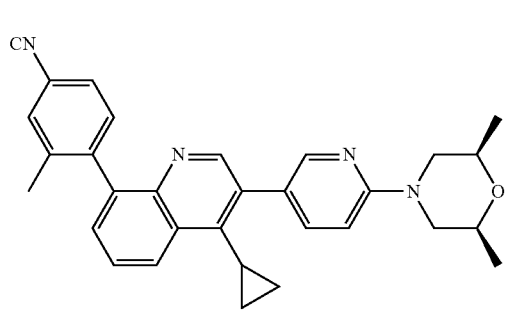
376
-continued
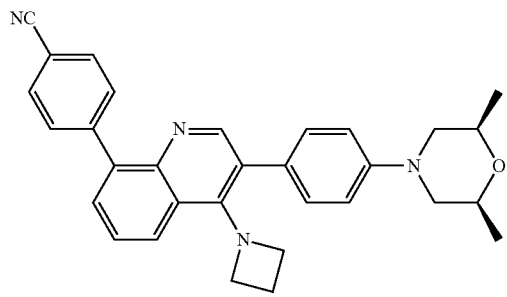
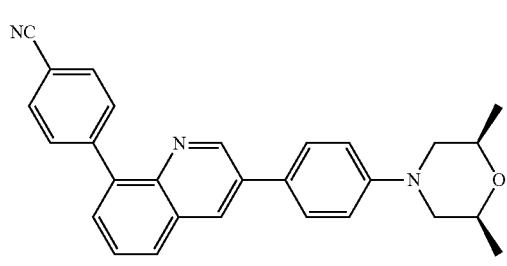
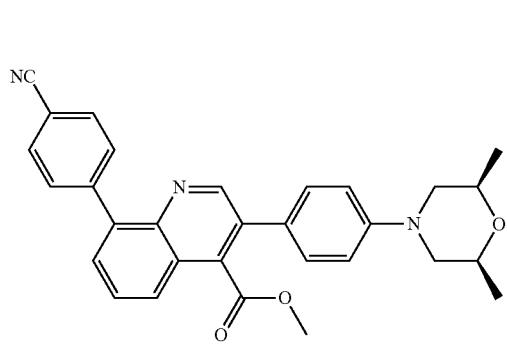
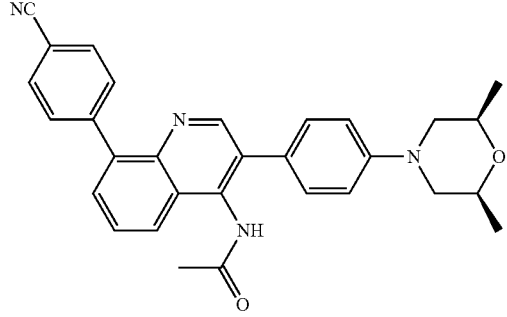
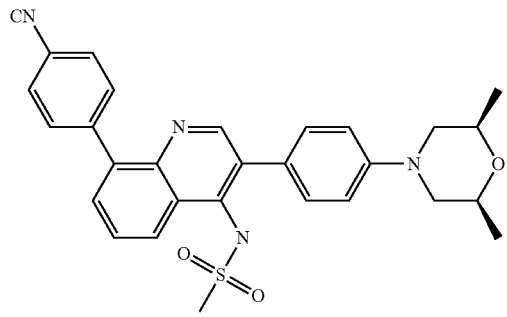

377
-continued
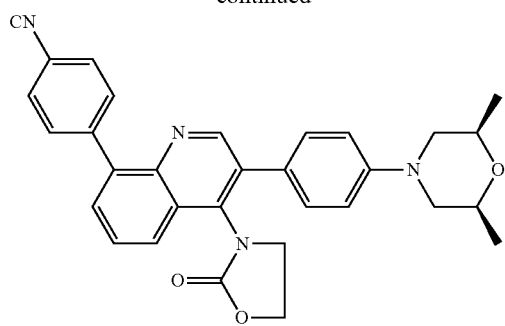
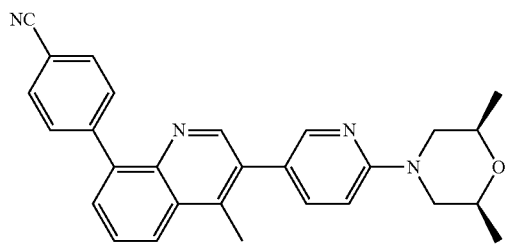
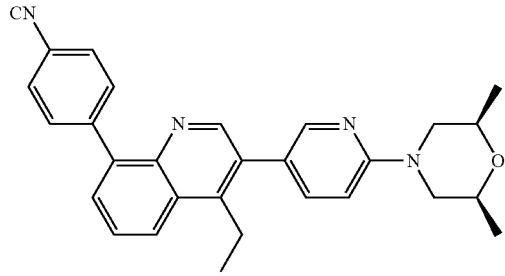
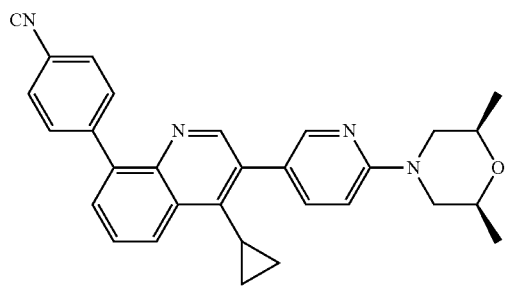
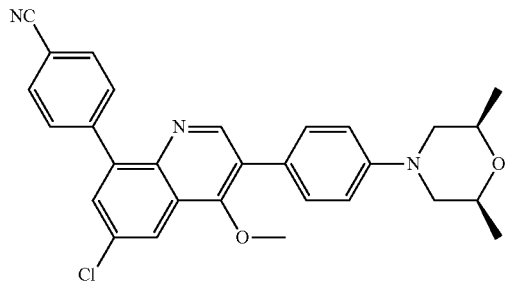
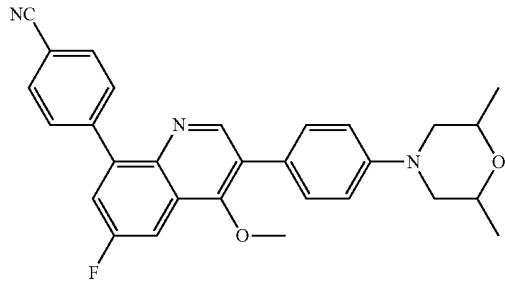
378
-continued
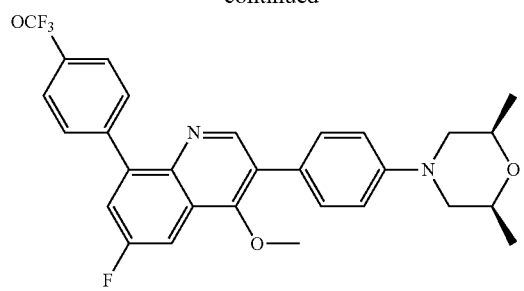
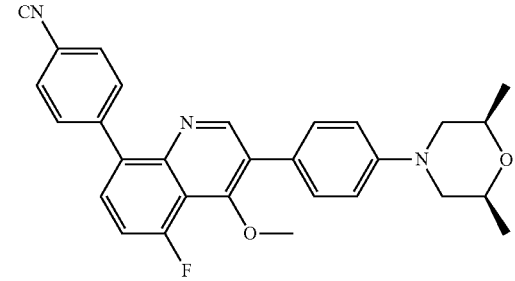
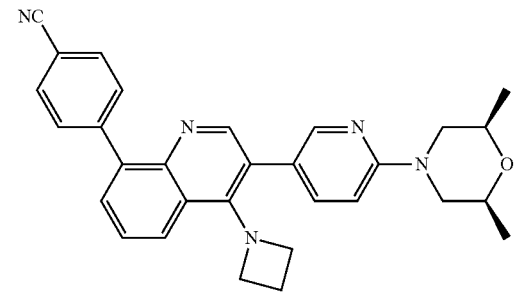
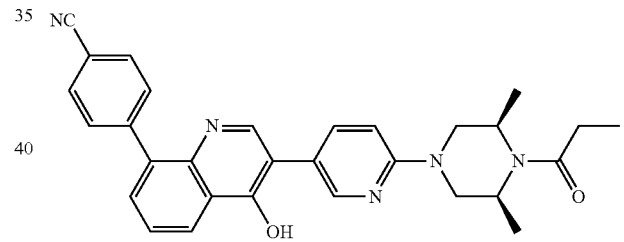
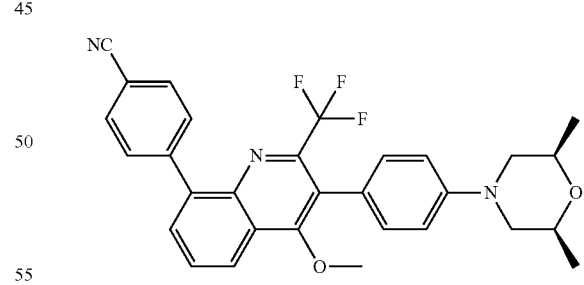
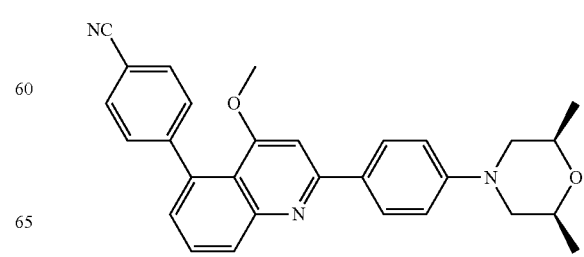

-continued
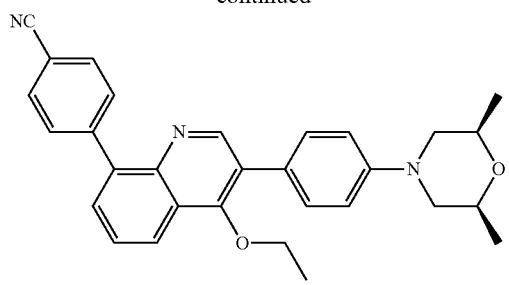
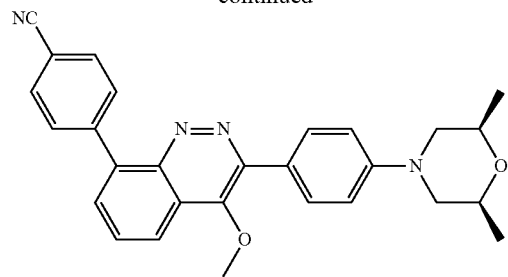
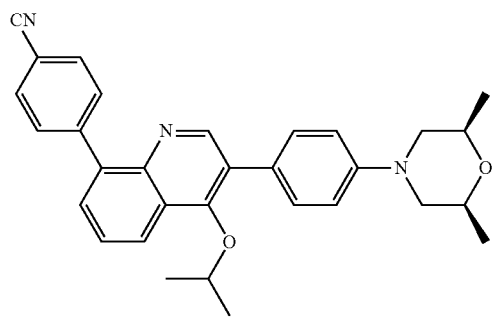
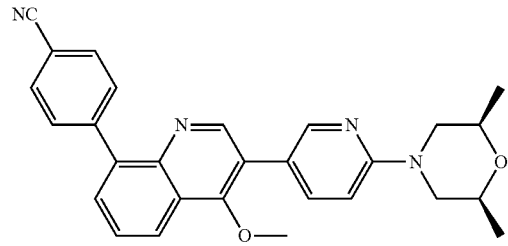
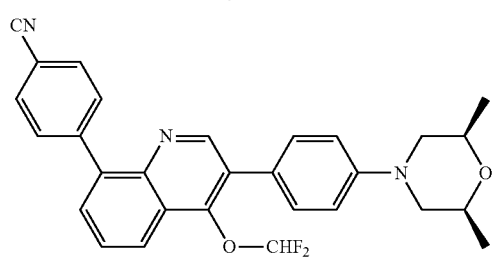
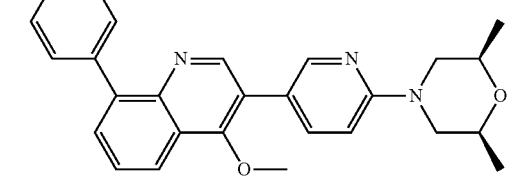
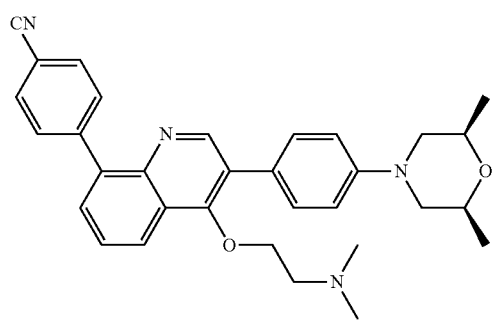
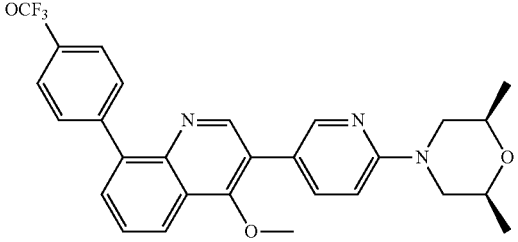
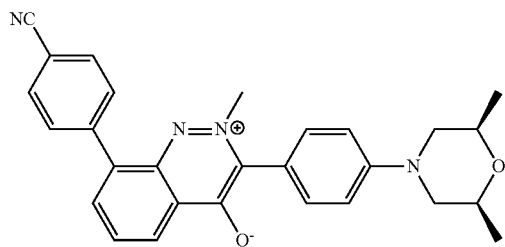
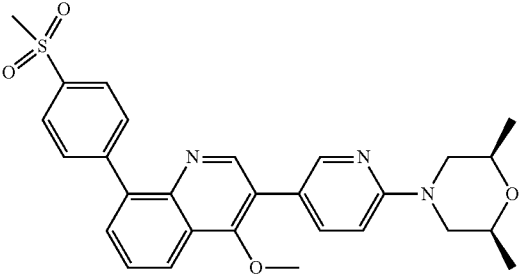
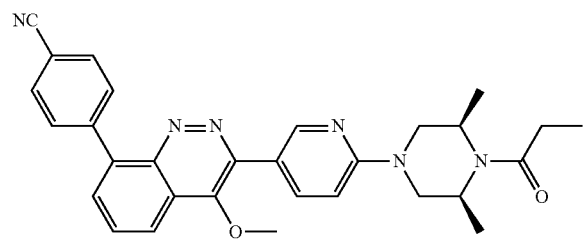
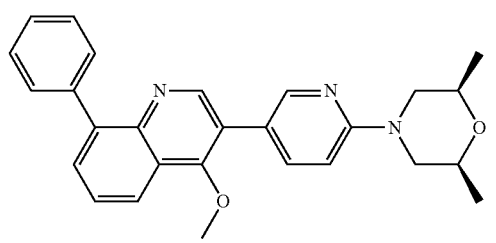

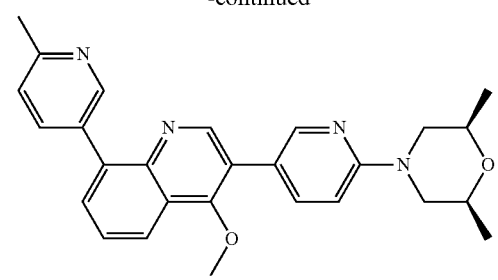
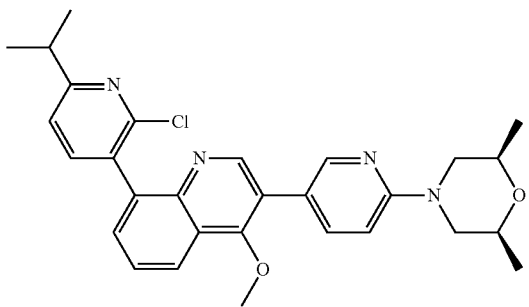
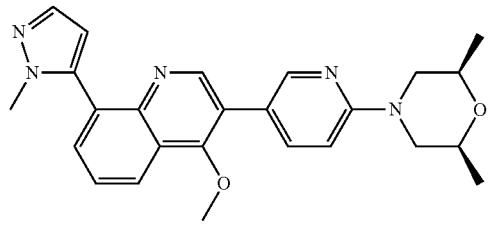
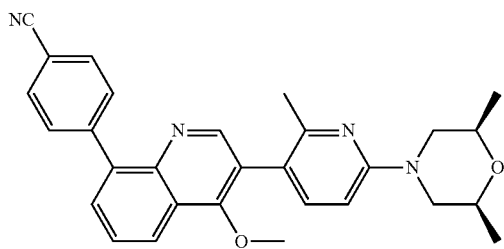
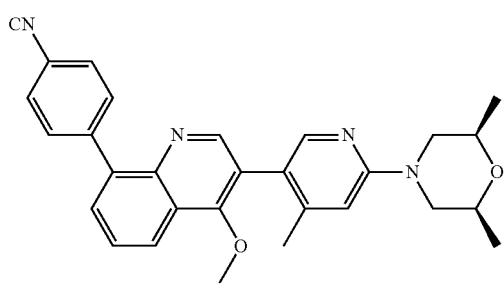
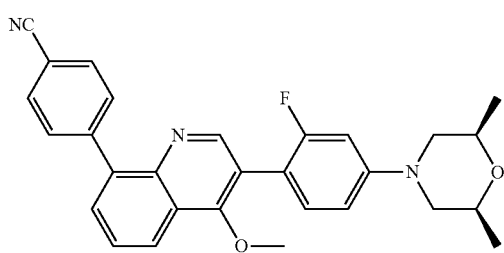
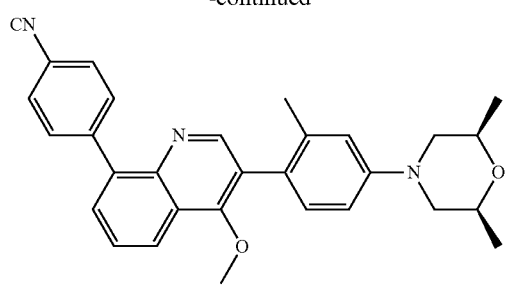
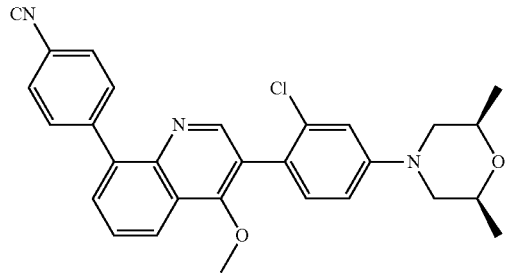
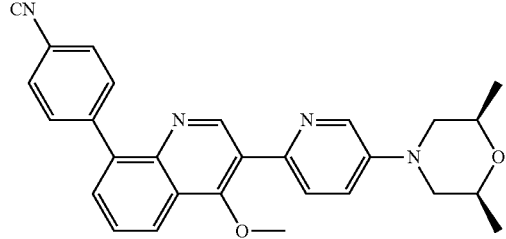
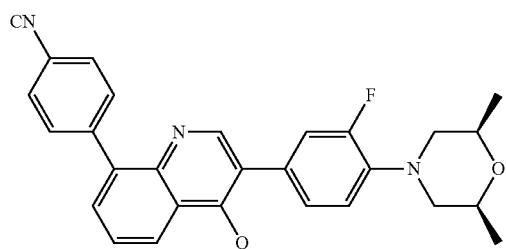
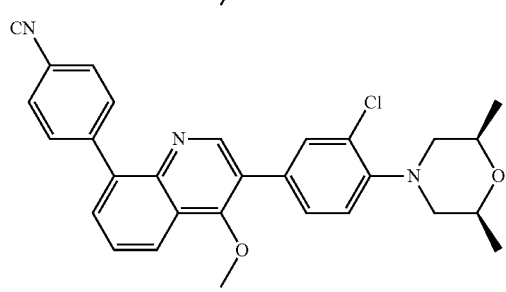
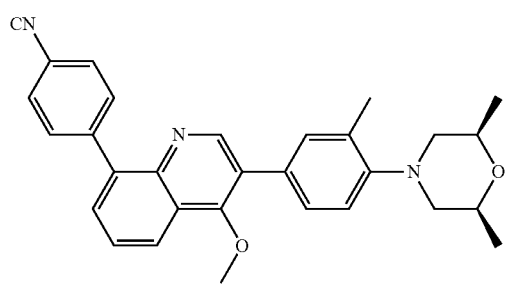

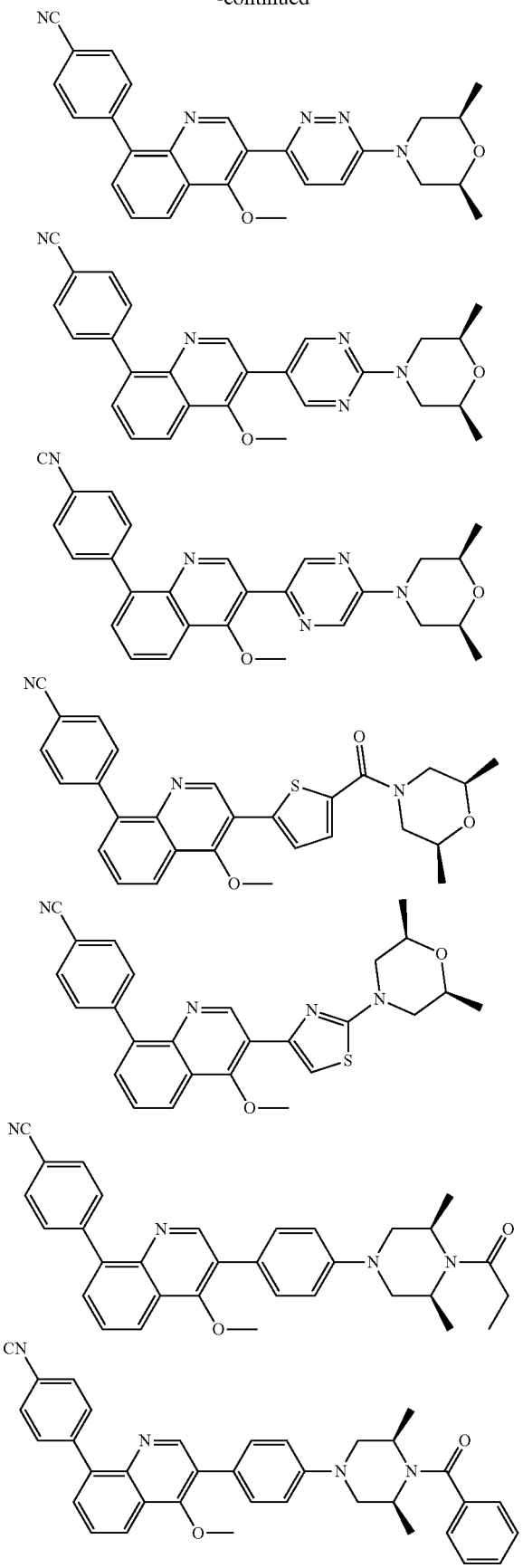
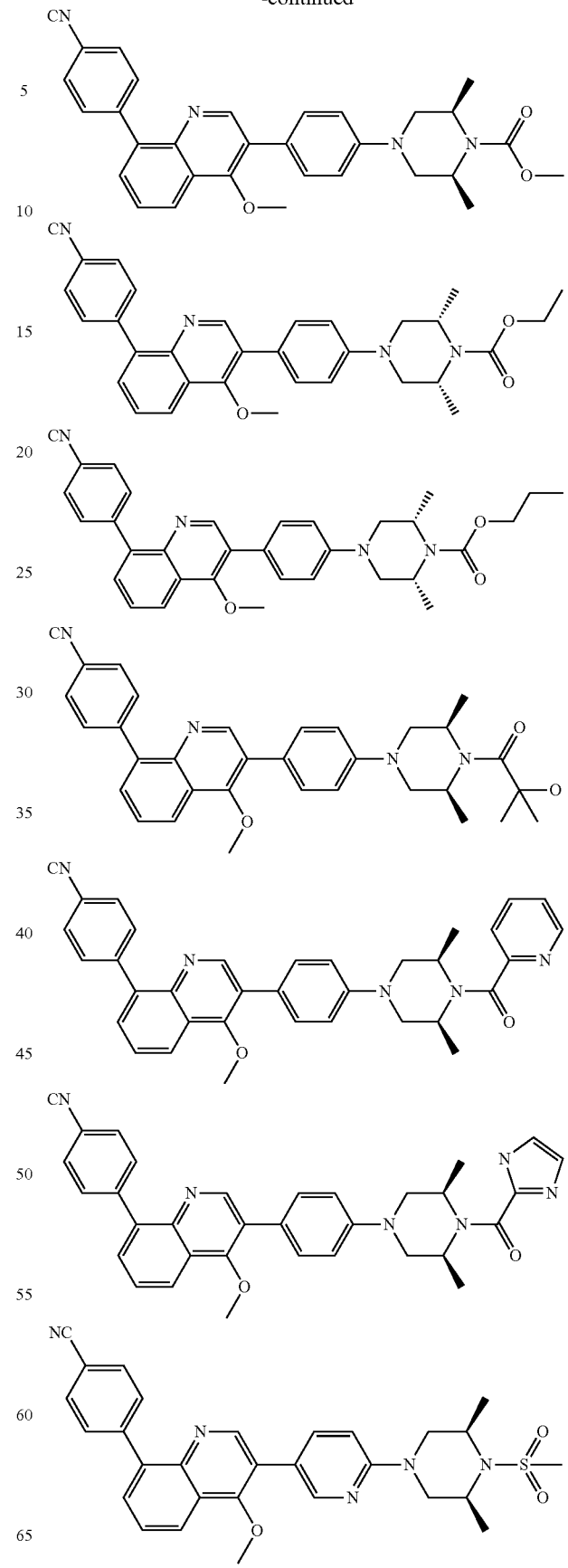

385
-continued
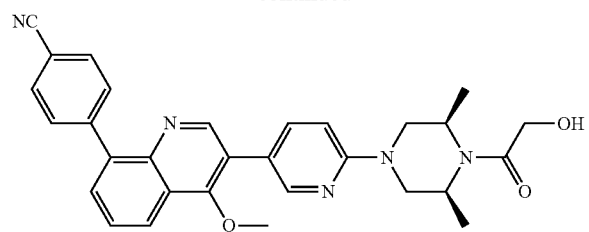
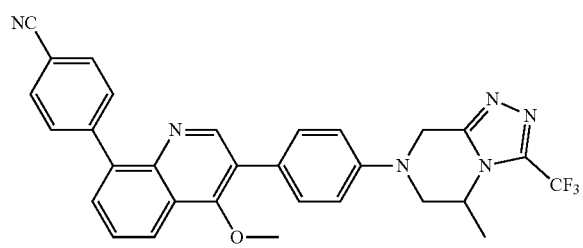
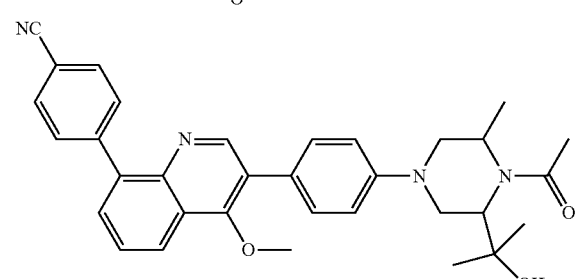
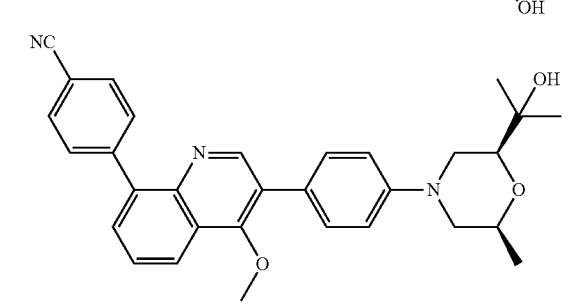
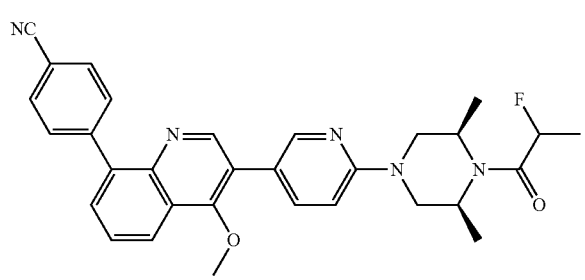
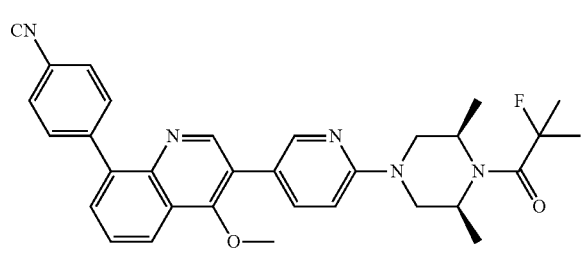
386
-continued
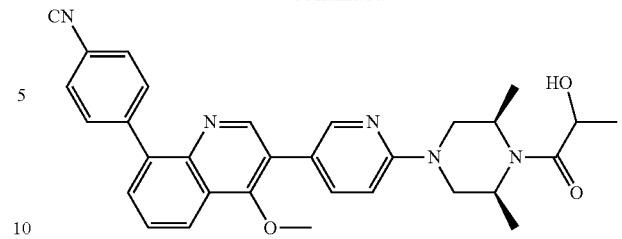
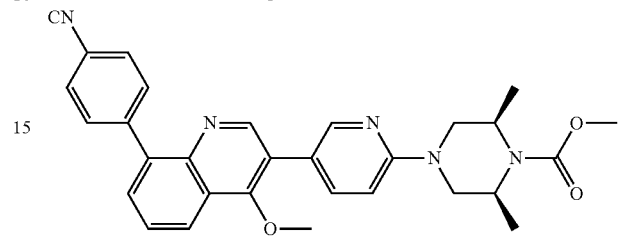
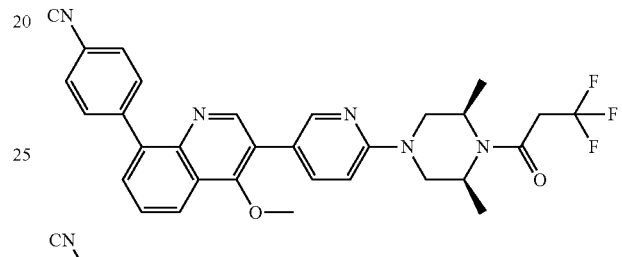
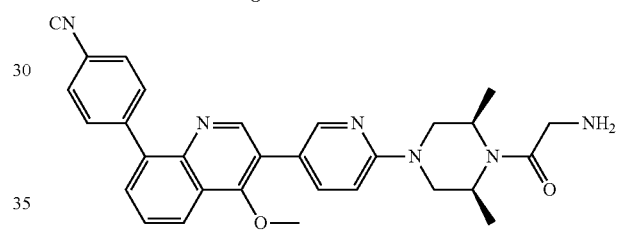
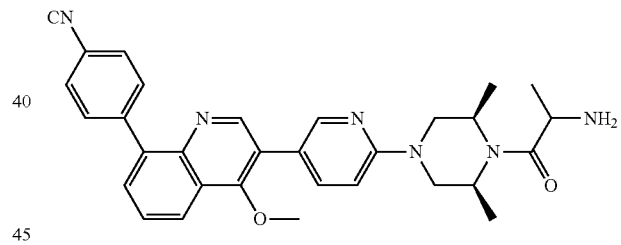
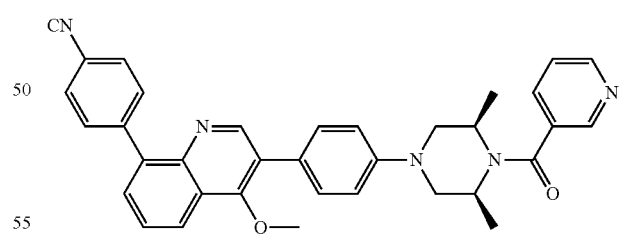
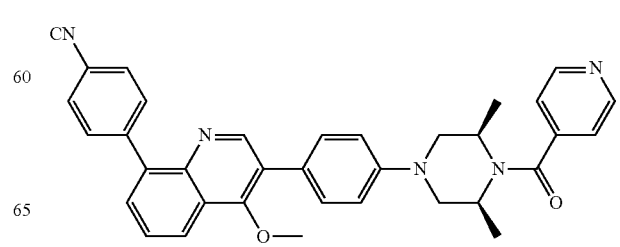

387
-continued
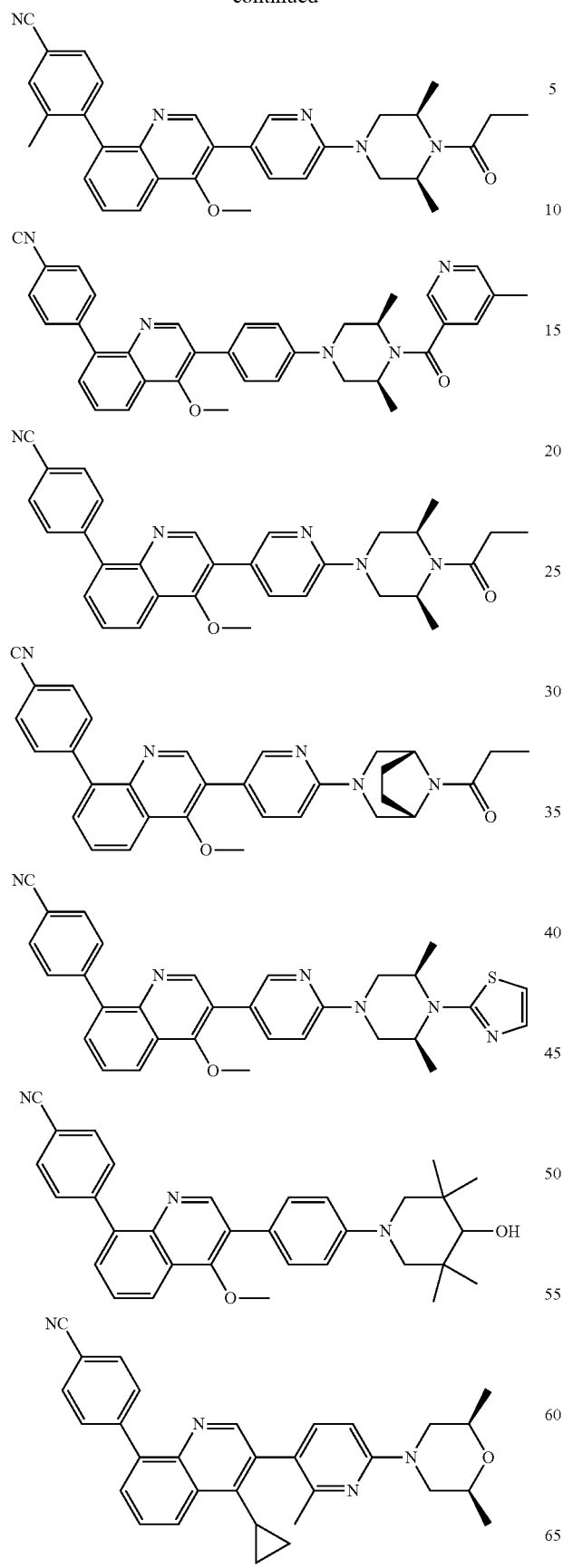
388
-continued
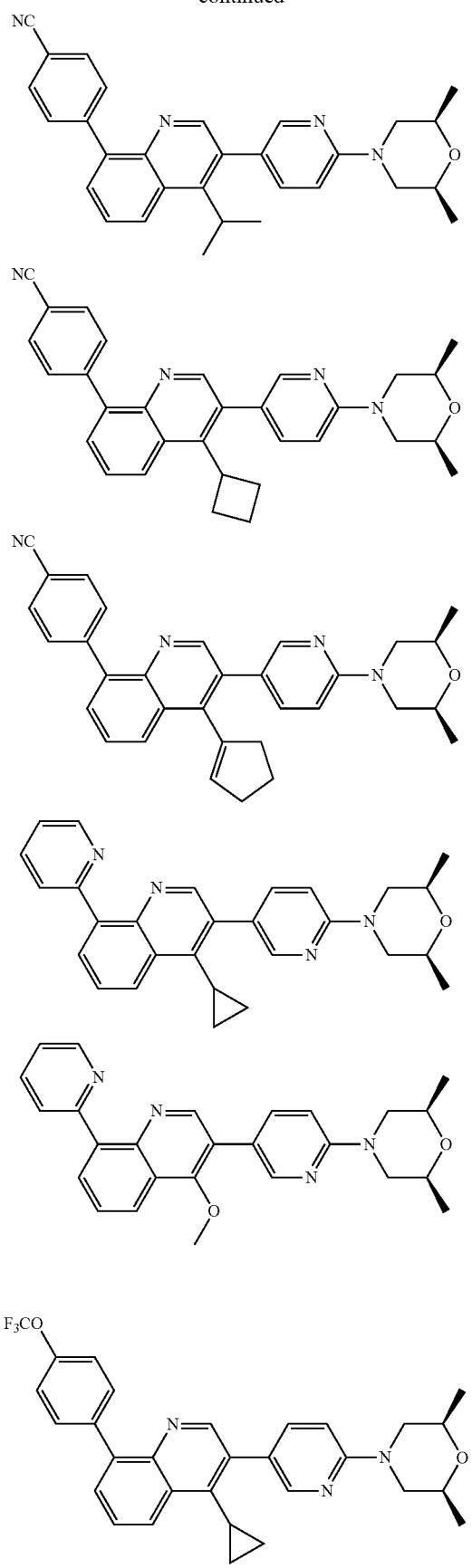

-continued

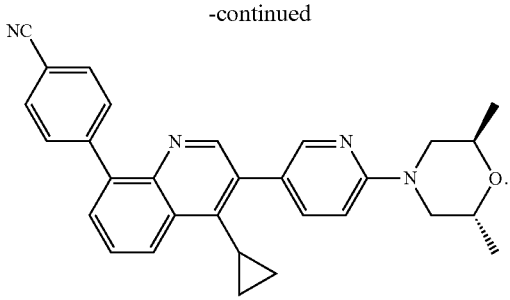

12. The compound represented by formula (I), or the pharmaceutically acceptable salt thereof according to claim 1, each of $R_{11-13}$, $R_{18-19}$ is independently selected from a methyl, a trifluoromethyl, a trifluoromethoxy, F, Cl, Br, I, CN, a methylamino carbonyl, a methylsulfonyl, a trifluoromethylsulfonyl, a trifluoromethoxy, a cyclopropyl, a morpholinylsulfonyl, a 2-imidazolyl, a dimethylamino, and a n-, iso- or neo-propyl;

or, each of $R_{25}$ is independently selected from F, Cl, Br, I, CN, OH, a methyl, an ethyl, an isopropyl, a methoxy, a trifluoromethyl, a difluoromethoxy, a n-, iso- or neo-propoxy, a cyclopropyl, a formamido, a methanesulfonylamino, a dimethylamino, a dimethylaminoethoxy, a methylsulfonyl, a carbomethoxy,

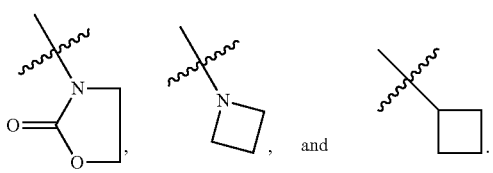 [SMILES: *N1CCOC1=O ; *N1CCC1 ; *C1CCC1]

13. The compound represented by formula (I), or the pharmaceutically acceptable salt thereof according to claim 5, wherein, B is selected from

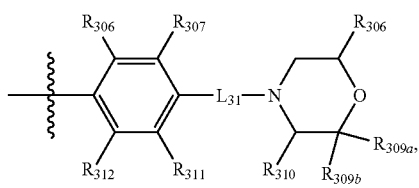

wherein, the $R_{308}$ and $R_{310}$ form a linking bond $CH_2$ together, $R_{308}$ and $R_{309a}$ form a linking bond $CH_2CH_2$ together;

or, each of $R_{306-308}$, $R_{309a}$, $R_{309b}$, $R_{310-312}$ is independently selected from a methyl, a cyclopropyl, $C(CH_3)_2(OH)$, $CH_2CH_2OH$, $CH_2N(CH_3)_2$, H, OH, $NH_2$, F, Cl, Br, I, and CN;

or, B is selected from

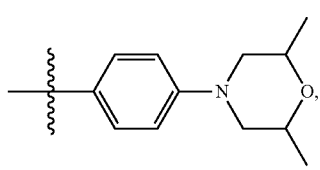

-continued

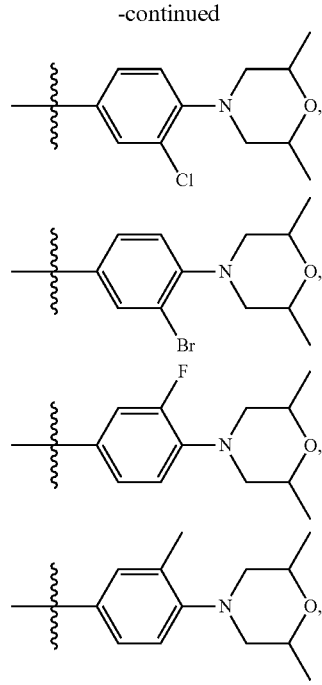

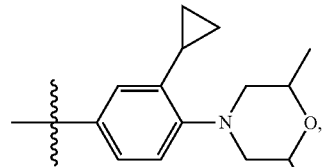

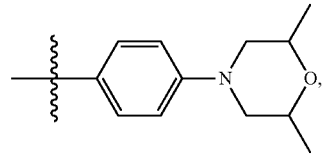

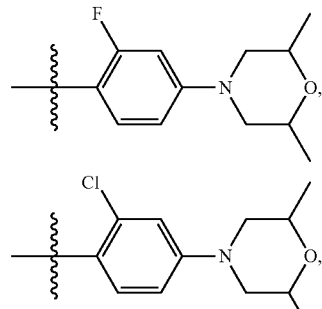

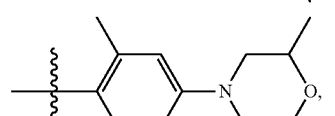

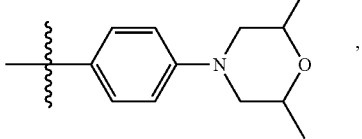

-continued

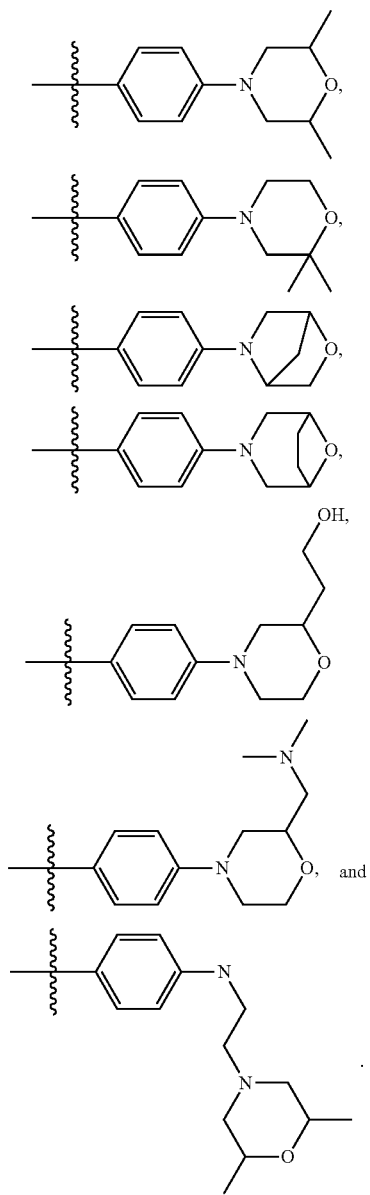

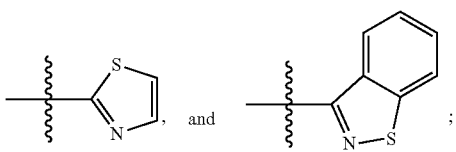 [SMILES: *c1nccs1 ; *c1nsc2ccccc12]

or, B is selected from

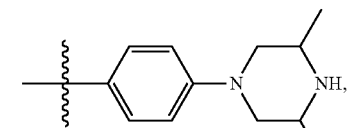

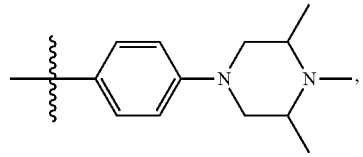

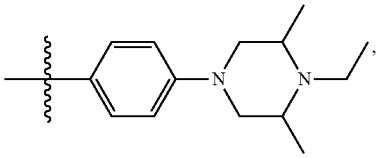

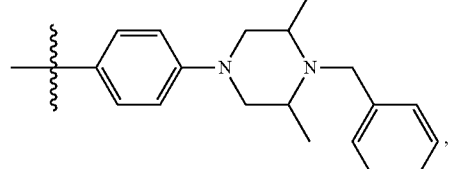

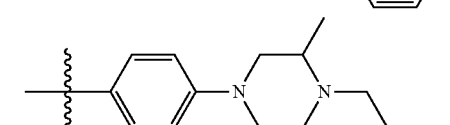

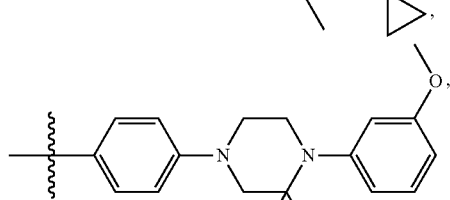

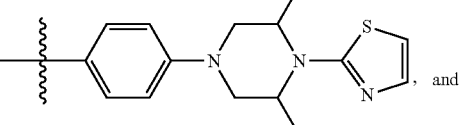

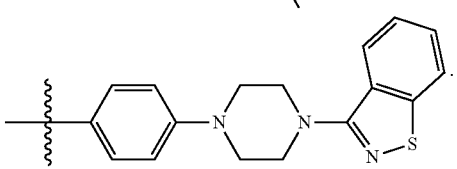

14. The compound represented by formula (I), or the pharmaceutically acceptable salt thereof according to claim 6, wherein, B is selected from

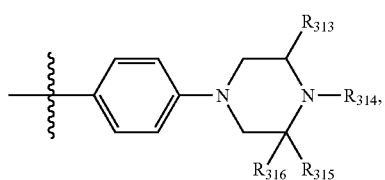

wherein, each of $R_{313}$, $R_{315}$, $R_{316}$ is independently selected from H, and a methyl;

$R_{314}$ is selected from H, a methyl, an ethyl, a phenyl methylene, a cyclopropyl methylene, a methoxyphenyl,

15. The compound represented by formula (I), or the pharmaceutically acceptable salt thereof according to claim 7, wherein B is selected from

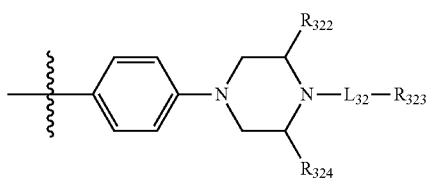

wherein, each of $R_{322}$, $R_{324}$ is independently selected from H, a methyl, a phenyl, and $C(CH_3)_2OH$;

$L_{32}$ is selected from $C(=O)$, and $S(=O)_2$;

or, $R_{323}$ is selected from a tert-butoxy, a methyl, a methoxy, an ethyl, an ethoxy, an propoxy, an isopropyl, a n-propyl, an isopropoxy, a cyclopropyl, a methylamino, a phenyl, a pyridyl, a 3-methyl pyridyl, an imidazolyl, and $C(CH_3)_2OH$;

or, B is selected from

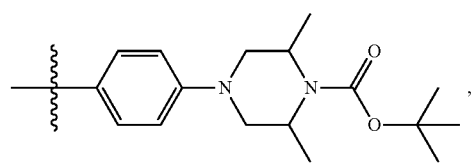

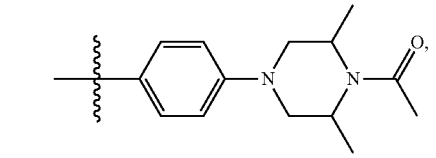

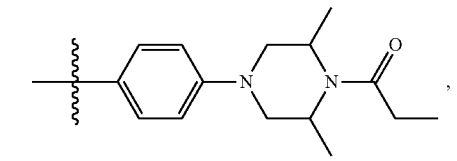

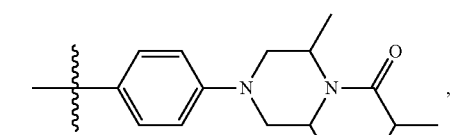

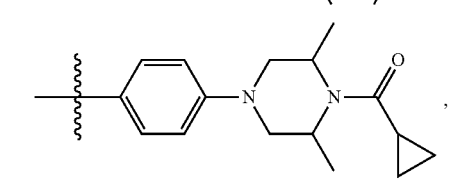

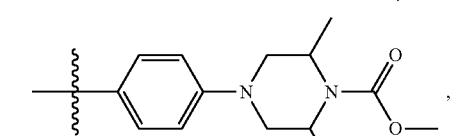

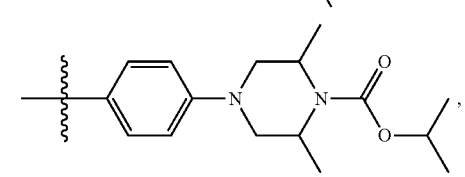

-continued

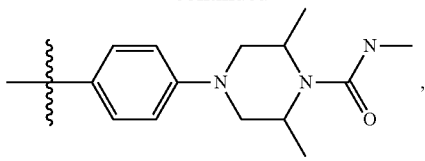

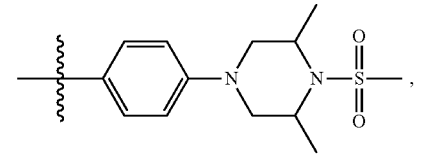

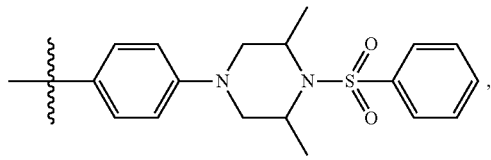

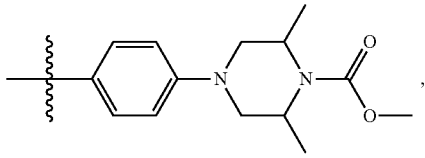

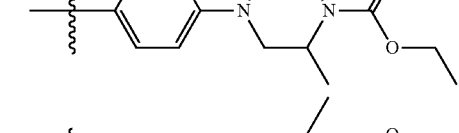

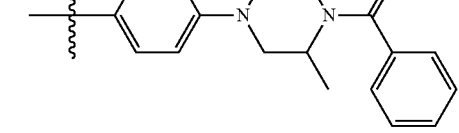

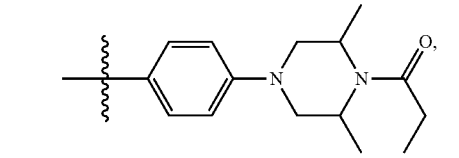

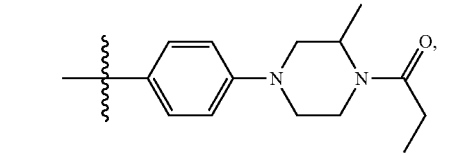

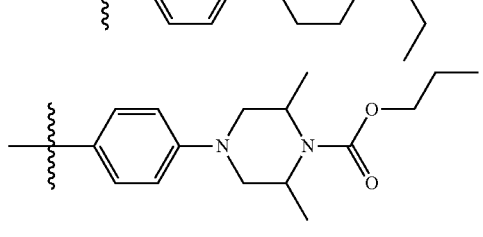

-continued

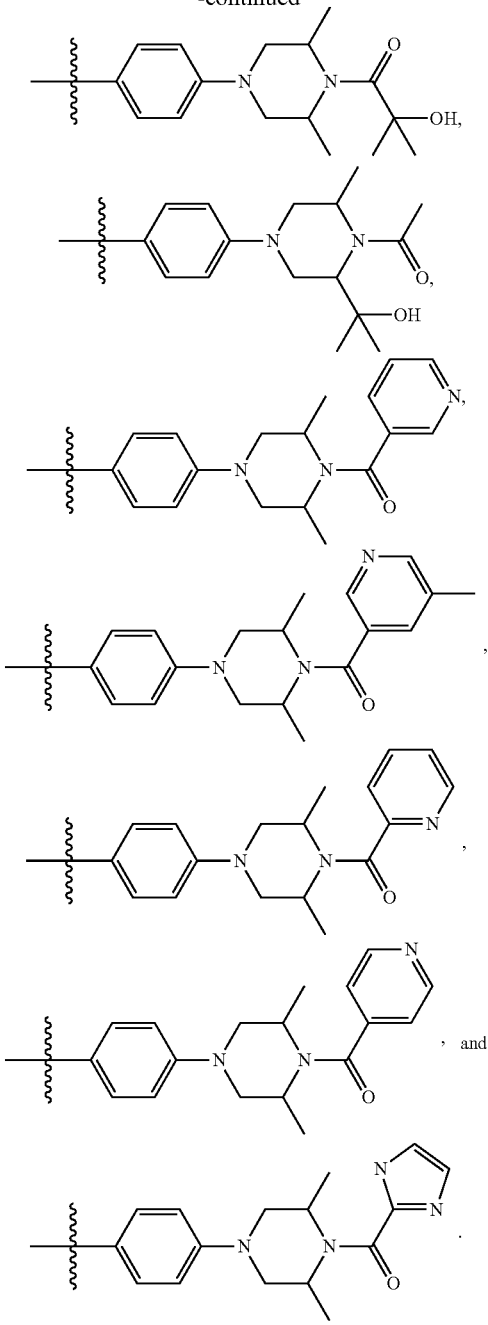

16. The compound represented by formula (I), or the pharmaceutically acceptable salt thereof according to claim 8, wherein B is selected from

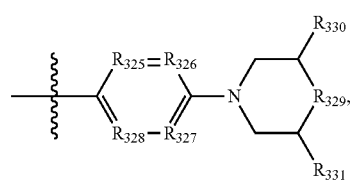

wherein one or two of $R_{325-328}$ is selected from N, the rest are selected from CH, CC(=O)OH and CCH$_3$;

$R_{329}$ is selected from N($R_{3014}$), and O;
$R_{3014}$ is selected from C(=O)$R_{3020}$, and

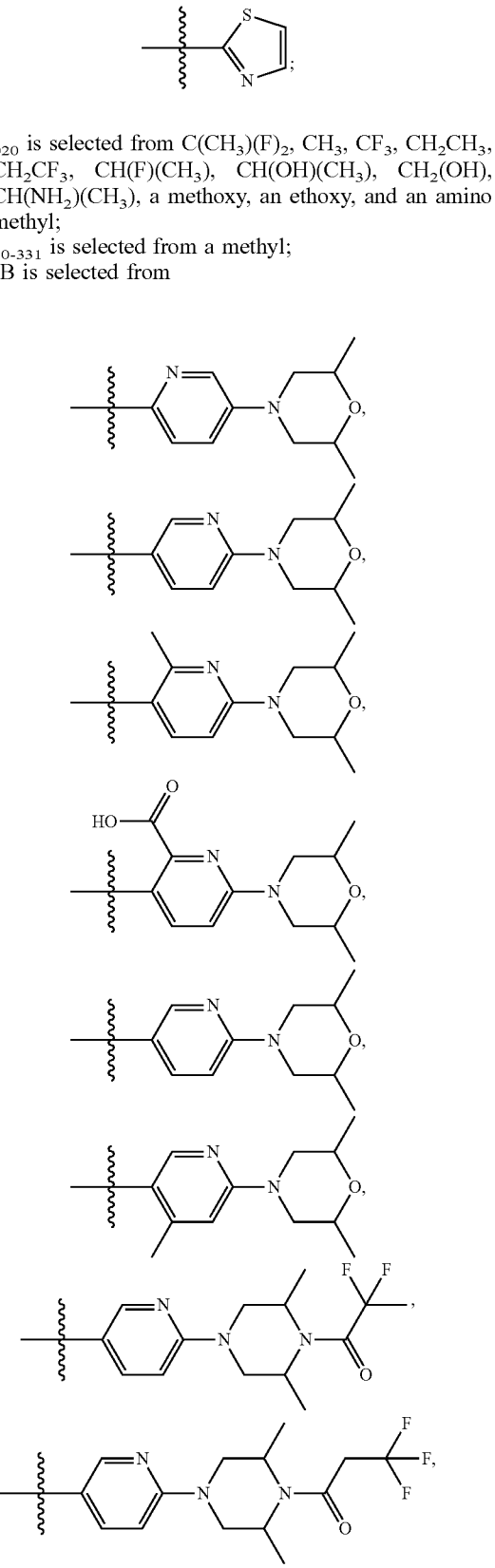

$R_{3020}$ is selected from C(CH$_3$)(F)$_2$, CH$_3$, CF$_3$, CH$_2$CH$_3$, CH$_2$CF$_3$, CH(F)(CH$_3$), CH(OH)(CH$_3$), CH$_2$(OH), CH(NH$_2$)(CH$_3$), a methoxy, an ethoxy, and an amino methyl;
$R_{330-331}$ is selected from a methyl;
or, B is selected from 397
-continued

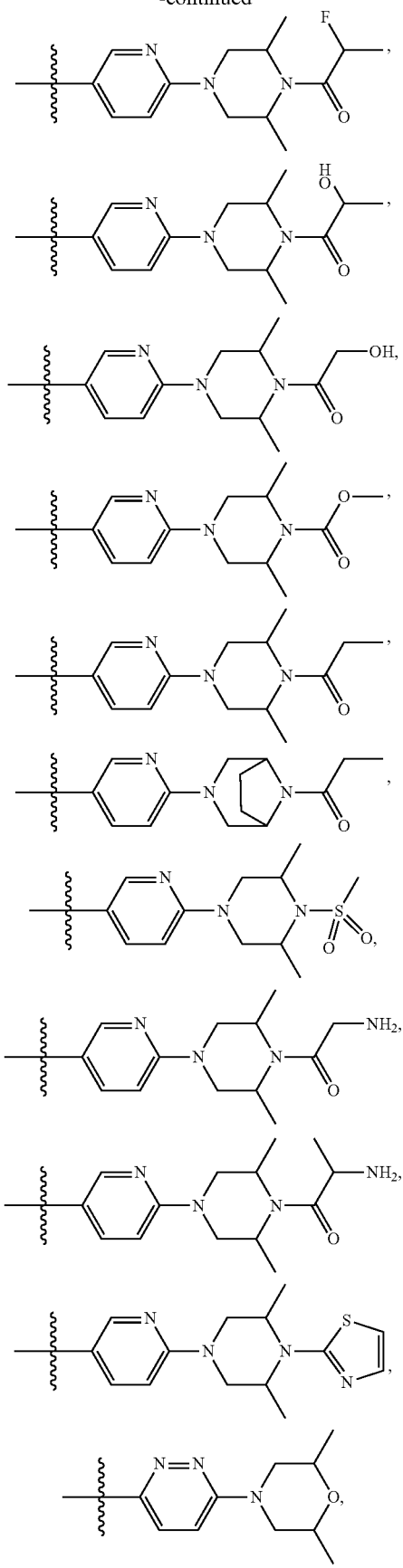

398
-continued

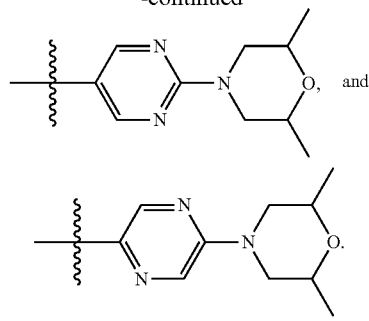

17. The compound represented by formula (I), or the pharmaceutically acceptable salt thereof according to claim 9, wherein B is selected from

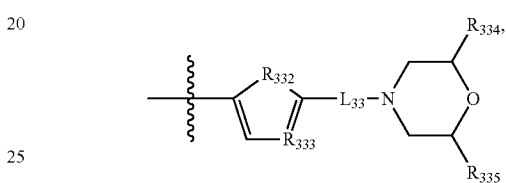

wherein, $R_{332}$ is selected from S, $R_{333}$ is selected from N and CH, $L_{33}$ is selected from a single bond, C(=O), each of $R_{334}$, $R_{335}$ is selected from a methyl;
or, B is selected from

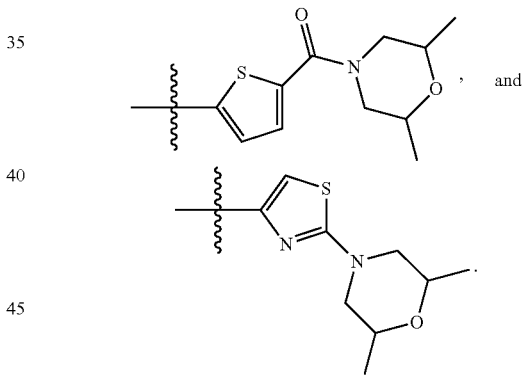

18. The compound represented by formula (I), or the pharmaceutically acceptable salt thereof according to claim 1, wherein the $C_{3-8}$ cyclic group or heterocyclic group or cycle-heteroatom group or heterocycle-heteroatom group is selected from a phenyl, a pyridyl, a thienyl, a furyl, an imidazolyl, an oxazolyl, a thiazolyl, and an isothiazolyl.

19. The compound represented by formula (I), or the pharmaceutically acceptable salt thereof according to claim 4, wherein B is selected from

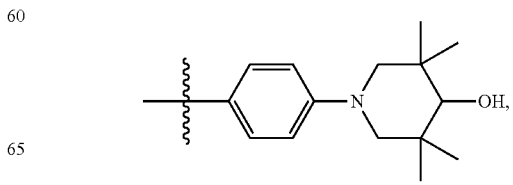

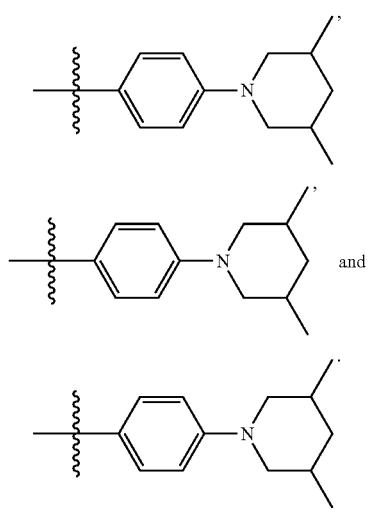
20. The compound represented by formula (I), or the pharmaceutically acceptable salt thereof according to claim 1, wherein $R_{31}$ and $R_{32}$, $R_{31}$ and $R_{33}$, $R_{31}$ and $R_{35}$, $E_{33}$ and $E_{34}$ form a linking bond $(CH_2)_{1-6}$ together, the linking bond being $(CH_2)_2$, $(CH_2)_3$, $(CH_2)_4$, or $(CH_2)_5$.
* * * * *

UNITED STATES PATENT AND TRADEMARK OFFICE
CERTIFICATE OF CORRECTION

PATENT NO. : 9,938,292 B2
APPLICATION NO. : 15/128064
DATED : April 10, 2018
INVENTOR(S) : Hao Wu et al.

Page 1 of 3

It is certified that error appears in the above-identified patent and that said Letters Patent is hereby corrected as shown below:

In the Claims

Column 357, the formula beginning at Line 35-40 reading:

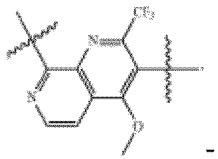

Should be read as:

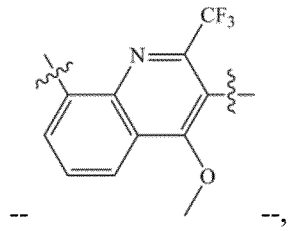

Column 361, the formula beginning at Line 5-10 reading:

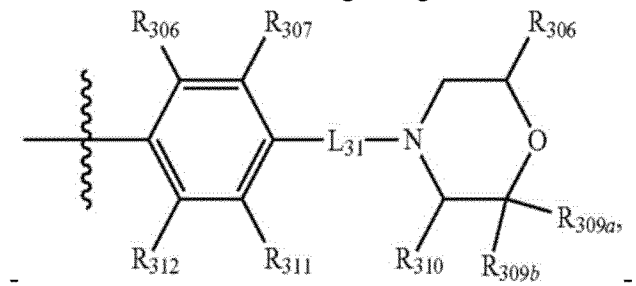

Signed and Sealed this
Nineteenth Day of July, 2022

Katherine Kelly Vidal

Katherine Kelly Vidal
*Director of the United States Patent and Trademark Office*

CERTIFICATE OF CORRECTION (continued)
U.S. Pat. No. 9,938,292 B2

Should be read as:

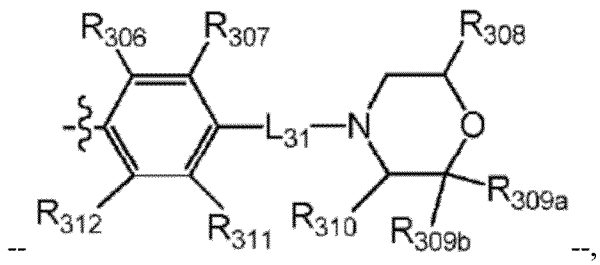

Column 374, the formula beginning at Line 5-10 reading:

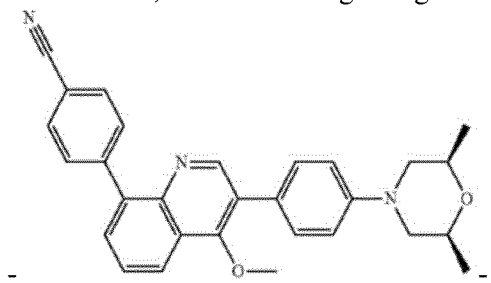

Should be read as:

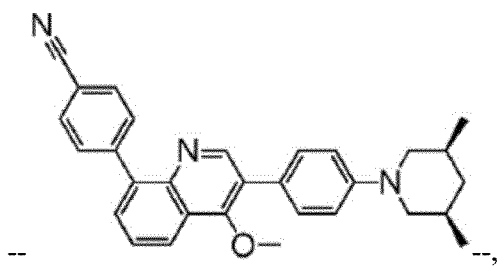

Column 385, the formula beginning at Line 55-65 reading:

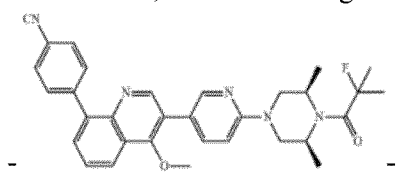

Should be read as:

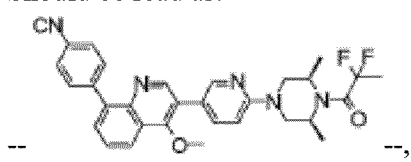

CERTIFICATE OF CORRECTION (continued)
U.S. Pat. No. 9,938,292 B2

Column 389, the formula beginning at Line 45 reading:

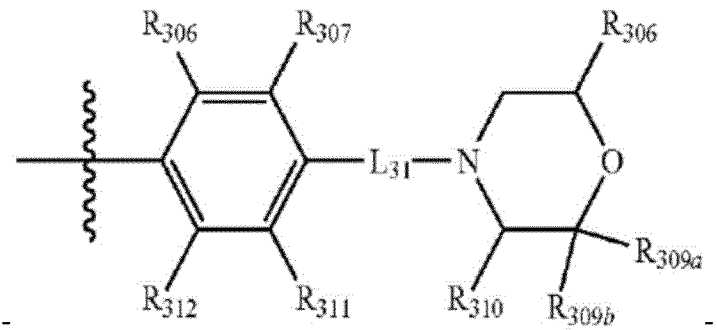

Should be read as: